US008889868B2

(12) United States Patent
Beusker et al.

(10) Patent No.: US 8,889,868 B2
(45) Date of Patent: Nov. 18, 2014

(54) CC-1065 ANALOGS AND THEIR CONJUGATES

(75) Inventors: Patrick Henry Beusker, Nijmegen (NL); Rudy Gerardus Elisabeth Coumans, Nijmegen (NL); Ronald Christiaan Elgersma, Nijmegen (NL); Wiro Michaël Petrus Bernardus Menge, Nijmegen (NL); Johannes Albertus Frederikus Joosten, Nijmegen (NL); Henri Johannes Spijker, Nijmegen (NL); Franciscus Marinus Hendrikus de Groot, Nijmegen (NL)

(73) Assignee: Syntarga BV, Nijmegen (NL)

( * ) Notice: Subject to any disclaimer, the term of this patent is extended or adjusted under 35 U.S.C. 154(b) by 235 days.

(21) Appl. No.: 13/126,920

(22) PCT Filed: Nov. 3, 2009

(86) PCT No.: PCT/NL2009/050660
§ 371 (c)(1),
(2), (4) Date: Apr. 29, 2011

(87) PCT Pub. No.: WO2010/062171
PCT Pub. Date: Jun. 3, 2010

(65) Prior Publication Data
US 2011/0207767 A1 Aug. 25, 2011

Related U.S. Application Data

(60) Provisional application No. 61/110,765, filed on Nov. 3, 2008, provisional application No. 61/140,213, filed on Dec. 23, 2008, provisional application No. 61/170,231, filed on Apr. 17, 2009.

(51) Int. Cl.
*A61K 31/4355* (2006.01)
*C07D 491/048* (2006.01)
*A61K 31/437* (2006.01)
*C07D 471/04* (2006.01)
*C07D 403/14* (2006.01)
*C07D 403/06* (2006.01)
*C07D 413/06* (2006.01)
*C07D 417/06* (2006.01)
*C07D 495/04* (2006.01)

(52) U.S. Cl.
CPC .......... *C07D 403/14* (2013.01); *C07D 491/048* (2013.01); *A61K 31/4355* (2013.01); *A61K 31/437* (2013.01); *C07D 403/06* (2013.01); *C07D 413/06* (2013.01); *C07D 417/06* (2013.01); *C07D 471/04* (2013.01); *C07D 495/04* (2013.01)
USPC ........... 546/113; 546/115; 546/121; 514/300; 514/302

(58) Field of Classification Search
CPC ............. C07D 491/048; C07D 471/04; A61K 31/4355; A61K 31/437
USPC .................. 546/113, 115, 121; 514/300, 302
See application file for complete search history.

(56) References Cited

U.S. PATENT DOCUMENTS

| | | |
|---|---|---|
| 5,475,092 A | 12/1995 | Chari |
| 5,502,068 A | 3/1996 | Lown |
| 5,585,499 A | 12/1996 | Chari |
| 5,629,430 A | 5/1997 | Terashima |
| 5,646,298 A | 7/1997 | Powell |
| 5,670,492 A | 9/1997 | Amishiro |
| 5,739,350 A | 4/1998 | Kelly |
| 5,843,937 A | 12/1998 | Wang |
| 5,846,545 A | 12/1998 | Chari |
| 7,223,837 B2 | 5/2007 | De Groot |
| 7,705,045 B2 | 4/2010 | De Groot |
| 2003/0050331 A1 | 3/2003 | Ng |
| 2005/0014700 A1* | 1/2005 | Boger ............................ 514/19 |
| 2005/0026987 A1 | 2/2005 | Boger |
| 2005/0148651 A1 | 7/2005 | Denny |
| 2007/0037739 A1 | 2/2007 | Wang |
| 2008/0279868 A1 | 11/2008 | Boyd |
| 2008/0311136 A1 | 12/2008 | Beusker et al. |

(Continued)

FOREIGN PATENT DOCUMENTS

| | | | |
|---|---|---|---|
| EP | 0 154 445 | A1 | 9/1985 |
| EP | 0154 445 | B1 | 5/1989 |

(Continued)

OTHER PUBLICATIONS

Boger "CC-1065 and the duocarmycins: Unraveling the keys to a new class of naturally derived DNA alkylating agents" Proc. Natl. Acad. Sci. USA vol. 92 Apr. 1995, pp. 3642-3649.*
Tietze et. al. "Determination of the Biological Activity and Structure Activity Relationships of Drugs Based on the Highly Cytotoxic Duocarmycins and CC-1065" Toxins 2009, 1, 134-150.*
Parrish J.P. et al., "Establishment of Substituent Effects in DNA Binding subunit of CBI Analogues of the Duocarmycins and CC-1065", Bioorganic & Medicinal Chemistry, Pergamon, GB, vol. 11, Jan. 1, 2003, pp. 3815-3838.
Atwell et al., "5-Amino-1-(chloromethyl)-1,2-dihydro-3H-benz[e]indoles:", J. Med. Chem., vol. 42, No. 17, Jan. 1, 1999, pp. 3400-3411.

(Continued)

*Primary Examiner* — David K O Dell
(74) *Attorney, Agent, or Firm* — Mark R. Buscher

(57) ABSTRACT

This invention relates to novel analogs of the DNA-alkylating agent CC-1065 and to their conjugates. Furthermore this invention concerns intermediates for the preparation of said agents and conjugates. The conjugates are designed to release their (multiple) payload after one or more activation steps and/or at a rate and time span controlled by the conjugate in order to selectively deliver and/or controllably release one or more of said DNA alkylating agents. The agents, conjugates, and intermediates can be used to treat an illness that is characterized by undesired (cell) proliferation. As an example, the agents and the conjugates of this invention may be used to treat a tumor.

14 Claims, 9 Drawing Sheets

(56) References Cited

U.S. PATENT DOCUMENTS

| | | | |
|---|---|---|---|
| 2009/0162372 | A1 | 6/2009 | King |
| 2009/0318668 | A1 | 12/2009 | Beusker et al. |
| 2010/0113476 | A1 | 5/2010 | Chen |
| 2011/0065767 | A1 | 3/2011 | Beusker et al. |
| 2011/0207767 | A1 | 8/2011 | Beusker |

FOREIGN PATENT DOCUMENTS

| | | | |
|---|---|---|---|
| EP | 0 65 360 | A1 | 6/1995 |
| EP | 0 702 014 | A1 | 3/1996 |
| WO | WO 88/04659 | | 6/1988 |
| WO | WO 90/02746 | | 3/1990 |
| WO | WO 91/16324 | | 10/1991 |
| WO | WO 95/31971 | | 11/1995 |
| WO | WO 97/07097 | | 2/1997 |
| WO | WO 97/12862 | | 4/1997 |
| WO | WO 97/32850 | | 9/1997 |
| WO | WO 97/44000 | | 11/1997 |
| WO | WO 97/44000 | A2 | 11/1997 |
| WO | WO 97/45411 | | 12/1997 |
| WO | WO 98/11101 | A2 | 3/1998 |
| WO | WO 98/25898 | | 6/1998 |
| WO | WO 98/52925 | | 11/1998 |
| WO | WO 99/19298 | | 4/1999 |
| WO | WO 01/83482 | | 11/2001 |
| WO | WO 02/30894 | | 4/2002 |
| WO | WO 02/059122 | | 8/2002 |
| WO | WO 02/067930 | | 9/2002 |
| WO | WO 02/067937 | | 9/2002 |
| WO | WO 02/068412 | | 9/2002 |
| WO | WO 02/096910 | A1 | 12/2002 |
| WO | WO 03/022806 | | 3/2003 |
| WO | WO 03/086318 | | 10/2003 |
| WO | WO 03/097635 | A1 | 11/2003 |
| WO | WO 2004/069201 | A2 | 8/2004 |
| WO | WO 2004/101767 | A2 | 11/2004 |
| WO | WO 2005/103040 | | 11/2005 |
| WO | 2005/112919 | | 12/2005 |
| WO | WO 2006/002895 | | 1/2006 |
| WO | WO 2006/043839 | | 4/2006 |
| WO | WO 2006/110476 | | 10/2006 |
| WO | WO 2007/038658 | A2 | 4/2007 |
| WO | WO 2007/051081 | | 5/2007 |
| WO | WO 2007/059404 | | 5/2007 |
| WO | WO 2007/089149 | | 8/2007 |
| WO | WO 2008/083312 | | 7/2008 |
| WO | WO 2008/103693 | A2 | 8/2008 |
| WO | WO 2009/026274 | | 2/2009 |
| WO | WO 2009/064908 | | 5/2009 |
| WO | WO 2009/073524 | | 6/2009 |
| WO | WO 2009/073533 | | 6/2009 |
| WO | WO 2009/073546 | | 6/2009 |
| WO | WO 2009/134977 | | 11/2009 |
| WO | WO 2010/062171 | A2 | 6/2010 |

OTHER PUBLICATIONS

Yuqiang Wang et al., "CC-1065 Analogues Bearing Different DNA-Binding Subunits:" J. Med. Chem., vol. 46, No. 4, Feb. 1, 2003, pp. 634-637.
Parrish J.P. et al., "Synthesis and Evaluation of N-aryl and N-alkenyl CBI derivatives", Bioorganic & Medicinal Chemistry, Pergamon, GB, vol. 12, No. 22, Nov. 15, 2004, pp. 5845-5856.
Dale L. Boger et al., "Synthesis and Evaluation of a Series of C3-Substituted CBI Analogues of CC-1065 and Duocarmycins", J. Org. Chem,, vol. 66, No. 15, Jul. 1, 2001, pp. 5163-5173.
Lutz F. Tietze et al., "Selective Treatment of Cancer: Synthesis, Biological Evaluation and Structure Elucidation of Novel Analogues of the Antibiotic CC-1065 and Duocarmycins", Chemistry—A European Journal, vol. 13, No. 16, May 25, 2007, pp. 4396-4409.
Wang et al., "Design, Synthesis, Cytotoxic Properties and Preliminary DNA Sequencing Evaluation of CPI-N-Methylpyrrole Hybrids.", Anti-Cancer Drug Design, Oxford Univ Press, vol. 11, Jan. 1, 1996, pp. 15-34.
Amishiro et al., "New Water-Soluble Duocarmycin Derivatives:", J. Med. Chem., vol. 42, No. 4, Feb. 1, 1999, pp. 669-676.
Schuster et al., "Synthesis of the First Spacer Containing Prodrug of a Duocarmycin Analogue and Determination of its Biological Activity", Organic & Biomolecular Chem., vol. 8, No. 8, Jan. 1, 2010, p. 1833.
Aristoff et al., "Synthesis of CBI-PDE-I-Dimer, . . . " J. Org. Chem., vol. 57, No. 23, 1992, pp. 6234-6239.
Bando and Sugiyama, "Synthesis and Biological Properties of Sequence-Specific DNA-Alkylating Pyrrole-Imidazole Polyamides" Acc. Chem. Res. 2006, 39, p. 935-944.
Boger et al., "Examination of the Role of the Duocarmycin SA Methoxy Substituents: . . . ", Biorg. Med. Chem. Lett., vol. 6, No. 18, pp. 2207-2210, 1996.
Boger et al., "Substituent Effects Within the DNA Binding Subunit of CBI Analogues of Duocarmycins and CC-1065" Bioorg. Med. Chem. Lett., vol. 11, pp. 2021-2024, 2001.
Boger et al., "CC-1065 and the Duocarmycins: Synthetic Stidies" Chem. Rev. 1987, 97, pp. 787-828.
Boyle et al., "Synthesis and Evaluation of Duocarmycin SA analogs incorporating the methyl . . . " Bioorg. Med. Chem. Lett. vol. 20, 2010, pp. 1854-1857.
Chavda et al., "A Novel Achiral seco-cyclopropylpyrido[e]indolone (CPyl) analog of CC-1065 . . . " Bioorg. Med. Chem. Lett., vol. 18, 2010, pp. 5016-5024.
Daniell et al., "Design, Synthesis, and Biological Evaluation of Achiral Analogs of Duocarmycin SA" Bioorg. Med. Chem. Lett., vol. 15, 2005, pp. 177-180.
Gauss et al., "Synthesis and Preliminary Evaluation of Duocarmycin analogues incorporating the . . . ", Tetrahedron, 65, 2009, pp. 6591-6599.
Jeffrey et al., "Design, Synthesis, and in Vitro Evaluation of Dipeptide-Based Antibody Minor Groove Binder Conjugates" J. Med. Chem. 2005, 48, 1344-1358.
Li and Sinha, "Studies Toward the Duocarmycin Prodrugs for the Antibody Prodrug Therapy Approach" Tetrahedron, 50, 2009, 2932-2935.
MacMillan et al., "Total Synthesis and Evaluation of iso-Duocarmycin SA and iso-Yatakemycin" J. AM. Chem. Soc. 2009, 131, 1187-1194.
Milbank et al., "Synthesis of 1-Substituted 3-(Chloromethyl)-6-aminoindoline . . . ", J.Med.Chem. 1999, 42, 649-658.
Purnell et al., "DNA Interstand Crosslinking agents: . . . " Bioorg. Med. Chem. Lett., 16, 2006, 5677-5681.
Robertson et al., "Synthesis and Evaluation of a series of C5'-Substituted Duocarmycin SA Analogs" Bioorg. Med. Chem Lett. 20, 2010, 2722-2725.
Suzawa et al., "Synthesis of a novel Duocarmycin Derivative DU-257 and . . . " Biorg. Med. Chem. Lett., 8, 2000, 2175-2184.
Tichenor et al., "Asymmetric Total Synthesis of (+)- and ent-(—)-Yatakemycin and Duocarmycon SA: . . . " J. AM. Chem. Soc. 2006, 128, 15683-15696.
Tichenor and Boger, "Yatakemycin: total synthesis, DNA alkylation, and biological properties" Nat. Prod. Rep., 2008, 25, 220-226.
Tietze et al., "Glycosidic Prodrugs of Highly Potent Bifunctional Duocarmycin Derivatives for Selective Treatment of Cancer" Angew Chem. Int. Ed. 2010, 49, 7336-7339.
Tietze and Krewer, "Novel Analogues of CC-1065 and the Duocarmycins for the Use in Targeted Tumour Therapies" Anti-Cancer Agents in Med. Chem., 2009, 9, 304-325.
Tietze et al., "Synthesis of a Novel Pentagastrin-Drug Conjugate for a Targeted Tumor Therapy" Chem. Eur. J. 2008, 14, 2811-2818.
Tietze et al., "Asymmetric Synthesis and Biological Evaluation of Glycosidic Prodrugs for a Selective Cancer Therapy" ChemMedChem 2008, 3, 1946-1955.
Wang et al., "Synthesis and Antitumor Activity of CBI-bearing Ester and Carbamte prodrugs of CC-1065" Bioorg. Med. Chem., 14, 2006, 7854-7861.
Wang et al., "Synthesis and Preliminary Biological Evaluations of CC-1065 Analogues: . . . " J. Med. Chem. 2000, 43, 1541-1549.
Amishiro et al., "Synthesis and Antitumor Activity of Duocarmycin Derivatives:" Bioorganic & Medicinal Chem., vol. 8, No. 7, Jul. 2000, pp. 1637-1643.

* cited by examiner

| Cmpd | X | Y | Cmpd | X | Y |
|---|---|---|---|---|---|
| a | CF₃ | H | g | OPr | H |
| b | F | H | h | O'Pr | H |
| c | CN | H | i | Cl | H |
| d | Et | H | j | OMe | H |
| e | OMe | Me | k | Me | Me |
| f | OEt | H | | | |

CC-1065 ANALOGS AND THEIR CONJUGATES

CROSS-REFERENCE TO RELATED APPLICATIONS

This application is the national phase of International (PCT) Patent Application Serial No. PCT/NL2009/050660, filed on Nov. 3, 2009, which claims priority to and the benefit of U.S. Ser. No. 61/110,765 filed on Nov. 3, 2008, U.S. Ser. No. 61/140,213 filed on Dec. 23, 2008, and U.S. Ser. No. 61/170,231 filed on Apr. 17, 2009, the disclosures of which are incorporated herein by reference.

FIELD OF THE INVENTION

This invention relates to novel analogs of the DNA-alkylating agent CC-1065 and to their conjugates. Furthermore this invention concerns intermediates for the preparation of said agents and conjugates. The conjugates are designed to release their (multiple) payload after one or more activation steps and/or at a rate and time span controlled by the conjugate in order to selectively deliver and/or controllably release one or more of said DNA-alkylating agents. The agents, conjugates, and intermediates can be used to treat an illness that is characterized by undesired (cell) proliferation. As an example, the agents and the conjugates of this invention may be used to treat a tumor.

BACKGROUND OF THE INVENTION

The duocarmycins, first isolated from a culture broth of *Streptomyces* species, are members of a family of antitumor antibiotics that also includes CC-1065. These extremely potent agents allegedly derive their biological activity from an ability to sequence-selectively alkylate DNA at the N3 of adenine in the minor groove, which initiates a cascade of events that terminates in an apoptotic cell death mechanism.[1]

Although CC-1065 has shown very potent cytotoxicity, it could not be used in the clinic because of serious delayed hepatotoxicity.[2] This observation led to the development of synthetic analogs of CC-1065 (see for CC-1065 derivatives for example Aristoff et al., *J. Org. Chem.* 1992, 57, 6234; Boger et al., *Bioorg. Med. Chem. Lett.* 1996, 6, 2207; Boger et al., *Chem. Rev.* 1997, 97, 787; Milbank et al., *J. Med. Chem.* 1999, 42, 649; Atwell et al., *J. Med. Chem.* 1999, 42, 3400; Wang et al., *J. Med. Chem.* 2000, 43, 1541; Boger et al., *Bioorg. Med. Chem. Lett* 2001, 11, 2021; Parrish et al., *Bioorg. Med. Chem.* 2003, 11, 3815; Daniell et al., *Bioorg. Med. Chem. Lett.* 2005, 15, 177; Tichenor et al., *J. Am. Chem. Soc.* 2006, 128, 15683; Purnell et al., *Bioorg. Med. Chem.* 2006, 16, 5677; Bando and Sugiyama, *Acc. Chem. Res.* 2006, 39, 935; Tichenor et al., *Nat. Prod. Rep.* 2008, 25, 220; MacMillan et al., *J. Am. Chem. Soc.* 2009, 131, 1187; Tietze et al., *Anti-Cancer Agents Med. Chem.* 2009, 9, 304; Gauss et al., *Tetrahedron* 2009, 65, 6591; EP 0154445; WO 88/04659; WO 90/02746; WO 97/12862; WO 97/32850; WO 97/45411; WO 98/52925; WO 99/19298; WO 01/83482; WO 02/067937; WO 02/067930; WO 02/068412; WO 03/022806; WO 2004/101767; WO 2006/043839; and WO 2007/051081), which generally showed to have similar cytotoxicity, but reduced hepatotoxicity. Still, however, these derivatives lack sufficient selectivity for tumor cells, as the selectivity of these agents—and cytotoxic agents in general—is for a certain part based on the difference in the rate of proliferation of tumor cells and normal cells, and therefore they also affect healthy cells that show a relatively high proliferation rate. This typically leads to severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modern drug development, targeting of cytotoxic drugs to the tumor site can therefore be considered one of the primary goals.

One promising approach to obtain increased selectivity for tumor cells or tumor tissue is to exploit the existence of tumor-associated antigens, receptors, and other receptive moieties, which can serve as a target. Such a target may be upregulated or to some degree be specifically present in tumor tissue or in closely associated tissue, such as neovascular tissue, with respect to other tissues in order to achieve efficient targeting. Many targets have been identified and validated and several methods to identify and validate targets have been developed.[3] By coupling a ligand, e.g. an antibody or antibody fragment, for such a tumor-associated antigen, receptor, or other receptive moiety to a therapeutic agent, this agent can be selectively targeted to tumor tissue.

Another promising approach to obtain selectivity for tumor cells or tumor tissue is to exploit the existence of tumor-associated enzymes. An enzyme that is mainly localized at the tumor site can convert a pharmacologically inactive prodrug, which consists of an enzyme substrate directly or indirectly linked to the toxic drug, to the corresponding drug in the vicinity of or inside the tumor. Via this concept a high concentration of toxic anticancer agent can be selectively generated at the tumor site. All tumor cells may be killed if the dose is sufficiently high, which may decrease development of drug-resistant tumor cells.

Enzymes can also be transported to the vicinity of or inside target cells or target tissue via for example antibody-directed enzyme prodrug therapy (ADEPT)[4], polymer-directed enzyme prodrug therapy (PDEPT) or macromolecular-directed enzyme prodrug therapy (MDEPT)[5], virus-directed enzyme prodrug therapy (VDEPT)[6], or gene-directed enzyme prodrug therapy (GDEPT)[7]. With ADEPT, for example, a non-toxic prodrug is selectively converted into a cytotoxic compound at the surface of target cells by an antibody-enzyme conjugate that has been pretargeted to the surface of those cells.

Yet another promising approach to obtain selectivity for tumor cells or tumor tissue is to exploit the enhanced permeability and retention (EPR) effect. Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.[8] By coupling a therapeutic agent directly or indirectly to a macromolecule, said agent can be selectively targeted to tumor tissue.

Besides efficient targeting, other important criteria for the successful application of targeted conjugates of cytotoxic agents in tumor therapy are that the one or more agents are released efficiently from the conjugate at the tumor site and that the conjugate is non-cytotoxic or only very weakly cytotoxic, whereas the cytotoxic agent itself exhibits highly potent cytotoxicity. Ideally, this leads to the generation of cytotoxic molecules only at the tumor site, which results in a greatly increased therapeutic index with respect to the untargeted cytotoxic agent. Another important criterion for a successful targeted conjugate is that the conjugate must have suitable pharmacological properties, such as sufficient stability in the circulation, low aggregation tendency, and good water solubility. Appropriate water-solubility and hydrophilicity of the drug and/or the linker may contribute to improved pharmacological properties.

Several conjugates of CC-1065 and derivatives have been described (see for conjugates of CC-1065 derivatives for example Suzawa et al., *Bioorg. Med. Chem.* 2000, 8, 2175; Jeffrey et al., *J. Med. Chem.* 2005, 48, 1344; Wang et al., *Bioorg. Med. Chem.* 2006, 14, 7854; Tietze et al., *Chem. Eur. J.* 2007, 13, 4396; Tietze et al., *Chem. Eur. J.* 2008, 14, 2811; Tietze et al., *Chem Med Chem* 2008, 3, 1946; Li et al., *Tetrahedron Lett.* 2009, 50, 2932; WO 91/16324; WO 94/04535; WO 95/31971; U.S. Pat. Nos. 5,475,092; 5,585,499; 5,646,298; WO 97/07097; WO 97/44000; U.S. Pat. No. 5,739,350; WO 98/11101; WO 98/25898; U.S. Pat. Nos. 5,843,937; 5,846,545; WO 02/059122; WO 02/30894; WO 03/086318; WO 2005/103040; WO 2005/112919; WO 2006/002895; WO 2006/110476; WO 2007/038658; WO 2007/059404; WO 2008/083312; WO 2008/103693; WO 2009/026274; and WO 2009/064908). In these conjugates, one or more of the favorable properties discussed above may be non-optimal.

Accordingly, there is still a clear need for conjugates of CC-1065 derivatives that show high cytotoxicity quotients (i.e., $IC_{50,\ conjugate}/IC_{50,\ parent\ drug}$), contain CC-1065 derivatives that have potent cytotoxicity and favorable pharmacological properties, and release the CC-1065 derivatives efficiently.

SUMMARY OF THE INVENTION

The present invention fulfils the above-mentioned need with a compound of formula (I) or (II):

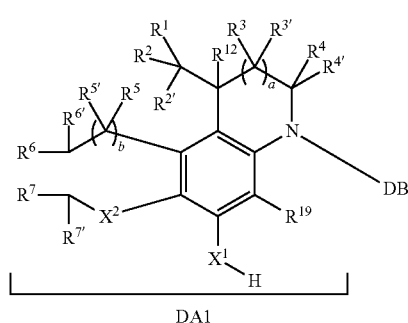

DA1

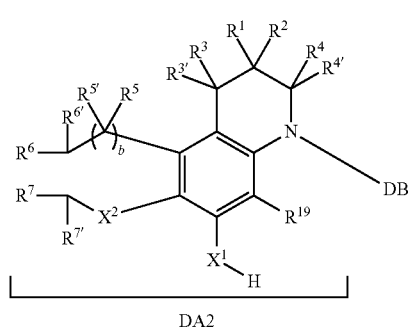

DA2 or a pharmaceutically acceptable salt, hydrate, or solvate thereof, wherein DB is a DNA-binding moiety and is selected from the group consisting of

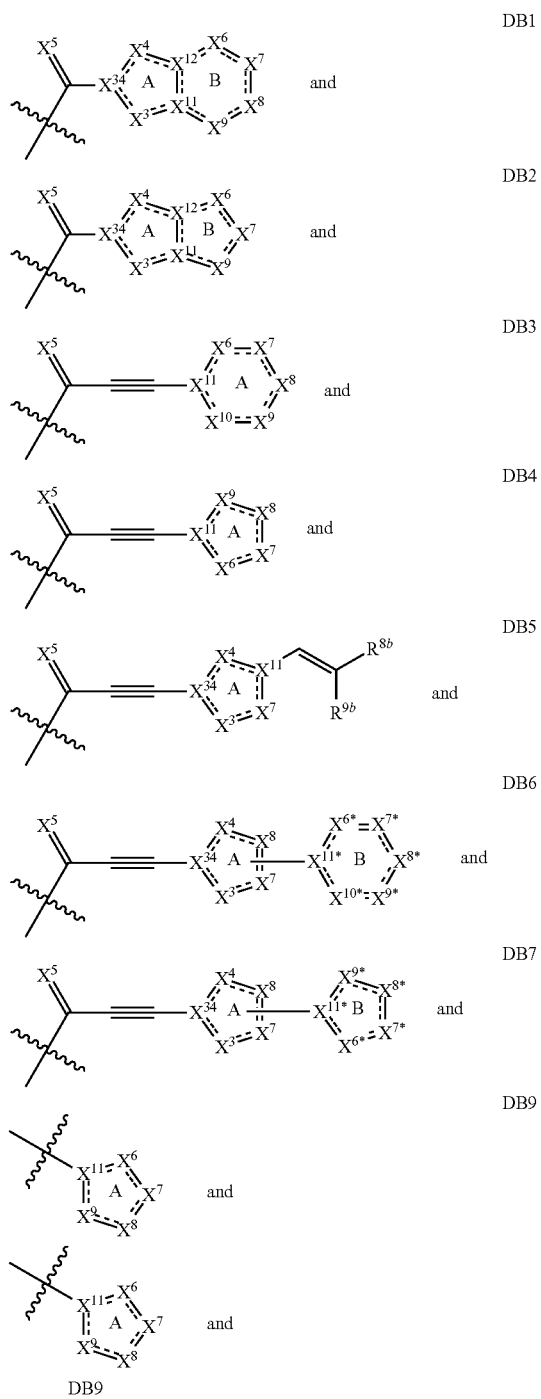

$R^1$ is a leaving group;
$R^2$, $R^{2'}$, $R^3$, $R^{3'}$, $R^4$, $R^{4'}$, $R^{12}$, and $R^{19}$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, and $N(R^a)C(O)N(R^b)R^c$, wherein
$R^a$, $R^b$, and $R^c$ are independently selected from H and optionally substituted $C_{1-3}$ alkyl or $C_{1-3}$ heteroalkyl, or $R^3+R^{3'}$ and/or $R^4+R^{4'}$ are independently selected from =O, =S, =NR$^{18}$, =C(R$^{18}$)R$^{18'}$, and =NR$^{18}$, R$^{18}$ and R$^{18'}$ being independently selected from H and optionally substituted $C_{1-3}$ alkyl, two or more of $R^2$, $R^{2'}$, $R^3$, $R^{3'}$, $R^4$, $R^{4'}$, and $R^{12}$ optionally being joined by one or more bonds to form one or more optionally substituted carbocycles and/or heterocycles;

$X^2$ is selected from O, C(R$^{14}$)(R$^{14'}$), and NR$^{14'}$, wherein R$^{14}$ and R$^{14'}$ have the same meaning as defined for R$^7$ and are independently selected, or R$^{14'}$ and R$^7$ are absent resulting in a double bond between the atoms designated to bear R$^7$ and R$^{14'}$;

$R^5$, $R^{5'}$, $R^6$, $R^{6'}$, $R^7$, and $R^{7'}$ are independently selected from H, OH, SH, NH$_2$, N$_3$, NO$_2$, NO, CF$_3$, CN, C(O)NH$_2$, C(O)H, C(O)OH, halogen, R$^e$, SR$^e$, S(O)R$^e$, S(O)$_2$R$^e$, S(O)OR$^e$, S(O)$_2$OR$^e$, OS(O)R$^e$, OS(O)$_2$R$^e$, OS(O)OR$^e$, OS(O)$_2$OR$^e$, OR$^e$, NHR$^e$, N(R$^e$)R$^f$, $^+$N(R$^e$)(R$^f$)R$^g$, P(O)(OR$^e$)(OR$^f$), OP(O)(OR$^e$)(OR$^f$), SiR$^e$R$^f$R$^g$, C(O)R$^e$, C(O)OR$^e$, C(O)N(R$^e$)R$^f$, OC(O)R$^e$, OC(O)OR$^e$, OC(O)N(R$^e$)R$^f$, N(R$^e$)C(O)R$^f$, N(R$^e$)C(O)OR$^f$, N(R$^e$)C(O)N(R$^f$)R$^g$, and a water-soluble group, wherein
  R$^e$, R$^f$, and R$^g$ are independently selected from H and optionally substituted (CH$_2$CH$_2$O)$_{ee}$CH$_2$CH$_2$X$^{13}$R$^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, X$^{13}$ is selected from O, S, and NR$^{f1}$, and R$^{f1}$ and R$^{e1}$ are independently selected from H and $C_{1-3}$ alkyl, one or more of the optional substituents in R$^e$, R$^f$, and/or R$^g$ optionally being a water-soluble group, two or more of R$^e$, R$^f$, and R$^g$ optionally being joined by one or more bonds to form one or more optionally substituted carbocycles and/or heterocycles, or $R^5+R^{5'}$ and/or $R^6+R^{6'}$ and/or $R^7+R^{7'}$ are independently selected from =O, =S, =NOR$^{e3}$, =C(R$^{e3}$)R$^{e4}$, and =NR$^{e3}$, R$^{e3}$ and R$^{e4}$ being independently selected from H and optionally substituted $C_{1-3}$ alkyl, or $R^{5'}+R^{6'}$ and/or $R^{6'}+R^{7'}$ and/or $R^{7'}+R^{14'}$ are absent, resulting in a double bond between the atoms designated to bear R$^{5'}$ and R$^{6'}$, and/or R$^{6'}$ and R$^{7'}$, and/or R$^{7'}$ and R$^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles;

$X^1$ is selected from O, S, and NR$^{13}$, wherein R$^{13}$ is selected from H and optionally substituted $C_{1-8}$ alkyl or $C_{1-8}$ heteroalkyl and not joined with any other substituent;

$X^3$ is selected from O, S, C(R$^{15}$)R$^{15'}$, —C(R$^{15}$)(R$^{15'}$)—C(R$^{15''}$)(R$^{15'''}$)—, —N(R$^{15}$)—N(R$^{15'}$)—, —C(R$^{15}$)(R$^{15'}$)—N(R$^{15''}$)—, —N(R$^{15''}$)—C(R$^{15}$)(R$^{15'}$)—, —C(R$^{15}$)(R$^{15'}$)—O—, —O—C(R$^{15}$)(R$^{15'}$)—, —C(R$^{15}$)(R$^{15'}$)—S—, —S—C(R$^{15}$)(R$^{15'}$)—, —C(R$^{15}$)=C(R$^{15'}$)—, =C(R$^{15}$)—C(R$^{15'}$)=, —N=C(R$^{15}$)—, =N—C(R$^{15'}$)=, —C(R$^{15}$)=N—, =C(R$^{15}$)—N=, —N=N—, =N—N=, CR$^{15}$, N, and NR$^{15}$, or in DB1 and DB2 —X$^3$— represents —X$^{3a}$ and X$^{3b}$—, wherein X$^{3a}$ is connected to X$^{34}$, a double bond is present between X$^{34}$ and X$^4$, and X$^{3b}$ is connected to X$^{11}$, wherein X$^{3a}$ is independently selected from H and optionally substituted (CH$_2$CH$_2$O)$_{ee}$CH$_2$CH$_2$X$^{13}$R$^{e1}$, $C_{1-8}$ alkyl, or $C_{1-8}$ heteroalkyl and not joined with any other substituent;

$X^4$ is selected from O, S, C(R$^{16}$)R$^{16'}$, NR$^{16}$, N, and CR$^{16}$;

$X^5$ is selected from O, S, C(R$^{17}$)R$^{17'}$, NOR$^{17}$, and NR$^{17}$, wherein R$^{17}$ and R$^{17'}$ are independently selected from H and optionally substituted $C_{1-8}$ alkyl or $C_{1-8}$ heteroalkyl and not joined with any other substituent;

$X^6$ is selected from CR$^{11}$, CR$^{11}$(R$^{11'}$), N, NR$^{11}$, O, and S;

$X^7$ is selected from CR$^8$, CR$^8$(R$^{8'}$), N, NR$^8$, O, and S;

$X^8$ is selected from CR$^9$, CR$^9$(R$^{9'}$), N, NR$^9$, O, and S;

$X^9$ is selected from CR$^{10}$, CR$^{10}$(R$^{10'}$), N, NR$^{10}$, O, and S;

$X^{10}$ is selected from CR$^{20}$, CR$^{20}$(R$^{20'}$), N, NR$^{20}$, O, and S;

$X^{11}$ is selected from C, CR$^{21}$, and N, or $X^{11}$—$X^{3b}$ is selected from CR$^{21}$, CR$^{21}$(R$^{2'}$), N, NR$^{21}$, O, and S;

$X^{12}$ is selected from C, CR$^{22}$, and N;

$X^{6*}$, $X^{7*}$, $X^{8*}$, $X^{9*}$, $X^{10*}$, and $X^{11*}$ have the same meaning as defined for $X^6$, $X^7$, $X^8$, $X^9$, $X^{10}$, and $X^{11}$, respectively, and are independently selected;

$X^{34}$ is selected from C, CR$^{23}$, and N;

the ring B atom of $X^{11*}$ in DB6 and DB7 is connected to a ring atom of ring A such that ring A and ring B in DB6 and DB7 are directly connected via a single bond;

═══ means that the indicated bond may be a single bond or a non-cumulated, optionally delocalized, double bond;

$R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ are each independently selected from H, OH, SH, NH$_2$, N$_3$, NO$_2$, NO, CF$_3$, CN, C(O)NH$_2$, C(O)H, C(O)OH, halogen, R$^h$, SR$^h$, S(O)R$^h$, S(O)$_2$R$^h$, S(O)OR$^h$, S(O)$_2$OR$^h$, OS(O)R$^h$, OS(O)$_2$R$^h$, OS(O)OR$^h$, OS(O)$_2$OR$^h$, OR$^h$, NHR$^h$, N(R$^h$)R$^i$, $^+$N(R$^h$)(R$^i$)R$^j$, P(O)(OR$^h$)(OR$^i$), OP(O)(OR$^h$)(OR$^i$), SiR$^h$R$^i$R$^j$, C(O)R$^h$, C(O)OR$^h$, C(O)N(R$^h$)R$^i$, OC(O)R$^h$, OC(O)OR$^h$, OC(O)N(R$^h$)R$^i$, N(R$^h$)C(O)R$^i$, N(R$^h$)C(O)OR$^i$, N(R$^h$)C(O)N(R$^i$)R$^j$, and a water-soluble group, wherein R$^h$, R$^i$, and R$^j$ are independently selected from H and optionally substituted (CH$_2$CH$_2$O)$_{ee}$CH$_2$CH$_2$X$^{13}$R$^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, one or more of the optional substituents in R$^h$, R$^i$, and/or R$^j$ optionally being a water-soluble group, two or more of R$^h$, R$^i$, and R$^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11'}$ and/or $R^{15}+R^{15'}$ and/or $R^{15''}+R^{15'''}$ and/or $R^{16}+R^{16'}$ and/or $R^{20}+R^{20'}$ and/or $R^{21}+R^{21'}$ are independently selected from =O, =S, =NOR$^{h1}$, =C(R$^{h1}$)R$^{h2}$, and =NR$^{h1}$, R$^{h1}$ and R$^{h2}$ being independently selected from H and optionally substituted $C_{1-3}$ alkyl, two or more of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ optionally being joined by one or more bonds to form one or more optionally substituted carbocycles and/or heterocycles;

$R^{8b}$ and $R^{9b}$ are independently selected and have the same meaning as $R^8$, except that they may not be joined with any other substituent;

one of $R^4$ and $R^{4'}$ and one of $R^{16}$ and $R^{16'}$ may optionally be joined by one or more bonds to form one or more optionally substituted carbocycles and/or heterocycles;

one of $R^2$, $R^{2'}$, $R^3$, and $R^{3'}$ and one of $R^5$ and $R^{5'}$ may optionally be joined by one or more bonds to form one or more optionally substituted carbocycles and/or heterocycles; and a and b are independently selected from 0 and 1.

In a further aspect, this invention relates to a compound of formula (I') or (II'):

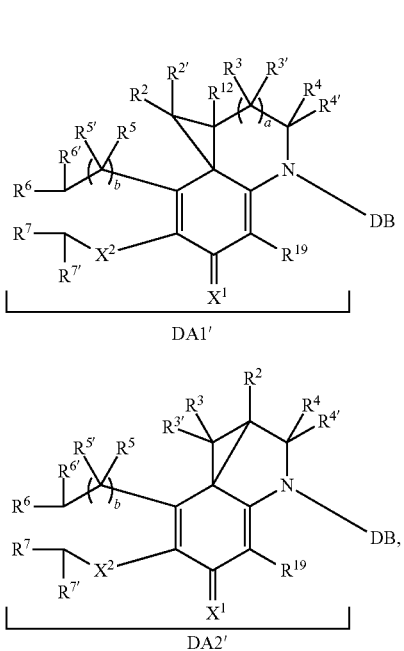

DA1'

DA2' which are formed through rearrangement of and concomitant elimination of H—R$^1$ from the corresponding compounds of formulae (I) and (II), which are seco compounds (FIG. 1). Said cyclopropyl ring-containing analogs are believed to be active species, allegedly being formed from compounds of formulae (I) and (II) in vivo via said rearrangement.

In a more specific embodiment, this invention relates to a compound of formula (I) or (II) as described hereinabove, wherein a) the DB moiety does not comprise a DA1, DA2, DA1', or DA2' moiety; and
b) ring B in DB1 is a heterocycle; and
c) if X$^3$ in DB1 represents —X$^{3a}$ and X$^{3b}$— and ring B is aromatic, then two vicinal substituents on said ring B are joined to form an optionally substituted carbocycle or heterocycle fused to said ring B; and
d) if X$^3$ in DB2 represents —X$^{3a}$ and X$^{3b}$— and ring B is aromatic, then two vicinal substituents on said ring B are joined to form an optionally substituted heterocycle fused to said ring B, an optionally substituted non-aromatic carbocycle fused to said ring B, or a substituted aromatic carbocycle which is fused to said ring B and to which at least one substituent is attached that contains a hydroxy group, a primary amino group, or a secondary amino group, the primary or secondary amine not being a ring atom in an aromatic ring system nor being part of an amide; and
e) if ring A in DB2 is a 6-membered aromatic ring, then substituents on ring B are not joined to form a ring fused to ring B; and
f) two vicinal substituents on ring A in DB8 are joined to form an optionally substituted carbocycle or heterocycle fused to said ring A to form a bicyclic moiety to which no further rings are fused; and
g) ring A in DB9 together with any rings fused to said ring A contains at least two ring heteroatoms.

In a further embodiment, this invention relates to a compound of formula (I) or (II) as described hereinabove, wherein at least one of the substituents R$^1$, R$^5$, R$^{5'}$, R$^6$, R$^{6'}$, R$^7$, R$^{7'}$, R$^{14}$, R$^{14'}$, R$^8$, R$^{8'}$, R$^9$, R$^{9'}$, R$^{10}$, R$^{10'}$, R$^{11}$, R$^{11'}$, R$^{15}$, R$^{15'}$, R$^{15''}$, R$^{15'''}$, R$^{16}$, R$^{16'}$, R$^{20}$, R$^{20'}$, R$^{21}$, R$^{21'}$, R$^{22}$, and R$^{23}$ contains a X$^{14}$(CH$_2$CH$_2$O)$_{ff}$CH$_2$CH$_2$X$^{14}$ moiety, wherein ff is selected from 1 to 1000 and each X$^{14}$ is independently selected from

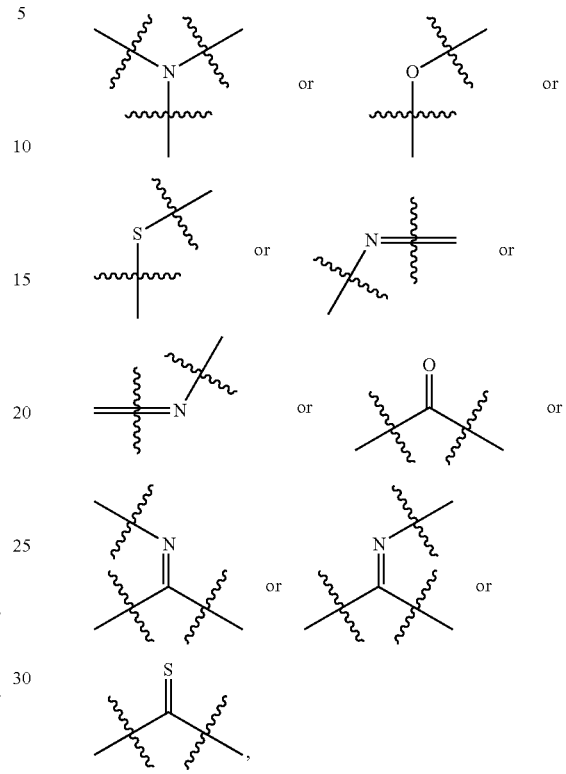

that is connected to the attachment site of said substituent either via a direct bond or via a moiety, being part of said same substituent, that does not comprise a disulfide, a hydrazone, a hydrazide, an ester, a natural amino acid, or a peptide containing at least one natural amino acid, and wherein if ring B in DB1 is an all-carbon ring, X$^3$ is O or NR$^{15}$, X$^4$ is CH, X$^{34}$ is C, there is only one X$^{14}$(CH$_2$CH$_2$O)$_{ff}$CH$_2$CH$_2$X$^{14}$ moiety present in said compound of formula (I) or (II) and said moiety is part of R$^6$, R$^7$, R$^8$, R$^{10}$, or R$^{15}$, then b=1 and ff is ≥5.

A compound of formula (I) or (II) or a conjugate thereof in which ff is larger than 1000 is encompassed by this invention.

In a further embodiment, this invention relates to a compound of formula (I) or (II) as described hereinabove, wherein at least one of the substituents R$^1$, R$^5$, R$^{5'}$, R$^6$, R$^{6'}$, R$^7$, R$^{7'}$, R$^{14}$, R$^{14'}$, R$^8$, R$^{8'}$, R$^9$, R$^{9'}$, R$^{10}$, R$^{10'}$, R$^{11}$, R$^{11'}$, R$^{15}$, R$^{15'}$, R$^{15''}$, R$^{15'''}$, R$^{16}$, R$^{16'}$, R$^{20}$, R$^{20'}$, R$^{21}$, R$^{21'}$, R$^{22}$, and R$^{23}$ contains a triazole moiety.

It is to be understood that if —X$^3$— represents —X$^{3a}$ and X$^{3b}$— in moieties DB1 and DB2 these moieties are actually represented by the following structures:

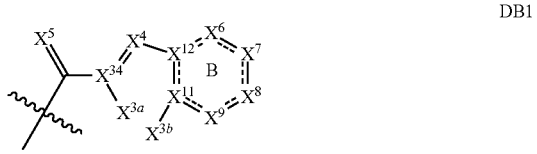

DB1

-continued

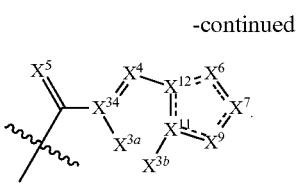
DB2

In another aspect, the present invention relates to a conjugate of a compound of formula (I), (II), (I'), or (II').

In yet another aspect, this invention relates to a compound of formula (III):

$$V^2 \!-\!\!\left(\!\!L^2\!-\!L\!\!\left(\!\!\begin{array}{c}V^1\\|\\Y\end{array}\!\!\right)_{\!p}\!\!\right)_{\!q}\!\!(Z)_z \qquad (III)$$

or a pharmaceutically acceptable salt, hydrate, or solvate thereof, wherein $V^2$ is either absent or a functional moiety;

each $L^2$ is independently absent or a linking group linking $V^2$ to L;

each L is independently absent or a linking group linking $L^2$ to one or more $V^1$ and/or Y;

each $V^1$ is independently absent or a conditionally-cleavable or conditionally-transformable moiety, which can be cleaved or transformed by a chemical, photochemical, physical, biological, or enzymatic process;

each Y is independently absent or a self-eliminating spacer system which is comprised of 1 or more self-elimination spacers and is linked to $V^1$, optionally L, and one or more Z;

each p and q are numbers representing a degree of branching and are each independently a positive integer;

z is a positive integer equal to or smaller than the total number of attachment sites for Z;

each Z is independently a compound of formula (I), (II), (I'), or (II') as defined hereinabove wherein one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ may optionally in addition be substituted by or be a substituent of formula (V):

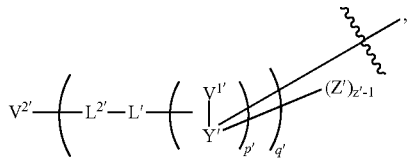
(V)

wherein each $V^{2'}$, $L^{2'}$, $L'$, $V^{1'}$, $Y'$, $Z'$, $p'$, $q'$, and $z'$ has the same meaning as defined for $V^2$, $L^2$, L, $V^1$, Y, Z, p, q, and z, respectively, and is independently selected, the one or more substituents of formula (V) being independently connected via $Y'$ to one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, and/or to one or more atoms bearing these R substituents;

each Z is independently connected to Y through either $X^1$, an atom in $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, or an atom bearing any of these R substituents; and at least $V^2$ or a $V^1$ is present.

It is noted that in a compound of formula (III), $V^2$ or a $V^1$ needs to be present. However, in the one or more moieties of formula (V) that are optionally present in Z, each $V^{2'}$ and $V^{1'}$ may be independently selected to be absent or present.

In a further aspect, this invention relates to a compound of formula (III), wherein $V^2$ is present and selected to be a targeting moiety and there is at least one group of formula (V) that contains a $V^{1'}$ moiety and either comprises a $V^{2'}$, $L^{2'}$, or $L'$ moiety that contains a $X^{14}(CH_2CH_2O)_{gg}CH_2CH_2X^{14}$ moiety, wherein gg is selected from 3 to 1000 and each $X^{14}$ is independently selected from

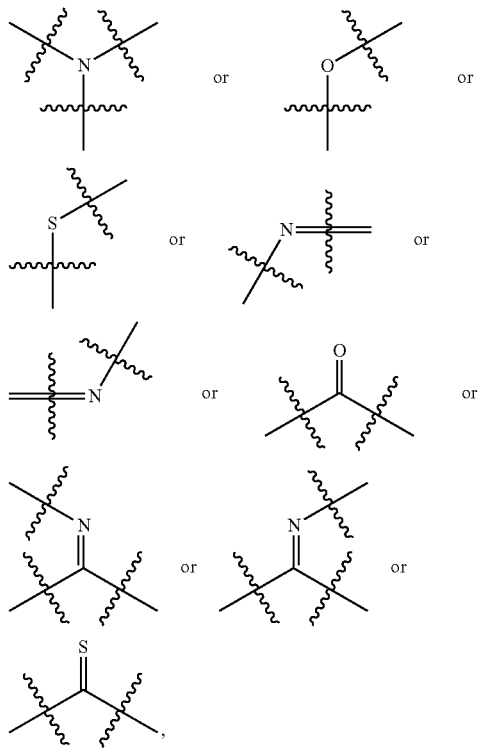

or said same group of formula (V) comprises at least 2 $X^{14}CH_2CH_2OCH_2CH_2X^{14}$ moieties, in which each $X^{14}$ is independently selected.

It is noted that the separate $X^{14}$ moieties in the —$CH_2CH_2X^{14}$ moieties that may be present in a compound of formula (III) are independently selected.

It is further noted that z does not represent a degree of polymerization; hence z does not indicate that a number of moieties Z are connected to one another.

It is further noted that if Y or Y' is connected to an atom bearing a specific R substituent instead of to this R substituent itself, this in fact means that this R substituent is absent if this is necessary to meet valency rules.

It is further noted that if $X^{14}$ in for example —$CH_2CH_2X^{14}$ represents

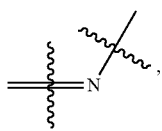 [SMILES: *N=*]

then —$CH_2CH_2X^{14}$ should be read as —$CH_2CHX^{14}$.

The present invention also relates to a compound of formula (IV):

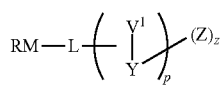

(IV)

or a pharmaceutically acceptable salt, hydrate, or solvate thereof, wherein

RM is a reactive moiety and L, $V^1$, Y, Z, p, and z are as defined hereinabove, except that L is now linking RM to one or more $V^1$ and/or Y, and $V^1$, Y, and Z may contain protecting groups, and the one or more $V^{2'}$-$L^{2'}$ moieties optionally present in Z as defined hereinabove may optionally and independently be RM' instead, which is a reactive moiety, and wherein, if there is more than 1 reactive moiety in (IV), some or all reactive moieties are the same or different. These linker-agent conjugates of formula (IV) may or may not be considered intermediates for compounds of formula (III).

In a further aspect, the present invention relates to a compound of formula (IV), wherein RM is a reactive moiety selected from carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate, and wherein at least one group of formula (V), being part of Z, contains a $V^{1'}$ moiety and either comprises a $V^{2'}$, $L^{2'}$, or L' moiety that contains a $X^{14}(CH_2CH_2O)_{gg}CH_2CH_2X^{14}$ moiety, wherein gg is selected from 3 to 1000 and each $X^{14}$ is independently selected from

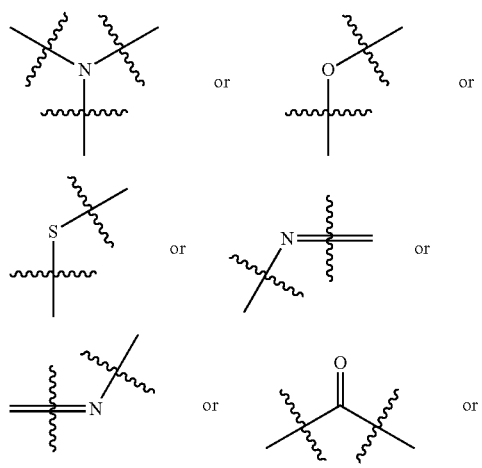

or said same group of formula (V) comprises at least 2 $X^{14}CH_2CH_2OCH_2CH_2X^{14}$ moieties, in which each $X^{14}$ is independently selected. These linker-agent conjugates of formula (IV) may or may not be considered intermediates for compounds of formula (III).

This invention relates to enantiomerically pure and/or diastereomerically pure compounds of formulae (I)-(IV) as well as to enantiomeric and/or diastereomeric mixtures of compounds of formulae (I)-(IV). This invention relates to pure compounds of formulae (I)-(IV) as well as to mixtures of isomers of compounds of formulae (I)-(IV).

Compounds of formulae (I) and (II) and their conjugates represent novel duocarmycin derivatives that preferably have novel DNA-binding moieties and/or preferably have heteroatoms at selected positions in the DNA-binding moiety or in substituents on the DNA-binding or DNA-alkylating moiety, or in one or more of the cleavable linkers attached to a compound of formula (I) or (II). These modifications are designed to improve pharmacological properties and cytotoxic activity compared to duocarmycin derivatives from the prior art.

In one embodiment, a compound of formula (I) or (II) contains a novel DNA-binding moiety. Without being bound by any theory, these novel DNA-binding moieties may contribute to the cytotoxic activity of compounds of formulae (I) and (II) by binding to DNA in a way similar to the DNA-binding moieties in CC-1065 analogs known from the prior art. The novel DNA binders may be more water-soluble, may have increased binding affinity, and/or may be metabolized with more ease in for example the liver, which is to lead to compounds of formulae (I) and (II) that have improved pharmacological properties, e.g., an increased therapeutic index, with respect to similar compounds from the prior art.

In another embodiment, a compound of formula (I) or (II) contains a triazole moiety. Without being bound by any theory, this heteroaromatic moiety may be incorporated in the molecule in such a way that it contributes to binding of a compound of formula (I) or (II) to the DNA of a target cell, thereby improving the activity of said compound. Although a same effect may be achieved by another (hetero)aromatic moiety, e.g., a phenyl ring, the triazole moiety has the additional advantage that it is a relatively polar group (with respect to other (hetero)aromatic moieties), which may lead to enhanced pharmacological properties (e.g., water solubility, hydrophilicity, aggregation behavior) of compounds of formulae (I) and (II) and their conjugates.

In another embodiment, a compound of formula (I) or (II) contains an oligoethylene glycol or polyethylene glycol moiety or a derivative thereof. Said oligoethylene glycol or polyethylene glycol moiety may either be branched or linear. Without being bound by any theory, this moiety may be incorporated in a compound of formula (I) or (II) to improve for example the physicochemical, biophysical, pharmacodynamic and/or pharmacokinetic properties of the compound,

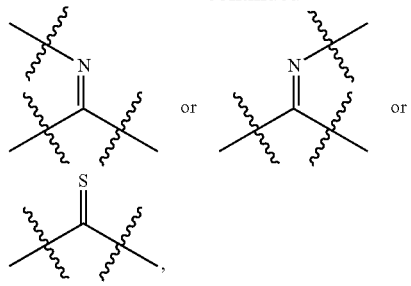

e.g., water solubility and aggregation behavior. Furthermore, due to the hydrophilic nature of the oligoethylene glycol or polyethylene glycol moiety, a compound of formula (I) or (II) may for example be more cytotoxic against multidrug-resistant tumor cells, as the compound is a bad substrate for efflux pumps. If a compound of formula (I) or (II) is incorporated in a conjugate, it may be that the oligoethylene glycol or polyethylene glycol moiety is located in between the promoiety, i.e., a moiety that is coupled to a compound of formula (I) or (II) to modify its properties and that is to be (partly) removed in vivo from said compound of formula (I) or (II), and the remainder of the compound of formula (I) or (II) or that it is located at a position somewhat opposite to the attachment site of the promoiety, thus placing the remainder of the compound of formula (I) or (II) in between the promoiety and the oligoethylene glycol or polyethylene glycol moiety. The latter situation may have the advantage that the hydrophobic (aromatic) core structure of the compound of formula (I) or (II) is more shielded from unfavorable interactions with its environment, e.g., an aqueous environment, thus for example reducing the amount of aggregate formation.

In another embodiment, the current invention relates to a conjugate of a compound of formula (I) or (II) according to one of the above embodiments and derivatives thereof. These conjugates contain one or more promoieties.

In another embodiment, a conjugate of a compound of formula (I) or (II) comprises at least two promoieties of which the first promoiety is an in vivo cleavable promoiety that comprises an oligoethylene glycol or polyethylene glycol moiety or a derivative thereof and the second promoiety comprises at least a targeting moiety. Such a conjugate has the relatively hydrophobic core structure of a compound of formula (I) or (II) or a derivative thereof placed in between the targeting promoiety and the oligoethylene glycol or polyethylene glycol-containing promoiety, thereby shielding the core structure from possibly unfavorable interactions with its environment.

Compounds of formulae (I) and (II) are suited for application in drug delivery purposes, including drug targeting and controlled release applications using compounds of formulae (III) and (IV).

DESCRIPTION OF THE INVENTION

Figure 1:
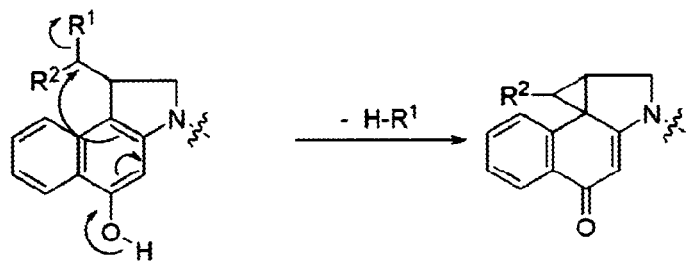
FIG. 1 illustrates the rearrangement of a seco compound to a cyclopropyl-containing compound.

The following detailed description is provided so that the invention may be more fully understood.

Definitions

Unless defined otherwise, all technical and scientific terms used herein have the same meaning as commonly understood by one of ordinary skill in the art.

The term "antibody", as used herein, refers to a full length immunoglobulin molecule, an immunologically active portion of a full-length immunoglobulin molecule, or a derivative of a full length immunoglobulin molecule or an active portion thereof, i.e., a molecule that contains an antigen-binding site that immunospecifically binds an antigen of a target of interest or part thereof, such targets including, but not limited to, tumor cells. The immunoglobulin can be of any type (e.g., IgG, IgE, IgM, IgD, IgA, or IgY), class (e.g., IgG1, IgG2, IgG3, IgG4, IgA1, or IgA2), or subclass. The immunoglobulin, or a derivative or active portion thereof, can be derived from any species, e.g., human, rodent (e.g., mouse, rat, or hamster), donkey, sheep, rabbit, goat, guinea pig, camelid, horse, cow, or chicken, but preferably, it is of human, murine, or rabbit origin, or it is derived from more than one species. Antibodies useful in the invention include, but are not limited to, monoclonal, polyclonal, bispecific, multispecific, human, humanized, chimeric, and engineered antibodies, single chain antibodies, Fv fragments, Fd fragments, Fab fragments, F(ab') fragments, F(ab')$_2$ fragments, dAb fragments, fragments produced by a Fab expression library, anti-idiotypic antibodies, isolated CDRs, and epitope-binding fragments of any of the above that immunospecifically bind to an antigen-of-interest.

The term "leaving group" refers to a group that can be substituted by another group in a substitution reaction. Such leaving groups are well-known in the art, and examples include, but are not limited to, a halide (fluoride, chloride, bromide, and iodide), azide, a sulfonate (e.g., an optionally substituted $C_{1-6}$ alkanesulfonate, such as methanesulfonate and trifluoromethanesulfonate, or an optionally substituted $C_{7-12}$ alkylbenzenesulfonate, such as p-toluenesulfonate), succinimide-N-oxide, p-nitrophenoxide, pentafluorophenoxide, tetrafluorophenoxide, a carboxylate, an aminocarboxylate (carbamate) and an alkoxycarboxylate (carbonate). For substitutions at saturated carbon, halides and sulfonates are preferred leaving groups. For substitutions at a carbonyl carbon a halide, succinimide-N-oxide, p-nitrophenoxide, pentafluorophenoxide, tetrafluorophenoxide, a carboxylate, or an alkoxycarboxylate (carbonate) may for example be used as a leaving group. The term "leaving group" also refers to a group that is eliminated as a consequence of an elimination reaction, e.g., an electronic cascade reaction or a spirocyclization reaction. In this instance, a halide, a sulfonate, azide, an aminocarboxylate (carbamate) or an alkoxycarboxylate (carbonate) may for example be used as a leaving group. Therefore, an agent or a derivative thereof released from a conjugate through a (multiple) self-elimination is defined as a leaving group according to this definition.

The term "active ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroxybenzotriazole, and 1-hydroxy-7-azabenzotriazole, and groups with comparable leaving capability. Unsubstituted alkyl-based alkoxy groups such as methoxy, ethoxy, isopropoxy, and t-butoxy do not qualify as good leaving groups and methyl, ethyl, isopropyl, and t-butyl esters are therefore not considered to be active esters.

The term "reactive moiety" herein refers to a functional group that can react with a second functional group under relatively mild conditions and without the need of prior functionalization of the reactive moiety. The reaction between the reactive moiety and said second functional group will only require the application of some heat, pressure, a catalyst, acid, and/or base. Examples of reactive moieties include, but are not limited to, carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

The term "promoiety" refers to a moiety that is coupled to a compound of formula (I) or (II) to modify its properties and that is to be (partly) removed in vivo from said compound of formula (I) or (II).

The term "water-soluble group" refers to a functional group that is well solvated in aqueous environments and that imparts improved water solubility to the compound to which it is attached. Examples of water-soluble groups include, but are not limited to, polyalcohols, straight chain or cyclic saccharides, primary, secondary, tertiary, or quaternary amines and polyamines, sulfate groups, sulfonate groups, sulfinate groups, carboxylate groups, phosphate groups, phosphonate groups, phosphinate groups, ascorbate groups, glycols, including polyethylene glycols, and polyethers. Preferred water-soluble groups are primary, secondary, tertiary, and quaternary amines, carboxylates, phosphates, —(CH$_2$CH$_2$O)$_{yy}$CH$_2$CH$_2$X$^{17}$R$^{yy}$, —(CH$_2$CH$_2$O)$_{yy}$CH$_2$CH$_2$X$^{17}$—, —X$^{17}$(CH$_2$CH$_2$O)$_{yy}$CH$_2$CH$_2$—, glycol, oligoethylene glycol, and polyethylene glycol, wherein yy is selected from 1 to 1000, X$^{17}$ is selected from O, S, and NR$^{zz}$, and R$^{zz}$ and R$^{yy}$ are independently selected from H and C$_{1-3}$ alkyl.

The term "substituted", when used as an adjective to "alkyl", "heteroalkyl", "cycloalkyl", "heterocycloalkyl", "aryl", "heteroaryl", or the like, indicates that said "alkyl", "heteroalkyl", "cycloalkyl", "heterocycloalkyl", "aryl", or "heteroaryl" group contains one or more substituents (introduced by substitution for hydrogen). Exemplary substituents include, but are not limited to, OH, =O, =S, =NR$^k$, =N—OR$^k$, SH, NH$_2$, NO$_2$, NO, N$_3$, CF$_3$, CN, OCN, SCN, NCO, NCS, C(O)NH$_2$, C(O)H, C(O)OH, halogen, R$^k$, SR$^k$, S(O)R$^k$, S(O)OR$^k$, S(O)$_2$R$^k$, S(O)$_2$OR$^k$, OS(O)R$^k$, OS(O)OR$^k$, OS(O)$_2$R$^k$, OS(O)$_2$OR$^k$, S(O)N(R$^k$)R$^l$, OS(O)N(R$^k$)R$^l$, S(O)$_2$N(R$^k$)R$^l$, OS(O)$_2$N(R$^k$)R$^l$, OP(O)(OR$^k$)(OR$^l$), P(O)(OR$^k$)(OR$^l$), OR$^k$, NHR$^k$, N(R$^k$)R$^l$, $^+$N(R$^k$)(R$^l$)R$^m$, Si(R$^k$)(R$^l$)(R$^m$), C(O)R$^k$, C(O)OR$^k$, C(O)N(R$^k$)R$^l$, OC(O)R$^k$, OC(O)OR$^k$, OC(O)N(R$^k$)R$^l$, N(R$^k$)C(O)R$^l$, N(R$^k$)C(O)OR$^l$, N(R$^k$)C(O)N(R$^l$)R$^m$, a water-soluble group, and the thio derivatives of these substituents, and protonated, charged, and deprotonated forms of any of these substituents, wherein R$^k$, R$^l$, and R$^m$ are independently selected from H and optionally substituted —(CH$_2$CH$_2$O)$_{yy}$CH$_2$CH$_2$X$^{17}$R$^{yy}$, C$_{1-15}$ alkyl, C$_{1-15}$ heteroalkyl, C$_{3-15}$ cycloalkyl, C$_{1-15}$ heterocycloalkyl, C$_{5-15}$ aryl, or C$_{1-15}$ heteroaryl, or a combination thereof, wherein yy is selected from 1 to 1000, X$^{17}$ is independently selected from O, S, and NR$^{zz}$, and R$^{zz}$ and R$^{yy}$ are independently selected from H and C$_{1-3}$ alkyl, two or more of R$^k$, R$^l$, and R$^m$ optionally being joined by one or more bonds to form one or more optionally substituted carbocycles and/or heterocycles. When there is more than one substituent, each substituent is independently selected. Two or more substituents may be connected to each other by replacement of one or more hydrogen atoms on each of the substituents by one or more connecting bonds, which may be single, double, or triple bonds, or, if resonance structures are possible, the bond order of said bonds may be different in two or more of these resonance structures. Two substituents may thus be joined under formation of one or more rings.

When substituents may be "joined by one or more bonds to form one or more optionally substituted carbocycles and/or heterocycles", this means that the substituents may be connected to each other through replacement of one or more hydrogen atoms on each of the substituents by one or more connecting bonds.

The term "aryl" as used herein refers to a carbocyclic aromatic substituent comprising 5 to 24 ring carbon atoms, which may be charged or uncharged and which may consist of one ring or two or more rings fused together. Examples of aryl groups include, but are not limited to, phenyl, naphthyl, and anthracenyl.

The term "heteroaryl" as used herein refers to a heterocyclic aromatic substituent comprising 1 to 24 ring carbon atoms and at least one ring heteroatom, e.g., oxygen, nitrogen, sulfur, silicon, or phosphorus, wherein nitrogen and sulfur may optionally be oxidized and nitrogen may optionally be quaternized, which may consist of one ring or two or more rings fused together. Heteroatoms may be directly connected to each other. Examples of heteroaryl groups include, but are not limited to, pyridinyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises 1 to 4 heteroatoms. It should be noted that "C$_1$ heteroaryl group" denotes that there is only one carbon present in the ring system of the heteroaromatic group (carbon atoms in optional substituents are thus not counted). An example of such a heteroaromatic group is a tetrazolyl group.

"Aryl" and "heteroaryl" groups also encompass ring systems in which one or more non-aromatic rings are fused to an aryl or heteroaryl ring or ring system.

The term "alkyl" as used herein refers to a straight chain or branched, saturated or unsaturated hydrocarbyl substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, 2-pentenyl, and 1-butynyl.

The term "heteroalkyl" as used herein refers to a straight chain or branched, saturated or unsaturated hydrocarbyl substituent in which at least one carbon atom is replaced by a heteroatom, e.g., by oxygen, nitrogen, sulfur, silicon, or phosphorus, wherein nitrogen and sulfur may optionally be oxidized and nitrogen may optionally be quaternized. Heteroatoms may be directly connected to each other. Examples include, but are not limited to, methoxy, ethoxy, propoxy, isopropoxy, n-butyloxy, tert-butyloxy, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein refers to a saturated or unsaturated non-aromatic cyclic hydrocarbyl substituent, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocycloalkyl" as used herein refers to a saturated or unsaturated non-aromatic cyclic hydrocarbyl substituent, which may consist of one ring or two or more rings fused together, wherein at least one carbon in one of the rings is replaced by a heteroatom, e.g., by oxygen, nitrogen, sulfur, silicon, or phosphorus, wherein nitrogen and sulfur may optionally be oxidized and nitrogen may optionally be quaternized. Heteroatoms may be directly connected to each other. Examples include, but are not limited to, tetrahydrofuranyl, pyrrolidinyl, piperidinyl, 1,4-dioxanyl, decahydroquinolinyl, piperazinyl, oxazolidinyl, and morpholinyl. It should be noted that "$C_1$ heterocycloalkyl group" denotes that there is only one carbon present in the ring system of the heterocycloalkane (carbon atoms in optional substituents are thus not counted). An example of such a group is a dioxiranyl group.

The number of carbon atoms that an "alkyl", "heteroalkyl", "cycloalkyl", "heterocycloalkyl", "aryl", "heteroaryl", and the like, may contain is indicated by a designation preceding said terms, i.e., $C_{1-10}$ alkyl means that said alkyl may contain from one to ten carbons (carbon atoms in optional substituents attached to this alkyl are not counted).

The term "carbocycle" herein refers to a saturated or unsaturated cycloalkane or arene moiety, wherein the terms "cycloalkane" and "arene" are defined as parent moieties of the "cycloalkyl" and "aryl" substituents, respectively, as defined hereinabove.

The term "heterocycle" herein refers to a saturated or unsaturated heterocycloalkane or heteroarene moiety, wherein the terms "heterocycloalkane" and "heteroarene" are defined as parent moieties of the "heterocycloalkyl" and "heteroaryl" substituents, respectively, as defined hereinabove.

The extension "-ylene" as opposed to "-yl" in for example "alkylene" as opposed to "alkyl" indicates that said for example "alkylene" is a divalent (or multivalent) moiety connected to one or more other moieties via at least one or more double bonds or two or more single bonds, as opposed to being a monovalent group connected to one moiety via one single bond in said for example "alkyl". The term "alkylene" therefore refers to a straight chain or branched, saturated or unsaturated hydrocarbylene moiety; the term "heteroalkylene" as used herein refers to a straight chain or branched, saturated or unsaturated hydrocarbylene moiety in which at least one carbon is replaced by a heteroatom; the term "arylene" as used herein refers to a carbocyclic aromatic moiety, which may consist of one ring or two or more rings fused together; the term "heteroarylene" as used herein refers to a carbocyclic aromatic moiety, which may consist of one ring or two or more rings fused together, wherein at least one carbon in one of the rings is replaced by a heteroatom; the term "cycloalkylene" as used herein refers to a saturated or unsaturated non-aromatic cyclic hydrocarbylene moiety, which may consist of one ring or two or more rings fused together; the term "heterocycloalkylene" as used herein refers to a saturated or unsaturated non-aromatic cyclic hydrocarbylene moiety, which may consist of one ring or two or more rings fused together, wherein at least one carbon in one of the rings is replaced by a heteroatom. Exemplary divalent moieties include those examples given for the monovalent groups hereinabove in which one hydrogen atom is removed.

The prefix "poly" in "polyalkylene", "polyheteroalkylene", "polyarylene", "polyheteroarylene", polycycloalkylene", "polyheterocycloalkylene", and the like, indicates that two or more of such "-ylene" moieties, e.g., alkylene moieties, are joined together to form a branched or unbranched multivalent moiety containing two or more attachment sites for adjacent moieties. Similarly, the prefix "oligo" in for example oligoethylene glycol indicates that two or more ethylene glycol moieties are joined together to form a branched or unbranched multivalent moiety. The difference between the prefixes "oligo" and "poly" is that the prefix "oligo" is most frequently used to denote a relatively small number of repeating units, while the prefix "poly" usually refers to a relatively large number of repeating units.

Certain compounds of the invention possess chiral centers and/or double bonds, and/or may have tautomers or atropisomers; the tautomeric, enantiomeric, diastereomeric, atropisomeric, and geometric mixtures of two or more isomers, in any composition, as well as the individual isomers (including tautomers and atropisomers) are encompassed within the scope of the present invention. Whenever the term "isomer" is used, it refers to an atropisomeric, tautomeric, enantiomeric, diastereomeric, and/or geometric isomer or to a mixture of two or more of these isomers, unless the context dictates otherwise.

The term "peptidomimetic" refers to a group or moiety that has a structure that is different from the general chemical structure of an amino acid or peptide, but functions in a manner similar to a naturally occurring amino acid or peptide. Therefore, a peptidomimetic is an amino acid mimic or peptide mimic.

The term "unnatural amino acid" is intended to represent the D stereoisomer of a naturally occurring amino acid.

The term "bond" herein refers to a covalent connection between two atoms and may refer to a single bond, a double bond, or a triple bond, or, if resonance structures are possible, the bond order of said bond may be different in two or more of these resonance structures. For example, if the bond is part of an aromatic ring, the bond may be a single bond in one resonance structure and a double bond in another resonance structure. If it is stated that a "double bond" or "triple bond" is present between two atoms, this double, or triple bond may be localized, but it may also be that this double or triple bond is delocalized, which means that only in one or some resonance structures a double or triple bond is indeed present between the two atoms, whereas the bond order may be different in one or more other resonance structures. At the same time, bonds marked as single bond in one resonance structure, may be double bonds in another resonance structure.

The compounds of the invention may also contain unnatural proportions of atomic isotopes at one or more atoms that constitute such compounds. All isotopic variations of the compounds of this invention, whether radioactive or not, are intended to be encompassed within the scope of this invention.

The phrase "pharmaceutically active salt" as used herein refers to a pharmaceutically acceptable organic or inorganic salt of a compound of the invention. For compounds containing one or more basic groups, e.g., an amine group, acid addition salts can be formed. For compounds containing one or more acidic groups, e.g., a carboxylic acid group, base addition salts can be formed. For compounds containing both acidic and basic groups, zwitterions may in addition be obtained as salts. When the compound of the invention comprises more than one charged atom or group, there may be multiple (distinct) counterions.

The phrase "pharmaceutically acceptable solvate" refers to an association of one or more solvent molecules with a compound of the invention. Examples of solvents that form pharmaceutically acceptable solvates include, but are not limited to, water, isopropyl alcohol, ethanol, methanol, DMSO, ethyl acetate, and acetic acid. When referring to water as a solvate, the term "hydrate" can be used.

The term "conjugate" hereinbelow refers to a compound of formula (III) or to a conjugate of a compound of formula (I) or (II) or a derivative thereof, unless the context dictates otherwise.

The term "linker-agent conjugate" hereinbelow refers to a compound of formula (IV), unless the context dictates otherwise.

The term "agent" hereinbelow refers to a compound of formula (I), (II), (I'), or (II'), unless the context dictates otherwise.

The term "core" or "core structure" of a moiety, for example the DNA-binding or DNA-alkylating moiety, refers to the structure that remains when all R substituents are removed from the formula representing said moiety.

The term "targeting moiety" refers to any moiety that specifically binds or reactively associates or complexes with a moiety specifically or in relative excess present at or near the target site, on, in, or near the target cell, or in (the proximity of) the target tissue or organ, e.g., a receptor, a receptor complex, substrate, antigenic determinant, or other receptive moiety, or that can target the conjugate to the target site via other mechanisms by virtue of its nature, e.g., through the EPR effect. Examples of a targeting moiety include, but are not limited to, an aptamer, an antibody or antibody fragment or derivative, a polymer, a dendrimer, a lectin, a biologic response modifier, an enzyme, a vitamin, a growth factor, a steroid, a sugar residue, an oligosaccharide residue, a carrier protein, and a hormone, or any combination thereof.

The phrase "moiety that improves the pharmacological properties of the compound" refers to a moiety that changes the pharmacological properties (e.g., pharmacodynamic, pharmacokinetic, physicochemical, and biopharmaceutic properties) of a compound of this invention in such a way that a better therapeutic effect can be obtained. The moiety can for example increase the water solubility, increase the circulation time, increase the therapeutic index, or reduce immunogenicity.

The term "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are each directly attached to the moiety immediately to the left of the corresponding opening bracket. For example, A-(B)$_b$ with b being a number representing a degree of branching means that b units B are all directly attached to A. This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_b$ with b being a number representing a degree of polymerization means that when b is 2, the formula reduces to A-B-B.

The term "single-release spacer" refers to a self-elimination spacer that can release one moiety upon self-immolation.

The term "multiple-release spacer" refers to a self-elimination spacer that can release two or more moieties upon (repetitive) self-immolation.

The term "electronic cascade spacer" refers to a self-elimination spacer, either branched or unbranched, which may self-eliminate through one or more 1,2+2n electronic cascade eliminations (n≥1).

The term "ω-amino aminocarbonyl cyclization spacer" refers to a self-elimination spacer that may eliminate through a cyclization process under formation of a cyclic ureum derivative.

The term "spacer system" refers to a single self-eliminating spacer moiety or to two or more of the same or different self-eliminating spacer moieties coupled together. A spacer system may be branched or unbranched and contain one or more attachment sites for Z as well as $V^1$ and optionally L.

In this document and in its claims, the verbs "to comprise", "to have", "to contain" and their conjugations are used in their non-limiting sense to mean that items that are "comprised", "had", or "contained" are included, but items non-specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

In the generic structures throughout this description and in the claims letters are used to define structural elements. Some of these letters can be mistaken to represent an atom, such as C, N, O, P, K, B, F, S, U, V, W, I, and Y. To avoid confusion whenever these letters do not represent an atom they are given in bold typeface.

When there are one or more adjectives and/or adjective phrases to a noun that is a) the first in a list of nouns or b) anywhere in the middle of a list of nouns and said noun and adjectives together are preceded by the word "and" or "or", the adjectives do not only bear on said noun, but on all following nouns separately, unless the context dictates otherwise. This for example means that the phrase "optionally substituted $C_{1-4}$ alkyl, $C_{1-4}$ heteroalkyl, $C_{3-7}$ cycloalkyl, or $C_{1-7}$ heterocycloalkyl" should be read as "optionally substituted $C_{1-4}$ alkyl, optionally substituted $C_{1-4}$ heteroalkyl, optionally substituted $C_{3-7}$ cycloalkyl, or optionally substituted $C_{1-7}$ heterocycloalkyl" and that the phrase "$C_{1-4}$ alkyl, $C_{1-4}$ heteroalkyl, and optionally substituted $C_{3-7}$ cycloalkyl, $C_{5-8}$ aryl, or $C_{1-7}$ heterocycloalkyl" should be read as "$C_{1-4}$ alkyl, $C_{1-4}$ heteroalkyl, and optionally substituted $C_{3-7}$ cycloalkyl, optionally substituted $C_{5-8}$ aryl, or optionally substituted $C_{1-7}$ heterocycloalkyl".

Throughout this description and in the claims molecular structures or parts thereof are drawn. As usual in such drawings bonds between atoms are represented by lines, in some cases, to indicate stereochemistry, by bold or broken or wedged lines. Usually a line ending in space (a "loose" end), i.e., at one end not having another line or specific atom connected to it, represents a $CH_3$ group. This is correct for the drawings representing the compounds of this invention. For those structures representing a structural element of the compounds of this invention a line ending in space may indicate the position of attachment of another structural element of the compound. This has been indicated with a wavy line perpendicular to and crossing the "loose" line.

Furthermore, the structures or parts thereof have been drawn, under the assumption that the structures are read from left to right, meaning that for example in the drawings of compounds of formula (III) $V^2$ (if present) is located on the left side and Z is located on the right side of such structures or parts thereof, unless the context implies otherwise.

The following abbreviations are used herein and have the indicated definitions: Ac: acetyl; AIBN: 2,2'-azobis(2-methylpropionitrile); Bn: benzyl; Boc: tert-butyloxycarbonyl; CBI: 1,2,9,9a-tetrahydrocyclopropa[c]benz[e]indol-4-one; DABCO: 1,4-diazabicyclo[2.2.2]octane; DBU: 1,8-diazabicyclo[5.4.0]undec-7-ene; DCC: N,N'-dicyclohexylcarbodiimide; DCM: dichloromethane; DMA: N,N-dimethylacetamide; DMAP: 4-dimethylaminopyridine; DMF: N,N-dimethylformamide; DiPEA: N,N-diisopropylethylamine; DPPA: diphenylphosphoryl azide; EDAC: 1-ethyl-3-(3-dimethylaminopropyl)carbodiimide; EtOAc: ethyl acetate; Fmoc: 9-fluorenylmethyloxycarbonyl; HATU: 2-(1H-7-azabenzotriazol-1-yl)-1,1,3,3-tetramethyl uronium hexafluorophosphate methanaminium; HOBt: N-hydroxybenzotriazole; PNPCl: p-nitrophenyl chloroformate; ppm: parts per million; py: pyridine; TEA: triethylamine; TFA: trifluoroacetic acid; TFAA: trifluoroacetic anhydride; THF: tetrahydrofuran; TsOH: p-toluenesulfonic acid; TsCl: p-toluenesulfonyl chloride; and TTMSS: tris(trimethylsilyl)silane.

Agents, Linker-agent Conjugates, and Conjugates

This invention relates to novel analogs of the DNA-alkylating agent CC-1065. The agents of the present invention are deemed to be used to treat an illness that is characterized by undesired (cell) proliferation. For example, an agent of this invention can be used to treat a tumor, cancer, an autoimmune disease, or an infectious disease.

The conjugates of the present invention are in one aspect deemed to be applicable to target agents of formulae (I) and (II) to a specific target site where the conjugate can be converted into one or more agents or be induced to be converted into one or more of said agents. This invention can furthermore find application in (non-specific) controlled release of one or more of said agents from a conjugate, with the aim of for example enhancing physicochemical, biopharmaceutic, pharmacodynamic, and/or pharmacokinetic properties.

Compounds of formulae (I) and (II) and their conjugates represent novel duocarmycin derivatives that preferably have novel DNA-binding moieties and/or preferably have heteroatoms at selected positions in the DNA-binding moiety or in substituents on the DNA-binding or DNA-alkylating moiety, or in one or more of the cleavable linkers attached to a compound of formula (I) or (II). These modifications are designed to improve pharmacological properties and cytotoxic activity compared to duocarmycin derivatives from the prior art.

In one embodiment, a compound of formula (I) or (II) contains a novel DNA-binding moiety. Without being bound by any theory, these novel DNA-binding moieties may contribute to the cytotoxic activity of compounds of formulae (I) and (II) by binding to DNA in a way similar to the DNA-binding moieties in CC-1065 analogs known from the prior art. The novel DNA binders may be more water-soluble, may have increased binding affinity, and/or may be metabolized with more ease in for example the liver, which is to lead to compounds of formulae (I) and (II) that have improved pharmacological properties, e.g., an increased therapeutic index, with respect to similar compounds from the prior art.

In another embodiment, a compound of formula (I) or (II) contains a triazole moiety. Without being bound by any theory, this heteroaromatic moiety may be incorporated in the molecule in such a way that it contributes to binding of a compound of formula (I) or (II) to the DNA of a target cell, thereby improving the activity of said compound. Although a same effect may be achieved by another (hetero)aromatic moiety, e.g., a phenyl ring, the triazole moiety has the additional advantage that it is a relatively polar group (with respect to other (hetero)aromatic moieties), which may lead to enhanced pharmacological properties (e.g., water solubility, hydrophilicity, aggregation behavior) of compounds of formulae (I) and (II) and their conjugates.

In another embodiment, a compound of formula (I) or (II) contains an oligoethylene glycol or polyethylene glycol moiety or a derivative thereof. Said oligoethylene glycol or polyethylene glycol moiety may either be branched or linear. Without being bound by any theory, this moiety may be incorporated in a compound of formula (I) or (II) to improve for example the physicochemical, biophysical, pharmacodynamic and/or pharmacokinetic properties of the compound, e.g., water solubility and aggregation behavior. Furthermore, due to the hydrophilic nature of the oligoethylene glycol or polyethylene glycol moiety, a compound of formula (I) or (II) may for example be more cytotoxic against multidrug-resistant tumor cells, as the compound is a bad substrate for efflux pumps. If a compound of formula (I) or (II) is incorporated in a conjugate, it may be that the oligoethylene glycol or polyethylene glycol moiety is located in between the promoiety, i.e., a moiety that is coupled to a compound of formula (I) or (II) to modify its properties and that is to be (partly) removed in vivo from said compound of formula (I) or (II), and the remainder of the compound of formula (I) or (II) or that it is located at a position somewhat opposite to the attachment site of the promoiety, thus placing the remainder of the compound of formula (I) or (II) in between the promoiety and the oligoethylene glycol or polyethylene glycol moiety. The latter situation may have the advantage that the hydrophobic (aromatic) core structure of the compound of formula (I) or (II) is more shielded from unfavorable interactions with its environment, e.g., an aqueous environment, thus for example reducing the amount of aggregate formation.

In another embodiment, the current invention relates to a conjugate of a compound of formula (I) or (II) and derivatives thereof. These conjugates contain one or more promoieties.

In another embodiment, a conjugate of a compound of formula (I) or (II) comprises at least two promoieties of which the first promoiety is an in vivo cleavable promoiety that comprises an oligoethylene glycol or polyethylene glycol moiety or a derivative thereof and the second promoiety comprises at least a targeting moiety. Such a conjugate has the relatively hydrophobic core structure of a compound of formula (I) or (II) or a derivative thereof placed in between the targeting promoiety and the oligoethylene glycol or polyethylene glycol-containing promoiety, thereby shielding the core structure from possibly unfavorable interactions with its environment.

Compounds of formulae (I) and (II) are suited for application in drug delivery purposes, including drug targeting and controlled release applications using compounds of formulae (III) and (IV).

Agents

In one aspect, the present invention provides a compound of formula (I) or (II):

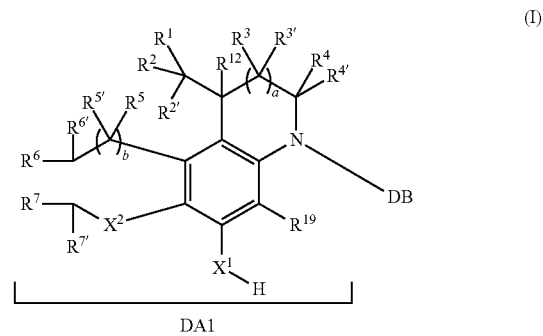

(I)

DA1

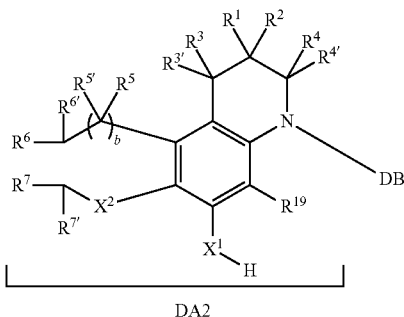

(II)

or a pharmaceutically acceptable salt, hydrate, or solvate thereof, wherein DB is a DNA-binding moiety and is selected from the group consisting of

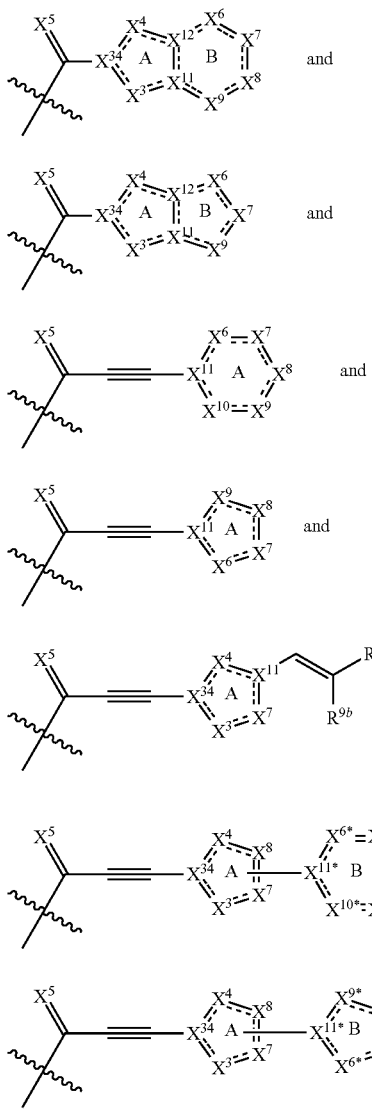

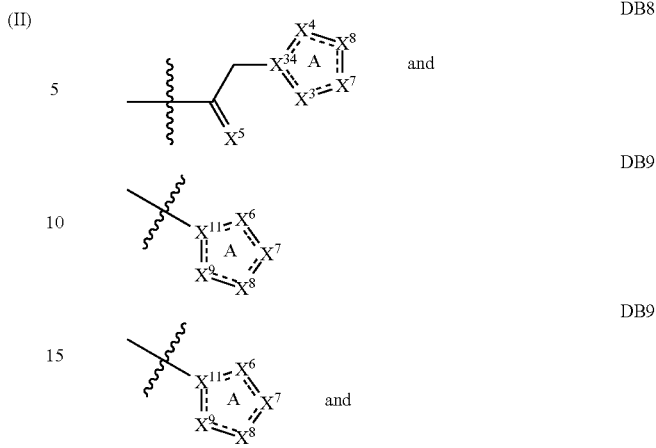

$R^1$ is a leaving group;

$R^2$, $R^{2'}$, $R^3$, $R^{3'}$, $R^4$, $R^{4'}$, $R^{12}$, and $R^{19}$ are independently selected from H, OH, SH, $NH_2$, $N_3$, $NO_2$, NO, $CF_3$, CN, $C(O)NH_2$, $C(O)H$, $C(O)OH$, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, and $N(R^a)C(O)N(R^b)R^c$, wherein $R^a$, $R^b$, and $R^c$ are independently selected from H and optionally substituted $C_{1-3}$ alkyl or $C_{1-3}$ heteroalkyl, or $R^3+R^{3'}$ and/or $R^4+R^{4'}$ are independently selected from =O, =S, =$NOR^{18}$, =$C(R^{18})R^{18'}$, and =$NR^{18}$, $R^{18}$ and $R^{18'}$ being independently selected from H and optionally substituted $C_{1-3}$ alkyl, two or more of $R^2$, $R^{2'}$, $R^3$, $R^{3'}$, $R^4$, $R^{4'}$, and $R^{12}$ optionally being joined by one or more bonds to form one or more optionally substituted carbocycles and/or heterocycles;

$X^2$ is selected from O, $C(R^{14})(R^{14'})$, and $NR^{14}$, wherein $R^{14}$ and $R^{14'}$ have the same meaning as defined for $R^7$ and are independently selected, or $R^{14'}$ and $R^{7'}$ are absent resulting in a double bond between the atoms designated to bear $R^{7'}$ and $R^{14'}$;

$R^5$, $R^{5'}$, $R^6$, $R^{6'}$, $R^7$, and $R^{7'}$ are independently selected from H, OH, SH, $NH_2$, $N_3$, $NO_2$, NO, $CF_3$, CN, $C(O)NH_2$, $C(O)H$, $C(O)OH$, halogen, $R^e$, $SR^e$, $S(O)R^e$, $S(O)_2R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, $N(R^e)C(O)N(R^f)R^g$, and a water-soluble group, wherein $R^e$, $R^f$, and $R^g$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, one or more of the optional substituents in $R^e$, $R^f$, and/or $R^g$ optionally being a water-soluble group, two or more of $R^e$, $R^f$, and $R^g$ optionally being joined by one or more bonds to form one or more optionally substituted carbocycles and/or heterocycles, or $R^5+R^{5'}$ and/or $R^6+R^{6'}$ and/or $R^7+R^{7'}$ are independently selected from $=O$, $=S$, $=NOR^{e3}$, $=C(R^{e3})R^{e4}$, and $=NR^{e3}$, $R^{e3}$ and $R^{e4}$ being independently selected from H and optionally substituted $C_{1-3}$ alkyl, or $R^{5'}+R^{6'}$ and/or $R^{6'}+R^{7'}$ and/or $R^{7'}+R^{14'}$ are absent, resulting in a double bond between the atoms designated to bear $R^{5'}$ and $R^{6'}$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles;

$X^1$ is selected from O, S, and $NR^{13}$, wherein $R^{13}$ is selected from H and optionally substituted $C_{1-8}$ alkyl or $C_{1-8}$ heteroalkyl and not joined with any other substituent;

$X^3$ is selected from O, S, $C(R^{15})R^{15'}$, $-C(R^{15})(R^{15'})-C(R^{15''})(R^{15'''})-$, $-N(R^{15})-N(R^{15'})-$, $-C(R^{15})(R^{15'})-N(R^{15''})-$, $-N(R^{15''})-C(R^{15})(R^{15'})-$, $-C(R^{15})(R^{15'})-O-$, $-O-C(R^{15})(R^{15'})-$, $-C(R^{15})(R^{15'})-S-$, $-S-C(R^{15})(R^{15'})-$, $-C(R^{15})=C(R^{15'})-$, $=C(R^{15})-C(R^{15'})=$, $-N=C(R^{15'})-$, $=N-C(R^{15'})=$, $-C(R^{15})=N-$, $=C(R^{15})-N=$, $-N=N-$, $=N-N=$, $CR^{15}$, N, and $NR^{15}$, or in DB1 and DB2 $-X^3-$ represents $-X^{3a}$ and $X^{3b}-$, wherein $X^{3a}$ is connected to $X^{34}$, a double bond is present between $X^{34}$ and $X^4$, and $X^{3b}$ is connected to $X^{11}$, wherein $X^{3a}$ is independently selected from H and optionally substituted $(CH_2CH_2O)_{ee}CH_2CH_2X^{13}R^{e1}$, $C_{1-8}$ alkyl, or $C_{1-8}$ heteroalkyl and not joined with any other substituent;

$X^4$ is selected from O, S, $C(R^{16})R^{16'}$, $NR^{16}$, N, and $CR^{16}$;

$X^5$ is selected from O, S, $C(R^{17})R^{17'}$, $NOR^{17}$, and $NR^{17}$, wherein $R^{17}$ and $R^{17'}$ are independently selected from H and optionally substituted $C_{1-8}$ alkyl or $C_{1-8}$ heteroalkyl and not joined with any other substituent;

$X^6$ is selected from $CR^{11}$, $CR^{11}(R^{11'})$, N, $NR^{11}$, O, and S;
$X^7$ is selected from $CR^8$, $CR^8(R^{8'})$, N, $NR^8$, O, and S;
$X^8$ is selected from $CR^9$, $CR^9(R^{9'})$, N, $NR^9$, O, and S;
$X^9$ is selected from $CR^{10}$, $CR^{10}(R^{10'})$, N, $NR^{10}$, O, and S;
$X^{10}$ is selected from $CR^{20}$, $CR^{20}(R^{20'})$, N, $NR^{20}$, O, and S;
$X^{11}$ is selected from C, $CR^{21}$, and N, or $X^{11}-X^{3b}$ is selected from $CR^{21}$, $CR^{21}(R^{21'})$, N, $NR^{21}$, O, and S;
$X^{12}$ is selected from C, $CR^{22}$, and N;
$X^{6*}$, $X^{7*}$, $X^{8*}$, $X^{9*}$, $X^{10*}$, and $X^{11*}$ have the same meaning as defined for $X^6$, $X^7$, $X^8$, $X^9$, $X^{10}$, and $X^{11}$, respectively, and are independently selected;
$X^{34}$ is selected from C, $CR^{23}$, and N;

the ring B atom of $X^{11*}$ in DB6 and DB7 is connected to a ring atom of ring A such that ring A and ring B in DB6 and DB7 are directly connected via a single bond;

=== means that the indicated bond may be a single bond or a non-cumulated, optionally delocalized, double bond;

$R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ are each independently selected from H, OH, SH, $NH_2$, $N_3$, $NO_2$, NO, $CF_3$, CN, $C(O)NH_2$, $C(O)H$, $C(O)OH$, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein $R^h$, $R^i$, and $R^j$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, one or more of the optional substituents in $R^h$, $R^i$, and/or $R^j$ optionally being a water-soluble group, two or more of $R^h$, $R^i$, and $R^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11'}$ and/or $R^{15}+R^{15'}$ and/or $R^{15''}+R^{15'''}$ and/or $R^{16}+R^{16'}$ and/or $R^{20}+R^{20'}$ and/or $R^{21}+R^{21'}$ are independently selected from $=O$, $=S$, $=NOR^{h1}$, $=C(R^{h1})R^{h2}$, and $=NR^{h1}$, $R^{h1}$ and $R^{h2}$ being independently selected from H and optionally substituted $C_{1-3}$ alkyl, two or more of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ optionally being joined by one or more bonds to form one or more optionally substituted carbocycles and/or heterocycles;

$R^{8b}$ and $R^{9b}$ are independently selected and have the same meaning as $R^8$, except that they may not be joined with any other substituent;

one of $R^4$ and $R^{4'}$ and one of $R^{16}$ and $R^{16'}$ may optionally be joined by one or more bonds to form one or more optionally substituted carbocycles and/or heterocycles;

one of $R^2$, $R^{2'}$, $R^3$, and $R^{3'}$ and one of $R^5$ and $R^{5'}$ may optionally be joined by one or more bonds to form one or more optionally substituted carbocycles and/or heterocycles; and a and b are independently selected from 0 and 1.

In a further aspect, this invention relates to a compound of formula (I') or (II'):

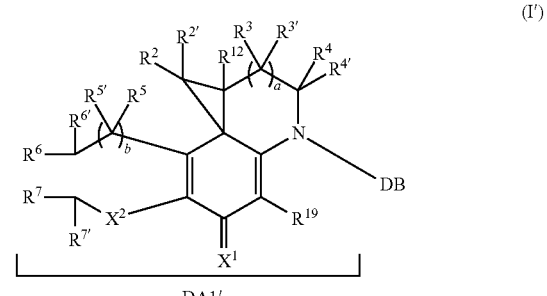

(I')

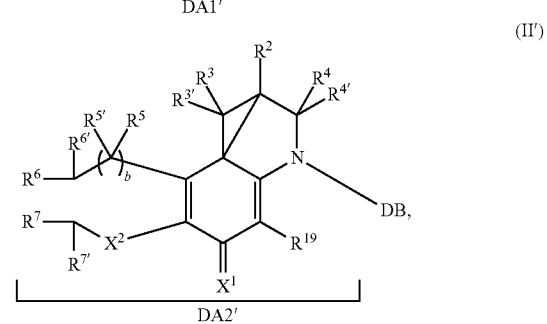

(II')

or a pharmaceutically acceptable salt, hydrate, or solvate thereof, wherein all substituents have the same meaning as described for compounds of formulae (I) and (II). Compounds of formulae (I) and (II) are alleged to be converted to (I') and (II'), respectively, in vivo with concomitant elimination of H—$R^1$, as schematically illustrated in FIG. 1 for a compound of formula (I).

Therefore, this invention relates to a compound of formula (I') or (II'), said compound comprising a cyclopropyl group, which can be formed through rearrangement of and concomitant elimination of H—$R^1$ from a compound of formula (I) or (II). All embodiments for a compound of formula (I) or (II) or a moiety thereof also hold for a compound of formula (I') or (II') or a moiety thereof, unless the context dictates otherwise.

In a more specific embodiment, this invention relates to a compound of formula (I) or (II) as described hereinabove, wherein a) the DB moiety does not comprise a DA1, DA2, DA1', or DA2' moiety; and b) ring B in DB1 is a heterocycle; and c) if $X^3$ in DB1 represents —$X^{3a}$ and $X^{3b}$— and ring B is aromatic, then two vicinal substituents on said ring B are joined to form an optionally substituted carbocycle or heterocycle fused to said ring B; and d) if $X^3$ in DB2 represents —$X^{3a}$ and $X^{3b}$— and ring B is aromatic, then two vicinal substituents on said ring B are joined to form an optionally substituted heterocycle fused to said ring B, an optionally substituted non-aromatic carbocycle fused to said ring B, or a substituted aromatic carbocycle which is fused to said ring B and to which at least one substituent is attached that contains a hydroxy group, a primary amino group, or a secondary amino group, the primary or secondary amine not being a ring atom in an aromatic ring system nor being part of an amide; and e) if ring A in DB2 is a 6-membered aromatic ring, then substituents on ring B are not joined to form a ring fused to ring B; and f) two vicinal substituents on ring A in DB8 are joined to form an optionally substituted carbocycle or heterocycle fused to said ring A to form a bicyclic moiety to which no further rings are fused; and g) ring A in DB9 together with any rings fused to said ring A contains at least two ring heteroatoms.

In a further more specific embodiment, this invention relates to a compound of formula (I) or (II) as described hereinabove, wherein at least one of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a $X^{14}(CH_2CH_2O)_{ff}CH_2CH_2X^{14}$ moiety, wherein ff is selected from 1 to 1000 and each $X^{14}$ is independently selected from

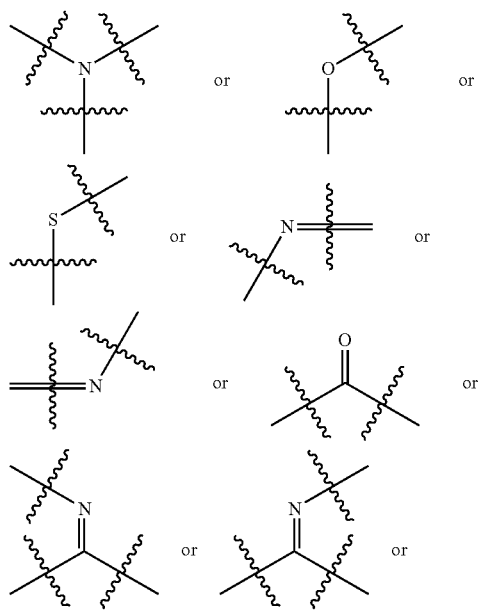

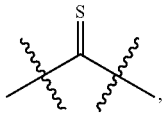

that is connected to the attachment site of said substituent either via a direct bond or via a moiety, being part of said same substituent, that does not comprise a disulfide, a hydrazone, a hydrazide, an ester, a natural amino acid, or a peptide containing at least one natural amino acid, and wherein if ring B in DB1 is an all-carbon ring, $X^3$ is O or $NR^{15}$, $X^4$ is CH, $X^{34}$ is C, there is only one $X^{14}(CH_2CH_2O)_{ff}CH_2CH_2X^{14}$ moiety present in said compound of formula (I) or (II) and said moiety is part of $R^6$, $R^7$, $R^8$, $R^{10}$, or $R^{15}$, then b=1 and ff is ≥5.

A compound of formula (I) or (II) or a conjugate thereof in which ff is larger than 1000 is encompassed by this invention.

In a further more specific embodiment, this invention relates to a compound of formula (I) or (II) as described hereinabove, wherein at least one of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a triazole moiety.

It should be understood that in this entire document, when referring to a compound of formula (I) or (II), this includes reference to a compound of formula (I') or (II'), respectively, unless structural parts of (I) and (II) not present in (I') and (II') are concerned or the context dictates otherwise. Similarly, when referring to a structural part (fragment), linker-agent conjugate, or conjugate derived from a compound of formula (I) or (II), this includes reference to a similar structural part (fragment), linker-agent conjugate, or conjugate derived from a compound of formula (I') or (II'), respectively, unless structural parts of (I) and (II) not present in (I') and (II') are concerned or the context dictates otherwise.

It should also be understood that when reference is made to a compound of formula (I) or (II) or a fragment, derivative, or conjugate thereof and the scope of $R^{2'}$ or $R^{12}$ is specified, this specification only affects a compound of formula (I) as $R^{2'}$ and $R^{12}$ are absent in a compound of formula (II). Therefore, wherever it reads "$R^{2'}$" or "$R^{12}$" in this document, one could read "$R^{2'}$ (if present)" or "$R^{12}$ (if present)", respectively. This holds as well for (other) substituents that may be present or absent in compounds of formulae (I) and (II) and their fragments, linker-agent conjugates, and conjugates.

It should further be understood that this invention relates to enantiomerically pure and/or diastereomerically pure compounds of formulae (I) and (II) as well as to enantiomeric and/or diastereomeric mixtures of compounds of formulae (I) and (II).

Considerations about substituent effects and the effects of linkers, DNA-alkylating units and DNA-binding units in compounds of formulae (I) and (II), their cyclopropyl-containing analogs, and their conjugates and linker-agent conjugates given in this document are presented without consenting to a specific mechanism of action for compounds of formulae (I) and (II), their cyclopropyl-containing analogs, and their linker-agent conjugates and conjugates.

Compounds of formula (I) and (II) can be considered to be built up of a DNA-binding unit (DB) and a DNA-alkylating unit (DA1, DA2, DA1', or DA2'), as indicated in the figures hereinabove. The DNA-alkylating unit of compounds of formulae (I) and (II) is considered to contain the site of alkylation. Alkylation of DNA may occur through attack of DNA on the carbon bearing $R^1$ in a compound of formula (I) or (II) or on that same carbon in the cyclopropyl-containing analog of said compound.

The DNA-binding unit of compounds of formulae (I) and (II) is considered to assist in efficient binding of these compounds to DNA. It may be coupled to the DNA-alkylating moiety via, for instance, an amide bond. Therefore in one embodiment, $X^5$ is O.

In one embodiment, this invention relates to a compound of formula (I). In another embodiment, this invention relates to a compound of formula (II).

$R^1$ in a compound of formula (I) or (II) is a leaving group.

In one embodiment, the leaving group $R^1$ is selected from halogen, azide ($N_3$), carboxylate [OC(O)R″], carbonate [OC(O)OR″], carbamate [OC(O)N(R″)R″$^1$], and OS(O)$_2$R$^o$, wherein R″R″$^1$, and R$^o$ are independently selected from H and optionally substituted $C_{1-10}$ alkyl, $C_{1-10}$ heteroalkyl, $C_{5-10}$ aryl, or $C_{1-10}$ heteroaryl. An optional substituent may be an oligoethylene glycol or a polyethylene glycol moiety. When the $R^1$ group comprises an oligoethylene glycol or polyethylene glycol moiety, i.e., a $X^{14}(CH_2CH_2O)_{\!f\!}CH_2CH_2X^{14}$ moiety, a compound of formula (I) or (II) or its conjugate may show improved physicochemical, biopharmaceutical, pharmacodynamic, and/or pharmacokinetic properties, which, as indicated hereinabove, may also be valid for the presence of oligoethylene glycol or polyethylene glycol moieties at other positions in a compound of formula (I) or (II). In addition, however, the relatively large size of the $R^1$ substituent may reduce non-specific alkylation of a compound of formula (I) or (II) or its conjugate. Furthermore, the $R^1$ group will be eliminated when the compound of formula (I) or (II) rearranges to a compound of formula (I′) or (II′). This means that the oligoethylene glycol or polyethylene glycol moiety may not have a negative effect on the cytotoxic potential of the compound of formula (I) or (II).

In one embodiment, $R^1$ is selected from halogen and OS(O)$_2$R$^o$. In another embodiment, the leaving group $R^1$ in a compound of formula (I) or (II) is a halogen. In another embodiment, $R^1$ is selected from chloro (Cl), bromo (Br), and iodo (I). In yet another embodiment, $R^1$ is chloro (Cl). In yet another embodiment, $R^1$ is bromo (Br). In yet another embodiment, $R^1$ is OS(O)$_2$R$^o$. In yet another embodiment, $R^1$ is OS(O)$_2$R$^o$ and R$^o$ contains a $X^{14}(CH_2CH_2O)_{\!f\!}CH_2CH_2X^{14}$ moiety. In yet another embodiment, $R^1$ is selected from OS(O)$_2$CF$_3$, OS(O)$_2$C$_6$H$_4$CH$_3$, and OS(O)$_2$CH$_3$.

By varying the leaving group $R^1$, one may tune the alkylating activity of the seco agents and affect the transformation rate of a seco agent to a cyclopropyl-containing agent of formula (I′) or (II′). If the leaving capability of $R^1$ is too good, this may cause the seco agent to become an aspecific alkylating agent, which may decrease the cytotoxicity quotient and therapeutic index of conjugates of compounds of formulae (I) and (II) as the agent may for example be able to alkylate while still being bound in the conjugate. On the other hand, if $R^1$ is too bad a leaving group, the seco agent may not close to form a cyclopropyl-containing agent, believed to be the active species, which may reduce its cytotoxicity and the cytotoxicity quotient. Therefore, in one embodiment, the Swain-Scott parameter s of the alkylating site is larger than 0.3. In other embodiments, the Swain-Scott parameter s is larger than 0.5 or 0.7 or 1.0.

The size of $R^1$ may affect the non-DNA alkylation rate of a compound of formula (I) or (II) or a conjugate thereof. If $R^1$ is a relatively bulky group, aspecific alkylation may be reduced as the carbon bearing $R^1$ is somewhat shielded.

Another means to tune the alkylating activity of the seco agents and their cyclopropyl-containing derivatives may be to somewhat shield the carbon to which the leaving group $R^1$ is attached or on which nucleophilic attack can occur by choosing at least one of $R^2$, $R^{2'}$, $R^3$, $R^{3'}$, $R^4$, $R^{4'}$, $R^5$, $R^{5'}$, $R^6$, $R^{6'}$, $R^{12}$, $R^{16}$, and $R^{16'}$ present to be other than hydrogen. Shielding of said carbon may reduce aspecific alkylation by compounds of formulae (I) and (II), their cyclopropyl-containing analogs, and their conjugates. Although introduction of steric hindrance may also affect the DNA alkylation rate, it may be reasonable to assume that aspecific alkylation may be affected relatively more than DNA alkylation as the latter occurs presumably after the agent is ideally positioned for nucleophilic attack being bound to the DNA minor groove. The carbon bearing $R^1$ in a compound of formula (II), being a secondary carbon atom (when $R^2$ is H), is already somewhat shielded in comparison to the carbon bearing $R^1$ in a compound of formula (I) when $R^2$ and $R^{2'}$ are both H. In this respect, a compound of formula (II) may be compared to a compound of formula (I) in which $R^{2'}$ is other than hydrogen. Further shielding may however be accomplished by choosing one or more of $R^2$, $R^3$, $R^{3'}$, $R^4$, $R^{4'}$, $R^5$, $R^{5'}$, $R^6$, $R^{6'}$, $R^{16}$, and $R^{16'}$ present to be other than hydrogen.

In one embodiment, $R^2$ and $R^{2'}$ are both hydrogen. In another embodiment, $R^{2'}$ is hydrogen and $R^2$ is not hydrogen. In another embodiment, $R^2$ is selected from $N_3$, $NO_2$, NO, $CF_3$, CN, C(O)NH$_2$, C(O)H, C(O)OH, halogen, $R^a$, SR$^a$, S(O)R$^a$, S(O)$_2$R$^a$, S(O)OR$^a$, S(O)$_2$OR$^a$, OS(O)R$^a$, OS(O)$_2$R$^a$, OS(O)OR$^a$, OS(O)$_2$OR$^a$, OR$^a$, N(R$^a$)R$^b$, $^+$N(R$^a$)(R$^b$)R$^c$, P(O)(OR$^a$)(OR$^b$), OP(O)(OR$^a$)(OR$^b$), SiR$^a$R$^b$R$^c$, C(O)R$^a$, C(O)OR$^a$, C(O)N(R$^a$)R$^b$, OC(O)R$^a$, OC(O)OR$^a$, OC(O)N(R$^a$)R$^b$, N(R$^a$)C(O)R$^b$, N(R$^a$)C(O)OR$^b$, and N(R$^a$)C(O)N(R$^b$)R$^c$, wherein R$^a$, R$^b$, and R$^c$ are independently selected from H and optionally substituted $C_{1-3}$ alkyl or $C_{1-3}$ heteroalkyl.

In one embodiment, $R^2$ is selected from optionally substituted $C_{1-3}$ alkyl and $C_{1-3}$ heteroalkyl. In another embodiment, $R^2$ is optionally substituted $C_{1-3}$ alkyl. In another embodiment, $R^2$ is selected from methyl, ethyl, propyl, and isopropyl. In another embodiment, $R^2$ is methyl.

In yet another embodiment, $R^2$ and $R^{2'}$ are both other than hydrogen. In one embodiment, both $R^2$ and $R^{2'}$ are methyl.

Alternatively, or simultaneously, steric shielding of the carbon bearing $R^1$ may be introduced by choosing one or more of $R^3$, $R^{3'}$, $R^4$, $R^{4'}$, $R^{12}$, $R^{16}$, and $R^{16'}$ present to be other than hydrogen. In one embodiment, $R^3$, $R^{3'}$, $R^4$, and $R^{4'}$ are each H. In another embodiment, $R^3$ and $R^{3'}$ are both H. In another embodiment, $R^4$ and $R^{4'}$ are both H. In another embodiment, one of $R^3$ and $R^{3'}$ is $C_{1-3}$ alkyl while the other is H. In another embodiment, one of $R^4$ and $R^{4'}$ is $C_{1-3}$ alkyl while the other is H. In another embodiment, one of $R^3$ and $R^{3'}$ is $C_{1-3}$ alkyl and one of $R^4$ and $R^{4'}$ is $C_{1-3}$ alkyl while the others are H. In another embodiment, both $R^3$ and $R^{3'}$ are independently $C_{1-3}$ alkyl. In another embodiment, both $R^4$ and $R^{4'}$ are independently $C_{1-3}$ alkyl. In another embodiment, one of $R^3$, $R^{3'}$, $R^4$, and $R^{4'}$ is methyl. In another embodiment, one of $R^4$ and $R^{4'}$ is methyl. In yet another embodiment, both $R^4$ and $R^{4'}$ are methyl. In yet other embodiments, one or both of $R^4$ and $R^{4'}$ are fluoro.

In one embodiment, $R^{12}$ is H. In another embodiment, $R^{12}$ is $C_{1-3}$ alkyl. In yet other embodiments, $R^{12}$ is methyl or ethyl. In yet another embodiment, $R^{12}$ equals C(R$^{2'}$)(R$^2$)R$^1$, which means that the carbon bearing $R^{12}$ bears two identical groups.

In another embodiment, $R^{16}$ and $R^{16'}$ are both H. In another embodiment, $R^{16}$ is H. In other embodiments, $R^{16}$ is fluoro (F) or methyl or ethyl.

The alkylating activity of a compound of formula (I) or (II) or its cyclopropyl-containing analog may also be affected by the nature of $X^1$. The nature of $X^1$ may affect the rate at which and the conditions under which the seco agents ring close to the cyclopropyl analogs and/or the rate at which the cyclopropyl ring is opened by nucleophilic attack (by DNA), and thus affect the alkylation behavior. In one embodiment, $X^1$ is O. In another embodiment, $X^1$ is $NR^{13}$.

The substituents $R^5$, $R^{5'}$, $R^6$, $R^{6'}$, $R^7$, $R^{7'}$, and $X^2$ as well as the size of the ring connected to the left-hand side of the ring bearing $X^1$ may for example, each independently or two or more taken together, affect the pharmacological properties of the agent, e.g., affect the water solubility, affect the aggregation behavior, affect the DNA alkylation process, and/or affect the DNA binding strength. Furthermore, especially $R^5$ and $R^{5'}$, and to some degree $R^6$ and $R^{6'}$ as well, may also affect the degree of shielding of the carbon on which nucleophilic attack should occur.

$R^5$ and $R^{5'}$ may both be H, or $R^5$ may be H while $R^{5'}$ is absent. In another embodiment, at least one of $R^5$ and $R^{5'}$ is not hydrogen nor absent. In another embodiment, $R^5$ is not hydrogen.

In one embodiment, $R^5$ is selected from OH, SH, $NH_2$, $N_3$, $NO_2$, NO, $CF_3$, CN, $C(O)NH_2$, C(O)H, C(O)OH, halogen, $R^{e2}$, $SR^{e2}$, $S(O)R^{e2}$, $S(O)_2R^{e2}$, $S(O)OR^{e2}$, $S(O)_2OR^{e2}$, $OS(O)R^{e2}$, $OS(O)_2R^{e2}$, $OS(O)OR^{e2}$, $OS(O)_2OR^{e2}$, $OR^{e2}$, $NHR^{e2}$, $N(R^{e2})R^{f2}$, $^+N(R^{e2})(R^{f2})R^{g2}$, $P(O)(OR^{e2})(OR^{f2})$, $OP(O)(OR^{e2})(OR^{f2})$, $SiR^{e2}R^{f2}R^{g2}$, $C(O)R^{e2}$, $C(O)OR^{e2}$, $C(O)N(R^{e2})R^{f2}$, $OC(O)R^{e2}$, $OC(O)OR^{e2}$, $OC(O)N(R^{e2})R^{f2}$, $N(R^{e2})C(O)R^{f2}$, $N(R^{e2})C(O)OR^{f2}$, and $N(R^{e2})C(O)N(R^{f2})R^{g2}$, wherein $R^{e2}$, $R^{f2}$, and $R^{g2}$ are independently selected from H and optionally substituted $C_{1-3}$ alkyl, $C_{1-3}$ heteroalkyl, $C_3$ cycloalkyl, or $C_{1-3}$ heterocycloalkyl, two or more of $R^{e2}$, $R^{f2}$, and $R^{g2}$ optionally being joined by one or more bonds to form one or more optionally substituted carbocycles and/or heterocycles.

In another embodiment, $R^5$ is selected from nitro, halogen, amino, cyano, hydroxy, and optionally substituted $C_{1-3}$ alkylamino, di($C_{1-3}$ alkyl)amino, $C_{1-3}$ alkylcarbonylamino, $C_{1-3}$ alkoxycarbonylamino, $C_{1-3}$ alkylaminocarbonylamino, $C_{1-3}$ alkyloxy, $C_{1-3}$ alkylcarbonyloxy, $C_{1-3}$ alkoxycarbonyloxy, $C_{1-3}$ alkylaminocarbonyloxy, or $C_{1-3}$ alkyl. In yet another embodiment, $R^5$ is optionally substituted linear $C_{1-3}$ alkyl. In another embodiment, $R^5$ is unsubstituted linear $C_{1-3}$ alkyl. In another embodiment, $R^5$ is selected from methyl, ethyl, propyl, isopropyl, nitro, $CF_3$, F, Cl, Br, cyano, methoxy, ethoxy, propoxy, isopropoxy, amino ($NH_2$), methylamino, formyl, hydroxymethyl, and dimethylamino. In another embodiment, $R^5$ is methyl, ethyl, methoxy, or ethoxy. In another embodiment, $R^5$ is methyl. In other embodiments, $R^5$ is ethyl or methoxy or ethoxy.

$R^6$ and $R^{6'}$ may both be hydrogen, or $R^6$ may be hydrogen while $R^{6'}$ is absent. In another embodiment, at least one of $R^6$ and $R^{6'}$ is not hydrogen nor absent. In another embodiment, $R^6$ is not hydrogen.

$R^5$ and $R^6$ may be joined to form, together with the two carbon atoms to which they are attached, an optionally substituted 5- or 6-membered ring. This ring may for example be a dihydropyrrole, dihydrofuran, cyclopentene, 1,3-dioxolene, pyrrolidine, tetrahydrofuran, cyclopentane, or 1,3-dioxolane moiety.

The substituents $R^{16}$ and $R^{16'}$ may affect the degree of shielding of the carbon on which nucleophilic attack can occur as well. In one embodiment $X^4$ is $CR^{16}$. In a further embodiment, $R^{16}$ is hydrogen. In yet another embodiment, $R^{16}$ is $C_{1-3}$ alkyl or $C_{1-3}$ heteroalkyl. In another embodiment, $R^{16}$ is methyl or ethyl. In yet another embodiment, $R^{16}$ is methyl. In yet another embodiment, $R^{16}$ is fluoro.

In one embodiment, $R^2$, $R^{2'}$, $R^3$, $R^{3'}$, $R^4$, $R^{4'}$, $R^5$, $R^{5'}$, $R^6$, $R^{6'}$, $R^{12}$, $R^{16}$, and $R^{16'}$ present are each hydrogen. In another embodiment $R^2$, $R^{2'}$, $R^3$, $R^{3'}$, $R^4$, $R^{4'}$, $R^5$, $R^{5'}$, $R^6$, $R^{6'}$, $R^{12}$, $R^{16}$, and $R^{16'}$ present are each hydrogen. In yet another embodiment, $R^2$, $R^{2'}$, $R^3$, $R^{3'}$, $R^4$, $R^{4'}$, $R^5$, $R^{5'}$, $R^6$, $R^{6'}$, $R^7$, $R^{7'}$, $R^{12}$, $R^{14}$, $R^{14'}$, $R^{16}$, $R^{16'}$, and $R^{19}$ present are each hydrogen. In yet another embodiment, $R^2$, $R^{2'}$, $R^3$, $R^{3'}$, $R^4$, $R^{4'}$, $R^5$, $R^{5'}$, $R^6$, $R^{6'}$, $R^7$, $R^{7'}$, $R^{12}$, $R^{14}$, $R^{14'}$, $R^{16}$, $R^{16'}$, and $R^{19}$ present are each hydrogen.

Although the alkylation rate and efficiency of compounds of formulae (I) and (II) may optionally be tuned in several ways, in one aspect of this invention, this may be achieved by introducing steric shielding choosing for a compound of formula (I) one or more of $R^2$, $R^{2'}$, $R^3$, $R^{3'}$, $R^4$, $R^{4'}$, $R^5$, $R^{5'}$, $R^6$, $R^{6'}$, $R^{12}$, $R^{16}$, and $R^{16'}$ present to be other than hydrogen and for a compound of formula (II) one or more of $R^2$, $R^3$, $R^{3'}$, $R^4$, $R^{4'}$, $R^5$, $R^{5'}$, $R^6$, $R^{6'}$, $R^{16}$, and $R^{16'}$ present to be other than hydrogen. Substituents should not cause too much steric hindrance, however, especially when more than one of these substituents is other than hydrogen, as this might adversely affect DNA alkylation. Furthermore, it may provide for less efficient binding in the DNA minor groove and may pose synthetic difficulties.

In one aspect of this invention, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a $X^{14}(CH_2CH_2O)_{ff}CH_2CH_2X^{14}$ moiety, wherein ff is selected from 1 to 1000 and each $X^{14}$ is independently selected from

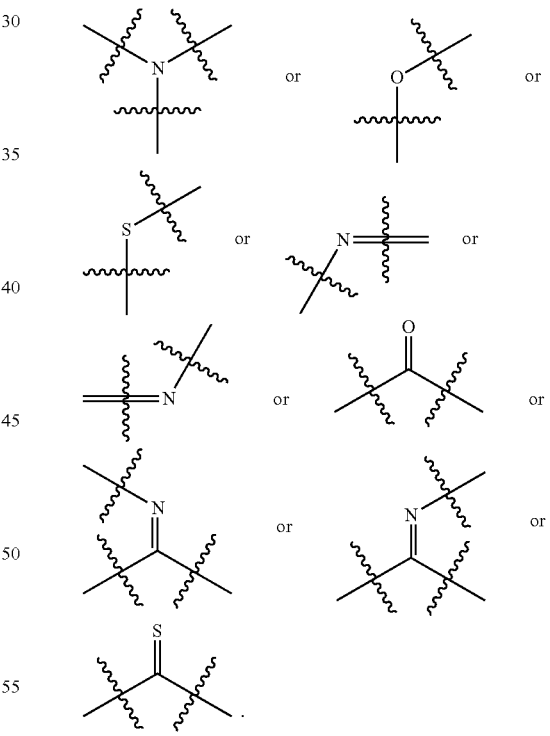

This moiety must be connected to the core of the DNA-alkylating moiety or DNA-binding moiety via a direct bond or via a linking unit that is part of said same R group and that does not comprise a disulfide, a hydrazone, a hydrazide, an ester, a natural amino acid, or a peptide containing at least one natural amino acid. Said linking unit should preferably be cleaved less than 20%, more preferably less than 10%, and most preferably less than 5% in 24 hours upon administration of a compound of formula (I) or (II) in vivo.

The $X^{14}(CH_2CH_2O)_{ff}CH_2CH_2X^{14}$ moiety may for example be selected to be
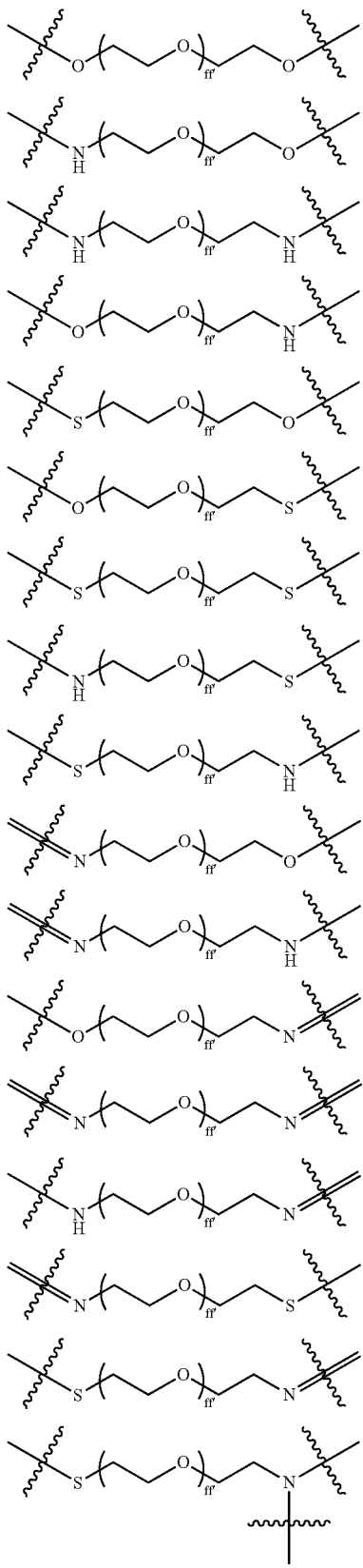
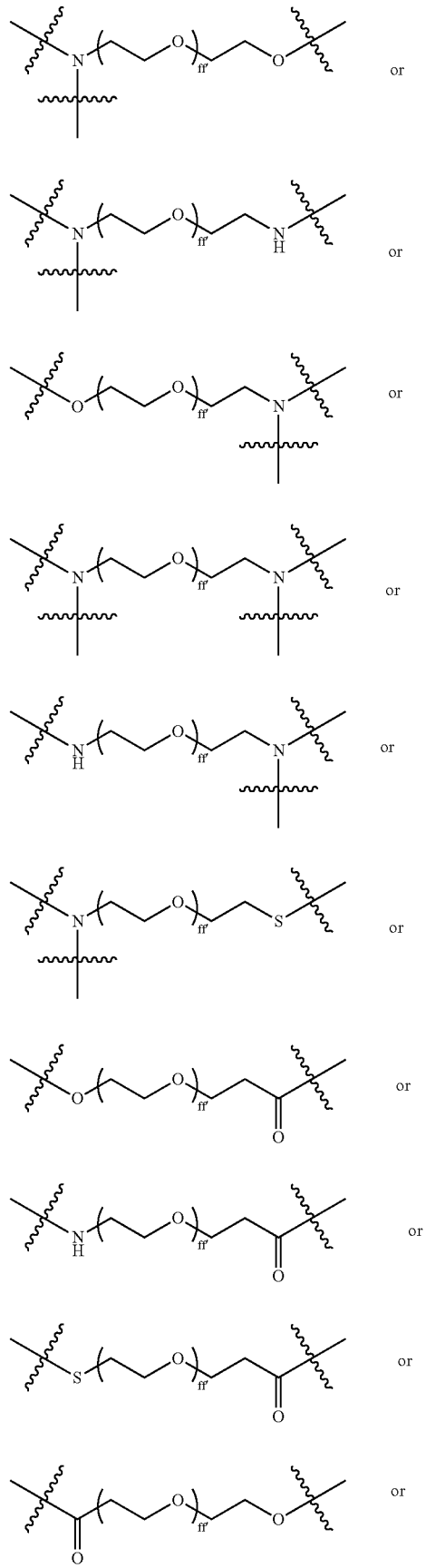

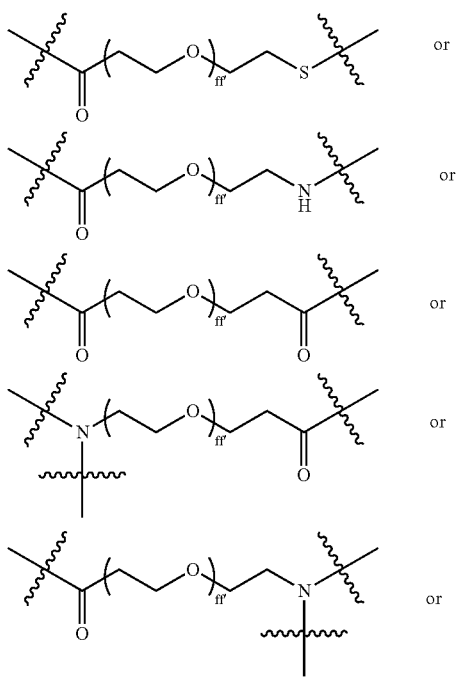

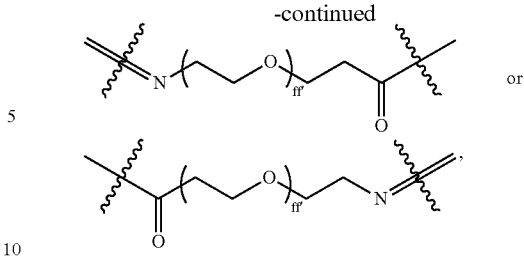

wherein ff is selected from 1 to 1000. In more specific embodiments, ff is selected from 1 to 100 or from 1 to 10. In other embodiments, ff is selected to be 1 or 2 or 3 or 4. In another embodiment, ff is 3 or 4.

The oligoethylene glycol or polyethylene glycol moiety or derivative thereof is connected via a linking unit to the core structure of a compound of formula (I) or (II). Such a linking unit may be a single bond, in which case the oligoethylene glycol or polyethylene glycol or derivative thereof is connected to the core structure via for example an amine, ether, or sulfide bond. Alternatively, the oligoethylene glycol or polyethylene glycol moiety or derivative thereof may be connected to the core structure via for example a carbamate, a carbonate, an amide, an alkyl, a heteroalkyl, an aryl, or a heteroaryl moiety, or a combination of any of these. In one embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ is selected from

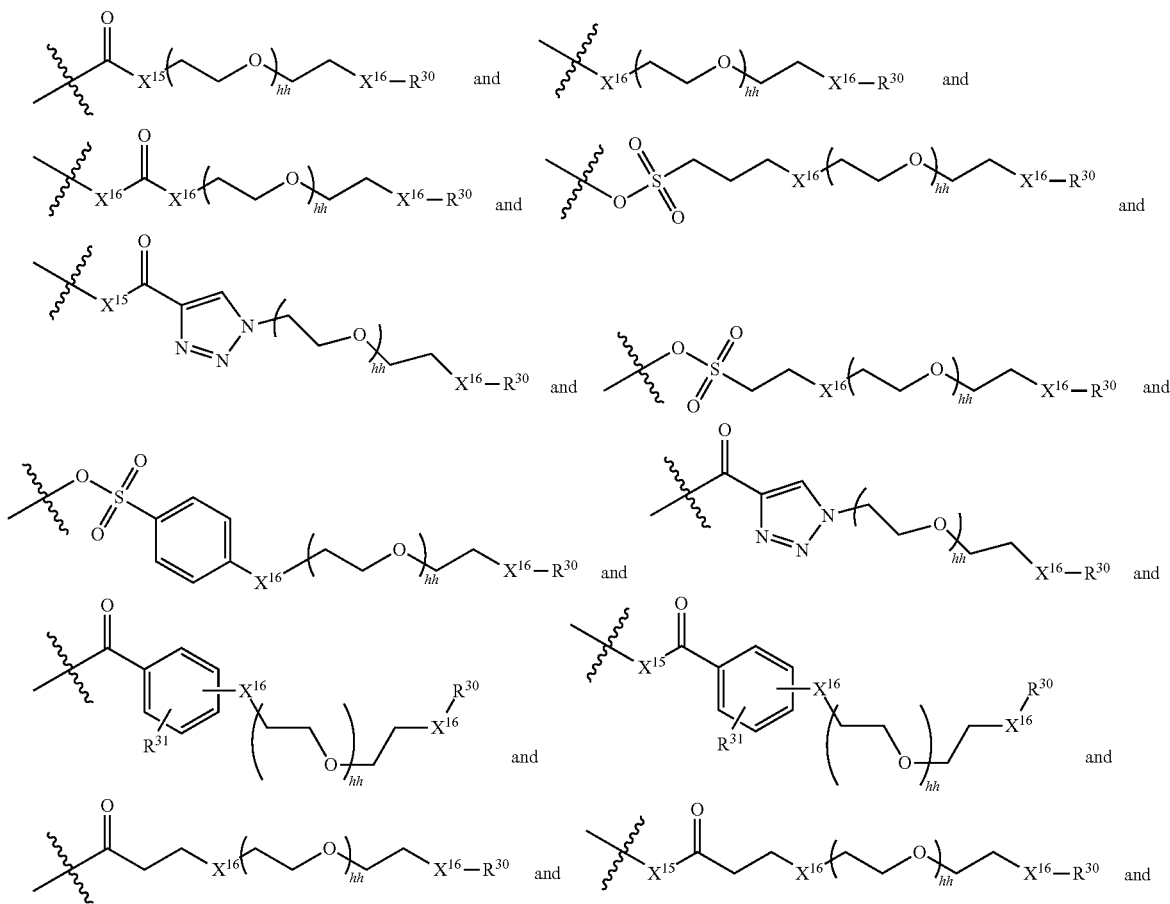

-continued

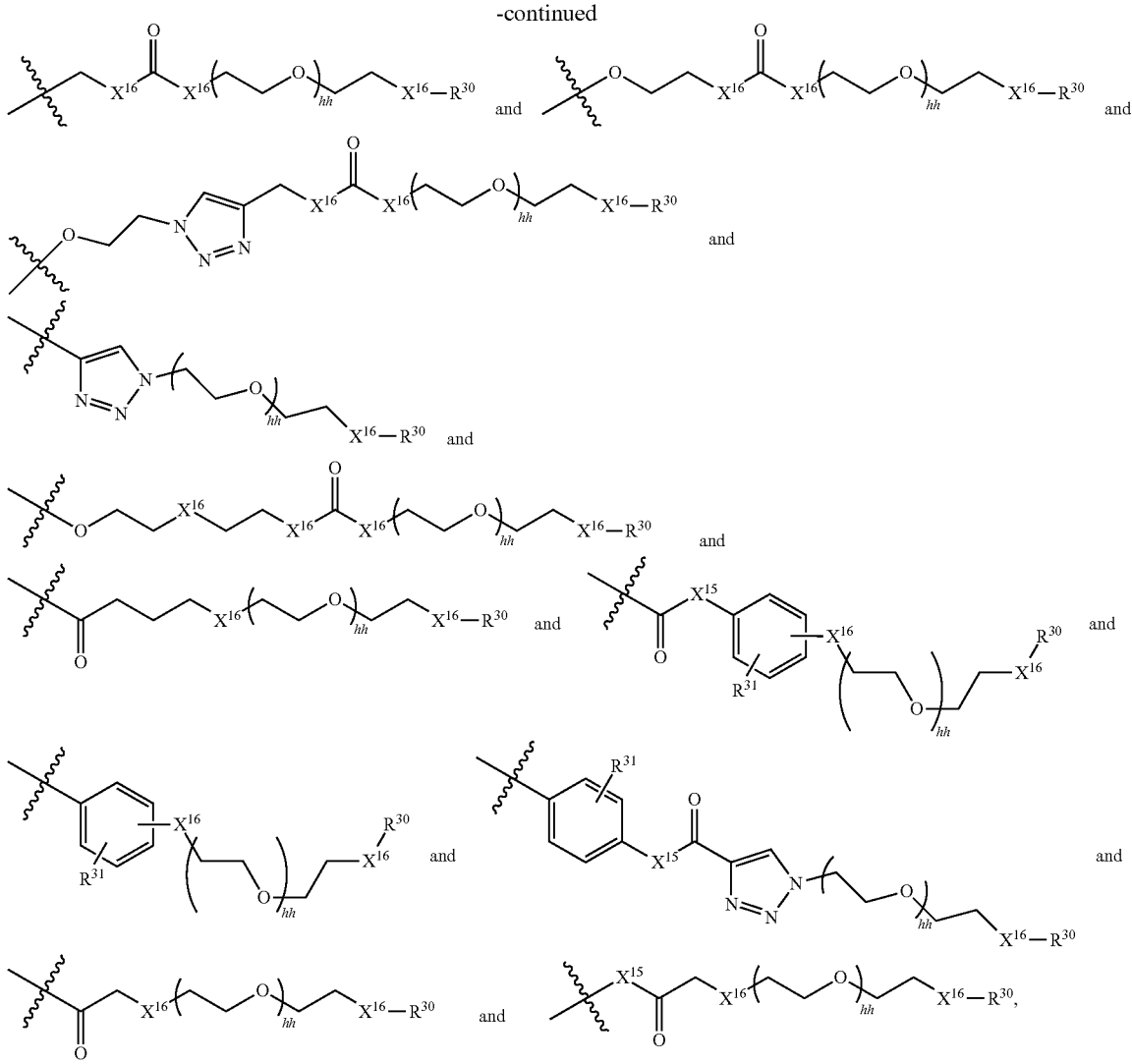

wherein hh is selected from 1 to 1000, $X^{15}$ is selected from S and $NR^{32}$, each $X^{16}$ is independently selected from O, S, and $NR^{34}$, $R^{30}$ is independently selected from H and optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, or $C_{1-10}$ heteroaryl, $R^{32}$, $R^{33}$, and $R^{34}$ are independently selected from H and $C_{1-3}$ alkyl, and $R^{31}$ has the same meaning as defined for $R^7$. $R^{30}$ may for example be selected from H, methyl, ethyl, methoxymethyl, p-aminobenzoyl, and p-aminoanilinocarbonyl.

In a further embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ is selected from

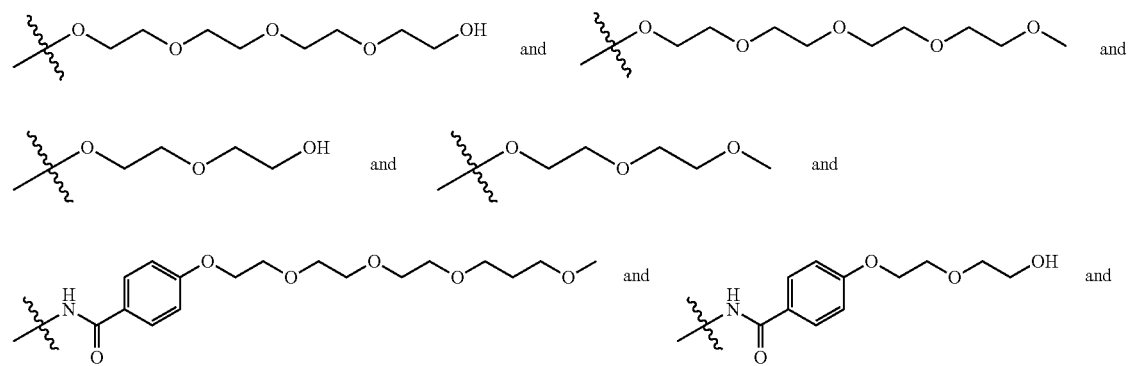

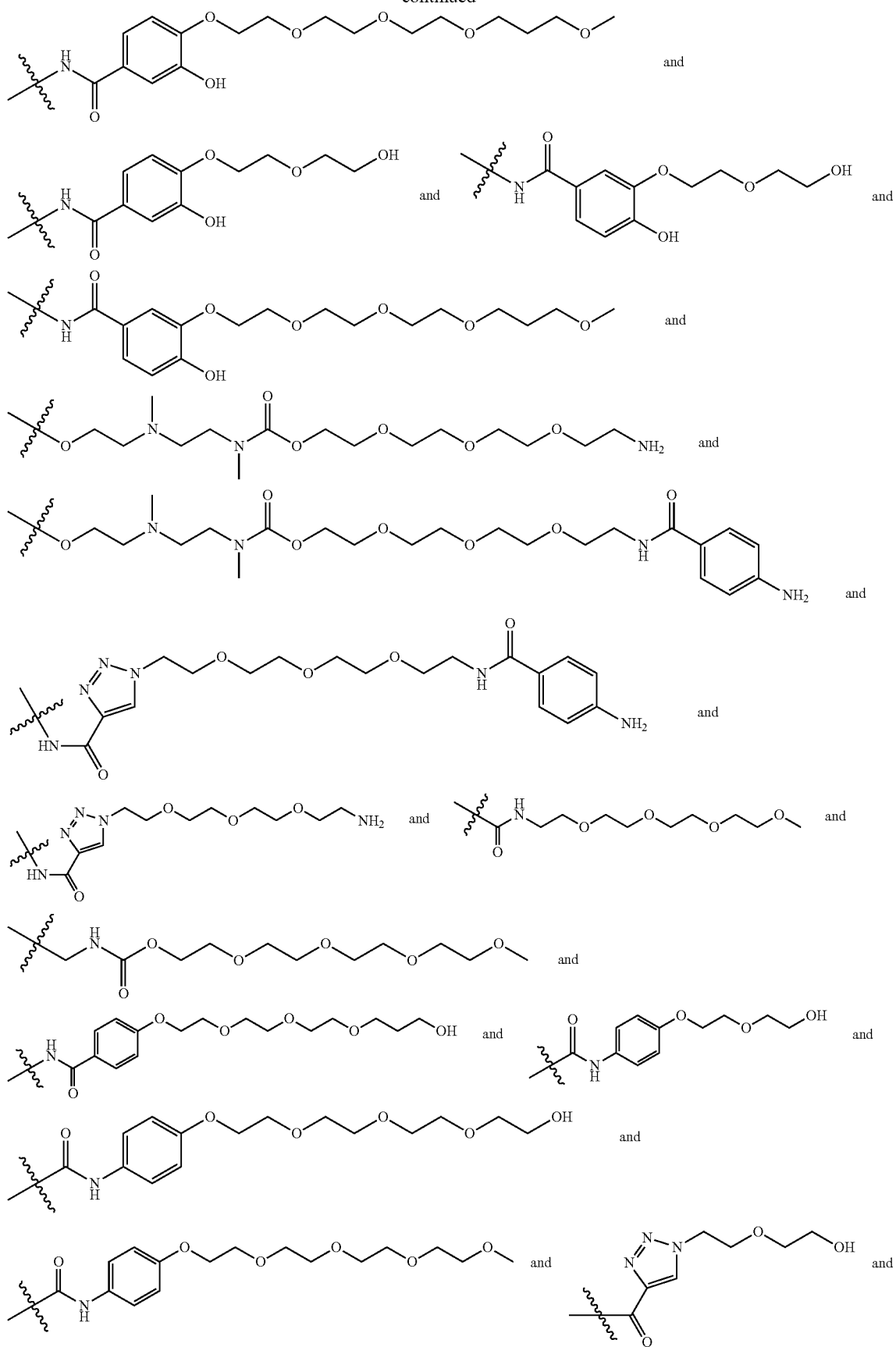

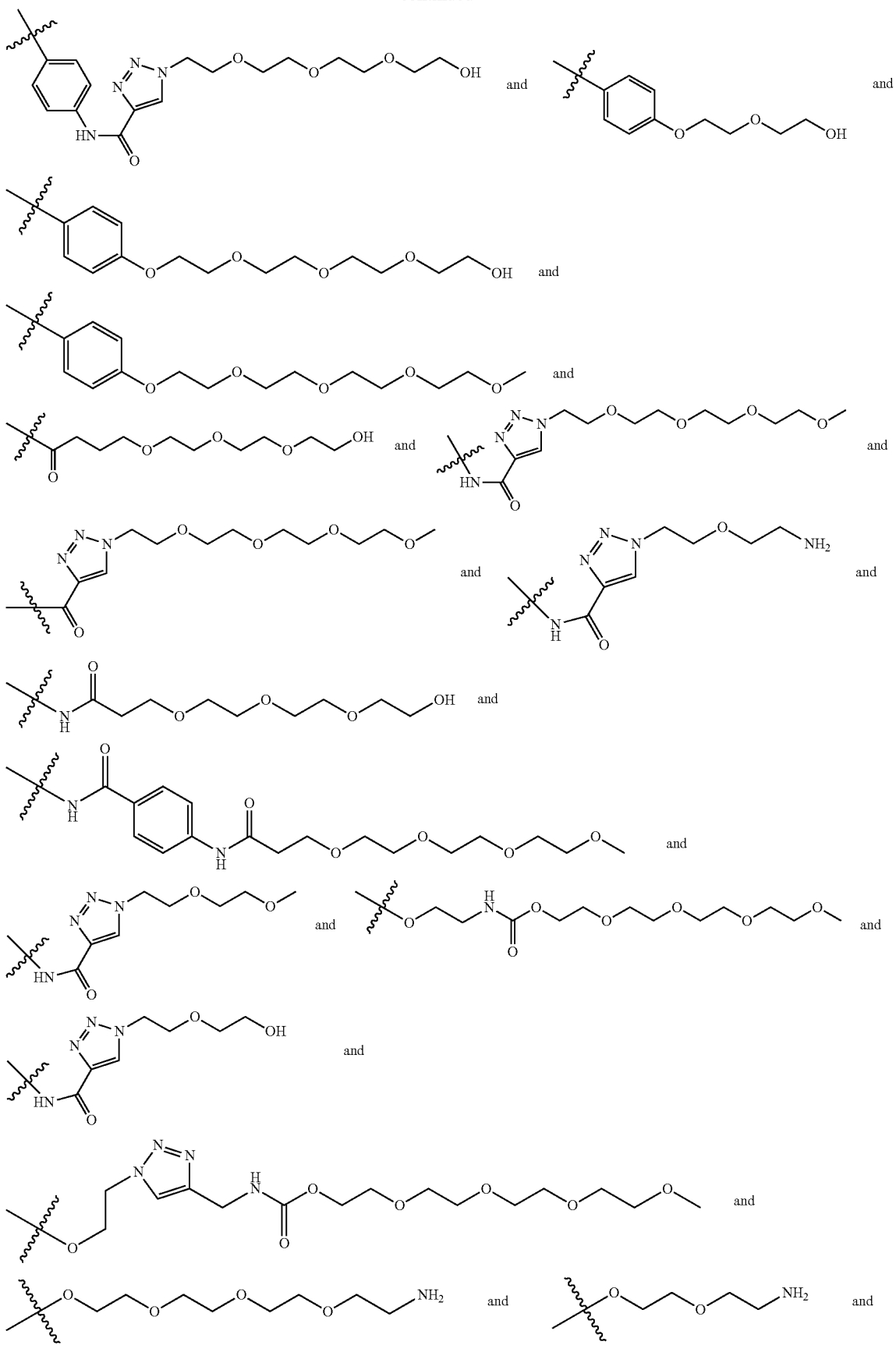

In another embodiment, $R^1$ is selected from

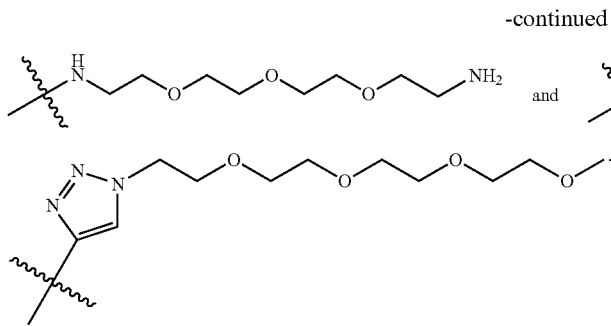

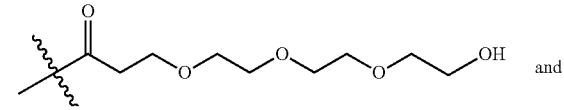

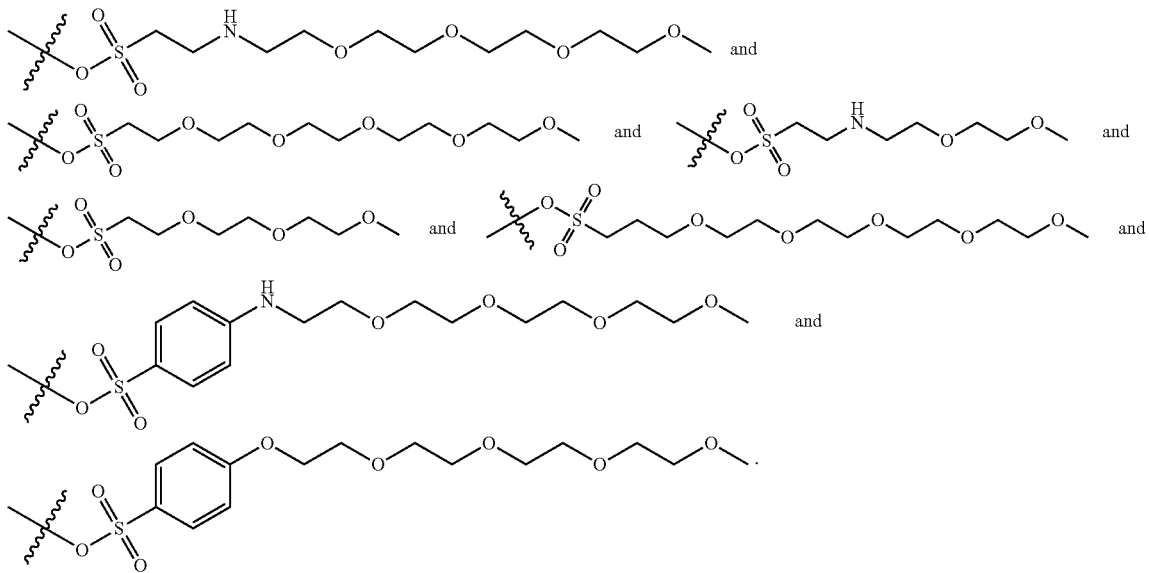

In one embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a $X^{14}(CH_2CH_2O)_{\!f\!f}CH_2CH_2X^{14}$ moiety. In another embodiment, at least one of $R^5$, $R^6$, $R^7$, and $R^{14}$ contains a $X^{14}(CH_2CH_2O)_{\!f\!f}CH_2CH_2X^{14}$ moiety. In yet another embodiment, at least one of $R^6$ and $R^7$ contains a $X^{14}(CH_2CH_2O)_{\!f\!f}CH_2CH_2X^{14}$ moiety. In yet another embodiment, at least one of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a $X^{14}(CH_2CH_2O)_{\!f\!f}CH_2CH_2X^{14}$ moiety. In yet another embodiment, at least one of $R^8$, $R^9$, $R^{10}$, $R^{11}$, $R^{20}$, $R^{21}$, and $R^{22}$ contains a $X^{14}(CH_2CH_2O)_{\!f\!f}CH_2CH_2X^{14}$ moiety. In yet another embodiment, at least one of $R^8$ and $R^9$ contains a $X^{14}(CH_2CH_2O)_{\!f\!f}CH_2CH_2X^{14}$ moiety. In yet another embodiment, at least $R^1$ contains a $X^{14}(CH_2CH_2O)_{\!f\!f}CH_2CH_2X^{14}$ moiety.

A compound of formula (I) or (II) may also contain 2 or more $X^{14}(CH_2CH_2O)_{\!f\!f}CH_2CH_2X^{14}$ moieties. In one embodiment, a compound of formula (I) or (II) contains 2 $X^{14}(CH_2CH_2O)_{\!f\!f}CH_2CH_2X^{14}$ moieties. In another embodiment, a compound of formula (I) or (II) contains 2 $X^{14}(CH_2CH_2O)_{\!f\!f}CH_2CH_2X^{14}$ moieties that are part of 2 separate R groups.

It may be beneficial to put the two or more $X^{14}(CH_2CH_2O)_{\!f\!f}CH_2CH_2X^{14}$ moieties at distant positions in the compound of formula (I) or (II) as this may shield the relatively hydrophobic core more efficiently.

Compounds of formulae (I) and (II) may contain one or more oligoethylene glycol or polyethylene glycol moieties or derivatives thereof. Such a moiety may improve the water solubility and aggregation behavior of a compound of formula (I) or (II) and may cause increased activity against multidrug-resistant targets. If a compound of formula (I) or (II) with such a moiety is incorporated in a conjugate, it may be that the oligoethylene glycol or polyethylene glycol moiety is located in between the promoiety and the remainder of the compound of formula (I) or (II) or that it is located at a position somewhat opposite to the attachment site of the promoiety, thus placing the remainder of the compound of formula (I) or (II) in between the promoiety and the oligoethylene glycol or polyethylene glycol moiety. The latter may be more beneficial for the water solubility of the conjugates. Improved water solubility of compounds of formulae (I) and (II) and their conjugates may lead to improved yields and purity of the conjugates during synthesis, for example due to reduced aggregate formation. Furthermore, a reduced tendency for aggregation and a higher purity of the conjugate may for example lead to fewer side effects after administration of the conjugate. In addition, the presence of one or more oligoethylene glycol and/or polyethylene glycol moieties in a conjugate may reduce excretion of the conjugate via the kidneys or liver, which increases the circulation time in the body.

In another aspect of this invention, compounds of formula (I) and (II) may contain one or more triazole rings. Incorporation of a 1,2,3-triazole ring may provide for a synthetic advantage as the two moieties that eventually may become attached to the 1,2,3-triazole ring may be attached to each other via said triazole ring using a mild and efficient cycloaddition reaction between an alkyne and azide moiety. Because the conditions for this cycloaddition reaction are very mild and are compatible with almost all functional groups, the reaction can be performed in one of the last steps of the synthetic route towards a compound of formula (I) or (II), its linker-agent conjugate, or conjugate, thus allowing for easy generation of series of compounds of formula (I) and (II) and their conjugates for SAR (structure-activity relationship) studies.

Preferably, the triazole moiety is located in such a way within the DNA-alkylating unit or DNA-binding unit that it can contribute to the binding of the compound to DNA. Additional DNA-binding moieties, such as indole or benzofuran moieties, that are connected to the DNA-binding or DNA-alkylating unit may increase the potency of the compound, allegedly through enhanced DNA binding. These additional aromatic moieties may however have a detrimental effect on pharmacological properties, such as water solubility. A triazole, being an aromatic group, may also enhance binding to DNA and thus increase cytotoxic potency of the compound, but as it is more polar than other aromatic moieties such as a phenyl ring, negative effects on pharmacological properties may be less pronounced.

In one embodiment, this invention relates to a compound of formula (I) or (II) wherein at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a triazole moiety.

In another embodiment, at least one of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a triazole moiety. In another embodiment, at least one of $R^8$, $R^9$, and $R^{10}$ contains a triazole moiety. In another embodiment, at least one of $R^8$ and $R^9$ contains a triazole moiety. In yet another embodiment, at least $R^8$ contains a triazole moiety.

In another embodiment, at least one of $R^5$, $R^{5'}$, $R^6$, $R^{6'}$, $R^7$, $R^{7'}$, $R^{14}$, and $R^{14'}$ contains a triazole moiety. In another embodiment, at least one of $R^6$, $R^{6'}$, $R^7$, and $R^{7'}$ contains a triazole moiety. In yet another embodiment, $R^1$ contains a triazole moiety.

For an optimum DNA-binding effect, the triazole moiety may be connected via a linker that keeps the triazole moiety in conjugation with or in close proximity to the core of the DNA-binding or DNA-alkylating unit. The linker may for example be a single bond, —N(R$^{35}$)C(O)—, —C(O)N(R$^{35}$)—, —C(O)—, —C(R$^{35}$)(R$^{36}$)—, —C(R$^{35}$)=C(R$^{36}$)—, —O—, —S—, or —N(R$^{35}$)—, wherein R$^{35}$ and R$^{36}$ are selected from H and optionally substituted $C_{1-4}$ alkyl or $C_{1-4}$ heteroalkyl, or be any other optionally substituted small linker that does not have more than 4 connecting atoms (e.g., the —N(R$^{20}$)C(O)— moiety has two connecting atoms: N and C) in between the DNA-binding unit or DNA-alkylating unit and the triazole ring.

The triazole ring may be a 1,2,3-triazole or a 1,2,4-triazole. In one embodiment, the triazole ring is a 1,2,3-triazole. In another embodiment, the triazole is a 1,2,4-triazole. A 1,2,3-triazole ring may be 4,5-, 1,5-, or 1,4-disubstituted. If the 1,2,3-triazole ring is 1,4-substituted, this means that the substituent that contains the 1,2,3-triazole ring has an extended form. If the 1,2,3-triazole ring is 4,5- or 1,5-substituted, the 1,2,3-triazole ring in fact forms a kind of turn and puts the two substituents on the triazole in close proximity to each other. The triazole ring may also be located at the end of the substituent, in which case the triazole ring is only monosubstituted. Substitution may in this case occur at N-1 or C-4. A 1,2,4-triazole may be 1,3-, 1,5-, or 3,5-disubstituted. A substituent that contains a 1,3- or 3,5-disubstituted 1,2,4-triazole has an extended form, whereas in a 1,5-disubstituted 1,2,4-triazole both substituents on the triazole are in close proximity to each other. The triazole ring may also be trisubstituted.

In one aspect, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ in a compound of formula (I) or (II) is

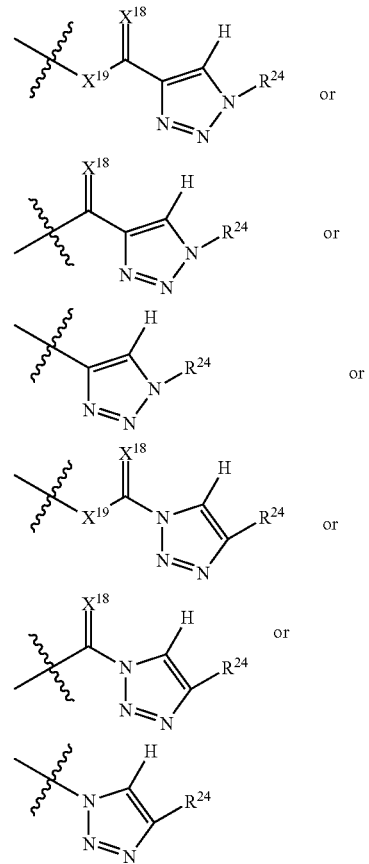

wherein $X^{18}$ and $X^{19}$ are selected from O, S, NR$^{25}$, H$_2$, and C(R$^{25}$)R$^{26}$, wherein R$^{25}$ and R$^{26}$ are selected from H and optionally substituted $C_{1-3}$ alkyl or $C_{1-3}$ heteroalkyl, and R$^{24}$ has the same meaning as $R^8$ and is independently selected.

$R^{24}$ may for example be selected from H and

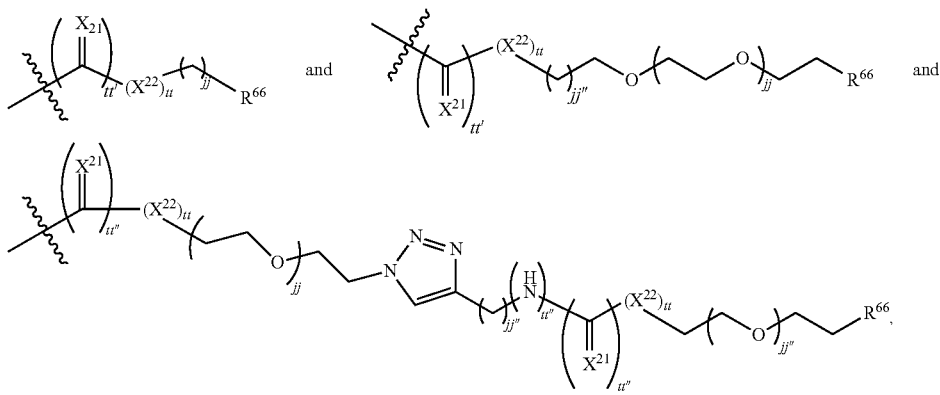

wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

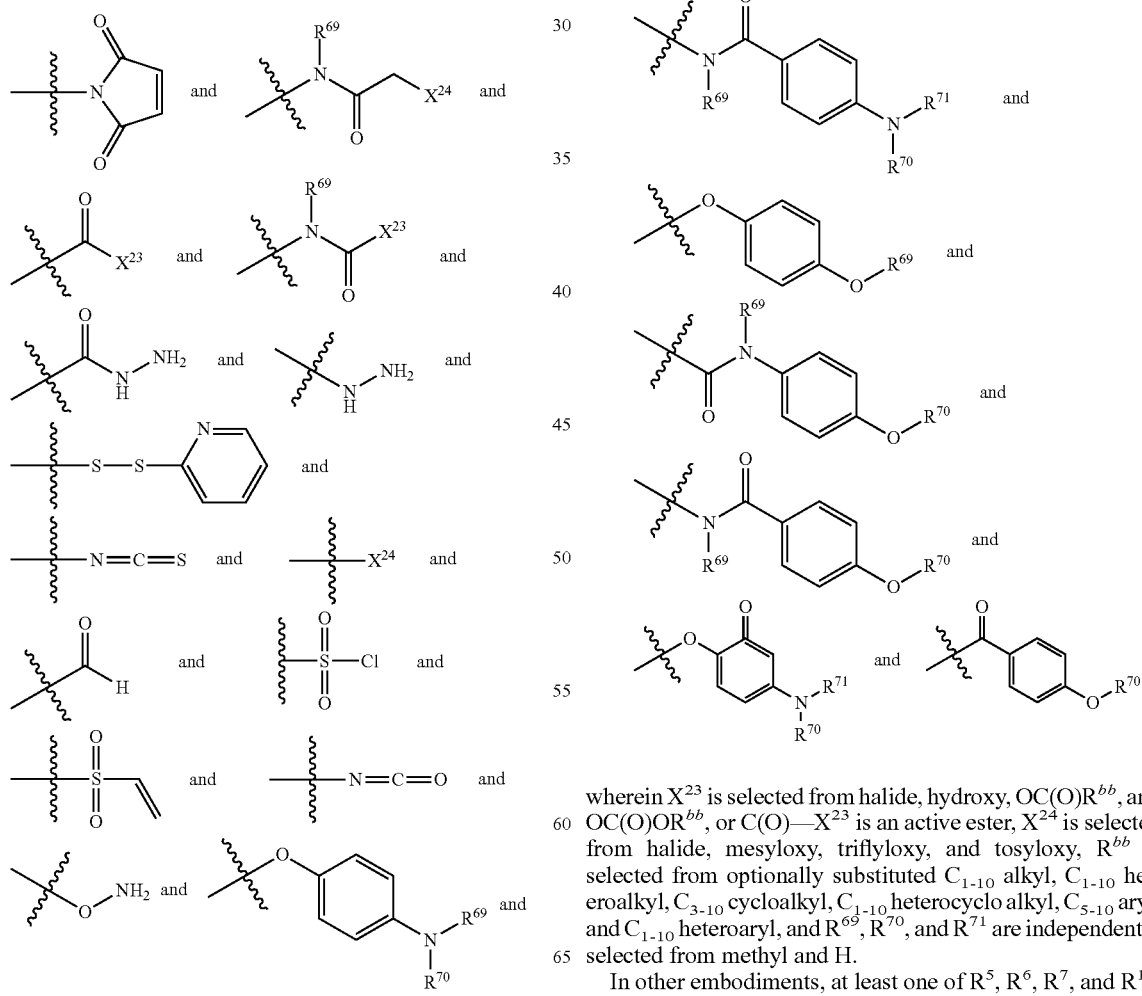

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In other embodiments, at least one of $R^5$, $R^6$, $R^7$, and $R^{14}$, or at least one of $R^8$, $R^9$, $R^{10}$ and $R^{11}$, or at least one of $R^6$ and $R^7$, or at least one of $R^8$ and $R^9$, or at least $R^8$, or at least $R^6$, or at least $R^7$ in a compound of formula (I) or (II) is

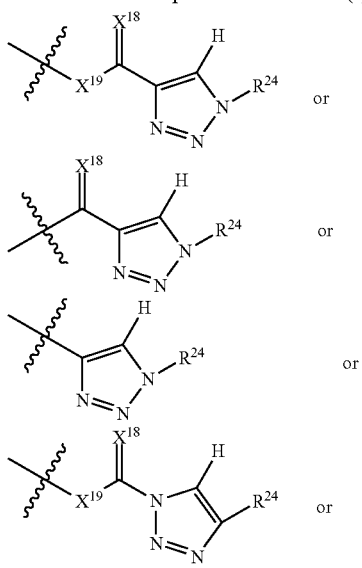

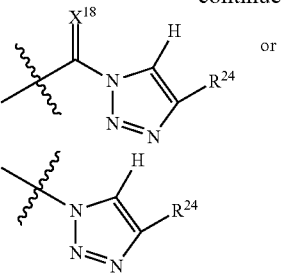

wherein $R^{24}$, $X^{18}$, and $X^{19}$ are as defined hereinabove.

In some embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, or at least one of $R^8$, $R^9$, $R^{10}$, and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

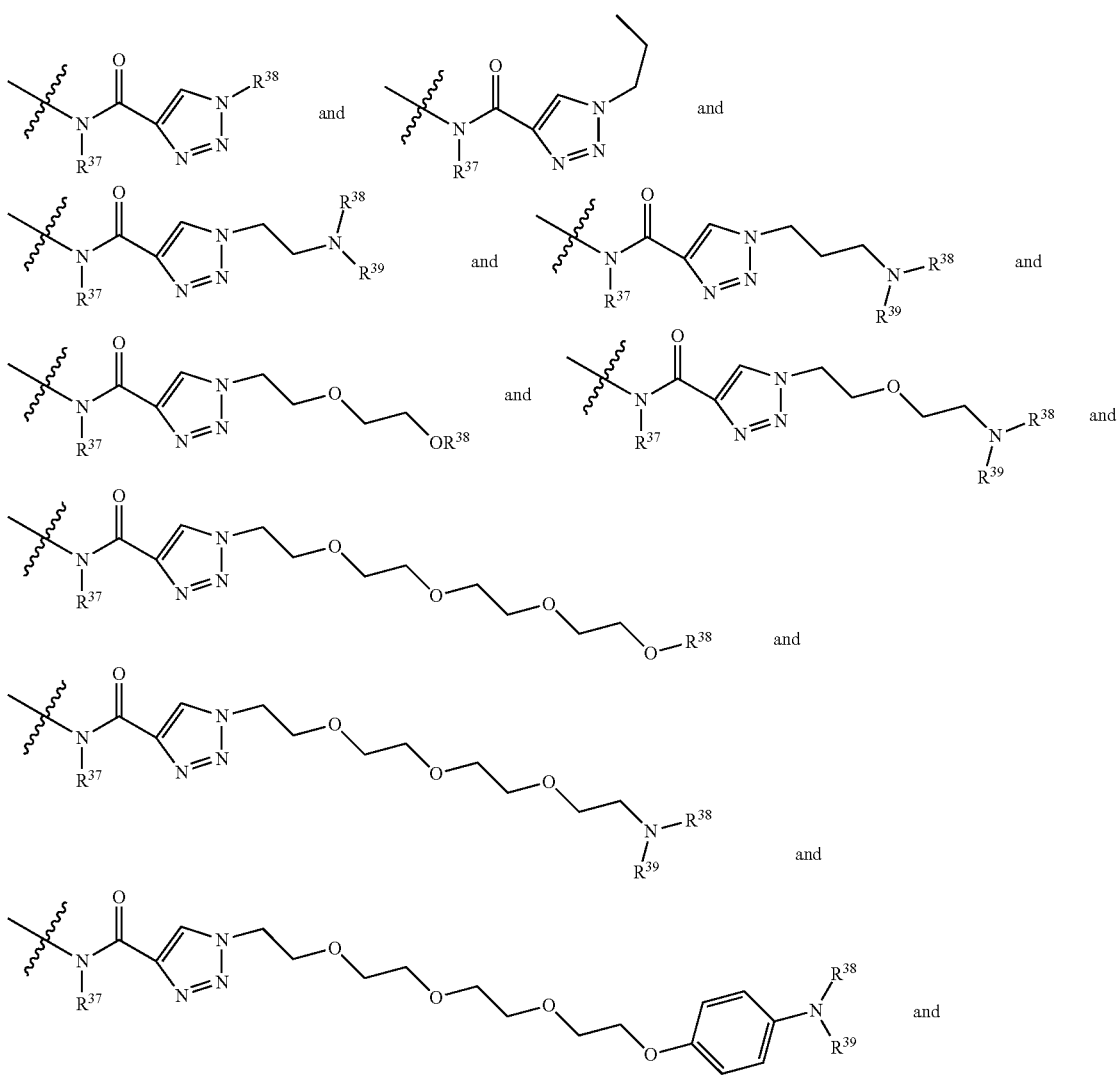

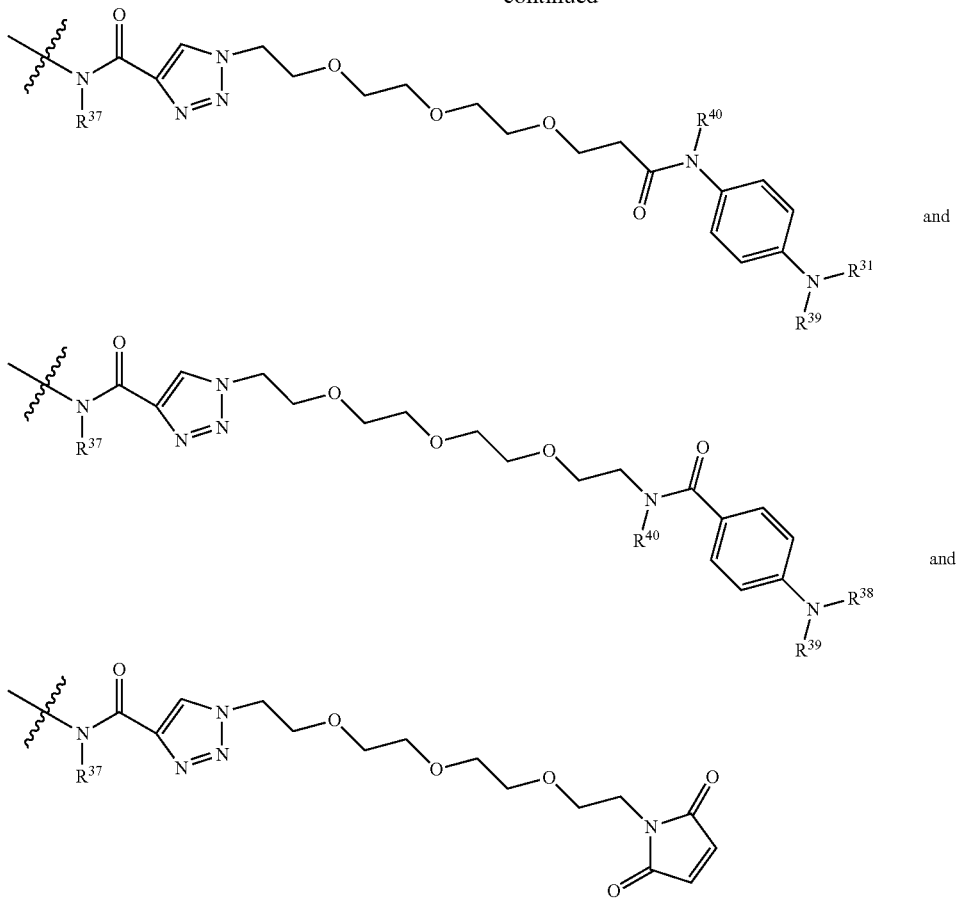

wherein $R^{37}$, $R^{38}$, $R^{39}$, and $R^{40}$ are independently selected from H and methyl.

In other embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, or at least one of $R^8$, $R^9$, $R^{10}$, and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

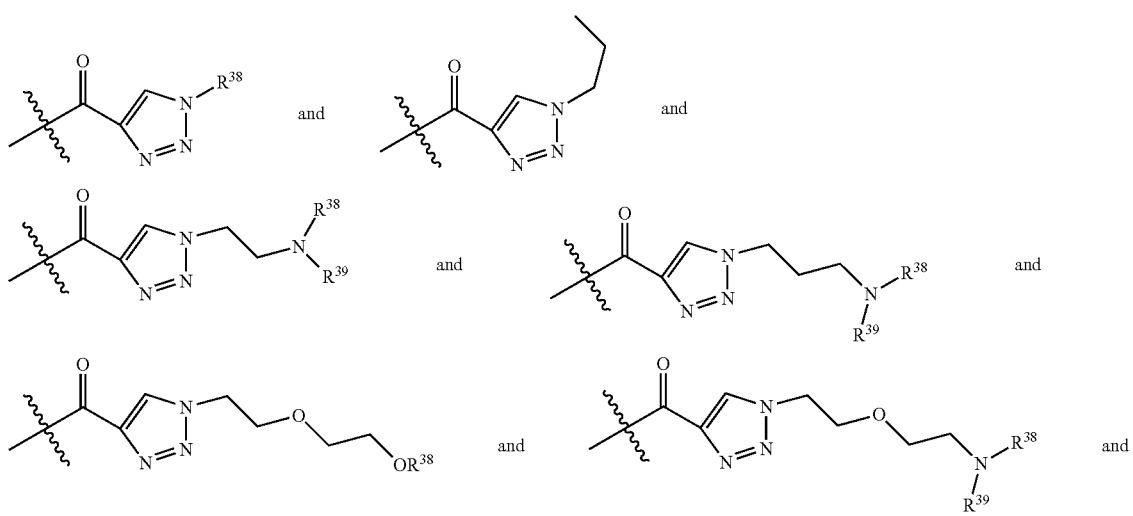

-continued
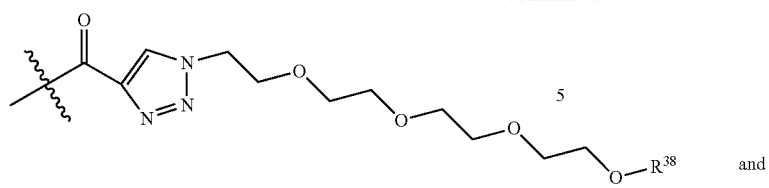 and
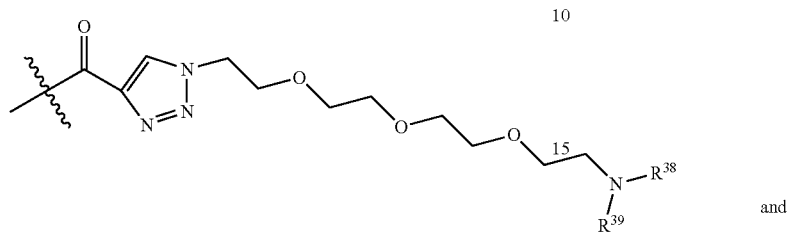 and
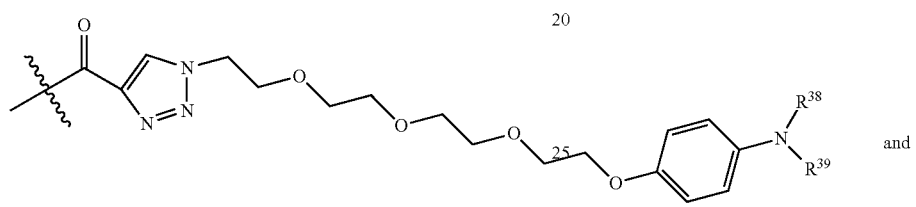 and
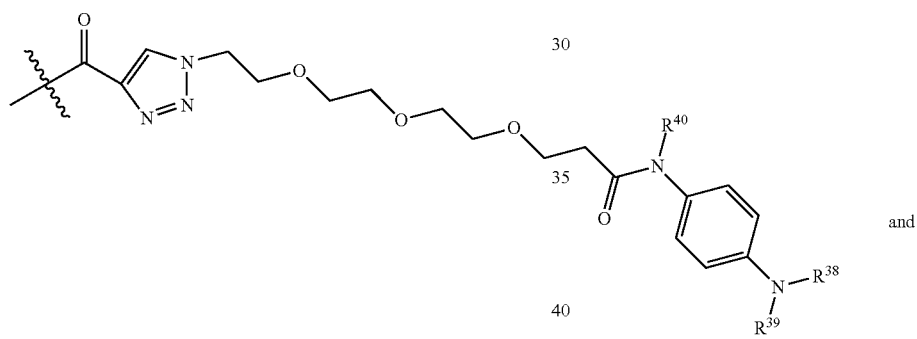 and
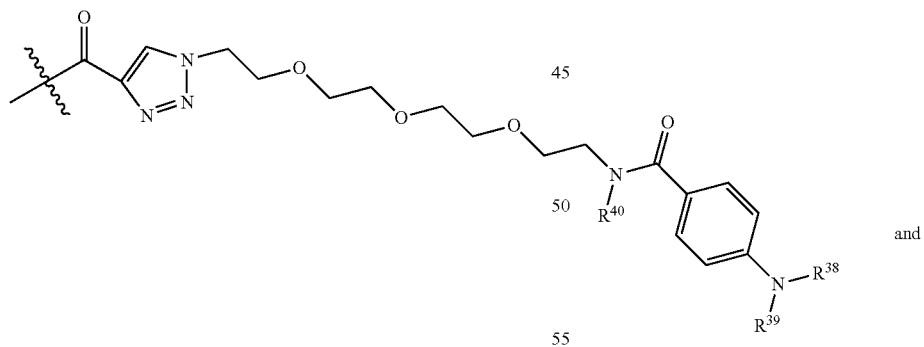 and
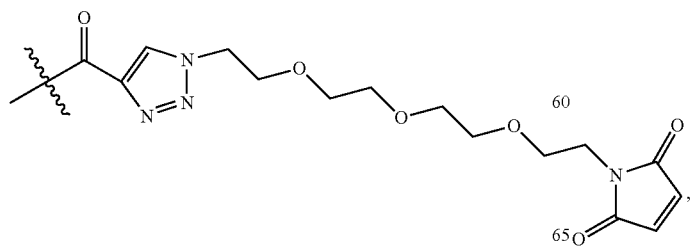, wherein $R^{38}$, $R^{39}$, and $R^{40}$ are independently selected from H and methyl.

In other embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, or at least one of $R^8$, $R^9$, $R^{10}$, and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

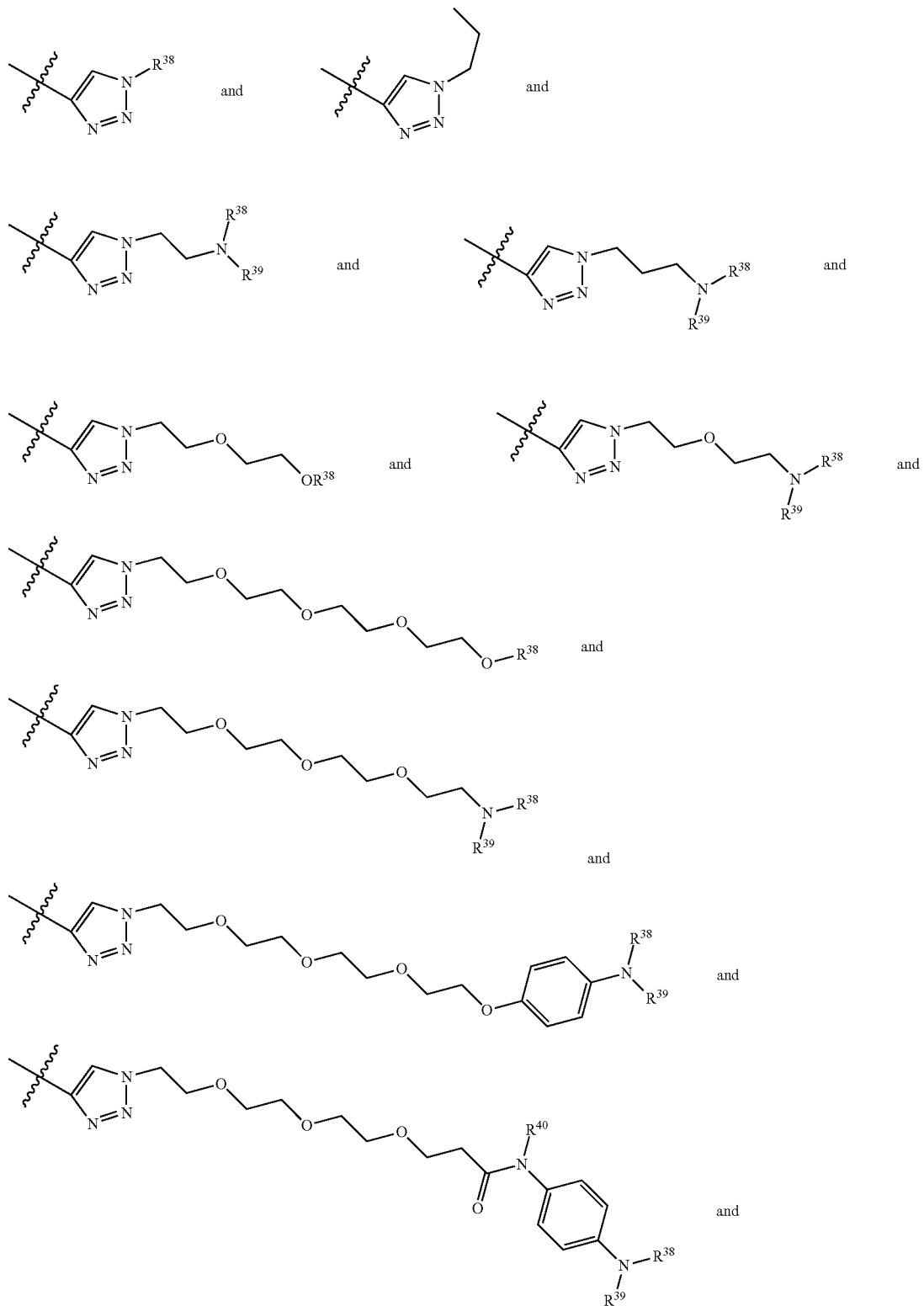

-continued

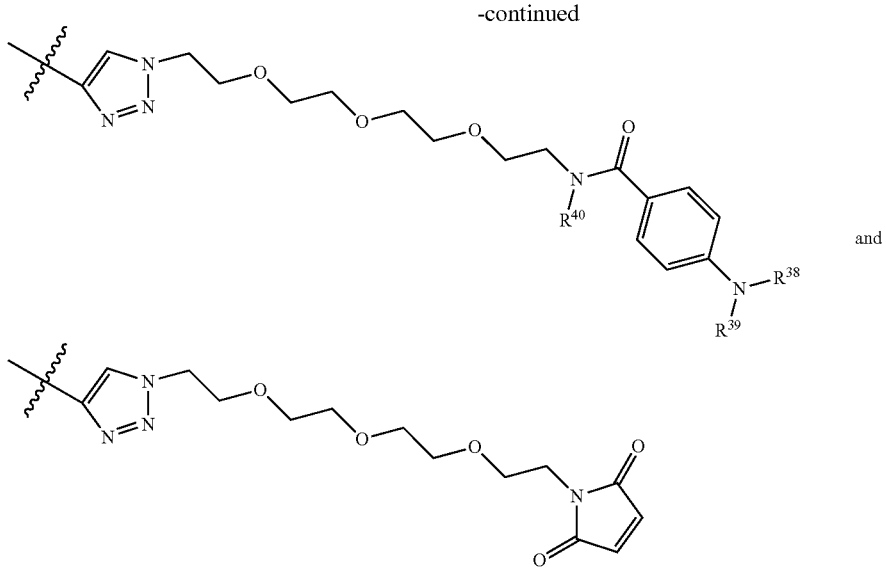

and wherein $R^{38}$, $R^{39}$, and $R^{40}$ are independently selected from H and methyl.

In other embodiments, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$, or at least one of $R^8$, $R^9$, $R^{10}$, and $R^{11}$, or at least one of $R^8$ and $R^9$, or at least $R^8$, or at least one of $R^5$, $R^6$, $R^7$, and $R^{14}$, or at least one of $R^6$ and $R^7$ in a compound of formula (I) or (II) is selected from

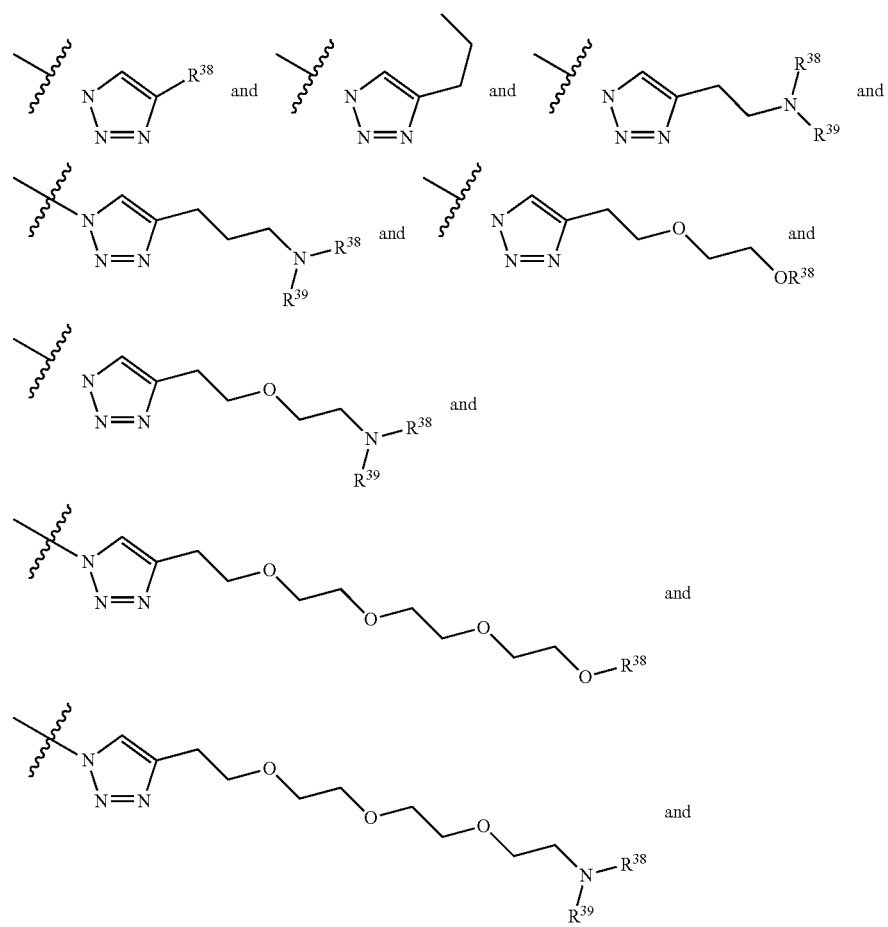

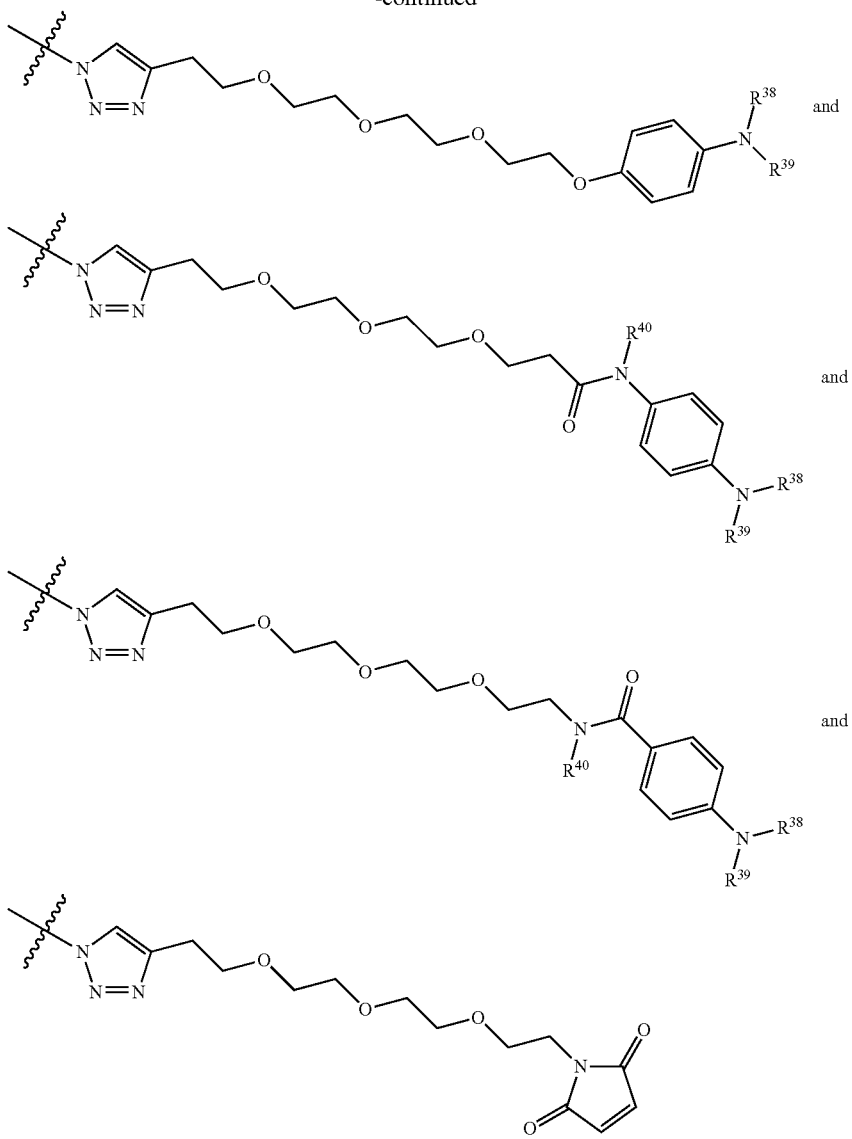

wherein R³⁸, R³⁹, and R⁴⁰ are independently selected from H and methyl.

In one aspect, compounds of formulae (I) and (II) are represented by compounds of formulae (Ib) and (IIb), respectively:

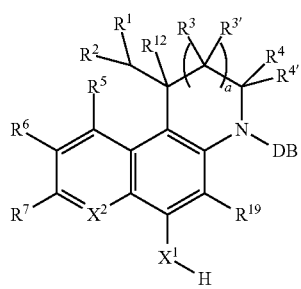
(Ib)

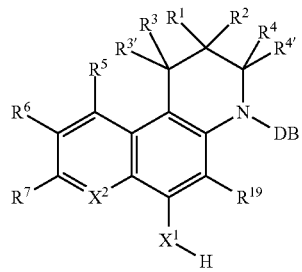
(IIb)

In one embodiment, $X^2$ in (Ib) or (IIb) is N.
In a preferred embodiment, $X^2$ in (Ib) or (IIb) is $CR^{14}$.
In a further embodiment, $X^2$ in (Ib) is $CR^{14}$ and a is 0.
In another embodiment, $X^2$ in (Ib) or (IIb) is CH.
In yet another embodiment, $R^5$ in (Ib) or (IIb) is selected from nitro, halogen, amino, cyano, hydroxy, and optionally substituted $C_{1-3}$ alkylamino, di($C_{1-3}$ alkyl)amino, $C_{1-3}$ alkylcarbonylamino, $C_{1-3}$ alkoxycarbonylamino, $C_{1-3}$ alkylaminocarbonylamino, $C_{1-3}$ alkyloxy, $C_{1-3}$ alkylcarbonyloxy, $C_{1-3}$ alkylaminocarbonyloxy, or $C_{1-3}$ alkyl. In yet another embodiment, $R^5$ in (Ib) or (IIb) is optionally substituted linear $C_{1-3}$ alkyl. In another embodiment, $R^5$ in (Ib) or (IIb) is unsubstituted linear $C_{1-3}$ alkyl. In another embodiment, $R^5$ in (Ib) or (IIb) is methyl. In other embodiments, $R^5$ in (Ib) or (IIb) is ethyl or methoxy or ethoxy.

In yet another aspect, compounds of formulae (I) and (II) are represented by compounds of formulae (Ic) and (IIc), respectively:

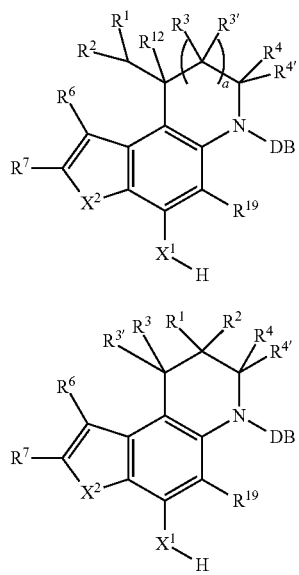

(Ic)

(IIc)

In one embodiment, $X^2$ in (Ic) or (IIc) is NH.

In yet another aspect, compounds of formulae (I) and (II) are represented by compounds of formulae (Id) and (IId), respectively:

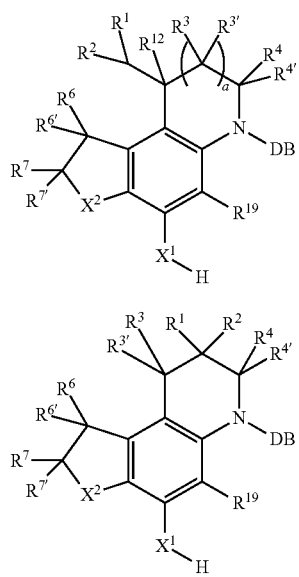

(Id)

(IId)

In one embodiment, $X^2$ in (Id) or (IId) is NH.

In another embodiment, compounds of formulae (I) and (II) are represented by (Ia) and (IIa), respectively:

DA1-DB                                       (Ia)

DA2-DB                                        (IIa)

wherein DA1 is

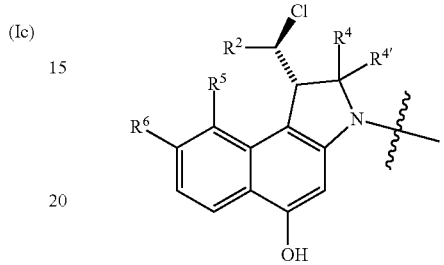

or an isomer or a mixture of isomers thereof.

In other embodiments, compounds of formulae (I) and (II) are represented by (Ia) and (IIa), respectively:

DA1-DB                                       (Ia)

DA2-DB                                        (IIa)

wherein DA1 is

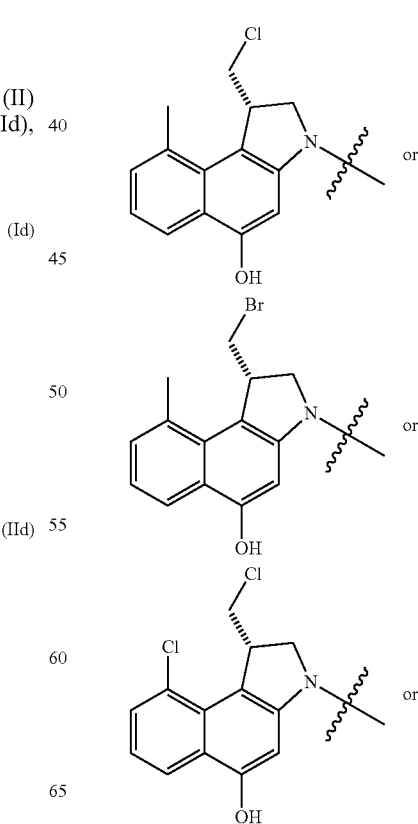

63
-continued
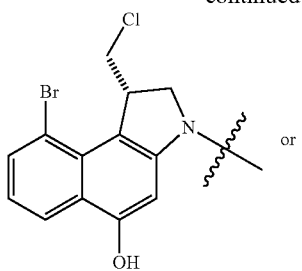
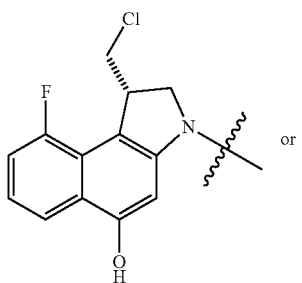
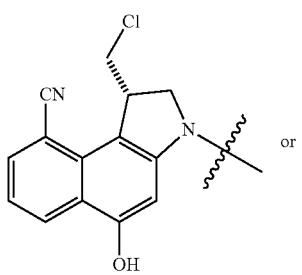
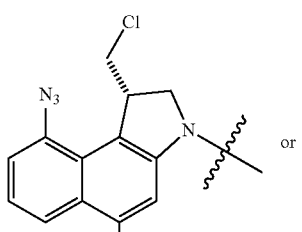
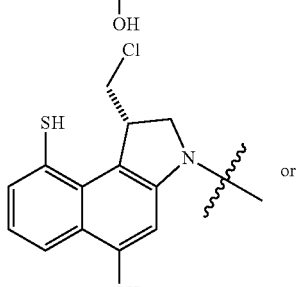
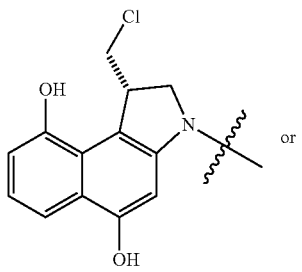
64
-continued
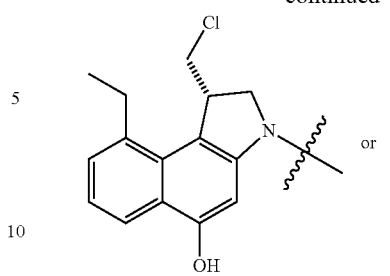
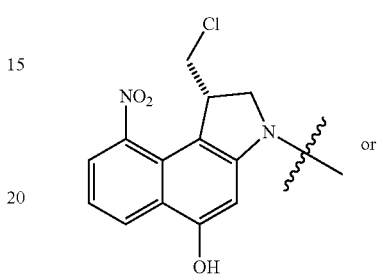
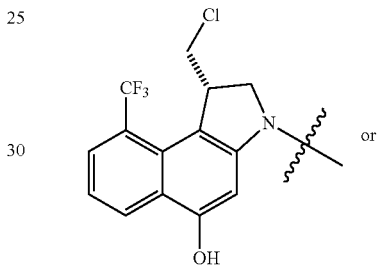
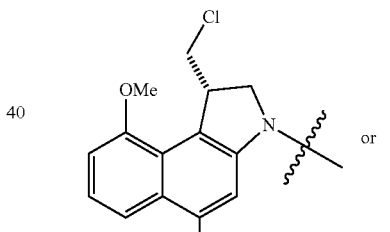
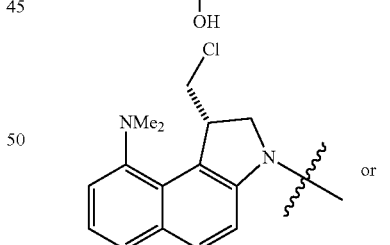
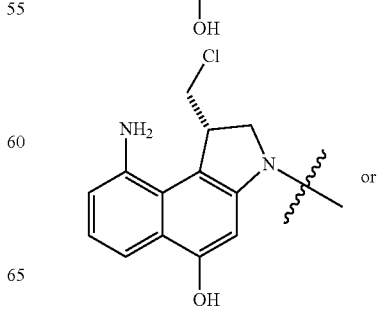

65
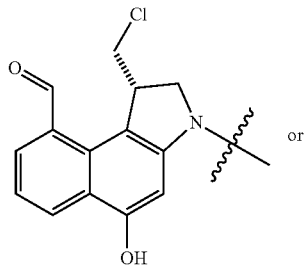
or
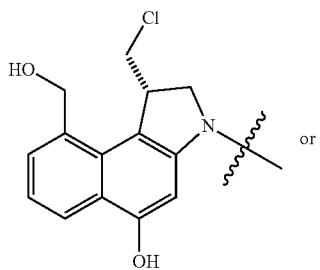
or
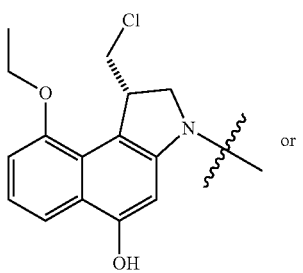
or
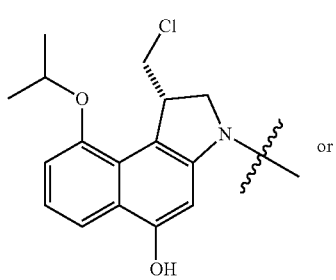
or
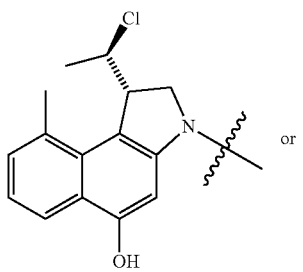
or
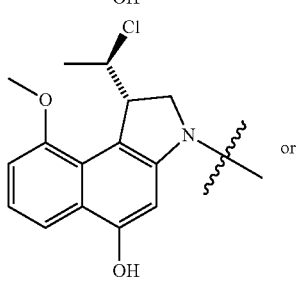
or
66
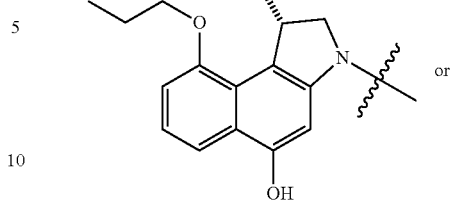
or
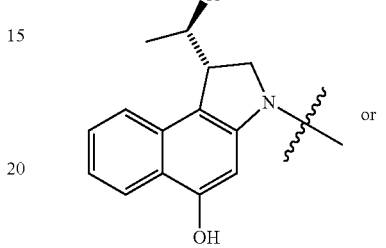
or
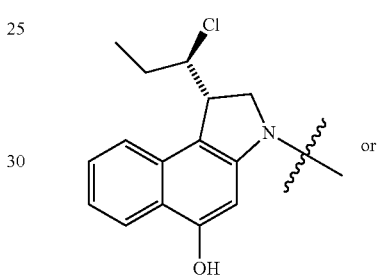
or
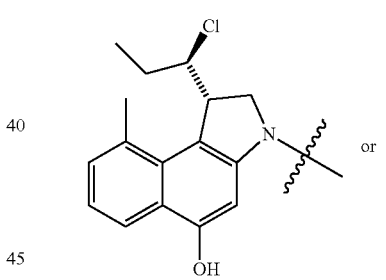
or
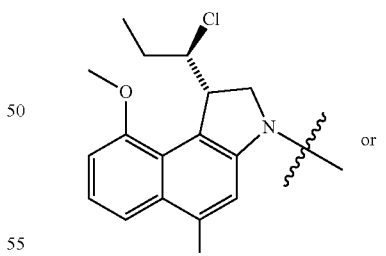
or
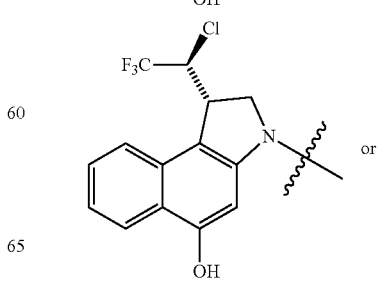
or 67
-continued
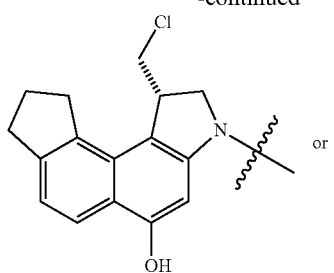
or
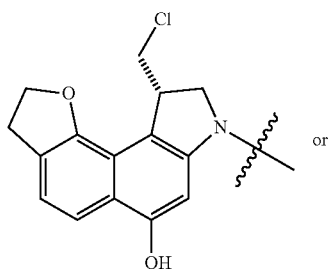
or
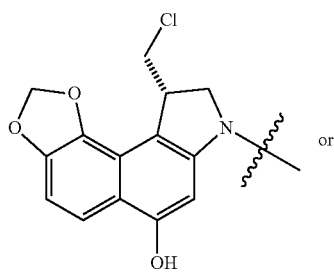
or
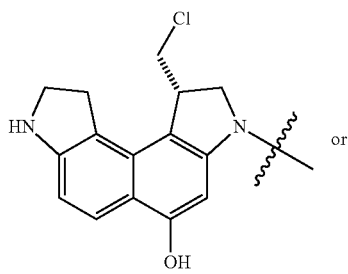
or
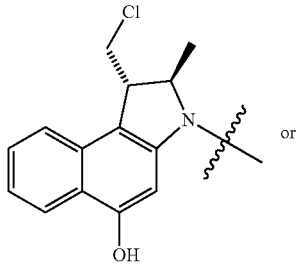
or
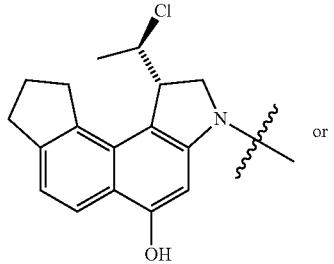
or
68
-continued
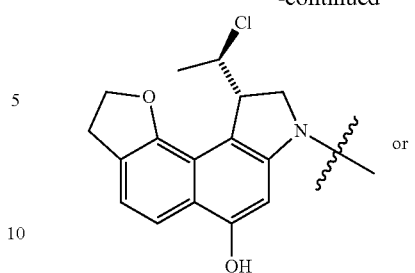
or
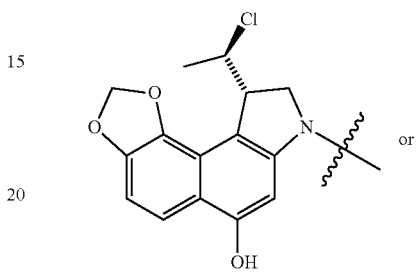
or
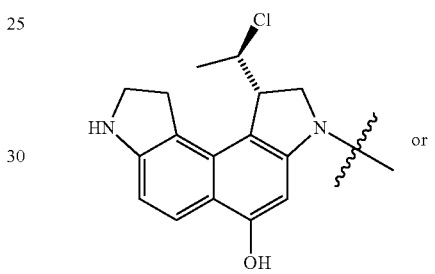
or
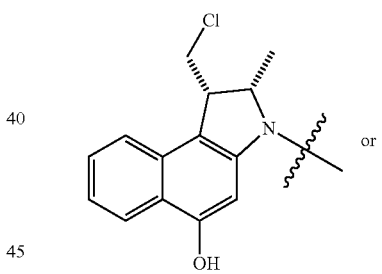
or
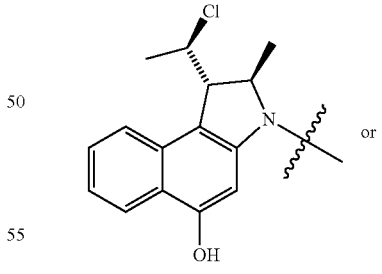
or
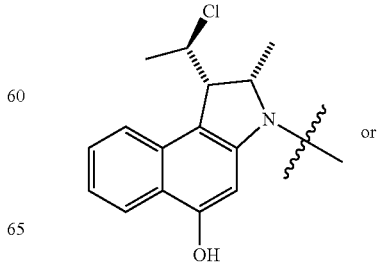
or

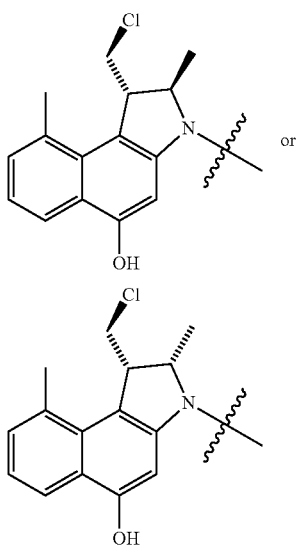
or an isomer of one of these, or a mixture of isomers.
In other embodiments, compounds of formulae (I) and (II) are represented by (Ia) and (IIa), respectively:
DA1-DB     (Ia)
DA2-DB     (IIa)
wherein DA1 is
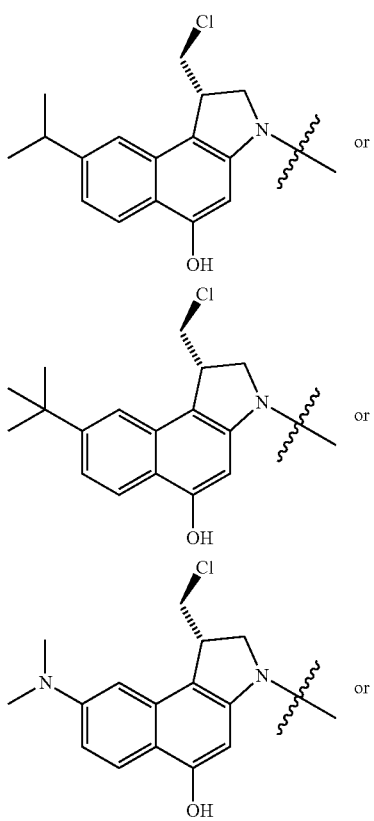
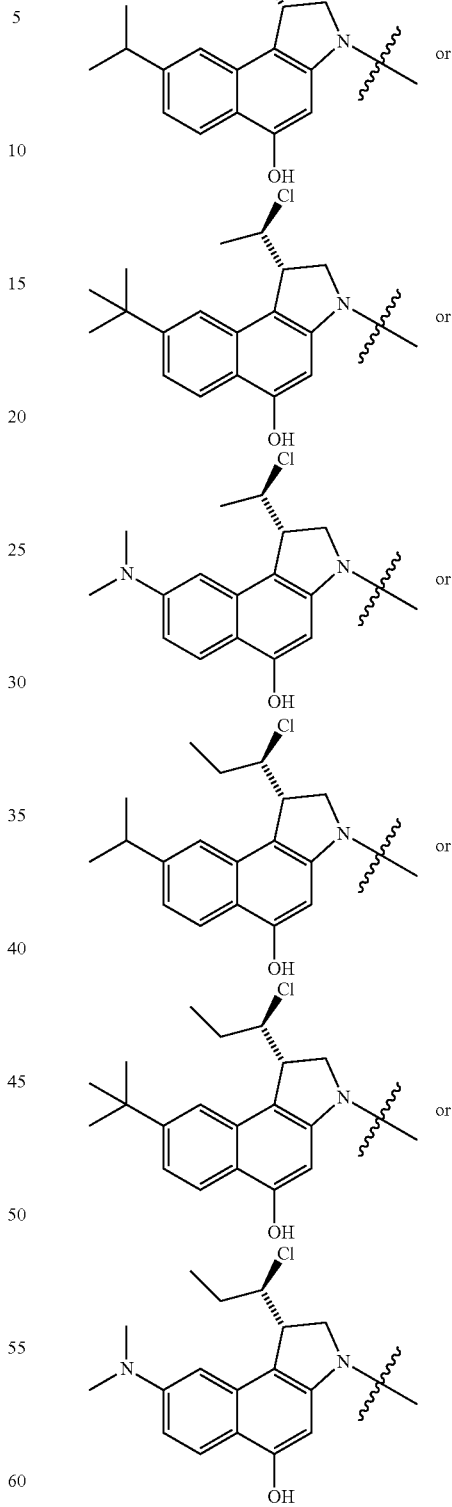
or an isomer of one of these, or a mixture of isomers.
In yet other embodiments, compounds of formulae (I) and (II) are represented by (Ia) and (IIa), respectively:
DA1-DB     (Ia)
DA2-DB     (IIa)

wherein DA1 is
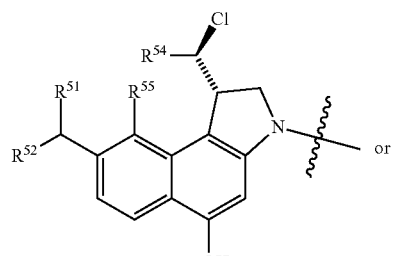
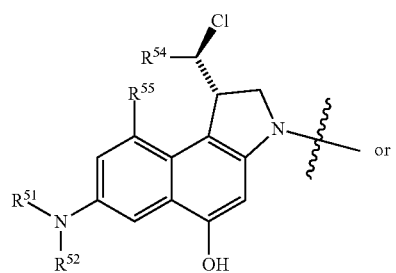
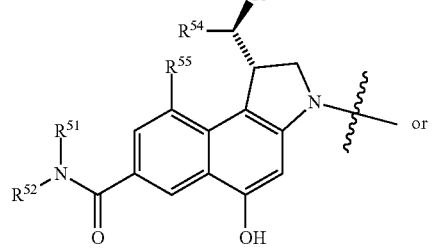
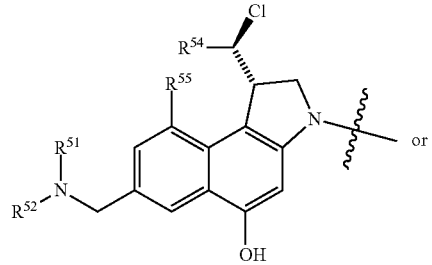
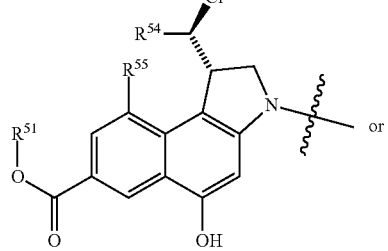
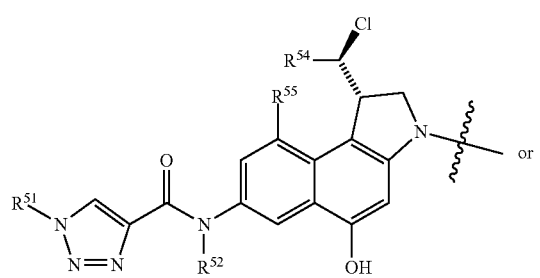
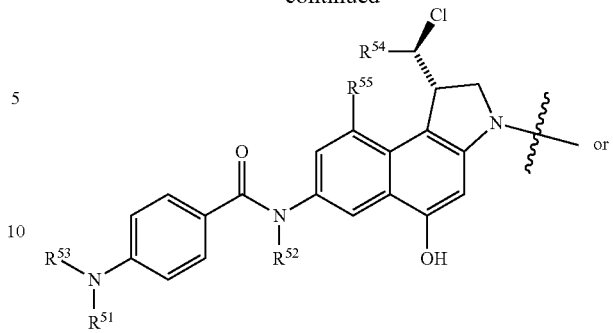
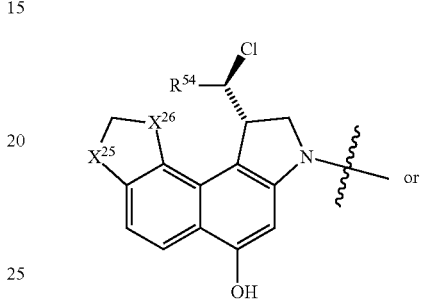
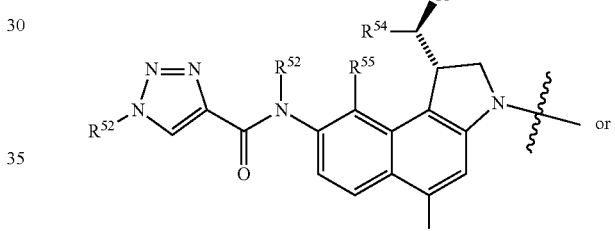
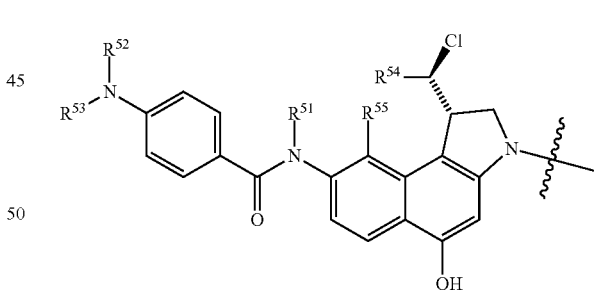
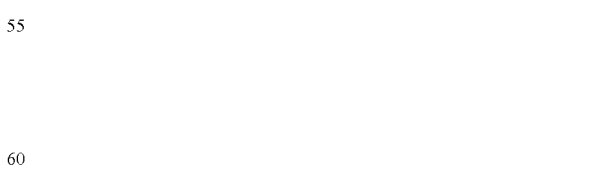
wherein $R^{54}$ is selected from H and optionally substituted $C_{1-3}$ alkyl (e.g., methyl or trifluoromethyl), $R^{55}$ is selected from H, methyl, ethyl, and methoxy, $X^{25}$ and $X^{26}$ are independently selected from O, S, $CH_2$, and $NR^{51}$, and $R^{51}$, $R^{52}$, and $R^{53}$ are independently selected from H, $C_{1-3}$ alkyl and

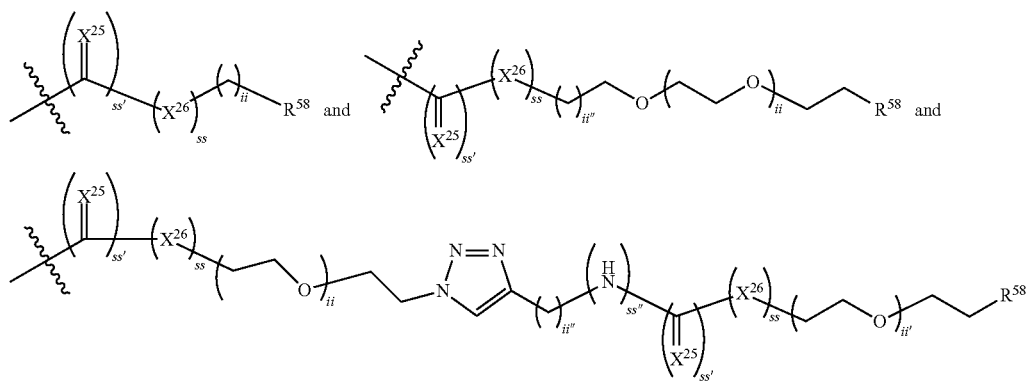

wherein ii, ii', and ii" are independently selected from 0 to 8, each ss, ss', and ss" is independently selected from 0 and 1, each $X^{25}$ and $X^{26}$ is independently selected from O, S, $NR^{56}$, $H_2$, and $C(R^{56})R^{57}$, wherein $R^{56}$ and $R^{57}$ are independently selected from H and optionally substituted $C_{1-3}$ alkyl or $C_{1-3}$ heteroalkyl, and $R^{58}$ is selected from H, COOH, $CO_2Me$, OH, OMe, $NR^{59}R^{60}$, $NR^{59}C(O)CH_3$, SH, SMe,

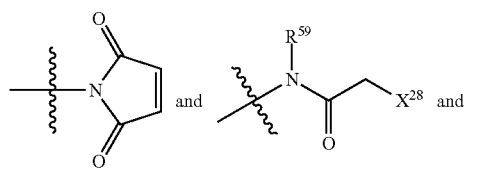

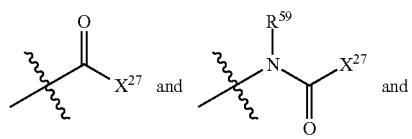

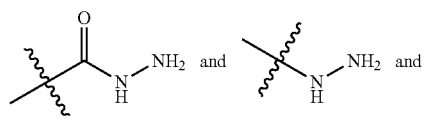

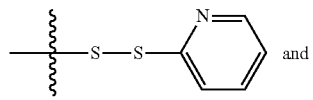

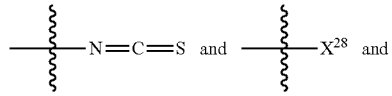

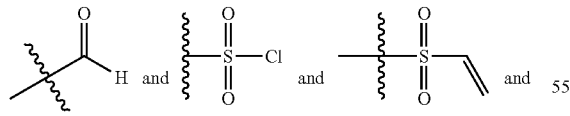

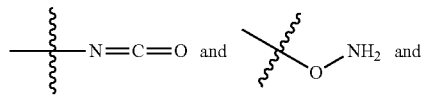

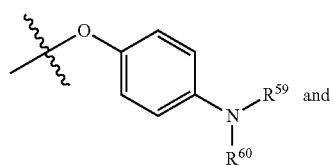

-continued

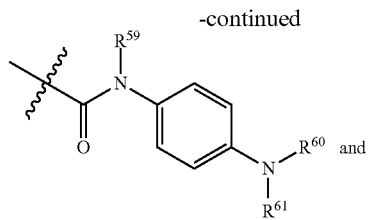

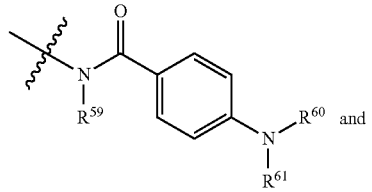

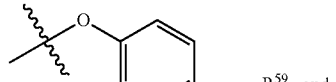

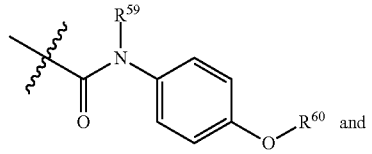

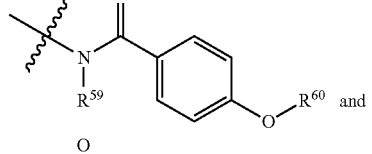

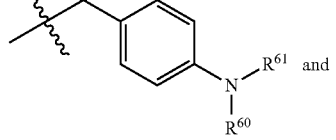

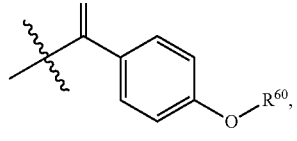

wherein $X^{27}$ is selected from halide, hydroxy, $OC(O)R^{aa}$, and $OC(O)OR^{aa}$, or $C(O)—X^{23}$ is an active ester, $X^{24}$ is selected from halide, mesyloxy, triflyloxy, and tosyloxy, $R^{aa}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl, and $R^{59}$, $R^{60}$, and $R^{61}$ are independently selected from methyl and H, or an isomer of one of these, or a mixture of isomers.

In another embodiment, a compound of formula (I) or (II) is

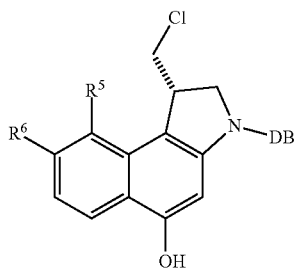

or an isomer thereof, or a mixture of isomers.

In another embodiment, a compound of formula (I) or (II) is

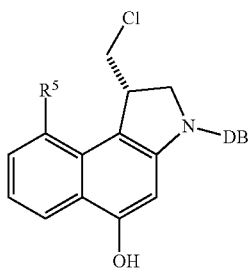

or an isomer thereof, or a mixture of isomers.

In other embodiments, a compound of formula (I) or (II) is

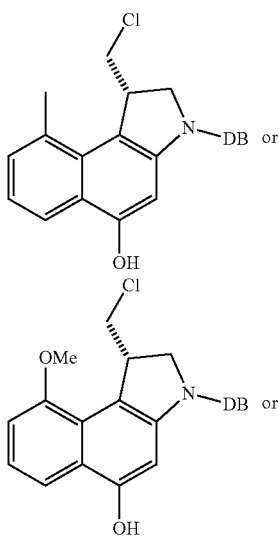

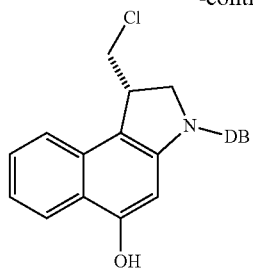

or an isomer of one of these, or a mixture of isomers.

In one embodiment, in a compound of formula (I) or (II), b=1. In another embodiment, b=0. In another embodiment, a=0. In yet another embodiment, a=0 and b=1.

Increased water solubility of a compound of formula (I) or (II) may not only be achieved through the introduction of water-soluble or polar groups, such as a triazole group or an oligoethylene glycol or polyethylene glycol moiety or a combination thereof, but may also be achieved through substitution of carbon ring atoms by heteroatoms, for example in the DNA-binding unit. Improved water solubility of compounds of formulae (I) and (II) and their conjugates may lead to improved yields and purity of the conjugates during synthesis, for example due to reduced aggregate formation. Furthermore, a reduced tendency for aggregation and a higher purity of the conjugate may for example lead to fewer side effects after administration of the conjugate.

Increased metabolic degradation, e.g., in the liver, may for example be achieved through the introduction of groups in the DNA-binding units that can be oxidized with relative ease, for example acetylene and alkene moieties. Oxidation of toxic compounds is one of the mechanisms by which a mammal may detoxify such compounds. If compounds of this invention are taken up in the liver, efficient detoxification may for example circumvent liver toxicity as a side effect.

Extension of the π-conjugated system in the DNA-binding moiety may increase the binding affinity of the DNA binder for DNA. The π system may be extended by the introduction of additional aromatic rings and/or conjugated double and/or triple bonds.

Promoieties may be connected to the DNA-binding units if a suitable functional group is present. This may for example be a hydroxyl group or a primary or secondary amino group. Coupling of a promoiety to the DNA-binding unit in addition to or instead of to the alkylating unit, e.g., to $X^1$, may provide advantages. For example, the presence of two promoieties may increase target-selective delivery and/or activation and/or reduce the amount of free agent in non-targeted areas, thereby reducing side effects and increasing the therapeutic index.

The DNA-binding unit DB in a compound of formula (I) or (II) is selected from structures DB1-DB9:

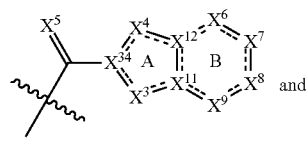

DB1

-continued

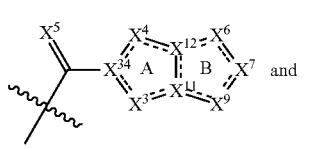
DB2

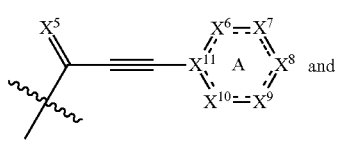
DB3

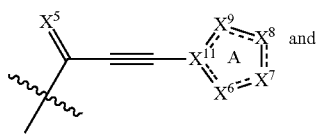
DB4

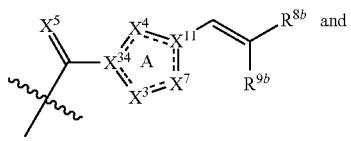
DB5

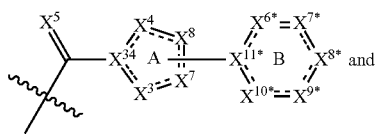
DB6

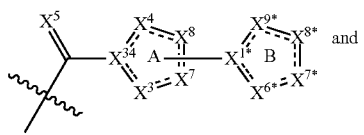
DB7

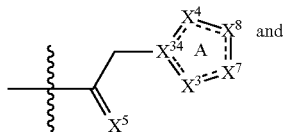
DB8

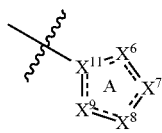
DB9

In one embodiment, the DNA-binding unit comprises at least two aromatic rings of which at least one contains at least one ring atom that is a heteroatom or the DNA-binding unit comprises at least a bicyclic aromatic system in which at least one ring atom is a heteroatom. In another embodiment, the DNA-binding unit comprises at least two aromatic rings and both contain at least one ring atom that is a heteroatom or the DNA-binding unit comprises at least a bicyclic aromatic system in which at least two ring atoms are a heteroatom.

In one aspect of this invention, a compound of formula (I) or (II) has a DNA-binding unit of formula DB1. This moiety comprises structures that at least contain a 6-membered ring B that is connected to the DNA-alkylating unit via a fused 5- or 6-membered ring A or vinyl group. The optional heteroatom in said ring B may provide for improved water solubility with respect to DNA binder analogs having an all-carbon ring. In one embodiment, ring B in unit DB1 contains a heteroatom.

Preferably, ring B is aromatic. It may for example be a phenyl, pyridine, pyrimidine, pyridazine, pyrazine, 1,3,5-triazine, 1,2,3,5-tetrazine, 1,2,3,4-tetrazine, pentazine, phosphinine, 1,3-diphosphinine, or 1,3-azaphosphinine moiety. Alternatively, this ring may be non-aromatic and either be unsaturated or completely saturated.

A compound of formula (I) or (II) wherein ring B is connected to the DNA-alkylating unit via a vinyl group may contain a handle that allows for detoxification by means of for example oxidation or hydration of the double bond.

The moiety DB1 may for example be

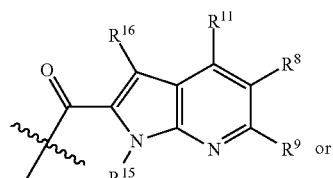
or

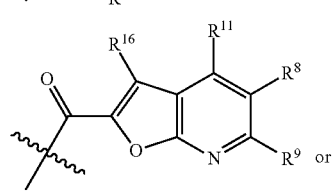
or

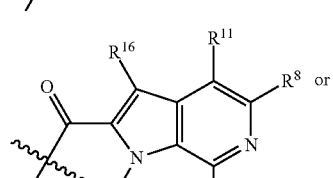
or

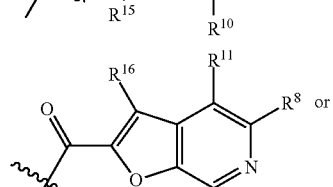
or

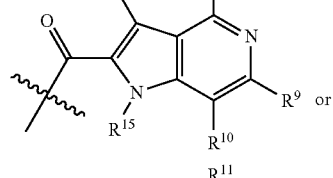
or

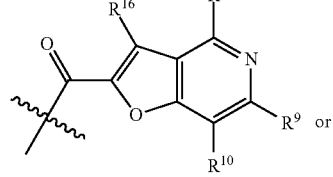
or

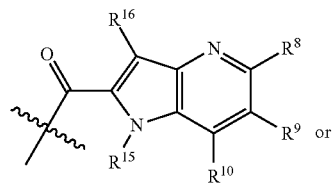
or

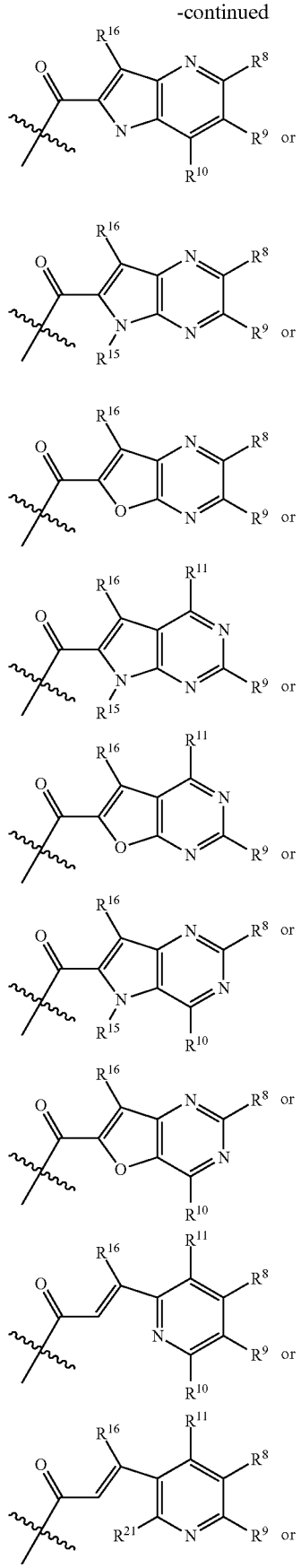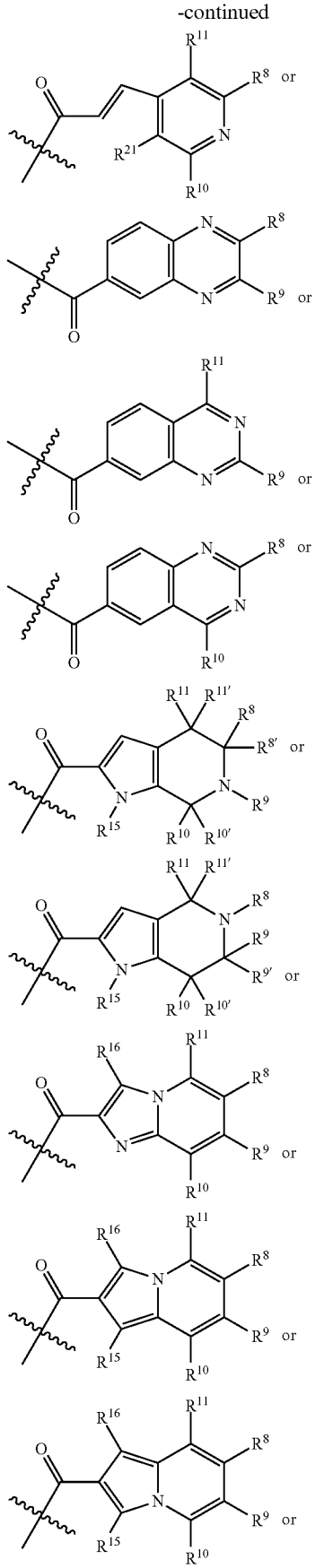

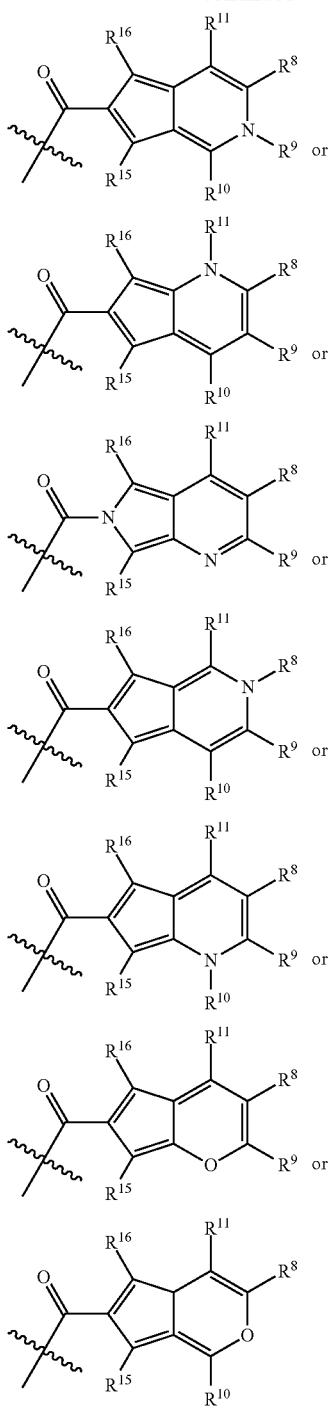
Moiety DB1 may for example also be
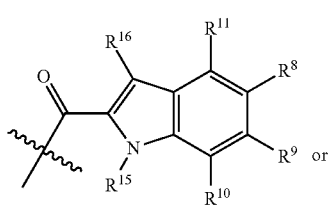
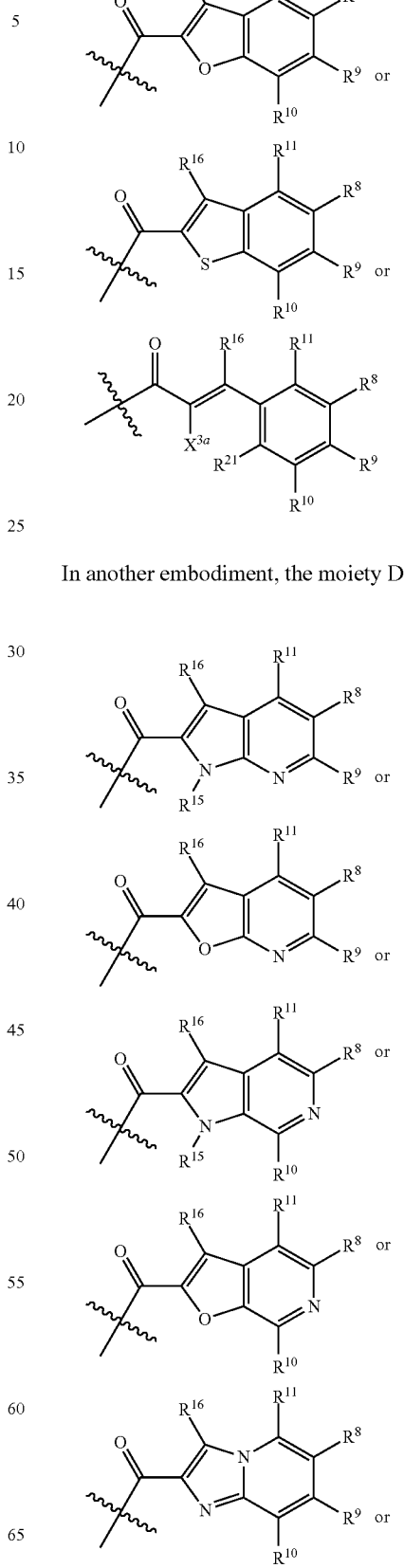
In another embodiment, the moiety DB1 may be

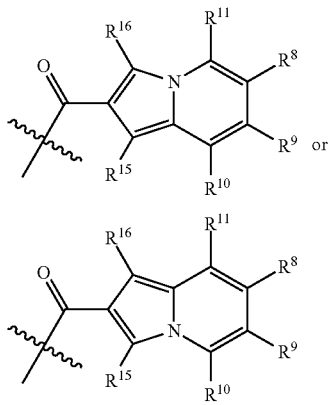
In a more specific embodiment, the moiety DB1 may for example be
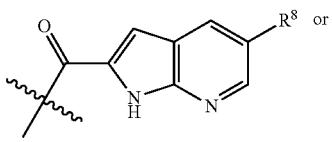
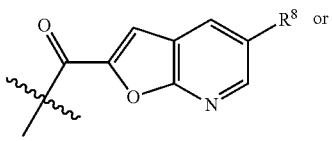
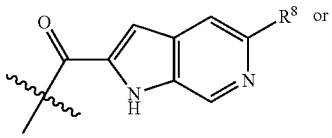
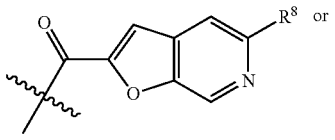
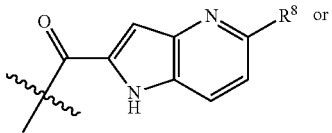
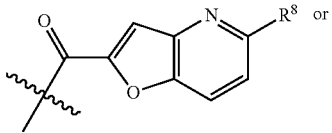
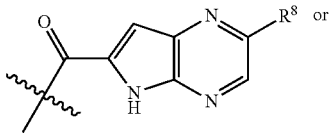
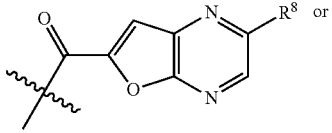
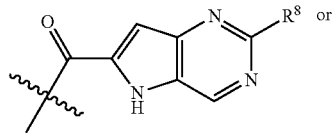
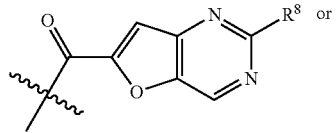
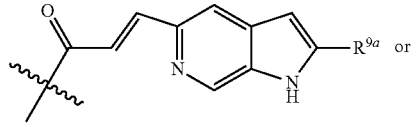
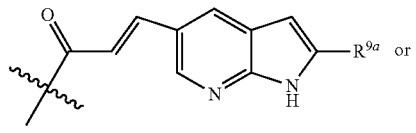
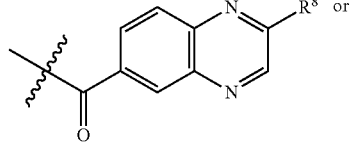
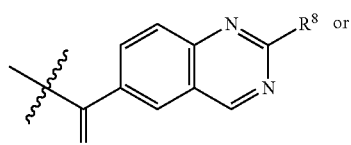
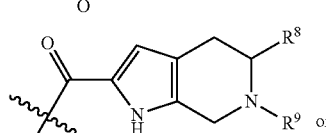
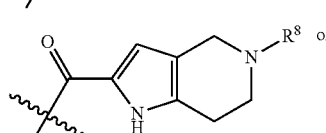
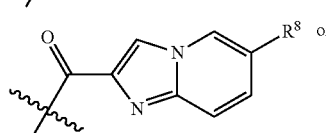
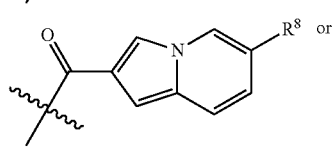
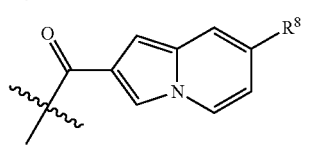
wherein $R^{9a}$ has the same meaning as defined for $R^9$ and is independently selected.

The moiety DB1 may for example also be
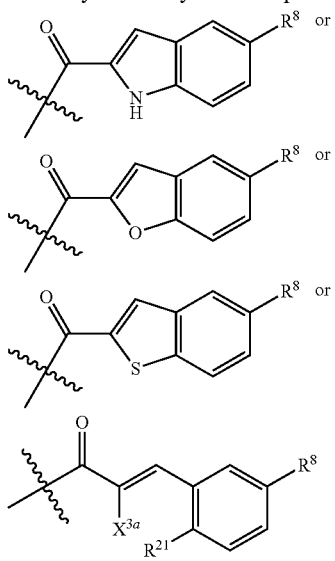
In the exemplary structures of DB1, $R^8$, $R^{8'}$, $R^9$, $R^{9'}$, $R^{9a}$, $R^{10}$, $R^{10'}$, $R^{11}$, $R^{11'}$, $R^{15}$, $R^{16}$, and $R^{21}$ may for example each independently be selected to be H, be or contain another moiety selected from structures DB1-DB9 or a derivative thereof, or be
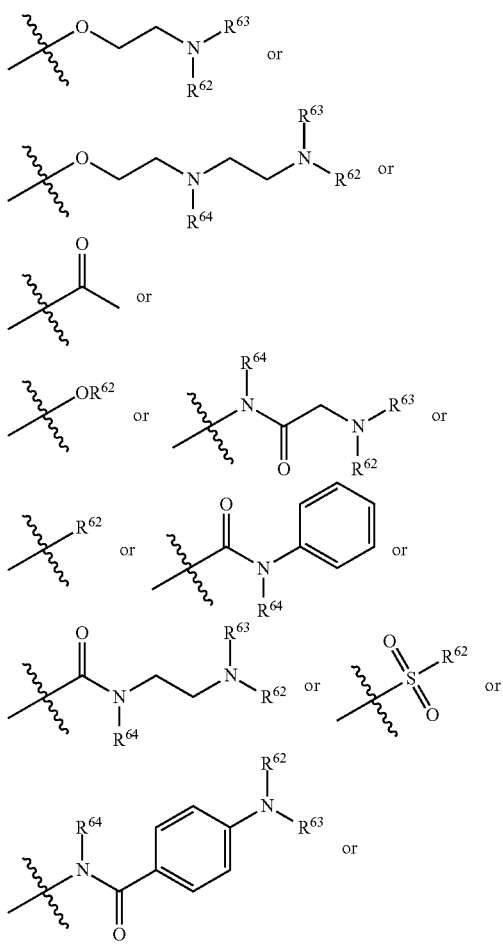
-continued
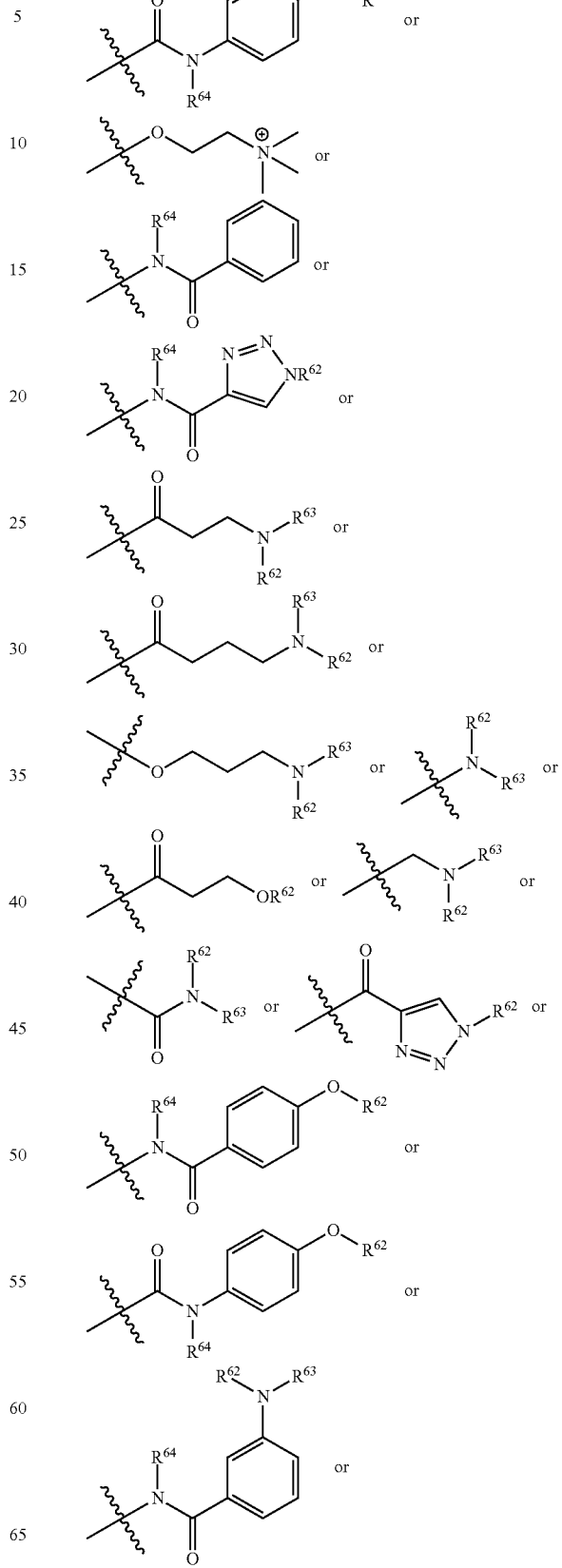

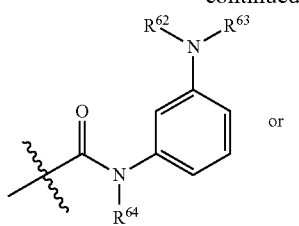 or
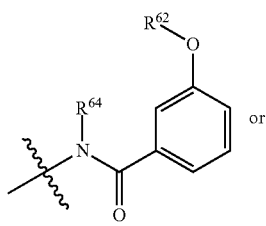 or
 or
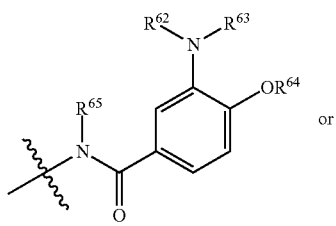 or
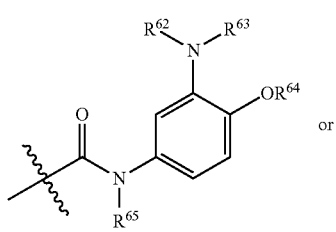 or
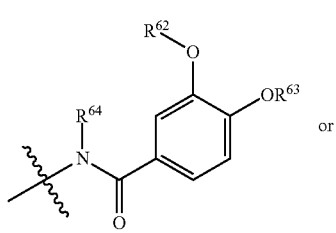 or
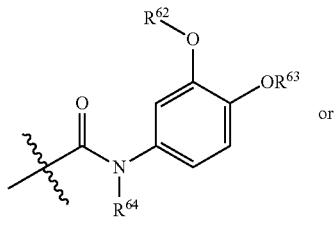 or
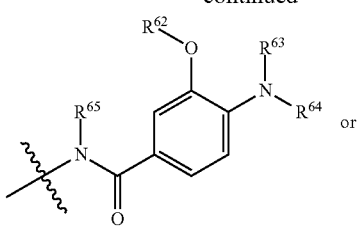 or
 or
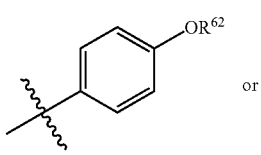 or
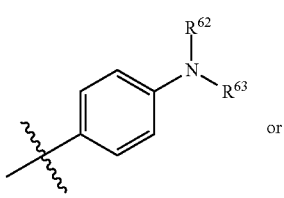 or
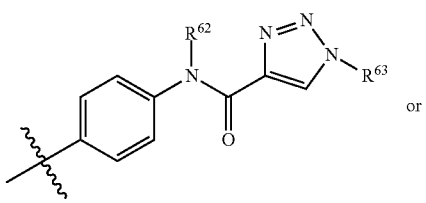 or
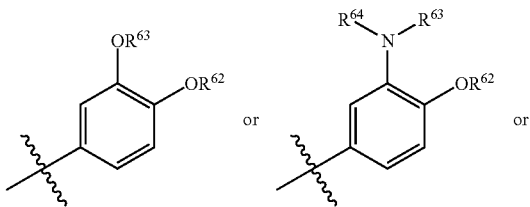 or
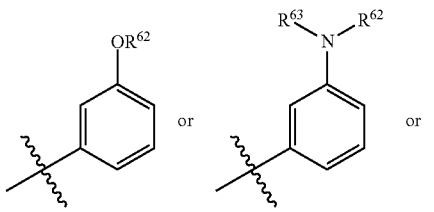 or
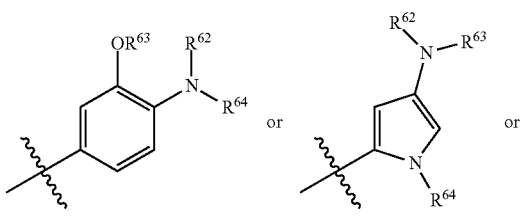

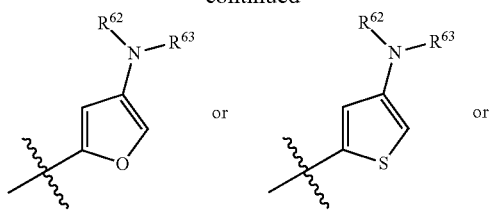
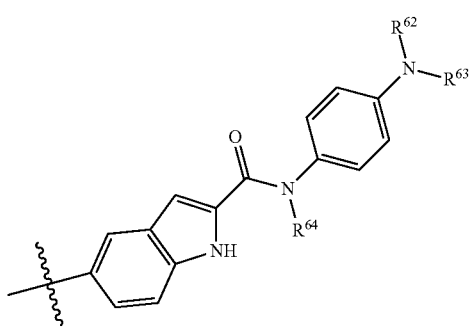
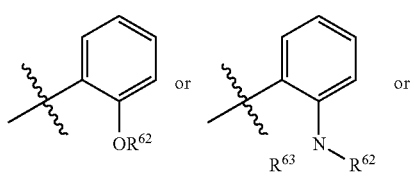
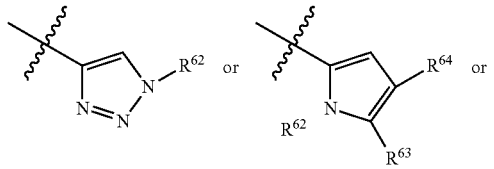
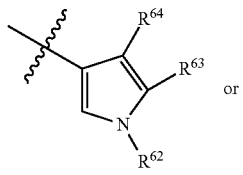
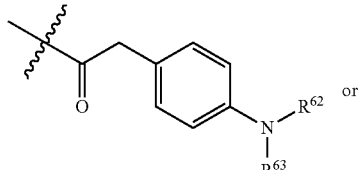
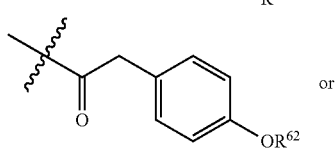
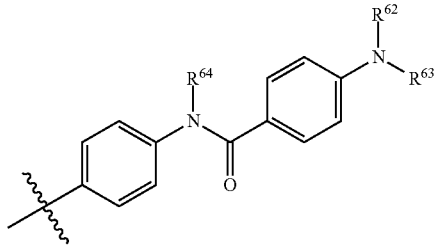
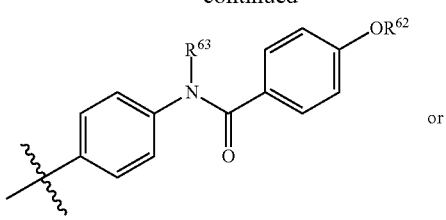
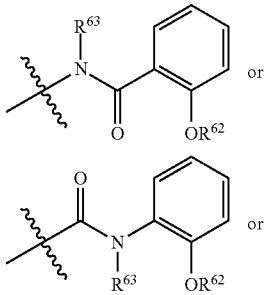
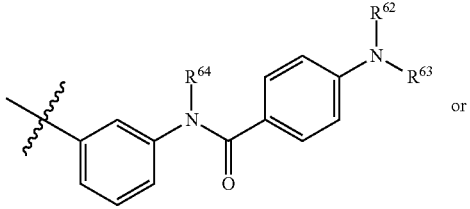
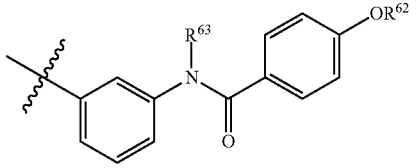
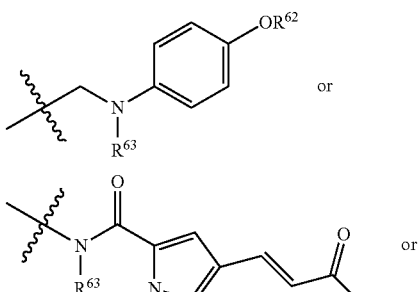
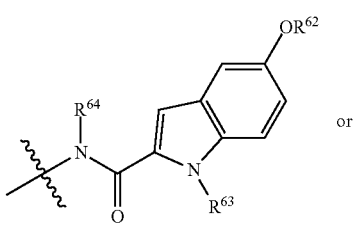
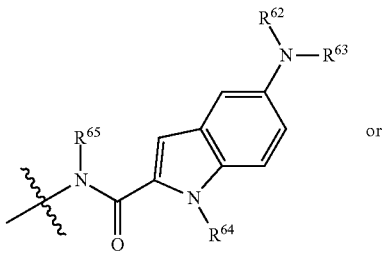

-continued

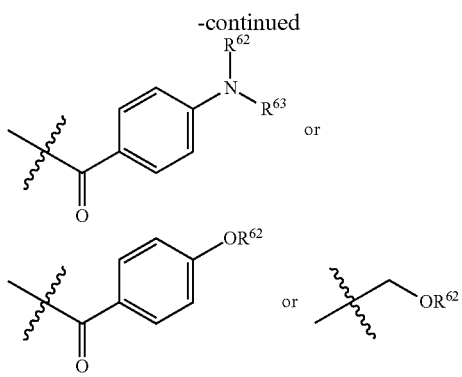

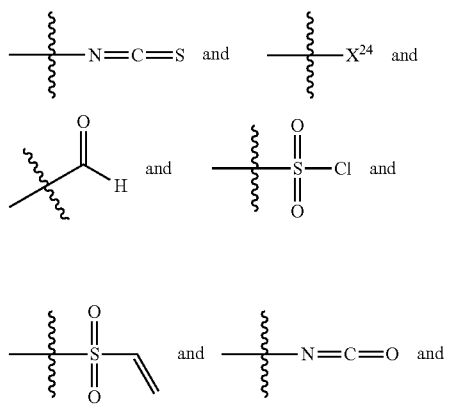

wherein $R^{62}$, $R^{63}$, $R^{64}$, and $R^{65}$ are independently selected from H, $C_{1-3}$ alkyl, and

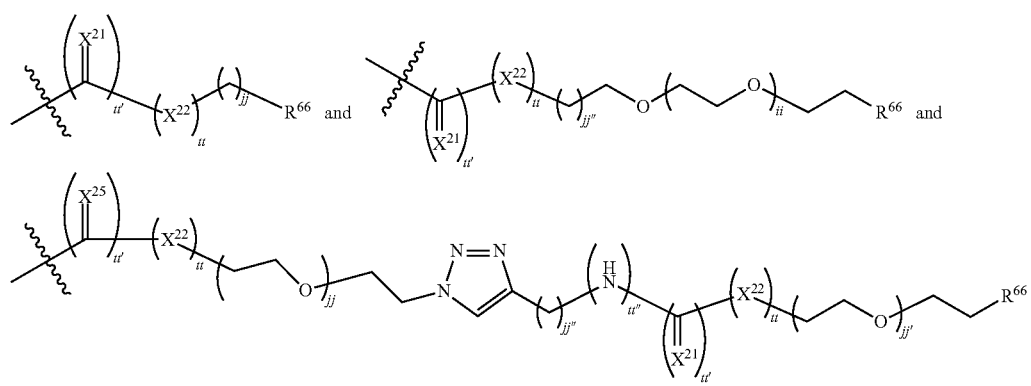

wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

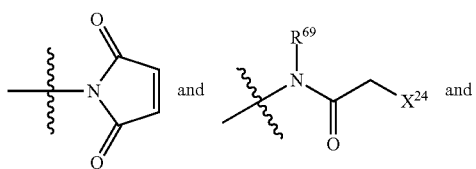

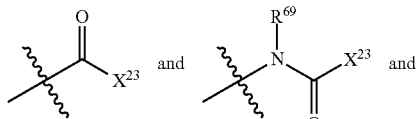

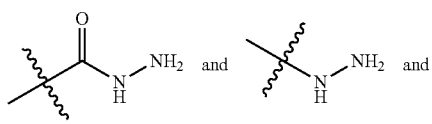

-continued

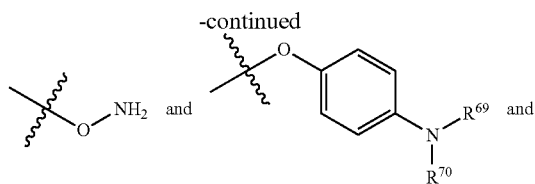

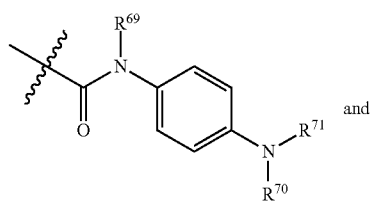

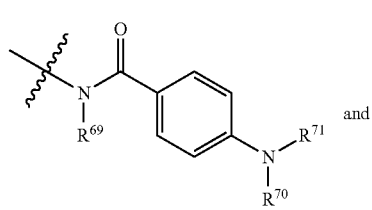

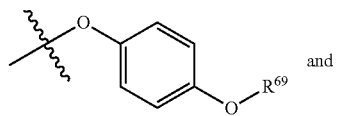

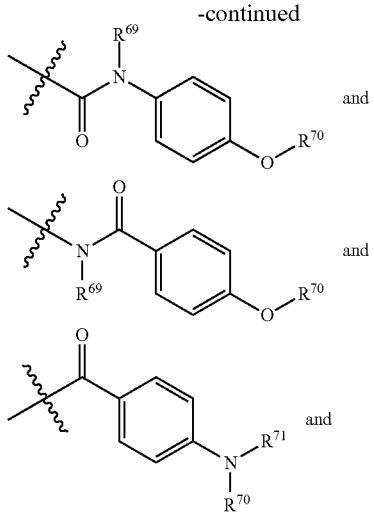

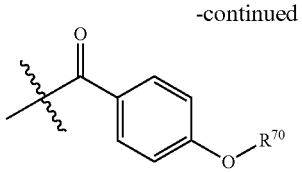

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, the moiety DB1 may for example be

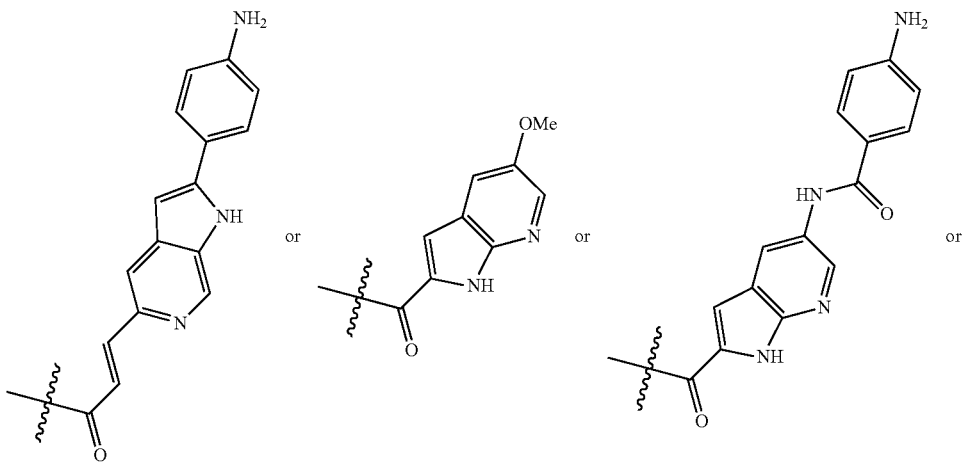

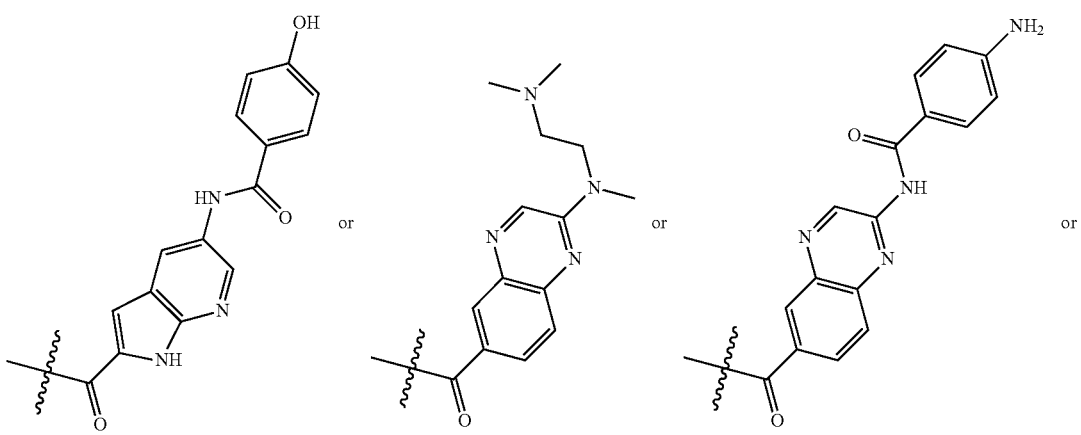

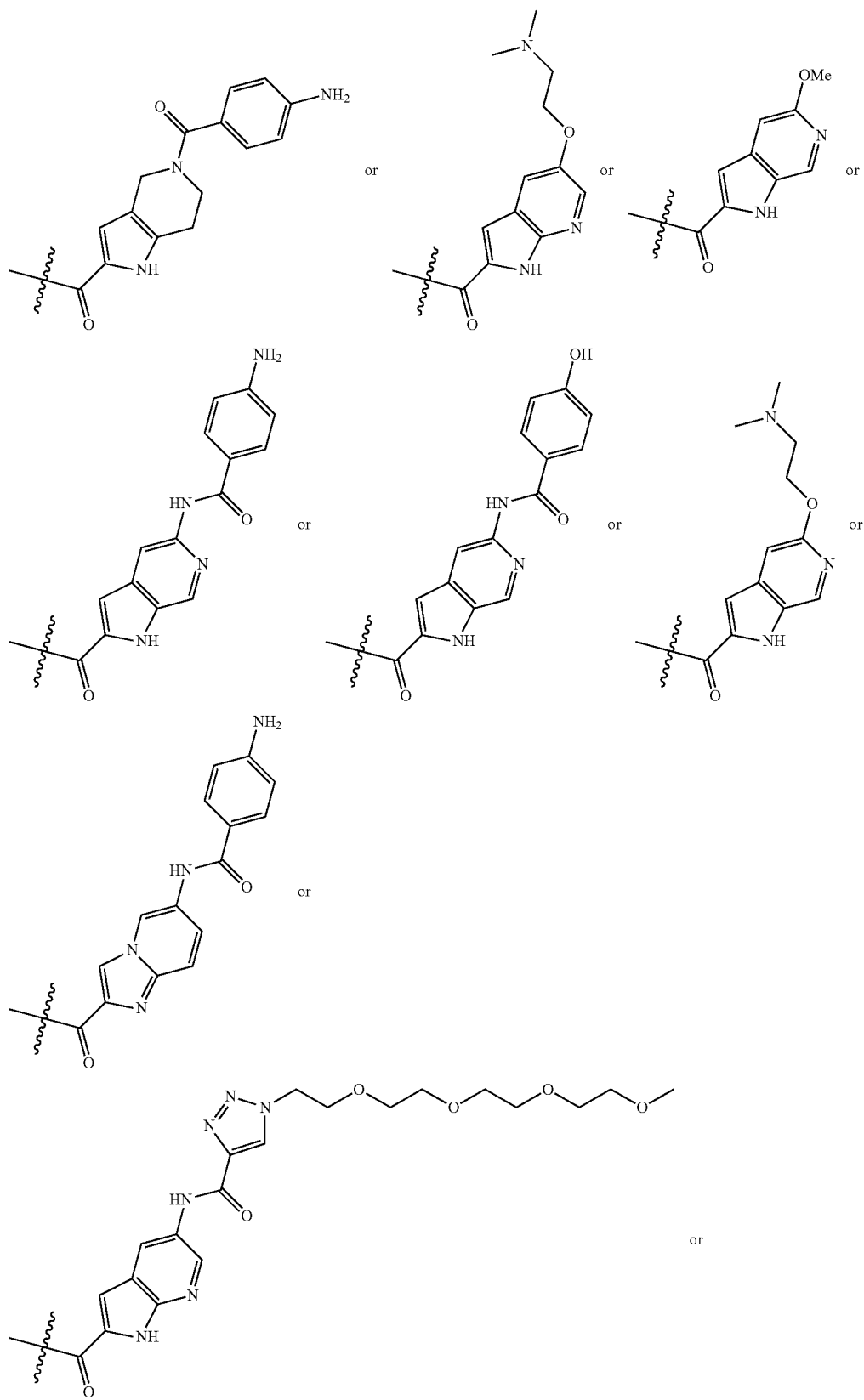

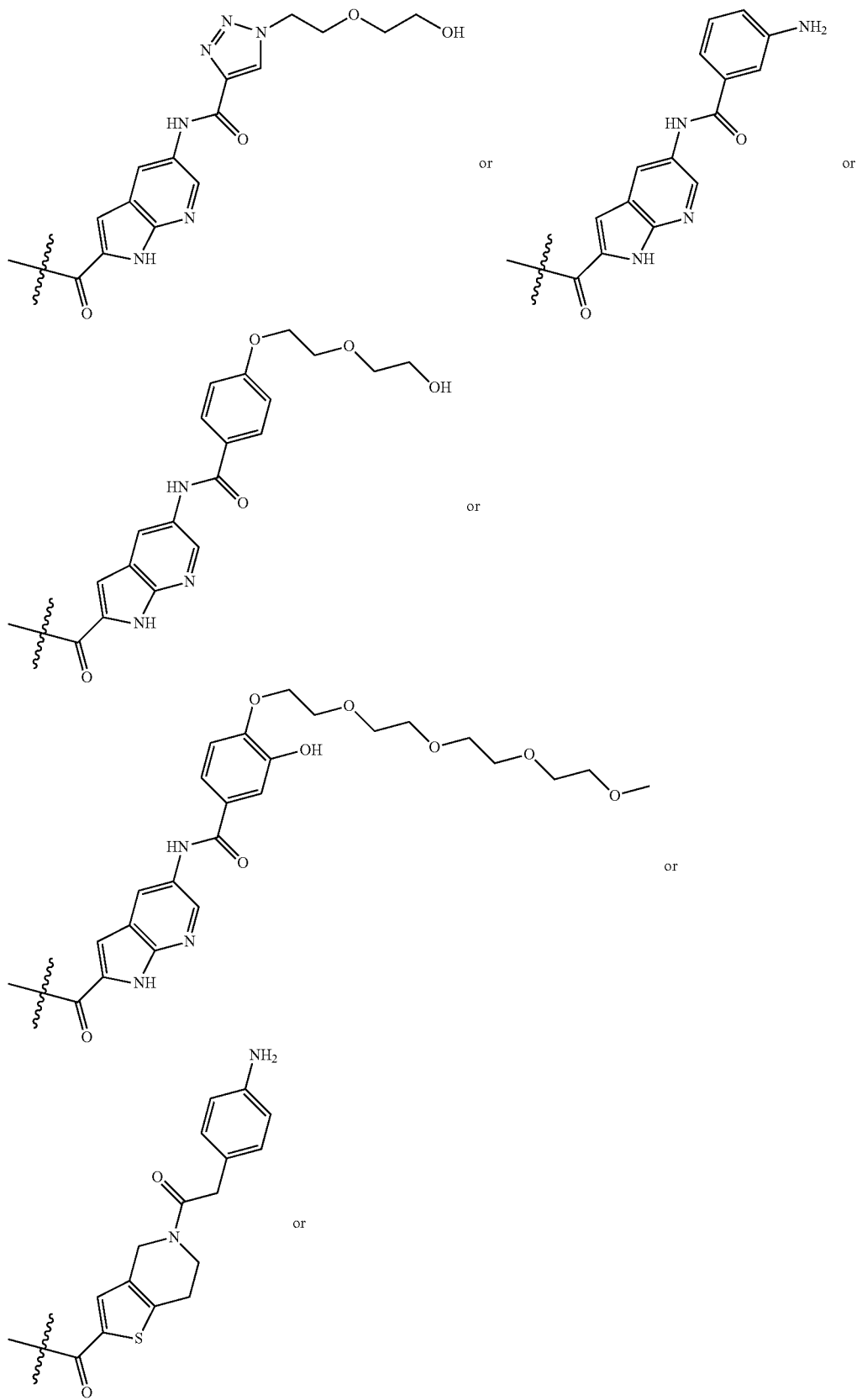

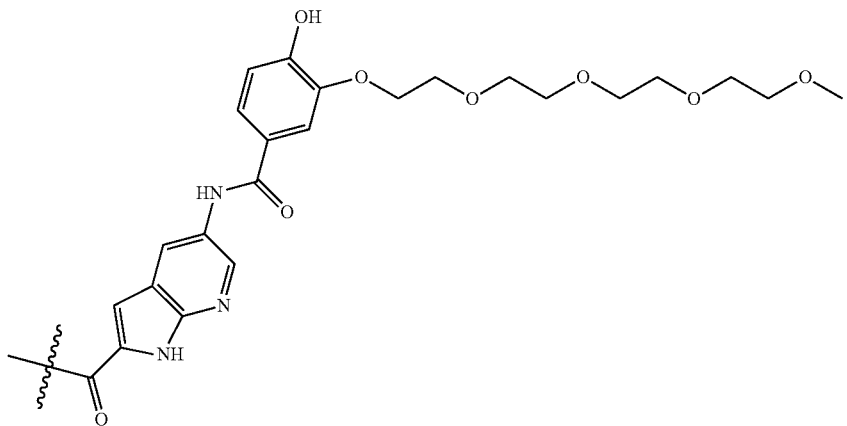
or
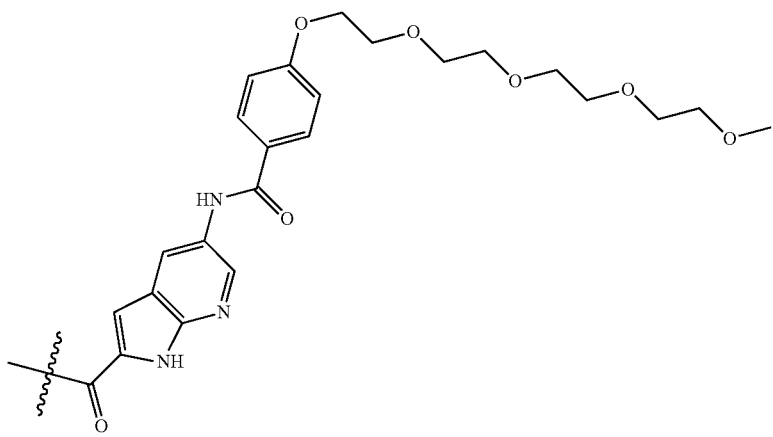
or
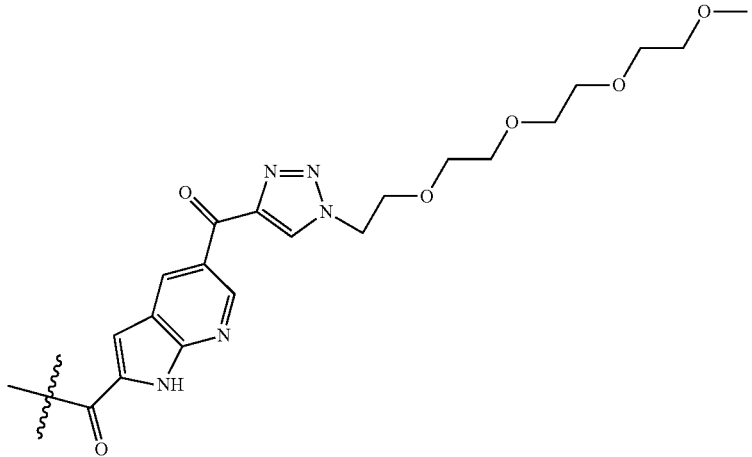
or
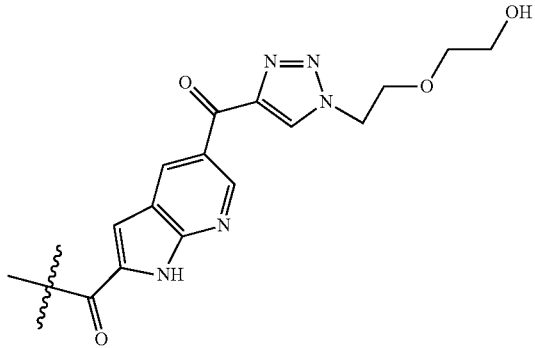
or

-continued
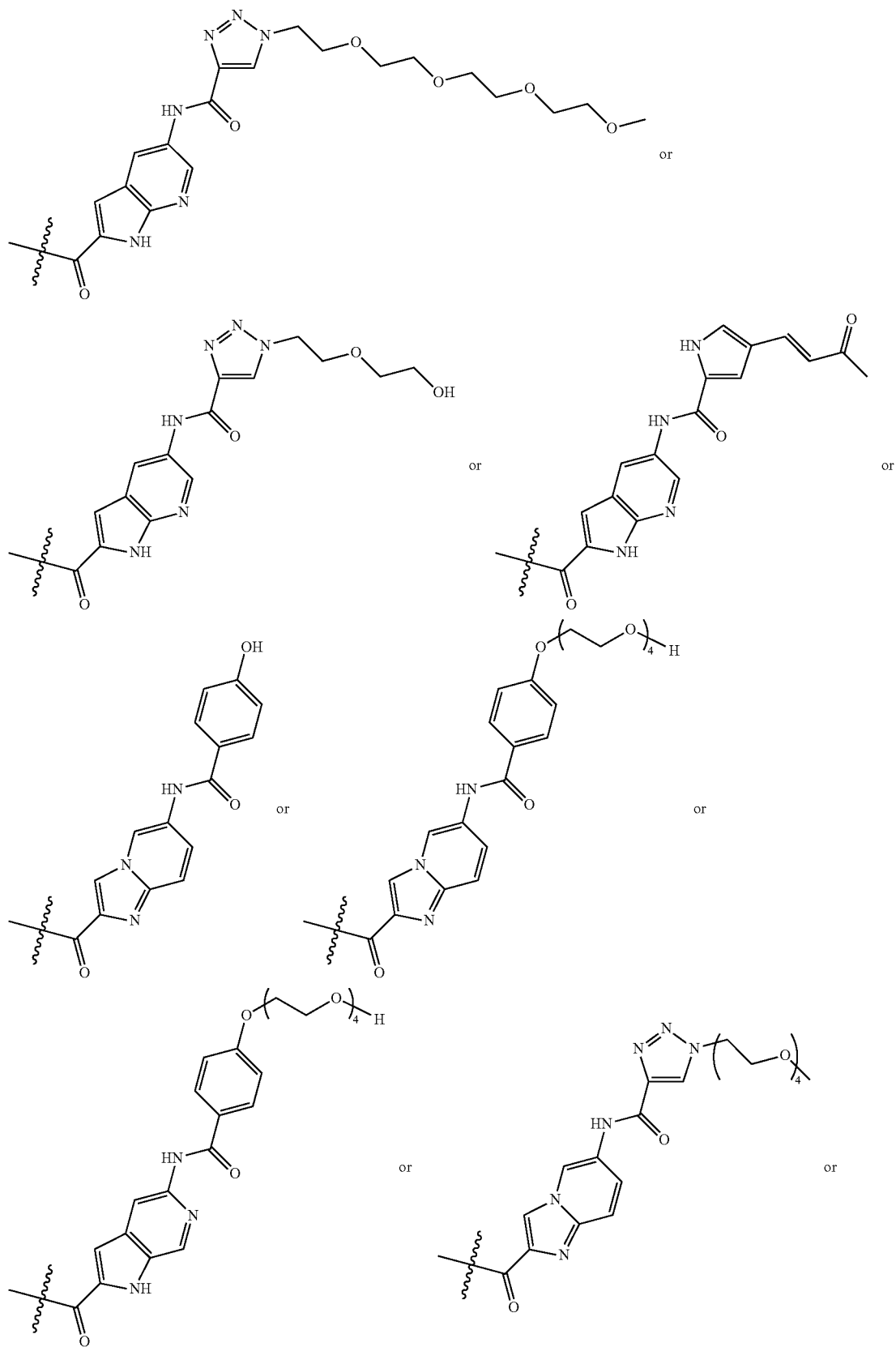

103 104
-continued
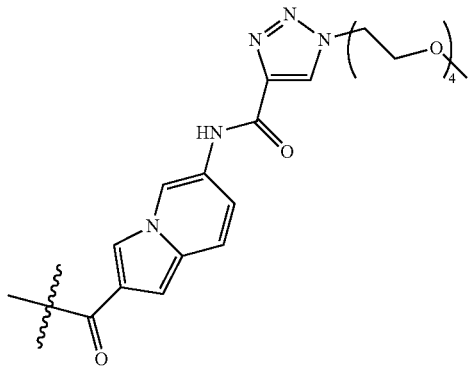 or 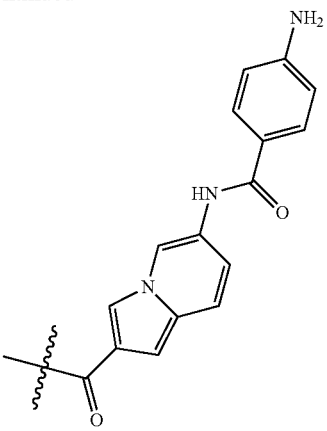 or
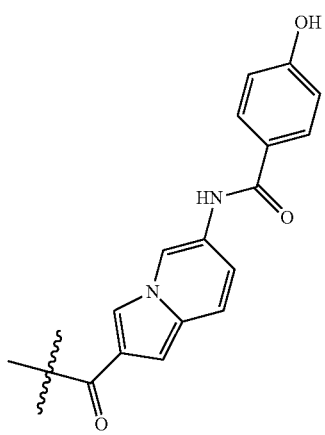 or 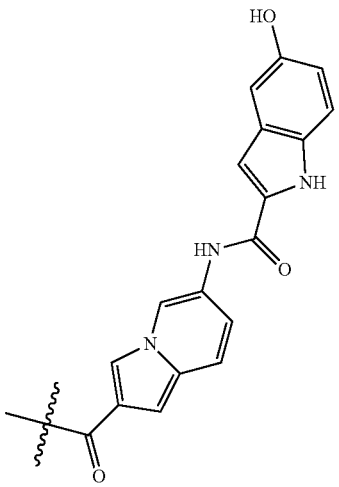 or 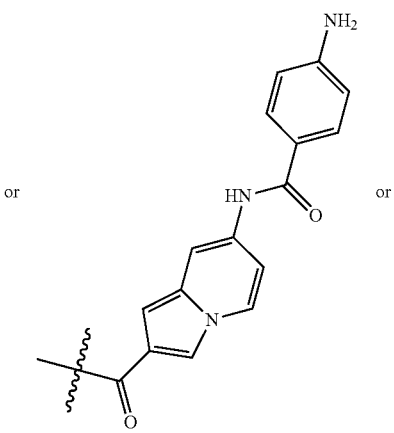 or
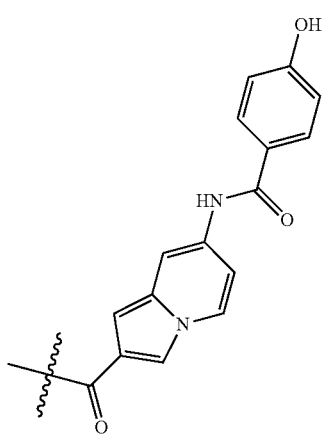 or 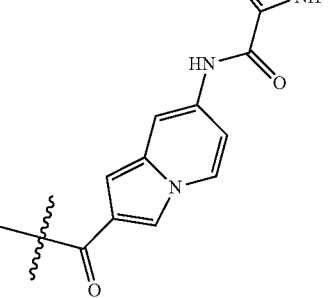 or 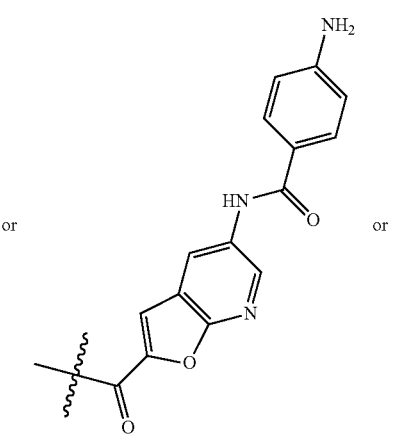 or -continued
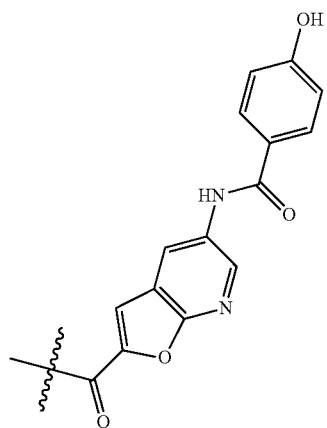 or 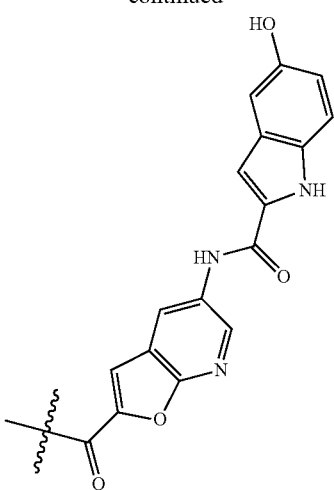 or
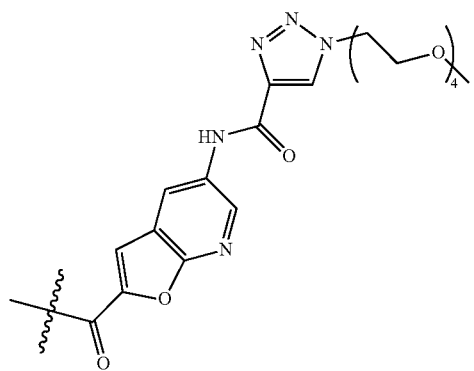 or 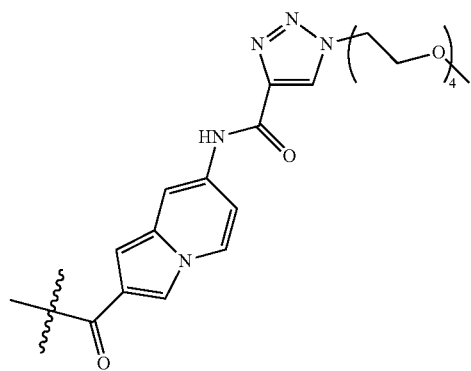 or
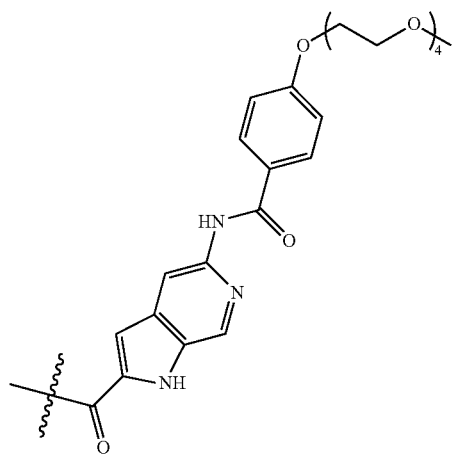 or 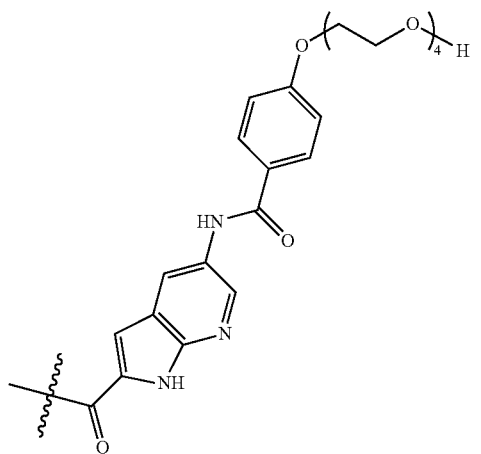 or -continued
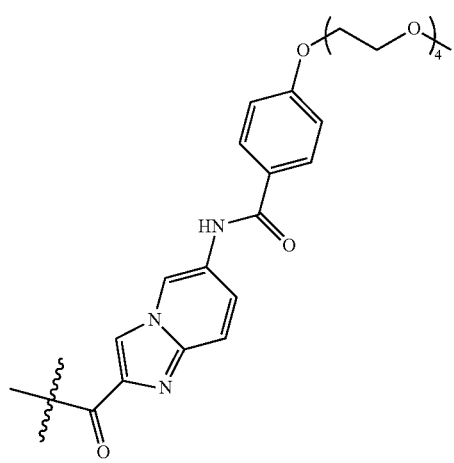 or 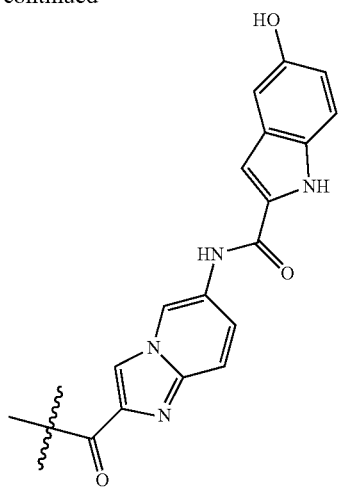 or
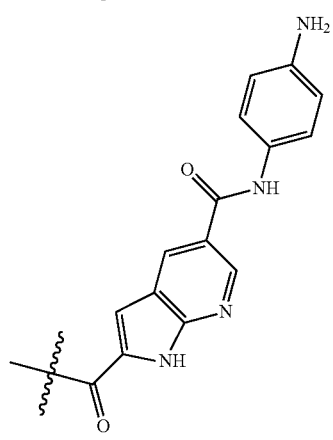 or 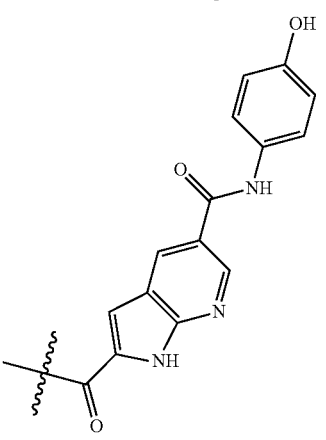 or
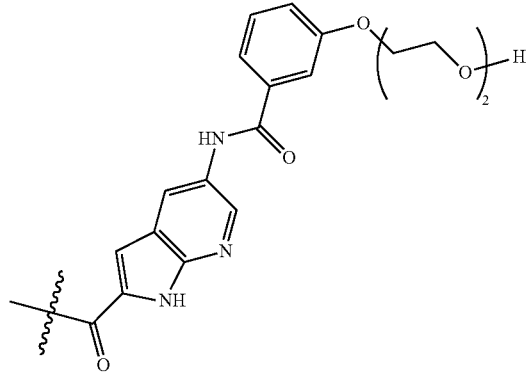 or 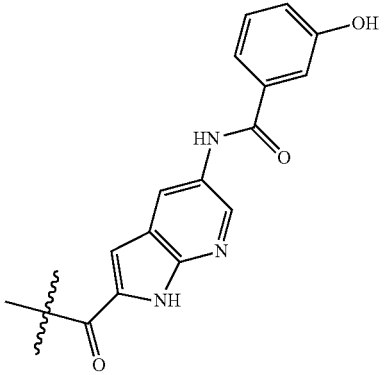 or
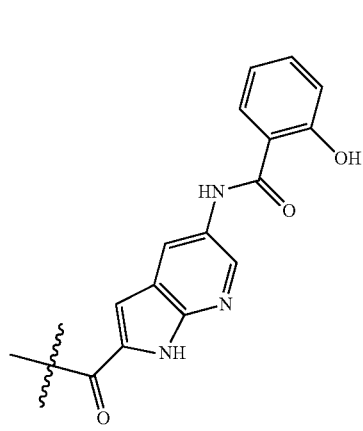 or 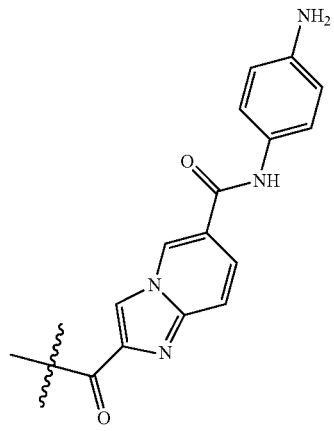 or -continued
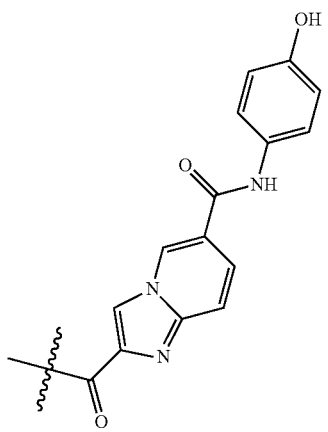 or 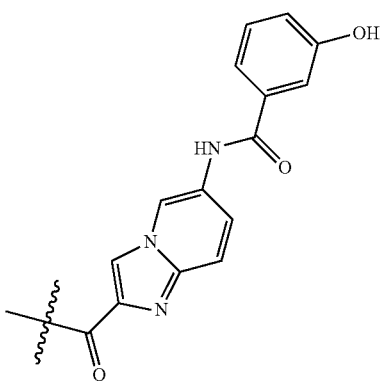 or
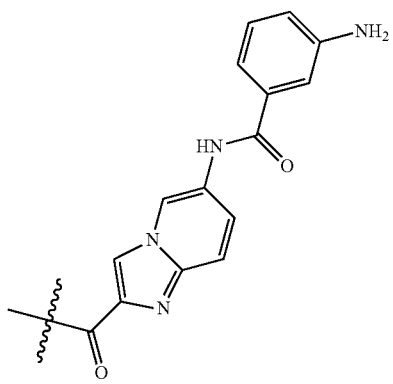 or 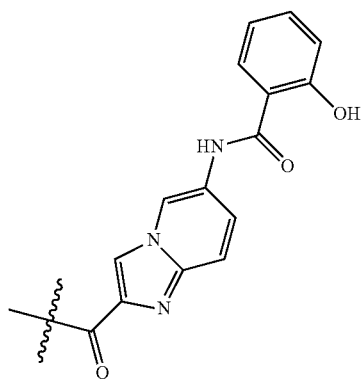 or
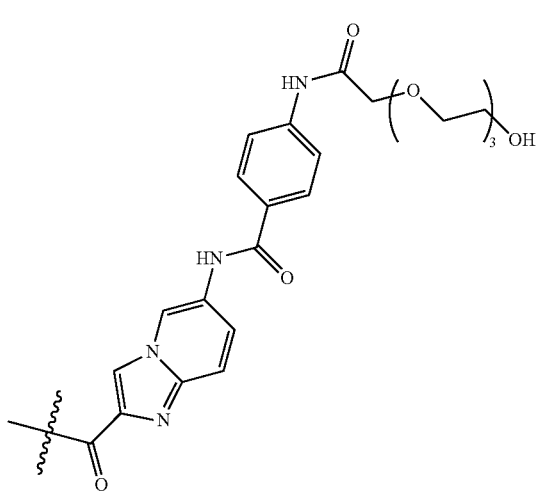 or 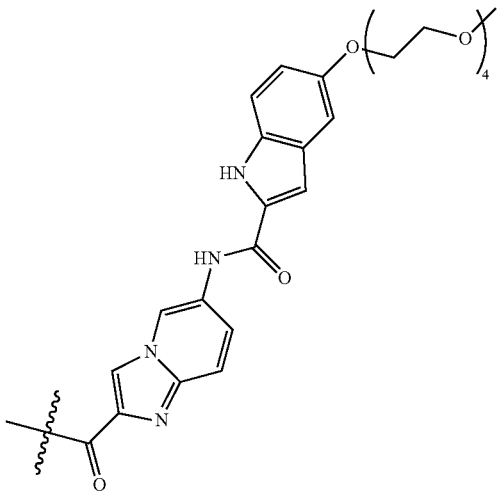 or
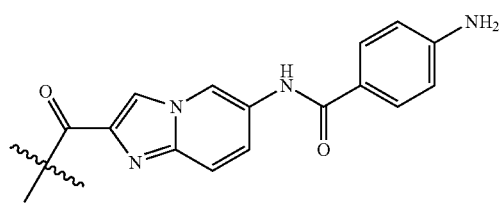

In another embodiment, the moiety DB1 may for example be
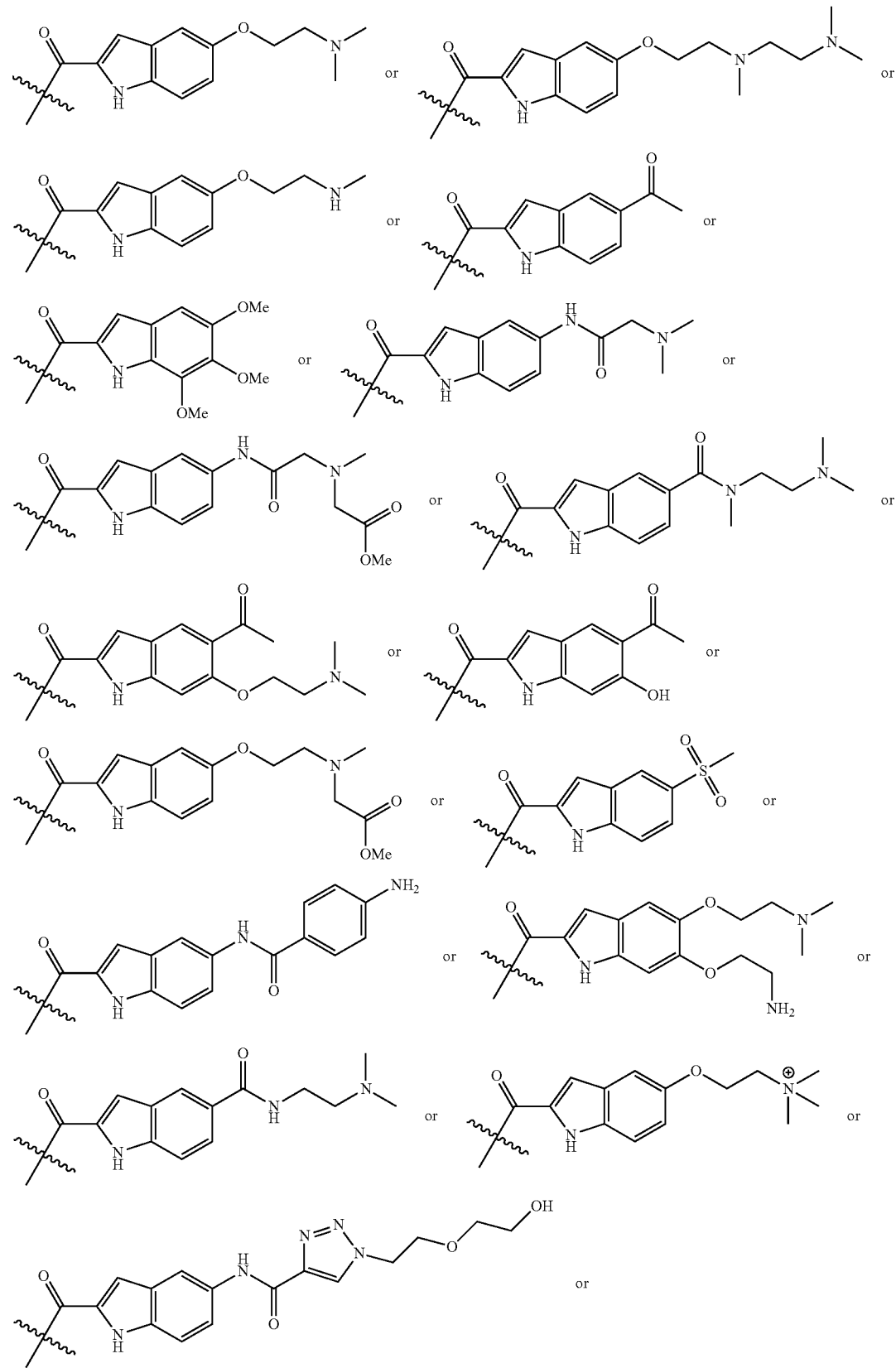

113
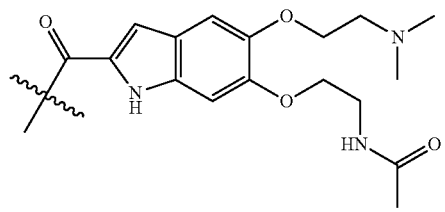 or
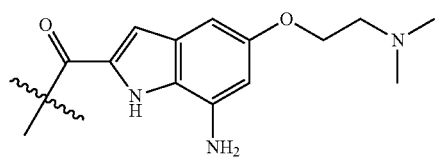 or
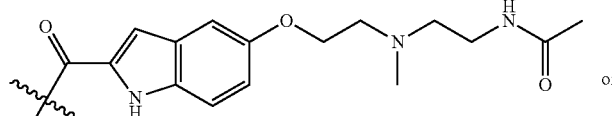 or
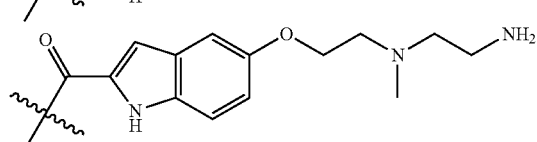 or
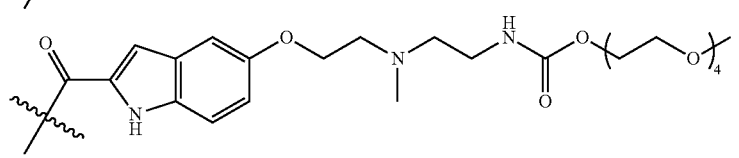 or
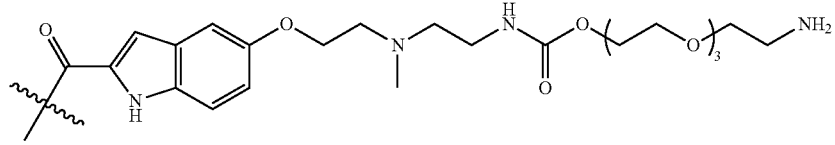 or
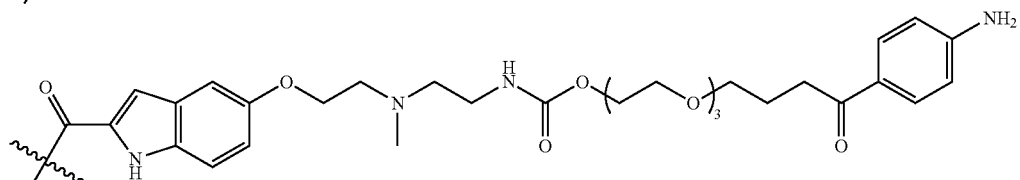 or
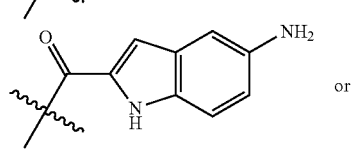 or
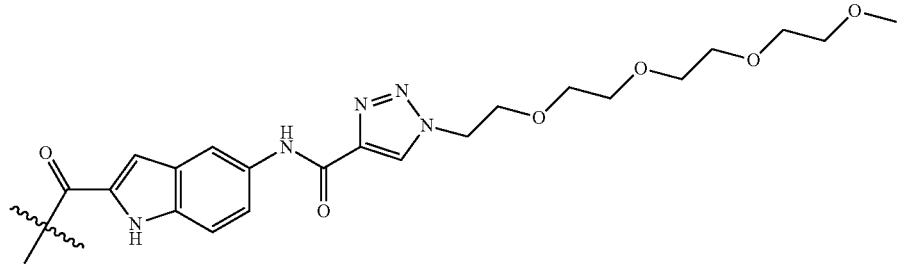 or
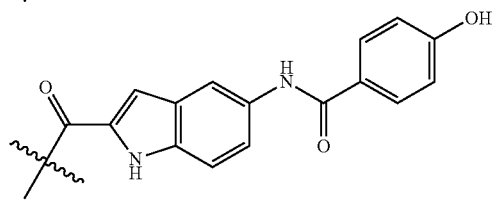 or
114
-continued
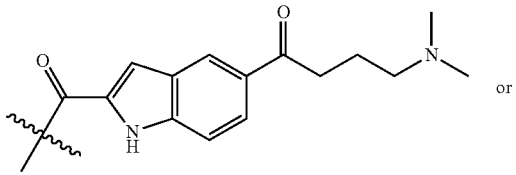 or
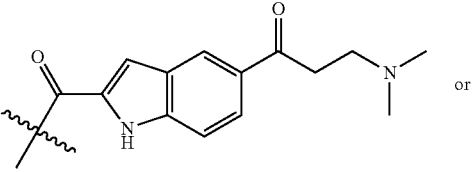 or
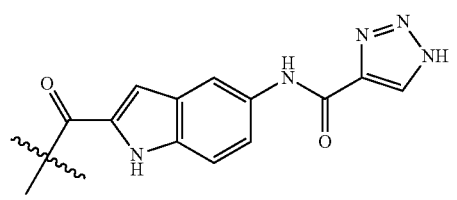 or

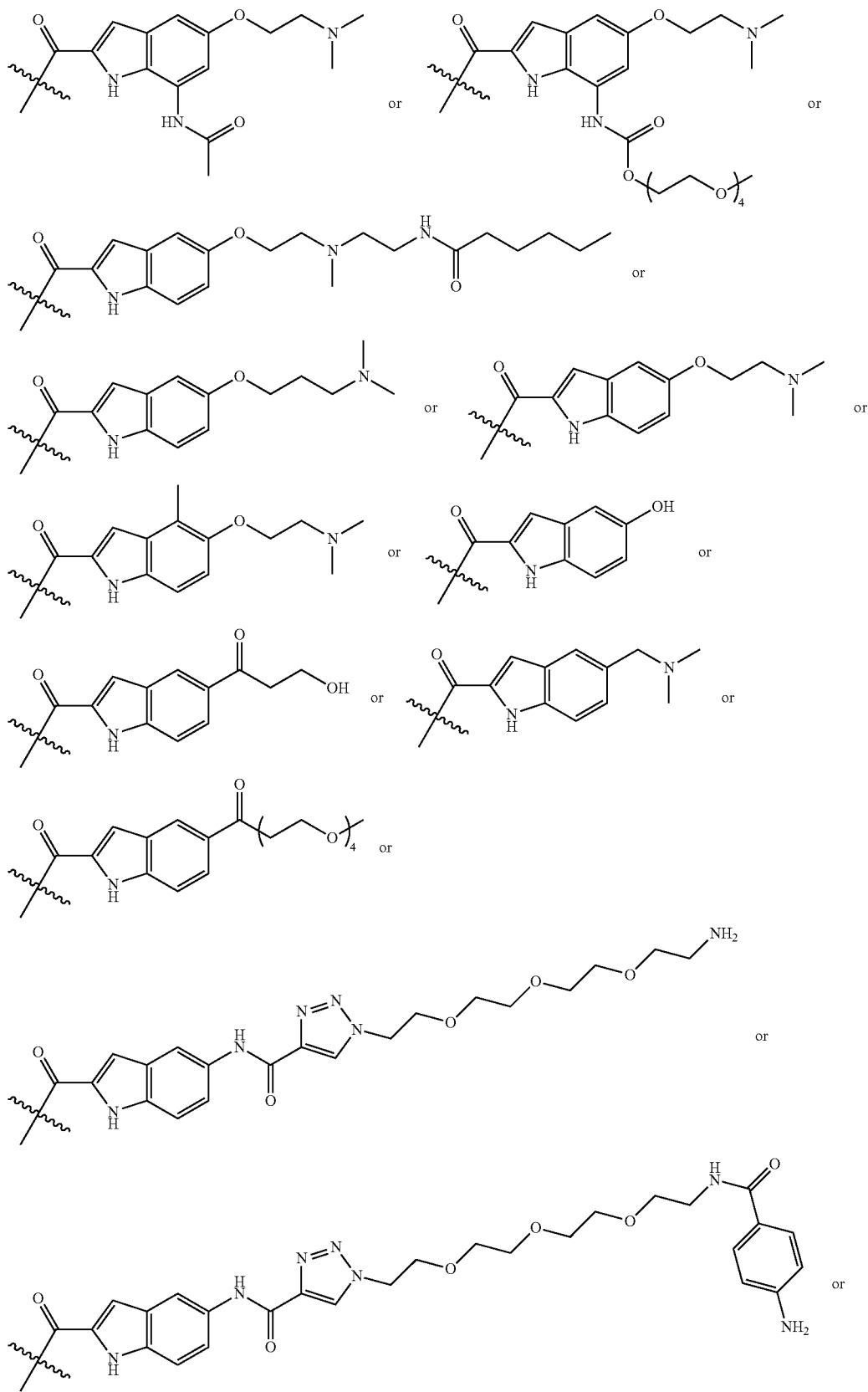

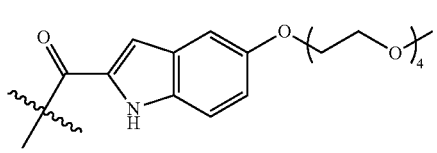 or 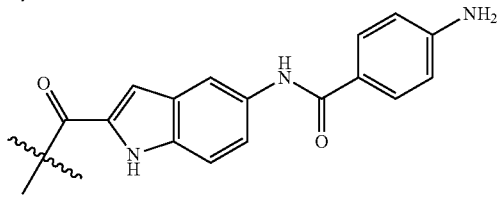

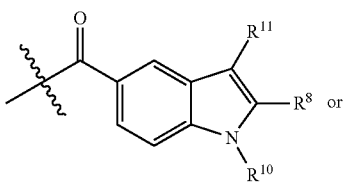

In another aspect of this invention, a compound of formula (I) or (II) has a DNA-binding unit of formula DB2. This moiety comprises structures that at least contain a 5-membered ring B that is connected to the DNA-alkylating unit via a fused 5- or 6-membered ring A or a vinyl group. Especially in the latter case, ring B may be fused to another heterocyclic or carbocyclic aromatic or non-aromatic ring in order to have an improved DNA-binding affinity. For reasons of increased water solubility, the fused ring may be a heterocycle, or a carbocycle substituted with relatively polar groups that at the same time may provide handles for coupling to promoieties. A DNA binder in which three or more rings are fused together to form an aromatic multicyclic system may be less favorable as this may increase the hydrophobicity and/or the aggregation tendency of the DNA-binder and therefore increase the hydrophobicity and/or the aggregation tendency of a compound of formula (I) or (II) and its conjugates. This may be especially true for multicyclic aromatic systems in which none or only one of the ring atoms is a heteroatom.

DNA binder DB2 may comprise an aromatic core structure. Alternatively, one or more rings may be non-aromatic and be either unsaturated or completely saturated.

A compound of formula (I) or (II) wherein ring B is connected to the DNA-alkylating unit via a vinyl group may contain a handle that allows for detoxification by means of for example oxidation or hydration of the double bond.

The moiety DB2 may for example be

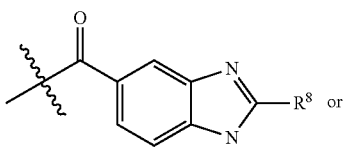

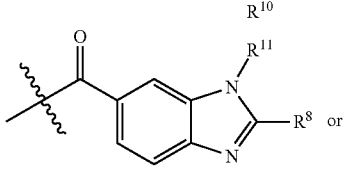

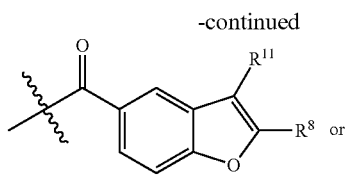

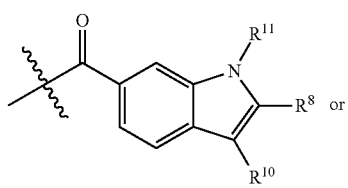

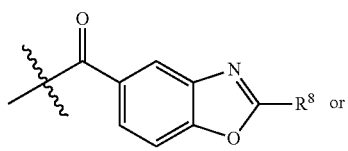

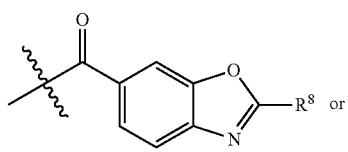

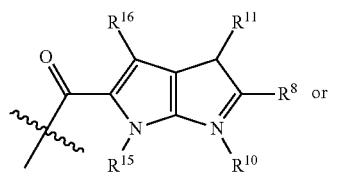

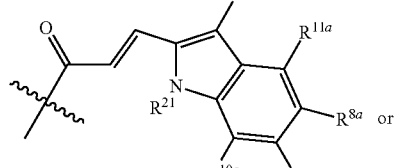

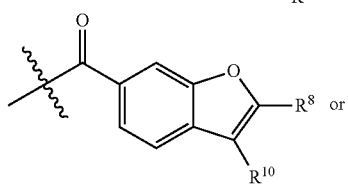

-continued
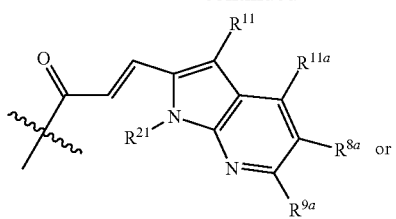
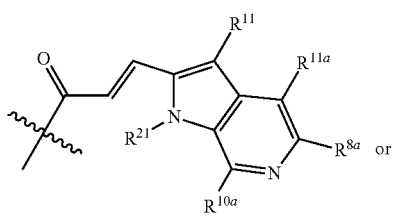
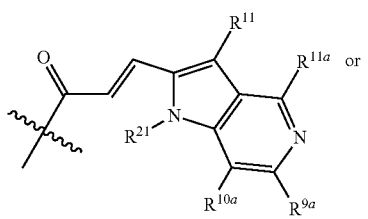
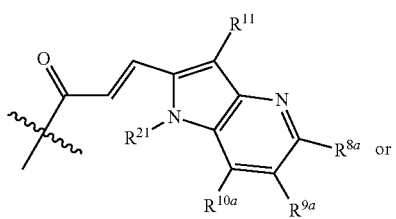
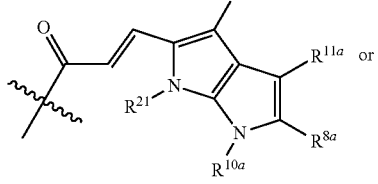
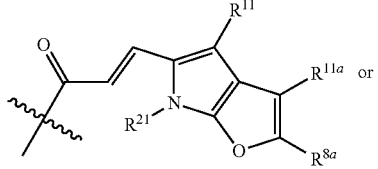
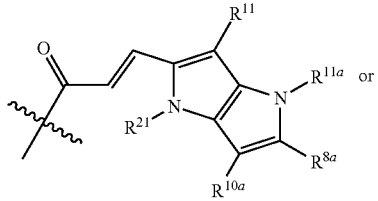
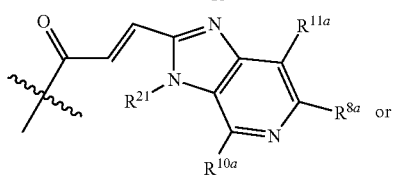
-continued
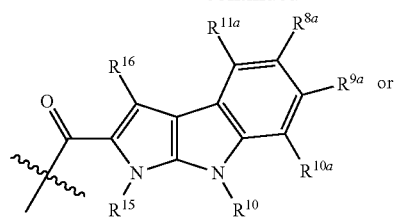
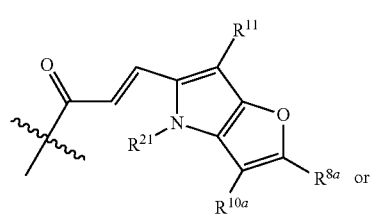
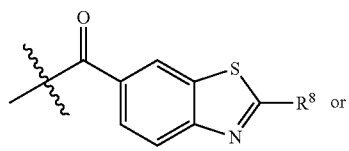
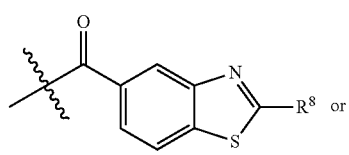
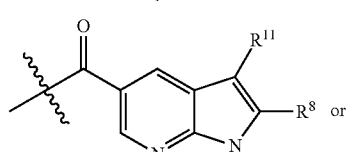
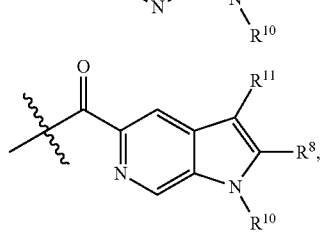
wherein $R^{8a}$, $R^{9a}$, $R^{10a}$, and $R^{11a}$, have the same meaning as defined for $R^8$, $R^9$, $R^{10}$, and $R^{11}$, respectively, and are independently selected.
In a more specific embodiment, the moiety DB2 may for example be
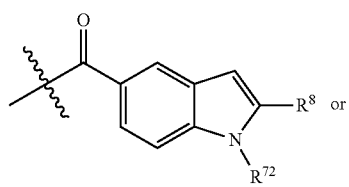
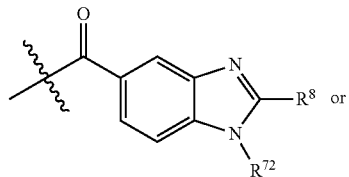

121
-continued
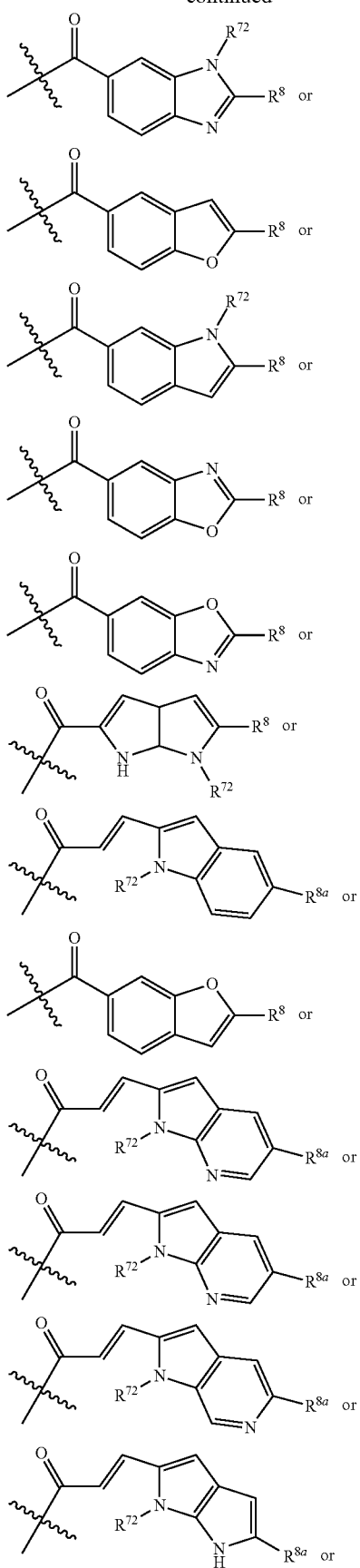
122
-continued
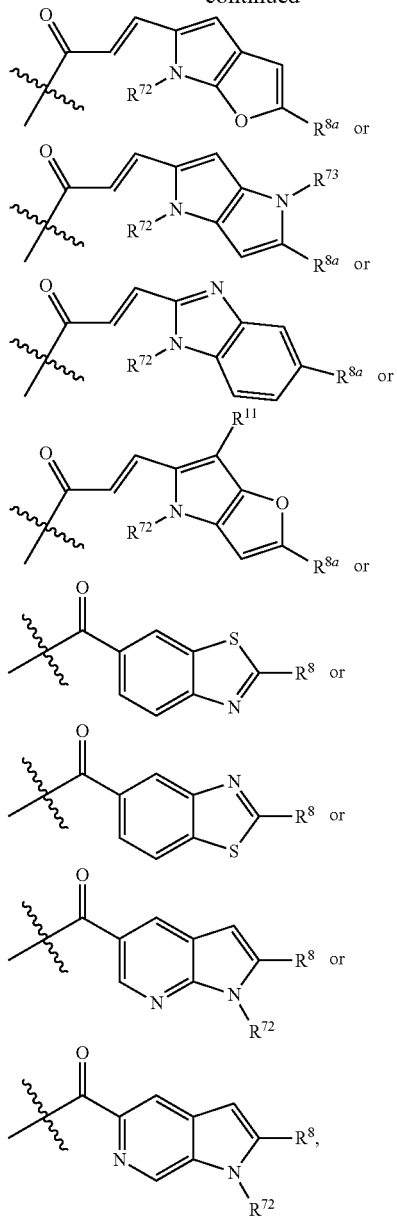
wherein $R^{72}$ and $R^{73}$ are independently selected from H and methyl.
In the exemplary structures of DB2, $R^8$, $R^{8a}$, $R^{9a}$, $R^{10}$, $R^{10a}$, $R^{11}$, $R^{11a}$, $R^{15}$, $R^{16}$, and $R^{21}$ may for example each independently be selected to be H, be or contain another moiety selected from structures DB1-DB9 or a derivative thereof, or be
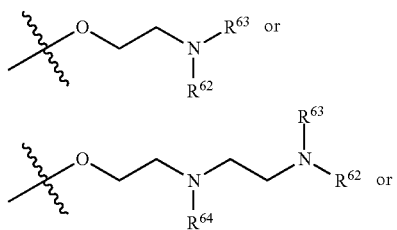

123
-continued
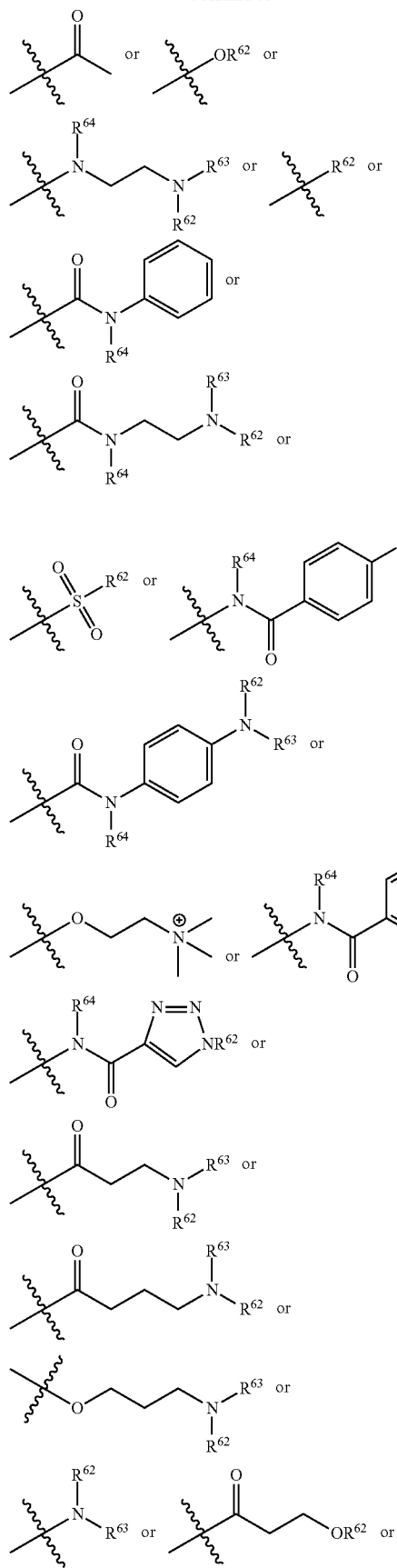
124
-continued
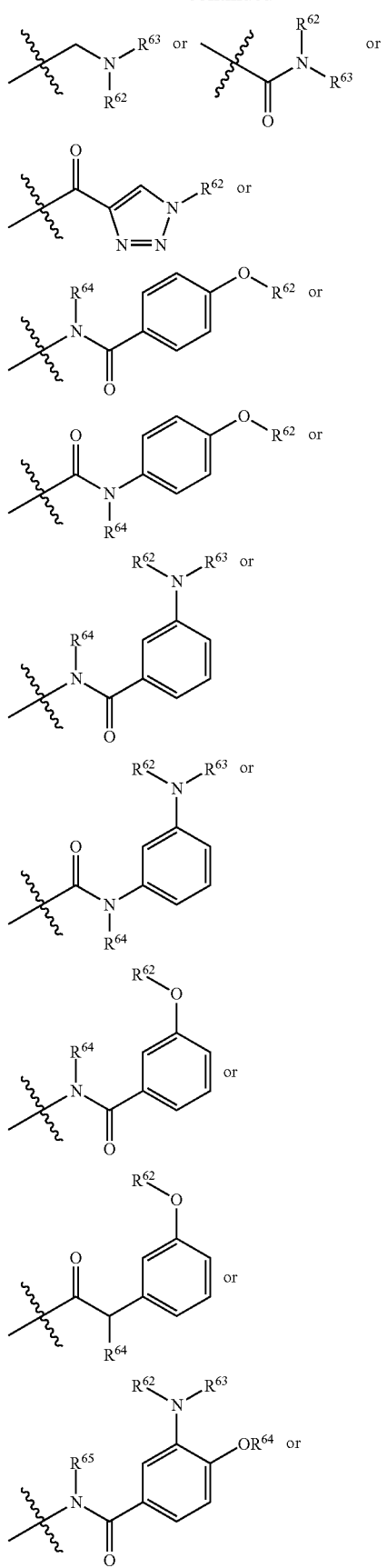

125
-continued
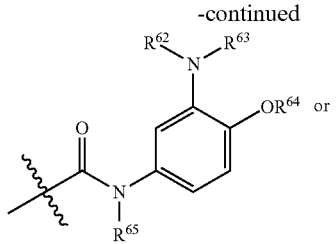
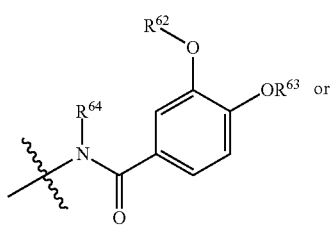
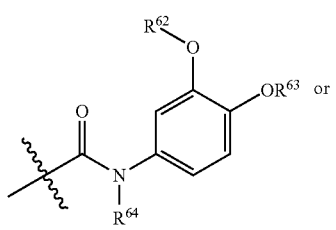

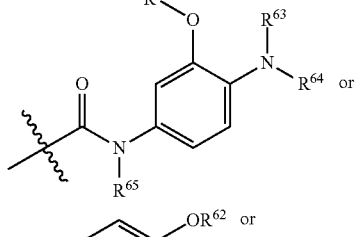
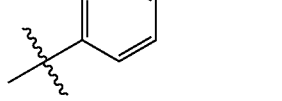
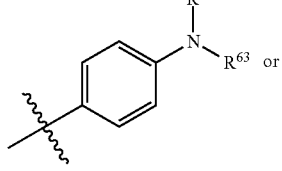
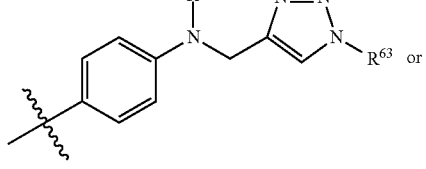
126
-continued
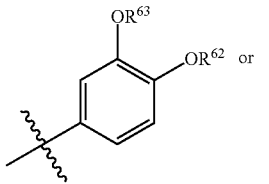
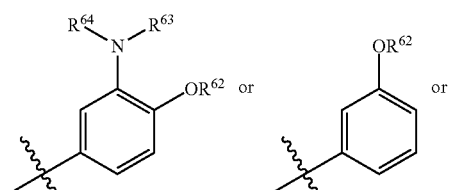
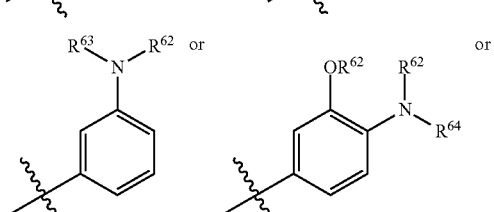
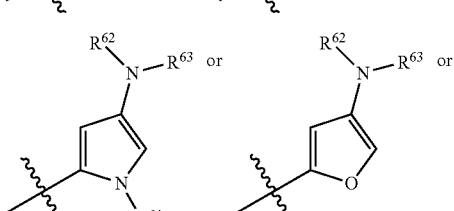
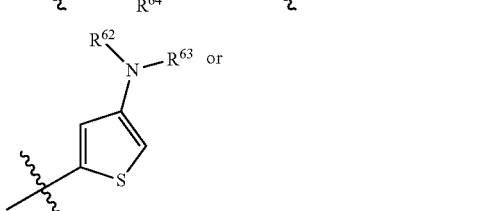
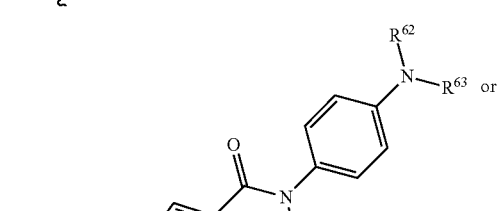
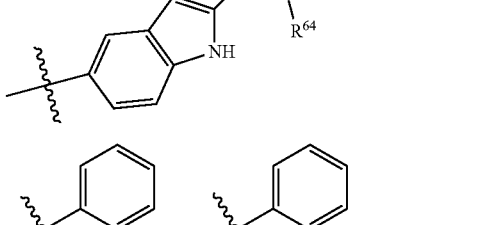
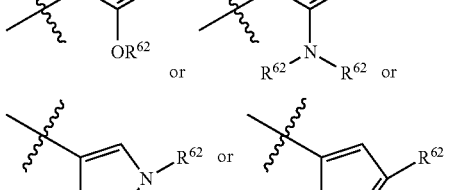
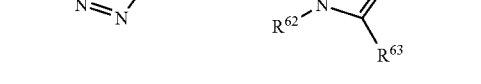

127
-continued
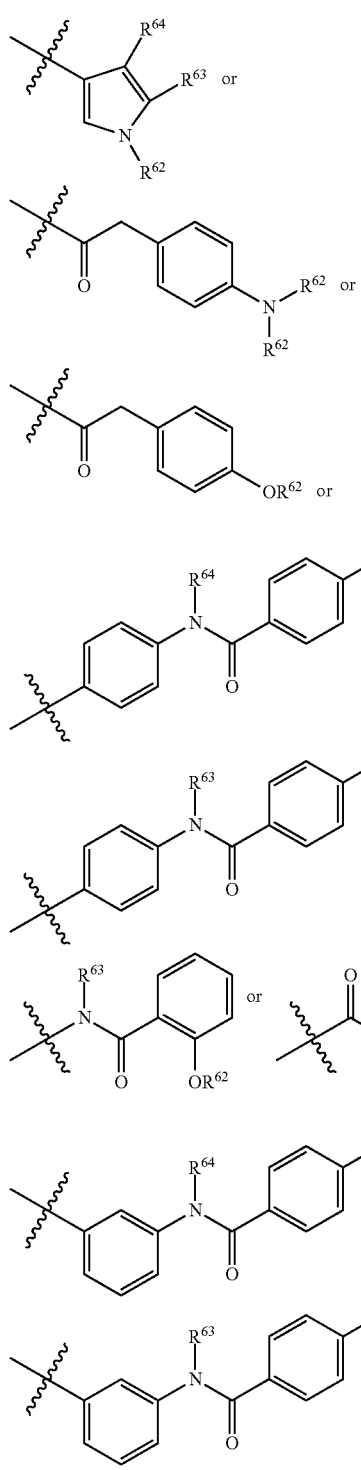
128
-continued
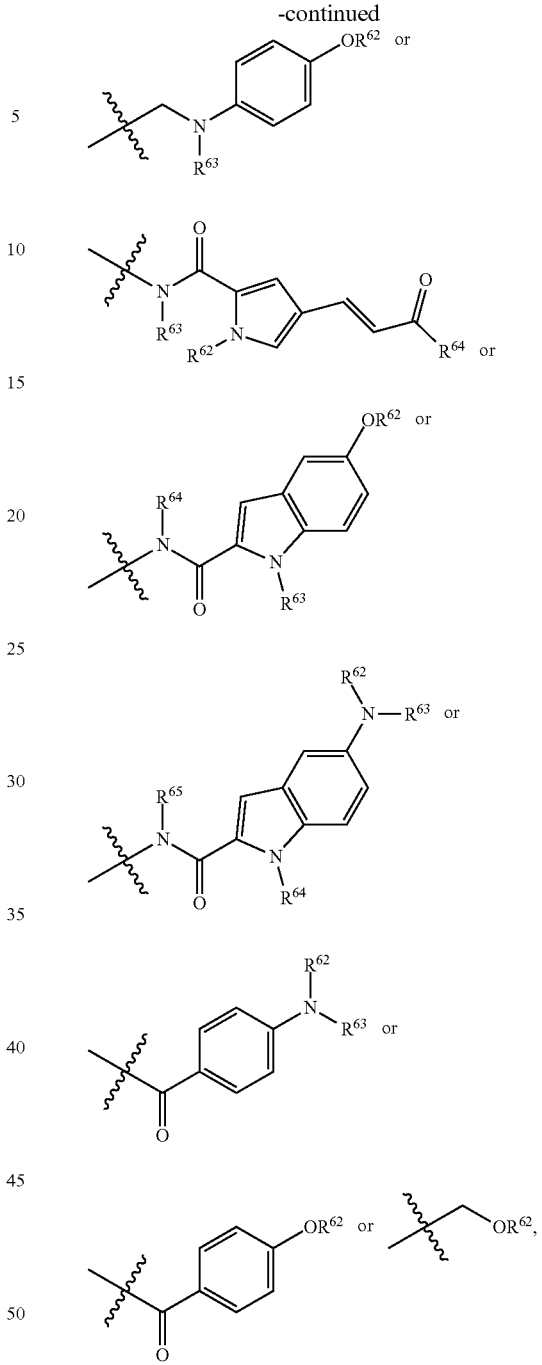
wherein $R^{62}$, $R^{63}$, $R^{64}$, and $R^{65}$ are independently selected from H, $C_{1-3}$ alkyl, and
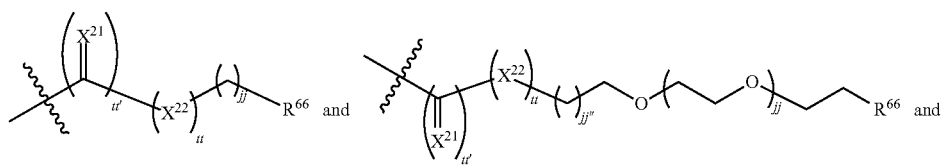

-continued

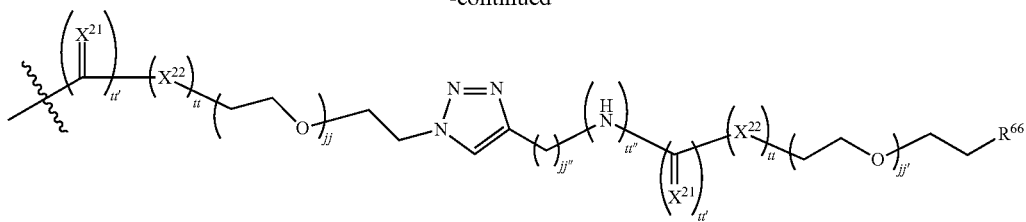

wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

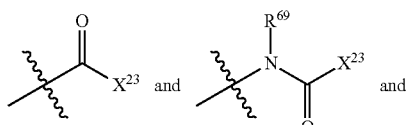

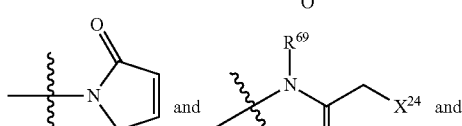

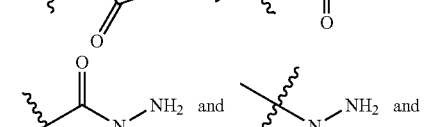

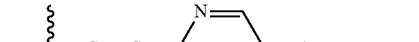

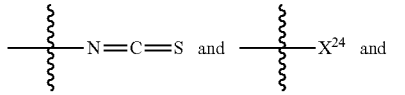

-continued

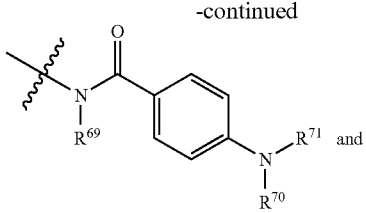

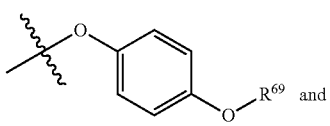

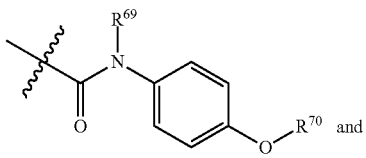

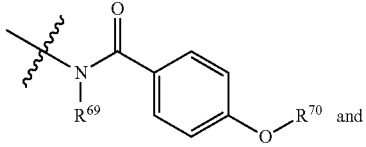

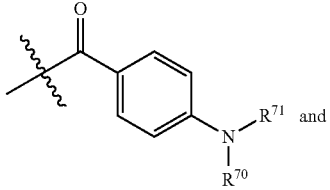

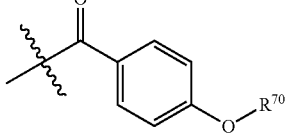

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl, and $R^{69}$, $R^{70}$, and $R^{71}$ are independently selected from methyl and H.

In a further embodiment, the moiety DB2 may for example be

131 132
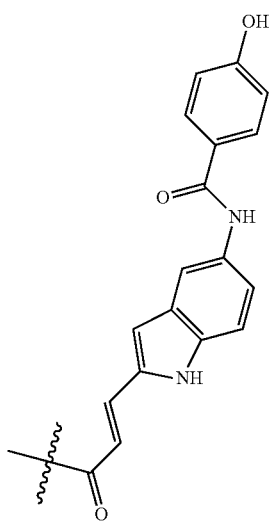 or 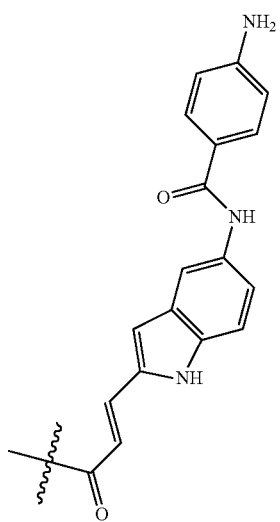 or 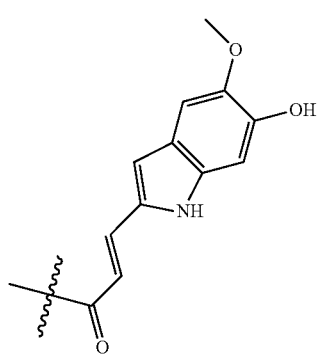 or
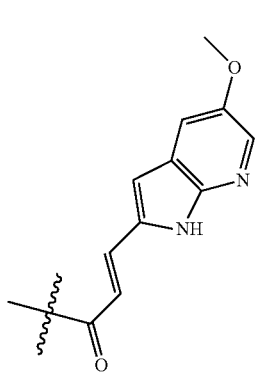 or 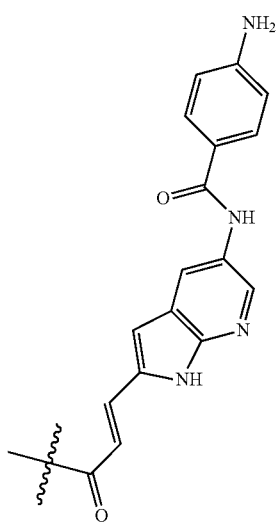 or 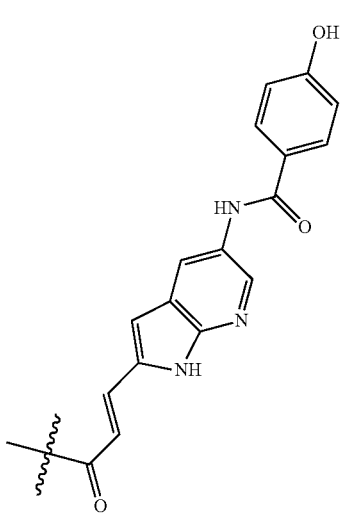 or
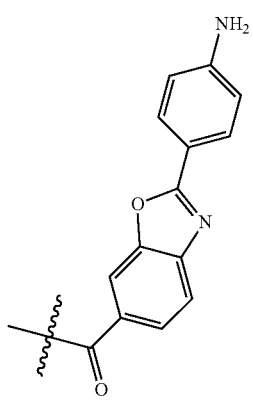 or 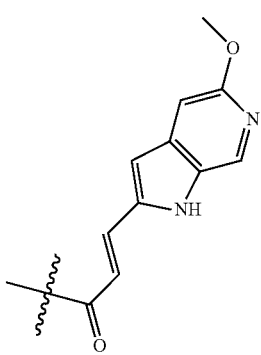 or 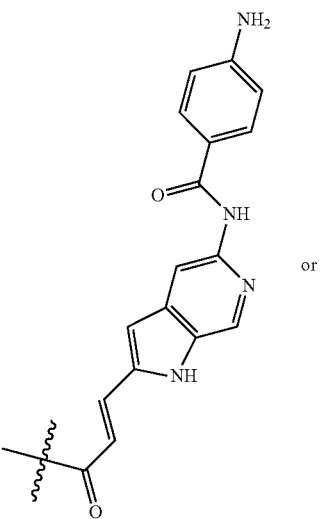

-continued
133
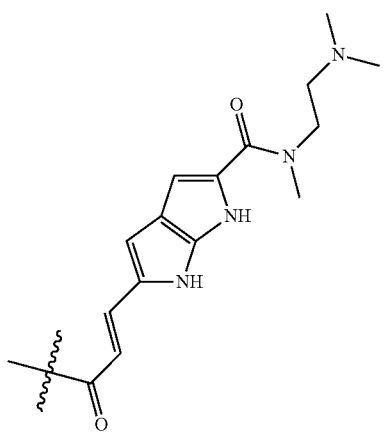 or
134
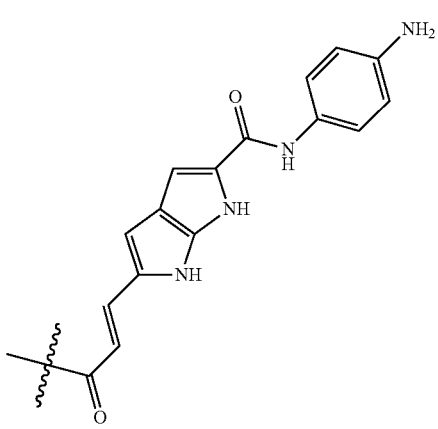 or
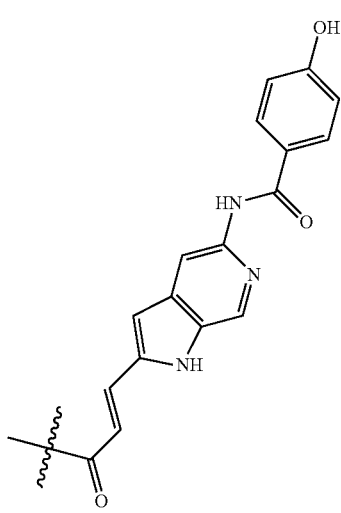 or
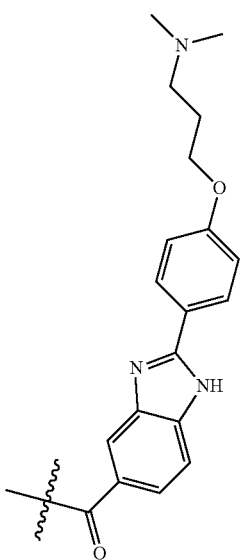 or
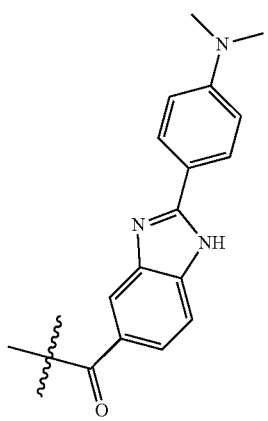 or
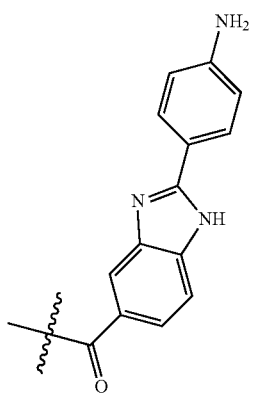 or
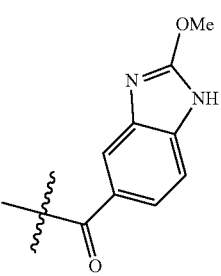 or
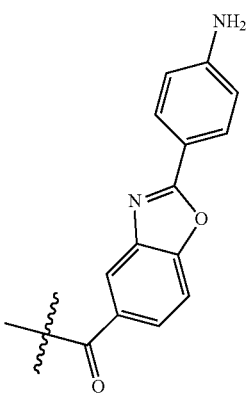 or 135 -continued 136
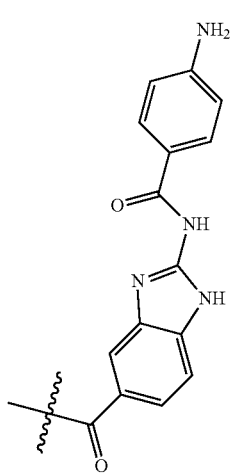
or
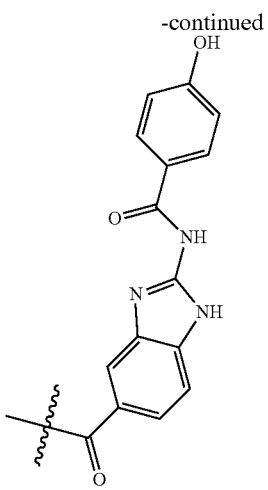
or
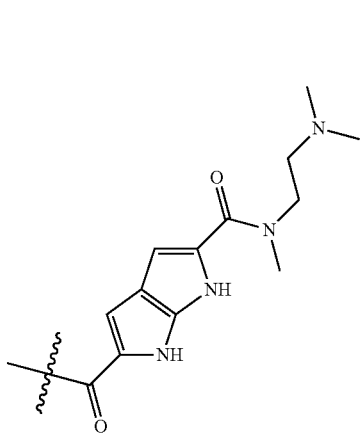
or
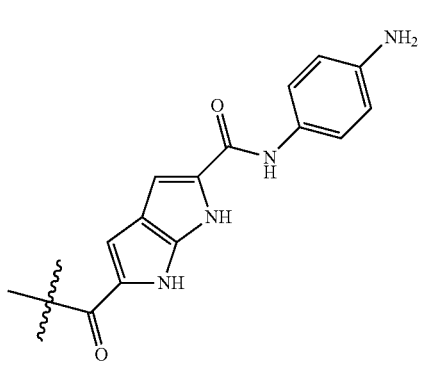
or
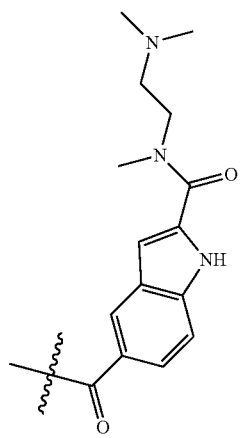
or
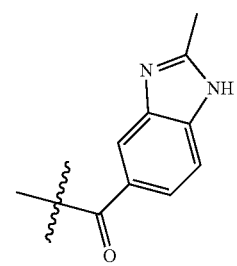
or
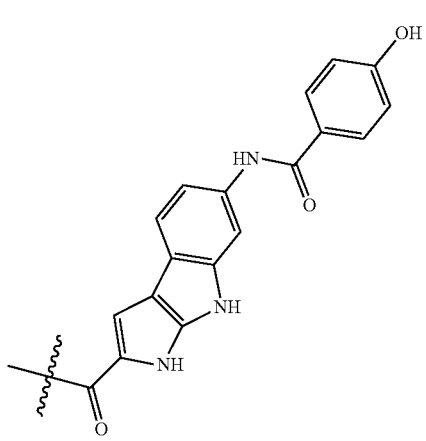
or
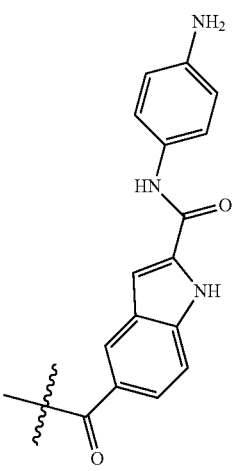
or
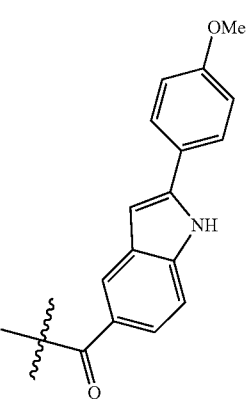
or

137
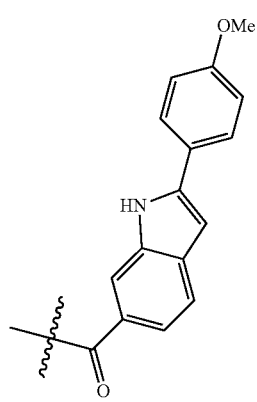 or 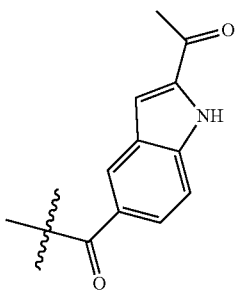 or
138
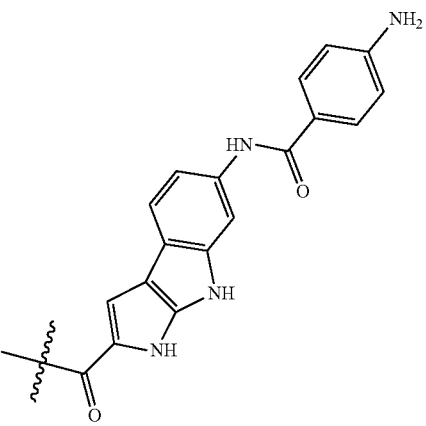 or
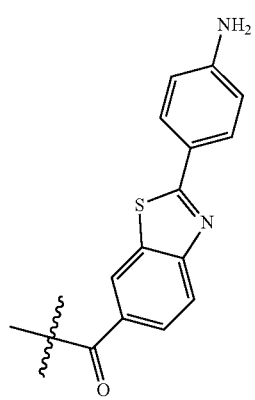 or 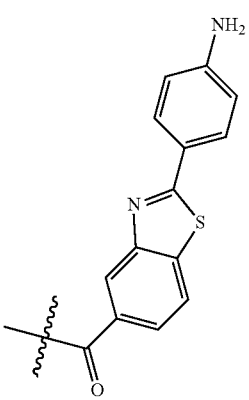 or 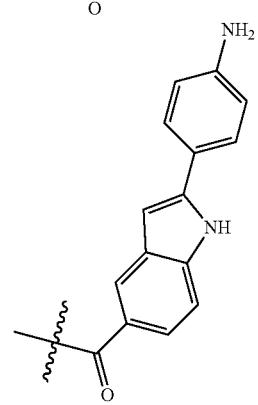 or
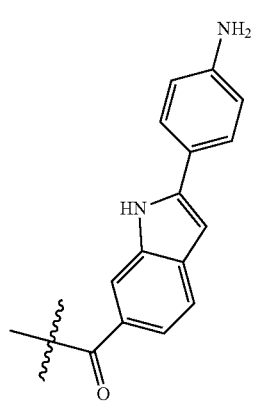 or 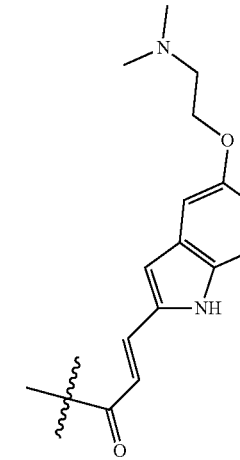 or 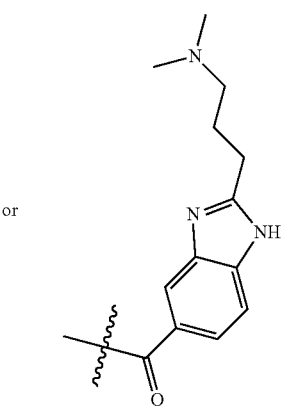 or
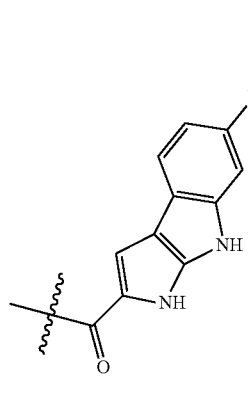 or 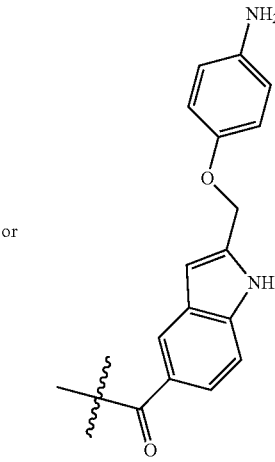 or 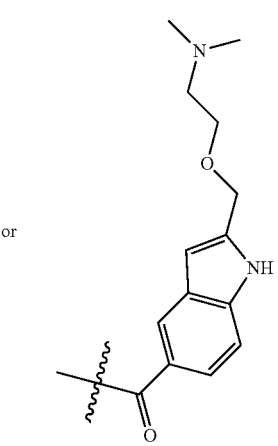 or -continued
139
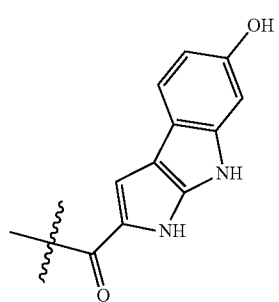 or 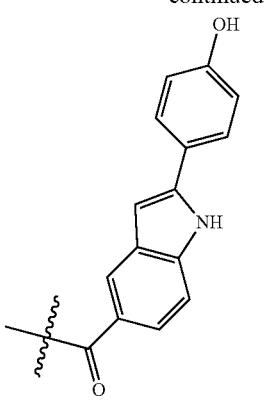 or 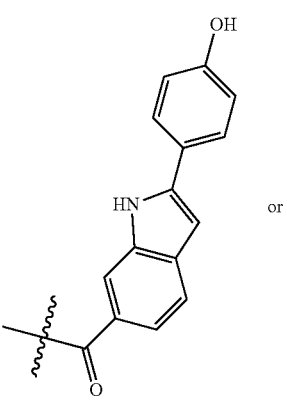
140
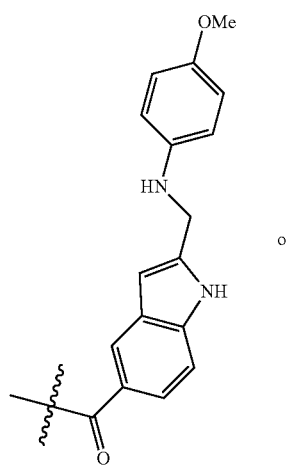 or 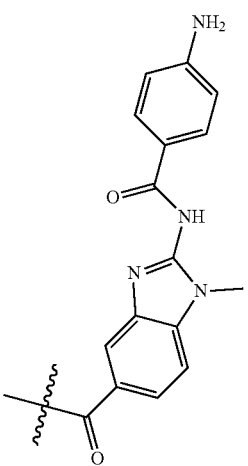 or 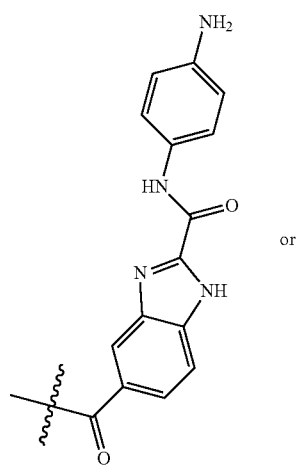
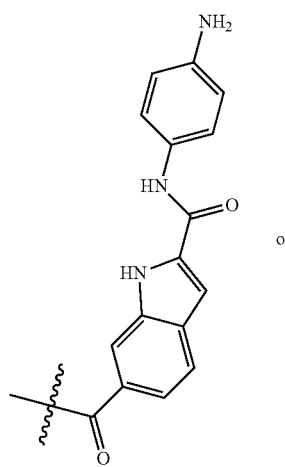 or 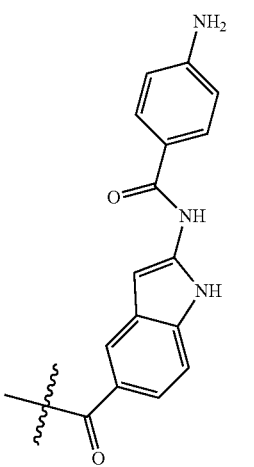 or 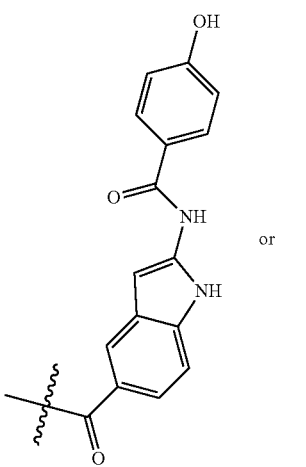

141
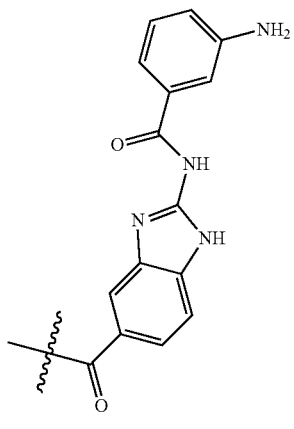
or
142
-continued
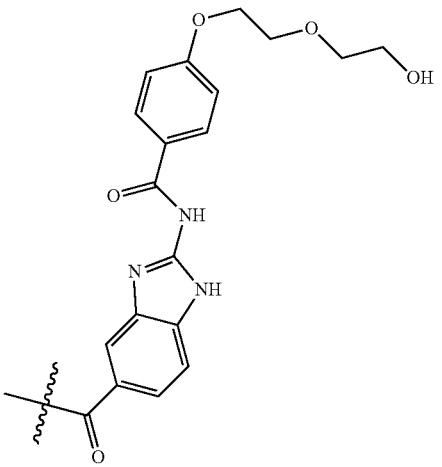
or
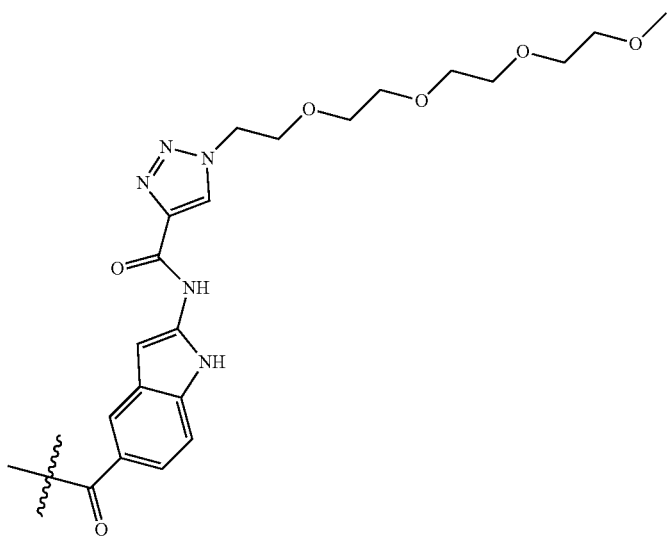
or
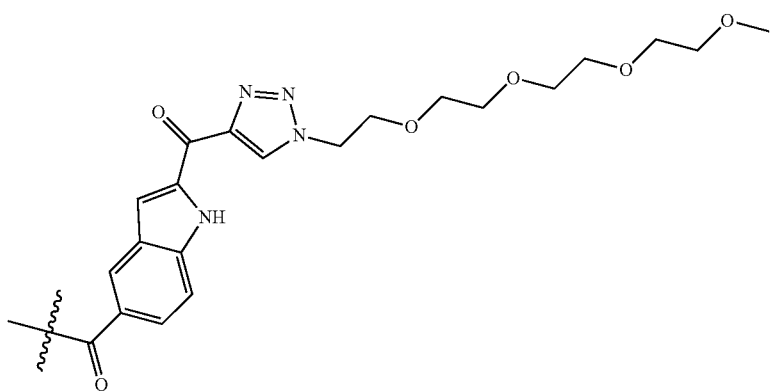
or

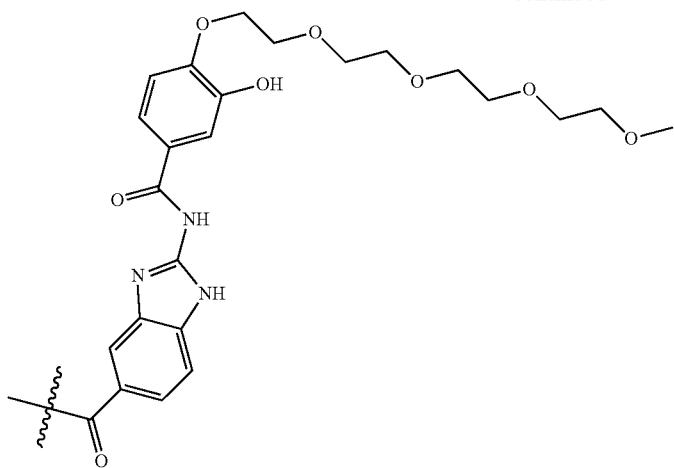
or
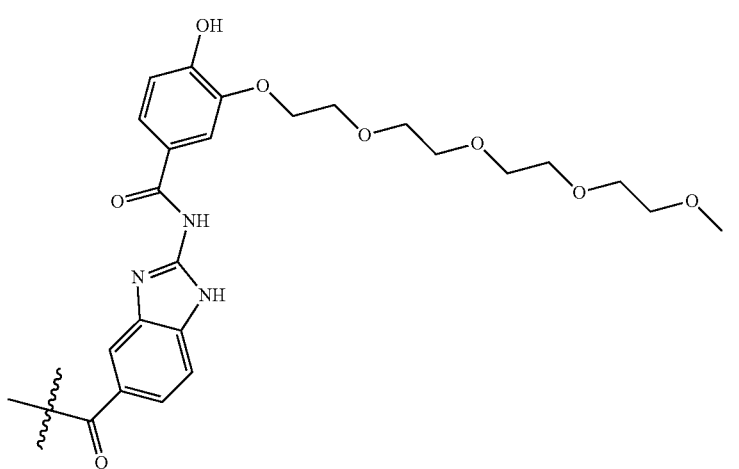
or
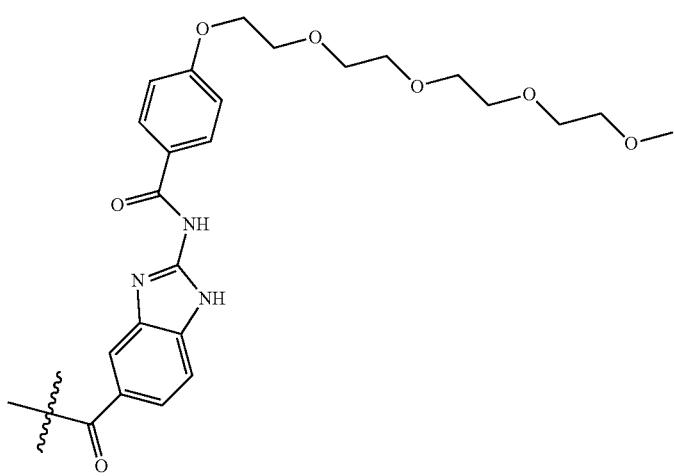
or 145 146
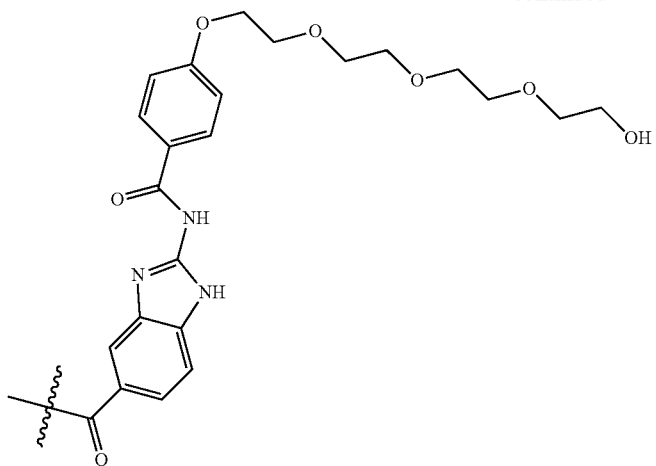 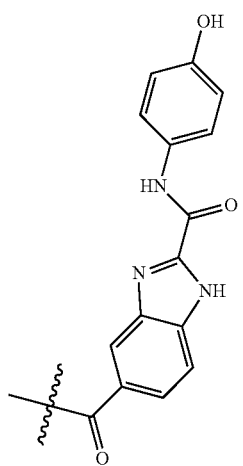
or
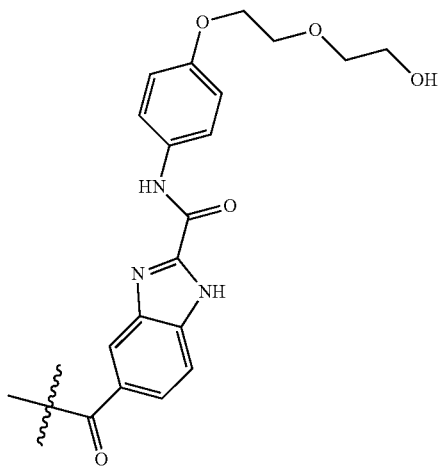
or
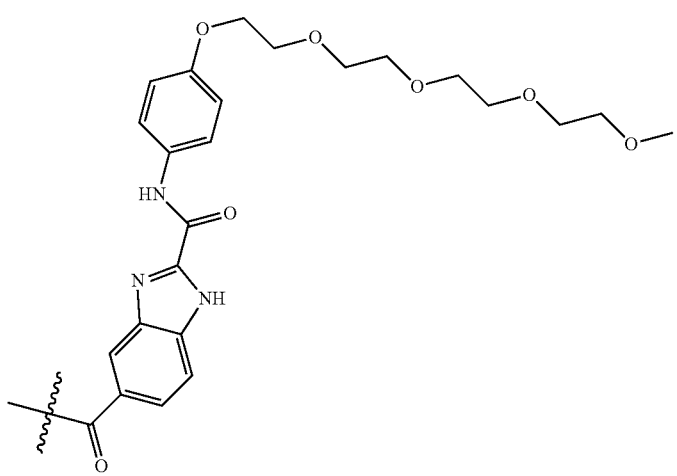
or -continued
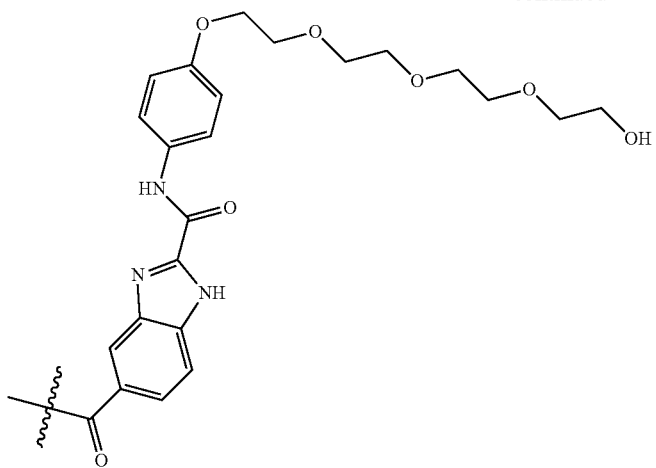
or
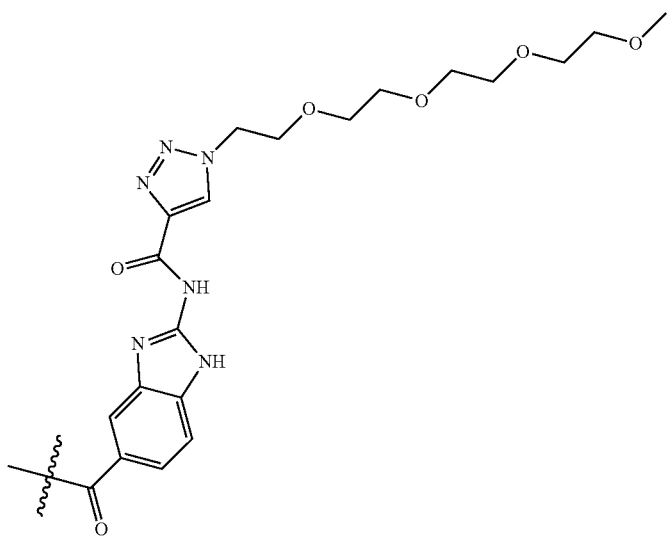
or
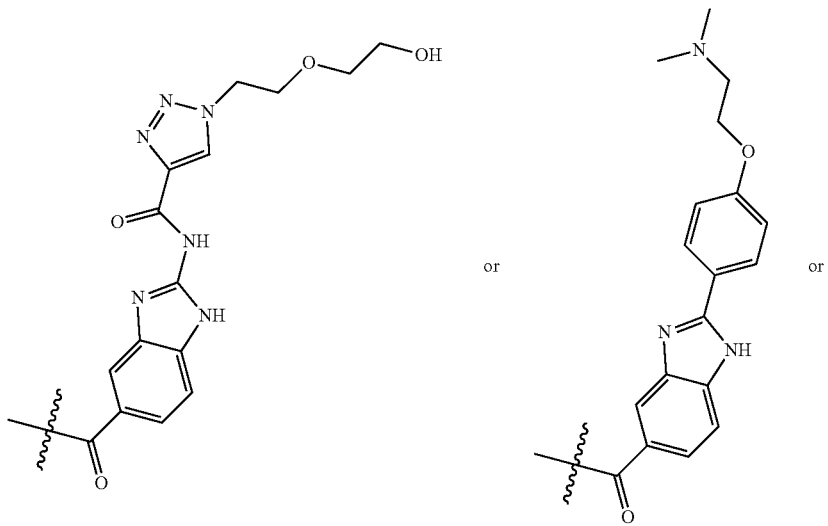
or -continued
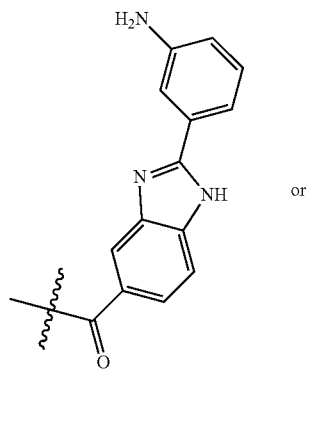 or 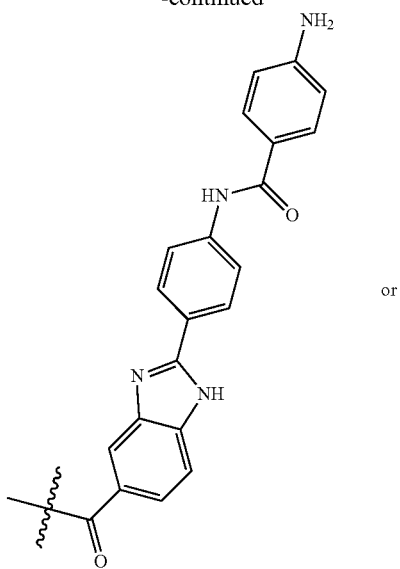 or
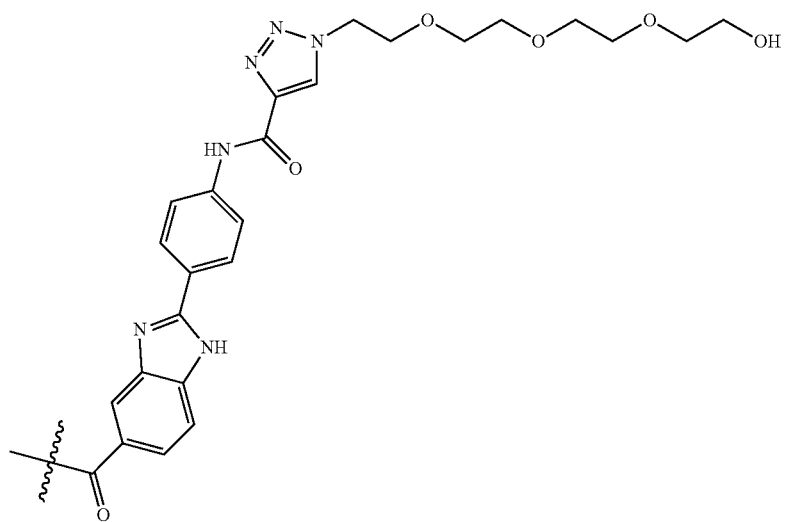 or
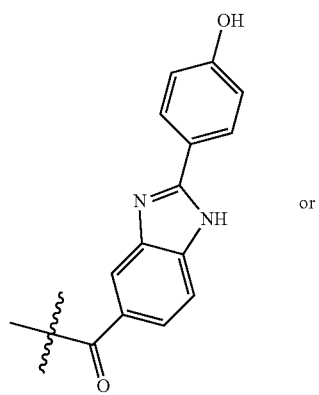 or 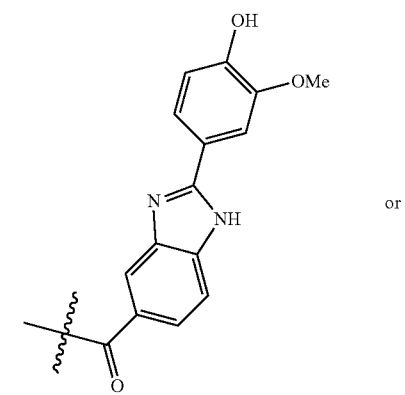 or 151 152
-continued
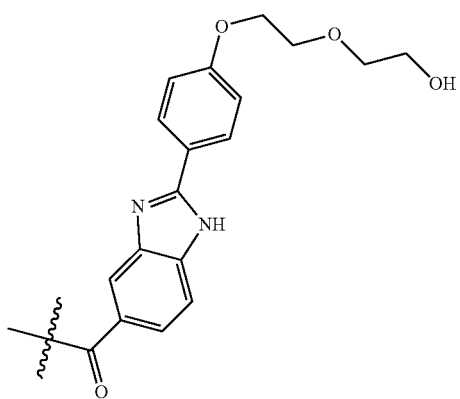
or
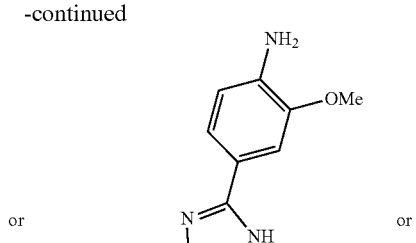
or
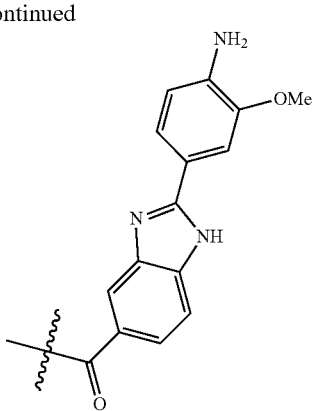
or
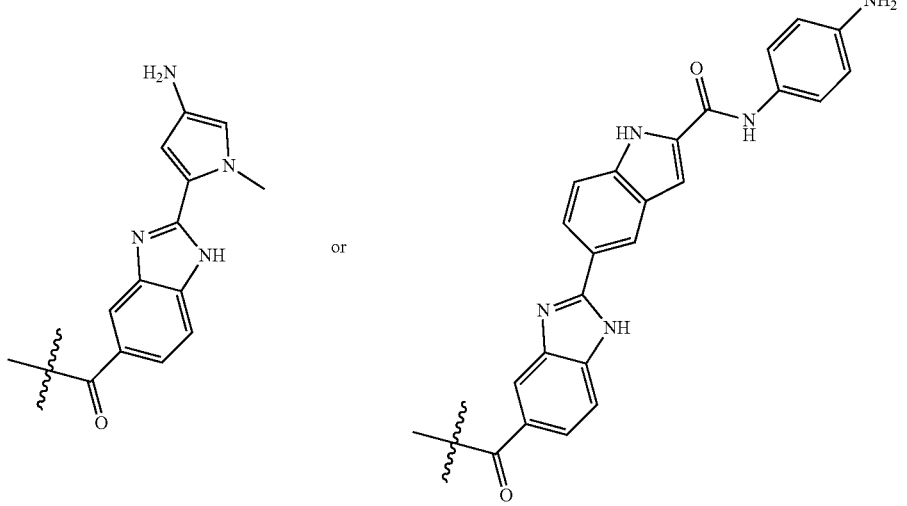
or
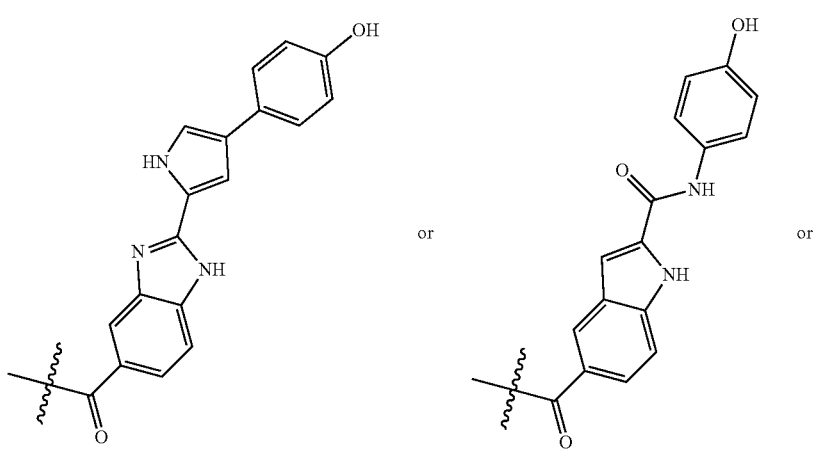

-continued
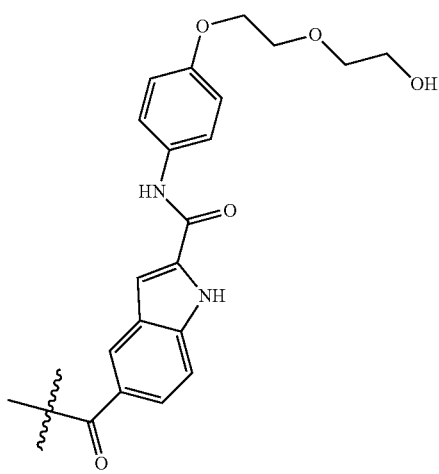
or
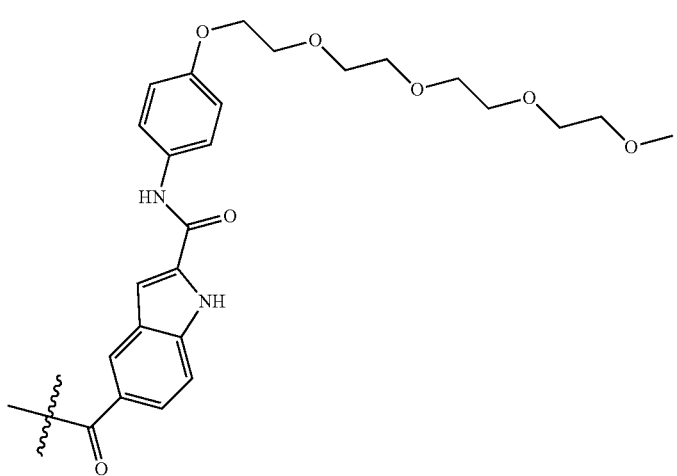
or
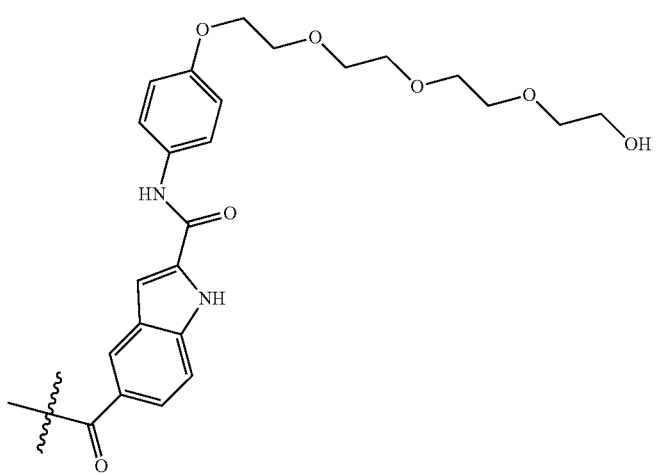
or

155
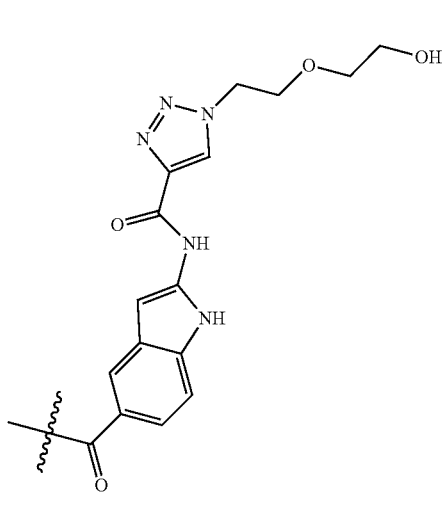 or 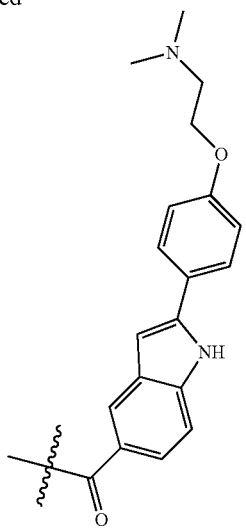
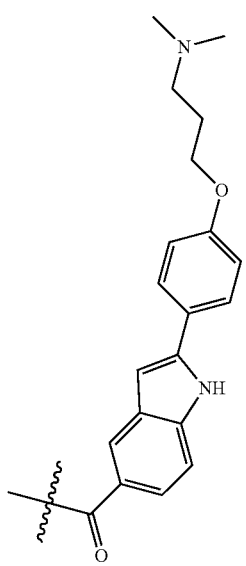 or 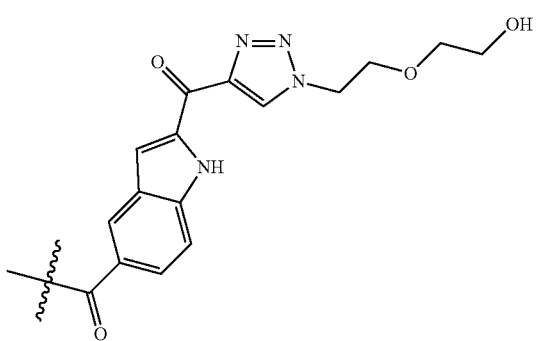 or
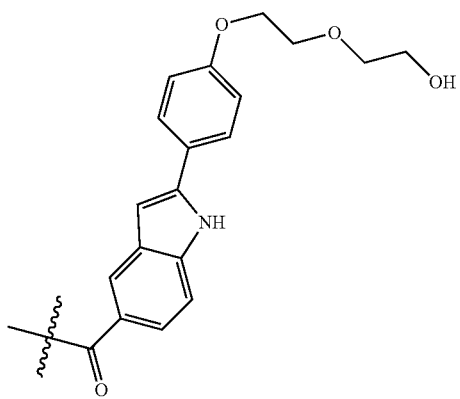 or 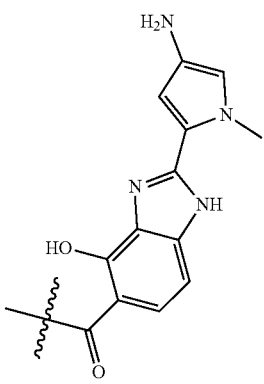

-continued
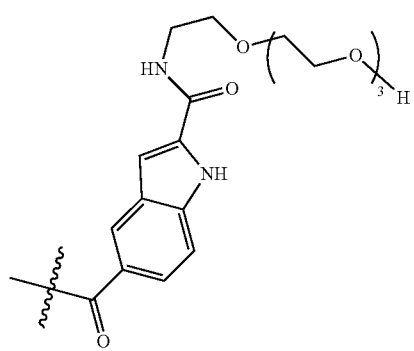
or
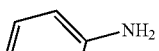
or
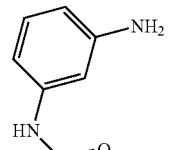
or
or
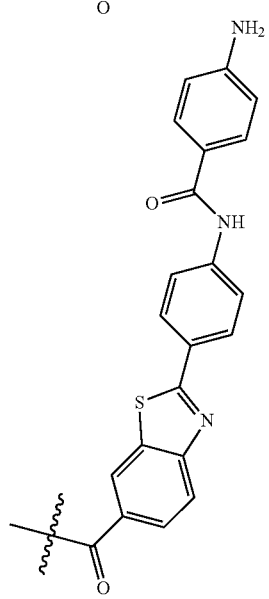
or
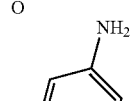
or
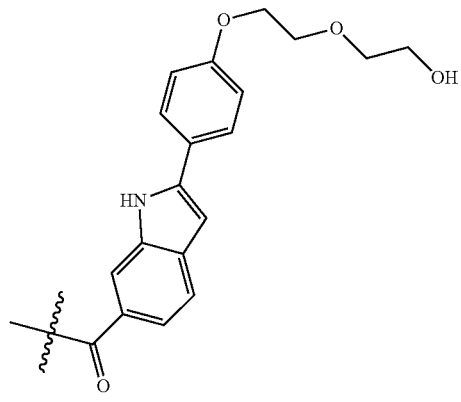
or
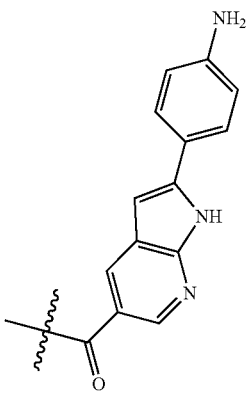
or

159
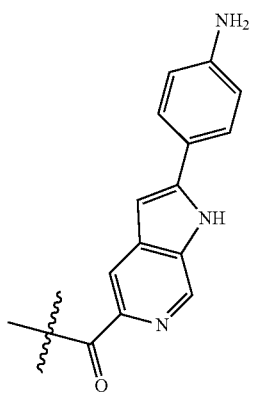
or
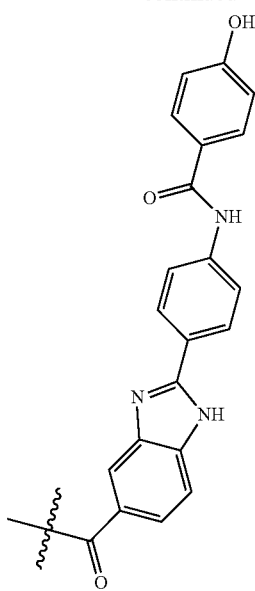
-continued
160
or
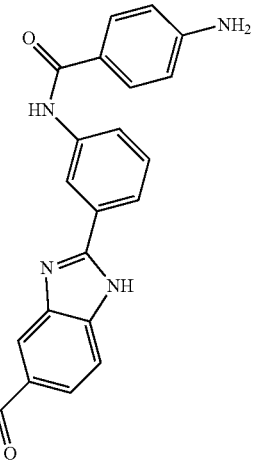
or
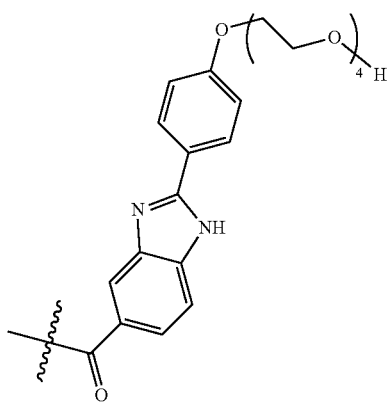
or
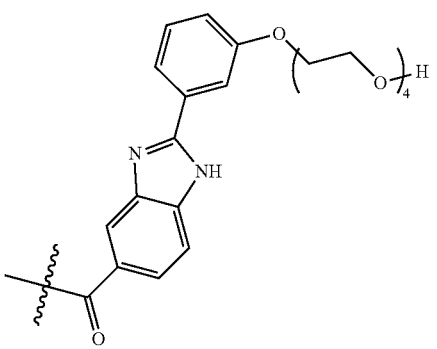
or
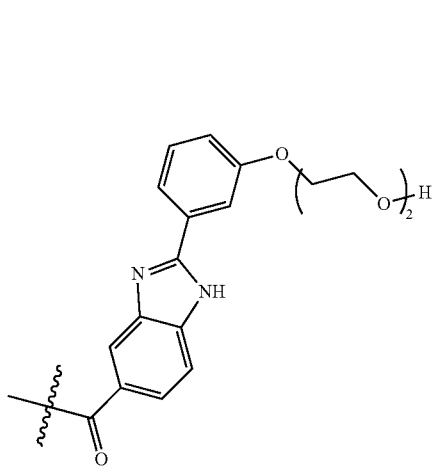
or
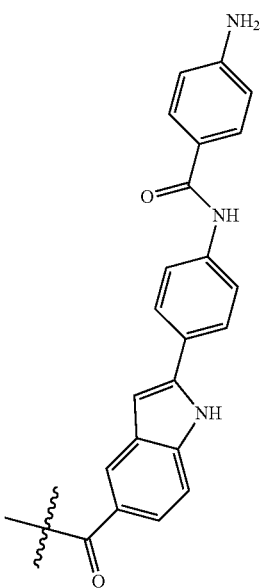
or -continued
161
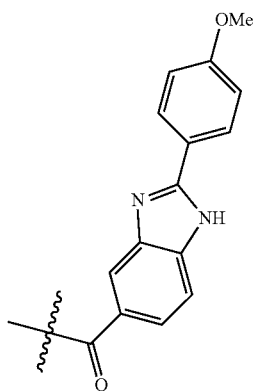 or 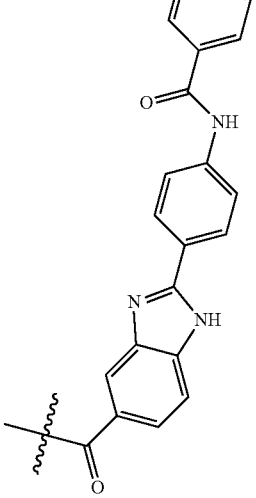 or
162
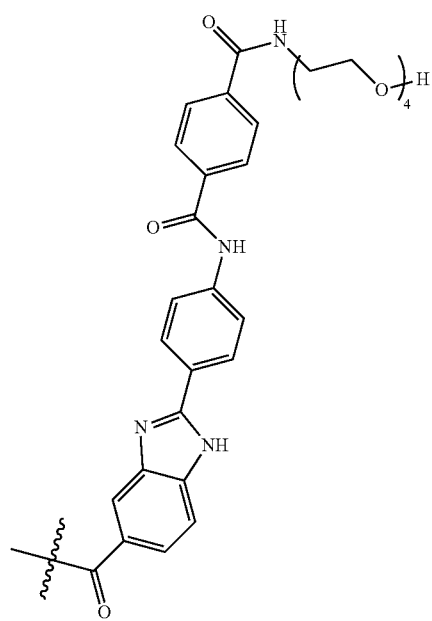 or 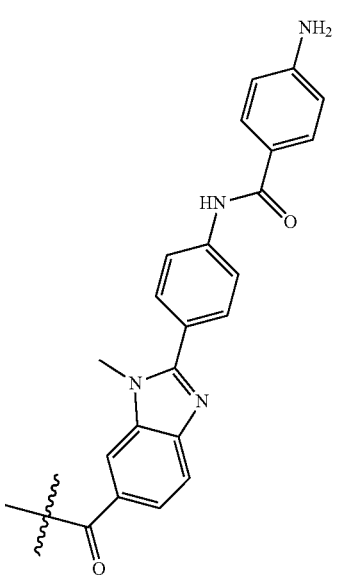 or -continued
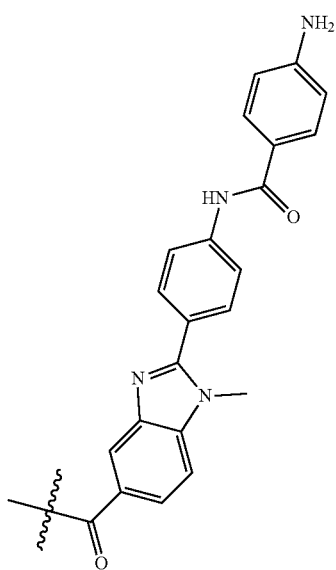 or 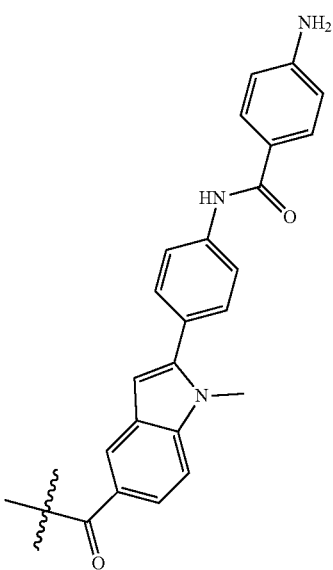 or
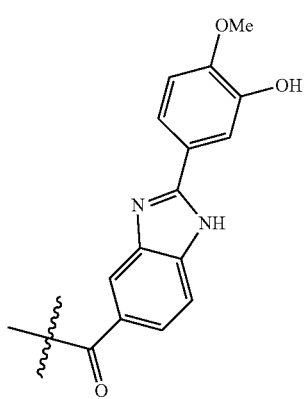 or 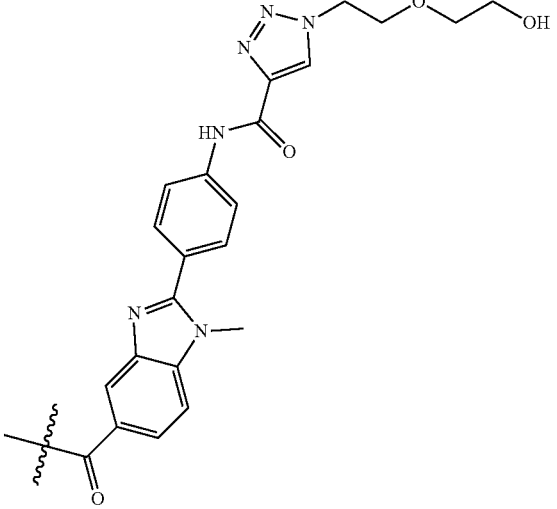 or
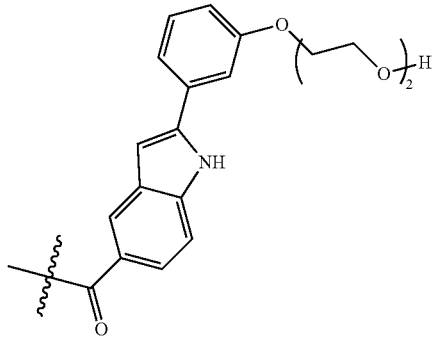 or 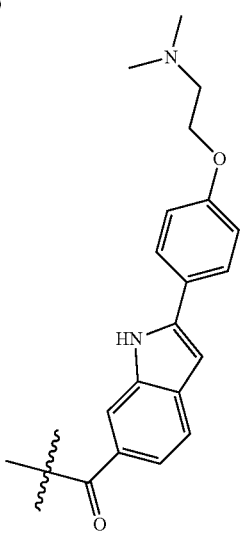 or 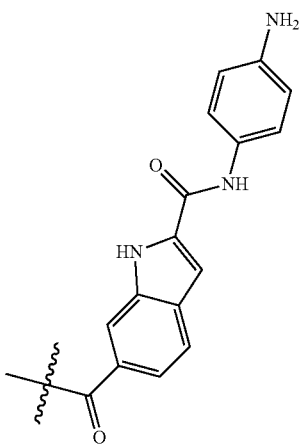
In another aspect of this invention, a compound of formula (I) or (II) has a DNA-binding unit of formula DB3 or DB4. These two moieties comprise structures that are built up of an acetylene moiety coupled to a 5- or 6-membered ring. This ring may be aromatic or non-aromatic. In the latter case, it may be either unsaturated or completely saturated. Furthermore, the 5- or 6-membered ring may be fused to one or more other rings to form an aromatic or non-aromatic ring system. Such a ring system is preferably flat as this may increase the DNA binding affinity. Either polar substituents or heteroatoms in the ring may provide for increased water solubility and may favorably affect the pharmacological properties of a compound of formula (I) or (II). The presence of an acetylene moiety in DNA-binding units DB3 and DB4 may provide for a handle that allows detoxification by means of for example oxidation or hydration.

The moiety DB3 may for example be

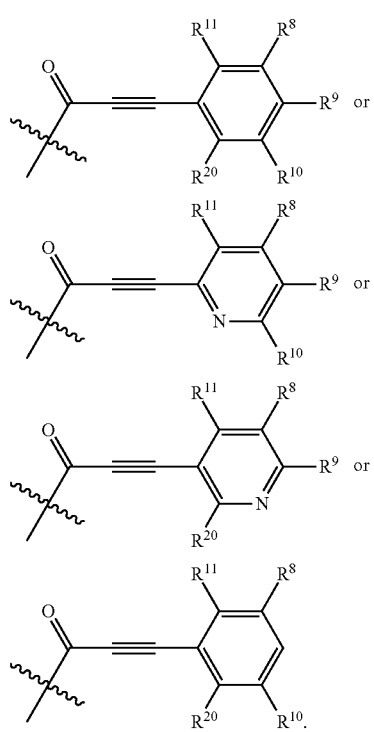

The moiety DB4 may for example be

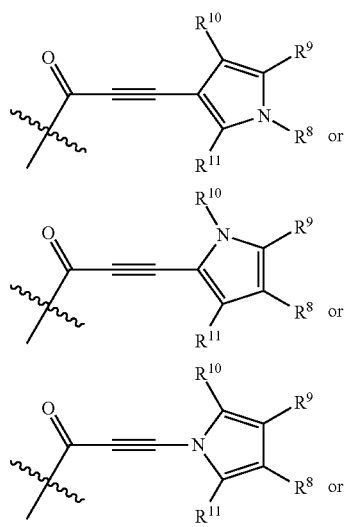

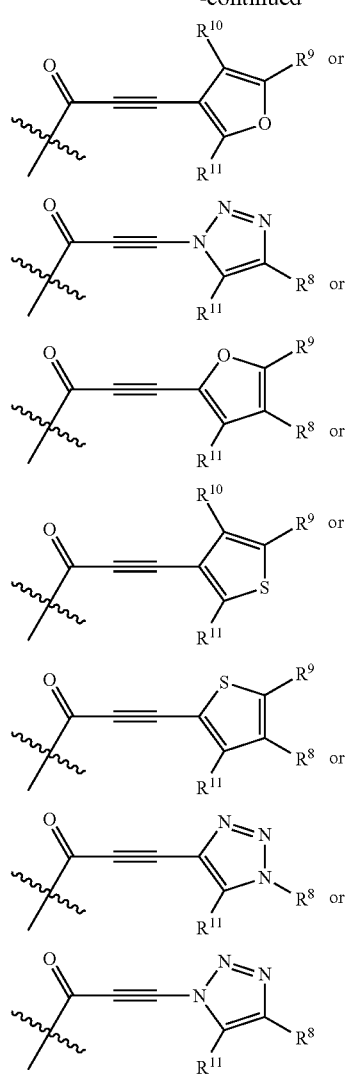

In a more specific embodiment, the moiety DB3 may for example be

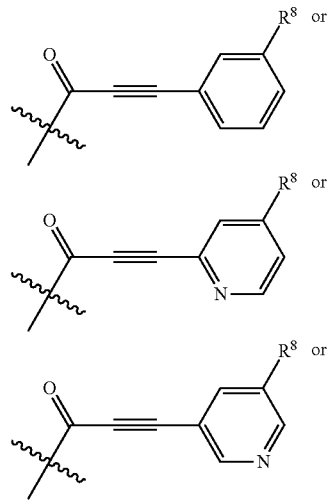

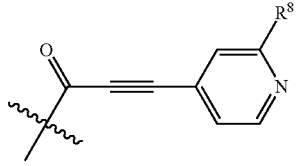
In another more specific embodiment, the moiety DB4 may for example be
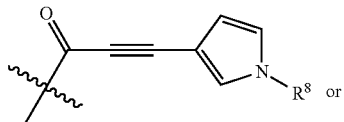
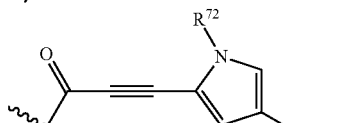
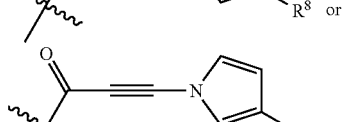
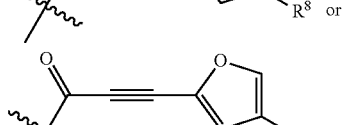
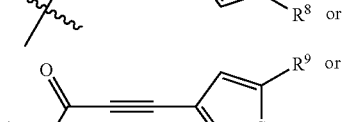
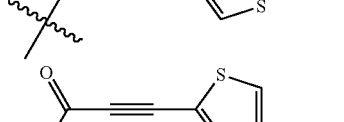
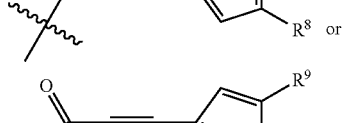
wherein $R^{72}$ is selected from H and methyl.
In the exemplary structures of DB3 and DB4, $R^8$, $R^9$, $R^{10}$, $R^{11}$, and $R^{20}$ may for example each independently be selected to be H, be or contain another moiety selected from structures DB1-DB9 or a derivative thereof, or be
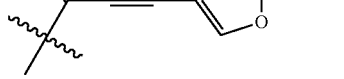
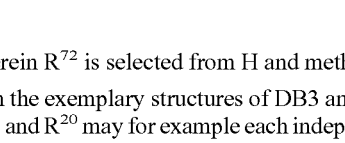
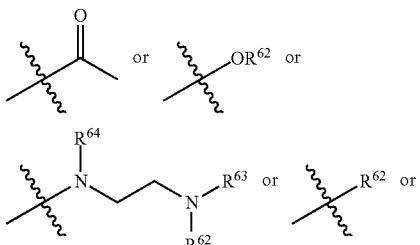
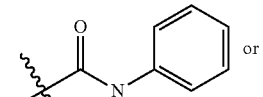
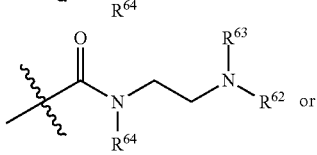
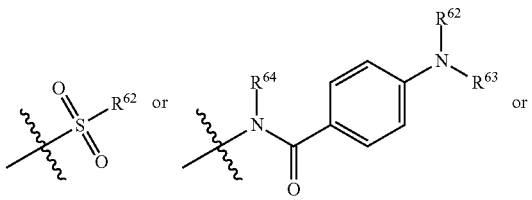
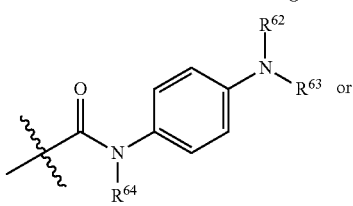
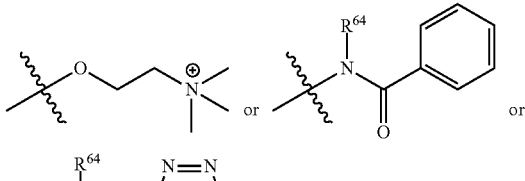
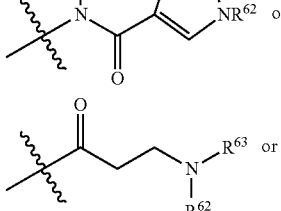
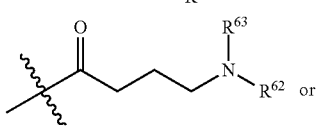
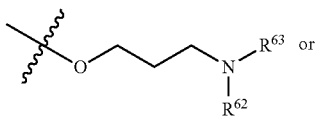
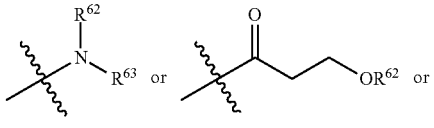

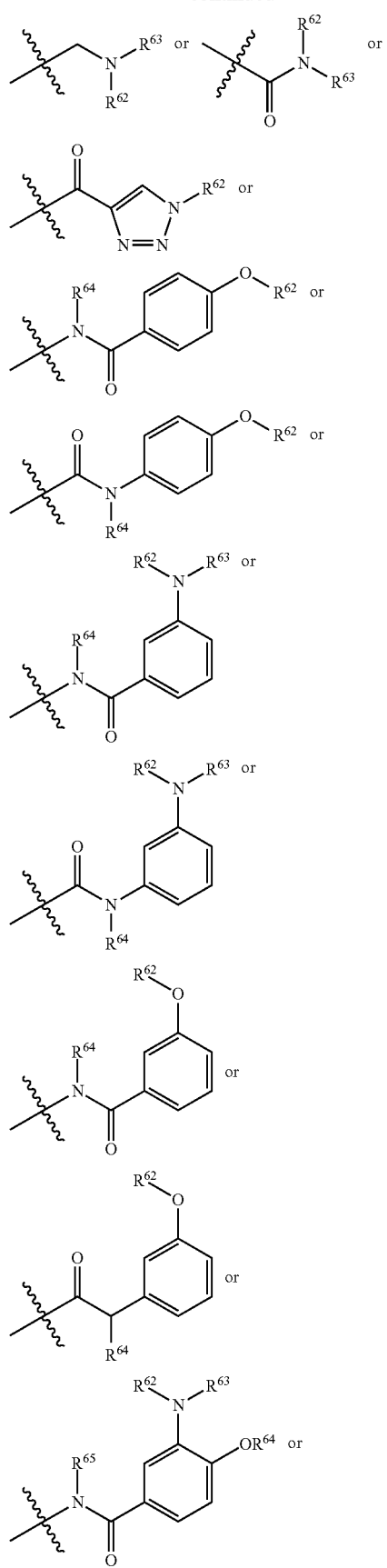
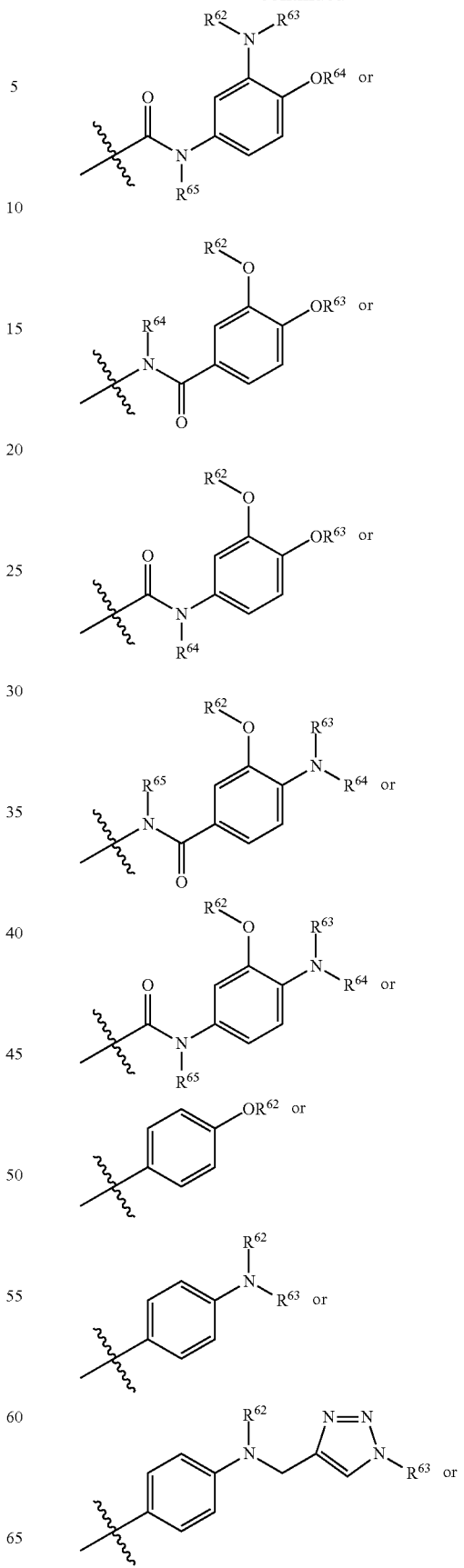

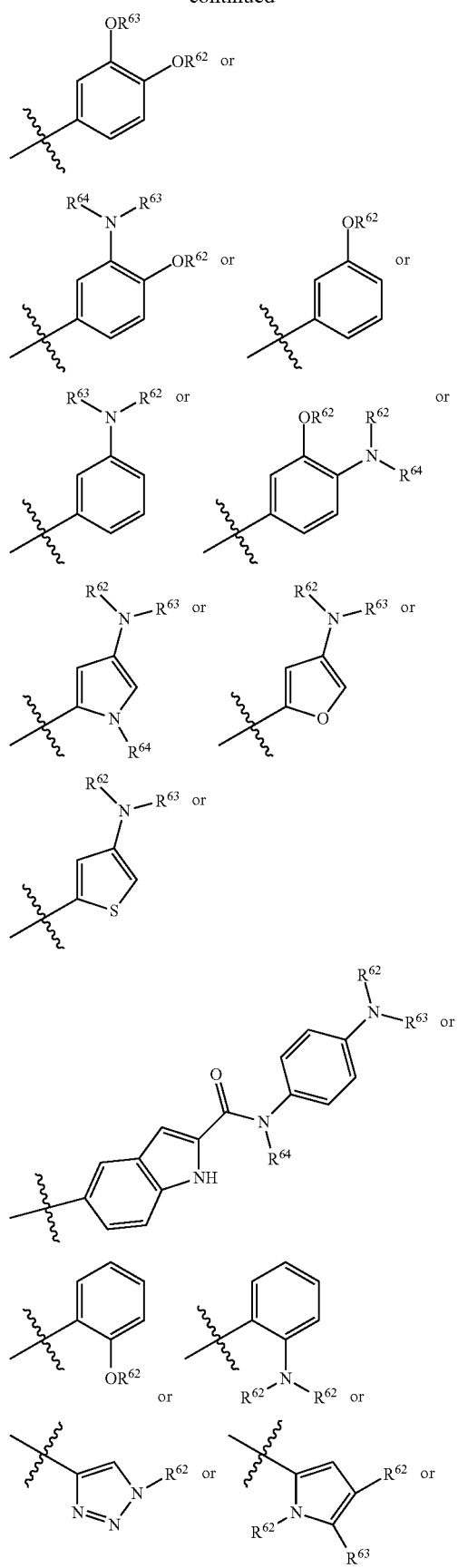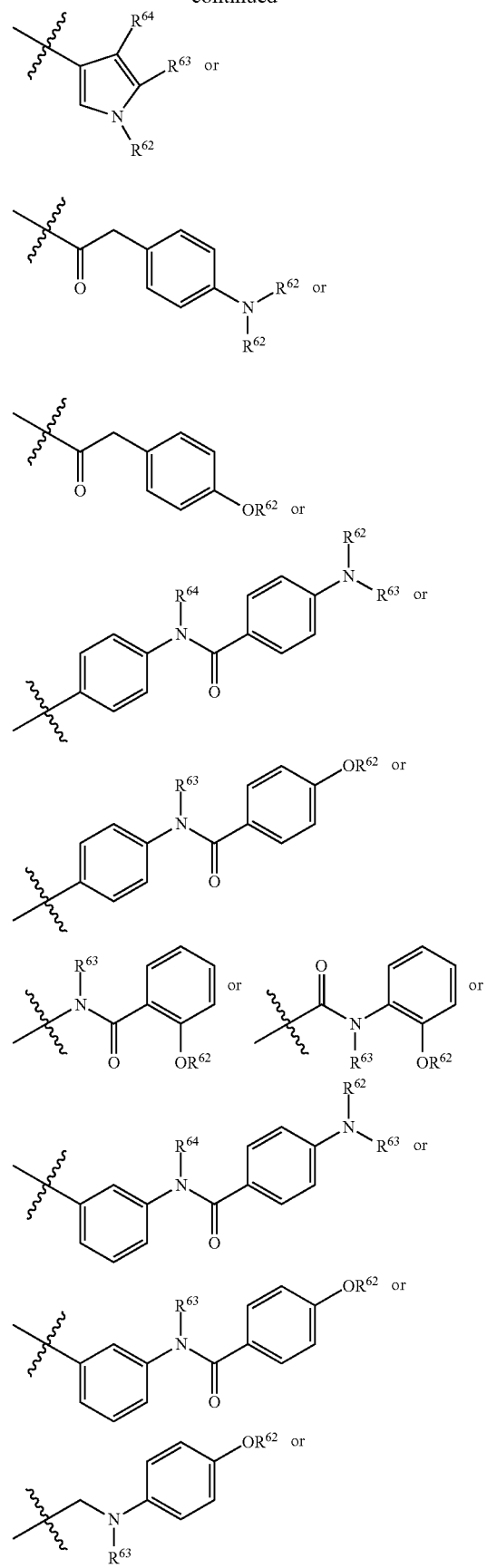

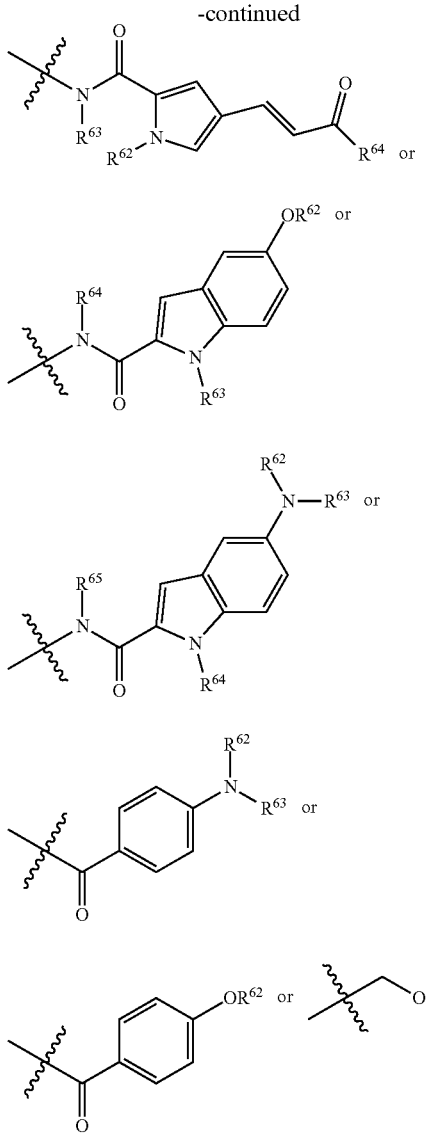

wherein R$^{62}$, R$^{63}$, R$^{64}$, and R$^{65}$ are independently selected from H, C$_{1-3}$ alkyl, and wherein jj, jj', and jj" are independently selected from 0 to 8, each tt, tt', and tt" is independently selected from 0 and 1, each X$^{21}$ and X$^{22}$ is independently selected from O, S, NR$^{67}$, H$_2$, and C(R$^{67}$)R$^{68}$, wherein R$^{67}$ and R$^{68}$ are independently selected from H and optionally substituted C$_{1-3}$ alkyl or C$_{1-3}$ heteroalkyl, and R$^{66}$ is selected from H, COOH, CO$_2$Me, OH, OMe, NR$^{69}$R$^{70}$, NR$^{69}$C(O)CH$_3$, SH, SMe,

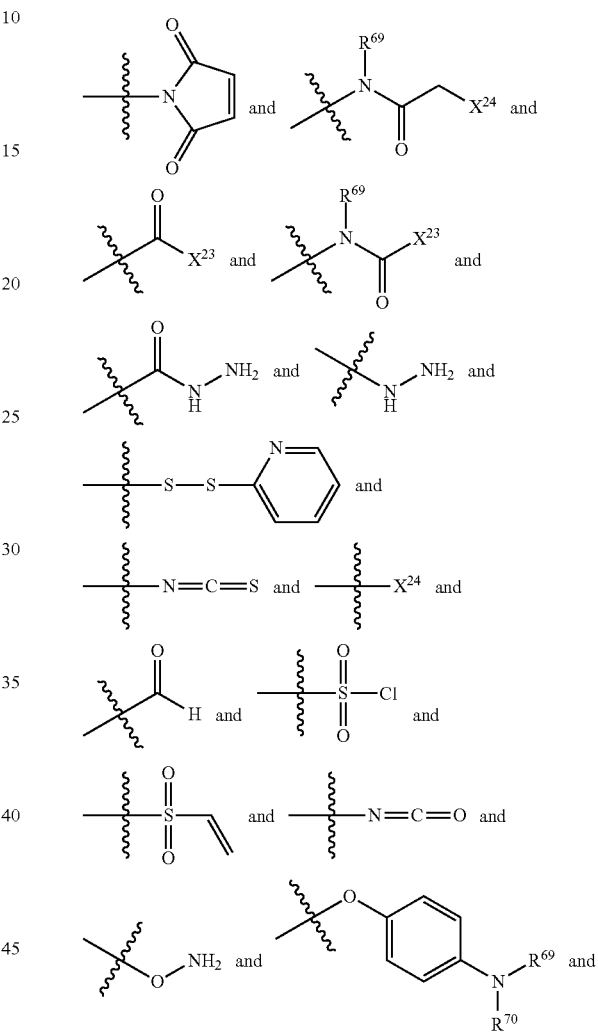

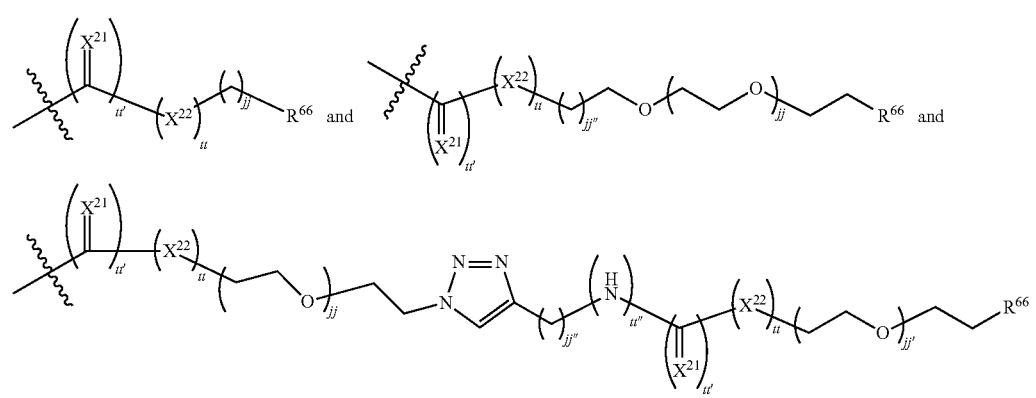

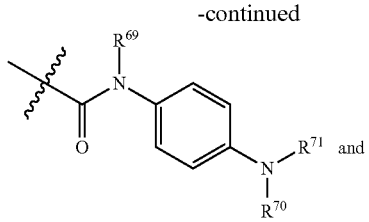 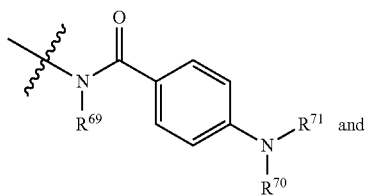 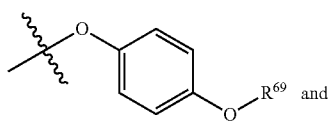 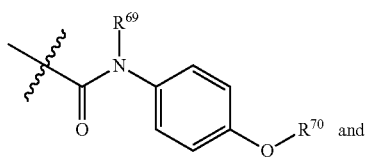 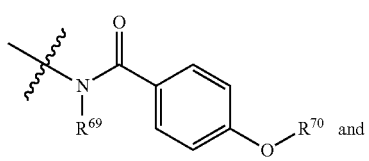 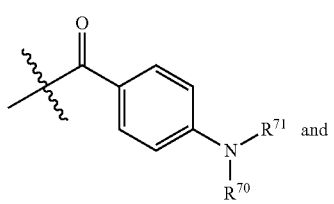 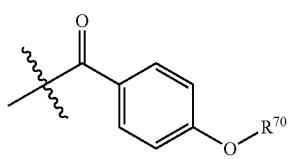

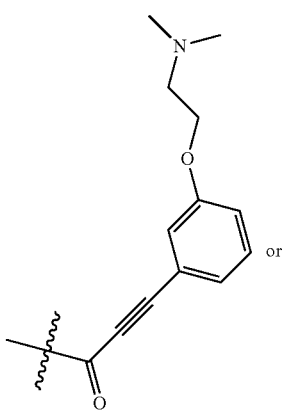 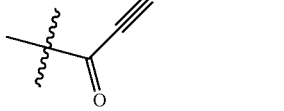 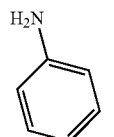 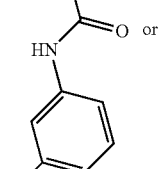 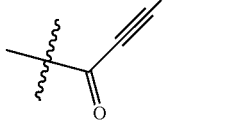 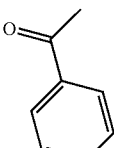 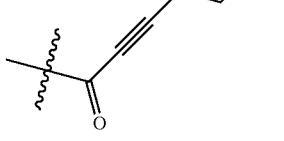 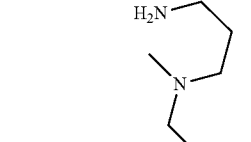 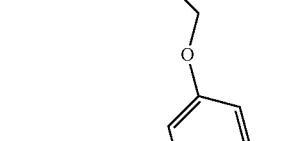 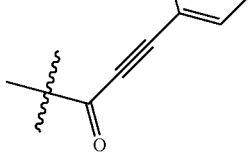

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl, and $R^{69}$, $R^{70}$, and $R^{71}$ are independently selected from methyl and H.

In a further embodiment, the moiety DB3 may for example be

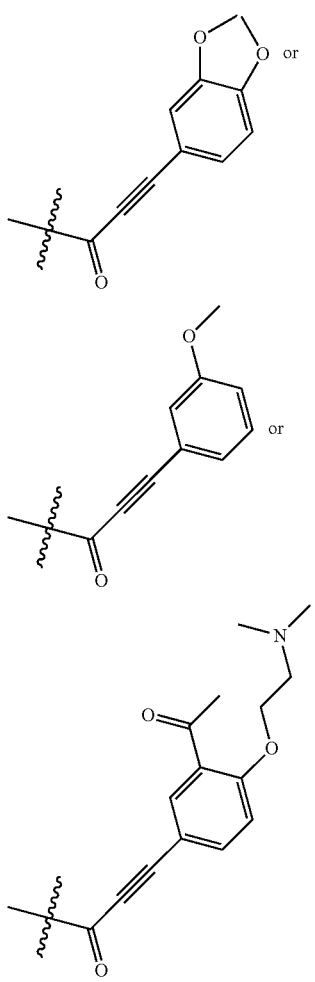

In yet a further embodiment, the moiety DB4 may for example be

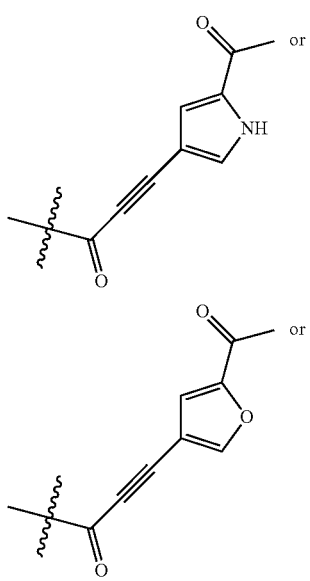

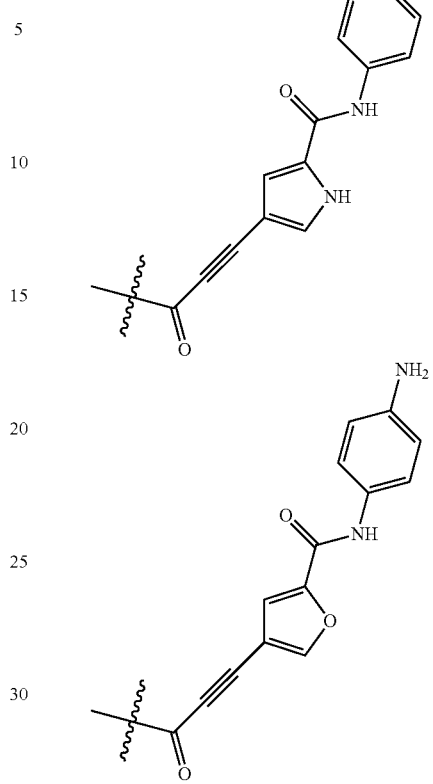

In another aspect of this invention, a compound of formula (I) or (II) has a DNA-binding unit of formula DB5. This moiety comprises structures that are built up of a 5-membered or 6-membered ring coupled to an optionally substituted vinyl moiety. The 5-membered or 6-membered ring may be aromatic or non-aromatic. In the latter case it may be either unsaturated or completely saturated. Polar substituents or heteroatoms in the ring and/or polar substituents on the vinyl group may provide for increased water solubility and favorably affect the pharmacological properties of a compound of formula (I) or (II). Aromatic substituents on the ring or vinyl moiety may increase the binding affinity. The presence of a vinyl moiety in DNA-binding unit DB5 may provide for a handle that allows detoxification by means of for example oxidation or hydration.

The moiety DB5 may for example be

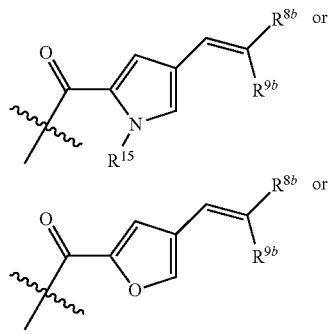

-continued
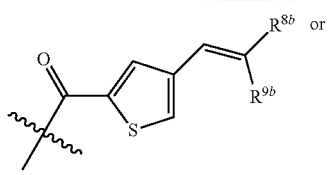
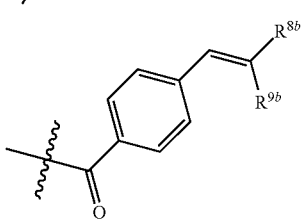
In the exemplary structures of DB5, $R^{8b}$, $R^{9b}$, and $R^{15}$ may for example each independently be selected to be H, be or contain another moiety selected from structures DB1-DB9 or a derivative thereof, or be
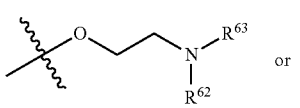
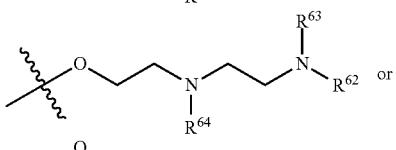
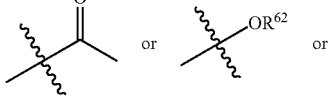
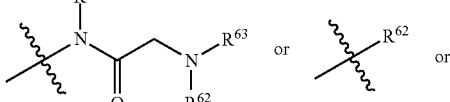
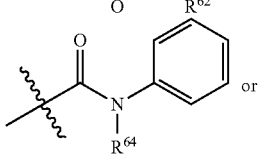
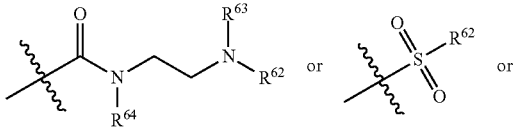
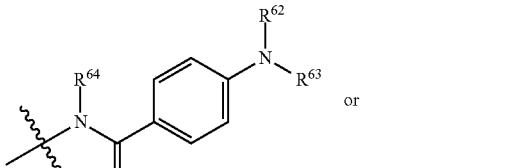
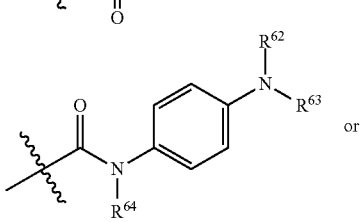
-continued
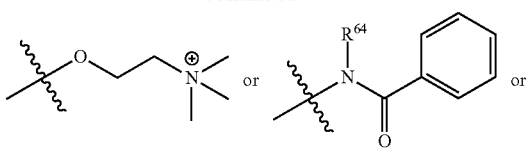
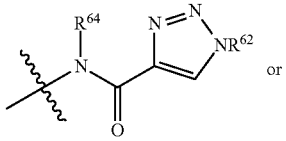
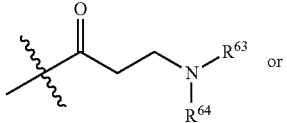
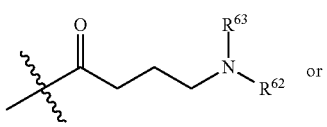
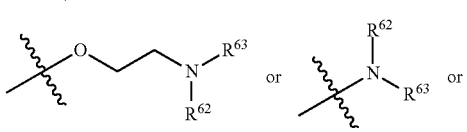
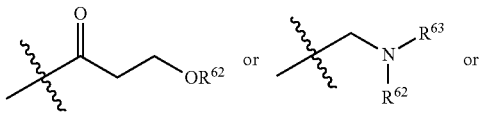
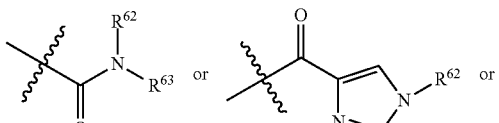
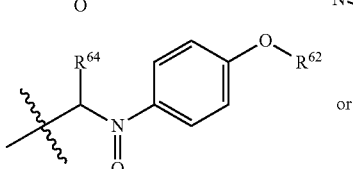
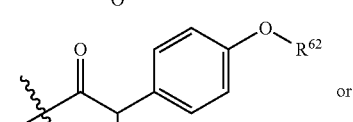
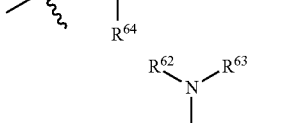
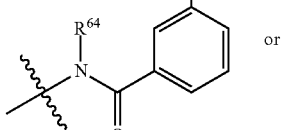
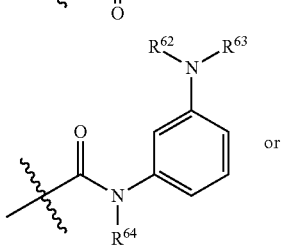

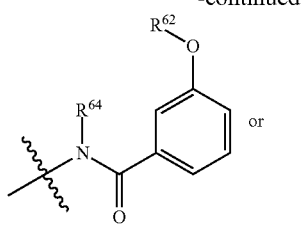
or
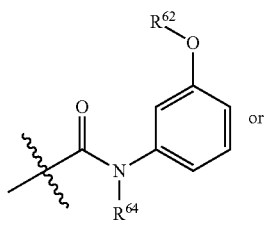
or
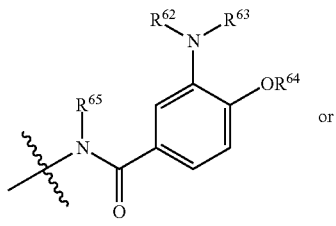
or
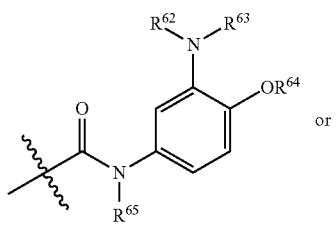
or

or
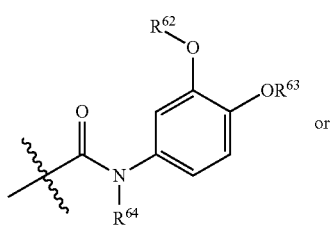
or
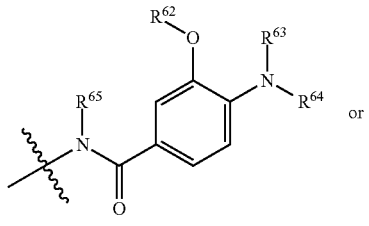
or
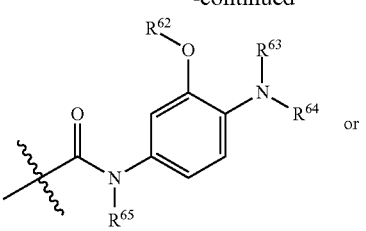
or
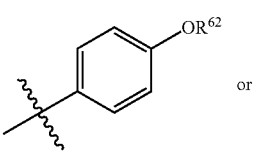
or
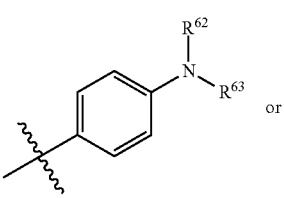
or
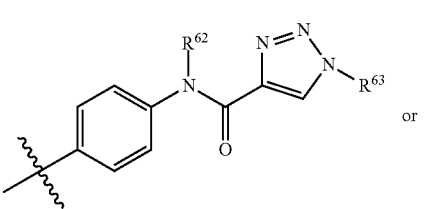
or
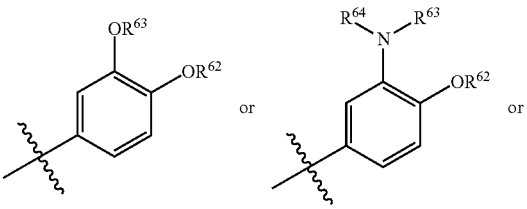
or
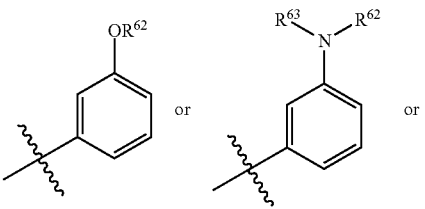
or
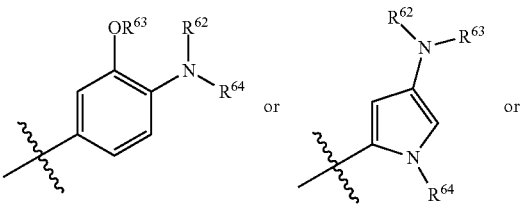
or
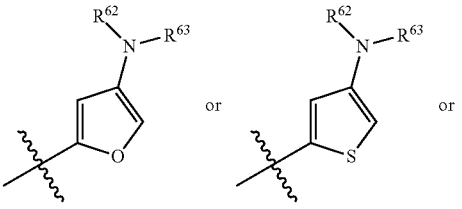
or -continued
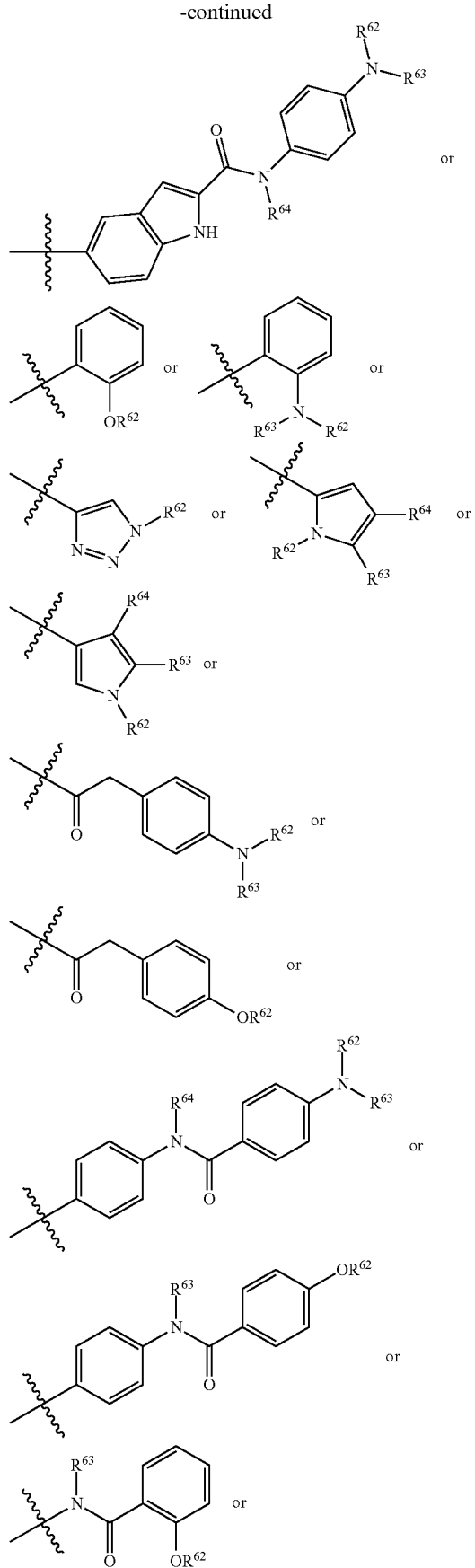
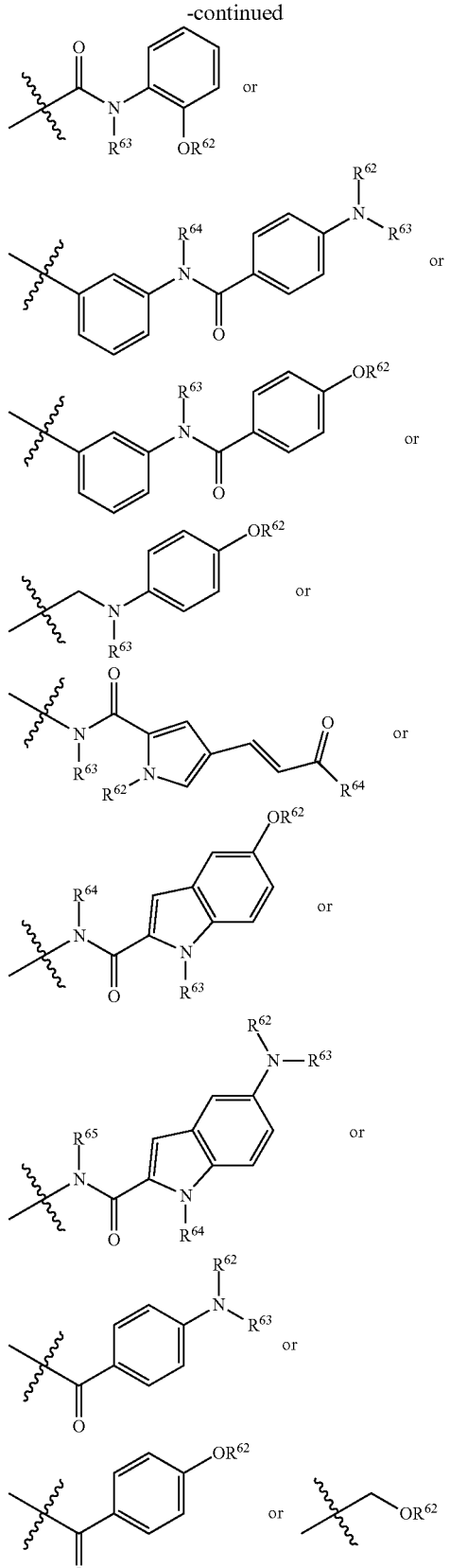
wherein $R^{62}$, $R^{63}$, $R^{64}$, and $R^{65}$ are independently selected from H, $C_{1-3}$ alkyl, and

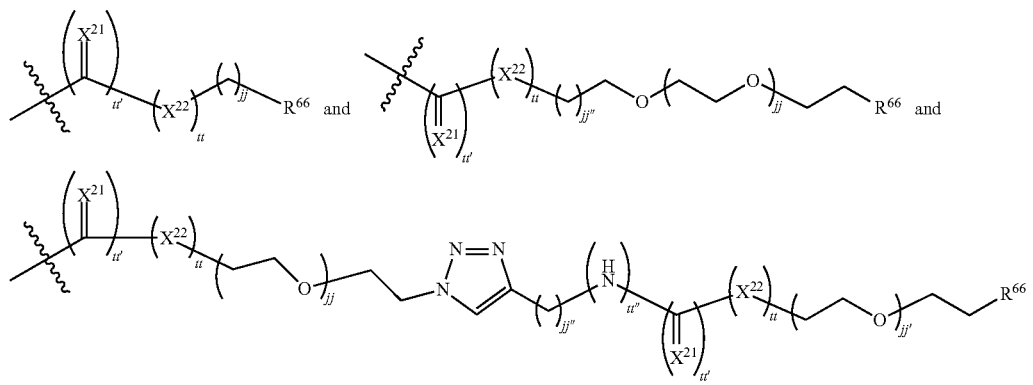

wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

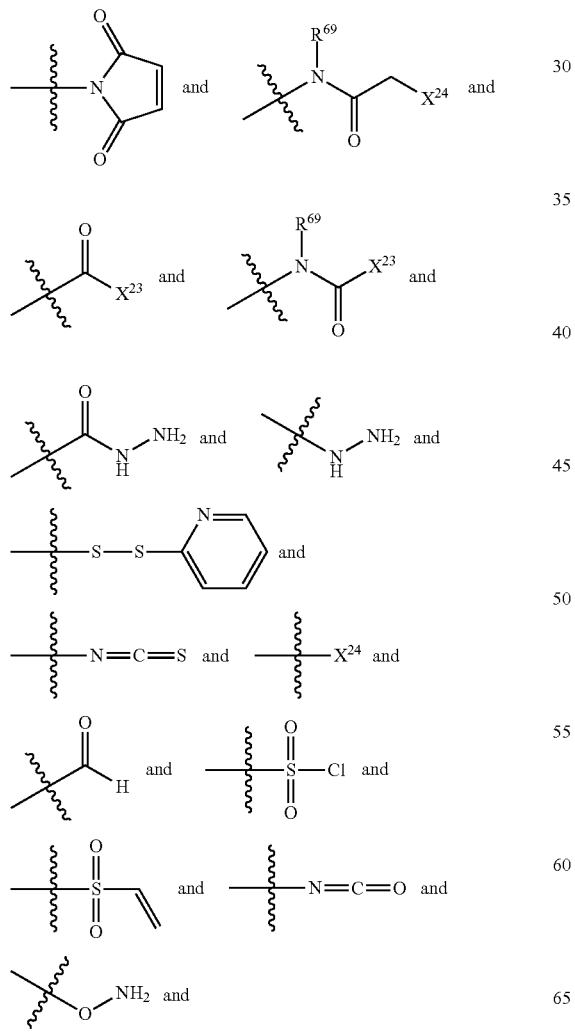

-continued

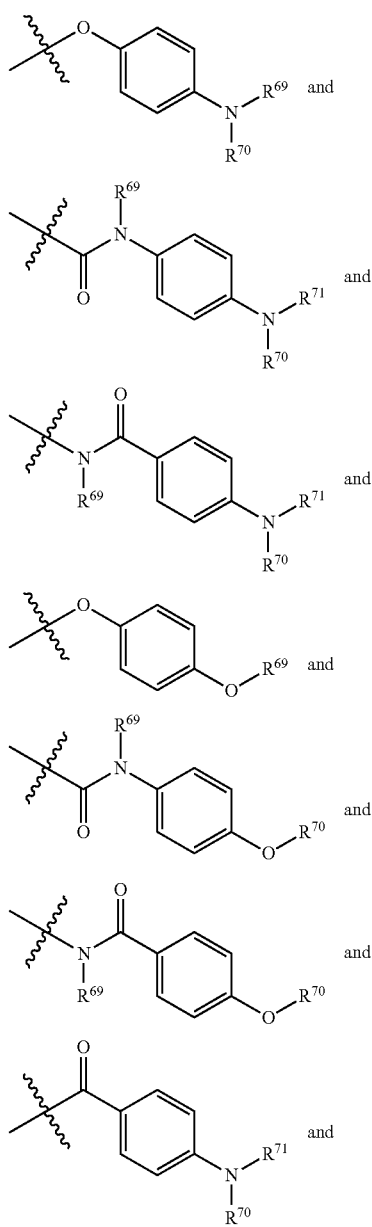

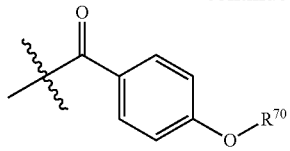

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl, and $R^{69}$, $R^{70}$, and $R^{71}$ are independently selected from methyl and H.

In a further embodiment, the moiety DB5 may for example be

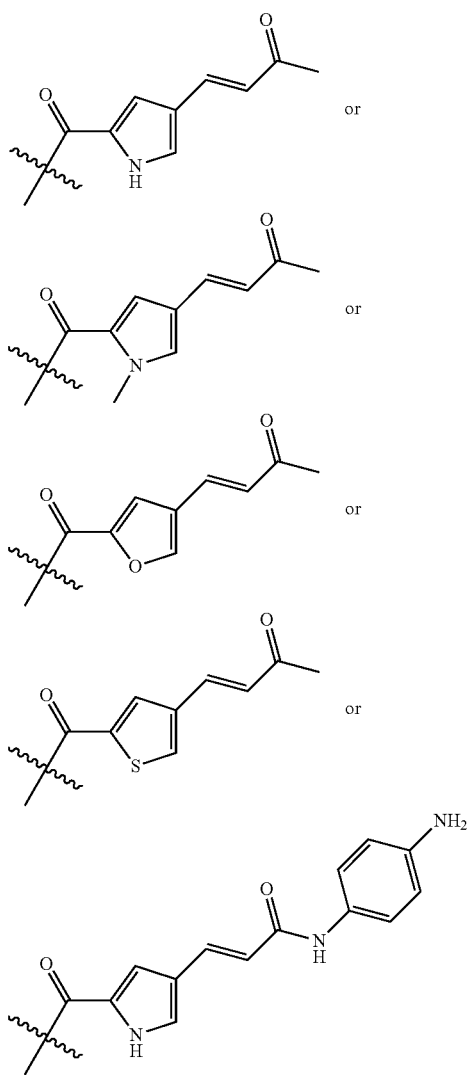

In another aspect of this invention, a compound of formula (I) or (II) has a DNA-binding unit of formula DB6 or DB7. These two moieties comprise structures that are built up of two 5- or 6-membered rings that are connected together via a direct single bond. These rings may each independently be aromatic or non-aromatic. In the latter case, they may be either unsaturated or completely saturated. Furthermore, ring B may be fused to one or more other rings to form an aromatic or non-aromatic ring system, which is preferably flat. This may increase the DNA binding affinity. Either polar substituents or heteroatoms in one or more of the rings may provide for increased water solubility and may favorably affect the pharmacological properties of a compound of formula (I) or (II).

The moiety DB6 may for example be

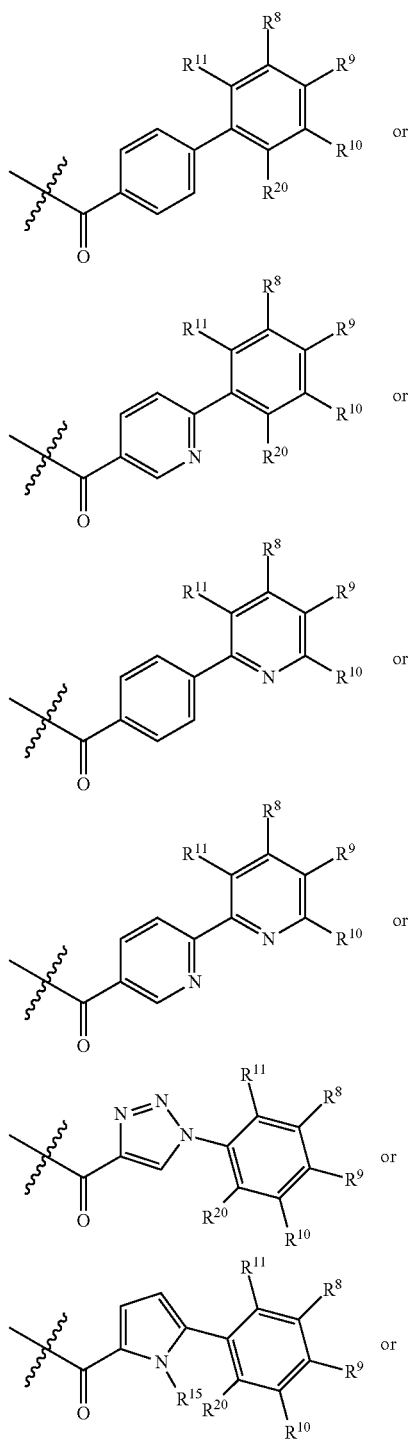

-continued
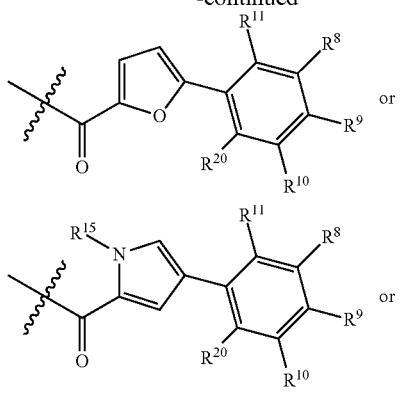
The moiety DB7 may for example be

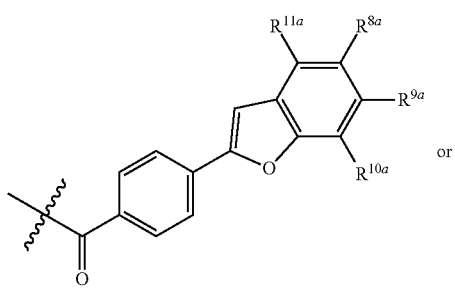

-continued
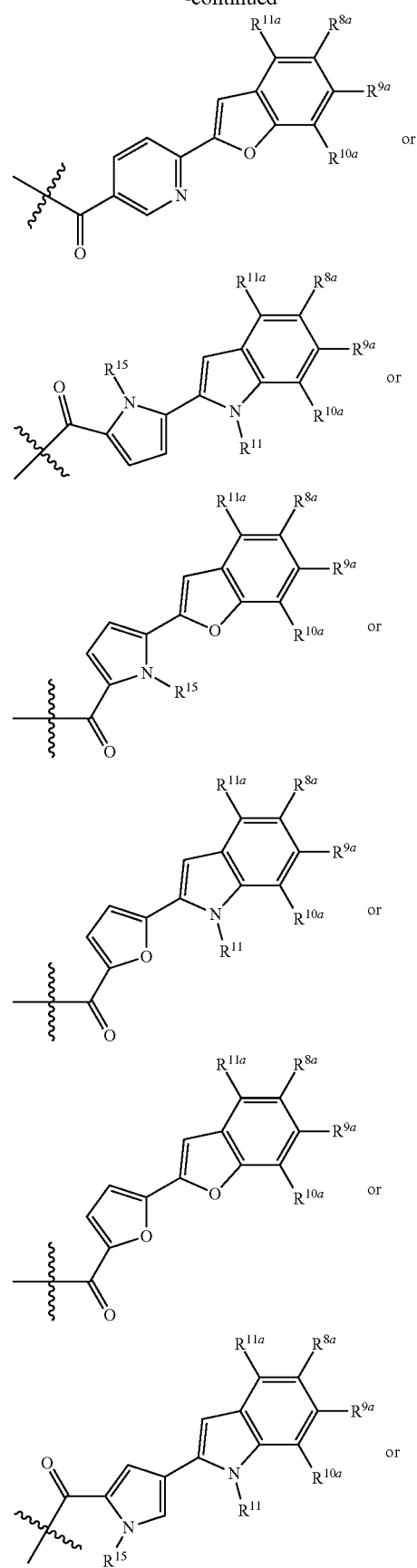

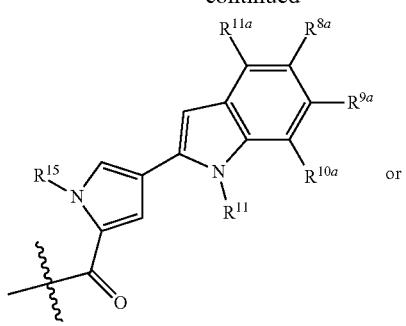
or
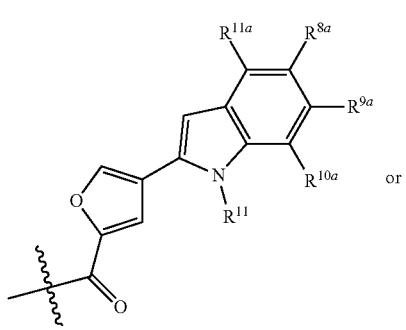
or
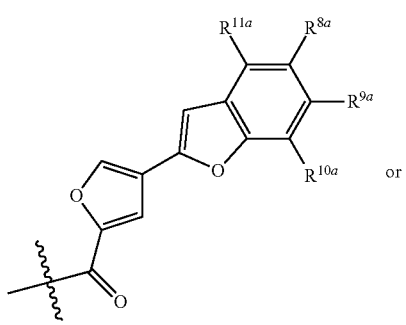
or
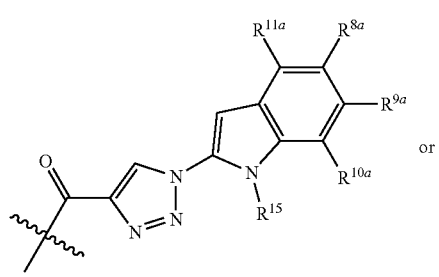
or
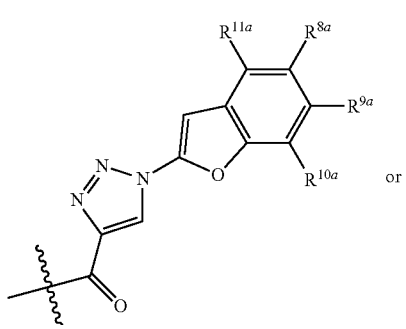
or
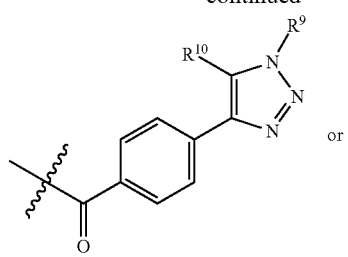
or
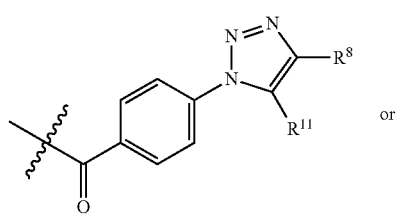
or
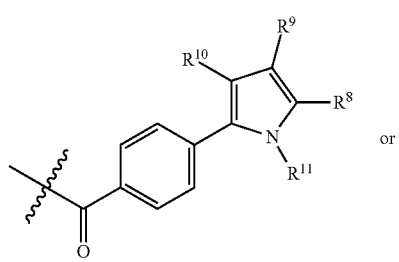
or
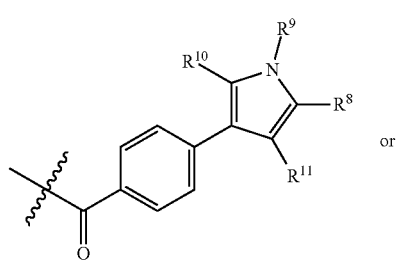
or
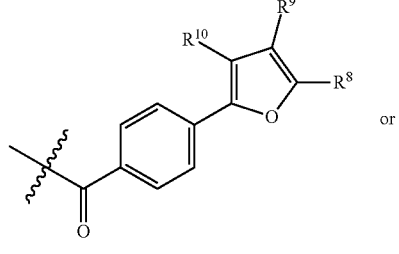
or
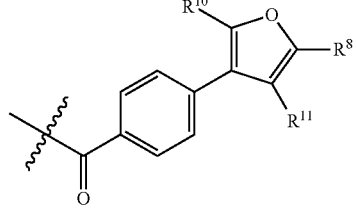
wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.
In a more specific embodiment, moiety DB6 may for example be

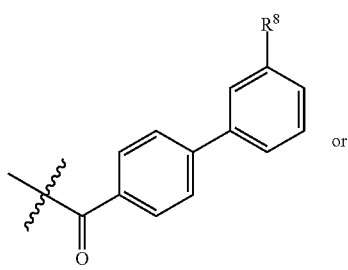 or
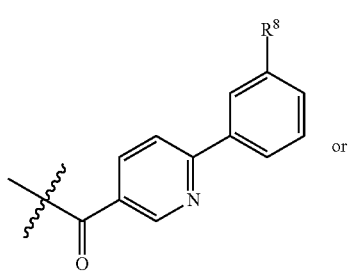 or
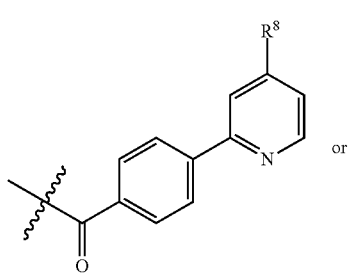 or
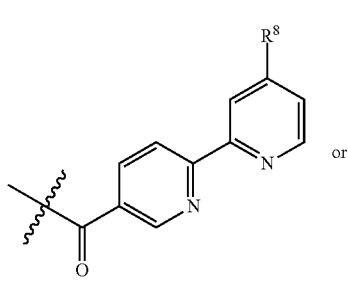 or
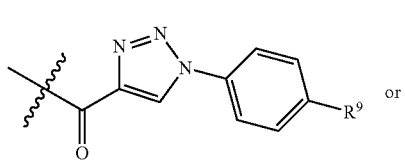 or
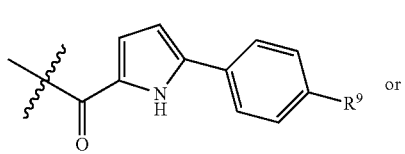 or
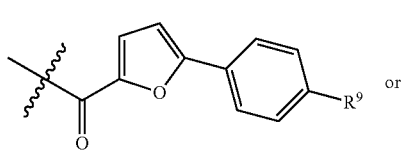 or
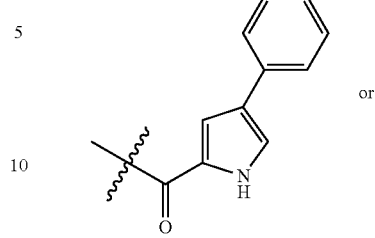 or
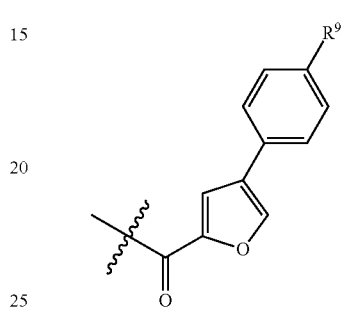
In another more specific embodiment, moiety DB7 may for example be
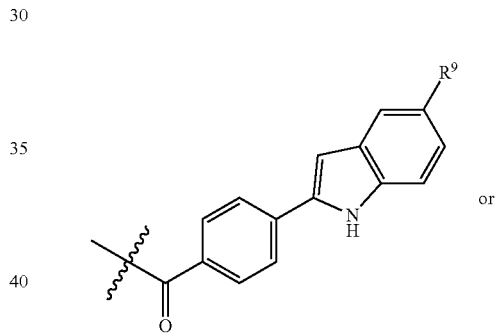 or
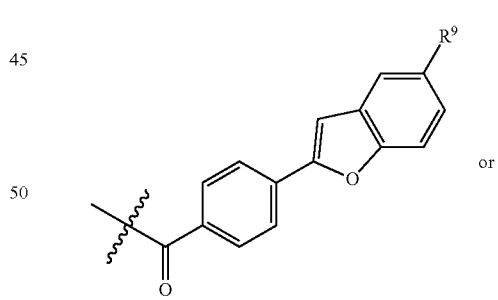 or
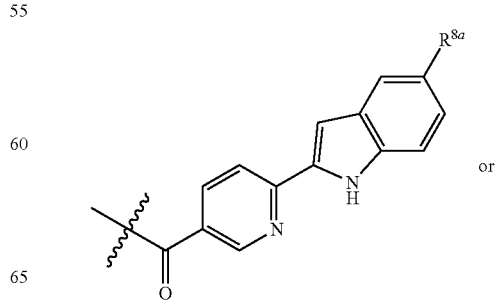 or -continued
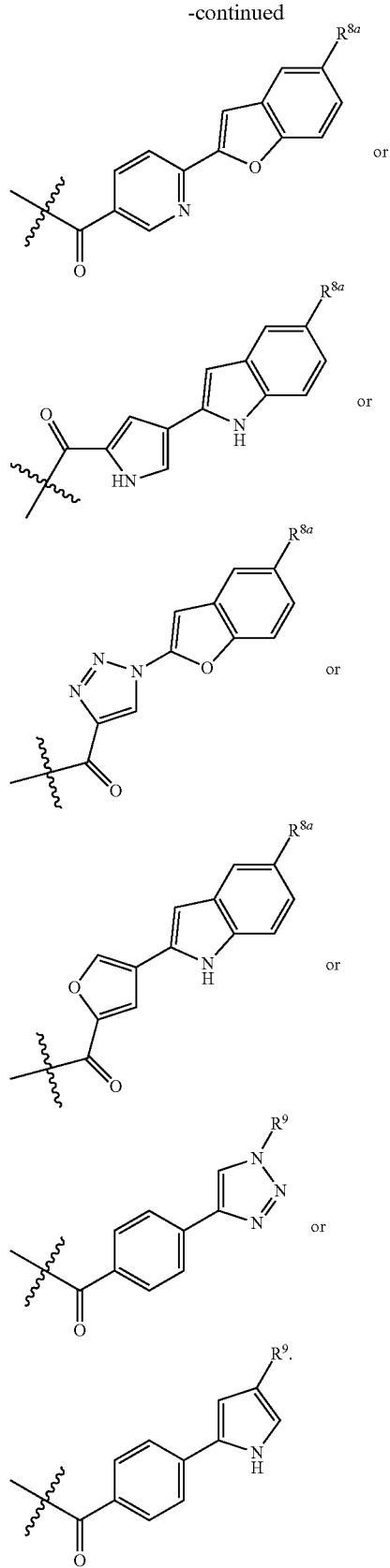
In the exemplary structures of DB6 and DB7, $R^8$, $R^{8a}$, $R^9$, $R^{9a}$, $R^{10}$, $R^{10a}$, $R^{11}$, $R^{11a}$, $R^{15}$, and $R^{20}$ may for example each independently be selected to be H, be or contain another moiety selected from structures DB1-DB9 or a derivative thereof, or be
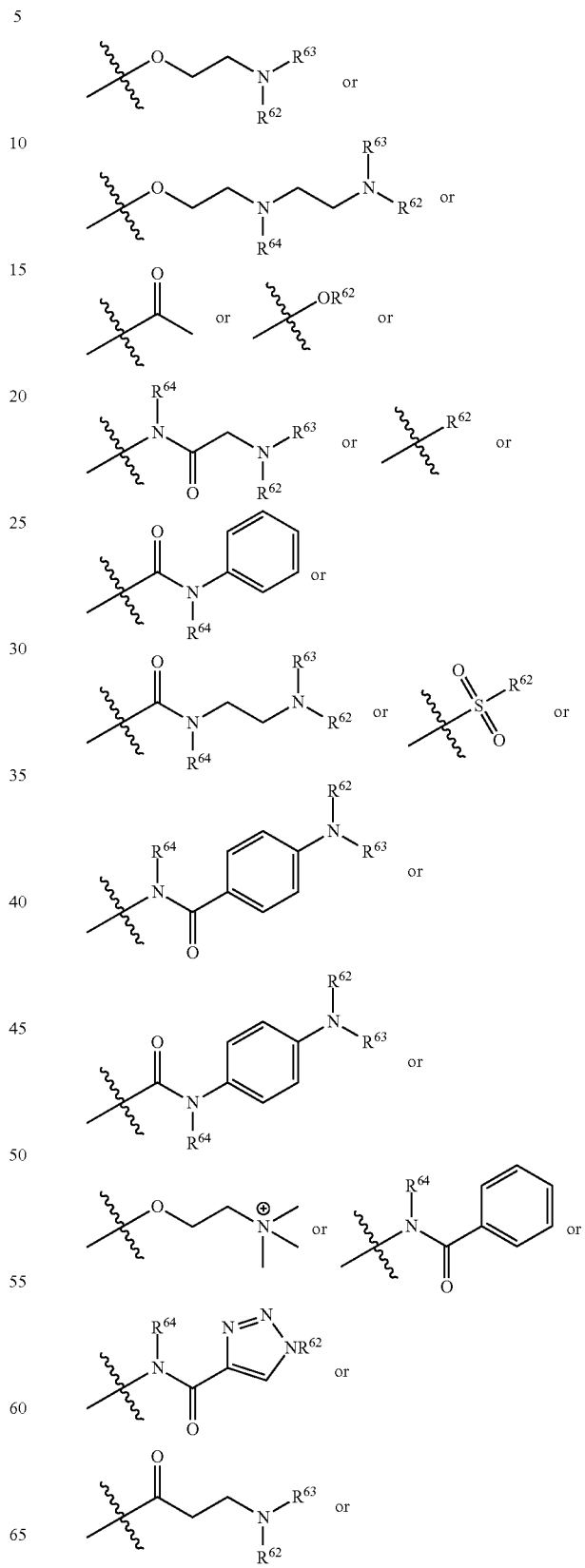

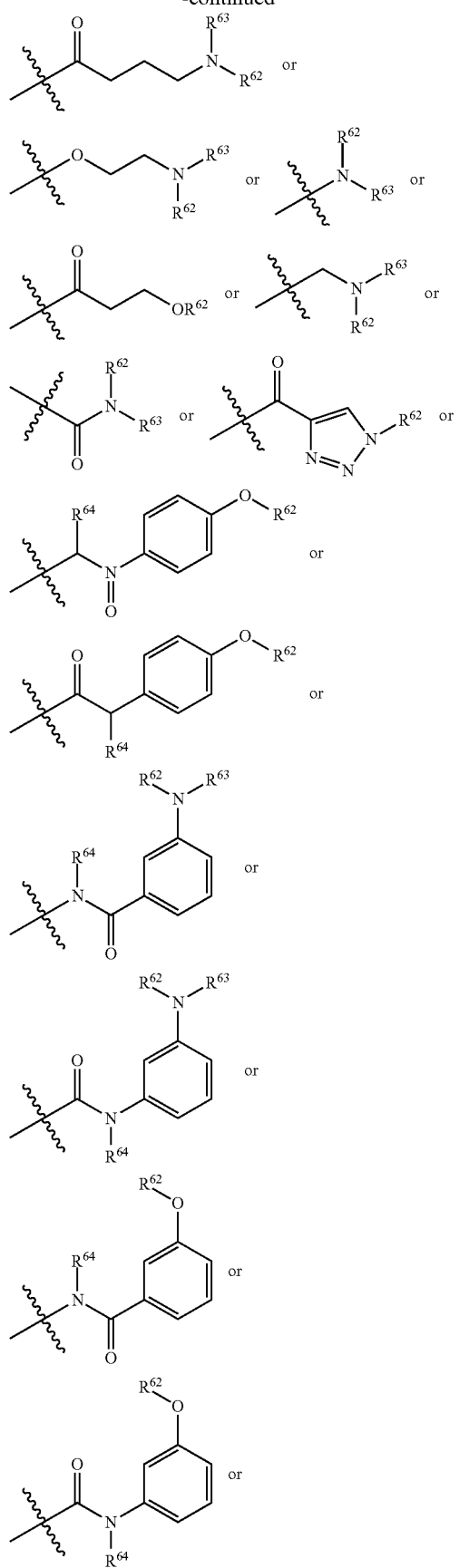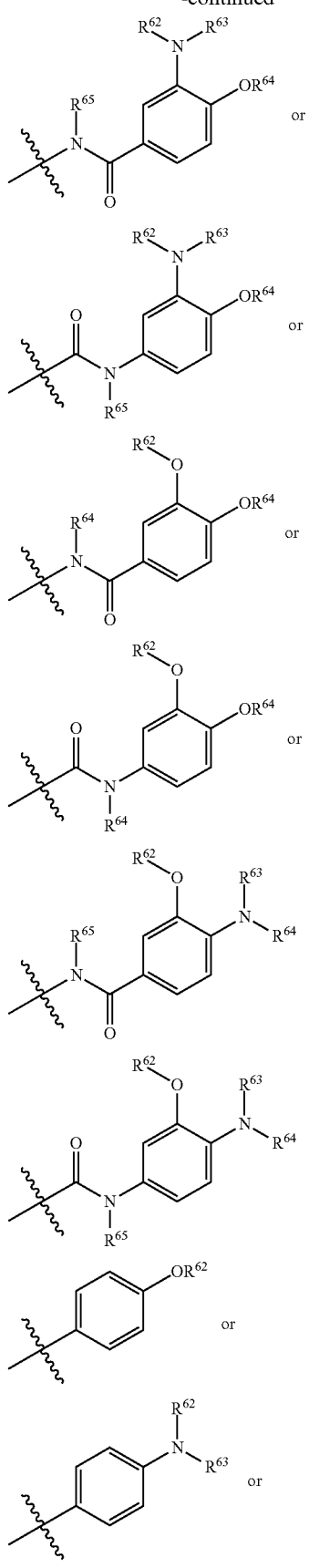

-continued

-continued wherein $R^{62}$, $R^{63}$, $R^{64}$, and $R^{65}$ are independently selected from H, $C_{1-3}$ alkyl, and wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe, -continued

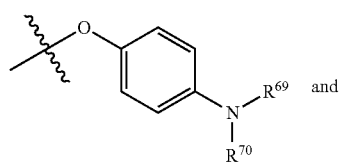
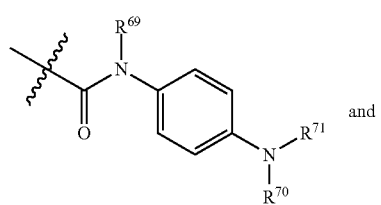
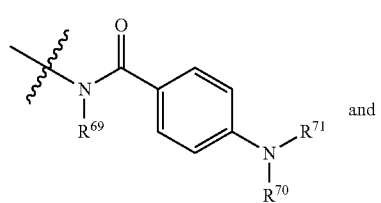
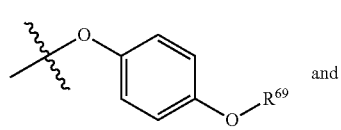
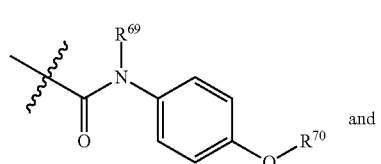
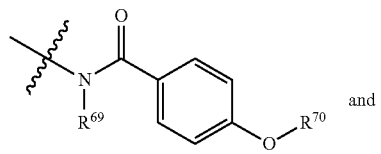
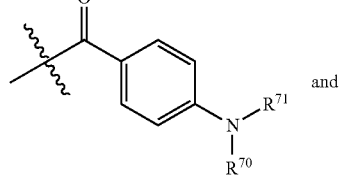
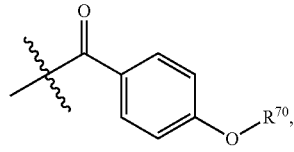

wherein $X^{23}$ is selected from halide, hydroxy, OC(O)$R^{bb}$, and OC(O)O$R^{bb}$, or C(O)—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocycloalkyl, $C_{5-10}$ aryl, and $C_{1-10}$ heteroaryl, and $R^{69}$, $R^{70}$, and $R^{71}$ are independently selected from methyl and H.

In a further embodiment, moiety DB6 may for example be

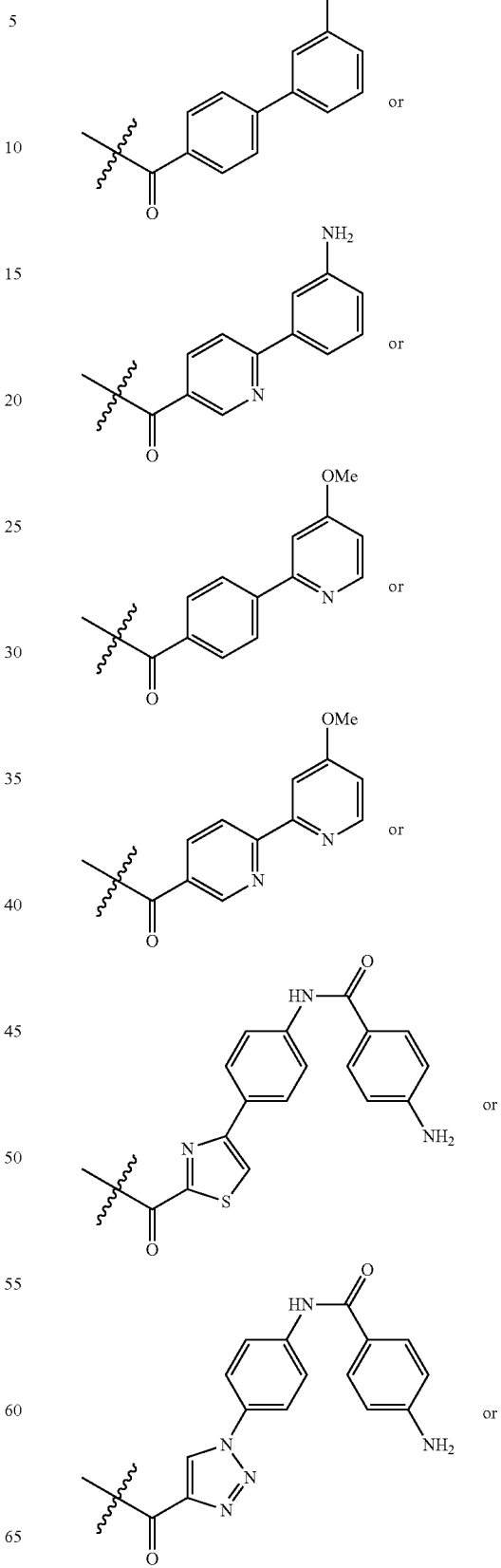

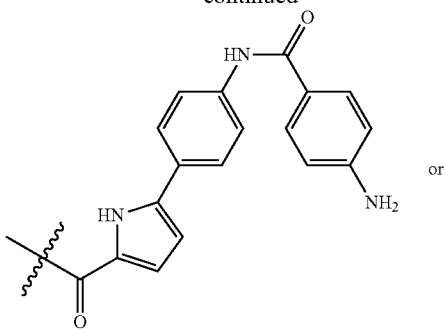
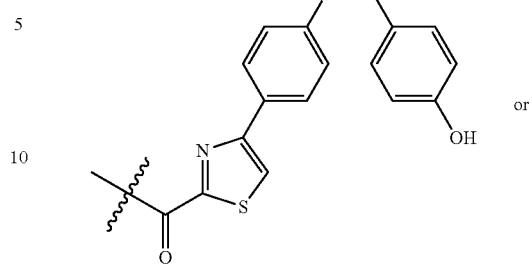
or
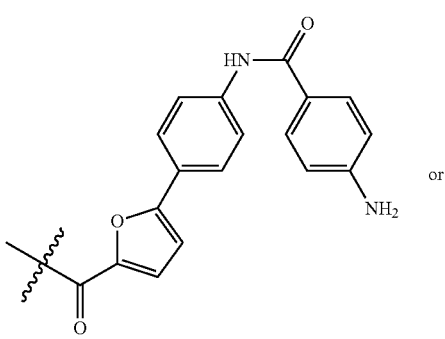
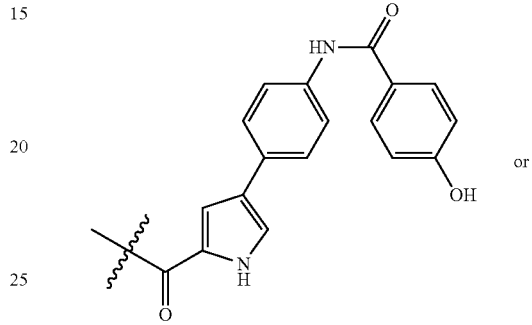
or
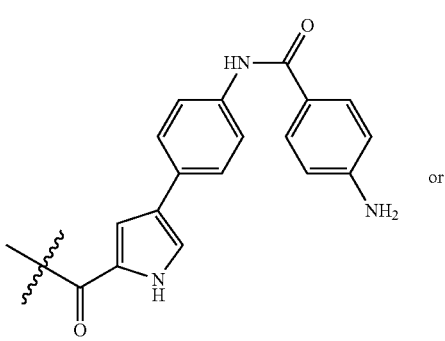
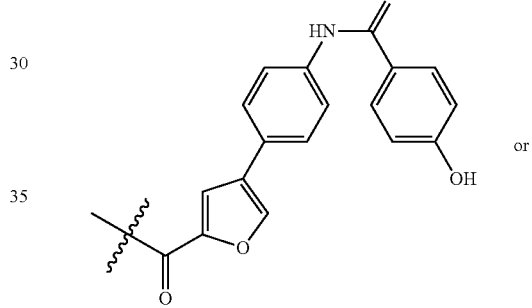
or
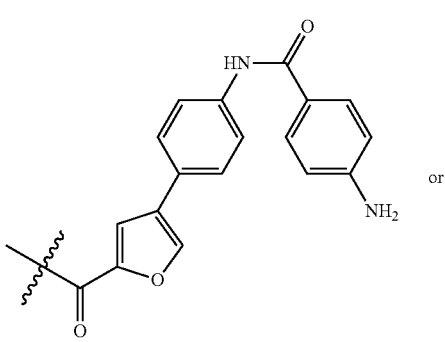
In another further embodiment, moiety DB7 may for example be
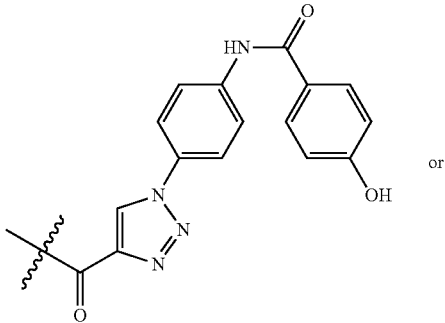
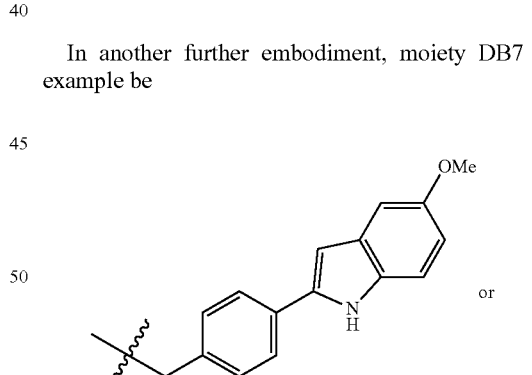
or
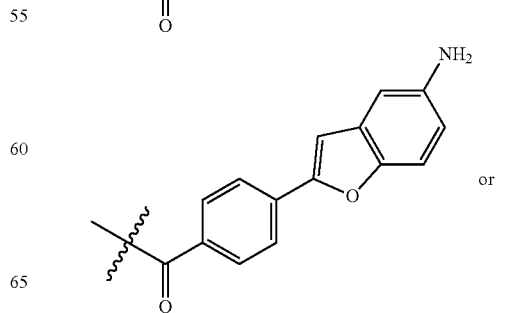
or -continued

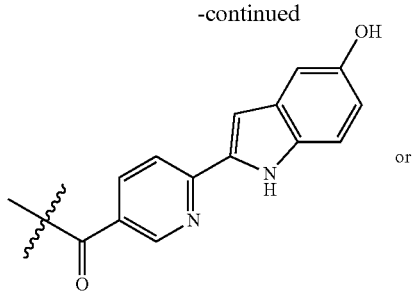 or

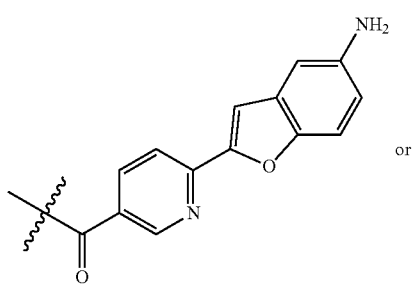 or

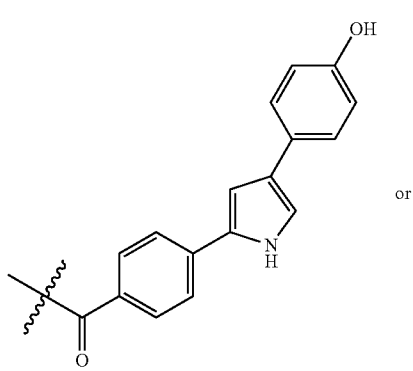 or

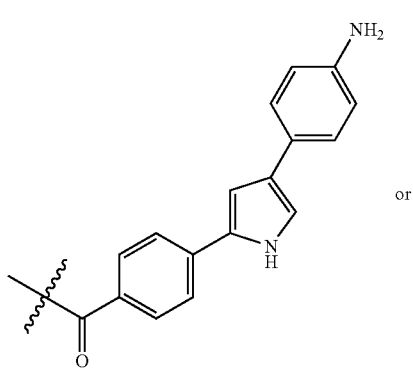 or

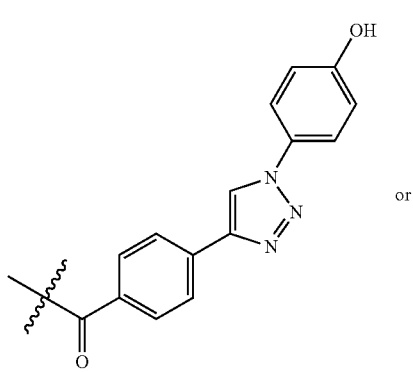 or

-continued

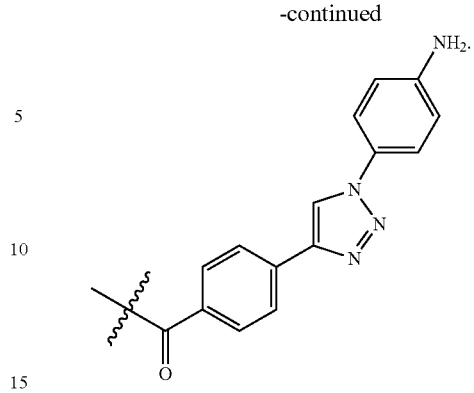

In another aspect of this invention, a compound of formula (I) or (II) has a DNA-binding unit of formula DB8. This moiety comprises structures that are built up of a monocyclic or multicyclic ring system coupled to the DNA-alkylating unit via a methylene unit. Preferably, the DB8 moiety comprises a bicyclic ring system. The ring system may be aromatic or non-aromatic. In the latter case it may be either unsaturated or completely saturated. Either polar substituents or heteroatoms in one or more of the rings may provide for increased water solubility and may favorably affect the pharmacological properties of a compound of formula (I) or (II).

The moiety DB8 may for example be

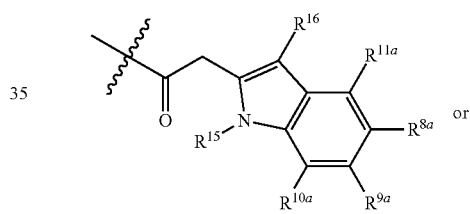 or

 or

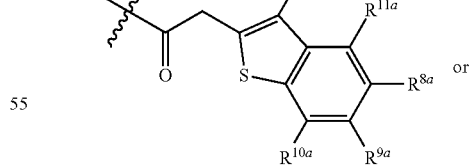 or

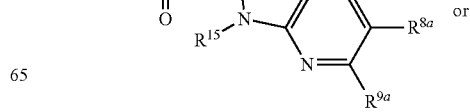 or

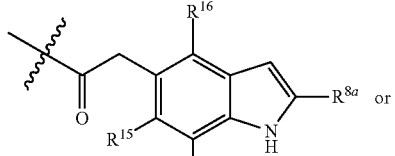
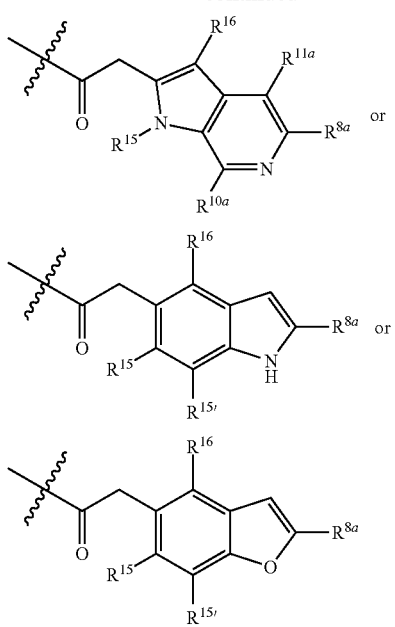
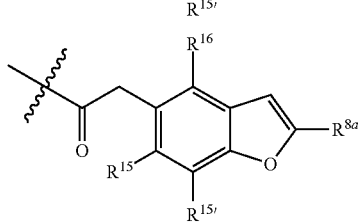

wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.

In the exemplary structures of DB8, $R^{8a}$, $R^{9a}$, $R^{10a}$, $R^{11a}$, $R^{15}$, $R^{15'}$, and $R^{16}$ may for example each independently be selected to be H, be or contain another moiety selected from structures DB1-DB9 or a derivative thereof, or be

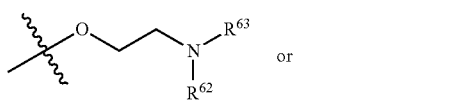
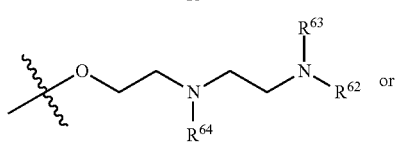
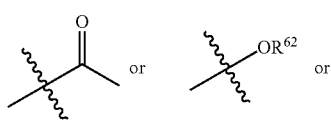
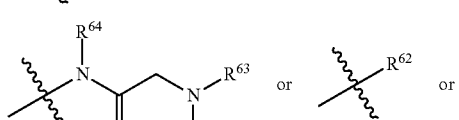
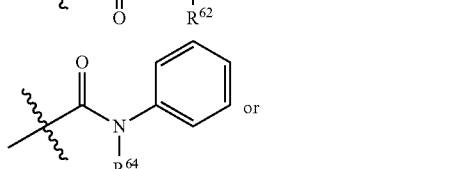
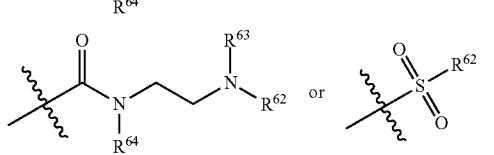

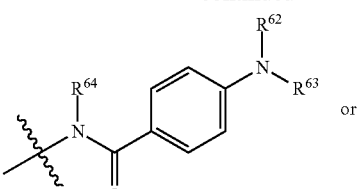
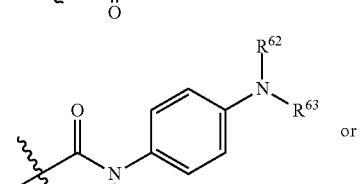
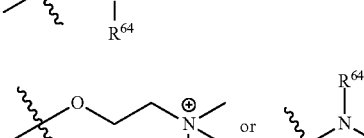
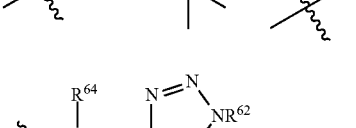
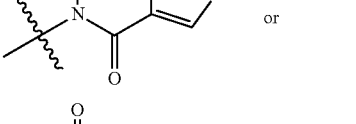
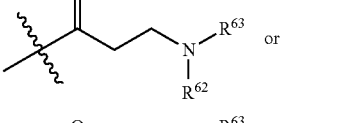
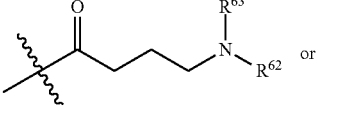
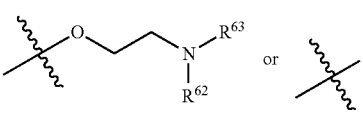
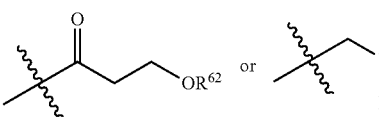
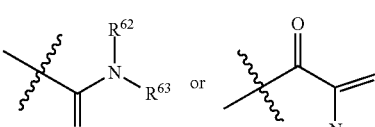
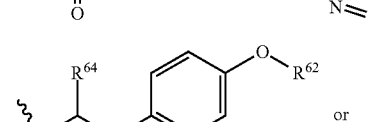
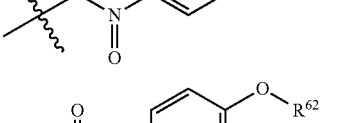
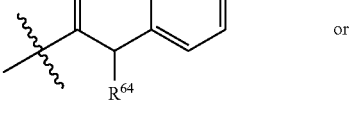

211
-continued
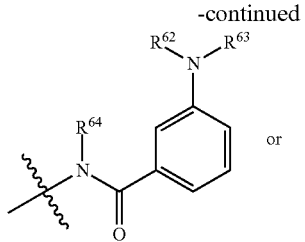 or
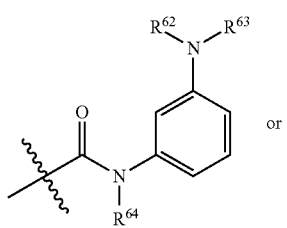 or
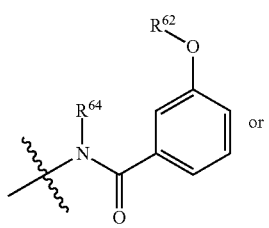 or
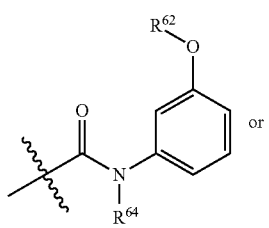 or
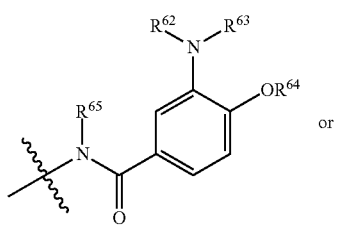 or
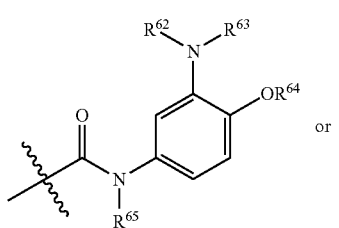 or
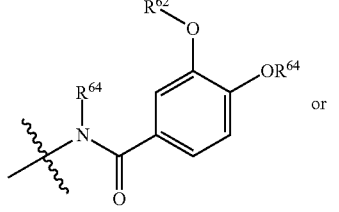 or
212
-continued
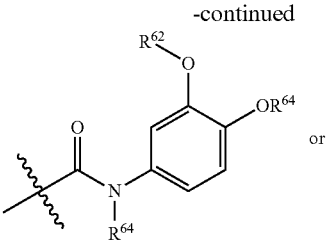 or
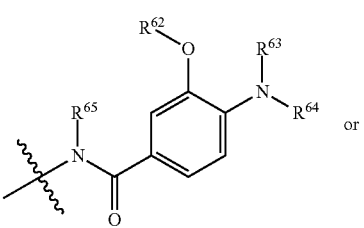 or
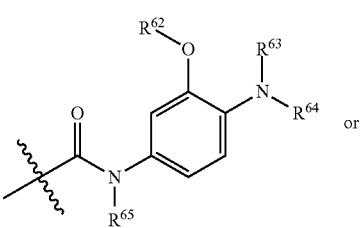 or
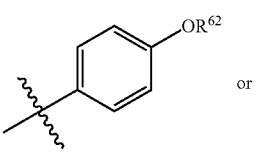 or
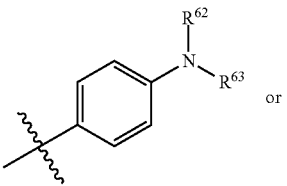 or
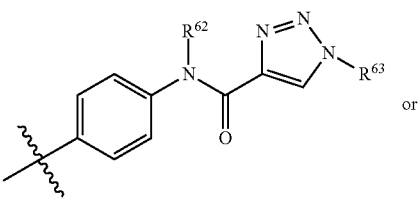 or
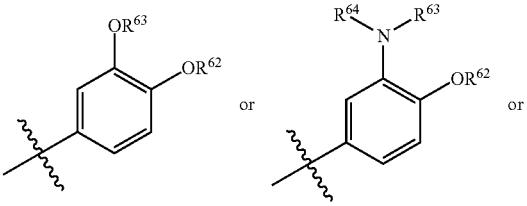 or
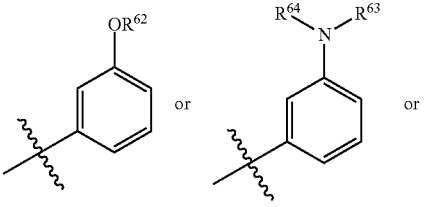 or

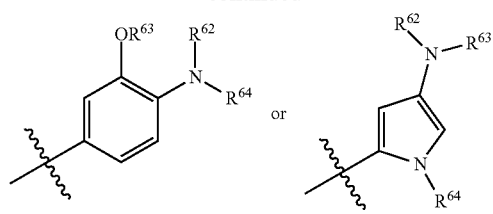 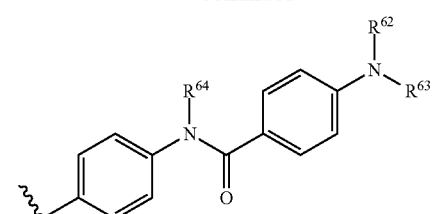
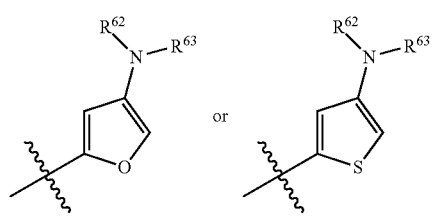 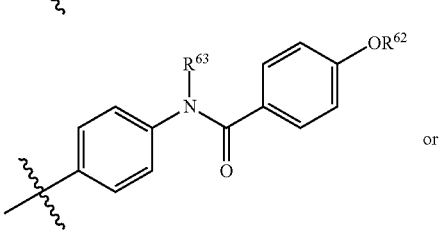
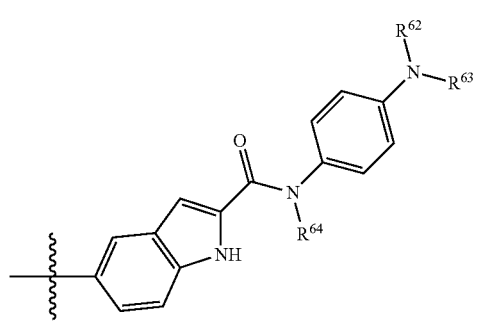 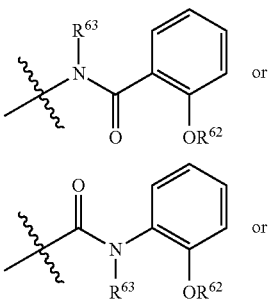
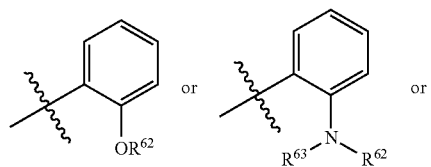 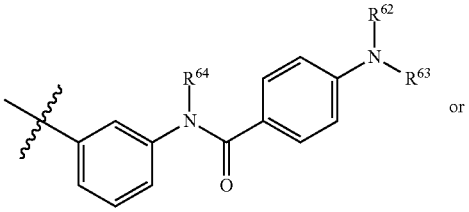
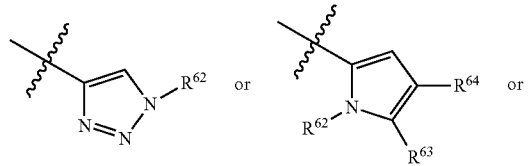 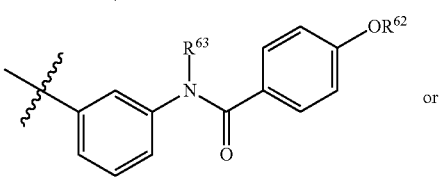
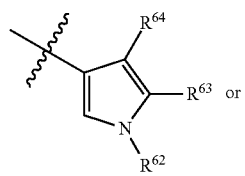 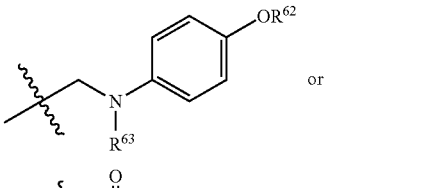
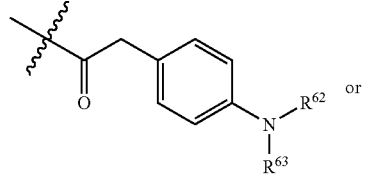 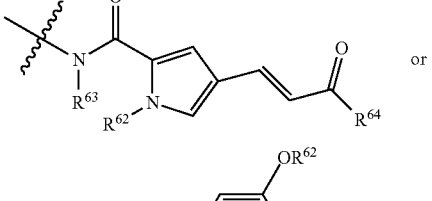
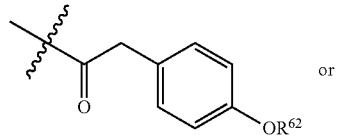 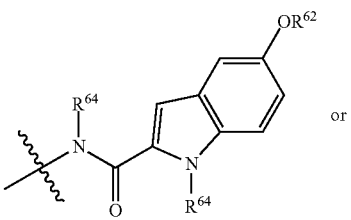

-continued

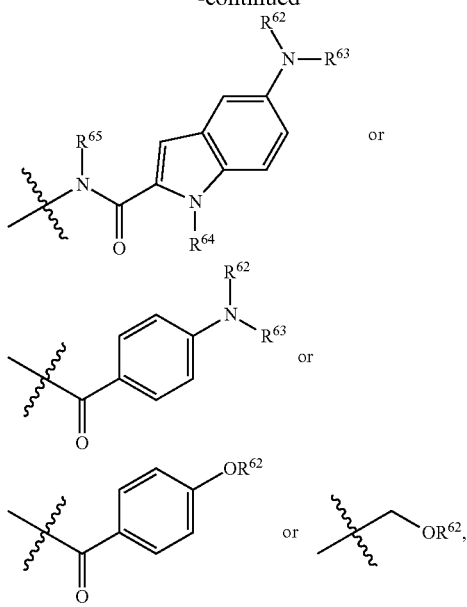

wherein $R^{62}$, $R^{63}$, $R^{64}$, and $R^{65}$ are independently selected from H, $C_{1-3}$ alkyl, and

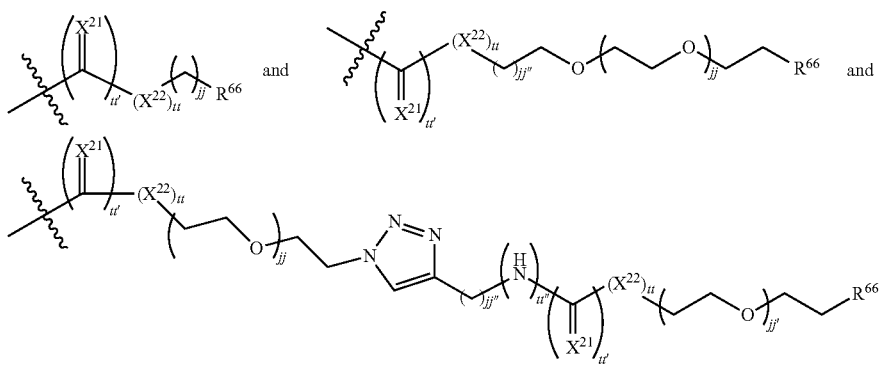

wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

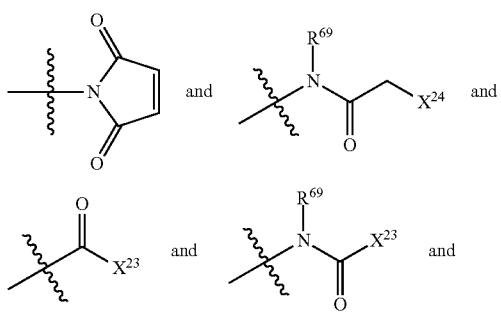

-continued

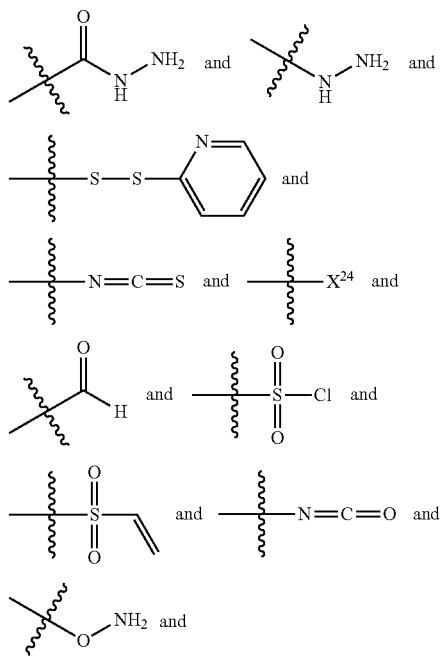

-continued

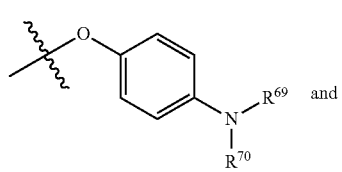

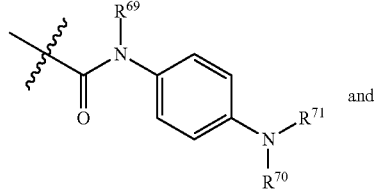

217
-continued

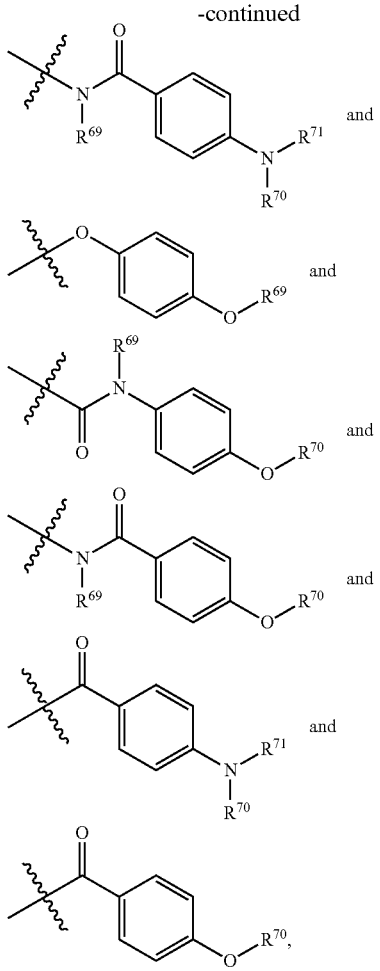

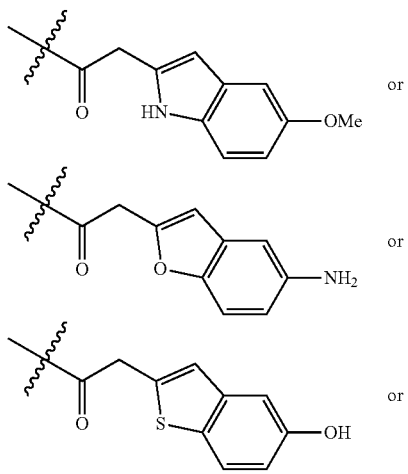

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl, and $R^{69}$, $R^{70}$, and $R^{71}$ are independently selected from methyl and H.

In a further embodiment, moiety DB8 may for example be

218
-continued

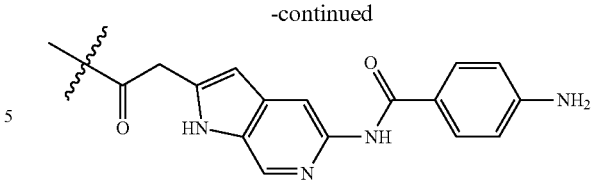

In another aspect of this invention, a compound of formula (I) or (II) has a DNA-binding unit of formula DB9. This moiety comprises structures that are built up of a 5-membered ring that is directly connected to the nitrogen atom of the DNA-alkylating unit via a single bond. The 5-membered ring may be connected or fused to one or more other rings to form a multicyclic ring system, which is preferably flat. This may increase the DNA binding affinity. The ring system may be aromatic or non-aromatic. In the latter case it may be either unsaturated or completely saturated. Either polar substituents or heteroatoms in one or more of the rings may provide for increased water solubility and may favorably affect the pharmacological properties of a compound of formula (I) or (II). In one embodiment, the DB9 moiety contains at least two ring heteroatoms.

The moiety DB9 may for example be

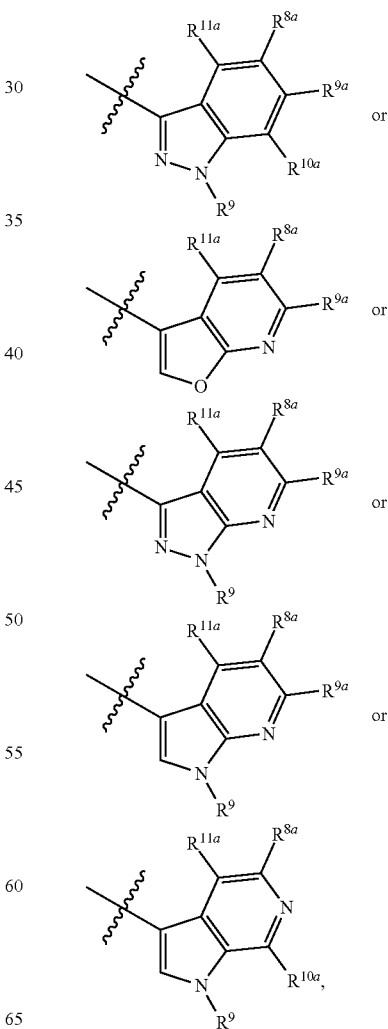

wherein $R^{8a}$, $R^{9a}$, $R^{10a}$, and $R^{11a}$ have the same meaning as defined for $R^8$, $R^9$, $R^{10}$, and $R^{11}$, respectively, and are independently selected.
In the exemplary structures of DB9, $R^{8a}$, $R^{9a}$, $R^{10a}$, $R^{11a}$, and $R^9$ may for example each independently be selected to be H, be or contain another moiety selected from structures DB1-DB9 or a derivative thereof, or be
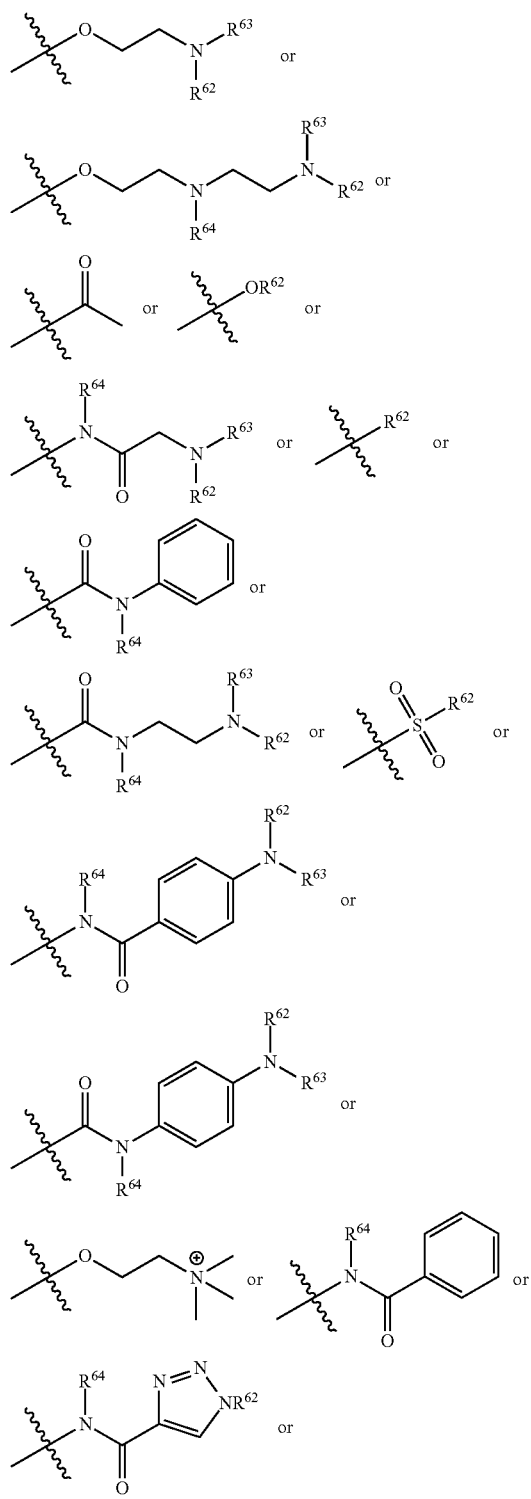
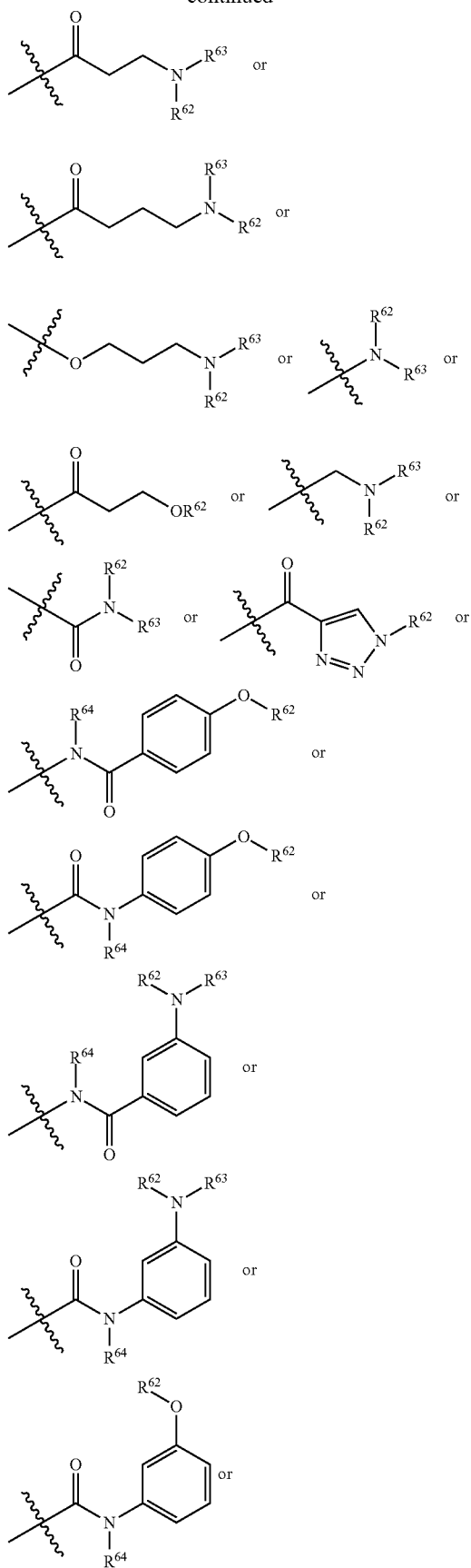

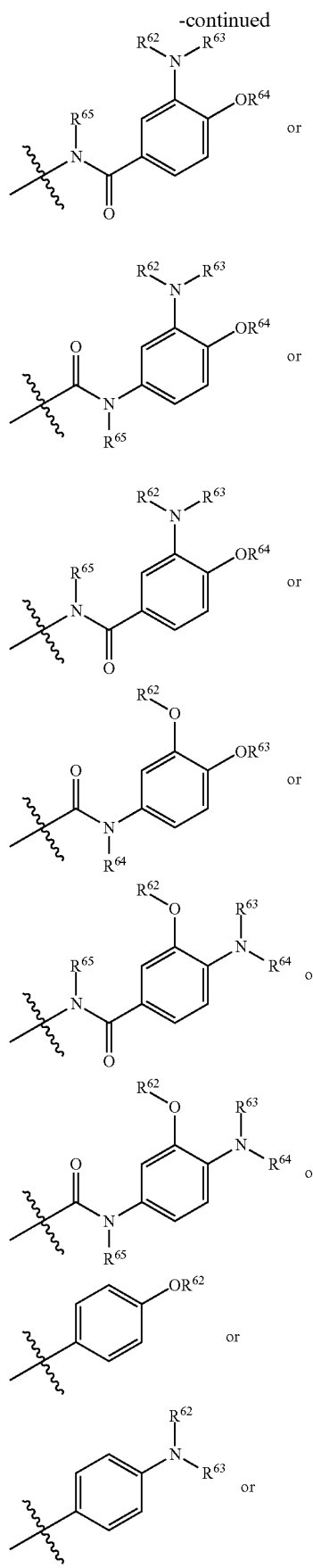
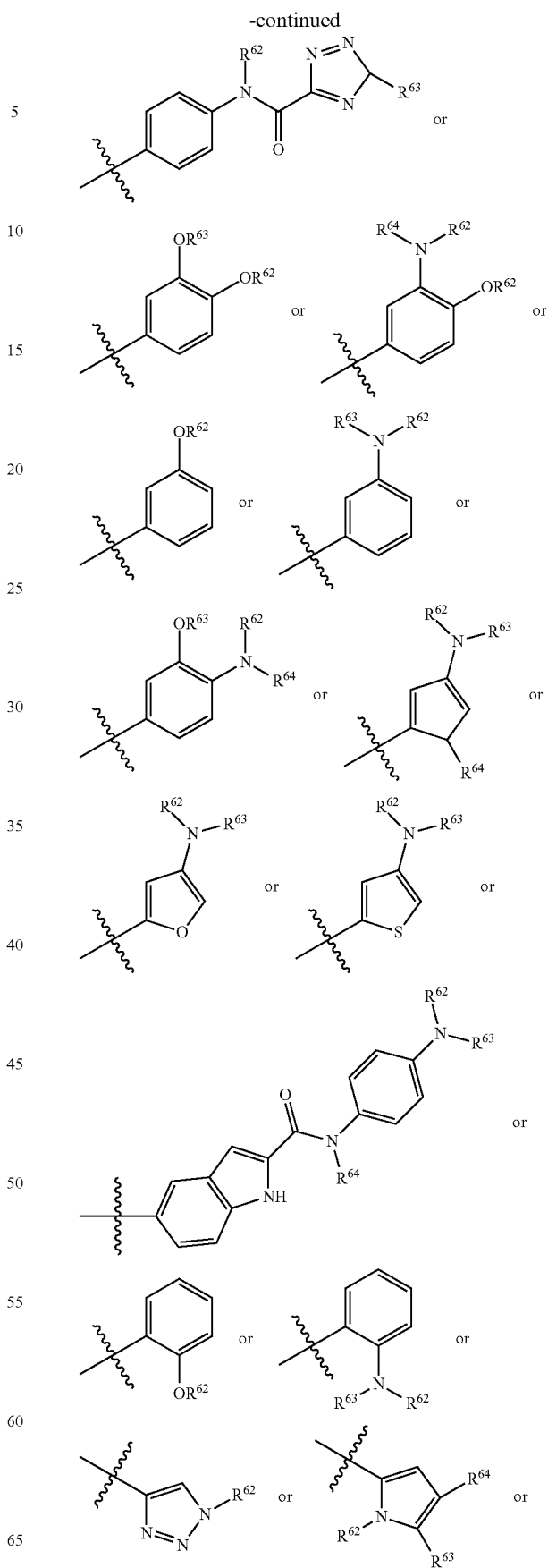

223
-continued
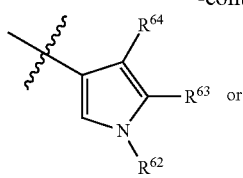 or
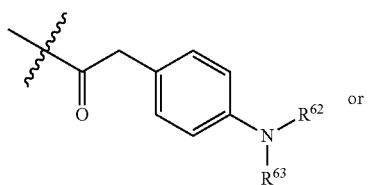 or
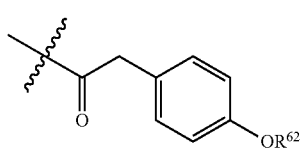 or
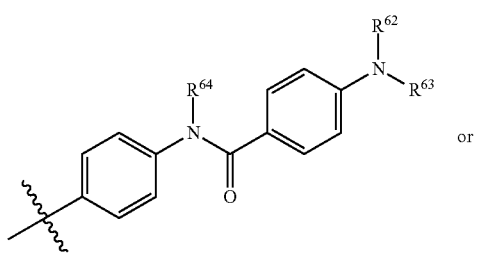 or
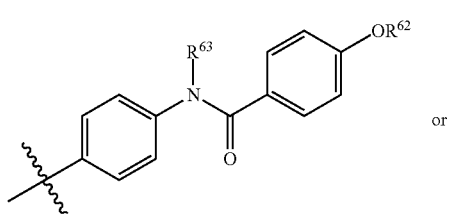 or
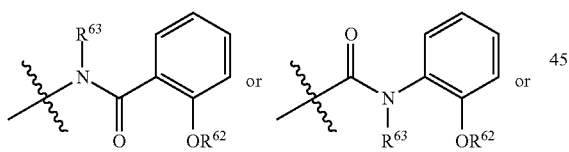 or
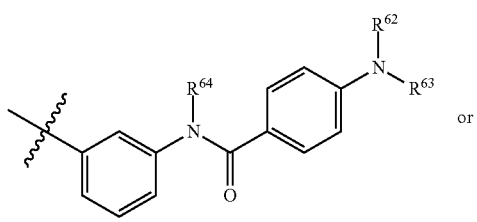 or
224
-continued
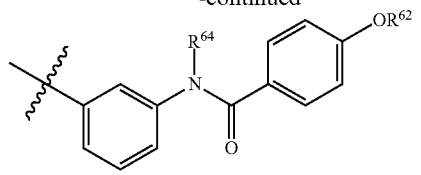 or
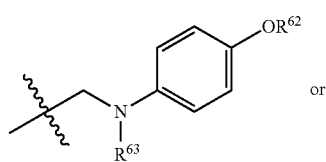 or
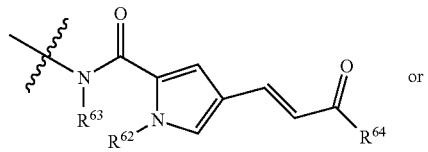 or
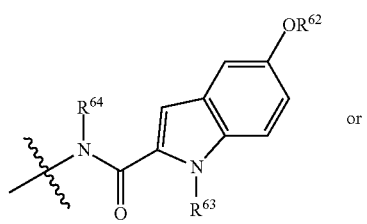 or
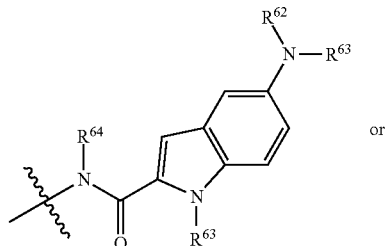 or
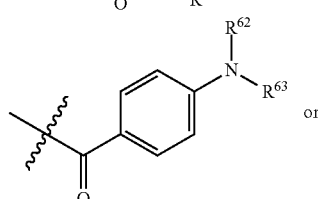 or
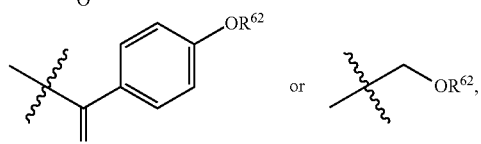,
wherein $R^{62}$, $R^{63}$, $R^{64}$, and $R^{65}$ are independently selected from H, $C_{1-3}$ alkyl, and
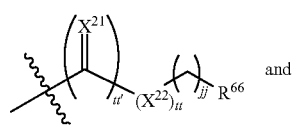 and 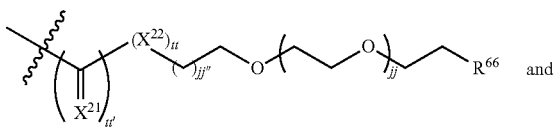 and -continued

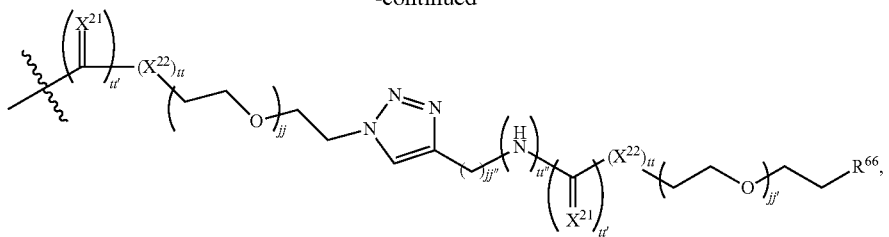

wherein jj, jj', and jj" are independently selected from 0 to 8, each tt, tt', and tt" is independently selected from 0 and 1, each $X^{21}$ and $X^{22}$ is independently selected from O, S, $NR^{67}$, $H_2$, and $C(R^{67})R^{68}$, wherein $R^{67}$ and $R^{68}$ are independently selected from H and optionally substituted $C_{1-3}$ alkyl or $C_{1-3}$ heteroalkyl, and $R^{66}$ is selected from H, COOH, $CO_2Me$, OH, OMe, $NR^{69}R^{70}$, $NR^{69}C(O)CH_3$, SH, SMe,

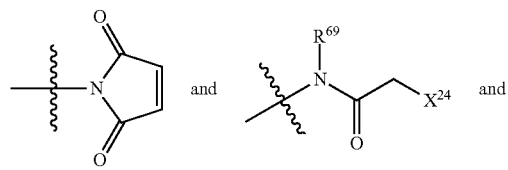

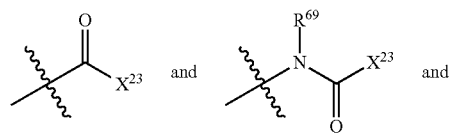

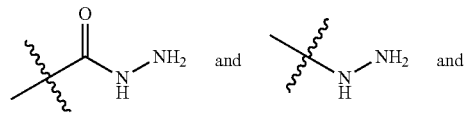

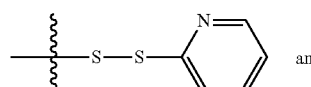

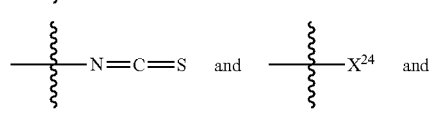

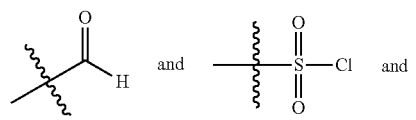

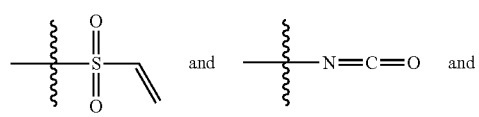

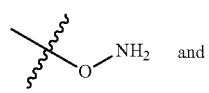

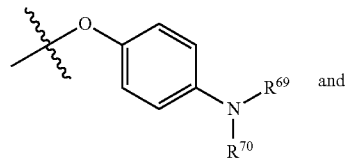

-continued

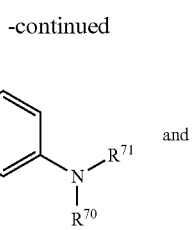

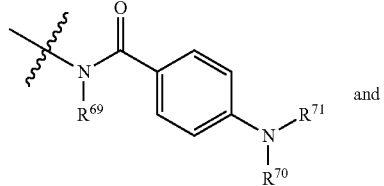

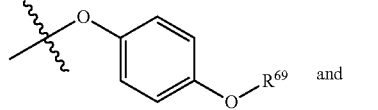

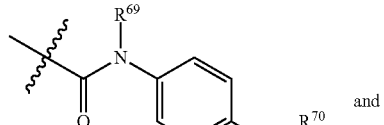

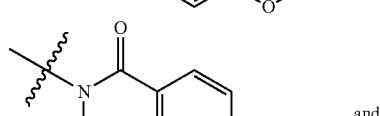

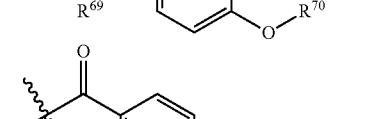

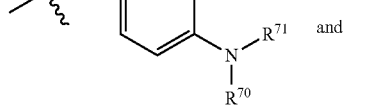

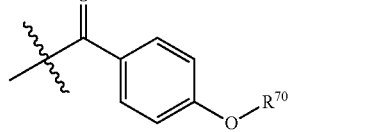

wherein $X^{23}$ is selected from halide, hydroxy, $OC(O)R^{bb}$, and $OC(O)OR^{bb}$, or $C(O)$—$X^{23}$ is an active ester, $X^{24}$ is selected from halide, mesyloxy, triflyloxy, and tosyloxy, $R^{bb}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl, and $R^{69}$, $R^{70}$, and $R^{71}$ are independently selected from methyl and H.

In a further embodiment, moiety DB9 may for example be

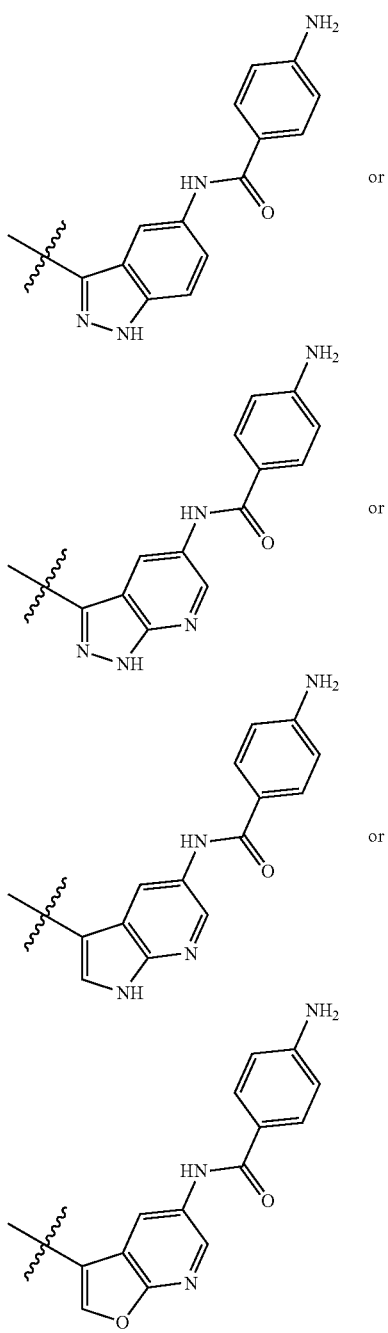

In one embodiment of this invention, the DB unit is DB1. In another embodiment, the DB unit is DB2. In yet another embodiment, the DB unit is DB3. In yet another embodiment, the DB unit is DB4. In yet another embodiment, the DB unit is DB5. In yet another embodiment, the DB unit is DB6. In yet another embodiment, the DB unit is DB7. In yet another embodiment, the DB unit is DB8. In yet another embodiment, the DB unit is DB9. In another embodiment, the DB unit is selected from DB1, DB2, DB3, DB4, DB5, DB6, and DB7. In another embodiment, the DB unit is selected from DB1, DB2, DB5, DB6, and DB7. In a further embodiment, DB is selected from DB1, DB2, DB6, and DB7. In yet a further embodiment, DB is selected from DB1 and DB2. In yet a further embodiment, DB is selected from DB6 and DB7.

In one embodiment, $R^5$, $R^{5'}$, $R^6$, $R^{6'}$, $R^7$, and $R^{7'}$ are independently selected from H, OH, SH, $NH_2$, $N_3$, $NO_2$, NO, $CF_3$, CN, $C(O)NH_2$, C(O)H, C(O)OH, halogen, $R^e$, $SR^e$, $S(O)R^e$, $S(O)_2R^e$, $S(O)R^e$, $S(O)OR^e$, $S(O)_2OR^e$, $OS(O)R^e$, $OS(O)_2R^e$, $OS(O)OR^e$, $OS(O)_2OR^e$, $OR^e$, $NHR^e$, $N(R^e)R^f$, $^+N(R^e)(R^f)R^g$, $P(O)(OR^e)(OR^f)$, $OP(O)(OR^e)(OR^f)$, $SiR^eR^fR^g$, $C(O)R^e$, $C(O)OR^e$, $C(O)N(R^e)R^f$, $OC(O)R^e$, $OC(O)OR^e$, $OC(O)N(R^e)R^f$, $N(R^e)C(O)R^f$, $N(R^e)C(O)OR^f$, and $N(R^e)C(O)N(R^f)R^g$, wherein $R^e$, $R^f$, and $R^g$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^e$, $R^f$, and $R^g$ optionally being joined by one or more bonds to form one or more optionally substituted carbocycles and/or heterocycles, or $R^5+R^{5'}$ and/or $R^6+R^{6'}$ and/or $R^7+R^{7'}$ are independently selected from =O, =S, =$NOR^{e3}$, =$C(R^{e3})R^{e4}$, and =$NR^{e3}$, $R^{e3}$ and $R^{e4}$ being independently selected from H and optionally substituted $C_{1-3}$ alkyl, or $R^{5'}+R^{6'}$ and/or $R^{6'}+R^{7'}$ and/or $R^{7'}+R^{14'}$ are absent, resulting in a double bond between the atoms designated to bear $R^{5'}$ and $R^{6'}$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined by one or more bonds to form one or more optionally substituted carbocycles and/or heterocycles.

In another embodiment, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ are each independently selected from H, OH, SH, $NH_2$, $N_3$, $NO_2$, NO, $CF_3$, CN, $C(O)NH_2$, C(O)H, C(O)OH, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, and $N(R^h)C(O)N(R^i)R^j$, wherein $R^h$, $R^i$, and $R^j$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, two or more of $R^h$, $R^i$, and $R^j$ optionally being joined by one or more bonds to form one or more optionally substituted carbocycles and/or heterocycles, or $R^8+R^{8'}$ and/or $R^9+R^{9'}$ and/or $R^{10}+R^{10'}$ and/or $R^{11}+R^{11' \text{ and/or } R15}+R^{15'}$ and/or $R^{15''}+R^{15'''}$ and/or $R^{16}+R^{16'}$ and/or $R^{20}+R^{20'}$ and/or $R^{21}+R^{21'}$ are independently selected from =O, =S, =$NOR^{h1}$, =$C(R^{h1})R^{h2}$, and =$NR^{h1}$, $R^{h1}$ and $R^{h2}$ being independently selected from H and optionally substituted $C_{1-3}$ alkyl, two or more of $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ optionally being joined by one or more bonds to form one or more optionally substituted carbocycles and/or heterocycles.

In another embodiment, $X^3$ is not represented by —$X^{3a}$ and $X^{3b}$—.

In a further embodiment, if DB is DB2 in a compound of formula (I) or (II), then $X^1$ is O.

In a further embodiment, if DB is DB2 in a compound of formula (I) or (II) and $X^3$ is represented by —$X^{3a}$ and $X^{3b}$—, then $X^1$ is O.

Any of the substituents present on any of the rings in DB1, DB2, DB3, DB4, DB5, DB6, DB7, DB8, and DB9 may be or comprise another DB1, DB2, DB3, DB4, DB5, DB6, DB7, DB8, or DB9 moiety or any other DNA-binding moiety. Such another DB moiety or DNA-binding moiety may be connected to the first DB moiety via for example an amide or ketone linkage.

In one embodiment, at least one ring in the DNA-binding moiety is aromatic. In another embodiment, at least one ring system is aromatic. In yet another embodiment, all rings in the DNA-binding moiety are aromatic or form an aromatic ring system. In yet another embodiment, the DNA-binding moiety contains at least a bicyclic aromatic moiety.

Substituents $R^1$ to $R^{23}$ may assist in improving the pharmacological properties of a compound of formula (I) or (II) or its conjugate, for example, its water solubility. This may for example be achieved by selecting one or more of the substituents $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{20}$, $R^{20'}$, $R^{21}$, $R^{21'}$, $R^{22}$, and $R^{23}$ to comprise or be an oligoethylene glycol or polyethylene glycol moiety or a triazole moiety. Alternatively or simultaneously, one or more of the substituents may comprise or be a water-soluble group. The presence of a water-soluble group may not only result in enhanced water solubility, but may also prevent a compound of formula (I) or (II) from crossing a biological barrier, especially when it is an apolar barrier, such as a cell membrane. This may be advantageous, especially when a compound of formula (I) or (II) is delivered into a targeted cell through conjugation to a targeting moiety before it is released from the conjugate as the compound of formula (I) or (II) will be unable to leave the cell. Even active transport via for example the P-glycoprotein pump may be (partially) impaired. When a compound of formula (I) or (II) is prematurely released from the conjugate, e.g., in the circulation, it may be unable or only moderately able to enter (non-targeted) cells aspecifically as its membrane translocation capabilities may be impaired by the water-soluble group. This may lead to increased selectivity and therefore to fewer side effects. In addition, at least in some instances, for example when the water-soluble group is positively charged under physiological conditions, the water-soluble group may also improve the binding affinity for DNA by means of favorable electrostatic interactions with the negatively charged phosphate groups.

A water-soluble group is a group that imparts increased solubility on a compound of formula (I) or (II) and/or a conjugate thereof. In one embodiment, water solubility of a compound of this invention carrying a water-soluble group is increased by more than 100% compared to the compound lacking said water-soluble group. In other embodiments, water solubility of a compound of this invention carrying a water-soluble group is increased by more than 75% or 50% or 25% or 10% compared to the compound lacking said water-soluble group. The water-soluble group may also contribute to prevent or reduce aggregation of compounds of this invention or to reduce side effects. Examples of water-soluble groups include, but are not limited to, $-NH_2$, $-NH-$, $-NHR^s$, $-NR^s-$, $-N(R^s)(R^t)-$, $-^+N(R^s)(R^t)-$, $-^+N(R^s)(R^t)(R^u)$, $-COOH$, $-OP(O)(OH)_2$, $-OP(O)(OH)O-$, $-OP(O)(OR^s)O-$, $-OP(O)(OH)OR^s$, $-OP(O)(OR^s)OR^t$, $-P(O)(OH)_2$, $-P(O)(OH)O-$, $-P(O)(OR^s)OH$, $-P(O)(OR^s)O-$, $-P(O)(OR^s)(OR^t)$, $-OS(O)_2OH$, $-OS(O)_2O-$, $-OS(O)_2OR^s$, $-S(O)_2OH$, $-S(O)_2O-$, $-S(O)_2OR^s$, $-OS(O)OH$, $-OS(O)O-$, $-OS(O)OR^s$, $-S(O)OH$, $-S(O)O-$, $-OS(O)-$, $-S(O)OR^s$, $-OS(O)_2-$, $-OS(O)_2R^s$, $-S(O)_2-$, $-S(O)_2R^s$, $-OS(O)R^s$, $-S(O)-$, $-S(O)R^s$, $-(OCH_2CH_2)_{v'}OH$, $-(OCH_2CH_2)_{v'}O-$, $-(OCH_2CH_2)_{v'}OR^s$, a sugar moiety, an oligosaccharide moiety, and an oligopeptide moiety, or a protonated or deprotonated form thereof and further any combination thereof, wherein $R^s$, $R^t$, and $R^u$ are independently selected from H and optionally substituted $C_{1-3}$ alkyl, two or more of $R^s$, $R^t$, and $R^u$ optionally being joined by one or more bonds to form one or more carbocycles and/or heterocycles, and $v'$ is an integer selected from 2 to 1000. The water-soluble group may be at any position within a substituent or may constitute the whole substituent. The water-soluble group may for example be located at any interior position, be part of the main chain, be part of a ring structure, be a functional group pending to the main chain or a ring, or be placed at the position at which the substituent is attached to the remainder of the agent.

In one embodiment, at least one of $R^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ contains a water-soluble group.

In another embodiment, at least one of $R^6$, $R^7$, $R^{14}$, $R^8$, $R^9$, and $R^{10}$ contains a water-soluble group.

In yet other embodiments, $R^8$ or $R^9$ or $R^{10}$ or $R^6$ or $R^7$ or $R^{14}$ contains a water-soluble group.

In one embodiment, the water-soluble group is a carboxylic acid group.

In another embodiment, the water-soluble group is an amino group.

In further embodiments, the water-soluble group is a primary or secondary or tertiary or quaternary amino (ammonium) group. In other embodiments, the water-soluble group is a primary or secondary or tertiary or quaternary aliphatic amino (ammonium) group.

A compound of formula (I) or (II) may not have a reactive moiety incorporated in its structure. On the other hand, as becomes clear from the above, a reactive moiety may be present in its structure that allows for reaction of a compound of formula (I) or (II) with another moiety. For example, a compound of formula (I) or (II) may be reacted with a targeting moiety or a linker-targeting moiety construct, e.g., an antibody or an antibody fragment, or an antibody-linker construct or an antibody fragment-linker construct, to prepare a targeting moiety-agent conjugate in one or more steps, which may or may not be a conjugate of formula (III). The formation of a targeting moiety-agent conjugate may not only be carried out through chemical synthesis, but may also occur in situ, i.e., upon administration of a compound of formula (I) or (II) in vivo. The compound of formula (I) or (II) may for example bind to endogenous proteins, e.g., albumin, upon administration.

Conjugates and Linker-Agent Conjugates

In another aspect, this invention relates to a conjugate of a compound of formula (I) or (II) that can be converted in vivo in one or more steps to a compound of formula (I) or (II), respectively. The conjugate may also be converted to a derivative of a compound of formula (I) or (II) in which a part of the promoiety attached to a compound of formula (I) or (II) in the conjugate remains attached to the compound of formula (I) or (II) after in vivo conversion. An alternative way of looking at this is that the remaining moiety of the linker is part of the compound of formula (I) or (II).

These conjugates may favorably affect the pharmacological properties and other characteristics of a compound of formula (I) or (II). In one embodiment, this invention relates to a conjugate comprising a compound of formula (I) or (II) conjugated to at least one promoiety. In another embodiment, this invention relates to a conjugate comprising a compound of formula (I) or (II) conjugated to a promoiety.

In a further embodiment, this invention relates to a compound of formula (III):

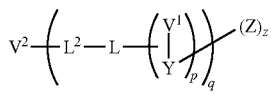
(III)

or a pharmaceutically acceptable salt, hydrate, or solvate thereof, wherein $V^2$ is either absent or a functional moiety;

each $L^2$ is independently absent or a linking group linking $V^2$ to L;

each L is independently absent or a linking group linking $L^2$ to one or more $V^1$ and/or Y;

each $V^1$ is independently absent or a conditionally-cleavable or conditionally-transformable moiety, which can be cleaved or transformed by a chemical, photochemical, physical, biological, or enzymatic process;

each Y is independently absent or a self-eliminating spacer system which is comprised of 1 or more self-elimination spacers and is linked to $V^1$, optionally L, and one or more Z;

each p and q are numbers representing a degree of branching and are each independently a positive integer;

z is a positive integer equal to or smaller than the total number of attachment sites for Z;

each Z is independently a compound of formula (I), (II), (I'), or (II') as defined hereinabove wherein one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, and $R^{23}$ may optionally in addition be substituted by or be a substituent of formula (V):

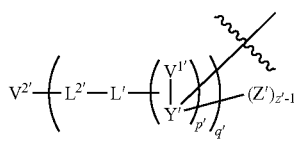
(V)

wherein each $V^{2'}$, $L^{2'}$, L', $V^{1'}$, Y', Z', p', q', and z' has the same meaning as defined for $V^2$, $L^2$, L, $V^1$, Y, Z, p, q, and z, respectively, and is independently selected, the one or more substituents of formula (V) being independently connected via Y' to one or more of $X^1$, $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, and/or to one or more atoms bearing these R substituents;

each Z is independently connected to Y through either $X^1$, an atom in $R^5$, $R^{5'}$, $R^6$, $R^{6'}$, $R^7$, $R^{7'}$, $R^{14}$, $R^{14'}$, $R^8$, $R^{8'}$, $R^9$, $R^{9'}$, $R^{10}$, $R^{10'}$, $R^{11}$, $R^{11'}$, $R^{15}$, $R^{15'}$, $R^{15''}$, $R^{15'''}$, $R^{16}$, $R^{16'}$, $R^{20}$, $R^{20'}$, $R^{21}$, $R^{21'}$, $R^{22}$, $R^{23}$, or an atom bearing any of these R substituents; and at least $V^2$ or a $V^1$ is present.

In a further aspect, this invention relates to a compound of formula (III), wherein $V^2$ is present and selected to be a targeting moiety and there is at least one group of formula (V) that contains a $V^{1'}$ moiety and either comprises a $V^{2'}$, $L^2$, or L' moiety that contains a $X^{14}(CH_2CH_2O)_{gg}CH_2CH_2X^{14}$ moiety, wherein gg is selected from 3 to 1000 and each $X^{14}$ is independently selected from

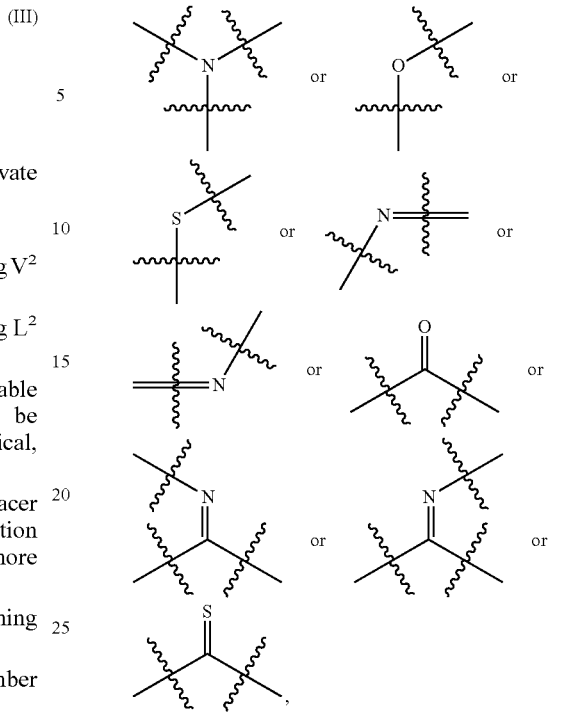

or said same group of formula (V) comprises at least 2 $X^{14}CH_2CH_2OCH_2CH_2X^{14}$ moieties, in which each $X^{14}$ is independently selected.

It should be understood from formula (III) that L can be connected to $V^1$ and/or to Y. If L is connected to Y, this means that both $V^1$ and L, as well as one or more Z, are connected to Y. If L is connected to $V^1$, this means that $V^1$ and one or more Z are connected to Y. L may also be connected to both $V^1$ and Y at the same time. If Y is absent, L is connected to $V^1$ or, if $V^1$ is absent, L is directly connected to Z.

The $V^2(-L^2-L(-(V^1-Y))_p)_q(Z)_{z-1}$ and one or more $V^{2'}(-L^{2'}-L'(-(V^{1'}-Y'))_{p'})_{q'}(Z')_{z'-1}$ moieties, wherein $L(-(V^1-Y))_p$ indicates that L can be connected to $V^1$ and/or to Y, connected to Z are herein referred to as promoieties.

The present invention also relates to a compound of formula (IV):

(IV)

or a pharmaceutically acceptable salt, hydrate, or solvate thereof, wherein

RM is a reactive moiety and L, $V^1$, Y, Z, p, and z are as defined hereinabove, except that L is now linking RM to one or more $V^1$ and/or Y, and $V^1$, Y, and Z may contain protecting groups, and the one or more $V^{2'}-L^{2'}$ moieties optionally present in Z as defined hereinabove may optionally and independently be RM' instead, which is a reactive moiety, and wherein, if there is more than 1 reactive moiety in (IV), some or all reactive moieties are the same or different. These linker-agent conjugates of formula (IV) may or may not be considered intermediates for compounds of formula (III). In a compound of formula (IV), RM must be present while $V^1$ may be either present or absent.

In a further aspect, the present invention relates to a compound of formula (IV), wherein RM is a reactive moiety selected from carbamoyl halide [—N(R)C(O)X], acyl halide [—C(O)X], active ester [—C(O)OR], anhydride [—C(O)OC(O)OR], α-haloacetyl [—C(O)CH$_2$X], α-haloacetamide [—N(R)C(O)CH$_2$X], maleimide, isocyanate [—N=C=O], isothiocyanate [—N=C=S], disulfide [—S—SR], thiol [—SH], hydrazine [—NH$_2$NH$_2$], hydrazide [—C(O)NH$_2$NH$_2$], sulfonyl chloride [—S(O)$_2$Cl], aldehyde [—C(O)H], methyl ketone [—C(O)CH$_3$], vinyl sulfone [—S(O)$_2$—CH=CH$_2$], halomethyl [—CH$_2$Cl], and methyl sulfonate [—CH$_2$OS(O)$_2$R], and wherein at least one group of formula (V), being part of Z, contains a $V^{1'}$ moiety and either comprises a $V^{2'}$, $L^{2'}$, or $L'$ moiety that contains a $X^{14}$(CH$_2$CH$_2$O)$_{gg}$CH$_2$CH$_2$X$^{14}$ moiety, wherein gg is selected from 3 to 1000 and each $X^{14}$ is independently selected from

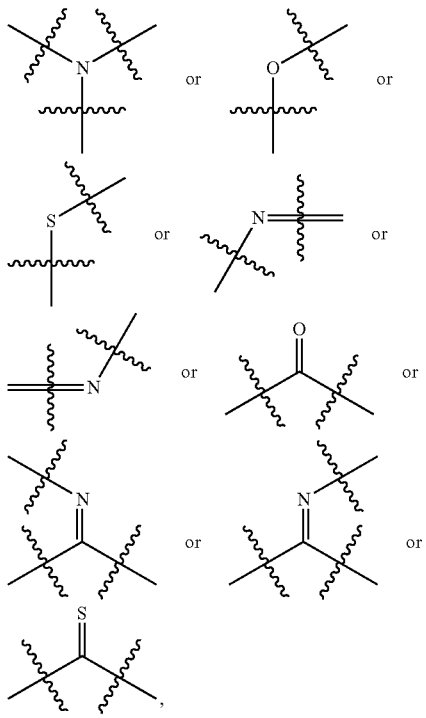

or said same group of formula (V) comprises at least 2 $X^{14}$CH$_2$CH$_2$OCH$_2$CH$_2$X$^{14}$ moieties, in which each $X^{14}$ is independently selected. These linker-agent conjugates of formula (IV) may or may not be considered intermediates for compounds of formula (III). In such a compound of formula (IV), RM must be present.

The RM-L(-($V^1$—Y))$_p$(Z)$_{z-1}$ and one or more RM'-L'(-($V^{1'}$—Y'))$_p$(Z')$_{z'-1}$ moieties, wherein L(-($V^1$—Y))$_p$ indicates that L can be connected to $V^1$ and/or to Y, connected to Z are herein referred to as promoieties.

It is noted that the separate $X^{14}$ moieties in the —CH$_2$CH$_2$X$^{14}$ moieties that may be present in a compound of formula (III) or (IV) are independently selected.

It is also noted that z does not represent a degree of polymerization; hence z does not indicate that a number of moieties Z are connected to one another.

It is further noted that if Y or Y' is connected to an atom bearing a specific R substituent instead of to this R substituent itself, this in fact means that this R substituent is absent if this is necessary to meet valency rules.

It is further noted that if $X^{14}$ in for example —CH$_2$CH$_2$X$^{14}$ represents

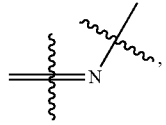 [SMILES: *N=*]

then —CH$_2$CH$_2$X$^{14}$ should be read as —CH$_2$CHX$^{14}$.

It should be understood that this invention relates to enantiomerically pure and/or diastereomerically pure compounds of formulae (III) and (IV) as well as to enantiomeric and/or diastereomeric mixtures of compounds of formulae (III) and (IV).

When a compound of formula (III) or (IV) contains attachment sites in Y for Z that are not coupled to Z, for instance as a consequence of an incomplete coupling reaction with Z during synthesis, these attachment sites are considered to be attached to H, OH, or a leaving group instead. If all of said attachment sites are connected to Z, then z equals the number of said attachment sites; otherwise, z is lower. Compounds of this invention may exist as a mixture, wherein each component of the mixture has a different z value. For example, the compound may exist as a mixture of two separate compounds, one compound wherein z is 4 and another compound wherein z is 3. Furthermore, for a given z, the compound may exist as a mixture of (constitutional) isomers as Z may be connected to distinct (sets of) attachment sites.

For reasons of clarity, when referring to the connections of one first moiety to other moieties within formula (III) or (IV), in general only those said other moieties are mentioned that are directly attached to said first moiety in formula (III) or (IV). It should be understood that if one of said other moieties is not present, said first moiety is actually connected to the moiety first in line that is present, unless explicitly stated otherwise. For example, if it is stated that "$V^1$ is cleaved from Y", this phrase actually means "$V^1$ is cleaved from Y, or from Z if Y is absent" and should be read as "$V^1$ is cleaved from Z" when reference is made to a compound lacking Y.

In a compound of formula (III) or (IV), Z may be conjugated to a promoiety through its water-soluble group, e.g., an oligoethylene glycol or polyethylene glycol moiety. In this way, the water-soluble group may contribute less to the water solubility of the compound of formula (III) or (IV), but may contribute again to the water solubility of Z upon removal of said promoiety.

In this document, whenever $V^2$, $L^2$, L, $V^1$, Y, Z, RM, p, q, or z is mentioned, it should be understood that the same can apply for each $V^{2'}$, $L^{2'}$, $L'$, $V^{1'}$, $Y'$, $Z'$, RM', p', q', or z', respectively, unless the context dictates otherwise.

The $V^1$ Moiety

In a compound of formula (III) or (IV), the $V^1$ moiety is a group that is conditionally cleavable or transformable. In other words, it is designed to be transformed and/or cleaved from Y by a chemical, photochemical, physical, biological, or enzymatic process upon being brought in or under a certain condition. This condition may for example be bringing a compound of the invention in an aqueous environment, which leads to hydrolysis of $V^1$, or bringing a compound of the invention in an environment that contains an enzyme that recognizes and cleaves $V^1$, or bringing a compound of the invention under reducing conditions, which leads to reduction and/or removal of $V^1$, or bringing a compound of the invention under oxidizing conditions, which leads to oxidation and/or removal of $V^1$, or bringing a compound of the invention in contact with radiation, e.g., UV light, which leads to transformation and/or cleavage, or bringing a compound of the invention in contact with heat, which leads to transformation and/or cleavage, or bringing a compound of the invention under reduced pressure, which leads to transformation, e.g., a retrocycloaddition, and/or cleavage, or bringing a compound of the invention under elevated or high pressure, which leads to transformation and/or cleavage. This condition may be met after administrating a compound of this invention to an animal, e.g., a mammal, for example a human: the condition may be met when the compound localizes to for example a specific organ, tissue, cell, subcellular target, or bacterial, viral, or microbial target, for example by the presence of internal factors (e.g., target-specific enzymes or hypoxia) or application of external factors (e.g., radiation, magnetic fields) or the condition may already be met directly upon administration (e.g., ubiquitous enzymes in the circulation).

Cleavage of $V^1$ means that the bond between $V^1$ and Y is broken. Transformation of $V^1$ means that $V^1$ is converted into a different moiety and this event may directly or indirectly lead to self-cleavage of $V^1$ from Y. Alternatively, transformation of $V^1$ may lead to formation of a $V^1$—Y moiety which is a self-immolative linker. In this case, Y only becomes self-immolative after transformation of $V^1$. The transformed $V^1$ moiety actually becomes (partially) part of Y. For example, oxidation of $V^1$ being a hydrogen atom to a hydroxyl group may lead to formation of a para- or ortho-hydroxybenzyloxycarbonyl $V^1$—Y moiety that self-eliminates. As another example, reduction of $V^1$ being a nitro group may lead to formation of a para- or ortho-aminobenzyloxycarbonyl $V^1$—Y moiety that self-eliminates.

Alternatively again, $V^1$ may be absent. In this instance, the promoiety is intended to be non-removable from Z and the whole promoiety or a part thereof (in case of degradation of a compound of formula (III) or (IV) at one or more other sites in the molecule) will stay connected to the one or more moieties Z. One alternative way to look at this is that the part of the promoiety that remains attached to the moiety Z is in fact a part of moiety Z.

A compound of this invention may contain more than one $V^1$ moiety per promoiety (p and/or q>1). These $V^1$ moieties may or may not be the same and may or may not require the same conditions for transformation and/or cleavage.

In one aspect of this invention, a conjugate is used to target one or more moieties Z to target cells. In this instance, a $V^1$ moiety may for example contain a substrate molecule that is cleaved by an enzyme present in the vicinity of the target cells or inside the target cells, for example tumor cells. $V^1$ can for example contain a substrate that is cleaved by an enzyme present at elevated levels in the vicinity of or inside the target cells as compared to other parts of the body, or by an enzyme that is present only in the vicinity of or inside the target cells.

It is important to recognize that if target site specificity is achieved solely based upon the selective transformation and/or cleavage of said $V^1$ at the target site, the condition causing the cleavage should preferably, at least to a certain degree, be target site-specific, whereas the presence of another target-specific moiety in the compound of the invention, for instance in a $V^2$ moiety, weakens or takes away this requirement. For example, when $V^2$ causes selective internalization into a target cell, an enzyme also present in other cells may transform and/or cleave $V^1$. However, cleavage should preferably not occur at a site distant from the target site. Therefore, the conjugate should not be exposed to enzymes or conditions that can cause cleavage of $V^1$ at sites other than the target site.

In one embodiment, transformation and/or cleavage of $V^1$ occur intracellularly. In another embodiment, transformation and/or cleavage of $V^1$ occur extracellularly. In another embodiment, transformation and/or cleavage of $V^1$ occur by a ubiquitous intracellular enzyme. In another embodiment, transformation and/or cleavage of $V^1$ occur by a ubiquitous extracellular enzyme.

In one embodiment, $V^1$ contains an amino acid, a di-, tri-, tetra-, or oligopeptide, or a peptidomimetic, which consists of an amino acid or amino acid sequence or mimetic thereof recognized and cleavable by a proteolytic enzyme, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment, $V^1$ is a peptide. In another embodiment, $V^1$ is a single amino acid. In another embodiment, $V^1$ is a dipeptide. In another embodiment, $V^1$ is a tripeptide. In another embodiment, $V^1$ is a tetrapeptide. In yet another embodiment, $V^1$ is a peptidomimetic.

In another embodiment, $V^1$ contains a β-glucuronide that is recognized by β-glucuronidase present in the vicinity of or inside tumor cells.

In one embodiment, $V^1$ contains a substrate for an enzyme.

In one embodiment, $V^1$ contains a substrate for an extracellular enzyme.

In another embodiment, $V^1$ contains a substrate for an intracellular enzyme.

In yet another embodiment, $V^1$ contains a substrate for a lysosomal enzyme.

In yet another embodiment, $V^1$ contains a substrate for the serine protease plasmin.

In yet another embodiment, $V^1$ contains a substrate for one or more of the cathepsins, for example cathepsin B.

In yet another embodiment, $V^1$ contains a substrate for a galactosidase.

In yet another embodiment, $V^1$ contains a substrate for quinone reductase NQO1.

In yet another embodiment, $V^1$ contains a hydrazide, hydrazone or imine moiety that is to be hydrolyzed intracellularly.

In yet another embodiment, $V^1$ contains a disulfide moiety that is to be cleaved intracellularly.

When $V^1$ is cleaved extracellularly, the one or more Z moieties may be released extracellularly. This may provide the advantage that these Z moieties are not only able to affect the cell(s) directly surrounding the site of activation (e.g., target-positive cells), but also cells somewhat further away from the site of activation (e.g., target-negative cells) due to diffusion (bystander effect), provided that the Z moieties are able to penetrate the cell membrane.

An enzyme to cleave $V^1$ can also be transported to the vicinity of or inside target cells or target tissue via for example antibody-directed enzyme prodrug therapy (ADEPT), polymer-directed enzyme prodrug therapy (PDEPT), macromolecular-directed enzyme prodrug therapy (MDEPT), virus-directed enzyme prodrug therapy (VDEPT), or gene-directed enzyme prodrug therapy (GDEPT). In these approaches, the enzyme that needs to cleave $V^1$ is transported to or induced to be produced at the target site before administration of the prodrug, e.g., a compound of formula (III) or (IV). In one embodiment, transformation and/or cleavage of $V^1$ occur through an enzyme linked to an antibody using the ADEPT approach.

In again another embodiment, $V^1$ contains a moiety, for example a nitrobenzyl moiety that can be transformed and/or cleaved by reduction under hypoxic conditions or by reduction by a nitroreductase. After reduction of the nitro group and cleavage of the resulting moiety via self-elimination, self-elimination of the spacer system Y, if present, leads to release of one or more moieties Z.

In one embodiment, the invention relates to a conjugate wherein $V^1$ is a single amino acid, a dipeptide, a tripeptide, a tetrapeptide, or an oligopeptide moiety comprised of natural L amino acids, unnatural D amino acids, or synthetic amino acids, or a peptidomimetic, or any combination thereof. In another embodiment, the invention relates to a compound wherein $V^1$ comprises a tripeptide. The tripeptide may be linked via its C-terminus to Y. In one embodiment, the C-terminal amino acid residue of the tripeptide is selected from alanine, arginine, citrulline, and lysine, the middle amino acid residue of the tripeptide is selected from alanine, valine, leucine, isoleucine, methionine, phenylalanine, cyclohexylglycine, tryptophan, and proline, and the N-terminal amino acid residue of the tripeptide is selected from any natural or unnatural amino acid.

In another embodiment, the invention relates to a compound wherein $V^1$ comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid.

In yet another embodiment, the invention relates to a compound wherein $V^1$ comprises a single amino acid. The amino acid may be linked via its carboxyl group to Y. In one embodiment, the amino acid is selected from alanine, arginine, citrulline, and lysine.

In one embodiment, when the α-amino group of the N-terminal amino acid of $V^1$ is not coupled to L, this amino acid may be functionalized with a suitable blocking group coupled to the α-amino group or may be an unnatural amino acid such that undesired premature degradation of $V^1$ by for example ubiquitous enzymes, e.g., exopeptidases, is prevented.

In a further embodiment, $V^1$ is selected from D-alanylphenylalanyllysine, D-valylleucyllysine, D-alanylleucyllysine, D-valylphenylalanyllysine, D-valyltryptophanyllysine, D-alanyltrypto-phanyllysine, alanylphenylalanyllysine, valylleucyllysine, alanylleucyllysine, valylphenyl-alanyllysine, valyltryptophanyllysine, alanyltryptophanyllysine, D-alanylphenylalanylcitrulline, D-valylleucylcitrulline, D-alanylleucylcitrulline, D-valylphenylalanylcitrulline, D-valyltryptophanylcitrulline, D-alanyltryptophanylcitrulline, alanylphenylalanylcitrulline, valylleucyl-citrulline, alanylleucylcitrulline, valylphenylalanylcitrulline, valyltryptophanylcitrulline, and alanyltryptophanylcitrulline.

In yet another embodiment, $V^1$ is selected from phenylalanyllysine, valyllysine, valylalanine, D-phenylalanylphenylalanyllysine, phenylalanylphenylalanyllysine, glycylphenylalanyllysine, alanyllysine, valylcitrulline, N-methylvalylcitrulline, phenylalanylcitrulline, isoleucylcitrulline, tryptophanyllysine, tryptophanylcitrulline, phenylalanylarginine, phenylalanylalanine, glycylphenylalanylleucylglycine, alanylleucylalanylleucine, alanylarginylarginine, phenylalanyl-$N^9$-tosylarginine, phenylalanyl-$N^9$-nitroarginine, leucyllysine, leucylcitrulline, and phenylalanyl-O-benzoylthreonine.

In a further embodiment, $V^1$ is selected from phenylalanyllysine, valyllysine, and valylcitrulline. Therefore, in one embodiment this invention relates to a compound wherein $V^1$ contains a substrate that can be cleaved by a proteolytic enzyme, plasmin, a cathepsin, cathepsin B, β-glucuronidase, a galactosidase, prostate-specific antigen (PSA), urokinase-type plasminogen activator (u-PA), a member of the family of matrix metalloproteinases, or an enzyme localized by means of directed enzyme prodrug therapy, such as ADEPT, VDEPT, MDEPT, GDEPT, or PDEPT, or wherein $V^1$ contains a moiety that can be cleaved or transformed through reduction under hypoxic conditions, through reduction by a nitroreductase, or through oxidation.

In another aspect of this invention, a conjugate of this invention is used primarily to improve the pharmacological properties of Z. When a promoiety does not need to be selectively removed at a target site, $V^1$ of said promoiety may for example be or contain a group that is cleaved by ubiquitous enzymes, e.g., esterases that are present in the circulation or intracellular enzymes, such as for example proteases and phosphatases, by pH-controlled intramolecular cyclization, or by acid-catalyzed, base-catalyzed, or non-catalyzed hydrolysis, or $V^1$ may for example be or contain a disulfide or form a disulfide with a neighboring moiety. $V^1$ may therefore, optionally together with the connecting atom(s) of L and/or Y, for example form a carbonate, carbamate, ureum, ester, amide, imine, hydrazone, hydrazide, oxime, disulfide, acetal, or ketal group that can be cleaved in vivo. This means that $V^1$, optionally together with the connecting atom(s) of L and/or Y, can for example also represent —OC(O)—, —C(O)O—, —OC(O)O—, —N(R$^v$)C(O)—, —C(O)N(R$^v$)—, —N(R$^v$)C(O)O—, —OC(O)N(R$^v$)—, —N(R$^v$)C(O)N(R$^w$)—, —C(O)—, —OC(R$^v$)(R$^w$)—, —C(R$^v$)(R$^w$)O—, —OC(R$^v$)(R$^w$)O—, —C(R$^v$)(R$^w$)—, —S—, —S—S—, —C=, =C—, —N=, =N—, —C=N—, —N=C—, —O—N=, =N—O—, —C=N—O—, —O—N=C—, —N(R$^v$)—N=, =N—N(R$^v$)—, —N(R$^v$)—N=C—, or —C=N—N(R$^v$)—, wherein R$^v$ and R$^w$ are independently selected from H and optionally substituted $C_{1-10}$ alkyl, $C_{1-10}$ heteroalkyl, $C_{1-10}$ heteroaryl, $C_{3-10}$ cycloalkyl, $C_{1-10}$ heterocycloalkyl, or $C_{5-10}$ aryl, R$^v$ and R$^w$ optionally being joined by one or more bonds to form one or more optionally substituted carbocycles and/or heterocycles.

$V^1$ may therefore for example be or contain, optionally together with the connecting atom(s) of L and/or Y, a peptide, an amino acid, a peptidomimetic, a disulfide, a monosaccharide or disaccharide or a derivative thereof, a nitroaromatic moiety, an imine, a hydrazide, or a hydrazone moiety.

If $V^1$ or $V^1$—Y represents a whole promoiety or L is connected to Y and not to $V^1$, $V^1$ may for example also be selected from a mono-, di-, or oligosaccharide, R$^p$—[O(R$^{p'}$O)P(O)]$_{pp}$—, R$^p$—C(O)—, R$^p$—OC(O)—, and R$^p$—N(R$^{p'}$)C(O)—, wherein pp is selected from 1 to 3 and each R$^p$ and R$^{p'}$ is independently selected from H and optionally substituted $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, R$^p$ and R$^{p'}$ optionally being joined by one or more bonds to form one or more optionally substituted carbocycles and/or heterocycles.

In one embodiment, $V^1$ is selected from phosphono, phenylaminocarbonyl, 4-(piperidin-1-yl)piperidin-1-ylcarbonyl, piperazin-1-ylcarbonyl, piperidin-1-ylcarbonyl, pyrrolidin-1-ylcarbonyl, and 4-methylpiperazin-1-ylcarbonyl.

$V^1$ itself may contribute to favorable pharmacological properties of the conjugate, for example through the presence of polar functional groups in $V^1$.

If a conjugate of this invention contains more than 1 promoiety, one of these promoieties may be used to target the conjugate to a target site (targeting promoiety), whereas another promoiety is used to improve the pharmacological properties. In this instance, the $V^1$ moiety in the targeting promoiety is preferably cleaved at the target site, for example through a target site-specific process such as an enzymatic cleavage by an enzyme predominantly present at the target site or through a more generic intracellular process which can only occur after target cell-selective internalization of the conjugate, whereas the promoiety that helps to improve the pharmacological properties may be cleaved either at the target site or systemically, for example by ubiquitous enzymes.

It should be noted that $V^1$, either in the form of an amino acid, a di-, tri-, tetra-, or oligopeptide, or in any other form, may contain protecting groups. Compounds of the invention comprising such a protected $V^1$ may not release any Z moiety when put under conditions that will transform and/or cleave the corresponding unprotected $V^1$. However, when said compounds are deprotected, such compounds will release one or more Z moieties when put under the appropriate conditions. Compounds comprising such a protected $V^1$ also fall under the scope of this invention. In particular the above can be envisioned for compounds of formula (IV). Suitable protecting groups for functional groups, in particular for amino acids, are well-known to the organic chemist and may for example be found in T. W. Greene, *Protective Groups in Organic Synthesis*, John Wiley & Sons, New York, 1981.

Compounds of formulae (III) and (IV) can be designed to eventually release a compound of formula (I) or (II), or a compound of formula (I') or (II'), after transformation and/or cleavage of the one or more $V^1$ and $V^{1'}$ moieties. Release of a compound of formula (I) or (II), a compound of formula (I') or (II'), or a derivative thereof (for example due to only partial degradation of the promoiety) from a conjugate of this invention via another mechanism is however not excluded from this invention.

In another aspect of this invention, a compound of formula (III) represents an intermediate for the preparation of a compound of formula (I) or (II) or another compound of formula (III). In this instance, for example, $V^2$, $L^2$, L, and Y are absent, p, q, and z all are 1, and the $V^1$ moiety may be a protecting group. There may or may not be one or more $V^{2'}(-L^{2'}-L'(-(V^{1'}-Y'))_{p'})_{q'}(Z')_{z'+1}$ moieties present, in which $V^{2'}$, $L^{2'}$, $L'$, and $Y'$ may or may not be absent, and p', q', and z' all may or may not be 1. In one embodiment, a compound of formula (III) is a compound of formula (I) or (II) to which a $V^1$ moiety is attached. In another embodiment, a compound of formula (III) is a compound of formula (I) or (II) to which a $V^1$ moiety and a $V^{2'}(-L^{2'}-L'(-(V^{1'}-Y'))_{p'})_{q'}(Z')_{z'-1}$ moiety are attached. In yet another embodiment, a compound of formula (III) is a compound of formula (I) or (II) to which a $V^1$ moiety and a $V^{1'}$ moiety are attached.

In one embodiment, $V^1$ is not a protecting group.

In another embodiment, $V^2$, $L^2$, L, and Y are absent, and p, q, and z all are 1.

In a further embodiment, $V^1$ is a chemically removable group.

In yet a further embodiment, $V^1$ is a chemically removable group connected to Z via $X^1$.

In yet another further embodiment, $V^1$ is a benzyl group connected to Z via $X^1$.

In another embodiment, $V^1$ is tert-butoxycarbonyl(methylamino)ethyl(methylamino)carbonyl.

In another embodiment, $V^1$ is 4-(tert-butoxycarbonyl)piperazine-1-carbonyl.

In one embodiment, $V^1$ is connected to L via more than one functional group on $V^1$.

In another embodiment, $V^1$ is connected to L via one functional group on $V^1$.

In another embodiment, $V^1$ is connected to L via a functional group in the side chain of one of the natural or unnatural amino acids of $V^1$.

In another embodiment, the N-terminal amino acid of $V^1$ is connected via its a amino group to L.

In another embodiment, $V^1$ is absent.

The Self-Eliminating Spacer System Y

The self-elimination spacer system Y, if present, links $V^1$ and optionally L to one or more moieties Z.

A self-elimination spacer system Y may be incorporated in a conjugate of this invention for example to improve the properties of Z or the conjugate in general, to provide for suitable coupling chemistries, and/or to create space between $V^1$ and Z.

A compound of this invention may contain more than one spacer system Y per promoiety. These moieties Y may or may not be the same.

After cleavage or transformation of $V^1$, the left-hand side of Y may become unblocked or a $V^1$—Y self-elimination moiety may be formed, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art.

In one aspect the invention is related to compounds wherein Y is $(W-)_w(X-)_x(A-)_s,$ wherein W and X are each a single-release 1,2+2n electronic cascade spacer (n≥1), being the same or different;

A is an ω-amino aminocarbonyl cyclization spacer that forms a cyclic ureum derivative upon cyclization;

s is 0 or 1;

w and x are numbers representing degree of polymerization and are independently an integer from 0 (included) to 5 (included).

According to a further embodiment of this invention, the 1,2+2n electronic cascade spacers W and X are independently a moiety having the formula:

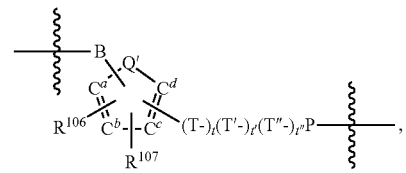

wherein

Q' is selected from $-R^{110}C=CR^{111}-$, S, O, $NR^{111}$, $-R^{111}C=N-$, and $-N=CR^{111}-$;

B is selected from $NR^{112}$, O, and S;

P is $C(R^{108})(R^{109})Q$;

$R^{106}$, $R^{107}$, B, and $(T-)_t(T'-)_{t'}(T''-)_{t''}P$ are connected to $C^a$, $C^b$, $C^c$, and $C^d$ in such a way that B and $(T-)_t(T'-)_{t'}(T''-)_{t''}P$ are connected to two adjacent carbon atoms or to $C^a$ and $C^d$, respectively;

Q is absent or $-O-C(O)-$;

t, t', and t" are numbers representing degree of polymerization and are independently an integer from 0 (included) to 5 (included);

T, T', and T" are independently selected from moieties having the formula:

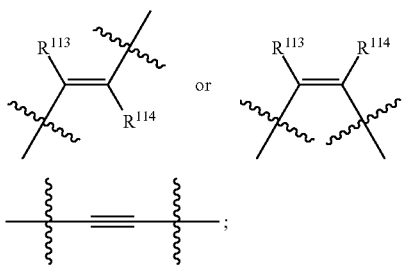

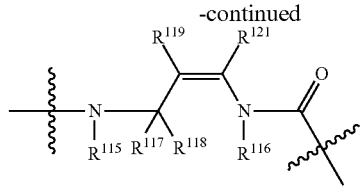

$R^{106}$, $R^{107}$, $R^{108}$, $R^{109}$, $R^{110}$, $R^{111}$, $R^{112}$, $R^{113}$, and $R^{114}$ are independently selected from H, OH, SH, $NH_2$, $N_3$, $NO_2$, NO, $CF_3$, CN, $C(O)NH_2$, C(O)H, C(O)OH, halogen, $R^y$, $SR^y$, $S(O)R^y$, $S(O)_2R^y$, $S(O)OR^y$, $S(O)_2OR^y$, $OS(O)R^y$, $OS(O)_2R^y$, $OS(O)OR^y$, $OS(O)_2OR^y$, $OR^y$, $NHR^y$, $N(R^y)R^{y1}$, $^+N(R^y)(R^{y1})R^{y2}$, $P(O)(OR^y)(OR^{y1})$, $OP(O)(OR^y)(OR^{y1})$, $C(O)R^y$, $C(O)OR^y$, $C(O)N(R^{y1})R^y$, $OC(O)R^y$, $OC(O)OR^y$, $OC(O)N(R^y)R^{y1}$, $N(R^{y1})C(O)R^y$, $N(R^{y1})C(O)OR^y$, and $N(R^{y1})C(O)N(R^{y2})R^y$, wherein $R^y$, $R^{y1}$, and $R^{y2}$ are independently selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^y$, $R^{y1}$, and $R^{y2}$ optionally being joined by one or more bonds to form one or more optionally substituted carbocycles and/or heterocycles, two or more of the substituents $R^{106}$, $R^{107}$, $R^{108}$, $R^{109}$, $R^{110}$, $R^{111}$, $R^{112}$, $R^{113}$, and $R^{114}$ optionally being joined by one or more bonds to form one or more optionally substituted carbocycles and/or heterocycles.

In the formulae above, Q may be O—C(O), but it may also be absent. For example, a compound with a benzyl ether linkage between self-elimination spacer and the group that leaves, the oxycarbonyl moiety thus being absent (Q is absent), has been reported to undergo self-elimination[9].

According to a further embodiment of the invention, the ω-amino aminocarbonyl cyclization elimination spacer A is a moiety having the formula:

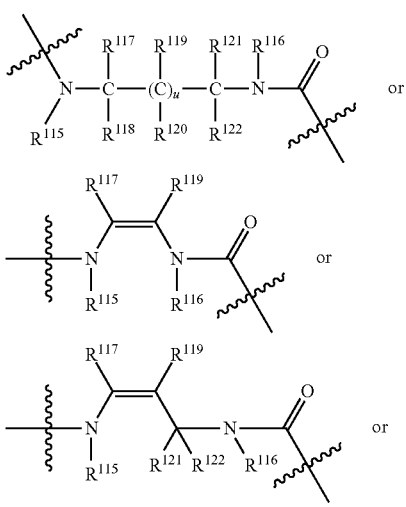

wherein u is an integer of 0 or 1;

$R^{115}$ and $R^{116}$ are independently selected from H and optionally substituted $C_{1-6}$ alkyl;

$R^{117}$, $R^{118}$, $R^{119}$, $R^{120}$, $R^{121}$, and $R^{122}$ are independently selected from H, OH, SH, $NH_2$, $N_3$, $NO_2$, NO, $CF_3$, CN, $C(O)NH_2$, C(O)H, C(O)OH, halogen, $R^z$, $SR^z$, $S(O)R^z$, $S(O)_2R^z$, $S(O)OR^z$, $S(O)_2OR^z$, $OS(O)R^z$, $OS(O)_2R^z$, $OS(O)OR^z$, $OS(O)_2OR^z$, $OR^z$, $NHR^z$, $N(R^z)R^{z1}$, $^+N(R^z)(R^{z1})R^{z2}$, $P(O)(OR^z)(OR^{z1})$, $OP(O)(OR^z)(OR^{z1})$, $C(O)R^z$, $C(O)OR^z$, $C(O)N(R^{z1})R^z$, $OC(O)R^z$, $OC(O)OR^z$, $OC(O)N(R^z)R^{z1}$, $N(R^{z1})C(O)R^z$, $N(R^{z1})C(O)OR^z$, and $N(R^{z1})C(O)N(R^{z2})R^z$, wherein $R^z$, $R^{z1}$, and $R^{z2}$ are independently selected from H and optionally substituted $(CH_2CH_2O)_{ee}CH_2CH_2X^{13}R^{e1}$, $C_{1-20}$ alkyl, $C_{1-20}$ heteroalkyl, $C_{3-20}$ cycloalkyl, $C_{1-20}$ heterocycloalkyl, $C_{5-20}$ aryl, or $C_{1-20}$ heteroaryl, wherein ee is selected from 1 to 1000, $X^{13}$ is selected from O, S, and $NR^{f1}$, and $R^{f1}$ and $R^{e1}$ are independently selected from H and $C_{1-3}$ alkyl, two or more of $R^z$, $R^{z1}$, and $R^{z2}$ optionally being joined by one or more bonds to form one or more optionally substituted carbocycles and/or heterocycles, two or more of the substituents $R^{115}$, $R^{116}$, $R^{117}$, $R^{118}$, $R^{119}$, $R^{120}$, $R^{121}$, and $R^{122}$ optionally being joined by one or more bonds to form one or more optionally substituted carbocycles and/or heterocycles.

Cyclization linker A may for example be selected from

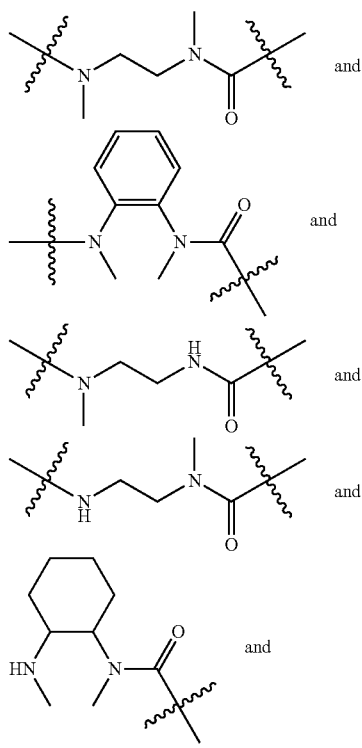

-continued
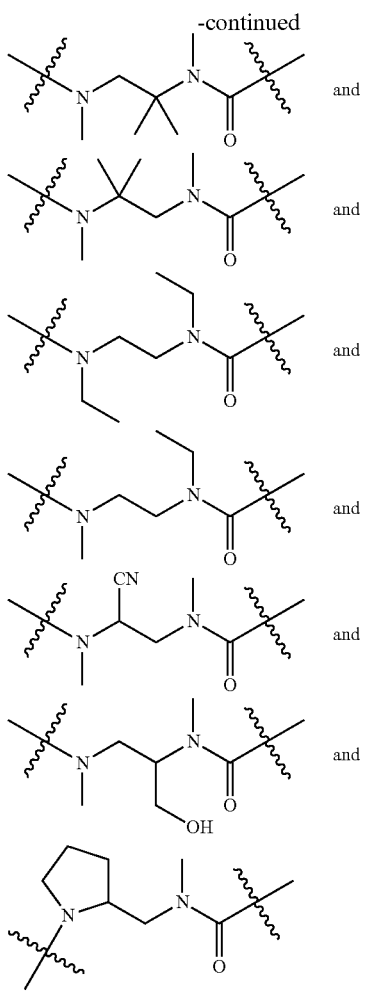
In a more specific embodiment, cyclization linker A may be selected from
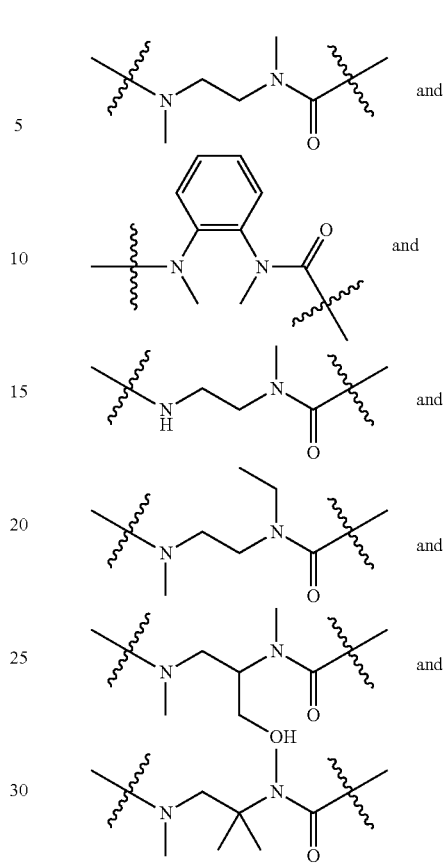
In one embodiment, Y is absent.
In another embodiment, this invention relates to a compound of formula (III) or (IV) wherein $X^1$ is O and Y is connected to $X^1$ via an ω-amino aminocarbonyl cyclization spacer being part of Y.
In one embodiment, the spacer system Y is selected from

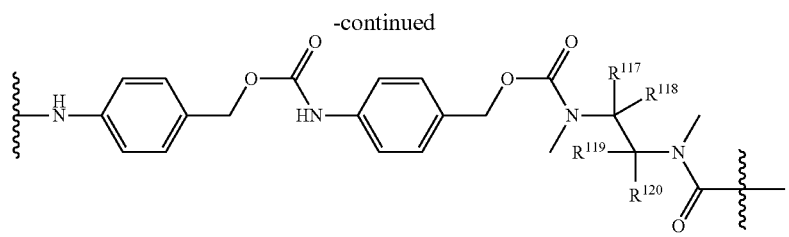

In another embodiment, the spacer system Y is

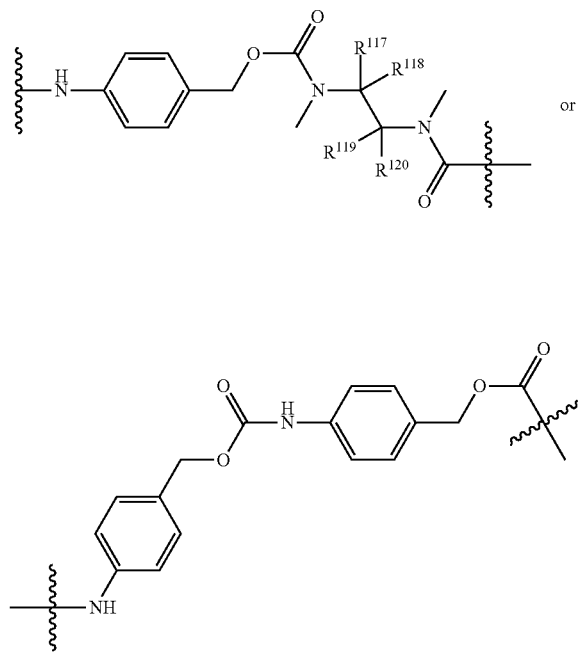

In another embodiment, the spacer system Y is

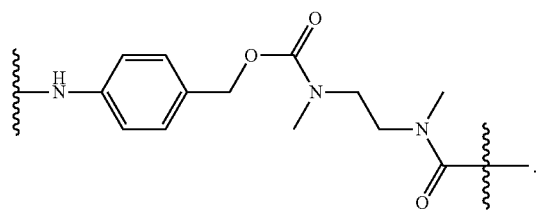 [SMILES: *Nc1ccc(COC(=O)N(C)CCN(C)C(*)=O)cc1]

Other examples of self-eliminating spacers include, but are not limited to, other spacers that can undergo cyclization[10], such as optionally substituted 4-aminobutyric acid amides, appropriately substituted bicyclo[2.2.1] and bicyclo[2.2.2] ring systems, 2-aminophenylpropionic acid amides, and "trimethyl-lock" cyclization spacers[11]. A glycine spacer in which an amine-containing leaving group is connected at the α-position is another useful spacer for the compounds of the invention.[12]

In a conjugate of this invention, a spacer system Y may be connected to more than one $V^1$ moiety. In this case, transformation and/or cleavage of one of these $V^1$ moieties may trigger the release of one or more Z moieties. When $V^1$ moieties that are transformed or cleaved under different conditions are connected to the same Y, release of one or more Z moieties may occur when a conjugate of this invention is brought under one of several distinct conditions if Y can undergo self-elimination in multiple ways. Alternatively, a spacer system Y may be used that requires to be triggered twice or even more times in order to self-eliminate. An example of such a self-elimination spacer is a bicine spacer.[13] When such a spacer is used in combination with different, selectively cleavable $V^1$ moieties connected to said spacer, selectivity of release of Z may be increased as two different conditions must be met before Z is released.

The Linking Group L

The linking group L links one or more $V^1$ and/or Y moieties to $L^2$ or RM. Synthesis may be more straightforward when L is connected to $V^1$ instead of Y and the compound may be less prone to premature degradation as $V^1$ may be more shielded. Connection of L to Y may have the advantage that $V^1$ may be transformed and/or cleaved with more ease. Other reasons to connect L to Y may for example be that (part of) Y remains bound to L upon cleavage of $V^1$, which prevents the release of reactive small molecules, and that the compound may display improved pharmacological properties, solubility, or aggregation behavior. L may be absent, which means that $V^1$ or Y is directly connected to either $L^2$ or RM. In another aspect, however, L is a linking group that functionally links or spaces the one or more $V^1$ and/or Y moieties and the $L^2$ or RM moiety. In a compound of formula (IV), spacing may make the reactive moiety RM more accessible to the reaction partner, for example when the functional moiety $V^2$ is being coupled. In a compound of formula (III), spacing may provide for a better accessibility of $V^1$, because $V^2$ is further away, which, especially in the case of enzymatic cleavage or transformation of $V^1$, may improve the rate at which $V^1$ is transformed and/or cleaved.

The linking group L must contain suitable functional groups at both of its ends to provide for selective coupling with the one or more $V^1$ and/or Y moieties and $L^2$ or RM.

The linking group L may be a water-soluble moiety or contain one or more water-soluble moieties, such that L contributes to the water solubility of a compound of formula (III) or (IV). L may also be a moiety or contain one or more moieties that reduce(s) aggregation of a compound of formula (III) or (IV), which may or may not be a moiety/moieties that also increase(s) the water solubility of a compound of formula (III) or (IV). The L moiety may contain an oligoethylene glycol or polyethylene glycol moiety or a derivative thereof. This moiety may for example improve the water solubility and/or reduce aggregation of a compound of formula (III) or (IV).

In one aspect, the L moiety is a linear, branched, or dendritic moiety, so that it can be connected to one or more $V^1$ and/or Y moieties. Branching can occur via one or more cyclic structures or at one or more branching atoms that may for example be carbon, nitrogen, silicon, or phosphorus.

The number of branches in L that are connected to $V^1$ and/or Y does not necessarily equal the total number of branches as in the coupling reaction with $V^1$ and/or Y not all branches may be coupled to $V^1$ and/or Y moieties due to incomplete chemical conversion. This means that L may contain branches that are not coupled to $V^1$ or Y, but instead end in for example a functional group, H, OH, or a leaving group.

Therefore, when L is branched, compounds of this invention may exist as a mixture, wherein each component of the mixture has a different p value. For example, the compound may exist as a mixture of two separate compounds, one compound wherein p is 2 and another compound wherein p is 3. Furthermore, for a given p, the compound may exist as a mixture of (constitutional) isomers as $V^1$ and/or Y may be connected to distinct (sets of) branches on L.

In one embodiment, L is absent.
In another embodiment, L is a linear linker.
In another embodiment, L is a linear linker containing a 1,2,3-triazole moiety. Such a linker may be built up through a cycloaddition reaction between a molecule containing an azide group and one containing an acetylene group.
In another embodiment, L is a branched linker.
In another embodiment, L is a dendritic linker. The dendritic structure may for example be built up through cycloaddition reactions between molecules containing one or more azide groups and ones containing one or more acetylene groups.
In one embodiment, p is 1.
In other embodiments, p is 2 or 3 or 4 or 6 or 8 or 9.
In another embodiment, L is represented by the formula:

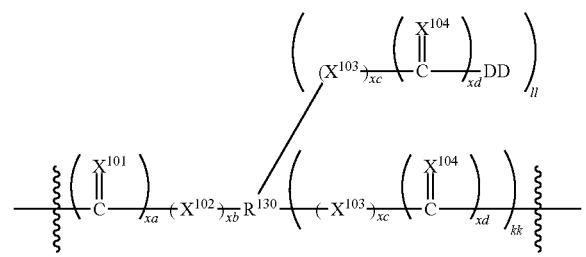

wherein $X^{101}$ and $X^{102}$ are each independently O, $NR^{131}$, or S;

Each $X^{103}$ and $X^{104}$ is independently O, $NR^{132}$, or S;

Each xa, xb, xc, and xd is independently 0 or 1;

kk is a number representing a degree of branching and is an integer selected from 1 (included) to 128 (included);

ll is a number representing a degree of branching and is an integer selected from 0 (included) to 127 (included);

kk+ll≤128;

Each DD is independently H, OH, or a leaving group;

$R^{130}$ is either a dendritic, branched, or unbranched multivalent moiety and selected from optionally substituted alkylene, oligoalkylene, or polyalkylene, and optionally substituted heteroalkylene, oligoheteroalkylene, or polyheteroalkylene, and optionally substituted arylene, oligoarylene, or polyarylene, and optionally substituted heteroarylene, oligoheteroarylene, or polyheteroarylene, and optionally substituted cycloalkylene, oligocycloalkylene, or polycycloalkylene, and optionally substituted heterocycloalkylene, oligoheterocycloalkylene, or polyheterocycloalkylene, and —$(CH_2CH_2O)_v$—, -alkylene-$(CH_2CH_2O)_v$—, —$(CH_2CH_2O)_v$-alkylene-, -alkylene-$(CH_2CH_2O)_v$-alkylene-, -heteroalkylene-$(CH_2CH_2O)_v$—, —$(CH_2CH_2O)_v$-heteroalkylene-, -heteroalkylene-$(CH_2CH_2O)_v$-alkylene-, -heteroalkylene-$(CH_2CH_2O)_v$-heteroalkylene-, -alkylene-$(CH_2CH_2O)_v$-heteroalkylene-, $X^{14}(CH_2CH_2O)_{gg}CH_2CH_2X^{14}$, a dendritic structure, and an oligopeptide, or any combination of two or more of the above;

$R^{131}$ and $R^{132}$ are independently selected from H, $C_{1-8}$ alkyl, and $C_{1-8}$ heteroalkyl;

v is selected from 1 (included) to 1000 (included).

In another embodiment, L is selected from

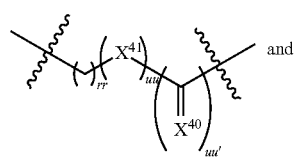 and 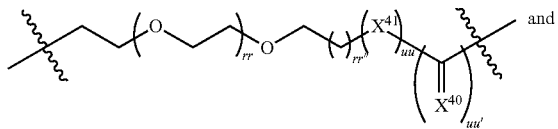 and

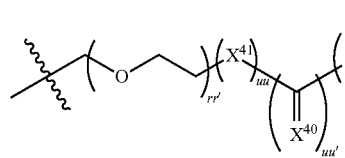 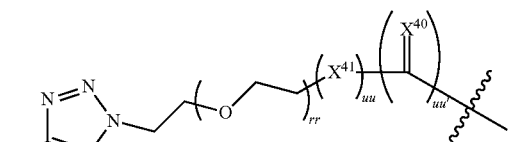

wherein rr, n', and rr" each independently range from 0 to 8, each $X^{40}$ and $X^{41}$ is independently selected from O, S, and $NR^{135}$, wherein $R^{135}$ is selected from H and $C_{1-3}$ alkyl, and each uu, uu', and uu" is independently selected from 0 and 1.
In another embodiment, L is selected from
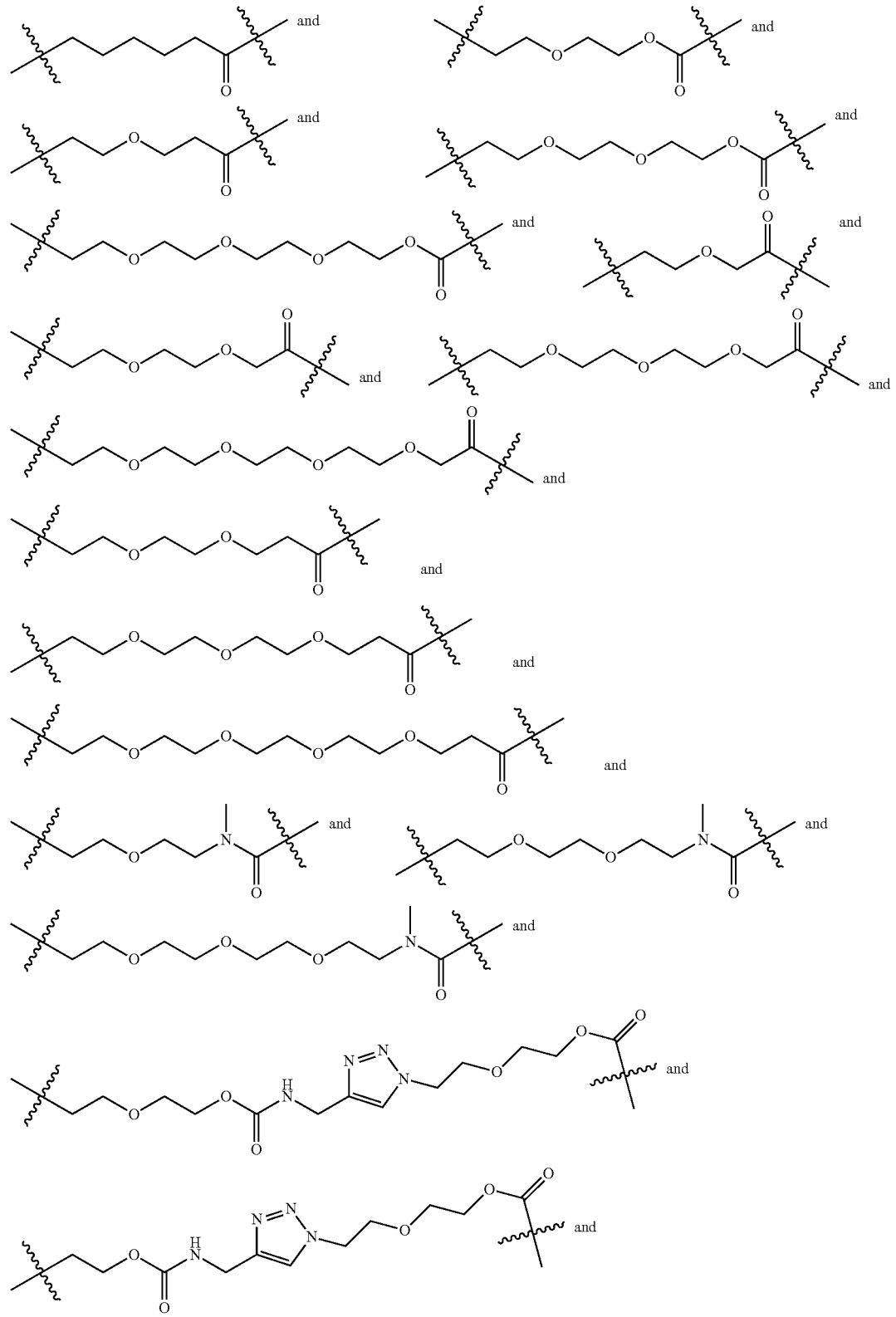

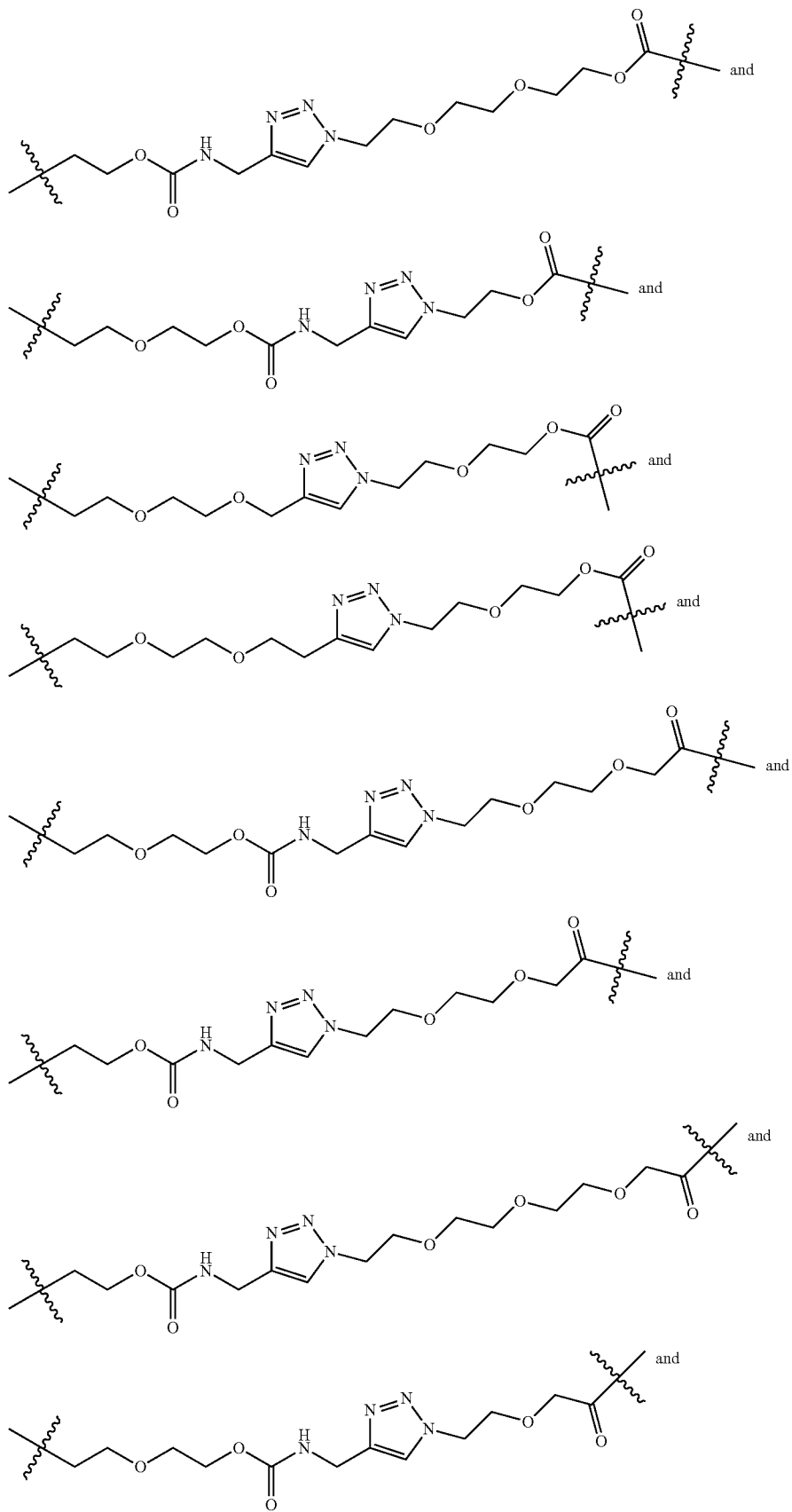

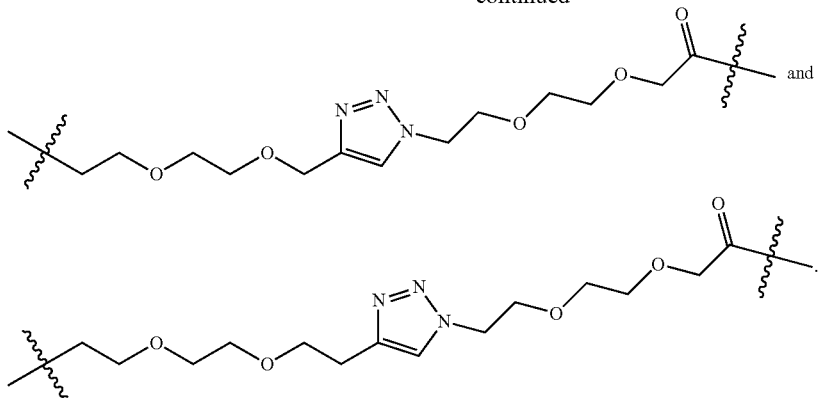
In yet another embodiment, L contains a $X^{14}(CH_2CH_2O)_{gg}CH_2CH_2X^{14}$ moiety that may for example be
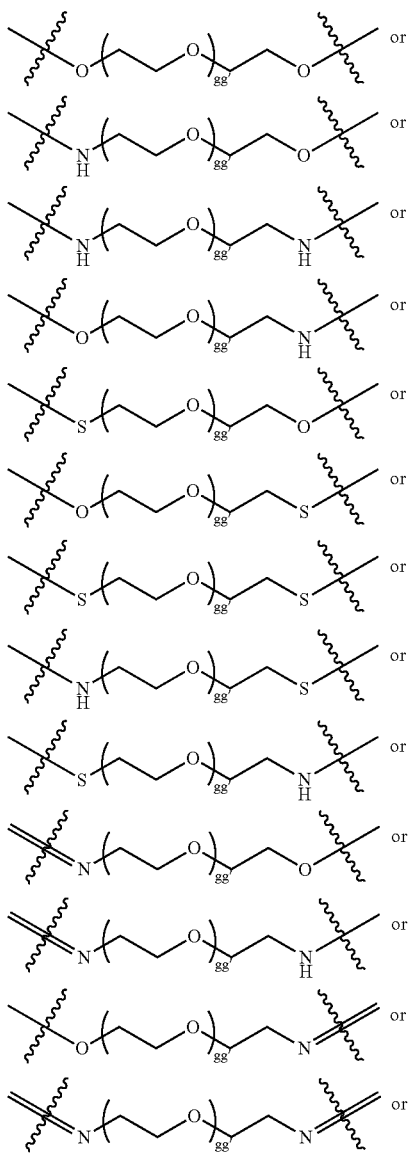
-continued
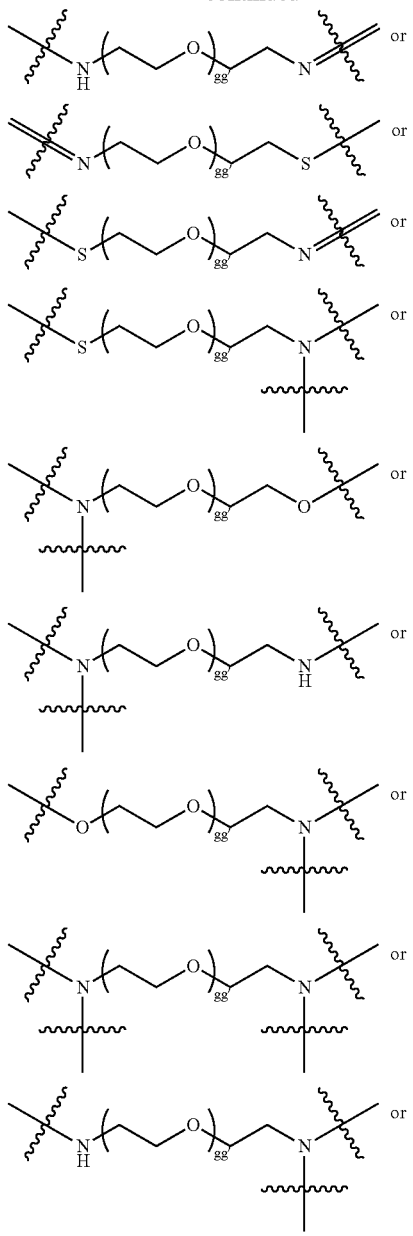

255
-continued
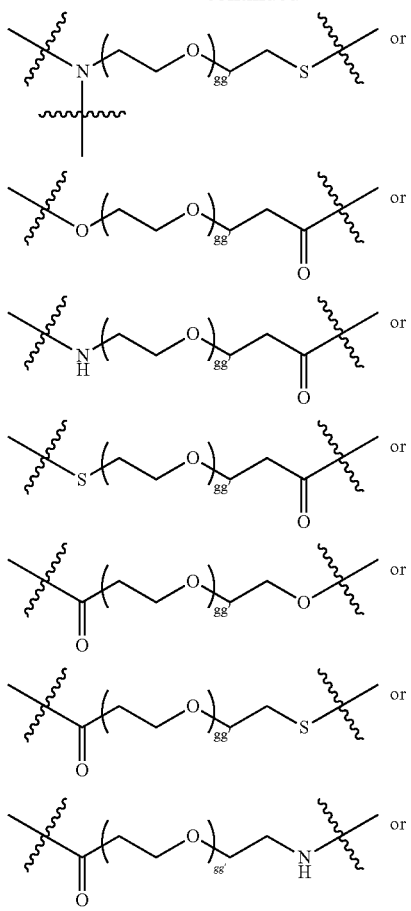
256
-continued
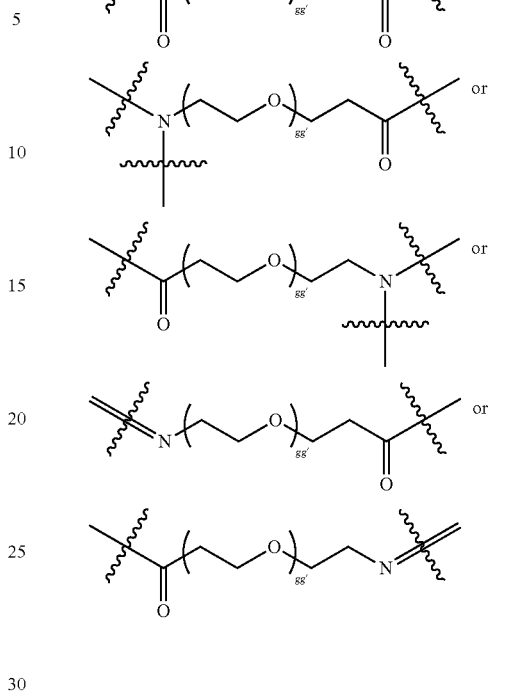
wherein gg' is selected from 3 to 1000. In other embodiments, gg' is selected from 3 to 500 or 100 or 50 or 10. In other embodiments, gg' is selected to be 3 or 4 or 5.
In another embodiment, L is selected from
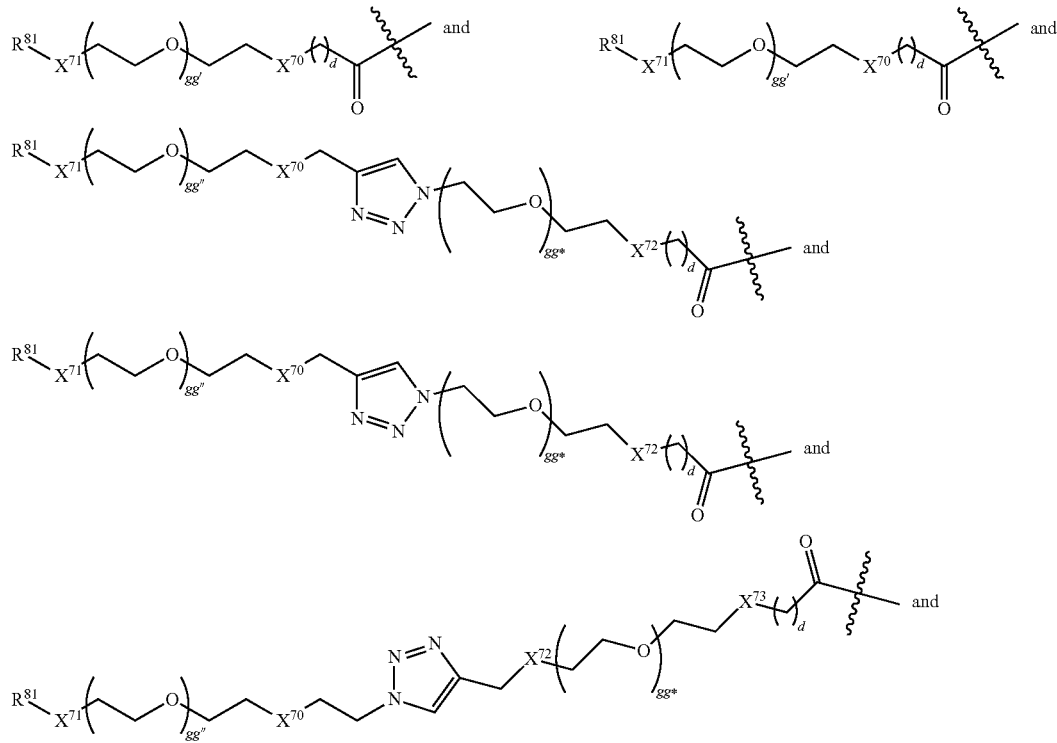

-continued

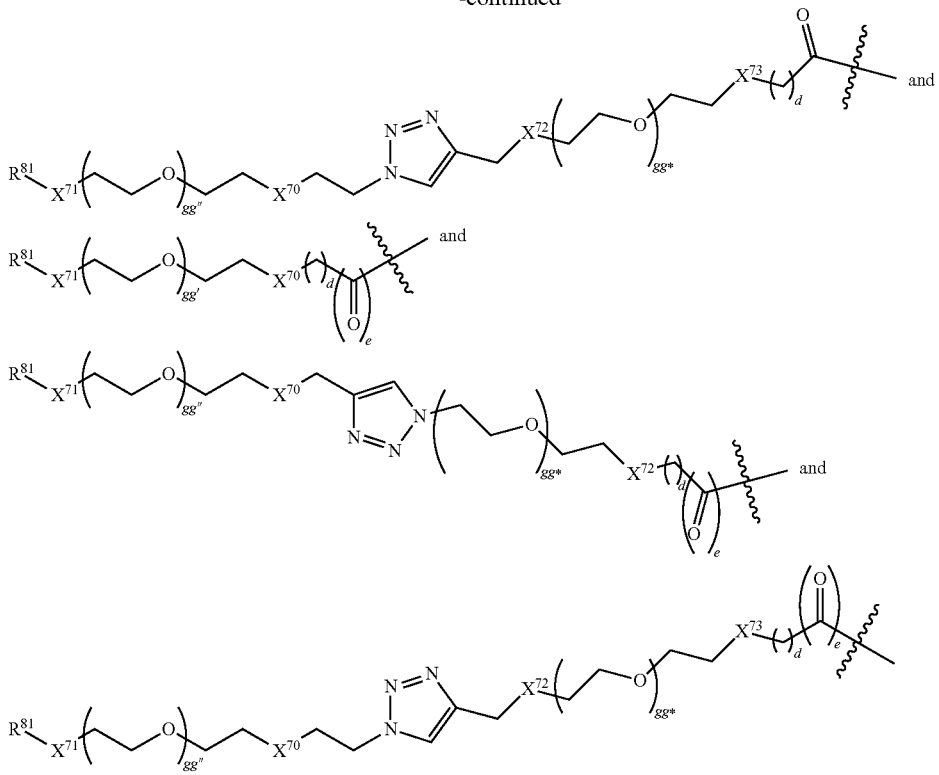

wherein $X^{70}$, $X^{71}$, $X^{72}$, and $X^{73}$ are independently selected from O, S, and $NR^{82}$, d is selected from 0 to 8, e is 0 or 1, gg" and gg* are independently selected from 1 to 1000, gg' is selected from 3 to 1000, and $R^{81}$ and $R^{82}$ are independently selected from H and optionally substituted $C_{1-3}$ alkyl.

The linkage between L and $V^1$ or Y may for example be an amide, a carbonate, or a carbamate linkage. Alternatively, when $V^1$ is a peptide in which the N-terminal amino acid is an amino acid mimic that carries an α-azido group instead of an α-amino group, the linkage between L and $V^1$ may be a triazole group formed through reaction of an acetylene group being part of L and the α-azido group of $V^1$.

The Reactive Moiety RM and the Linking Group $L^2$

The reactive moiety RM in a compound of formula (IV) is connected to the linking group L and is able to react with a suitable functional group on a reaction partner.

In one embodiment of this invention, the reactive moiety RM is designed to react with a functional group on the moiety $V^2$, which results in formation of a compound of formula (III). In this reaction, the moiety RM is transformed into the moiety $L^2$. In another embodiment, the reactive moiety RM is designed to react with a complementary moiety in situ, e.g., in vivo, for example with serum albumin, to give a compound that may or may not be a compound of formula (III).

In one aspect of this invention, the reactive moiety RM contains an electrophilic group that reacts with a nucleophilic group on the reaction partner, for example $V^2$, e.g., a thiol group, an amino group, or a hydroxy group.

In another aspect of this invention, the reactive moiety RM contains a nucleophilic group that reacts with an electrophilic group on the reaction partner, for example $V^2$, e.g., an aldehyde group.

In another aspect of the invention, the reactive moiety RM contains a cycloaddition partner moiety, e.g., an alkene, a diene, a 1,3-dipole, or a 1,3-dipolarophile, that reacts with a suitable complementary cycloaddition partner moiety on the reaction partner, for example $V^2$, e.g., a diene, an alkene, a 1,3-dipolarophile, or a 1,3-dipole.

In another aspect of the invention, the reactive moiety RM contains a group that can be coupled with a suitable complementary group on the reaction partner, for example $V^2$, under metal-catalyzed, biocatalyzed, or enzyme-catalyzed conditions, e.g., palladium-catalyzed conditions.

In one aspect of the invention, the reactive moiety RM is, without limitation,

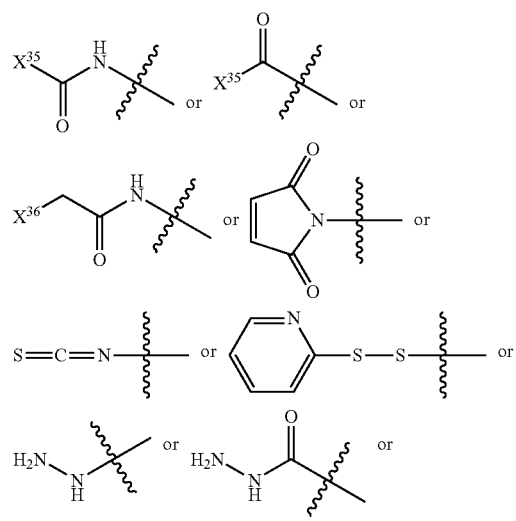

-continued

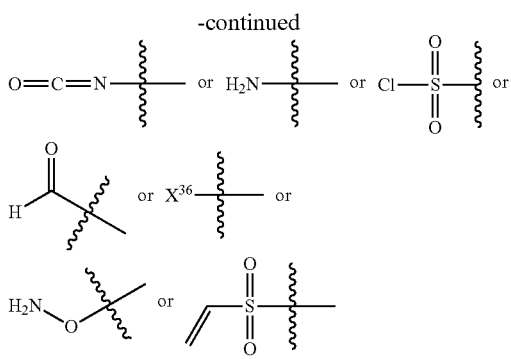

wherein $X^{35}$ is selected from halide, hydroxy, $OC(O)R^{dd}$, and $OC(O)OR^{dd}$, or $C(O)$—$X^{35}$ is an active ester, $X^{36}$ is selected from halide, mesyloxy, triflyloxy, and tosyloxy, and $R^{dd}$ is selected from optionally substituted $C_{1-10}$ alkyl, $C_{1-10}$ heteroalkyl, $C_{3-10}$ cycloalkyl, $C_{1-10}$ heterocyclo alkyl, $C_{5-10}$ aryl, and $C_{1-10}$ heteroaryl.

In one embodiment, the moiety RM is selected from

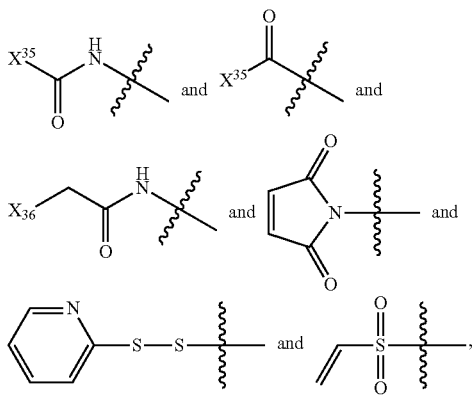

which makes it able to react with a thiol group on the reaction partner, for example moiety $V^2$.

In another embodiment, the moiety RM is

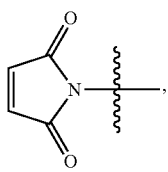 [SMILES: *N1C(=O)C=CC1=O]

which makes it able to react with a thiol group on the reaction partner, for example moiety $V^2$.

In another embodiment, the moiety RM is selected from

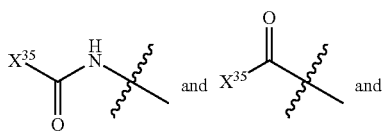

-continued

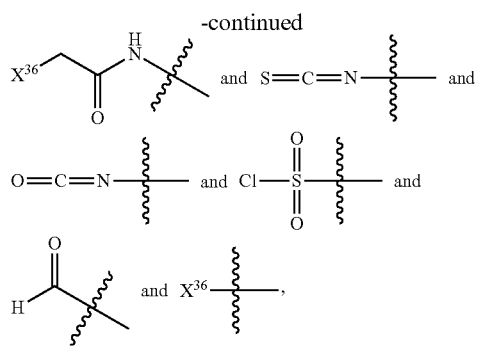

which makes it able to react with an amino group, e.g., a primary or secondary amino group, on the reaction partner, for example moiety $V^2$.

In another embodiment, the moiety RM is selected from

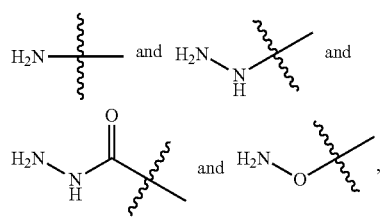

which makes it able to react with an aldehyde group on the reaction partner, for example moiety $V^2$.

The linking group $L^2$ in a compound of formula (III) represents the remainder of RM when the reactive moiety RM has reacted with $V^2$. This group then links the moiety $V^2$ with L. The group that remains may be a bond, meaning that $L^2$ is absent. Typically, however, $L^2$ is a linking group. When a compound of formula (III) is formed other than via a compound of formula (IV), $L^2$ does not represent the remainder of RM, but may represent a similar or the same moiety and in addition be selected from for example optionally substituted $C_{1-10}$ alkylene, $C_{1-10}$ heteroalkylene, $C_{3-10}$ cycloalkylene, $C_{1-10}$ heterocycloalkylene, $C_{5-10}$ arylene, and $C_{1-10}$ heteroarylene. The $L^2$ moiety may optionally comprise a $X^{14}(CH_2CH_2O)_{gg}CH_2CH_2X^{14}$ moiety.

In one embodiment, the moiety $L^2$ is absent.

In another embodiment, the moiety $L^2$ is, without limitation,

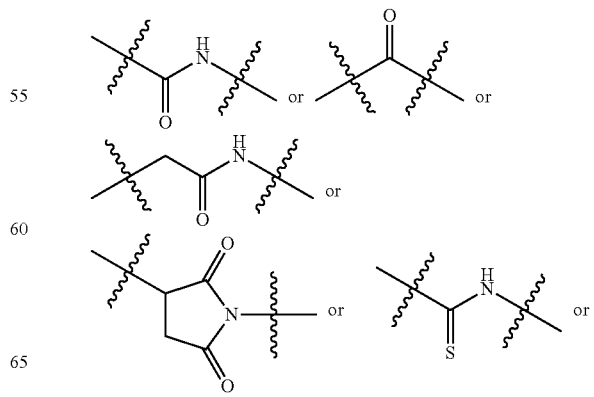

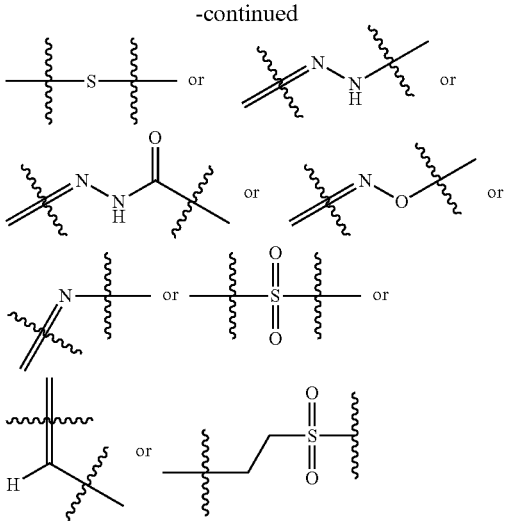

In a further embodiment, the moiety $L^2$ is

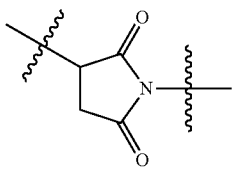 [SMILES: *C1CC(=O)N(*)C1=O]

The Moiety $V^2$

The moiety $V^2$ is a functional moiety, which means that it adds additional functionality to a compound of the invention.

In one embodiment, $V^2$ is a targeting moiety. In another embodiment, the $V^2$ moiety is a moiety that improves the pharmacological properties of a compound of the invention. In yet another embodiment, the $V^2$ moiety is a moiety that causes accumulation of a compound of the invention at a target site. In yet another embodiment, the $V^2$ moiety is a moiety that improves the aqueous solubility of a compound of the invention. In yet another embodiment, the $V^2$ moiety is a moiety that increases the hydrophobicity of a compound of the invention. In yet another embodiment, the $V^2$ moiety is a moiety that reduces extravasation of a compound of the invention. In yet another embodiment, the $V^2$ moiety is a moiety that reduces excretion of a compound of the invention. In yet another embodiment, the $V^2$ moiety is a moiety that reduces the immunogenicity of a compound of the invention. In yet another embodiment, the $V^2$ moiety is a moiety that enhances the circulation time of a compound of the invention. In yet another embodiment, the $V^2$ moiety is a moiety that enhances the ability of a compound of the invention to cross a biological barrier, e.g., a membrane, cell wall, or the blood-brain barrier. In yet another embodiment, the $V^2$ moiety is a moiety that enhances the ability of a compound of the invention to internalize. In yet another embodiment, the $V^2$ moiety is a moiety that enables a compound of the invention to internalize. In yet another embodiment, the $V^2$ moiety is a moiety that causes the compounds of the invention to aggregate. In yet another embodiment, the $V^2$ moiety is a moiety that reduces aggregation of a compound of the invention. In yet another embodiment, the $V^2$ moiety is a moiety that causes a compound of the invention to form micelles or liposomes. In yet another embodiment, the $V^2$ moiety is a moiety that causes complexation of a compound of the invention to another molecule, e.g., a biomolecule. In yet another embodiment, the $V^2$ moiety is a polynucleotide moiety that complexes with a complementary nucleotide sequence, for example RNA or DNA. In yet another embodiment, the $V^2$ moiety is a moiety that causes a compound of the invention to bind, associate, interact, or complex to another moiety, for example a (functionalized) surface or solid support.

In another embodiment, $V^2$ exhibits two or more different functions. The $V^2$ moiety may for example be a targeting moiety and at the same time improve the pharmacological properties, including water solubility.

In one aspect of the invention, the moiety $V^2$ includes within its scope any unit that binds or reactively associates or complexes with a receptor, a receptor complex, antigen, or other moiety associated with a given target cell population. $V^2$ can be any molecule that binds to, complexes with, or reacts with a moiety of a cell population sought to be therapeutically or otherwise biologically modified. The $V^2$ moiety acts to deliver the one or more moieties Z to the particular target cell population with which $V^2$ reacts or to which $V^2$ binds. Such $V^2$ moieties include, but are not limited to, aptamers, full-length antibodies and antibody fragments and derivatives thereof, lectins, biologic response modifiers, enzymes, vitamins, growth factors, steroids, nutrients, sugar residues, oligosaccharide residues, hormones, and any derivatives thereof, or any combination of any of these. Upon binding, reactively associating, or complexing, the compounds of the invention may or may not be internalized. If internalization occurs, transformation and/or cleavage of $V^1$ preferably occur inside the target cell.

Useful non-immunoreactive protein, polypeptide, or peptide $V^2$ moieties include, but are not limited to, transferrin, epidermal growth factors ("EGF"), bombesin, gastrin and its derivatives, gastrin-releasing peptide, platelet-derived growth factor, IL-2, IL-6, transforming growth factors ("TGF"), such as TGF-a and TGF-P, tumor growth factors, vaccinia growth factor ("VGF"), insulin and insulin-like growth factors I and II, lectins, and apoprotein from low density lipoprotein.

Useful polyclonal antibody $V^2$ moieties are heterogeneous populations of antibody molecules. Various procedures well-known in the art may be used for the production of polyclonal antibodies to an antigen-of-interest.

Useful monoclonal antibody $V^2$ moieties are homogeneous populations of antibodies to a particular antigen (e.g., a cancer cell antigen). A monoclonal antibody (mAb) to an antigen-of-interest can be prepared by using any technique known in the art which provides for the production of monoclonal antibody molecules.

Useful monoclonal antibody $V^2$ moieties include, but are not limited to, human monoclonal antibodies, humanized monoclonal antibodies, or chimeric human-mouse (or other species) monoclonal antibodies. Monoclonal antibodies may be made by any of numerous techniques known in the art.

The $V^2$ moiety can also be a bispecific antibody. Methods for making bispecific antibodies are known in the art.

The $V^2$ moiety can be a functionally active fragment, derivative, or analog of an antibody that immunospecifically binds to an antigen on a target cell, e.g., a cancer cell antigen. In this regard, "functionally active" means that the fragment, derivative, or analog is able to elicit anti-anti-idiotype antibodies that recognize the same antigen that the antibody from which the fragment, derivative, or analog is derived, recognizes.

Other useful $V^2$ moieties comprise fragments of antibodies including, but not limited to, F(ab')$_2$ fragments, which contain the variable region, the light chain constant region, and the CH1 domain of the heavy chain, which can be produced by pepsin digestion of the antibody molecule, and Fab fragments, which can be generated by reducing the disulfide bridges of the F(ab')$_2$ fragments. Other useful $V^2$ moieties are heavy chain and light chain dimers of antibodies, or any minimal fragment thereof such as Fvs or single chain antibodies (SCAs), domain antibodies, anticalins, affibodies, nanobodies, and any other molecules with the same, similar, or comparable specificity as the parent antibody.

Additionally, recombinant antibodies, such as chimeric and humanized monoclonal antibodies, comprising both human and non-human portions, which can be made using standard recombinant DNA techniques, are useful $V^2$ moieties. A chimeric antibody is a molecule in which different portions are derived from different animal species, such as those having a variable region derived from a murine monoclonal and a human immunoglobulin constant region. Humanized antibodies are antibody molecules from non-human species having one or more complementarity determining regions (CDRs) from the non-human species and a framework region from a human immunoglobulin molecule.

Completely human antibodies are particularly desirable as $V^2$ moieties. Such antibodies can for example be produced using transgenic mice that are incapable of expressing endogenous immunoglobulin heavy and light chains genes, but which can express human heavy and light chain genes.

In other embodiments, the $V^2$ moiety is a fusion protein of an antibody, or a functionally active fragment or derivative thereof, for example one in which the antibody is fused via a covalent bond (e.g., a peptide bond) at either the N-terminus or the C-terminus to an amino acid sequence of another protein (or portion thereof, preferably at least a 10, 20, or 50 amino acid portion of the protein) that is not the antibody. Preferably, the antibody or fragment thereof is covalently linked to the other protein at the N-terminus of the constant domain.

The $V^2$ moiety antibodies include analogs and derivatives that are modified, i.e., by the covalent attachment of any type of molecule as long as such covalent attachment permits the antibody to retain its antigen-binding immunospecificity. For example, but not by way of limitation, derivatives and analogs of antibodies include those that have been further modified, e.g., by glycosylation, acetylation, pegylation, disulfide reduction, phosphylation, amidation, derivatization by known protecting or blocking groups, proteolytic cleavage, linkage to another protein, etc. Additionally, the analog or derivative can contain one or more unnatural amino acids.

The $V^2$ moiety antibodies include antibodies having modifications (e.g., substitutions (for example cysteine to serine or serine to cysteine), deletions, or additions), for example in amino acid residues that interact with Fc receptors. In particular, they include antibodies having modifications in amino acid residues identified as involved in the interaction between the Fc domain and the FcRn receptor. Modifications may also be introduced to be able to couple the antibody to linker-agent conjugates at specific positions on the antibody.

In a specific embodiment, an antibody immunospecific for a cancer or tumor antigen is used as a $V^2$ moiety in accordance with the compounds, compositions, and methods of the invention.

Antibodies immunospecific for a cancer cell antigen can be obtained commercially or produced by any method known to one of skill in the art, such as chemical synthesis or recombinant expression techniques. The nucleotide sequences encoding antibodies immunospecific for a cancer cell antigen can be obtained, e.g., from the GenBank database or a database like it, a commercial or other source, literature publications, or by routine cloning and sequencing.

Examples of antibodies available for the treatment of cancer that may be useful for incorporation into conjugates of this invention include, but are not limited to, HERCEPTIN (trastuzumab), which is a humanized anti-HER2 monoclonal antibody for the treatment of patients with metastatic breast cancer; RITUXAN (rituximab), which is a chimeric anti-CD20 monoclonal antibody for the treatment of patients with non-Hodgkin's lymphoma; OvaRex (oregovomab), which is a murine antibody for the treatment of ovarian cancer; Panorex (edrecolomab), which is a murine IgG$_{2a}$ antibody for the treatment of colorectal cancer; IMC-BEC2 (mitumomab), which is a murine IgG antibody for the treatment of lung cancer; IMC-C225 (erbitux), which is a chimeric IgG antibody for the treatment of head and neck cancer; Vitaxin, which is a humanized antibody for the treatment of sarcoma; Campath I/H (alemtuzumab), which is a humanized IgG1 antibody for the treatment of chronic lymphocytic leukemia (CLL); SGN-70, which is a humanized anti-CD70 antibody for the treatment of hematologic malignancies; Smart M195, which is a humanized IgG antibody for the treatment of acute myeloid leukemia (AML); J591, which is a murine antibody against prostate specific membrane antigen; LymphoCide (epratuzumab), which is a humanized IgG antibody for the treatment of non-Hodgkin's lymphoma; SGN-33, which is a humanized anti-CD33 antibody for the treatment of acute myeloid leukemia; Smart ID 10, which is a humanized antibody for the treatment of non-Hodgkin's lymphoma; Oncolym, which is a murine antibody for the treatment of non-Hodgkin's lymphoma; Allomune, which is a humanized anti-CD2 mAb for the treatment of Hodgkin's disease or non-Hodgkin's lymphoma; Avastin (bevacizumab), which is a humanized anti-VEGF antibody for the treatment of lung and colorectal cancers; SGN-40, which is a humanized anti-CD40 antibody for the treatment of multiple myeloma; SGN-30, which is a chimeric anti-CD30 antibody for the treatment of Hodgkin's disease; CEAcide, which is a humanized anti-CEA antibody for the treatment of colorectal cancer; IMC-1C11, which is an anti-KDR chimeric antibody for the treatment of colorectal cancer, lung cancers, and melanoma; and Cetuximab, which is an anti-EGFR chimeric antibody for the treatment of epidermal growth factor positive cancers. Other antibodies useful in the treatment of cancer include, but are not limited to, antibodies against the following antigens: CA125, CA9, CA6, CA15-3, CA19-9, L6, Lewis Y, Lewis X, alpha fetoprotein, CA 242, placental alkaline phosphatase, prostate specific antigen (PSA), prostate specific membrane antigen (PSMA), prostatic acid phosphatase, epidermal growth factor receptors, interleukin receptors, insulin-like growth factor receptors, CanAg, DAF, PEM, IRTA-2, IRTA-4, AFP, HER2, EGFR, VEGFR1, VEGFR2, MAGE-1, LUCA1, LUCA2, MAGE-2, MAGE-3, MAGE-4, ED-B, MADCAM, MCP-1, TAT226, VLA-4, C3B, anti-transferrin receptor, Syndecan-1, ROBO4, STEAP-1, CMET, Eph receptor tyrosine kinases, PSCA, CLL-1, TNF-α, FAP-α, IFN-α, EphA2, EphB2, EphB4, EGFL-7, DLL-4, RS7, 4-1BB, TENB2, FLT3, p97, FGF19, FGFR2, glypican-3, P53, RON, GFR-α3, FDF03, TSLPR, MUC1-KLH, MUC18, B7H4, PTK7, RG-1, MUC16, CSAP, PSMA, 5T4, EpCAM, IGF1R, CCR2, CCR5, CTLA4, CLCA-1, DRS, CEA, CXCR-4, GD2, gp100, GD3 ganglioside, L243, HMGB1, GPC-3, MART1, IL-2 receptor, CD2, CD3, CD4, CD20, CD43, CD44, CD30, CD55, CD151, CD154, CD19, CD23, CD79, CD52, CD25, CD46, CD56, CD59, CD7, CD138, CD74, CD133, CD80, CD63, CD64, CD66, CD140b, CD32, CD33, CD37, CD22, Apo-2, ERBB4, HLA-DR, HLA-DR10, human chorionic gonadotropin, CD38, CD40, CD70, mucin, P21, MPG, and Neu oncogene product. Many other internalizing or non-internalizing antibodies that bind to tumor-associated antigens can be used in this invention as a $V^2$ moiety, some of which have been reviewed[14].

In some embodiments, the antibody is an anti-nuclear antibody or an antibody that can bind to a receptor or receptor complex expressed on a target cell. The receptor or receptor complex can comprise an immunoglobulin gene superfamily member, an integrin, a chemokine receptor, a TNF receptor superfamily member, a cytokine receptor, a major histocompatibility protein, a complement control protein, or a lectin.

In another specific embodiment, an antibody immunospecific for an antigen associated with an autoimmune disease is used as a $V^2$ moiety in accordance with the compounds, compositions, and methods of the invention. In another specific embodiment, an antibody immunospecific for a viral or microbial antigen is used as a $V^2$ moiety in accordance with the compounds, compositions, and methods of the invention. As used herein, the term "viral antigen" includes, but is not limited to, any viral peptide or polypeptide protein that is capable of eliciting an immune response. As used herein, the term "microbial antigen" includes, but is not limited to, any microbial peptide, polypeptide, protein, saccharide, polysaccharide, or lipid that is capable of eliciting an immune response.

New antibodies are continually being discovered and developed, and the present invention provides that these new antibodies may also be incorporated into a compound of this invention.

$V^2$ can react with the reactive moiety RM via for example a heteroatom on $V^2$. Heteroatoms that may be present on $V^2$ include, without limitation, sulfur (in one embodiment, from a sulfhydryl group), oxygen (in one embodiment, from a carboxyl or hydroxyl group), and nitrogen (in one embodiment, from a primary or secondary amino group). $V^2$ may also react via for example a carbon atom (in one embodiment, from a carbonyl group). These atoms can be present on $V^2$ in $V^2$'s natural state, for example a naturally occurring antibody, or can be introduced into $V^2$ via (chemical) modification.

Free sulfhydryl groups can be generated in an antibody or antibody fragment by reduction of the antibody (fragment) with a reducing agent such as dithiothreitol (DTT) or tris(2-carboxyethyl)phosphine (TCEP). In this way, modified antibodies can be obtained that can have from 1 to about 20 sulfhydryl groups, but typically between about 1 and about 9 sulfhydryl groups.

Alternatively, $V^2$ can have one or more carbohydrate groups that can be chemically modified to contain one or more sulfhydryl groups. As another alternative, sulfhydryl groups can be generated by reaction of amino groups, for example from lysine moieties, on $V^2$ with 2-iminothiolane (Traut's reagent), N-succinimidyl S-acetylthioacetate (SATA), or another sulfhydryl-generating reagent.

In one embodiment, the $V^2$ moiety is a receptor-binding moiety.

In another embodiment, the $V^2$ moiety is an antibody or an antibody fragment or a derivative thereof.

In another embodiment, the $V^2$ moiety is a monoclonal antibody or a fragment or derivative thereof.

In one embodiment, $V^2$ has one or more sulfhydryl groups and $V^2$ reacts with one or more RM moieties of one or more compounds of formula (IV) via one or more of these sulfhydryl groups' sulfur atoms to form a compound of formula (III) in which one or more compounds of formula (IV) have thus been incorporated.

In yet another embodiment, $V^2$ contains one or more disulfide bonds that can be chemically reduced to sulfhydryl groups (two for each disulfide bond), which can then be reacted with one or more reactive moieties RM to form a compound of formula (III).

In another embodiment, $V^2$ contains about 1 to about 3 sulfhydryl groups, which can be reacted with one or more reactive moieties RM to form a compound of formula (III).

In another embodiment, $V^2$ contains about 3 to about 5 sulfhydryl groups, which can be reacted with one or more reactive moieties RM to form a compound of formula (III).

In another embodiment, $V^2$ contains about 7 to about 9 sulfhydryl groups, which can be reacted with one or more reactive moieties RM to form a compound of formula (III).

In another embodiment, $V^2$ can have one or more carbohydrate groups that can be chemically modified to have one or more sulfhydryl groups. $V^2$ reacts with RM moieties via these one or more sulfhydryl groups' sulfur atoms to form a compound of formula (III).

In another embodiment, $V^2$ can have one or more lysine groups that can be chemically modified to have one or more sulfhydryl groups, which can be reacted with one or more reactive moieties RM to form a compound of formula (III).

Reactive moieties that can react with a sulfhydryl group include, but are not limited to, carbamoyl halide, acyl halide, α-haloacetamide, halomethyl ketone, vinyl sulfone, maleimide, and 2-disulfanylpyridine.

In yet another embodiment, $V^2$ can have one or more carbohydrate groups that can be oxidized to provide one or more aldehyde groups. The corresponding aldehyde(s) can then react with one or more reactive moieties RM to form a compound of formula (III). Reactive moieties that can react with an aldehyde group on $V^2$ include, but are not limited to, hydrazine, hydrazide, amine, and hydroxylamine.

In yet another embodiment, $V^2$ can have one or more amino groups, e.g., from lysine residues, which can be reacted with one or more reactive moieties RM to form a compound of formula (III). Reactive moieties that can react with an amino group include, but are not limited to, carbamoyl halide, α-haloacetamide, acyl halide, aldehyde, sulfonyl chloride, alkyl halide, alkyl sulfonate, isocyanate, and isothiocyanate.

A conjugate of formula (III) may exist as a mixture, wherein each component of the mixture has a different q value. For example, the compound may exist as a mixture of two separate compounds, one compound wherein q is 2 and another compound wherein q is 3. As another example, a compound may exist as a mixture of 5 separate compounds, in which q is 1, 2, 3, 4, and 5, respectively. As yet another example, a compound may exist as a mixture of more than 5 separate compounds. Such mixtures might further be "contaminated" with unconjugated $V^2$. When analyzing the compound of formula (III) it is understood that q may be the (rounded) average number of $L^2$-L(-($V^1$—Y))$_p$(Z)$_{z/q}$ units per $V^2$ moiety. Furthermore, for a given q, the compound may exist as a mixture of (constitutional) isomers as the q $L^2$-L(-($V^1$—Y))$_p$(Z)$_{z/q}$ moieties may be connected to distinct (sets of) functional groups on $V^2$. It should be noted that the number of Z moieties in each unit only equals z/q if all units are the same and/or contain the same number of Z moieties.

In one embodiment, the $V^2$ moiety is connected to $L^2$ via a sulfur atom of $V^2$.

In another embodiment, the $V^2$ moiety is connected to $L^2$ via a sulfur atom and q ranges from about 1 to about 20.

In another embodiment, the $V^2$ moiety is connected to $L^2$ via a sulfur atom and q ranges from about 1 to about 9.

In another embodiment, the $V^2$ moiety is connected to $L^2$ via a sulfur atom and q ranges from about 1 to about 3.

In another embodiment, the $V^2$ moiety is connected to $L^2$ via a sulfur atom and q is about 2.

In another embodiment, the $V^2$ moiety is connected to $L^2$ via a sulfur atom and q ranges from about 3 to about 5.

In another embodiment, the $V^2$ moiety is connected to $L^2$ via a sulfur atom and q is about 4.

In another embodiment, the $V^2$ moiety is connected to $L^2$ via a sulfur atom and q ranges from about 7 to about 9.

In another embodiment, the $V^2$ moiety is connected to $L^2$ via a sulfur atom and q is about 8.

In one embodiment, a compound of formula (III) exists as a mixture of separate compounds.

In one embodiment, a compound of formula (III) exists as a mixture of separate compounds wherein q for three compounds is 1, 2, and 3, respectively.

In one embodiment, a compound of formula (III) exists as a mixture of separate compounds wherein q for three compounds is 3, 4, and 5, respectively.

In one embodiment, a compound of formula (III) exists as a mixture of separate compounds wherein q for three compounds is 5, 6, and 7, respectively.

In one embodiment, a compound of formula (III) exists as a mixture of separate compounds wherein q for three compounds is 7, 8, and 9, respectively.

In another embodiment, the $V^2$ moiety is connected to $L^2$ via a nitrogen atom of $V^2$.

In yet another embodiment, the $V^2$ moiety is connected to $L^2$ via a carbon atom of $V^2$.

In another aspect of this invention, the $V^2$ moiety includes any unit that causes accumulation of compounds of the invention at the target site or in the vicinity thereof by a mechanism other than binding or reactively associating or complexing with a receptor, antigen, or other receptive moiety associated with a given target site, e.g., a target cell population. One way to achieve this is for example to use a large macromolecule as a $V^2$ moiety, which targets to solid tumor tissue through the enhanced permeability and retention (EPR) effect. Ringsdorf reported use of polymers to target antitumor agents to tumors.[15] Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.

The $V^2$ moiety may for example be a branched or unbranched polymer, such as for example poly[N-(2-hydroxypropyl)methacrylamide] (HPMA), hydroxyethyl starch (HES), poly(2-hydroxyethyl methacrylate) (HEMA), polyglutamic acid or poly-L-glutamic acid (PG), carboxymethyldextran (CMDex), a polyacetal, chitosan, a polypeptide, an oligoethylene glycol or polyethylene glycol (PEG), or a copolymer, such as an HPMA copolymer, an HPMA-methacrylic acid copolymer, a HEMA-methacrylic acid copolymer, a CMDex copolymer, a β-cyclodextrin copolymer, a PEG copolymer, or a poly(lactic-co-glycolic) acid copolymer.[16] In this document both polymer and copolymer are referred to as polymer.

The polymer may be connected to $L^2$ via any suitable functional group, which can be located at one or both ends of the polymer, meaning that in the conjugate q ranges from 1 to 2, or alternatively, the functional groups may (also) be located on groups pendant on the polymer such that $L^2$ is (also) connected to the polymer via these pendant groups with q typically ranging from 1 to about 1000. Optionally, the polymer may also contain an additional targeting group that can bind or reactively associate or complex with a receptive moiety, e.g., an antibody or antibody derivative, bonded to the polymer either via a pendant group or end group, such that improved targeting to the target site is achieved.

Alternatively, the $V^2$ moiety may be a dendrimer or a protein or protein fragment, e.g., serum albumin, which has no targeting properties except for its ability to accumulate at the target site because of its size or molecular weight.

In one embodiment, the $V^2$ moiety contains a polymer.

In another embodiment, the $V^2$ moiety is a polymer.

In another embodiment, the $V^2$ moiety is a polymer and q ranges from 1 to about 1000.

In other embodiments, the $V^2$ moiety is a polymer and q ranges from 1 to about 500 or 400 or 300 or 200 or 100 or less than 100.

In another embodiment, the $V^2$ moiety is a polymer and q ranges from 1 to 2.

In another embodiment, the $V^2$ moiety is a polymer and q is 1.

In a specific embodiment, the $V^2$ moiety is an oligoethylene glycol or a polyethylene glycol or a derivative thereof.

In another embodiment, the $V^2$ moiety is a dendrimer, a protein, or a protein fragment.

In another embodiment, $V^2$ is absent.

In another embodiment, the $V^2$ moiety is a moiety that is able to transport the conjugate across a biological barrier, e.g., a cell membrane, either with or without prior binding, associating, or complexing with a receptor or receptor complex. In one embodiment, the $V^2$ moiety is a Tat peptide or a derivative, fragment, or analog thereof, or a moiety that has similar transmembrane delivery properties. In another embodiment, the $V^2$ moiety is a protein or protein fragment, an antibody or an antibody fragment, a receptor-binding or peptide vector moiety, or a polymeric or dendritic moiety, or any combination thereof, to which is attached a Tat peptide or a derivative, fragment, or analog thereof, or a moiety that has similar transmembrane delivery properties.

Thus, in one aspect of the invention, the moiety $V^2$ is a targeting moiety and is selected from the group consisting of a protein or protein fragment, an antibody or an antibody fragment, a receptor-binding or peptide vector moiety, and a polymeric or dendritic moiety, and any combination or derivative thereof.

In another aspect of the invention, the $V^2$ moiety is a moiety that improves the pharmacological properties of a conjugate of the invention. For example, the moiety $V^2$ can be chosen such that the water solubility of the conjugate is (further) improved. This can be achieved by choosing $V^2$ to be a hydrophilic moiety. Alternatively, the $V^2$ moiety can be used for example to increase the residence time of the compound in the circulation, to reduce extravasation and/or excretion, to reduce aggregation, and/or to reduce the immunogenicity of the compound. This may for example be achieved by choosing $V^2$ to be or contain a polyethylene glycol or oligoethylene glycol or derivative thereof. When the moiety $V^2$ is a moiety that improves the pharmacological properties of a compound of the invention and $V^1$ is a moiety that can be cleaved or transformed aspecifically and there are no $V^{1'}$ and $V^{2'}$ moieties, the compound solely serves to improve the (pharmacological) properties of the one or more Z moieties.

In one embodiment, $V^2$ is a moiety that improves the pharmacological properties and $V^1$ is a moiety that can be cleaved or transformed specifically.

In another embodiment, $V^2$ is an oligoethylene glycol or a polyethylene glycol or a derivative thereof and $V^1$ is a moiety that can be cleaved or transformed specifically.

In another embodiment, $V^2$ is a moiety that improves the pharmacological properties and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved by ubiquitous enzymes.

In another embodiment, $V^2$ is an oligoethylene glycol or a polyethylene glycol or a derivative thereof and $V^1$ is a hydrolyzable moiety.

In another embodiment, $V^2$ contains a $X^{14}(CH_2CH_2O)_{gg}CH_2CH_2X^{14}$ moiety.

In one aspect of this invention, the $V^2$ moiety is represented by formula (VI):

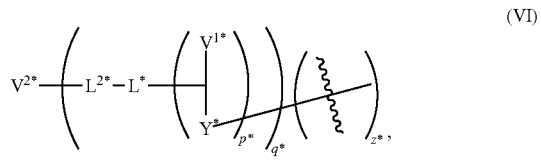
(VI)

wherein $V^{2*}$, $L^{2*}$, $L^*$, $V^{1*}$, $Y^*$, $p^*$, $q^*$, and $z^*$ have the same meaning as $V^2$, $L^2$, $L$, $V^1$, $Y$, $p$, $q$, and $z$, respectively, as defined in this document and are selected independently, except that $Y^*$ is connected to $L^2$. It should be noted that $z^*$ actually equals q, assuming that all $Y^*$ is indeed connected to $L^2$. When a compound of formula (III) contains a $V^2$ moiety represented by formula (VI), the one or more $L^2$ moieties are thus connected to $Y^*$.

Use of a $V^2$ moiety of formula (VI) in a conjugate of formula (III) implicates that two conditionally-cleavable or conditionally-transformable moieties may be present in between the functional moiety $V^2$ and Z, and therefore two separate cleavages/transformations may be required to release Z. The requirement that two different conditions need to have been met—in consecutive order—before one or more Z are released might favorably affect the properties of the conjugate. For instance, it may increase the targeting efficiency and therapeutic index of the conjugate. The two transformations/cleavages may occur at different extracellular/intracellular locations. The moiety to be removed by the second cleavage or as a consequence of the second transformation may for example be used to help transport Z from a first extracellular or intracellular location (where the first cleavage has occurred) to a second extracellular or intracellular location, or to stabilize Z until it is closer to its target, or to (temporarily) increase the water solubility of Z. In order to increase the targeting efficiency and/or therapeutic index using this concept, the second transformation and/or cleavage should only occur after the first transformation and/or cleavage have occurred. If the second transformation and/or cleavage can also occur before the first transformation and/or cleavage have occurred, an improved targeting efficiency and/or an improved therapeutic index due to this concept seems unlikely.

It will be apparent that a $V^2$ moiety of formula (VI) or a promoiety containing such a $V^2$ cannot only be useful in conjugates of a compound of formula (I) or (II), but may be used in similar conjugates of other therapeutic agents, diagnostic moieties, and the like.

A compound of formula (III) containing a $V^2$ moiety of formula (VI) may be prepared from a compound of formula (III) containing a $V^2$ moiety of formula (VII):

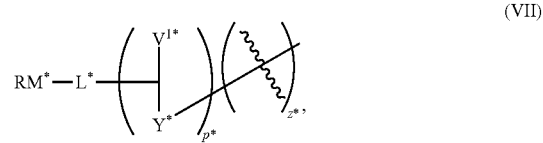
(VII)

wherein RM* has the same meaning as RM and is selected independently.

It should be understood that in this document, whenever $V^2$, $L^2$, L, $V^1$, Y, RM, p, q, or z is mentioned, the same can apply for each $V^{2*}$, $L^{2*}$, $L^*$, $V^{1*}$, $Y^*$, RM*, $p^*$, $q^*$, or $z^*$, respectively, unless the context dictates otherwise.

It should be understood that the functional moiety $V^2$ can have several functional properties combined. For example, $V^2$ can be a moiety that improves the pharmacological properties of a compound of this invention and at the same time be or contain a targeting moiety.

Conjugates of this invention may contain one or more promoieties. These promoieties may be the same or different. The presence of two or more promoieties may favorably affect the properties of the conjugate. For instance, it may improve the water solubility and/or increase the targeting efficiency of the conjugate. Furthermore, if in a targeted conjugate there are two promoieties and the promoiety required for targeting is prematurely cleaved from Z, for example in the circulation, the second promoiety attenuates the cytotoxicity of Z.

In one embodiment, when there are two or more promoieties, said promoieties are different from each other. The two or more different promoieties may have different functions and may be removed under different conditions and at different extracellular/intracellular locations.

In one embodiment, there is one promoiety linked to Z. In another embodiment, there is one promoiety linked to Z via $X^1$. In another embodiment, there are two promoieties linked to Z. In another embodiment, there are two promoieties linked to Z, of which one is connected via $X^1$. In another embodiment, there are two promoieties linked to Z, of which one is connected via $X^1$ and the other to the DNA-alkylating unit. In another embodiment, there are two promoieties linked to Z, of which one is connected via $X^1$ and the other to the DNA-binding unit. In another embodiment, there are two promoieties linked to Z, of which one is connected to the DNA-binding unit and the other to the DNA-alkylating unit. In yet another embodiment, there are three promoieties linked to Z. In yet another embodiment, there are three promoieties linked to Z, of which one is connected via $X^1$.

In one aspect of this invention, a compound of formula (III) comprises at least 2 promoieties. The first promoiety contains at least a targeting moiety and the second comprises at least a $X^{14}(CH_2CH_2O)_{gg}CH_2CH_2X^{14}$ moiety or 2 $X^{14}CH_2CH_2OCH_2CH_2X^{14}$ moieties, and $V^1$ of said same second promoiety is present. Similarly, a compound of formula (IV) may comprise at least 2 promoieties. The first promoiety contains at least a reactive moiety RM2 and the second comprises at least a $X^{14}(CH_2CH_2O)_{gg}CH_2CH_2X^{14}$ moiety or $2X^{14}CH_2CH_2OCH_2CH_2X^{14}$ moieties, and $V^{1'}$ of said same second promoiety is present. Said second promoieties of compounds of formulae (III) and (IV) may for example be represented by

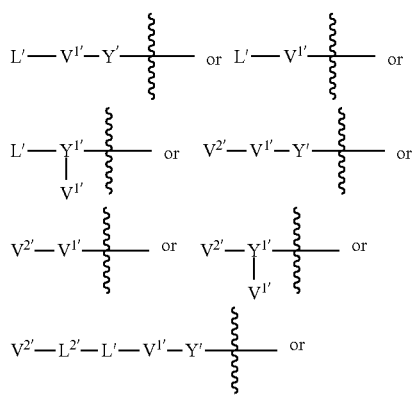
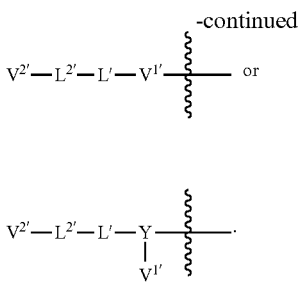
In one embodiment, said second promoiety is selected from
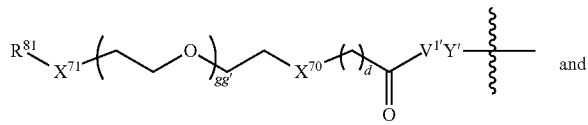
and
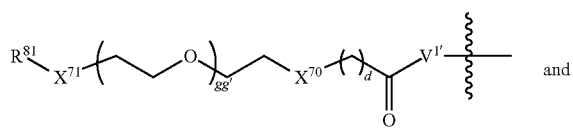
and
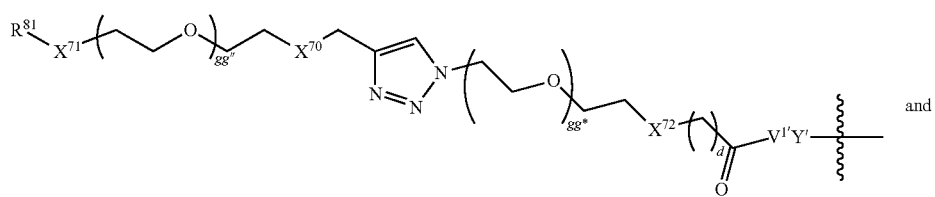
and
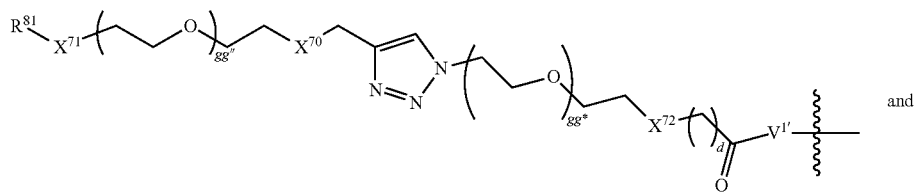
and
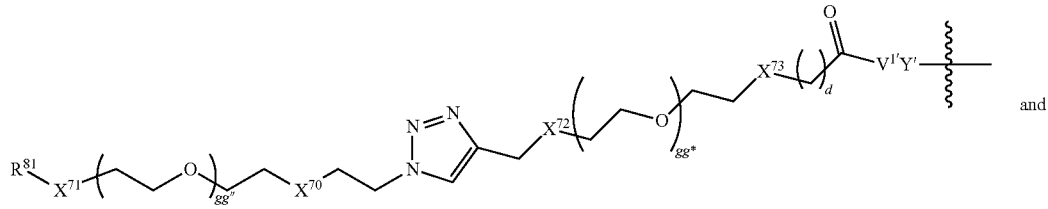
and
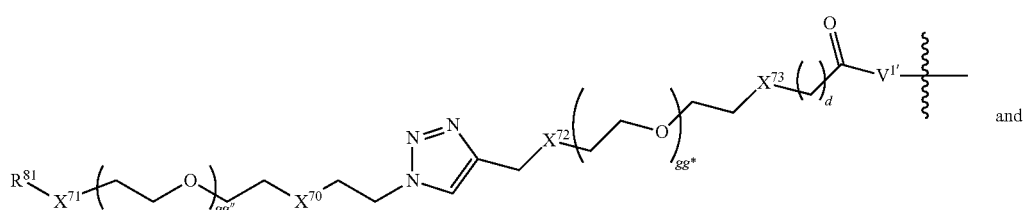
and
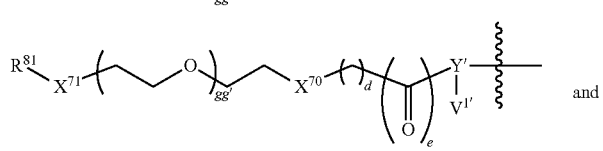
and -continued

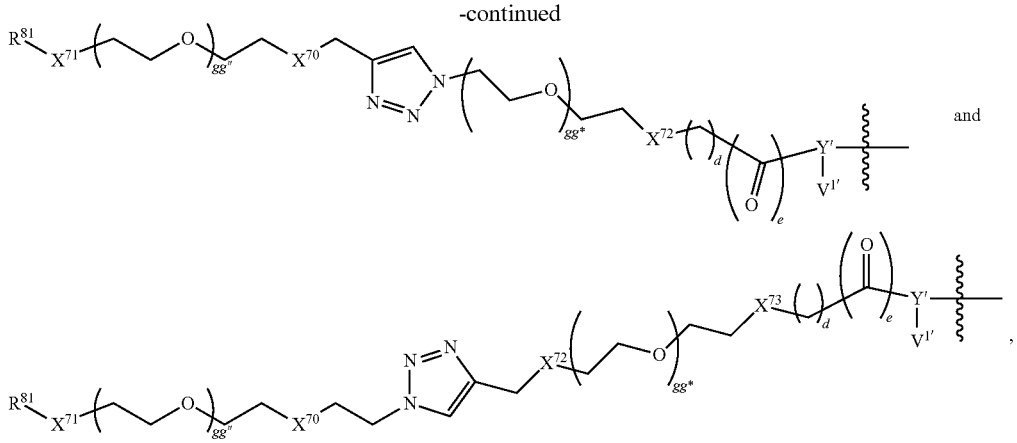

wherein $X^{70}$, $X^{71}$, $X^{72}$, and $X^{73}$ are independently selected from O, S, and $NR^{82}$, d is selected from 0 to 8, e is 0 or 1, gg" and gg* are independently selected from 1 to 1000, gg' is selected from 3 to 1000, and $R^{81}$ and $R^{82}$ are independently selected from H and optionally substituted $C_{1-3}$ alkyl.

In another embodiment, said second promoiety is selected from

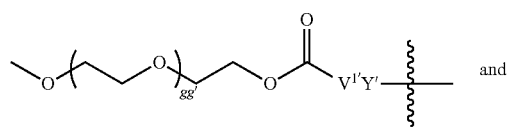 and

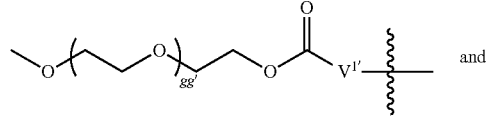 and

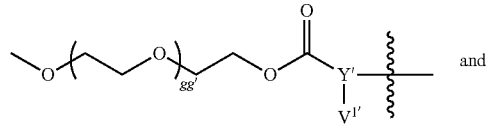 and

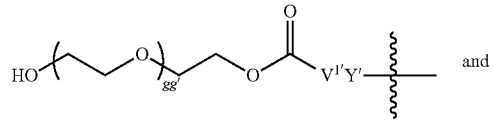 and

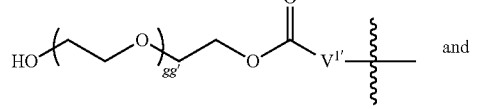 and

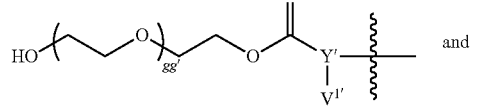 and

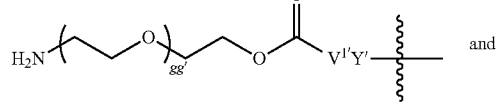 and

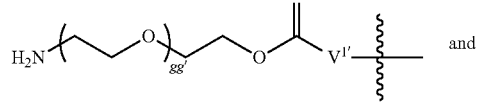 and

-continued

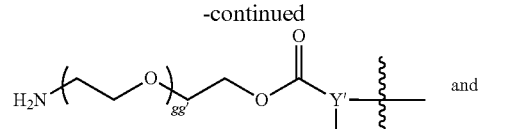 and

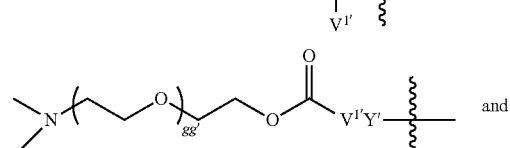 and

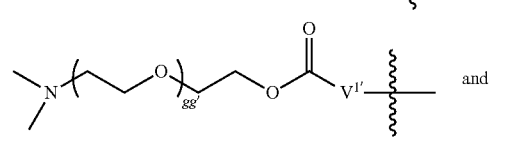 and

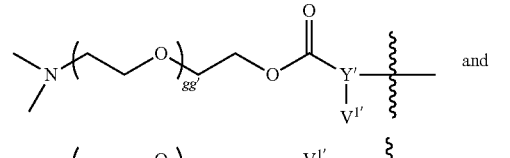 and

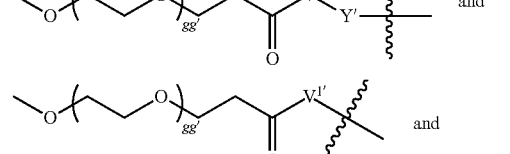 and

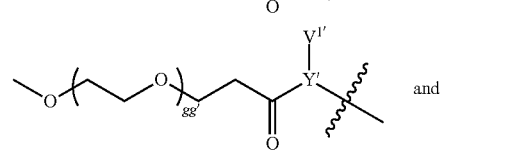 and

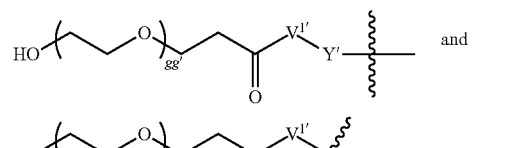 and

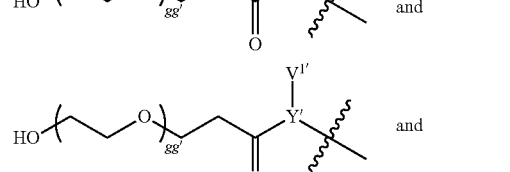 and

275
-continued
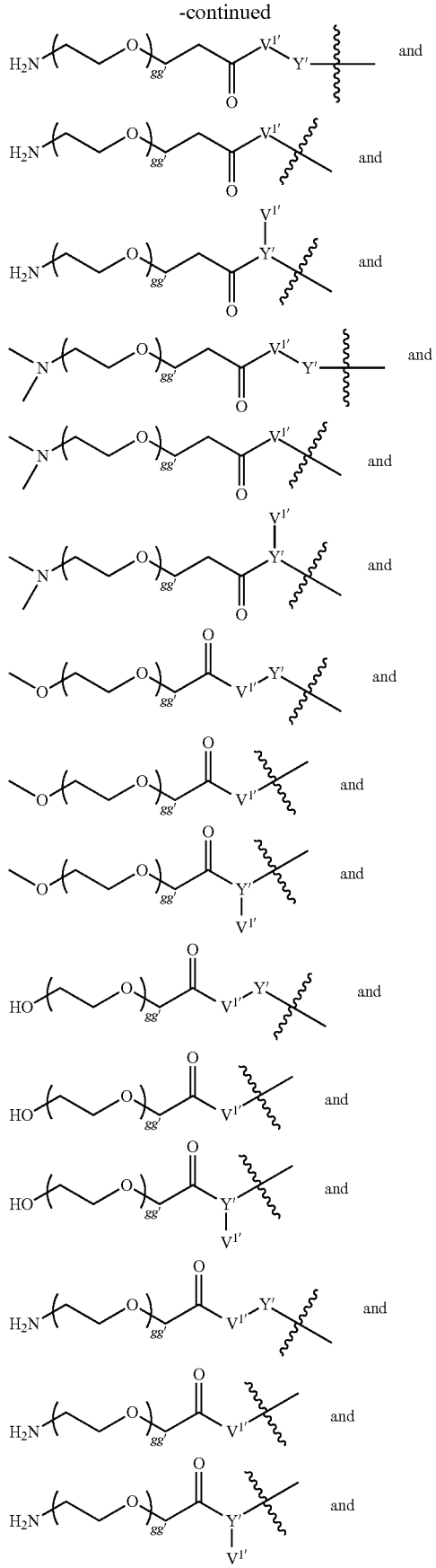
276
-continued
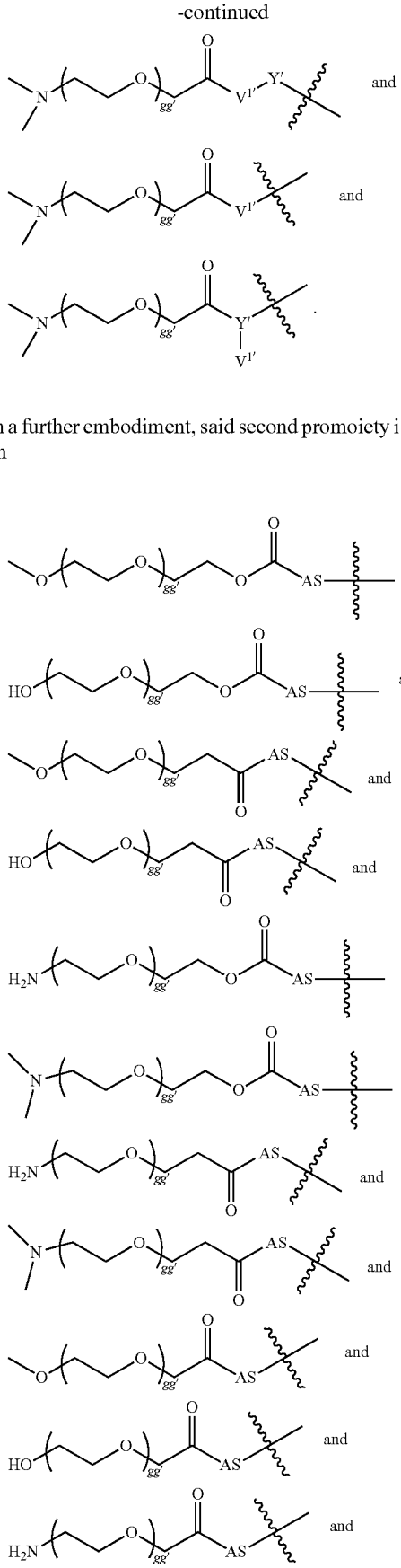
In a further embodiment, said second promoiety is selected from

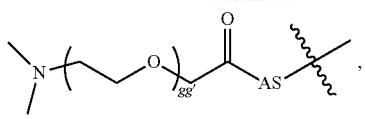

wherein AS is

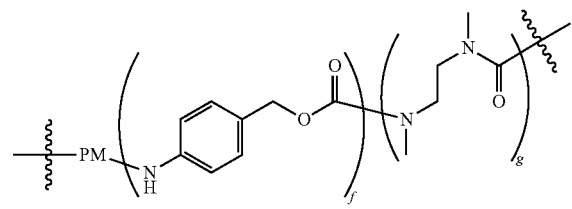

wherein f is 0, 1, or 2, g is 0 or 1, and PM is an amino acid or a peptide coupled with its N-terminus to L'.

In further embodiments, said second promoiety is selected from

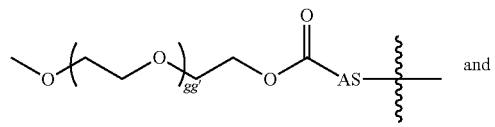

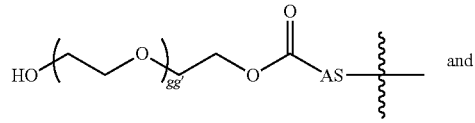

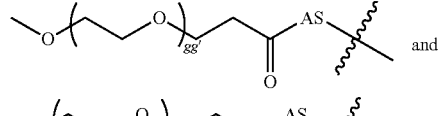

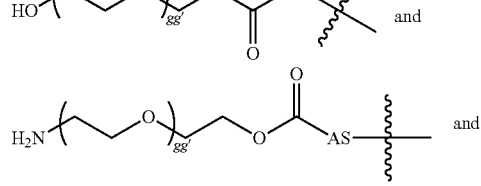

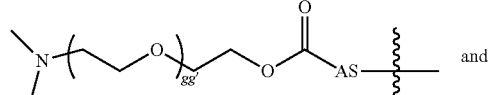

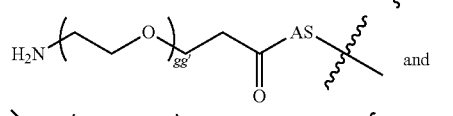

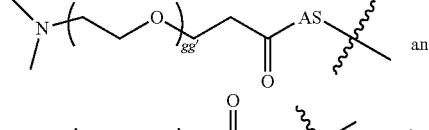

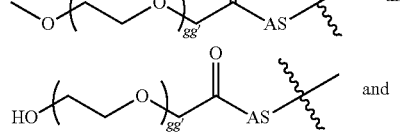

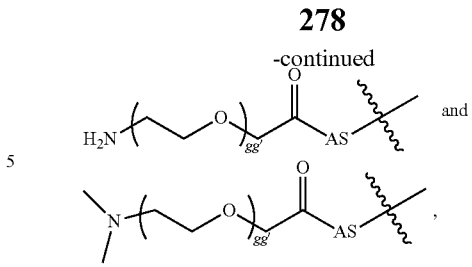

wherein AS is

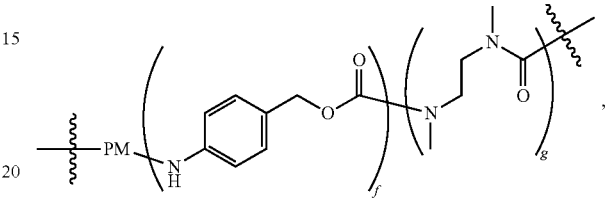

wherein f is 0, 1, or 2, g is 0 or 1, PM is selected from valylcitrulline, valyllysine, phenylalanyllysine, alanylphenylalanyllysine, and D-alanylphenylalanyllysine coupled with its N-terminus to L', and gg' is selected from 3 to 1000 or 500 or 100 or 50 or 10 or 5.

In one embodiment, a compound of formula (III) is represented by a compound of formula (III-1) or (III-2):

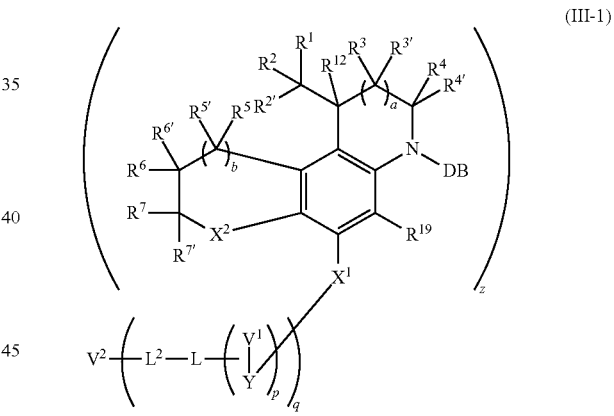

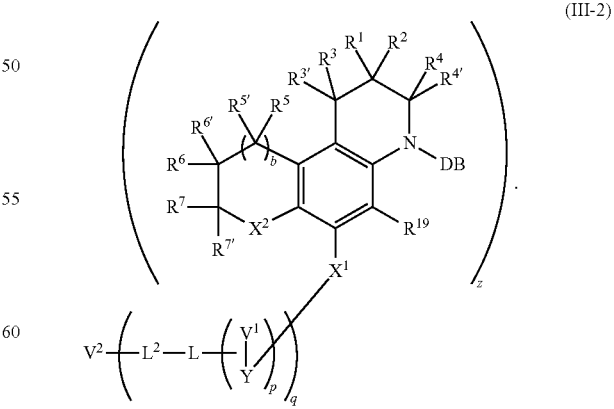

In another embodiment, a compound of formula (III) is represented by a compound of formula (III-3a) or (III-4a), wherein the DNA-binding moiety is DB1:

(III-3a) (III-3b)

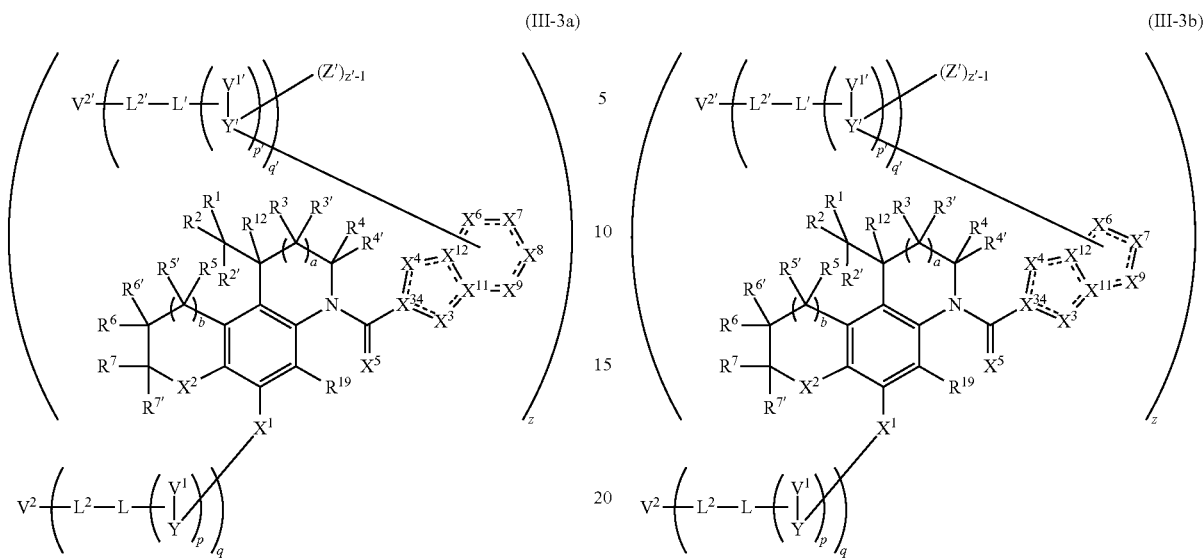

(III-4a) (III-4b)

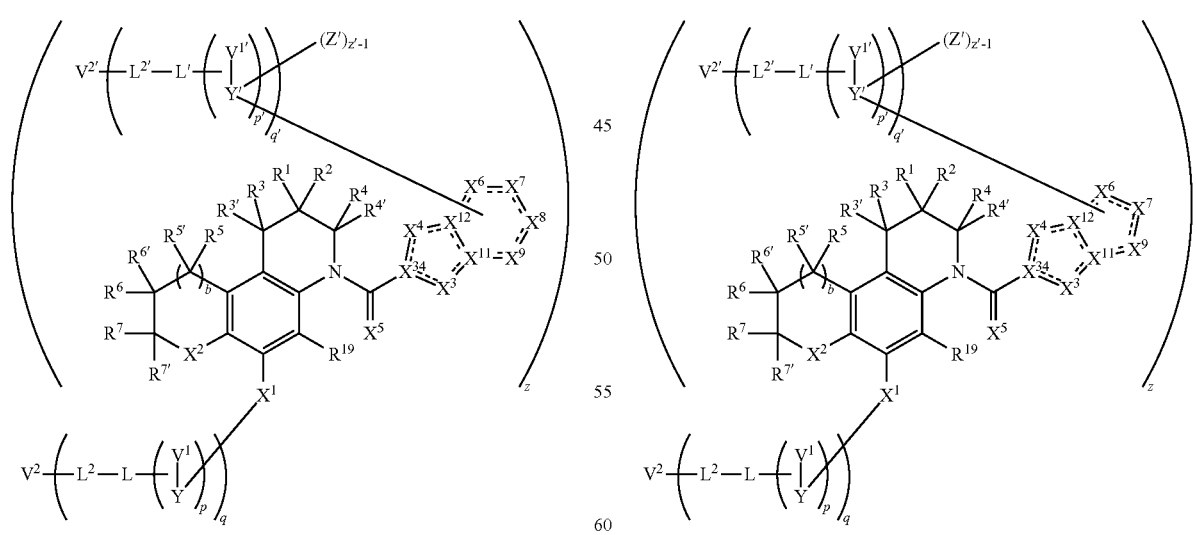

wherein Y' is connected to an atom being part of $X^3$, $X^{34}$, $X^4$, $X^6$, $X^7$, $X^8$, $X^9$, $X^{11}$, or $X^{12}$.

In another embodiment, a compound of formula (III) is represented by a compound of formula (III-3b) or (III-4b), wherein the DNA-binding moiety is DB2:

wherein Y' is connected to an atom being part of $X^3$, $X^{34}$, $X^4$, $X^6$, $X^7$, $X^9$, $X^{11}$, or $X^{12}$.

In another embodiment, a compound of formula (III) is represented by a compound of formula (III-3c) or (III-4c), wherein the DNA-binding moiety is DB3:

(III-3c) (III-3d)

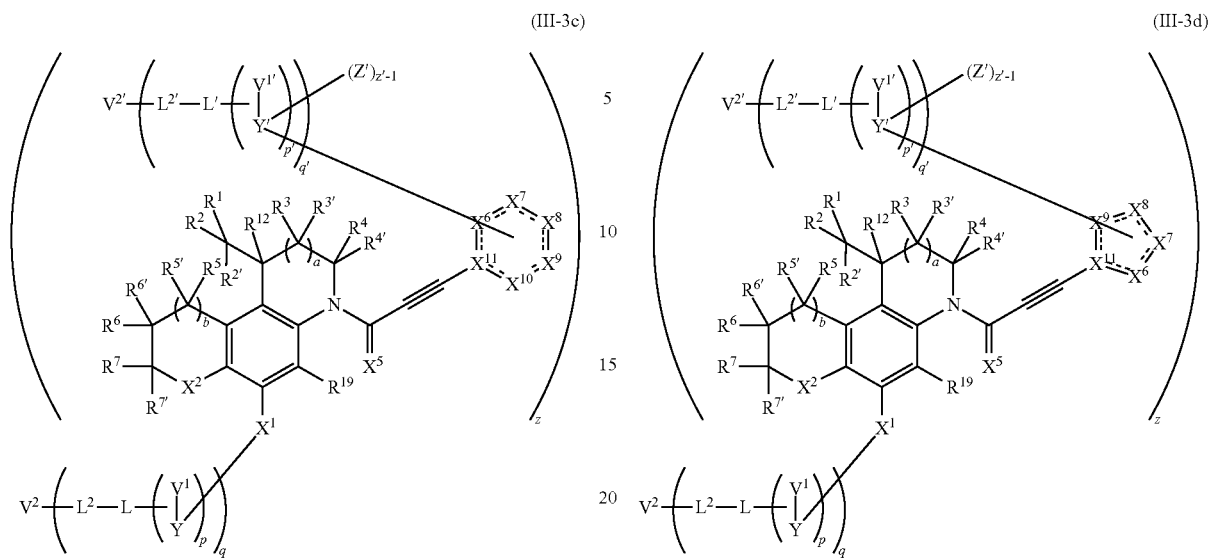

(III-4c) (III-4d)

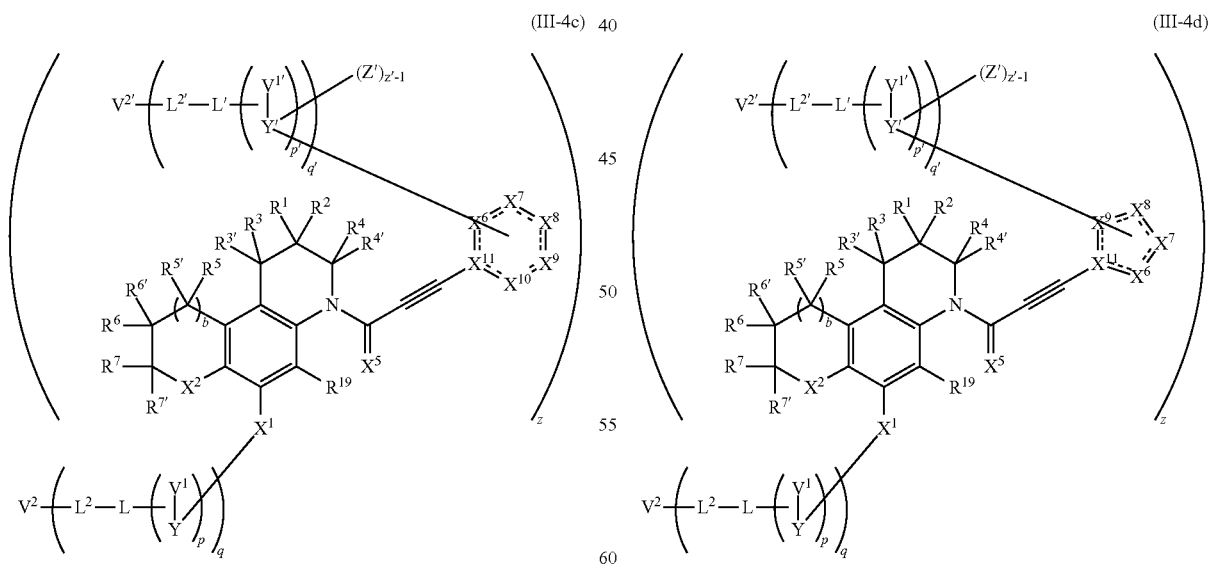

wherein Y' is connected to an atom being part of $X^6$, $X^7$, $X^8$, $X^9$, $X^{10}$, or $X^{11}$.

In another embodiment, a compound of formula (III) is represented by a compound of formula (III-3d) or (III-4d), wherein the DNA-binding moiety is DB4:

wherein Y' is connected to an atom being part of $X^6$, $X^7$, $X^8$, $X^9$, or $X^{11}$.

In another embodiment, a compound of formula (III) is represented by a compound of formula (III-3e) or (III-4e), wherein the DNA-binding moiety is DB5:

(III-3e)

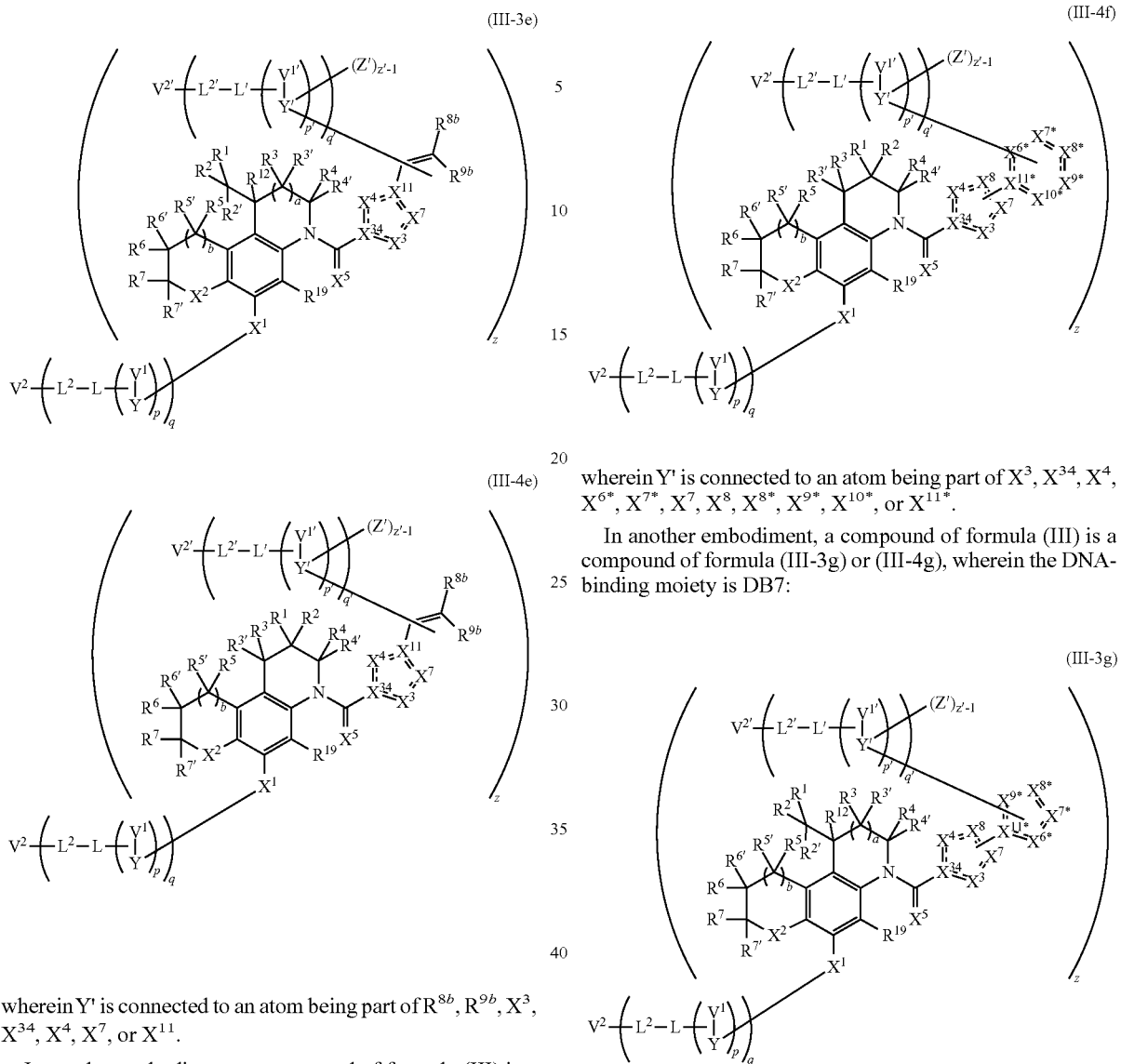

(III-4e)

wherein Y' is connected to an atom being part of $R^{8b}$, $R^{9b}$, $X^3$, $X^{34}$, $X^4$, $X^7$, or $X^{11}$.

In another embodiment, a compound of formula (III) is a compound of formula (III-3f) or (III-4f), wherein the DNA-binding moiety is DB6:

(III-3f)

(III-4f)

wherein Y' is connected to an atom being part of $X^3$, $X^{34}$, $X^4$, $X^{6*}$, $X^{7*}$, $X^7$, $X^8$, $X^{8*}$, $X^{9*}$, $X^{10*}$, or $X^{11*}$.

In another embodiment, a compound of formula (III) is a compound of formula (III-3g) or (III-4g), wherein the DNA-binding moiety is DB7:

(III-3g)

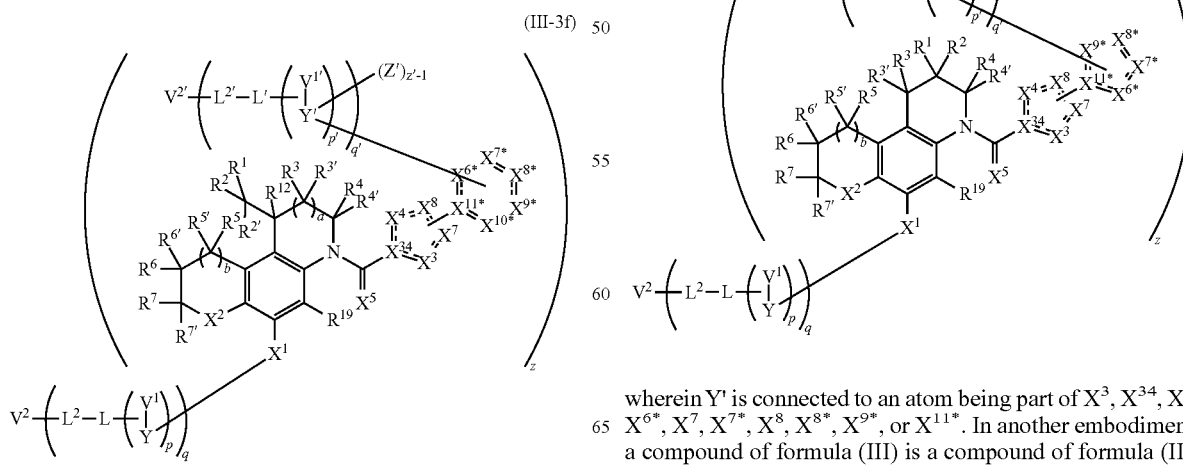

(III-4g)

wherein Y' is connected to an atom being part of $X^3$, $X^{34}$, $X^4$, $X^{6*}$, $X^7$, $X^{7*}$, $X^8$, $X^{8*}$, $X^{9*}$, or $X^{11*}$. In another embodiment, a compound of formula (III) is a compound of formula (III-3h) or (III-4h), wherein the DNA-binding moiety is DB8:

(III-3h)

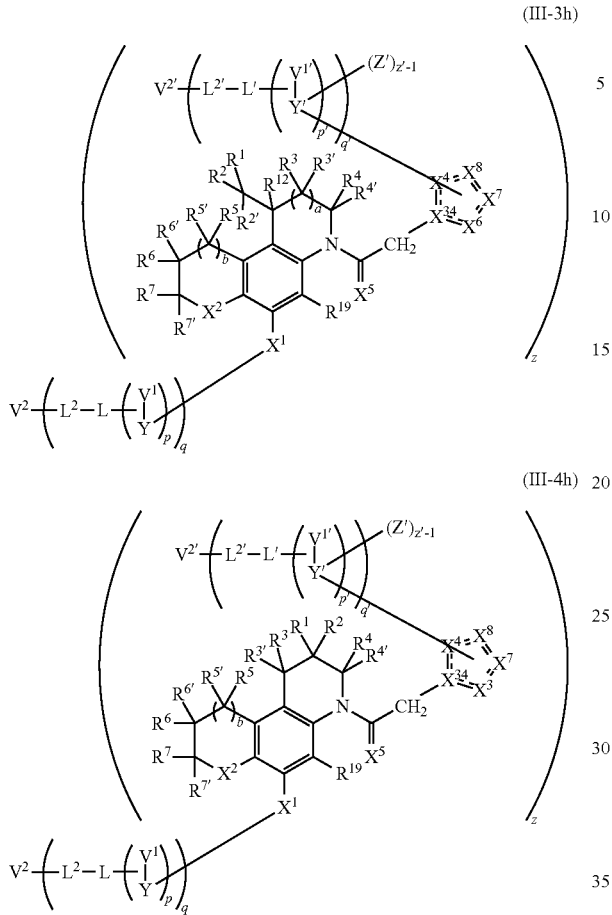

(III-4h)

wherein Y' is connected to an atom being part of $X^3$, $X^{34}$, $X^4$, $X^7$, or $X^8$.

In another embodiment, a compound of formula (III) is represented by a compound of formula (III-3i) or (III-4i), wherein the DNA-binding moiety is DB9:

(III-3i)

(III-4i)

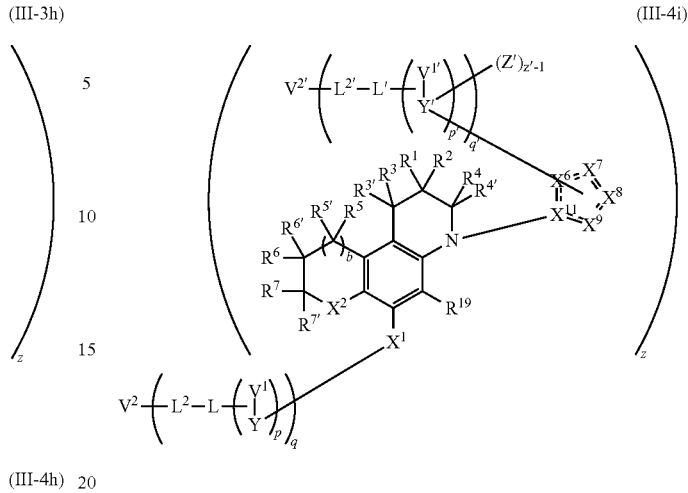

wherein Y' is connected to an atom being part of $X^6$, $X^7$, $X^8$, $X^9$, or $X^{11}$.

This invention further relates to compounds of formulae (III-3j)-(III-3r) and (III-4j)-(III-4r), which are identical to compounds of formulae (III-3a)-(III-3i) and (III-4a)-(III-4i), respectively, except that the two promoieties have switched places, Y now being connected to an atom in the DNA-binding unit and Y' being connected to $X^1$.

It is noted that if in any of compounds of formulae (III-3a)-(III-3i) and (III-4a)-(III-4i) Y' is connected to a ring atom being part of ring A or ring B instead of to an atom in an R substituent connected to said ring atom, this in fact means that such an R substituent is absent if this is necessary to meet valency rules. The same holds for Y in compounds of formulae (III-3j)-(III-3r) and (III-4j)-(III-4r).

In another embodiment, a compound of formula (III) is represented by a compound of formula (III-5a) or (III-6a):

(III-5a)

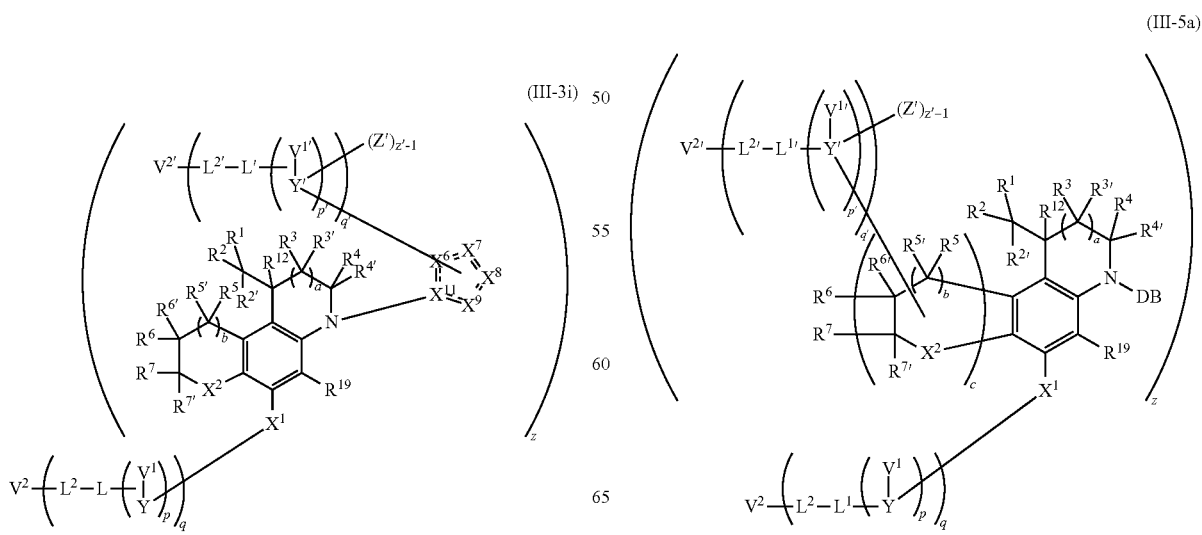

-continued

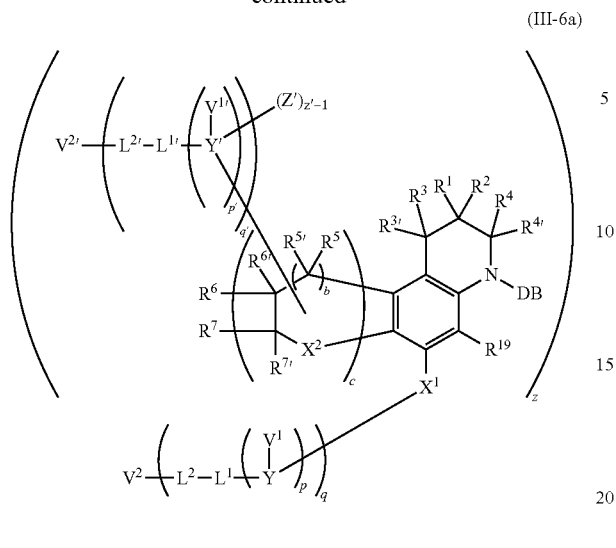

(III-6a)

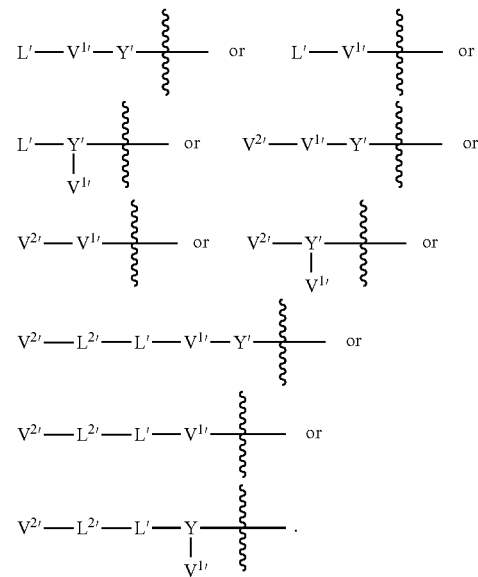

wherein Y' is connected to an atom being part of $R^5$, $R^{5'}$, $R^6$, $R^{6'}$, $R^7$, $R^{7'}$, $R^{14}$, $R^{14'}$, $X^2$ or to any of the atoms bearing these R substituents.

In a further embodiment, a compound of formula (III) is represented by compounds of formulae (III-5b) and (III-6b), which are identical to compounds (III-5a) and (III-6a), respectively, except that the two promoieties have switched places, Y now being connected to an atom in the DNA-alkylating unit and Y' being connected to $X^1$.

When Y' in compounds of formulae (III-5a) and (III-6a) is connected to a ring atom instead of to an atom in an R substituent connected to said ring atom, this in fact means that such an R substituent is absent if this is necessary to meet valency rules. The same holds for Y in compounds of formulae (III-5b) and (III-6b).

In one embodiment, the $V^{2'}(-L^{2'}-L'(-(V^{1'}-Y'))_{p'})_{q'}(Z')_{z'-1}$ moiety in any of compounds of formulae (III-3a)-(III-3r), (III-4a)-(III-4r), (III-5a), (III-5b), (III-6a), and (III-6b) is represented by In another embodiment, the $V^{2'}(-L^{2'}-L'(-(V^{1'}-Y'))_{p'})_{q'}(Z')_{z'-1}$ moiety in any of compounds of formulae (III-3a)-(III-3r), (III-4a)-(III-4r), (III-5a), (III-5b), (III-6a), and (III-6b) is represented by

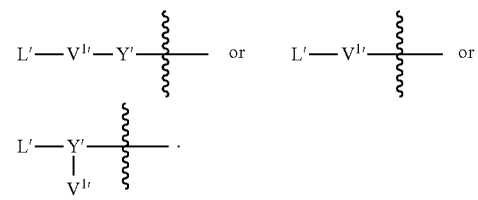

In a further embodiment, the $V^{2'}(-L^{2'}-L'(-(V^{1'}-Y'))_{p'})_{q'}(Z')_{z'-1}$ moiety in any of compounds of formulae (III-3a)-(III-3r), (III-4a)-(III-4r), (III-5a), (III-5b), (III-6a), and (III-6b) is selected from

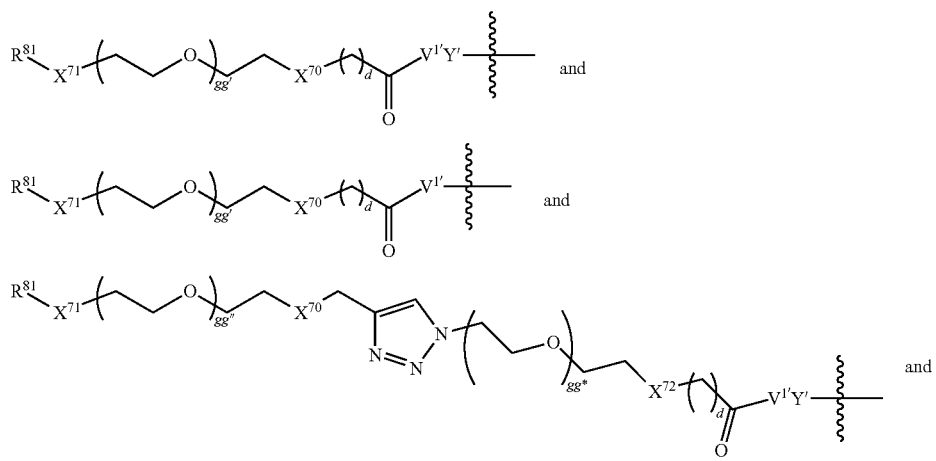

-continued

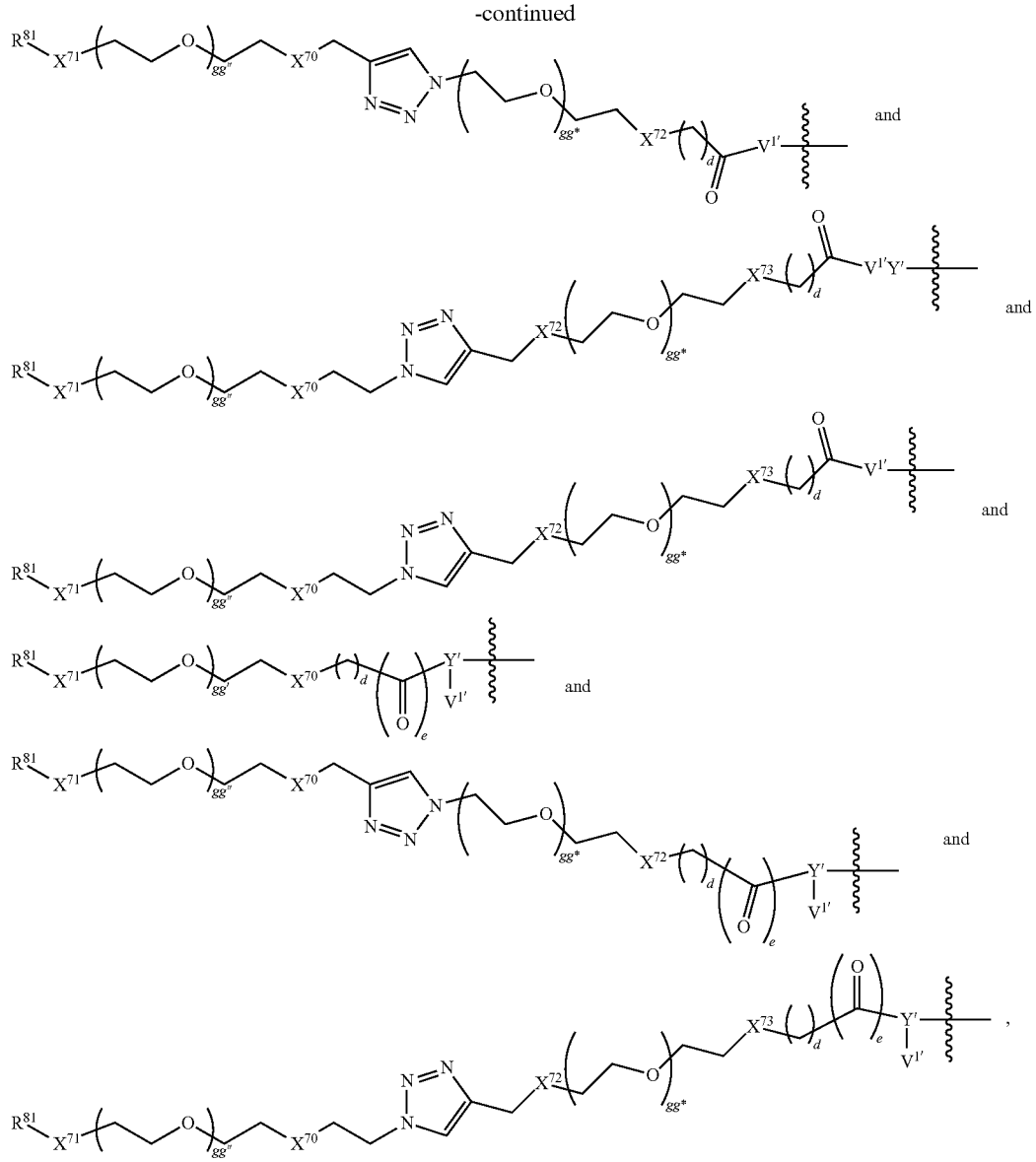

wherein $X^{70}$, $X^{71}$, $X^{72}$, and $X^{73}$ are independently selected from O, S, and $NR^{82}$, d is selected from 0 to 8, e is 0 or 1, gg" and gg* are independently selected from 1 to 1000, gg' is selected from 3 to 1000, and $R^{81}$ and $R^{82}$ are independently selected from H and optionally substituted $C_{1-3}$ alkyl.

In one embodiment, p is an integer from 1 (included) to 128 (included). In another embodiment, q is an integer from 1 (included) to 1000 (included). In other embodiments, p is an integer from 1 (included) to 64 (included) or 32 (included) or 16 (included) or 8 (included) or 4 (included) or 2 (included), or p is 1. In other embodiments, q is an integer from 1 (included) to 500 (included) or 400 (included) or 300 (included) or 200 (included) or 100 (included) or 16 (included) or 8 (included) or 6 (included) or 4 (included) or 2 (included), or q is 1.

In one embodiment, if more than 1 promoiety is connected to a first Z and in one of the promoieties there is more than one attachment site for Z moieties, then the other ones of said promoieties connected to said first Z each contain a single attachment site for a Z moiety.

In one embodiment, a compound of formula (III) is represented by

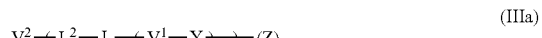
(IIIa)

In one embodiment, p in a compound of formula (IIIa) is 1.
In another embodiment, in a compound of formula (IIIa) p is 1 and z equals q, which reduces formula (IIIa) to:

In another embodiment, a compound of formula (IIIa) is represented by

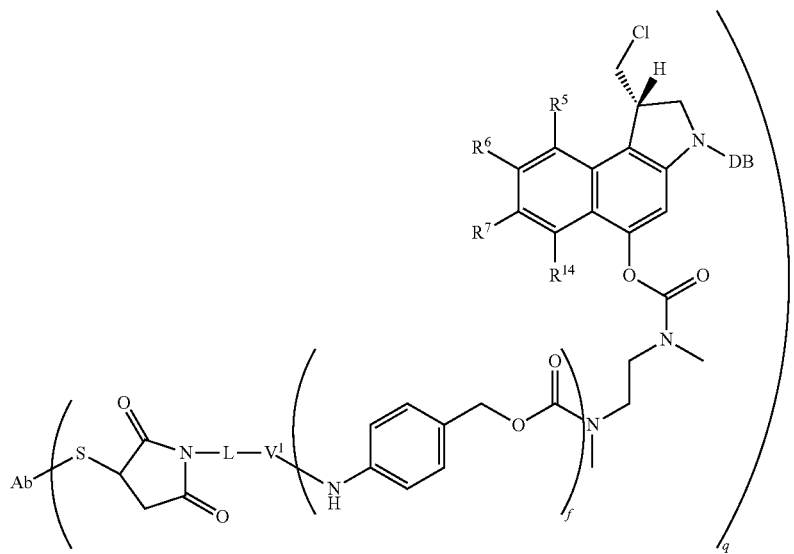

or by an isomer, or by a mixture of isomers, wherein $R^5$, $R^6$, $R^7$, $R^{14}$, and DB are as previously defined, $V^1$ is selected from valylcitrulline, valyllysine, phenylalanyllysine, alanylphenylalanyllysine, and D-alanylphenylalanyllysine, f is 1 or 2, L is selected from

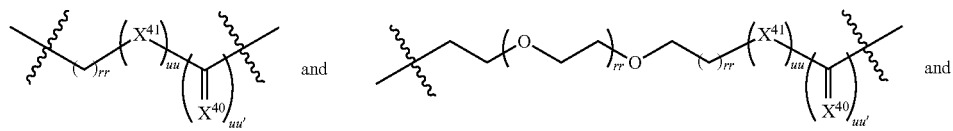

and

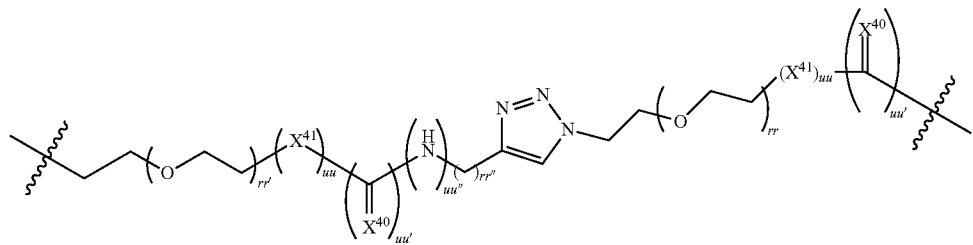

q ranges from 1 to 20, rr, rr', and rr" each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, and Ab is an antibody or a fragment or derivative thereof.

In another embodiment, a compound of formula (IIIa) is represented by

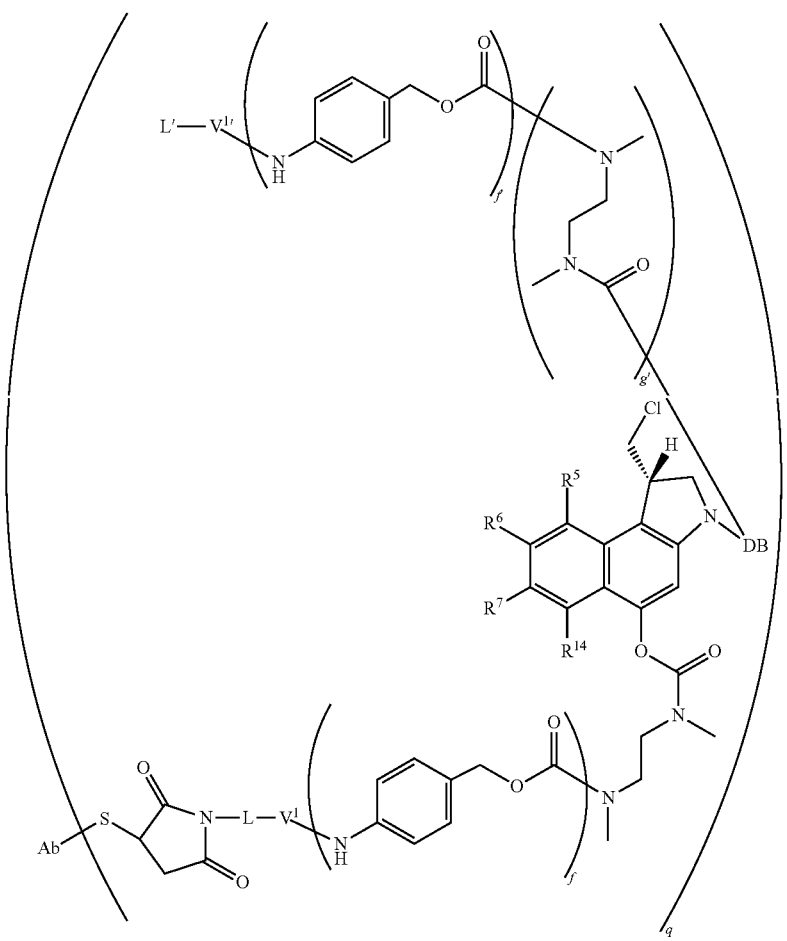

or by an isomer, or by a mixture of isomers, wherein $R^5$, $R^6$, $R^7$, $R^{14}$, and DB are as previously defined, $V^1$ and $V^{1'}$ are independently selected from valylcitrulline, valyllysine, phenylalanyllysine, alanylphenylalanyllysine, and D-alanylphenylalanyllysine, f is 1 or 2, f is 0, 1, or 2, g' is 0 or 1, the dimethylaminoethylene group—or the p-aminobenzyloxycarbonyl group if g' is 0, or the $V^{1'}$ group if f is 0 as well—is connected to an atom in DB, L is selected from q ranges from 1 to 20, rr, rr', and rr'' each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu'' is independently selected from 0 and 1, Ab is an antibody or a fragment or derivative thereof, and L' is selected from

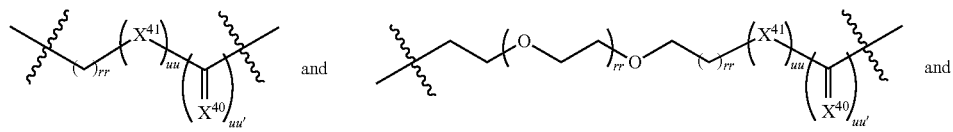

and

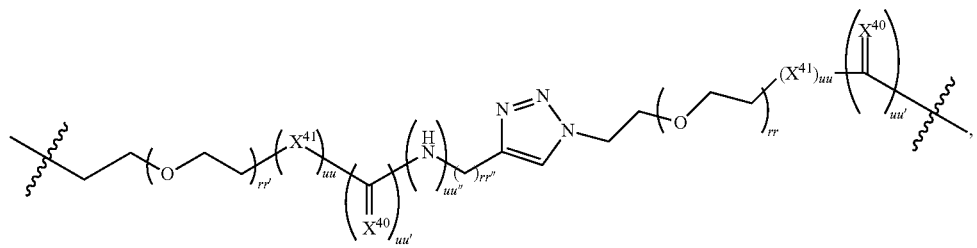

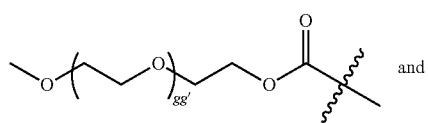 and
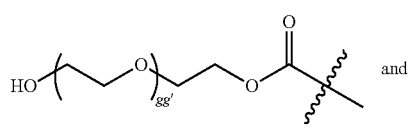 and
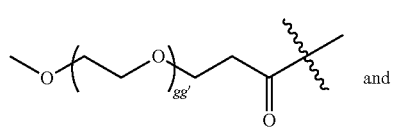 and
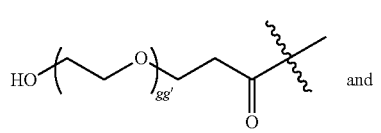 and
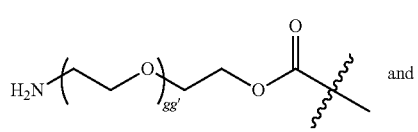 and
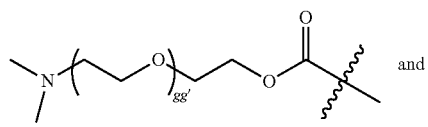 and
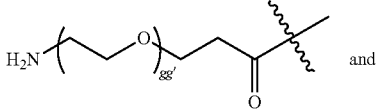 and
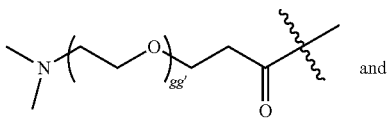 and
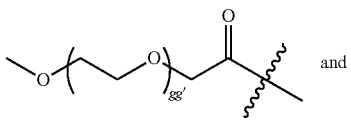 and
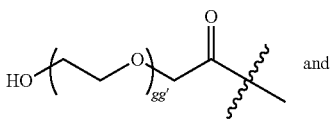 and
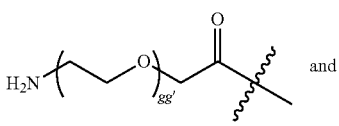 and
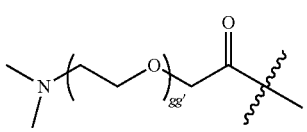 and
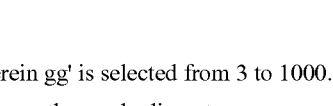
wherein gg' is selected from 3 to 1000.
In another embodiment, a compound of formula (IIIa) is represented by
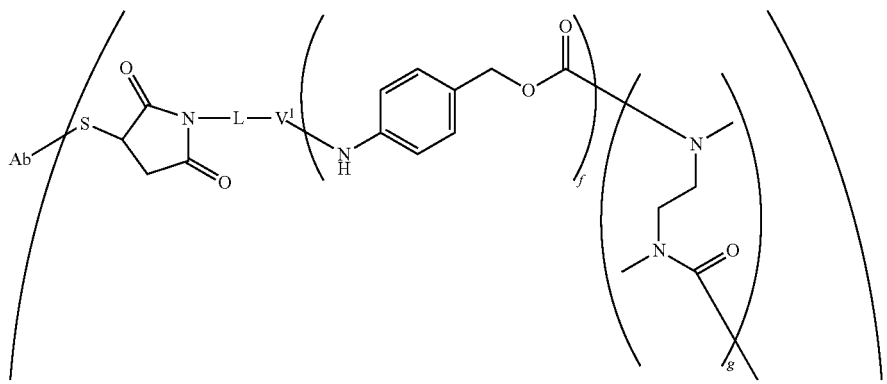

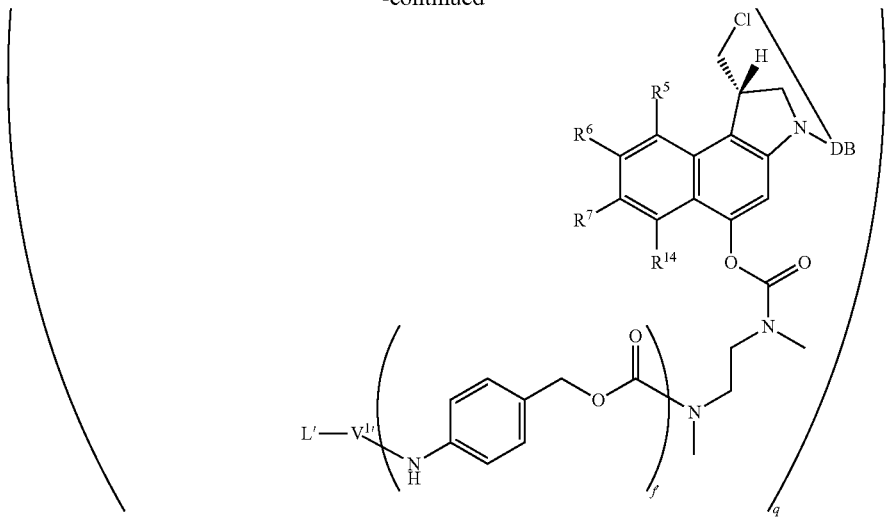

or by an isomer, or by a mixture of isomers, wherein $R^5$, $R^6$, $R^7$, $R^{14}$, and DB are as previously defined, $V^1$ and $V^{1'}$ are independently selected from valylcitrulline, valyllysine, phenylalanyllysine, alanylphenylalanyllysine, and D-alanylphenylalanyllysine, f is 0, 1, or 2, f' is 1, or 2, g is 0 or 1, the dimethylaminoethylene group—or the p-aminobenzyloxycarbonyl group if g is 0, or the $V^1$ group if f is 0 as well—is connected to an atom in DB. L is selected from

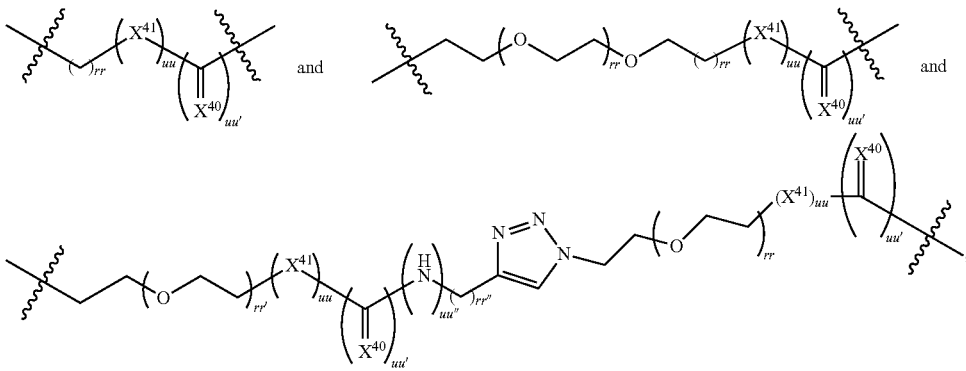

q ranges from 1 to 20, rr, rr', and rr" each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, Ab is an antibody or a fragment or derivative thereof, and L' is selected from

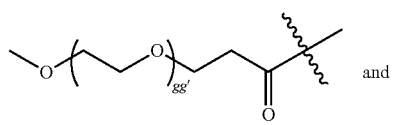

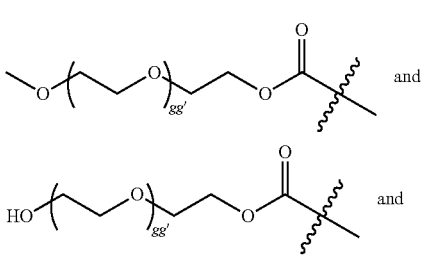

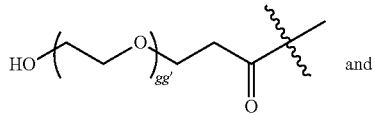

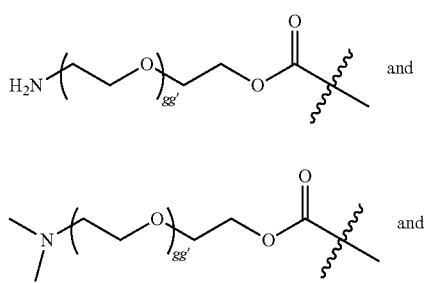

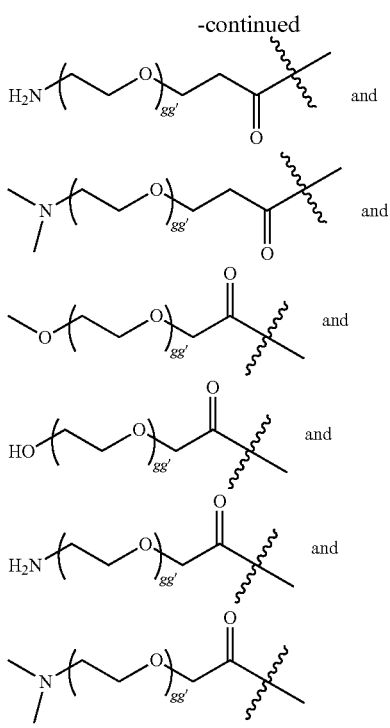

wherein gg' is selected from 3 to 1000.

In another embodiment, a compound of formula (III) is represented by

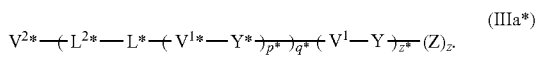
(IIIa*)

In one embodiment, p* in a compound of formula (IIIa*) is 1.

In another embodiment, in a compound of formula (IIIa*) p* is 1 and z* equals q*.

In another embodiment, in a compound of formula (IIIa*) p* is 1 and z* as well as z equal q*, which reduces formula (IIIa*) to:

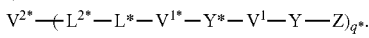

In another embodiment, a compound of formula (III) is represented by

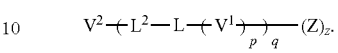
(IIIb)

In one embodiment, p in a compound of formula (IIIb) is 1.
In another embodiment, p in a compound of formula (IIIb) is 1 and z equals q, which reduces formula (IIIb) to:

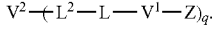

In another embodiment, a compound of formula (III) is represented by

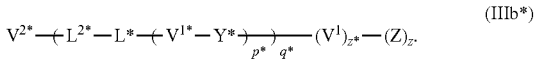
(IIIb*)

In one embodiment, p* in a compound of formula (IIIb*) is 1.

In another embodiment, in a compound of formula (IIIb*) p* is 1 and z* equals q*.

In yet another embodiment, in a compound of formula (IIIb*) p* is 1 and z* as well as z equal q*, which reduces formula (IIIb*) to:

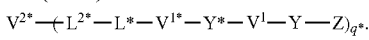

In another embodiment, $V^1$ in a compound of formula (IIIb*) is an enzyme-cleavable substrate. In a further embodiment, $V^1$ can be cleaved by an intracellular enzyme. In another embodiment, $V^1$ is an optionally substituted N,N-dialkylaminocarbonyl group wherein the two alkyl groups may be the same or different and optionally be connected to each other to form an optionally substituted heterocycle. In yet another embodiment, $V^1$ is piperazinocarbonyl. Such a $V^1$ group may be cleaved enzymatically, for example by carboxylesterases.

In another embodiment, a compound of formula (IIIb*) is represented by

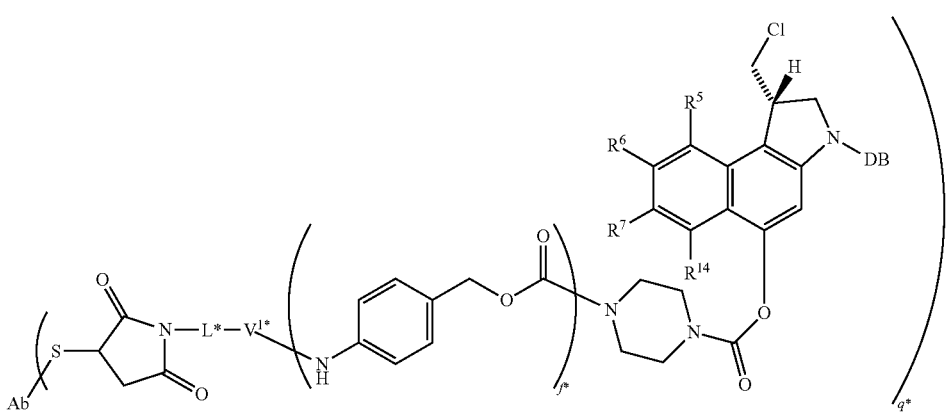

or by an isomer, or by a mixture of isomers, wherein $R^5$, $R^6$, $R^7$, $R^{14}$, and DB are as previously defined, $V^{1*}$ is selected from valylcitrulline, valyllysine, phenylalanyllysine, alanylphenylalanyllysine, and D-alanylphenylalanyllysine, f* is 1 or 2, L* is selected from

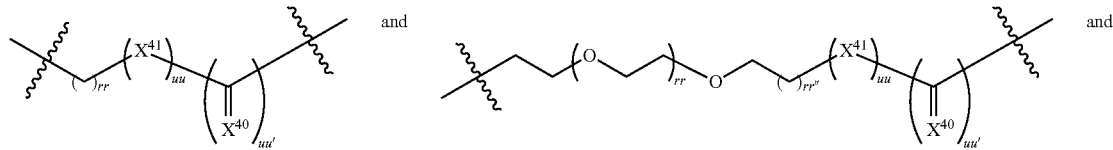

and

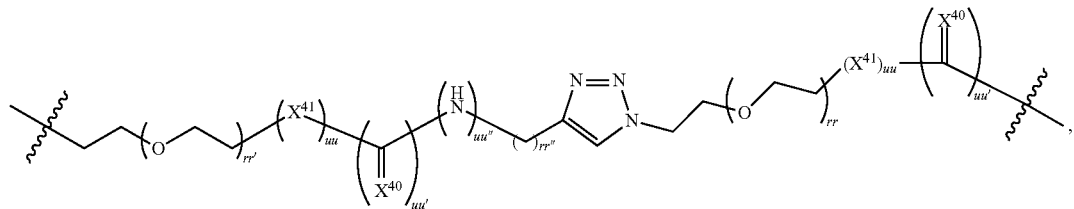

q* ranges from 1 to 20, rr, rr', and rr" each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, and Ab is an antibody or a fragment or derivative thereof.

In another embodiment, a compound of formula (III) is represented by $$V^2\text{---}(L^2\text{---}L\text{---}V^1\text{---}Z)_{q'}$$ (IIIc)

In yet another embodiment, a compound of formula (III) is represented by $$V^1\text{---}Z$$ (IIId).

In one embodiment, a compound of formula (IIId) is represented by

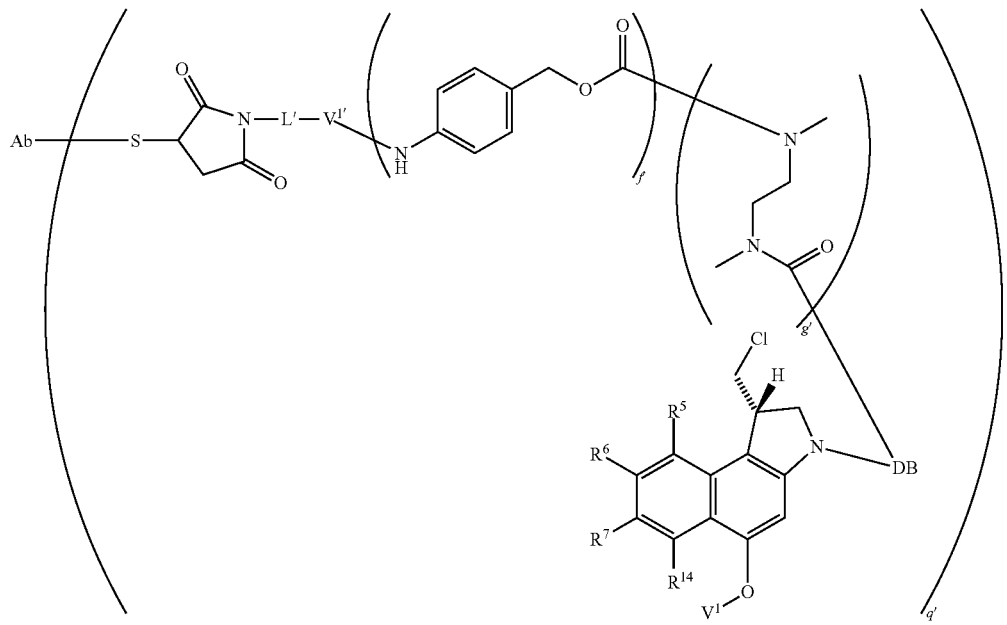

or by an isomer, or by a mixture of isomers, wherein $R^5$, $R^6$, $R^7$, $R^{14}$, and DB are as previously defined, f' is 0, 1, or 2, g' is 0 or 1, $V^{1'}$ is selected from valylcitrulline, valyllysine, phenylalanyllysine, alanylphenylalanyllysine, and D-alanylphenylalanyllysine or is absent, the dimethylaminoethylene group—or the p-aminobenzyloxycarbonyl group if g' is 0, or the $V^{1'}$ group if f' is 0 as well, or the L' group if the $V^{1'}$ group is absent as well—is connected to an atom in DB, L' is selected from

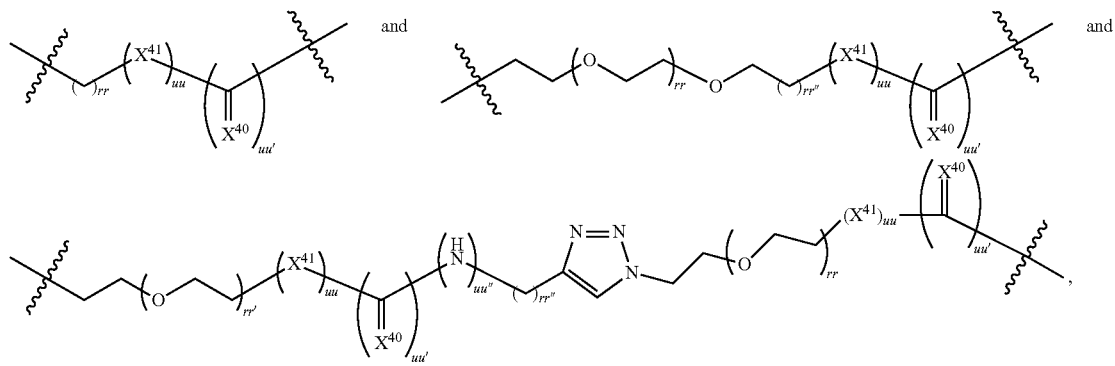

and q' ranges from 1 to 20, rr, n', and rr'' each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu'' is independently selected from 0 and 1, Ab is an antibody or a fragment or derivative thereof, and $V^1$ is selected from a mono-, di-, or oligosaccharide or a derivative thereof and

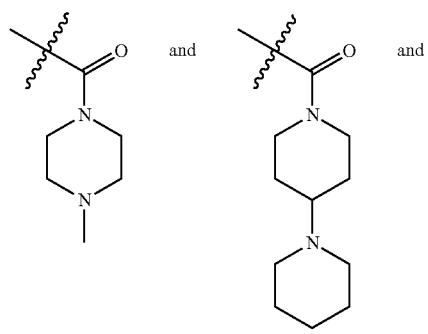

and

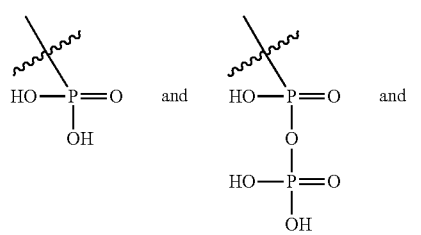

and

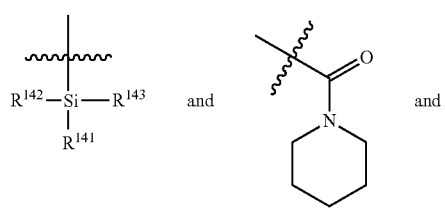

and

-continued

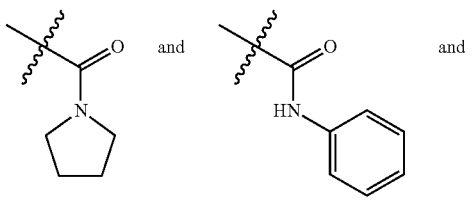

and

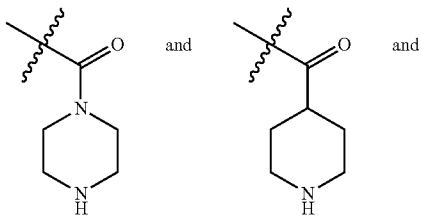

and

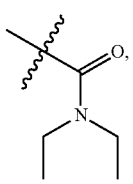

wherein $R^{141}$, $R^{142}$, and $R^{143}$ are independently selected from H and optionally substituted $C_{1-8}$ alkyl, $C_{1-8}$ heteroalkyl, $C_{3-8}$ cycloalkyl, $C_{1-8}$ heterocycloalkyl, $C_{5-8}$ aryl, or $C_{1-8}$ heteroaryl.

In another embodiment, a compound of formula (IIId) is represented by

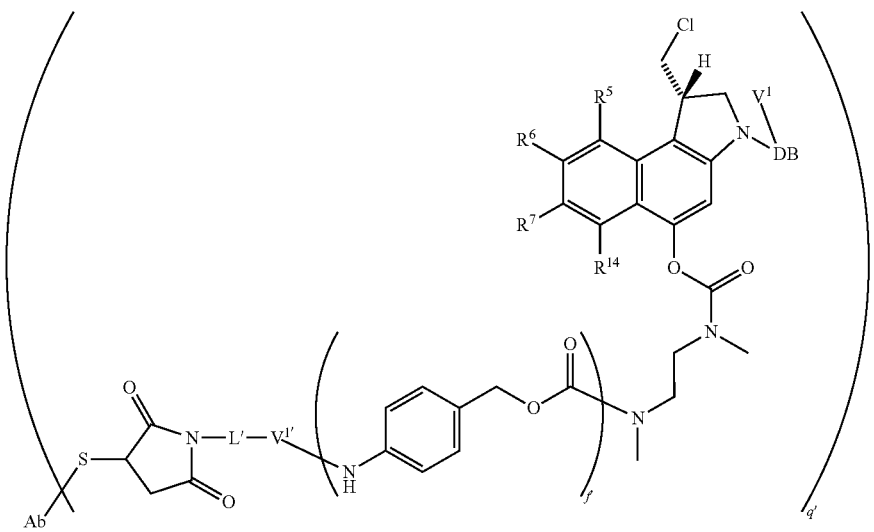

or by an isomer, or by a mixture of isomers, wherein $R^5$, $R^6$, $R^7$, $R^{14}$, and DB are as previously defined, f' is 1 or 2, $V^{1'}$ is selected from valylcitrulline, valyllysine, phenylalanyllysine, alanylphenylalanyllysine, and D-alanylphenylalanyllysine, L' is selected from

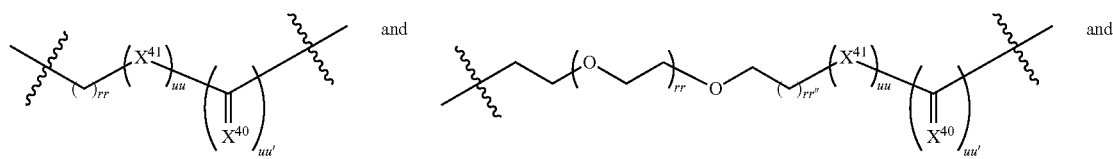

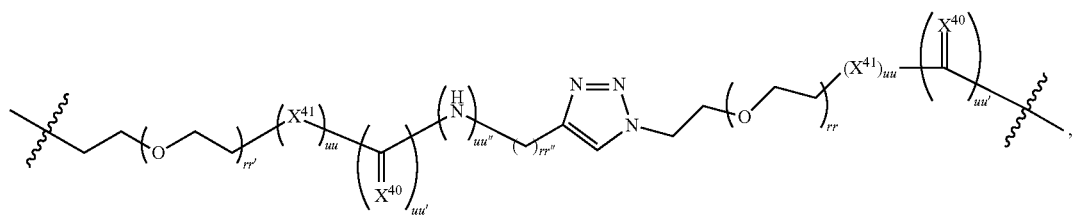

q' ranges from 1 to 20, rr, rr', and rr" each independently range from 0 to 8, each $X^{40}$ and $X^{41}$ is independently selected from O, S, and $NR^{135}$, wherein $R^{135}$ is selected from H and $C_{1-3}$ alkyl, each uu, uu', and uu" is independently selected from 0 and 1, Ab is an antibody or a fragment or derivative thereof, and $V^1$ is coupled to an atom of DB and is selected from a mono-, di-, or oligosaccharide or a derivative thereof and

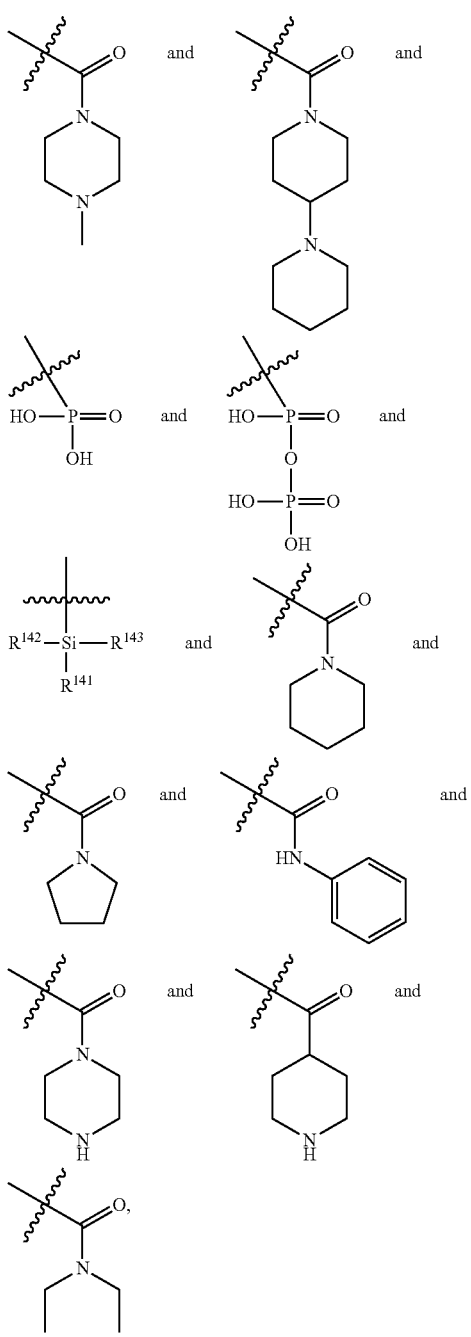

wherein $R^{141}$, $R^{142}$, and $R^{143}$ are independently selected from H and optionally substituted $C_{1-8}$ alkyl, $C_{1-8}$ heteroalkyl, $C_{3-8}$ cycloalkyl, $C_{1-8}$ heterocycloalkyl, $C_{5-8}$ aryl, or $C_{1-8}$ heteroaryl.

In yet another embodiment, a compound of formula (III) is represented by

$$V^2\text{-}L^2\text{-}L\text{-}Z \qquad (IIIe).$$

Synthesis of Compounds of the Invention

Compounds of formulae (I)-(IV) can be conveniently prepared in a way for some part analogous to compounds reported in WO 01/83448, WO 02/083180, WO 2004/043493, WO 2007/018431, WO 2007/089149, and WO 2009/017394.

Figure 2:
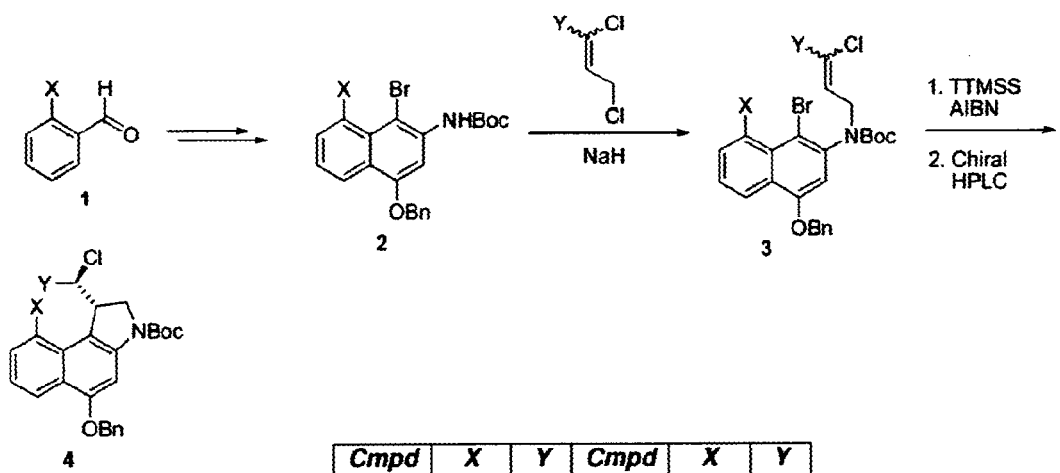
FIG. 2 depicts the synthesis of alkylating moieties 4a-4k.
Figure 3:
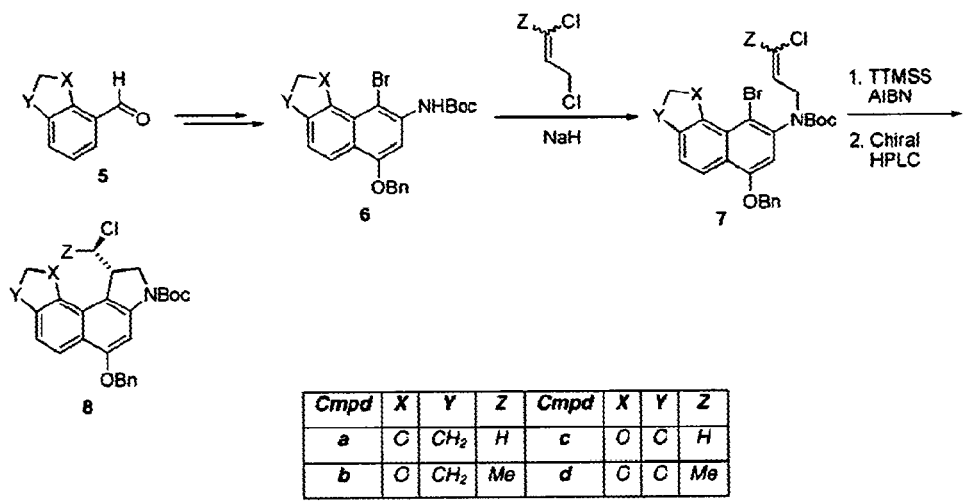
FIG. 3 shows the synthesis of alkylating moieties 8a-8d.
Figure 4:
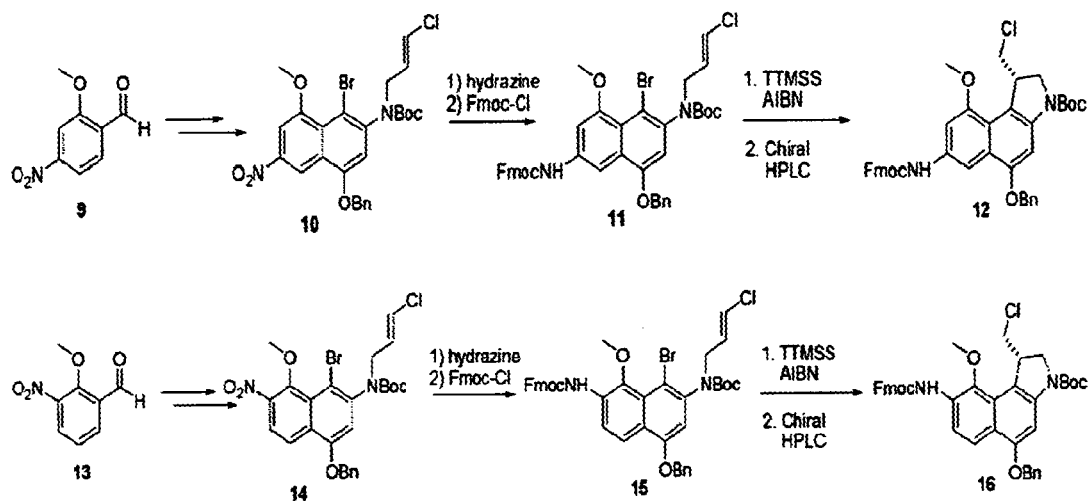
FIG. 4 illustrates the synthesis of alkylating moieties 12 and 16.

FIGS. 2-4 describe the syntheses of some protected DA units. These protected DA units can generally be prepared from commercially available substituted benzaldehydes.

Figure 5:
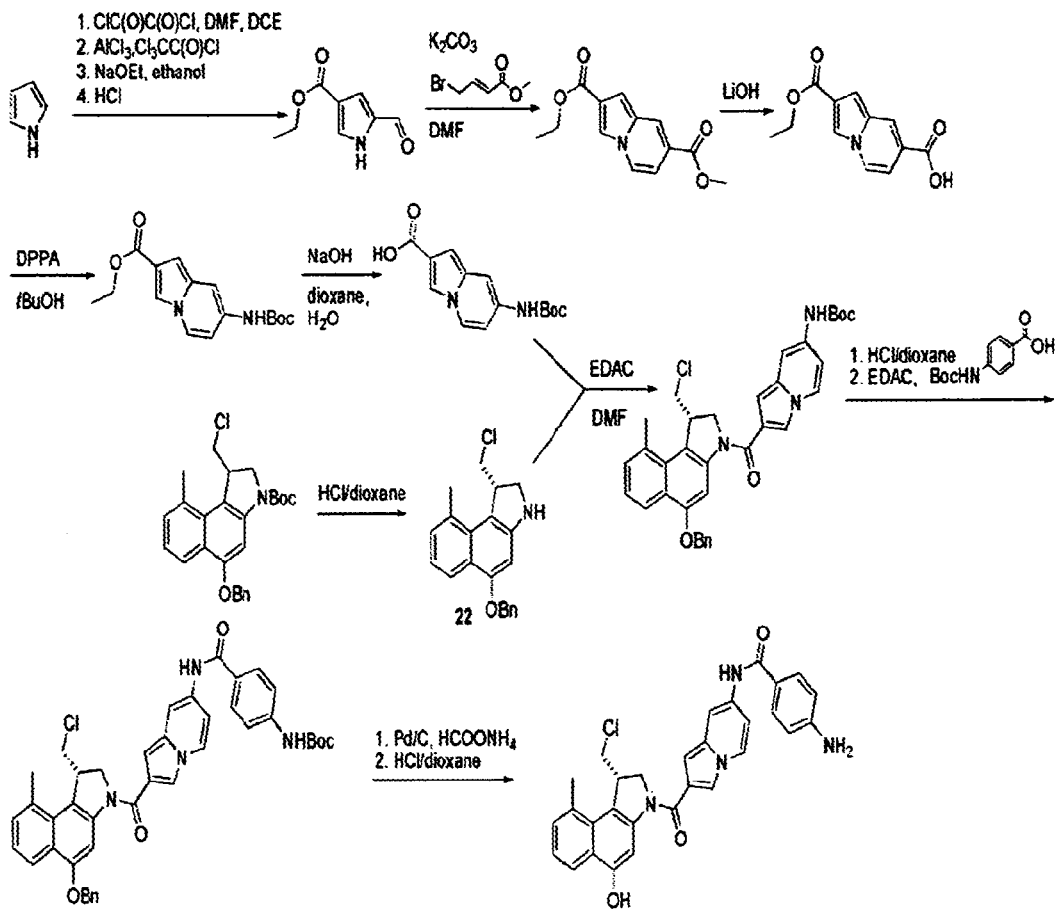
FIG. 5 illustrates the synthesis of duocarmycins containing a 7-substituted indolizine.
Figure 6:
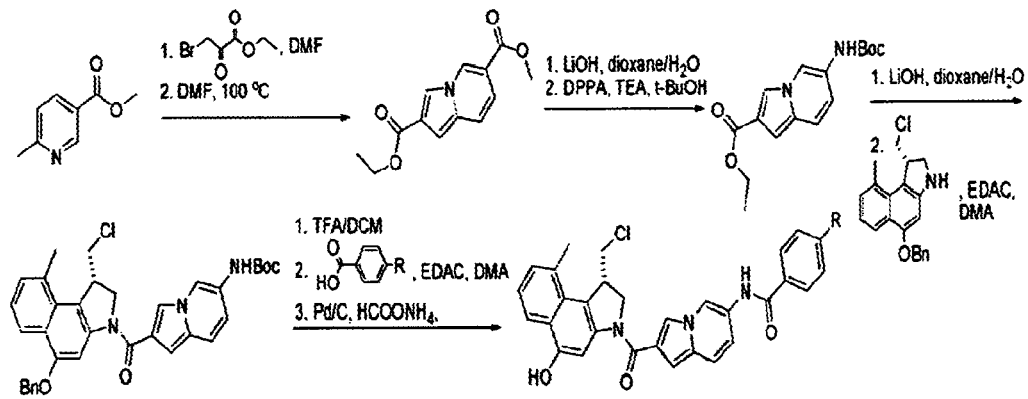
FIG. 6 depicts the synthesis of duocarmycins containing a 6-substituted indolizine.
Figure 7:
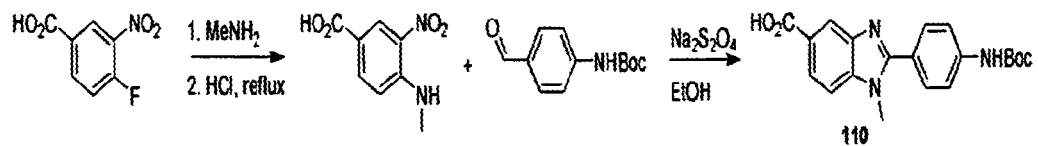
FIG. 7 shows the synthesis of compound 110.
Figure 8:
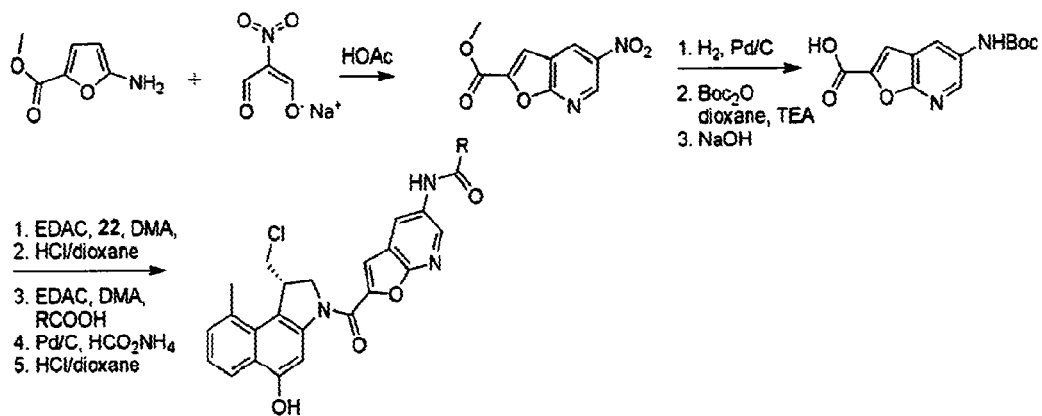
FIG. 8 shows the synthesis of duocarmycins containing a 7-azabenzofuran.
Figure 9:
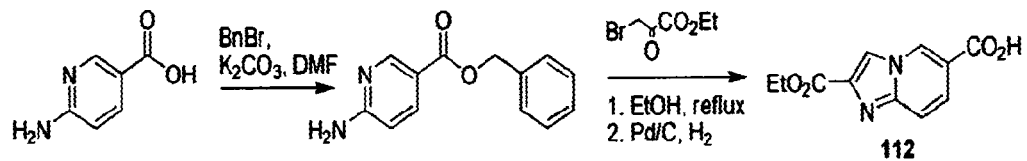
FIG. 9 illustrates the synthesis of compound 112.

The DB moieties can generally be prepared in a few steps from commercially available starting materials in good yields. Coupling with suitable DA units provides agents in a few steps. The synthesis of indolizine-containing agents has been depicted in FIGS. 5 and 6. The synthesis of 7-azabenzofuran-containing agents is shown in FIG. 8. FIGS. 7 and 9 depict the synthesis of two other DB units. Further syntheses have been described in the Examples.

Figure 10:
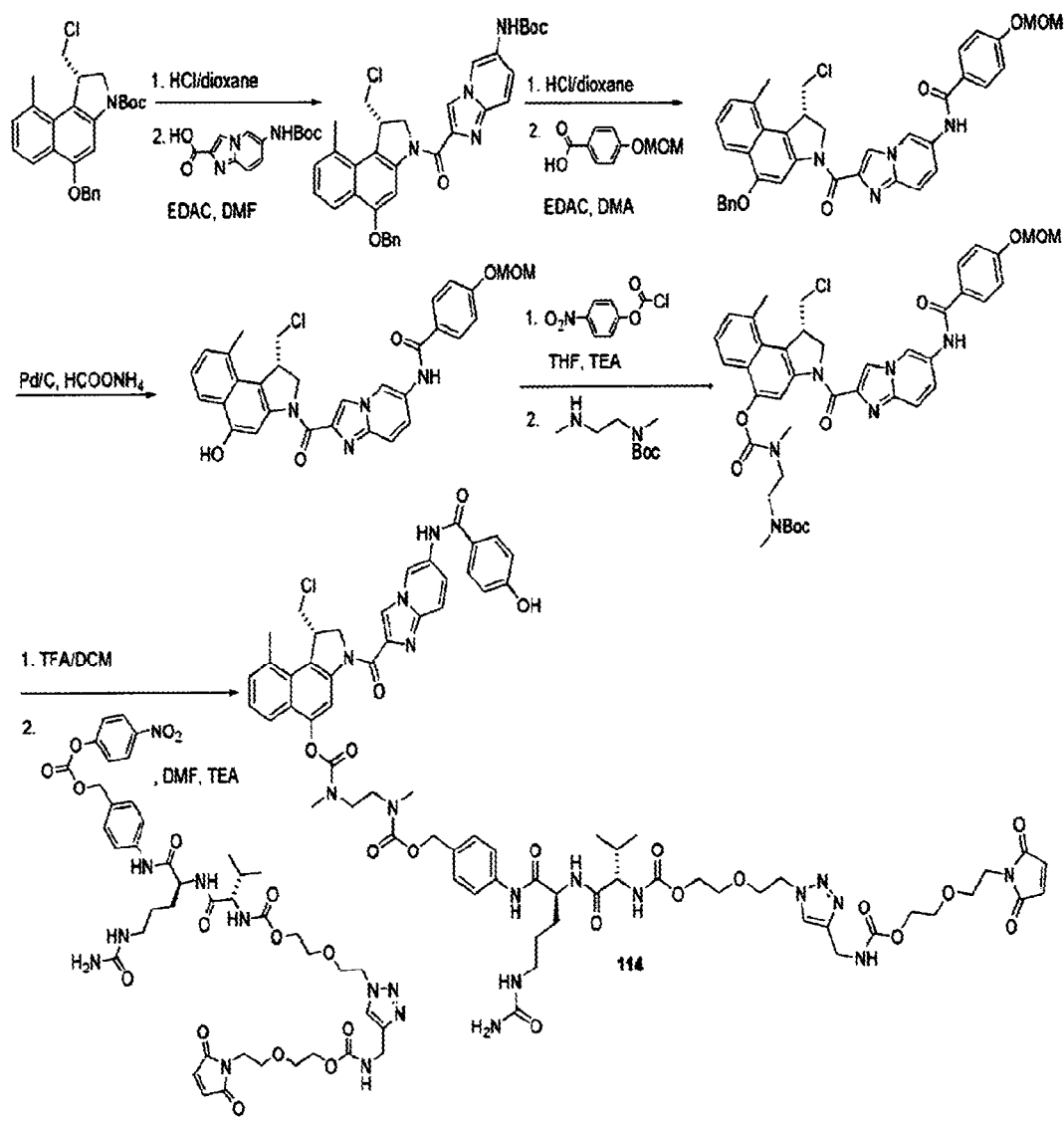
FIG. 10 depicts the synthesis of linker-agent conjugate 114.
Figure 11:
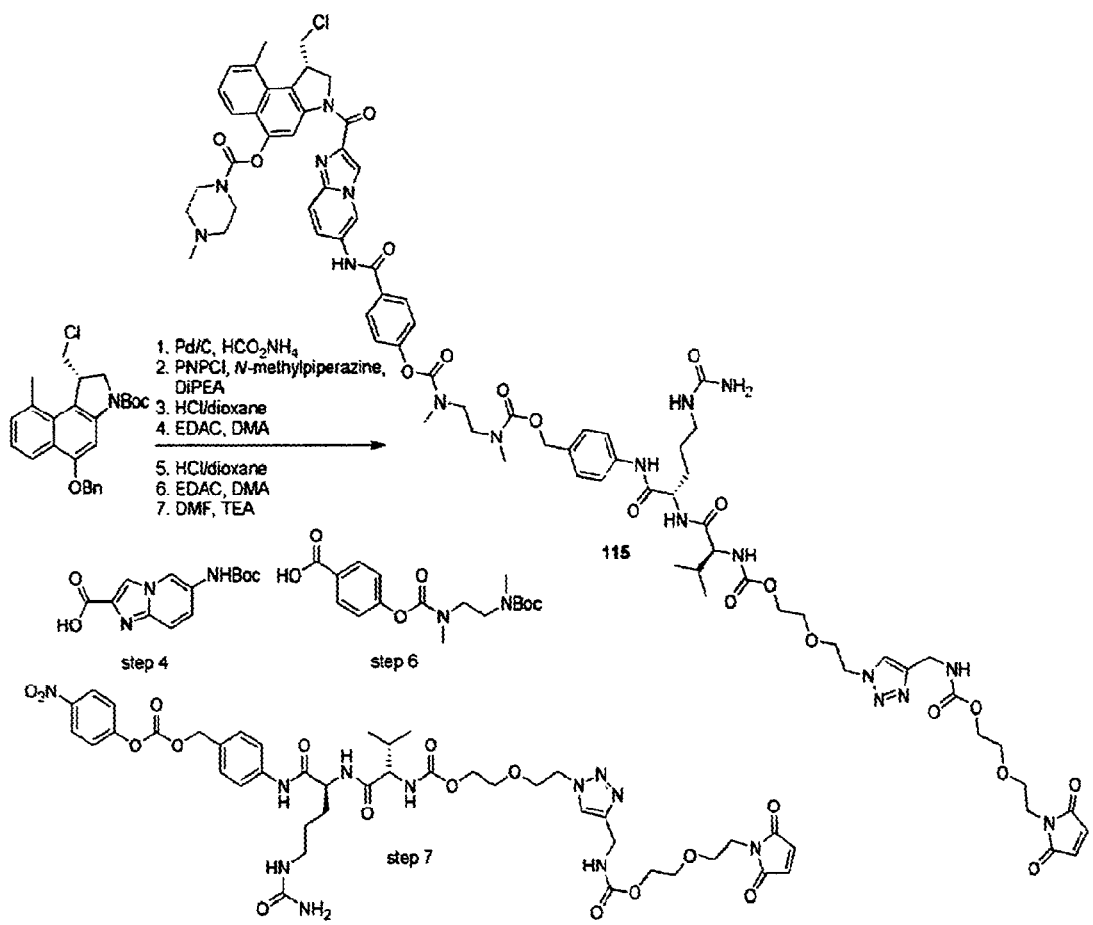
FIG. 11 shows the synthesis of linker-agent conjugate 115.
Figure 12:
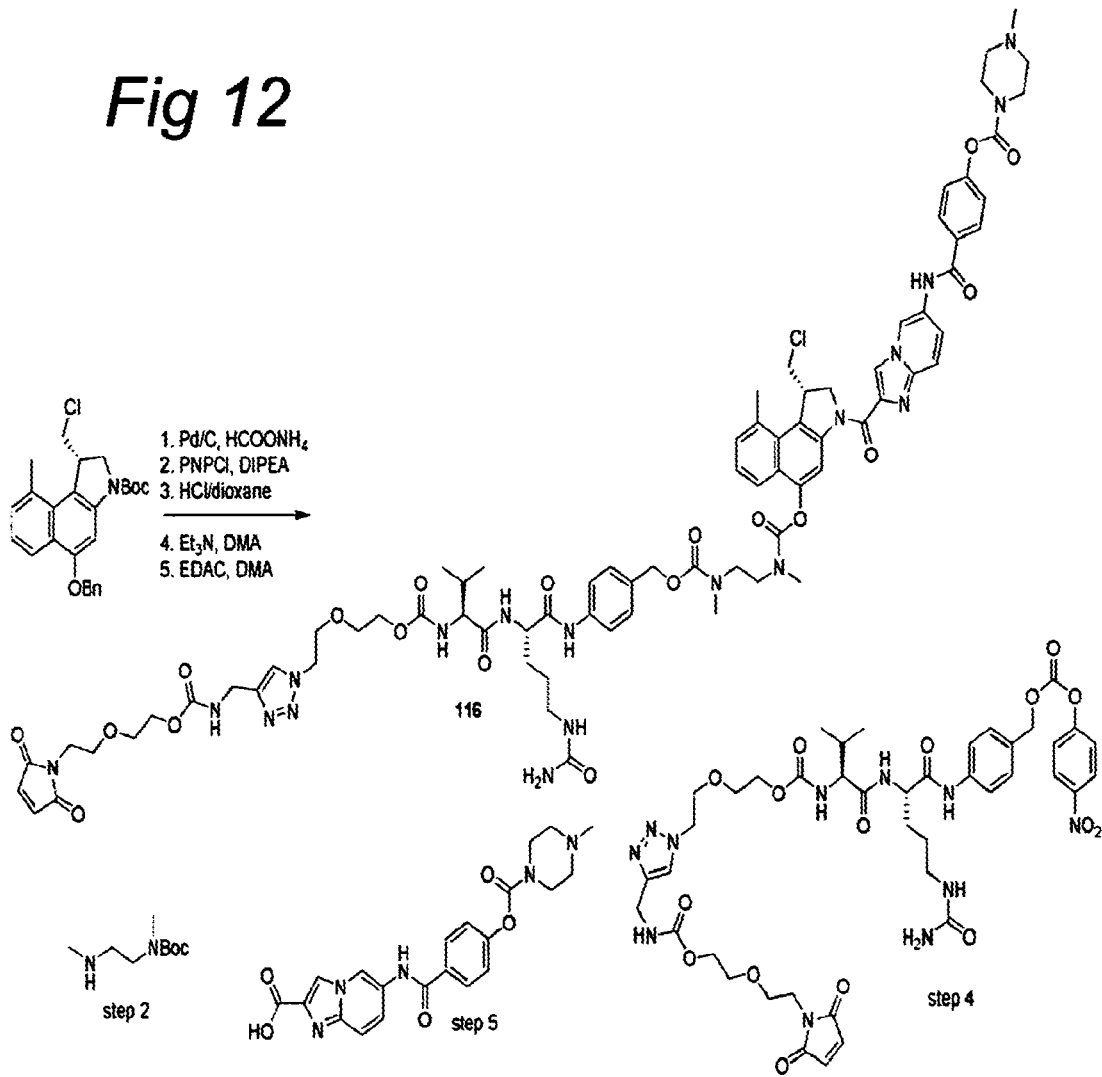
FIG. 12 illustrates the synthesis of linker-agent conjugate 116.
Figures 1, 13:
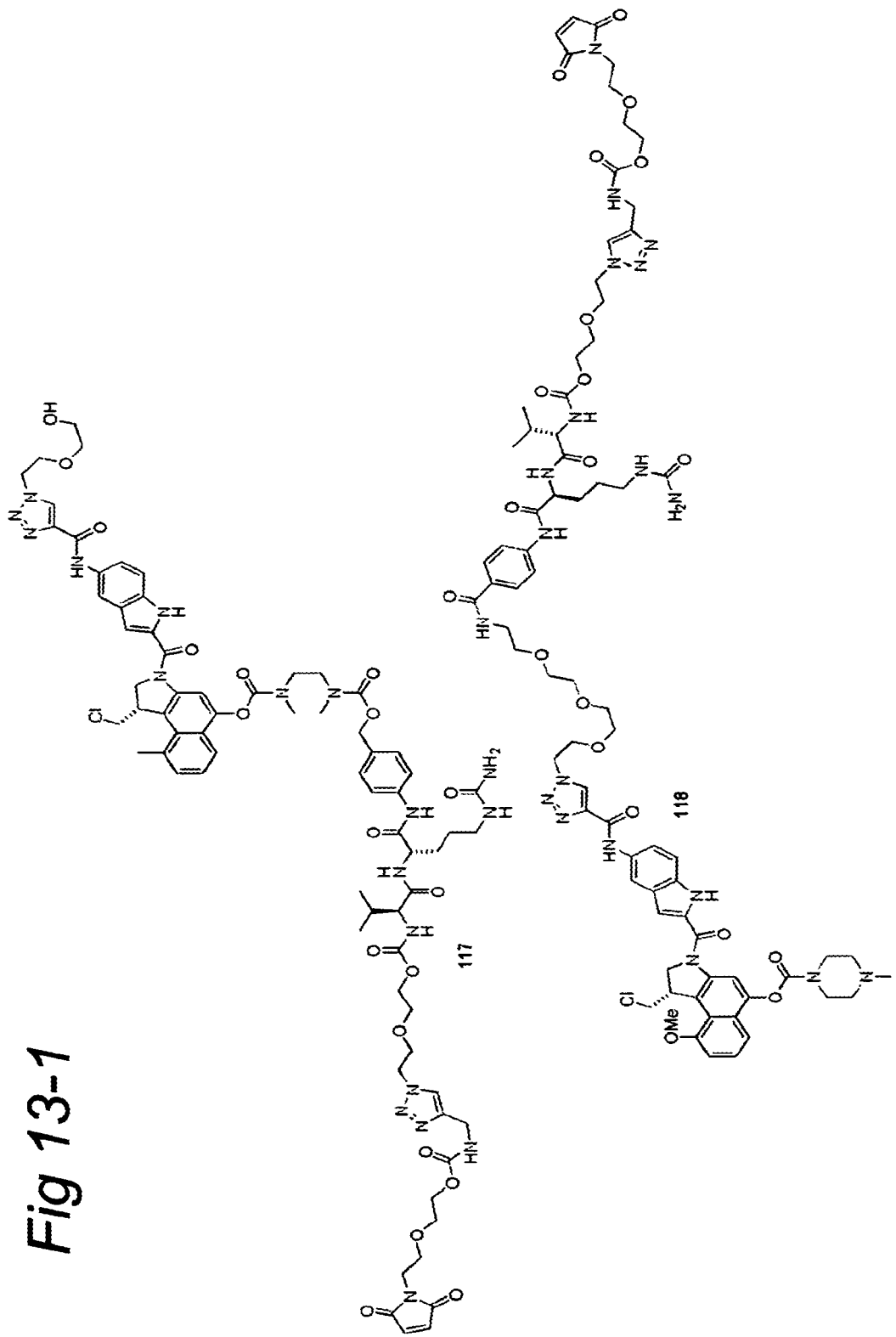
FIG. 13 depicts linker-agent conjugates 117, 118, 119, and 120.
Figures 2, 13:
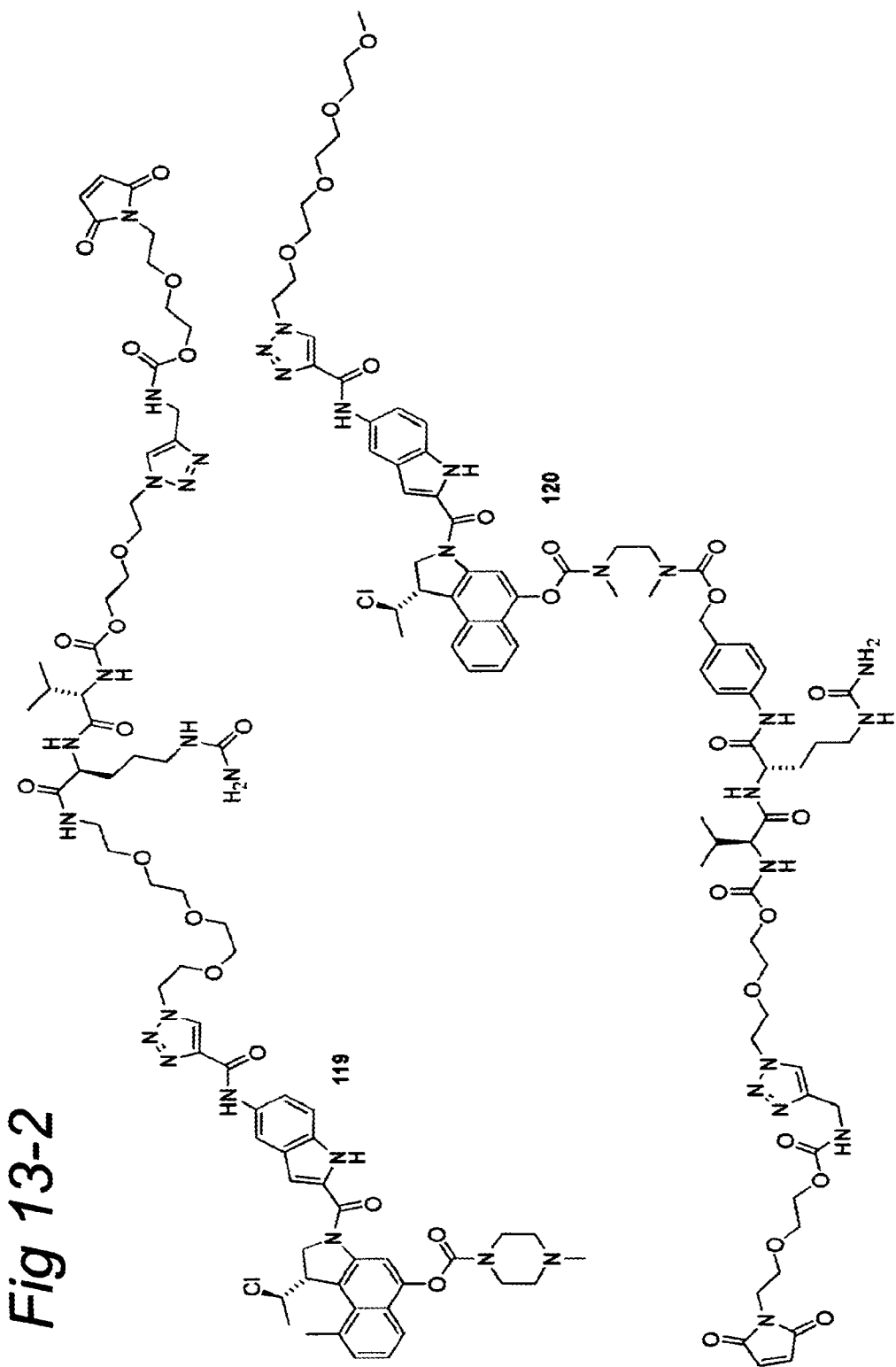

Linker-agent conjugates can be prepared by combining a DB unit, a DA unit, and one or more promoieties. The synthesis of linker-agent conjugates 114, 115, and 116 has been depicted in FIGS. 10, 11, and 12, respectively. Additional exemplary linker-agent conjugates have been depicted in FIG. 13.

In one embodiment, a compound of formula (I) or (II) is used to prepare a compound of formula (III). In another embodiment, a compound of formula (I) or (II) is used to prepare a compound of formula (IV). In another embodiment, a compound of formula (IV) is used to prepare a compound of formula (III). In another embodiment, a compound of formula (III) wherein $V^1$ is a protecting group is used to prepare another compound of formula (III) wherein $V^1$ is an in vivo cleavable/transformable moiety.

Uses, Methods, and Compositions

In one aspect, this invention relates to use of a compound of formula (I) or (II) for the preparation of a compound of formula (III).

In another aspect, this invention relates to use of a compound of formula (IV) for the preparation of a compound of formula (III).

In yet another aspect, this invention relates to use of a compound of formula (I) or (II) for the preparation of a compound of formula (IV).

In yet another aspect, this invention relates to use of a compound of formula (III) wherein $V^1$ is a protecting group for the preparation of another compound of formula (III) wherein $V^1$ is an in vivo cleavable/transformable moiety.

In yet another aspect, the invention relates to the use of any of the compounds defined hereinabove for the manufacture of a pharmaceutical composition for the treatment of a mammal being in need thereof. In one embodiment, the invention relates to the use of any of the compounds defined hereinabove for the manufacture of a pharmaceutical composition for the treatment or prevention of a tumor in a mammal.

The invention also relates to any of the compounds defined hereinabove as a medicament or an active component or active substance in a medicament.

In a further aspect, the invention relates to a process for preparing a pharmaceutical composition containing a compound as defined hereinabove, to provide a solid or a liquid formulation for administration orally, topically, or by injection. Such a method or process at least comprises the step of mixing the compound with a pharmaceutically acceptable carrier.

In one embodiment, a compound of the invention is used to treat or prevent an illness characterized by undesired proliferation. In another embodiment, a compound of the invention is used to treat or prevent an illness characterized by undesired cell proliferation. In another embodiment, a compound of the invention is used to treat or prevent a tumor. In yet another embodiment, a compound of the invention is used to treat or prevent an inflammatory disease. In yet another embodiment, a compound of the invention is used to treat or prevent an autoimmune disease. In yet another embodiment, a compound of the invention is used to treat or prevent a bacterial, viral, or microbial infection.

In a further embodiment, this invention relates to a method of treating a mammal having an illness characterized by undesired (cell) proliferation with a compound of this invention. In another embodiment, this invention relates to a method of treating a mammal carrying a tumor with a compound of this invention. In yet another embodiment, this invention relates to a method of treating a mammal having an inflammatory disease with a compound of this invention. In yet another embodiment, this invention relates to a method of treating a mammal having an autoimmune disease with a compound of this invention. In yet another embodiment, this invention relates to a method of treating a mammal having a bacterial, viral, or microbial infection with a compound of this invention.

In a further embodiment, the invention relates to a method of treating a mammal being in need thereof, whereby the method comprises the administration of a pharmaceutical composition comprising a compound of this invention to the mammal in a therapeutically effective dose.

In one embodiment, the invention relates to a method of treating or preventing a tumor in a mammal, whereby the method comprises the administration of a pharmaceutical composition comprising a compound of this invention to the mammal in a therapeutically effective dose.

In another embodiment, the invention relates to a method of treating or preventing an inflammatory disease in a mammal, whereby the method comprises the administration of a pharmaceutical composition comprising a compound of this invention to the mammal in a therapeutically effective dose.

In another embodiment, the invention relates to a method of treating or preventing an autoimmune disease in a mammal, whereby the method comprises the administration of a pharmaceutical composition comprising a compound of this invention to the mammal in a therapeutically effective dose.

In another embodiment, the invention relates to a method of treating or preventing a bacterial, viral, or microbial infection in a mammal, whereby the method comprises the administration of a pharmaceutical composition comprising a compound of this invention to the mammal in a therapeutically effective dose.

The invention also relates to pharmaceutical compositions comprising the compounds of the invention as defined hereinabove. A compound of the invention may be administered in purified form together with a pharmaceutical carrier as a pharmaceutical composition. The preferred form depends on the intended mode of administration and therapeutic application. The pharmaceutical carrier can be any compatible, non-toxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds of the invention. Such physiologically acceptable compounds include, for example, carbohydrates, such as glucose, sucrose, or dextrans, antioxidants, such as ascorbic acid or glutathione, chelating agents, low molecular weight proteins, or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion, or other known desirable features are red iron oxide, silica gel, sodium lauryl sulfate, titanium dioxide, edible white ink, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art and described in more detail in various sources, including, for example, Remington's Pharmaceutical Science[17].

A compound of the invention may also be used in combination therapy, in which a compound of this invention is used in combination with one or more other therapeutic agents. Combination of two or more therapeutics may favorably affect treatment outcome. The agents may be administered either sequentially or concomitantly. Therefore, in one embodiment this invention relates to use of a compound of this invention or a pharmaceutical composition comprising a compound of this invention in combination therapy.

The invention is further exemplified by the following examples. These examples are for illustrative purposes only and are not intended to limit the scope of the invention.

EXAMPLES

Example 1

General Procedure for the Alkylation of Compounds 2 and 6

To a suspension of NaH (2.5 equiv.) in DMF was added a solution of bromonaphthalene 2 or 6 in DMF and the resultant mixture was stirred for 1 h at room temperature. Alkene (1.6 equiv.) was added and the mixture was stirred for another 2 h at room temperature. The reaction was slowly quenched with saturated aqueous NH$_4$Cl and the resultant mixture was extracted with EtOAc. The organic layer was washed with water and brine, dried (Na$_2$SO$_4$), filtered, and concentrated. The crude product was purified using column chromatography to afford the alkylated naphthalene 3 or 7.

General Procedure for the Radical Ring Closure of Compounds 3, 7, 11, and 15

A solution of naphthalene 3, 7, 11, or 15 in toluene was brought under a nitrogen atmosphere by bubbling nitrogen through the solution for 10 minutes, AIBN (0.25 equiv.) and TTMSS (1.1 equiv.) were added, and the mixture was stirred at 80° C. for 4 h. The reaction mixture was cooled to room temperature, water was added, and the resultant mixture was extracted with EtOAc. The organic layer was dried (Na$_2$SO$_4$), filtered, and concentrated. The crude product was recrystallized from heptane and further purified by column chromatography to provide compound 4, 8, 12, or 16 as a racemic mixture. Separation of the enantiomers was carried out by chiral HPLC (Chiralpak IA, heptanes/DCM).

Compound 4a: $^1$H NMR (300 MHz, CDCl$_3$), δ (ppm): 1.61 (9 H, s, Boc), 3.11 (1 H, t, J=9.9 Hz, H-10), 3.52 (1 H, d, J=9.9 Hz, H-10), 3.98 (1 H, ddd, J=1.5 Hz, 7.3 Hz, 11.1 Hz, H-2), 4.08 (1 H, m, H-1), 4.30 (1 H, d, J=11.1 Hz, H-2), 5.28 (2 H, s, OCH$_2$Ph), 7.30-7.55 (6 H, m, OCH$_2$Ph, H-7), 7.97 (1 H, d, J=6.9 Hz, H-6), 8.06 (1 H, bs, H-4), 8.58 (1 H, d, J=8.4 Hz, H-8);

Compound 4b: $^1$H NMR (300 MHz, CDCl$_3$), δ (ppm): 1.61 (9 H, s, Boc), 3.42 (1 H, t, J=10.0 Hz, H-10), 3.91 (1 H, d, J=10.0 Hz, H-10), 4.00-4.10 (2 H, m, H-1, H-2), 4.29 (1 H, d, J=10.2 Hz, H-2), 5.26 (2 H, s, OCH$_2$Ph), 7.10-7.55 (7 H, m, OCH$_2$Ph, H-7, H-8), 7.92 (1 H, bs, H-4), 8.06 (1 H, d, J=8.1 Hz, H-6);

Compound 4c: $^1$H NMR (300 MHz, CDCl$_3$), δ (ppm): 1.61 (9 H, s, Boc), 3.50 (1 H, dd, J=9.2 Hz, 11.2 Hz, H-10), 3.97 (1 H, dd, J=2.8 Hz, 11.2 Hz, H-10), 4.08 (1 H, dd, J=8.4 Hz, 11.8 Hz, H-2), 4.34 (1 H, d, J=11.8 Hz, H-2), 4.55-4.65 (1 H, m, H-1), 5.27 (2 H, s, OCH$_2$Ph), 7.33 (1 H, dd, J=7.2 Hz, 8.4 Hz, H-7), 7.35-7.55 (5 H, m, OCH$_2$Ph), 7.91 (1 H, dd, J=1.3 Hz, 7.2 Hz, H-6), 8.00 (1 H, bs, H-4), 8.55 (1 H, dd, J=1.3 Hz, 8.4 Hz, H-6);

Compound 4d: $^1$H NMR (300 MHz, CDCl$_3$), δ (ppm): 1.29 (3 H, t, J=7.2 Hz, 9-CH$_3$), 1.61 (9 H, s, Boc), 2.96 (1 H, m, 9-CH$_2$), 3.19 (1 H, m, 9-CH$_2$), 3.23 (1 H, t, J=10.6 Hz, H-2a), 3.60 (1 H, m, H-2b), 3.99 (2 H, m, H-10), 4.30 (1 H, d, J=10.6 Hz, H-1), 5.26 (2 H, s, OCH$_2$Ph), 7.23-7.45 (7 H, m, 7-H, 8-H, OCH$_2$Ph), 7.91 (1 H, bs, H-4), 8.25 (1 H, m, H-6);

Compound 4e: $^1$H NMR (300 MHz, CDCl$_3$), δ (ppm): 1.64-1.57 (12 H, m, C(CH$_3$)$_3$, 10-CH$_3$), 3.88-4.00 (4 H, m, 9-OCH$_3$, H-2a), 4.17 (1 H, dt, J=9.3, 2.3 Hz, H-1), 4.28 (1 H, bs, J=9.6 Hz, H-2b), 4.53 (1 H, dq, J=7.1, 1.9 Hz, H-10), 5.25 (2 H, s, OCH$_2$Ph), 6.81 (1 H, d, J=7.7 Hz, H-8), 7.20 (1 H, t, J=8.1 Hz, H-7), 7.30-7.60 (5 H, m, OCH$_2$Ph), 7.91 (1 H, d, J=8.6 Hz, H-6), 7.96 (1 H, bs, H-4);

Compound 4f: $^1$H NMR (300 MHz, CDCl$_3$), δ (ppm): 1.57 (3 H, t, CH$_2$CH$_3$), 1.60 (9 H, s, (CH$_3$)$_3$), 3.30 (1 H, dd), 3.97 (2 H, m), 4.16 (2 H, dd, J=1.5 Hz, 7.2 Hz), 4.28 (2 H, q, CH$_2$CH$_3$), 5.25 (2 H, s, OCH$_2$Ph), 6.82 (1 H, d, J=7.5 Hz, H-8), 7.20 (1 H, dd, J=7.8 Hz, 8.4 Hz, H-7), 7.37-7.54 (3 & 2 H, 2×m, OCH$_2$Ph), 7.87 (1 H, d, J=8.4 Hz, H-6), 7.89 (1 H, bs, H-4); MS (ESI) m/z=468 [M+H]$^+$;

Compound 4g: $^1$H NMR (300 MHz, CDCl$_3$), δ (ppm): 1.12 (3 H, OCH$_2$CH$_3$), 1.60 (9 H, s, (CH$_3$)$_3$), 1.98 (2 H, m, OCH$_2$CH$_2$CH$_3$), 3.29 (1 H, dd), 3.97 (3 H, m), 4.06 (1 H, m), 4.29 (2 H, m), 5.24 (2 H, s, OCH$_2$Ph), 6.81 (1 H, d, J=7.8 Hz, H-8), 7.19 (1 H, J=7.8 Hz, 8.4 Hz, H-7), 7.33-7.54 (3 & 2 H, 2×m, OCH$_2$Ph), 7.87 (1 H, d, J=8.4 Hz, H-6), 7.89 (1 H, bs, H-4);

Compound 4h: $^1$H NMR (300 MHz, CDCl$_3$), δ (ppm): 1.49 (6 H, dd, J=5.7 Hz, 10.8 Hz, 2×CH$_3$), 1.60 (9 H, s, Boc), 3.29 (1 H, t, J=10.5 Hz, H-10a), 3.91-4.02 (2 H, m, H-1, H-10b), 4.22-4.36 (2 H, m, H-2a, H-2b), 4.74-4.82 (1 H, m, OCH), 5.25 (2 H, s, OCH$_2$Ph), 6.83 (1 H, d, J=7.5 Hz, H-8), 7.16-7.58 (6 H, m, H-7, OCH$_2$Ph), 7.82-7.91 (2 H, m, H-6, H-4);

Compound 4i: $^1$H NMR (300 MHz, CDCl$_3$), δ (ppm): 1.61 (9 H, s, (CH$_3$)$_3$), 3.31 (1 H, t), 3.99 (2 H, m), 4.31 (1 H, d), 4.60 (1 H, m), 5.25 (2 H, s, OCH$_2$Ph), 7.19 (1 H, dd), 7.39-7.55 (6 H, m), 7.96 (1 H, bs, H-4), 8.25 (1 H, d);

Compound 4j: $^1$H NMR (300 MHz, CDCl$_3$), δ (ppm): 1.60 (9 H, s, (CH$_3$)$_3$), 3.31 (1 H, dd, J=10.2 Hz), 3.90-4.00 (2 H, m), 3.96 (3 H, s, OCH$_3$), 4.25 (2 H, m), 5.24 (2 H, s, OCH$_2$Ph), 6.83 (1 H, d, J=7.5 Hz, H-8), 7.20 (1 H, dd, J=7.8 Hz, 8.4 Hz, H-7), 7.34-7.54 (3 & 2 H, 2×m, OCH$_2$Ph), 7.87 (1 H, d, H-6), 7.89 (1 H, bs, H-4);

Compound 4k: $^1$H NMR (400 MHz, CDCl$_3$), δ (ppm): 1.56-1.61 (12 H, m, Boc, 10-CH$_3$), 2.69 (3 H, s, 9-CH$_3$), 3.99-4.08 (2 H, m, H-2, H-10), 4.18-4.3 (2 H, m, H-2, H-1), 5.26 (2 H, bs, OCH$_2$Ph), 7.18-7.28 (2 H, m, Ar—H), 7.34-7.44 (3 H, m, Ar—H), 7.54 (2 H, d, J=6.5 Hz, Ar—H), 7.97 (1 H, bs, H-4), 8.23 (1 H, d, J=7.8 Hz, H-8); MS (ESI) m/z=396 [M+H]$^+$;

Compound 8a: $^1$H NMR (300 MHz, CDCl$_3$), δ (ppm): 1.60 (9 H, s, Boc), 3.28-3.44 (3 H, m, dihydrofuran+H-2), 3.96-4.18 (3 H, m, H-2, H-1, H-10), 4.22-4.32 (1 H, m, H-10), 4.73 (2 H, dt, J=1.8, 9.0 Hz, dihydrofuran), 5.24 (2 H, s, OCH$_2$Ph), 7.18 (1 H, d, J=8.4 Hz, H-7), 7.30-7.55 (5 H, m, OCH$_2$Ph), 7.81 (1 H, bs, H-4), 7.81 (1 H, d, J=8.4 Hz, H-6);

Compound 8b: $^1$H NMR (400 MHz, CDCl$_3$), δ (ppm): 1.55-1.66 (12 H, m, Boc+10-Me), 3.26-3.42 (2 H, m, dihydrofuran), 3.92-4.02 (2 H, m, H-2), 4.22-4.34 (1 H, m, H-1), 4.60-4.72 (3 H, m, dihydrofuran+H-10), 5.25 (2 H, s, OCH$_2$Ph), 7.17 (1 H, d, J=8.4 Hz, H-7), 7.32-7.58 (5 H, m, OCH$_2$Ph), 7.83 (1 H, bs, H-4), 7.84 (1 H, d, J=8.4 Hz, H-6);

Compound 8c: $^1$H NMR (300 MHz, CDCl$_3$), δ (ppm): 1.60 (9 H, s, Boc), 3.38-3.47 (1 H, m, H-2), 3.94-4.11 (3 H, m, H-2, H-1, H-10), 4.22-4.31 (1 H, m, H-10), 5.24 (2 H, s, OCH$_2$Ph), 6.09 (1 H, d, J=1.5 Hz, dioxymethylene), 6.15 (1 H, d, J=1.5 Hz, dioxymethylene), 7.00 (1 H, d, J=8.9 Hz, H-7), 7.32-7.56 (5 H, m, OCH$_2$Ph), 7.70 (1 H, bs, H-4), 7.87 (1 H, d, J=8.9 Hz, H-6);

Compound 8d: $^1$H NMR (400 MHz, CDCl$_3$), δ (ppm): 1.56-1.64 (12 H, m, Boc+10-Me), 3.85-3.90 (1 H, m, H-2), 3.96-4.04 (1 H, m, H-2), 4.23-4.33 (1 H, m, H-1), 4.58-4.66 (1 H, m, H-10), 5.24 (2 H, s, OCH$_2$Ph), 6.07 (1 H, d, J=1.3 Hz, dioxymethylene), 6.12 (1 H, d, J=1.3 Hz, dioxymethylene), 7.00 (1 H, d, J=8.9 Hz, H-7), 7.32-7.56 (5 H, m, OCH$_2$Ph), 7.75 (1 H, bs, H-4), 7.89 (1 H, d, J=8.9 Hz, H-6);

Compound 12: $^1$H NMR (300 MHz, CDCl$_3$), δ (ppm): 1.60 (9H, s, Boc), 3.32 (1 H, t, J=10.2 Hz, H-10), 3.86-4.01 (2 H, m, H1, H-10), 3.99 (3 H, s, OMe), 4.18-4.30 (3 H, m, H-2, H-Fmoc), 4.53 (2 H, d, J=6.8 Hz, H-Fmoc), 5.21 (2 H, s, OCH$_2$Ph), 6.82 (1 H, bs, NH), 7.28-7.55 (11 H, m, OCH$_2$Ph, H-Fmoc), 7.61 (1 H, s, H-8), 7.64 (1 H, s, H-6), 7.90 (1 H, bs, H-4);

Compound 16: $^1$H NMR (300 MHz, CDCl$_3$), δ (ppm): 1.61 (9 H, s, Boc), 3.26 (1 H, t, J=9.9 Hz, H-10a), 3.77 (3 H, s, OMe), 3.86-3.99 (2 H, m, H-10b, H-2a), 4.06-4.13 (1 H, m, H-1), 4.24-4.34 (2 H, m, H-2b, H-Fmoc), 4.60 (2 H, d, J=6.9 H, H-Fmoc), 5.25 (2 H, s, OCH$_2$Ph), 7.26-7.45 (8 H, m), 7.50-7.54 (2 H, d), 7.64 (2 H, d), 7.78 (2 H, d), 8.04-8.10 (2 H, m).

Example 2
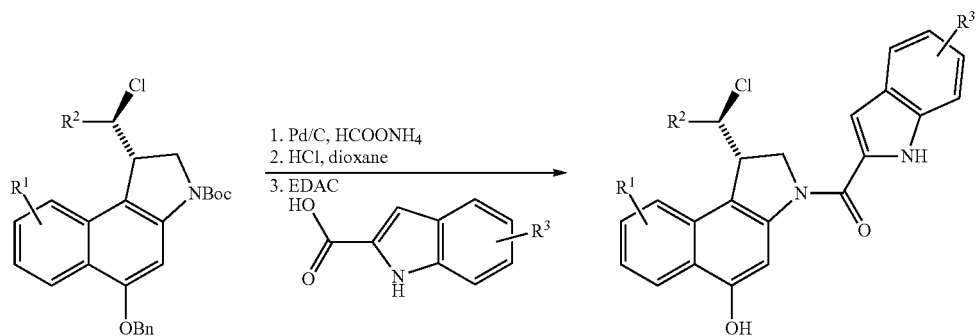
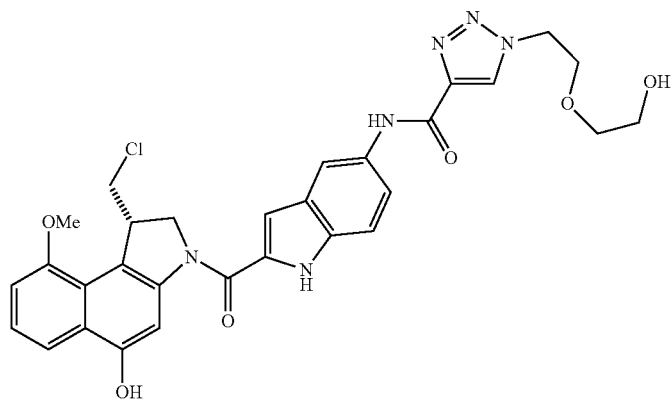
17
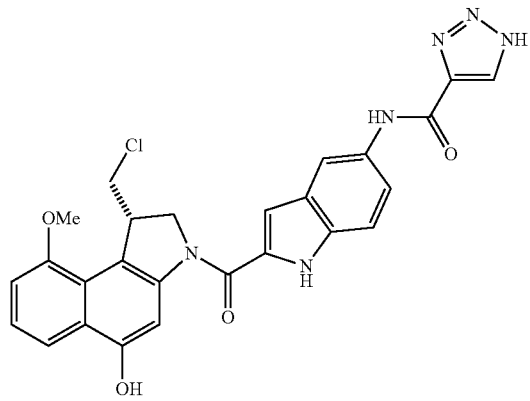
18
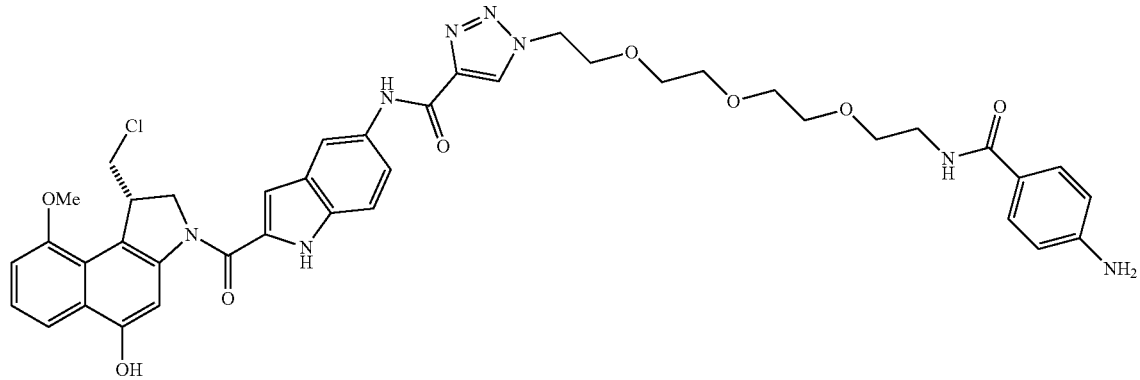
19

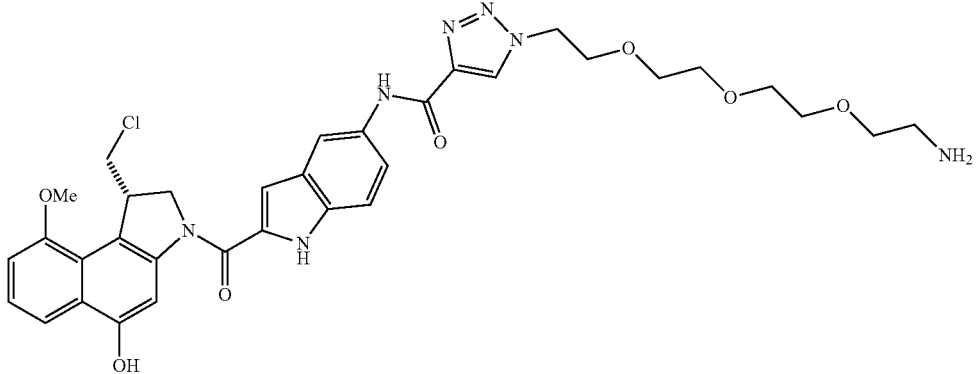

20

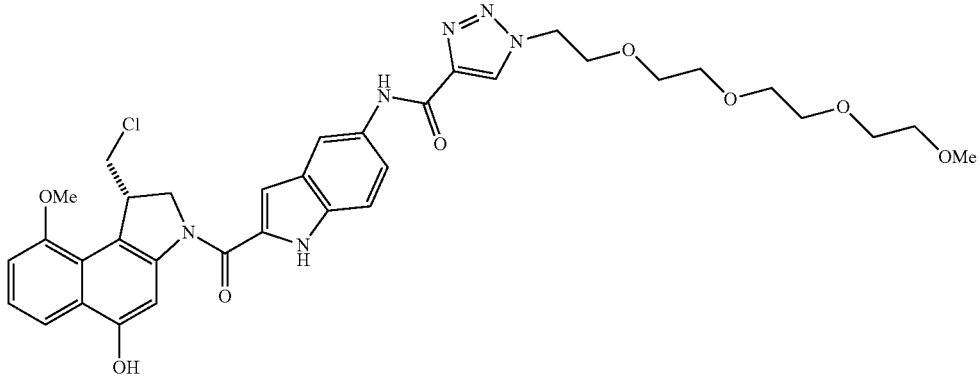

21

General Procedure for Amine Deprotection, Coupling, and Debenzylation

The N-Boc-O-Bn-protected seco CBI derivative was dissolved in 4 M HCl/dioxane and stirred at ambient temperature until TLC indicated completion of the reaction. The reaction mixture was concentrated in vacuo and further dried under high vacuum. The residue was dissolved in dry DMF, the solution was cooled to 0° C., and EDC (2.0 equiv.) and functionalized, optionally Boc-protected indole-2-carboxylate (1.5 equiv) were added. The reaction mixture was allowed to warm to ambient temperature overnight, after which it was concentrated in vacuo. The residue was taken up in water/EtOAc, saturated aqueous $NaHCO_3$ was added, and the mixture was extracted with EtOAc. The combined organic layers were washed with brine, dried ($Na_2SO_4$), filtered, and concentrated in vacuo. Flash chromatography afforded the benzyl-protected agent. This compound was dissolved in methanol, and Pd/C (10% Pd, 0.2 equiv.) and $HCOONH_4$ (10 equiv.) were added. The reaction mixture was stirred at 40° C. until TLC indicated completion of the reaction. The reaction mixture was cooled to room temperature and filtered over a bed of Celite. The Celite was thoroughly rinsed with MeOH and the combined filtrate was concentrated in vacuo. Flash chromatography afforded the pure agent, optionally still protected with a Boc group. Removal of this Boc group was carried out by dissolving the compound in 4 M HCl in dioxane. The mixture was stirred until TLC indicated completion of the reaction. The reaction mixture was concentrated to afford the pure compound.

Compound 17: $^1$H NMR ($CD_3OD$, 400 MHz), δ (ppm): 3.46 (1 H, m), 3.94-3.99 (4 H, m), 4.38 (1 H, m), 4.57 (1 H, m), 4.69 (1 H, m), 6.95 (1 H, d, J=8 Hz), 7.14 (1 H, s), 7.26 (1 H, t, J=8 Hz), 7.52 (2 H, m), 7.79 (1 H, d, J=8 Hz), 7.85 (1 H, bs), 8.11 (1 H, s), 8.37 (1 H, s); MS (ESI) m/z=517 [M+H]$^+$;

Compound 18: $^1$H NMR (300 MHz, DMSO-$d_6$), δ (ppm): 3.44-3.50 (4 H, m, H-2", H-3"), 3.62 (1 H, dd, J=8.1 Hz, 10.4 Hz, H-10), 3.88 (2 H, t, J=5.0 Hz, H-4"), 3.88-3.98 (4 H, m, H-10, OMe), 3.93-4.00 (4 H, m, H-10, OMe), 4.27-4.37 (1 H, m, H-1), 4.54 (d, J=10.4 Hz, H-2), 4.60-4.75 (3 H, m, H-1", H-2), 7.00 (1 H, d, J=7.8 Hz, H-8), 7.17 (1 H, d, J=1.3 Hz, H-3'), 7.28 (1 H, dd, J=7.8 Hz, 8.2 Hz, H-7), 7.45 (1 H, d, J=8.9 Hz, H-7'), 7.64 (1 H, dd, J=1.9 Hz, 8.9 Hz, H-6'), 7.71 (1 H, d, J=8.2 Hz, H-6), 8.00 (1 H, s, H-4), 8.21 (1 H, d, J=1.5 Hz, H-4'), 8.69 (1 H, s, triazolyl-H), 10.32 (1 H, s, NH), 10.40 (1 H, s, OH), 11.70 (1 H, s, NH), MS (ESI) m/z=605 [M+H]$^+$;

Compound 19: $^1$H NMR (300 MHz, $CDCl_3$), δ (ppm): 3.5 (12 H, m), 3.9 (3 H, t, J=4.2 Hz), 4.0 (3 H, s, 9-$OCH_3$), 4.3 (1 H, t, J=7.6 Hz, H-2a) 4.5 (1 H, d, J=11.0 Hz, H-2b) 4.6 (4 H, t, J=4.8 Hz), 6.6 (2 H, d, J=8.2 Hz), 7.0 (1 H, d, J=8.2 Hz, H-8), 7.2 (1 H, s, H-3'), 7.3 (1 H, t, J=7.6 Hz, H-7), 7.5 (1 H, d, J=9.0 Hz, H-6'), 7.6 (2 H, d, J=8.5 Hz), 7.6 (1 H, d, J=9.0 Hz), 7.7 (1 H, d, J=8.2 Hz, H-6), 8.0 (2 H, s, CH), 8.2 (1 H, s, H-4), 8.7 (1 H, s, H-4'), 10.3 (1 H, s, NH), 10.4 (1 H, s, NH), 11.7 (1 H, s, NH); MS (ESI) m/z=811.3 [M+H]$^+$;

Compound 20: $^1$H NMR (300 MHz, DMSO-$d_6$), δ (ppm): 2.94 (2 H, sextet, $CH_2NH_3$), 3.48-3.66 (15 H, m, $CH_2$), 3.89 (2 H, t, $CH_2$), 3.92-4.03 (4 H, m), 4.33 (1 H, t, J=7.5 Hz), 4.53 (1 H, d, J=11 Hz), 4.65 (2 H, t, J=4.6 Hz), 4.72 (1 H, d, J=15 Hz), 7.0 (1 H, d, J=7.5 Hz), 7.18 (1 H, s), 7.28 (1 H, t, J=8.1 Hz), 7.46 (1 H, d, J=8 Hz), 7.64 (1 H, d, J=9.9 Hz), 7.71 (1 H, d, J=9.3 Hz), 7.93 (3 H, s), 8.00 (1 H, s), 8.2 (1 H, s), 8.7 (1 H, s), 10.3 (1 H, s), 10.4 (1 H, s), 11.7 (1 H, s);

Compound 21: $^1$H NMR (300 MHz, $CD_3OD$), δ (ppm): 3.48-3.64 (13 H, m), 3.95 (2 H, m, (C=O)—$CH_2$), 4.00 (4 H, m, $OCH_3$, H-10), 4.40 (1 H, m, H-1), 4.68 (5 H, m, H-2+ (C=O)$CH_2CH_2$), 6.97 (1 H, d, J=7.3 Hz), 7.17 (1 H, s), 7.28 (1 H, t, J=7.9 Hz), 7.53 (2 H, m), 7.80 (1 H, d, J=8.2 Hz), 7.84 (1 H, m), 8.13 (1 H, s), 8.55 (1 H, s); MS (ESI) m/z=707.3 [M+H]$^+$, 729.3 [M+Na]$^+$.

Example 3
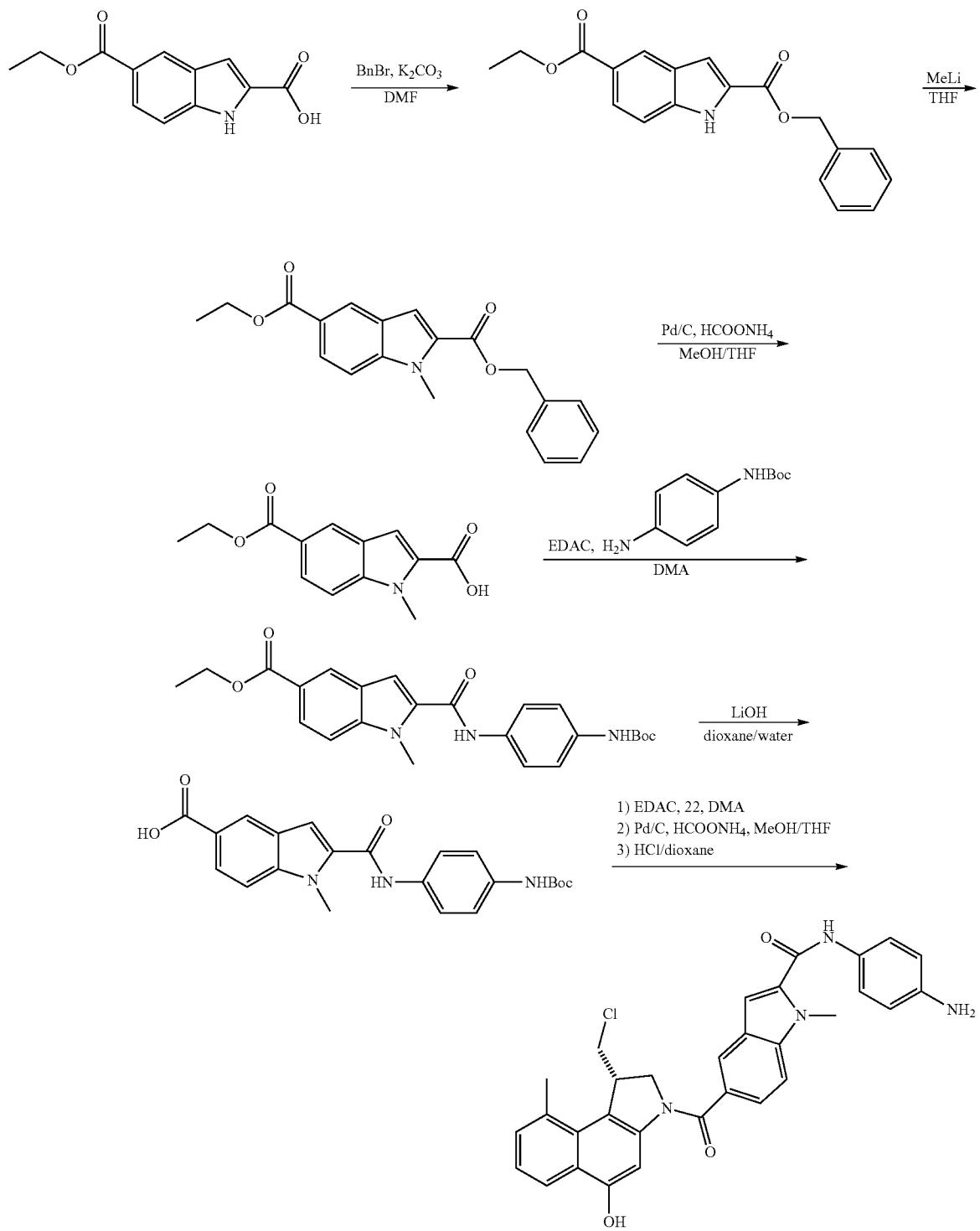
Compound 30: ¹H NMR (400 MHz, DMSO-d₆), δ (ppm): 2.76 (3 H, s, 9-Me), 3.50 (1 H, m, H-10), 3.78 (1 H, d, J=10.8 Hz, H-10), 4.00-4.10 (4 H, m, H-1, NCH), 4.13-4.20 (1 H, m, H-2), 4.33-4.39 (1 H, m, H-2), 7.19-7.28 (3 H, m, H7, Ph-H), 7.33 (1 H, d, J=7.0 Hz, H-8), 7.45 (1 H, s, H-3'), 7.58-7.75 (3 H, m, H-4, H6', H7'), 7.85 (2 H, d, J=8.6 Hz, Ph-H), 8.02 (1 H, d, J=8.0 Hz, H-6), 8.06 (1 H, s, H-4'), 9.45 (2 H, bs, NH₂), 10.38 (1 H, s, OH), 10.52 (1 H, s, NH); MS (ESI) m/z=539 [M+H]⁺.

319
Example 4
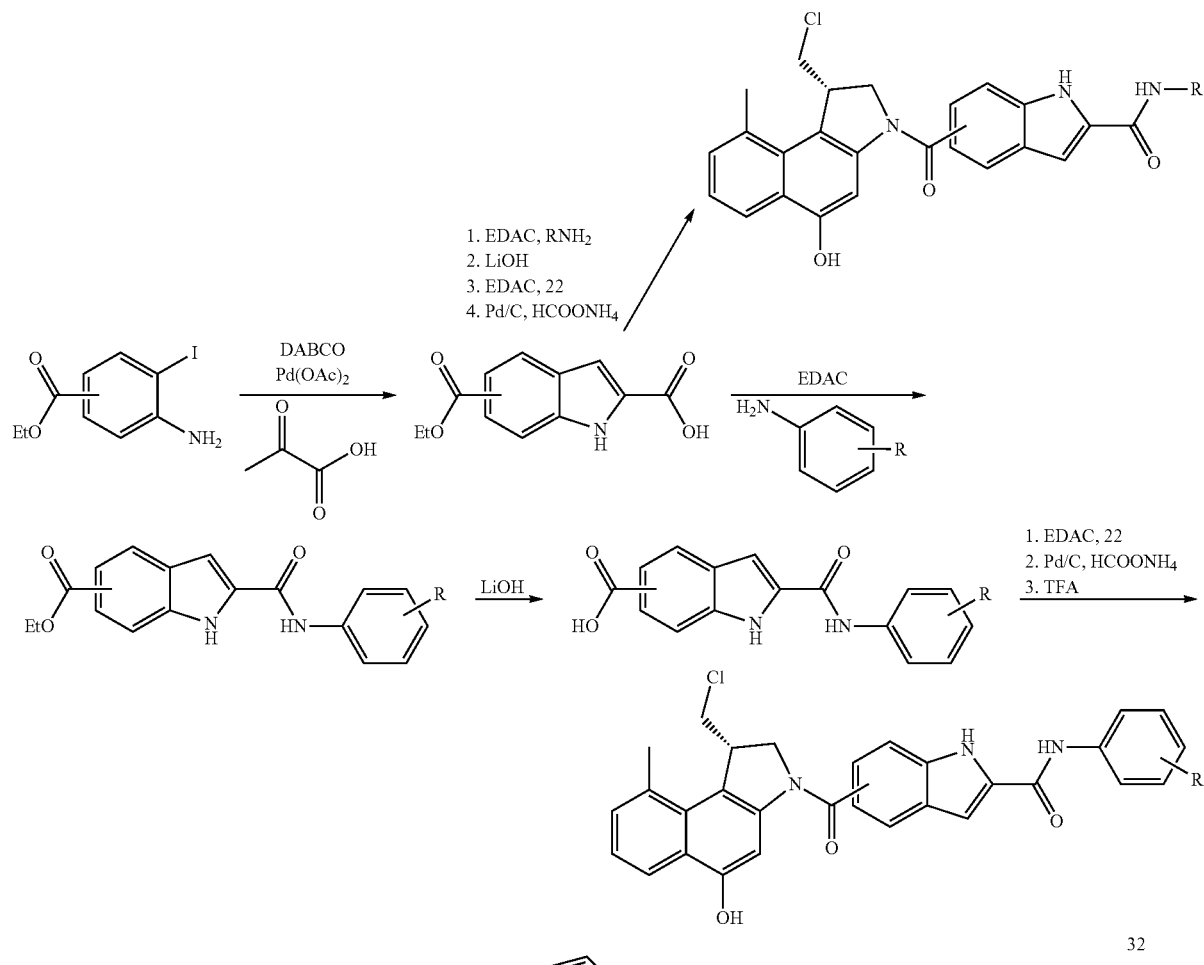
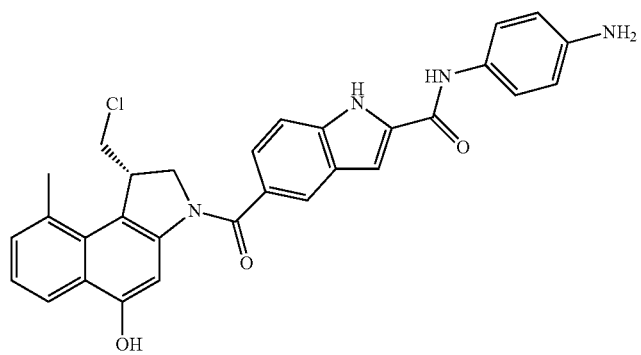
32
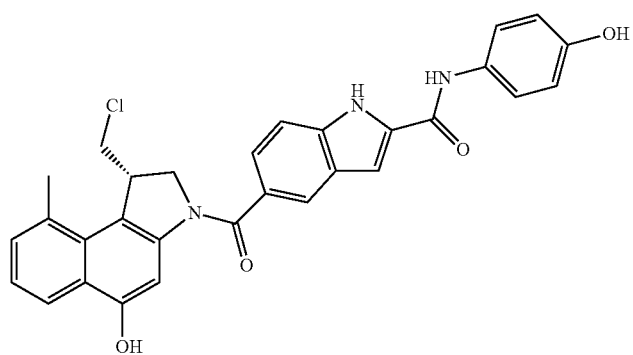
37

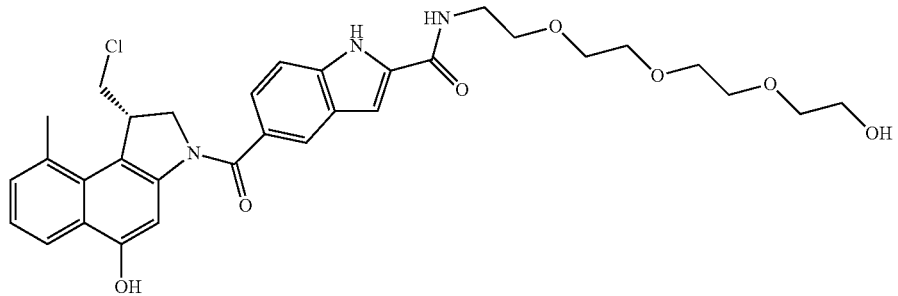
46
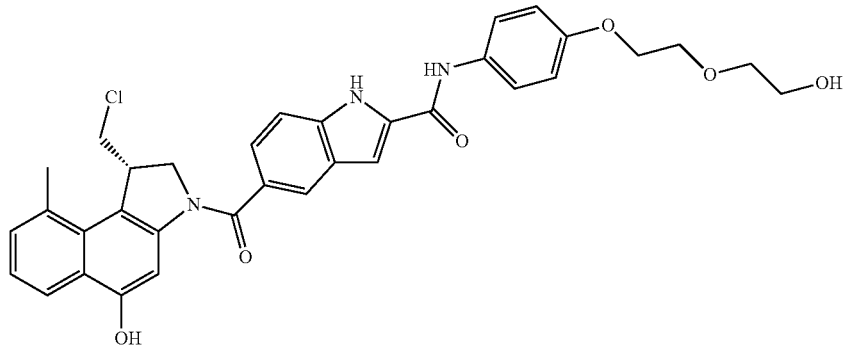
38
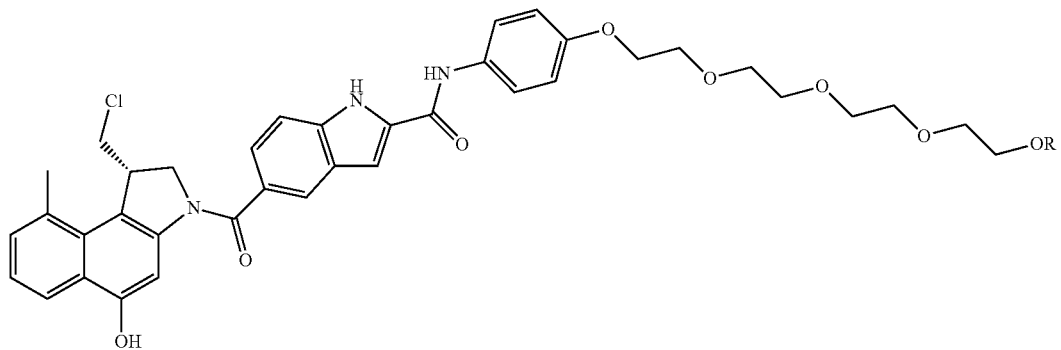
39 R = H
42 R = Me
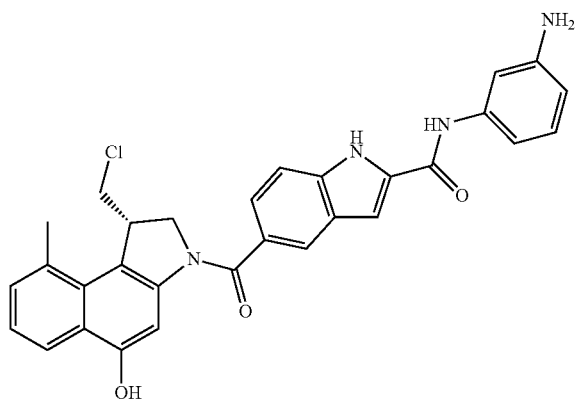
43

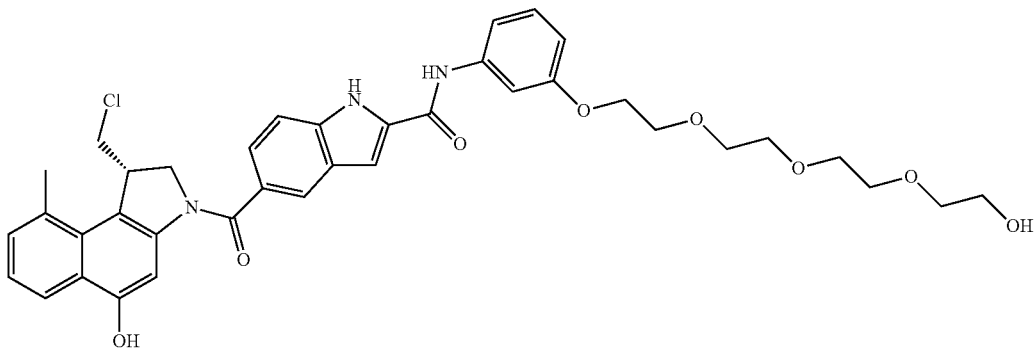

44

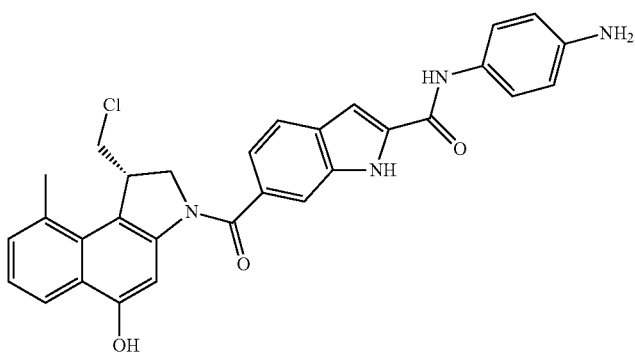

45

Compound 32: ¹H NMR (300 MHz, DMSO), δ (ppm): 2.75 (3 H, s, 9-Me), 3.51 (1 H, t, J=9.0 Hz, H-10), 3.77 (1 H, d, J=11.7 Hz, H-10), 4.06 (1 H, m, H-2), 4.17 (1 H, t, J=9.9 Hz, H-2), 4.34-4.39 (1 H, m, H-1), 7.10 (2 H, d, J=8.7 Hz, H-2"), 7.21 (1 H, t, J=6.9 Hz, H-7), 7.32 (1 H, d, J=6.9 Hz, H-8), 7.49-7.61 (4 H, m, H-4, H-3', H-6', H-7'), 7.75 (2 H, d, J=8.7 Hz, H-1"), 8.02 (1 H, d, J=7.8 Hz, H-6), 8.06 (1 -H, s, H-4'), 10.31 (1 H, s, NH), 10.37 (1 H, s, OH), 12.03 (1 H, s, NH); MS (ESI) m/z=525.2 [M+H]⁺;

Compound 37: ¹H NMR (300 MHz, DMSO), δ (ppm): 2.75 (3 H, s, 9-Me), 3.51 (1 H, t, J=10.5 Hz, H-10), 3.77 (1 H, d, J=10.8 Hz, H-10), 4.06 (1 H, d, J=9.9 Hz, H-2), 4.16 (1 H, t, J=10.5 Hz, H-2), 4.33-4.39 (1 H, m, H-1), 6.77 (1 H, d, J=9.0 Hz, H-2"), 7.21 (1 H, t, J=7.2 Hz, H-7), 7.32 (1 H, d, J=6.6 Hz, H-8), 7.44-7.61 (6 H, m, H-4, H-3', H-6', H-7', H-1"), 8.00-8.04 (2 H, m, H-6, H-4'), 9.27 (1 H, s, OH), 10.11 (1 H, s, NH), 10.36 (1 H, s, OH), 11.99 (1 H, s, NH); MS (ESI) m/z=526.3 [M+H]⁺;

Compound 38: ¹H NMR (300 MHz, DMSO), δ (ppm): 2.76 (3 H, s, 9-Me), 3.47-3.56 (5 H, m, H-10), 3.73-3.79 (3 H, m, H-10), 4.03-4.10 (3 H, m, H-2), 4.16 (1 H, t, J=7.8 Hz, H-2), 4.33-4.39 (1 H, m, H-1), 4.62 (1 H, m, OH), 6.97 (2 H, d, J=9.0 Hz, H-2"), 7.23 (1 H, t, J=7.8 Hz, H-7), 7.32 (1 H, d, J=6.9 Hz, H-8), 7.49-7.58 (4 H, m, H-4, H-3', H-6', H-7'), 7.72 (2 H, d, J=9.0 Hz, H-1"), 8.00-8.05 (2 H, m, H-6, H-4'), 10.23 (1 H, s, NH), 10.36 (1 H, s, OH), 12.04 (1 H, s, NH); MS (ESI) m/z=614.5 [M+H]⁺;

Compound 39: ¹H NMR (300 MHz, DMSO), δ (ppm): 2.76 (3 H, s, 9-Me), 3.39-3.58 (13 H, m, H-10), 3.73-3.79 (3 H, m, H-10), 4.04-4.10 (3 H, m, H-2), 4.16 (1 H, t, J=9.0 Hz, H-2), 4.33-4.39 (1 H, m, H-1), 4.57 (1 H, t, J=5.4 Hz, OH), 6.98 (2 H, d, J=9.0 Hz, H-2"), 7.22 (1 H, t, J=7.2 Hz, H-7), 7.31 (1 H, d, J=6.9 Hz, H-8), 7.48-7.58 (4 H, m, H-4, H-3', H-6', H-7'), 7.71 (2 H, d, J=9.0 Hz, H-1"), 8.00-8.05 (2 H, m, H-6, H-4'), 10.22 (1 H, s, NH), 10.36 (1 H, s, OH), 12.03 (1 H, s, NH); MS (ESI) m/z=724.5 [M+H]⁺;

Compound 42: ¹H NMR (300 MHz, DMSO), δ (ppm): 2.76 (3 H, s, 9-Me), 3.24 (3 H, s, OMe), 3.40-3.61 (13 H, m, H-10), 3.73-3.80 (3 H, m, H-10), 4.04-4.10 (3 H, m, H-2), 4.17 (1 H, t, J=7.8 Hz, H-2), 4.34-4.40 (1 H, m, H-1), 6.97 (2 H, d, J=9.0 Hz, H-2"), 7.21 (1 H, t, J=6.6 Hz, H-7), 7.32 (1 H, d, J=6.6 Hz, H-8), 7.49-7.58 (4 H, m, H-4, H-3', H-6', H-7'), 7.71 (2 H, d, J=9.0 Hz, H-1"), 8.00-8.05 (2 H, m, H-6, H-4'), 10.21 (1 H, s, NH), 10.37 (1 H, s, OH), 12.02 (1 H, s, NH); MS (ESI) m/z=738.5 [M+H]⁺;

Compound 43: ¹H NMR (300 MHz, DMSO), δ (ppm): 2.76 (3 H, s, 9-Me), 3.51 (1 H, m, H-10), 3.78 (1 H, m, H-10), 4.6 (1 H, d, J=10.5 Hz, H-2), 4.17 (1 H, t, J=8.1 Hz, H-2), 4.34-4.37 (1 H, m, H-1), 6.72 (1 H, m, H-4"), 7.12-7.79 (9 H, m, H-7, H-8, H-4, H-3', H-6', H-7', H-2", H-3", H-6"), 8.00-8.05 (2 H, m, H-6 , H-4'), 10.39 (2 H, s, NH, OH), 12.12 (1 H, s, NH); MS (ESI) m/z=525.6 [M+H]⁺;

Compound 44: ¹H NMR (300 MHz, DMSO), δ (ppm): 2.76 (3 H, s, 9-Me), 3.39-3.62 (13 H, m, H-10), 3.75-3.79 (3 H, m, H-10), 4.04-4.21 (4 H, m, H-2, H-2), 4.33-4.37 (1 H, m, H-1), 4.55 (1 H, bs, OH), 6.72 (1 H, m, H-4"), 7.20-7.33 (3 H, m, H-7, H-8, H-3"), 7.41 (1 H, d, J=8.1 Hz, H-2"), 7.50-7.59 (5 H, m, H-4, H-3', H-6', H-7', H-6"), 8.00-8.06 (2 H, m, H-6, H-4'), 10.26 (1 H, s, NH), 10.37 (1 H, s, OH), 12.05 (1 H, s, NH); MS (ESI) m/z=702.7 [M+H]⁺;

Compound 45: ¹H NMR (300 MHz, DMSO), δ (ppm): 2.75 (3 H, s, 9-Me), 3.51 (1 H, t, J=10.2 Hz, H-10), 3.77 (1 H, d, J=10.2 Hz, H-10), 4.04 (1 H, m, H-2), 4.18 (1 H, m, H-2), 4.34-4.39 (1 H, m, H-1), 7.04 (2 H, m, NH₂), 7.17-7.24 (3 H, m, H-7, H-2"), 7.30-7.35 (3 H, m, H-8, H-4', H-5'), 7.51-7.54 (3 H, m, H-3', H-1"), 7.30-7.80 (2 H, m, 4-H, H-7'), 8.01 (1 H, d, J=8.4 Hz, H-6), 10.41 (2 H, m, OH, NH), 12.14 (1 H, s, NH); MS (ESI) m/z=525.3 [M+H]⁺;

Compound 46: ¹H NMR (300 MHz, DMSO), δ (ppm): 2.75 (3 H, s, 9-Me), 3.37-3.59 (17 H, m, H-10), 3.73 (1 H, d, J=10.2 Hz, H-10), 4.04 (1 H, d, J=11.1 Hz, H-2), 4.16 (1 H, t, J=7.8 Hz, H-2), 4.32-4.38 (1 H, m, H-1), 4.56 (1 H, t, J=5.4 Hz, OH), 7.19-7.26 (2 H, m, H-7, H-3'), 7.31 (1 H, d, J=7.2 Hz, H-8), 7.46-7.54 (3 H, m, H-4, H-6', H-7'), 7.98-8.03 (2 H, m, H-6, H-4'), 8.64 (1 H, t, J=5.7 Hz, NH), 10.35 (1 H, s, OH), 11.88 (1 H, s, NH); MS (ESI) m/z=610.5 [M+H]$^+$.
Example 5
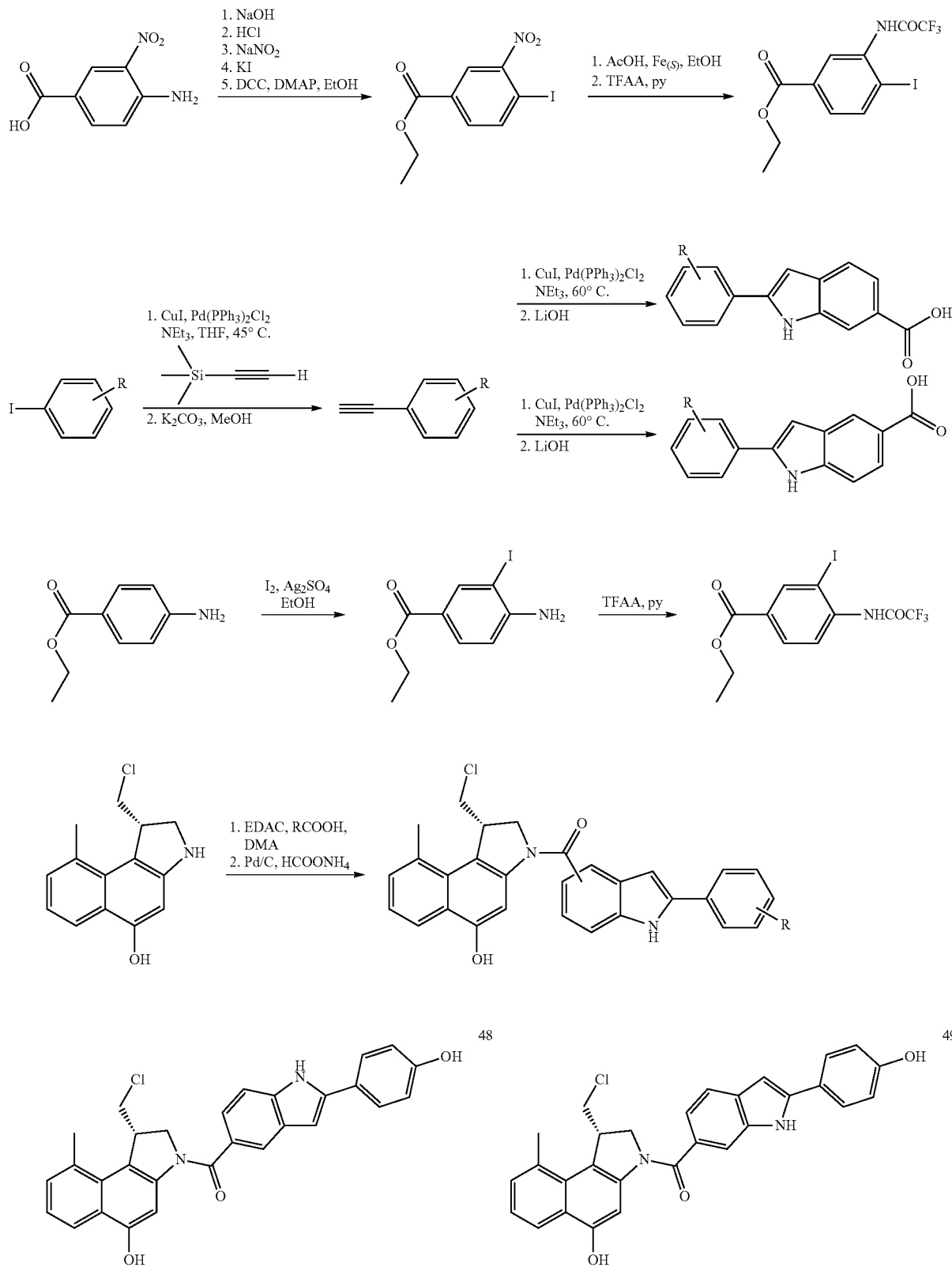

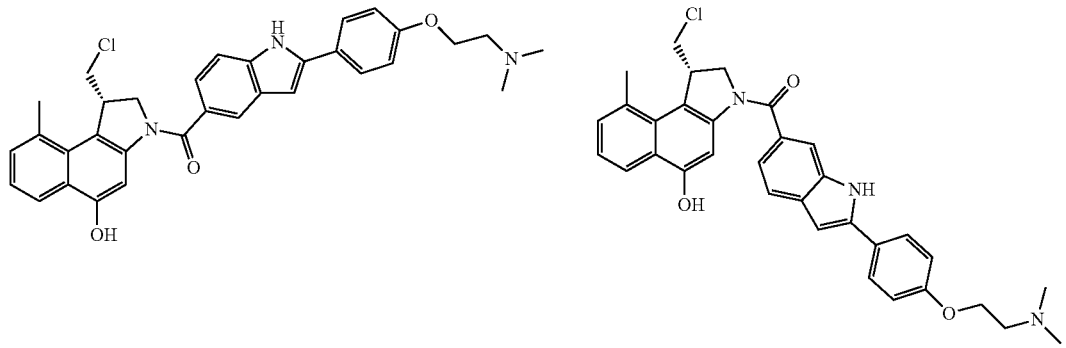
50
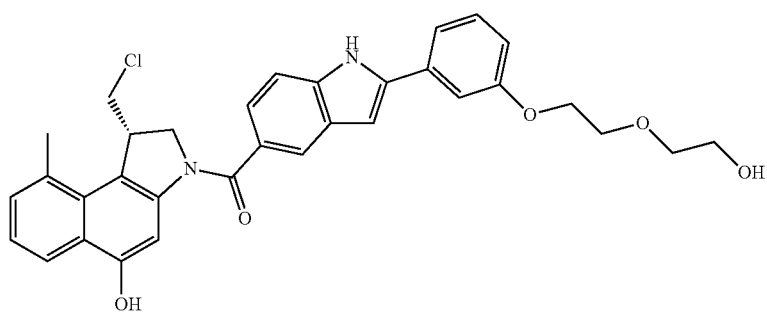
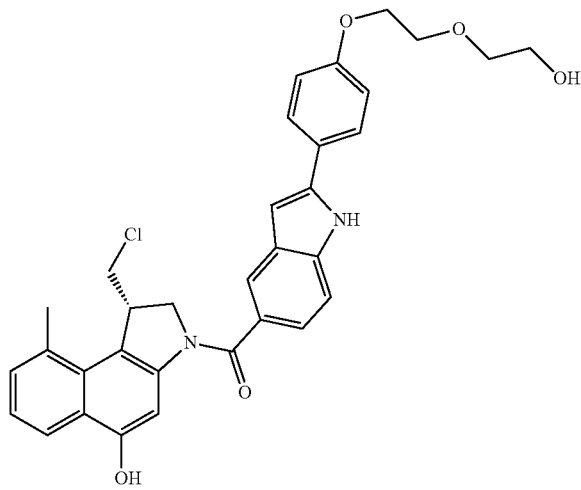
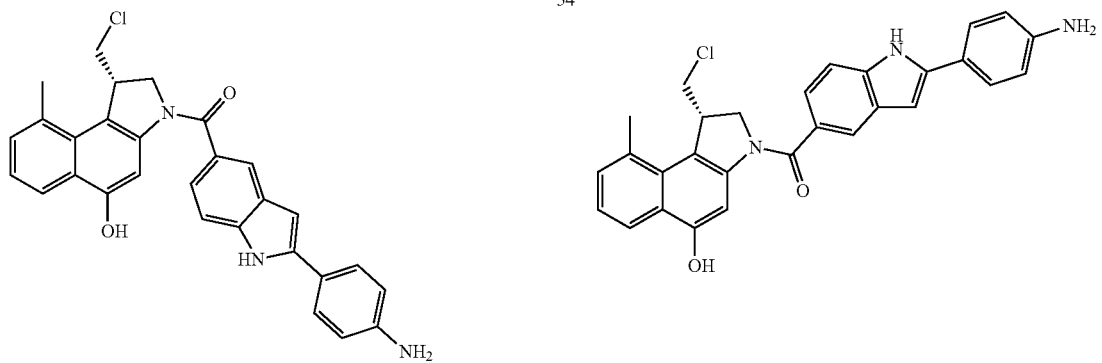

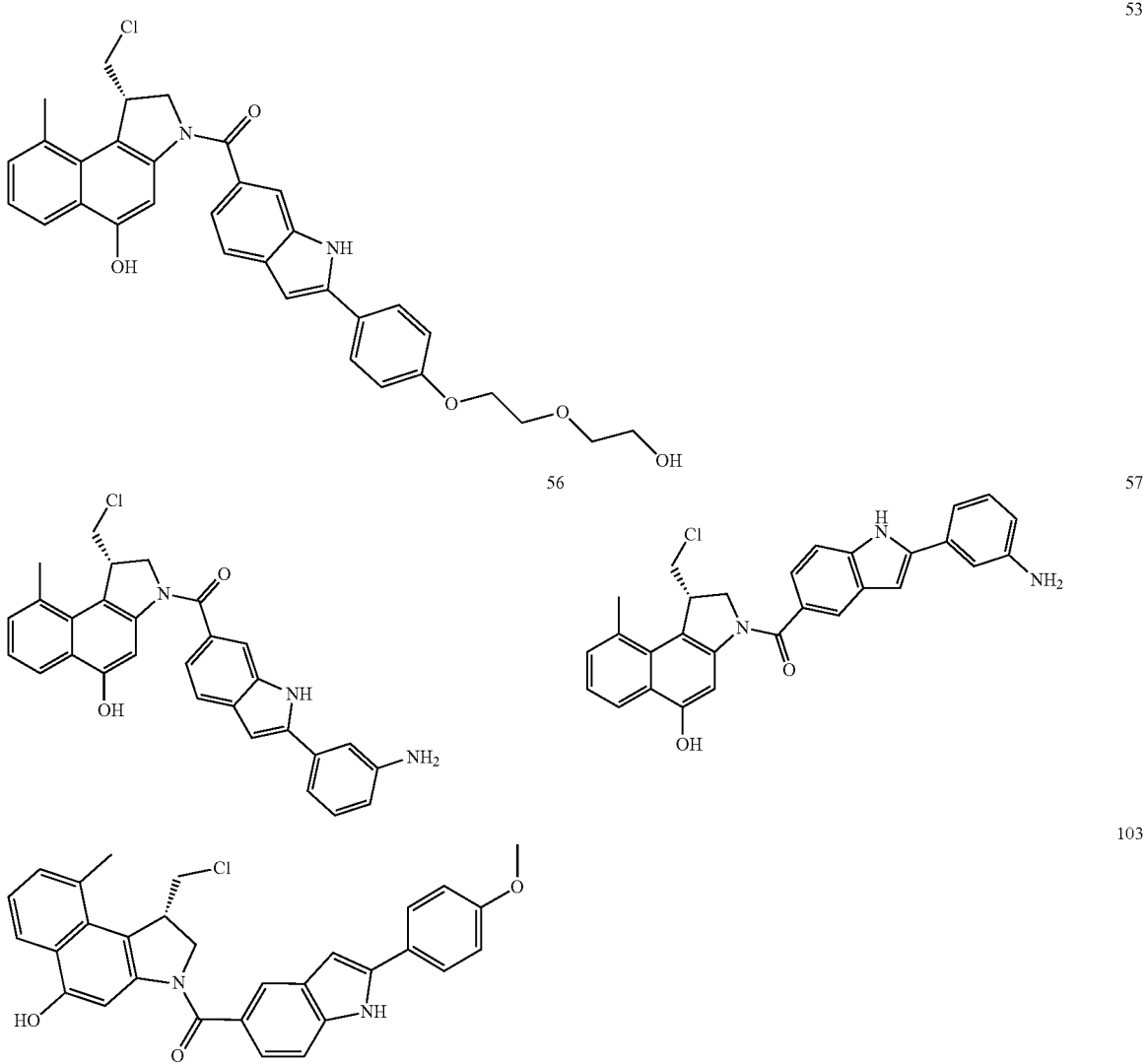

Compound 31: ¹H NMR (400 MHz, DMSO-d₆), δ (ppm): 2.79 (3 H, s, 9-Me), 3.45-3.55 (5 H, m, H-10, 2×OCH₂), 3.75-3.80 (3 H, m, H-10, OCH₂), 4.08 (1 H, d, J=11.0 Hz, H-2), 4.13-4.19 (3 H, m, H-1, OCH₂), 4.36 (1 H, dd, J=7.3 Hz, J=10.8 Hz, H-2), 4.63 (1 H, s, OH), 6.90 (1 H, d, J=2.0 Hz, H-3') 7.07 (2 H, d, J=8.9 Hz, Ph-H), 7.21 (1 H, dd, J=7.0 Hz, J=8.3 Hz, H-7), 7.32 (1 H, d, J=7.0 Hz, H-8), 7.37 (1 H, dd, J=1.5 Hz, J=8.4 Hz, H-7'), 7.47 (1 H, d, J=8.5 Hz, H-6'), 7.56 (1 H, s, H-4), 7.80-7.85 (3 H, m, Ph-H, H-4'), 8.01 (1 H, d, J=8.4 Hz, H-6), 10.34 (1 H, s, OH), 11.74 (1 H, s, NH); MS (ESI) m/z=571 [M+H]⁺;

Compound 48: ¹H NMR (300 MHz, DMSO), δ (ppm): 2.75 (3 H, s, 9-Me), 3.48 (1 H, t, J=10.2 Hz, H-10), 3.77 (1 H, d, J=10.2 Hz, H-10), 4.08 (1 H, d, J=10.5 Hz, H-2), 4.17 (1 H, t, J=8.1 Hz, H-2), 4.34-4.39 (1 H, m, H-1), 6.81 (1 H, s, H-3'), 6.87 (2 H, d, J=8.7 Hz, H-2''), 7.20 (1 H, t, J=6.9 Hz, H-7), 7.30-7.37 (2 H, m, H-8, H-7'), 7.45 (1 H, d, J=8.4 Hz, H-6'), 7.55 (1 H, bs, H-4), 7.71 (2 H, d, J=8.7 Hz, H-1''), 7.82 (1 H, s, H-4'), 8.01 (1 H, d, J=8.4 Hz, H-6), 9.69 (1 H, s, OH), 10.35 (1 H, s, OH), 11.66 (1 H, s, NH); MS (ESI) m/z=483.4 [M+H]⁺;

Compound 49: ¹H NMR (300 MHz, DMSO), δ (ppm): 2.76 (3 H, s, 9-Me), 3.50 (1 H, t, J=9.6 Hz, H-10), 3.77 (1 H, d, J=11.1 Hz, H-10), 4.08 (1 H, d, J=11.1 Hz, H-2), 4.17 (1 H, t, J=7.8 Hz, H-2), 4.31-4.37 (1 H, m, H-1), 6.81 (1 H, s, H-3'), 6.88 (2 H, d, J=8.7 Hz, H-2''), 7.20 (1 H, t, J=7.2 Hz, H-7), 7.21-7.32 (2 H, m, H-8, H-4'), 7.51-7.59 (2 H, m, H-4, H-5'), 7.65 (1 H, s, H-7'), 7.72 (2 H, d, J=8.7 Hz, H-1''), 8.01 (1 H, d, J=8.4 Hz, H-6), 9.71 (1 H, s, OH), 10.35 (1 H, s, OH), 11.65 (1 H, s, NH); MS (ESI) m/z=483.4 [M+H]⁺;

Compound 50: ¹H NMR (300 MHz, DMSO), δ (ppm): 2.76 (3 H, s, 9-Me), 2.86 (6 H, s, N—(CH₃)₂), 3.51 (1 H, m, H-10, NCH₂), 3.77 (1 H, m, H-10), 4.07 (1 H, m, H-2), 4.16 (1 H, m, H-2), 4.34-4.42 (3 H, m, H-1, OCH₂), 6.81 (1 H, m, H-3'), 6.87 (2 H, m, H-2''), 7.20 (1 H, m, H-7), 7.30-7.37 (2 H, m, H-8, H-7'), 7.45 (1 H, m, H-6'), 7.55 (1 H, bs, H-4), 7.86 (3 H, m, H-4', H-1''), 8.01 (1 H, m, H-6), 10.35 (1 H, s, OH), 11.80 (1 H, s, NH); MS (ESI) m/z=554.5 [M+H]⁺;

Compound 51: ¹H NMR (300 MHz, DMSO-D₆), δ (ppm): 2.72 (3 H, s, 9-Me), 2.81 (6 H, s, N(CH₃)₂), 3.17 (2 H, m, NCH₂), 3.78 (1 H, d, H-10), 4.05 (1 H, d, H-2), 4.16 (1 H, t, H-2), 4.32 (1 H, t, H-1), 4.39 (2 H, t, OCH₂), 6.89 (1 H, s), 7.12 (2 H, d), 7.20 (1 H, t), 7.28 (2 H, t), 7.58 (2 H, d), 7.67 (1 H, s), 7.88 (2 H, d), 8.00 (1 H, d, J=8.2 Hz, H-6), 10.36 (1 H, s, OH), 11.88 (1 H, s, NH); MS (ESI) m/z=554.7 [M+H]⁺;

Compound 52: ¹H NMR (300 MHz, DMSO), δ (ppm): 2.76 (3 H, s, 9-Me), 3.47-3.56 (4 H, m, H-10), 3.76-3.81 (3 H, m, H-10), 4.07 (1 H, d, J=10.8 Hz, H-2), 4.14-4.20 (3 H, m, H-2), 4.34-4.36 (1 H, m, H-1), 4.62-4.66 (1 H, m, OH), 6.91-6.95 (1 H, m, H-4″), 7.06 (1 H, s, H-3′), 7.21 (1 H, t, J=6.9 Hz, H-7), 7.31 (1 H, d, J=6.6 Hz, H-8), 7.36-7.42 (2 H, m, H-6′, H-6″), 7.47-7.58 (4 H, m, H-4, H-7′, H-2″, H-3″), 7.88 (1 H, s, H-4′), 8.02 (1 H, d, J=8.1 Hz, H-6), 10.35 (1 H, s, OH), 11.83 (1 H, s, NH); MS (ESI) m/z=571.5 [M+H]⁺;

Compound 53: ¹H NMR (300 MHz, DMSO-D₆), δ (ppm): 2.73 (3 H, s, 9-Me), 3.49 (4 H, m, 2 CH₂), 3.78 (3 H, CH₂), 4.11 (4 H, m, CH₂), 4.31 (1 H, dd), 4.59 (1 H, t), 6.87 (1 H, s), 7.04 (2 H, d), 7.17 (1 H, t), 7.28 (2 H, t), 7.58 (2 H, d), 7.64 (1 H, s), 7.81 (2 H, d), 8.00 (1 H, d, J=7.7 Hz, H-6), 10.33 (1 H, s, OH), 11.70 (1 H, s, NH); MS (ESI) m/z=571.7 [M+H]⁺;

Compound 54: ¹H NMR (300 MHz, DMSO-D₆), δ (ppm): 2.73 (3 H, s, 9-Me), 3.76 (2 H, m), 4.07 (1 H, dd), 4.13 (1 H, t), 4.32 (1 H, t), 6.74 (3 H, m), 7.18 (1 H, t), 7.29 (3 H, m) 7.39 (1 H, m) 7.59 (2 H, d), 7.77 (1 H, s), 7.99 (1 H, d J=7.9 Hz, H-6), 10.31 (1 H, s, OH), 11.55 (1 H, s, NH); MS (ESI) m/z=482.6 [M+H]⁺;

Compound 55: ¹H NMR (300 MHz, DMSO), δ (ppm): 2.76 (3 H, s, 9-Me), 3.46-3.53 (1 H, m, H-10), 3.76-3.79 (1 H, m, H-10), 4.09-4.20 (2 H, m, 2×H-2), 4.32-4.37 (1 H, m, H-1), 6.77-8.82 (3 H, m, H-3′, H-2″), 7.21-7.33 (3 H, H-7, H-8, H-4′), 7.51-7.59 (2 H, m, H-4, H-5′), 7.63-7.67 (3 H, m, H-7′, H-1″), 8.02 (1 H, d, J=8.4 Hz, H-6), 10.35 (1 H, s, OH), 11.59 (1 H, s, NH); MS (ESI) m/z=482.5 [M+H]⁺;

Compound 56: ¹H NMR (300 MHz, DMSO-D₆), δ (ppm): 2.73 (3 H, s, 9-Me), 3.73 (2 H, m), 4.04 (1 H, m), 4.14 (1 H, t), 4.34 (1 H, t), 6.73 (1 H, m), 6.87 (1 H, s), 7.23 (6 H, m) 7.37 (1 H, d, J=8.22 Hz) 7.46 (2 H, d, J=8.37 Hz), 7.86 (1 H, s), 7.99 (1 H, d, J=8.1 Hz, H-6), 10.33 (1 H, s, OH), 11.76 (1 H, s, NH); MS (ESI) m/z=482.6 [M+H]⁺;

Compound 57: ¹H NMR (300 MHz, DMSO), δ (ppm): 2.76 (3 H, s, 9-Me), 3.47-3.53 (1 H, m, H-10), 3.77-3.81 (1 H, m, H-10), 4.10 (1 H, d, J=10.8 Hz, H-2), 4.18 (1 H, t, J=7.5 Hz, H-2), 4.31-4.35 (1 H, m, H-1), 6.75 (1 H, m, H-4″), 6.87 (1 H, s, H-3′), 7.19-7.33 (5 H, m, H-7, H-8, H-5′, H-2″, H-3″), 7.51-7.68 (3 H, m, H-4, H-4′, H-6′), 8.02 (1 H, d, J=7.5 Hz, H-6), 10.36 (1 H, s, OH), 11.76 (1 H, s, NH); MS (ESI) m/z=482.6 [M+H]⁺;

Compound 103: ¹H NMR (300 MHz, DMSO-d₆), δ (ppm): 2.75 (3 H, s, 9-Me), 3.49 (1 H, m, H-10), 3.75 (1 H, m, H-10), 3.82 (3 H, s, MeO), 4.08 (1 H, d, J=10.9 Hz, H-2), 4.16 (1 H, m, H-2), 4.35 (1 H, m, H-1), 6.89 (1 H, s, H-3′), 7.06 (2 H, d, J=8.6 Hz, H-3″), 7.21 (1 H, t, J=7.6 Hz, H-7), 7.31 (1 H, d, J=6.8 Hz, H-8), 7.37 (1 H, d, J=8.4 Hz, H-6′), 7.47 (1 H, d, J=8.4 Hz, H-7′), 7.55 (1 H, bs, H-4), 7.83 (2 H, d, J=8.6 Hz, H-3″), 8.02 (1 H, d, J=7.7 Hz, H-6), 10.34 (1 H, bs, OH), 11.73 (1 H, s, NH); MS (ESI) m/z=497 [M+H]⁺.

Example 6

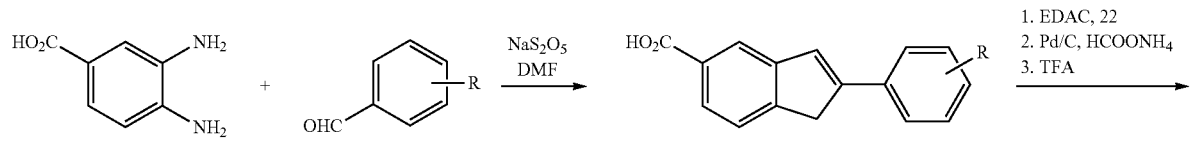

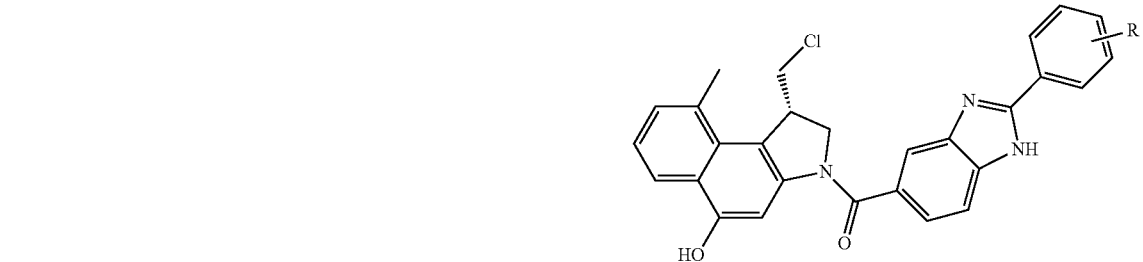

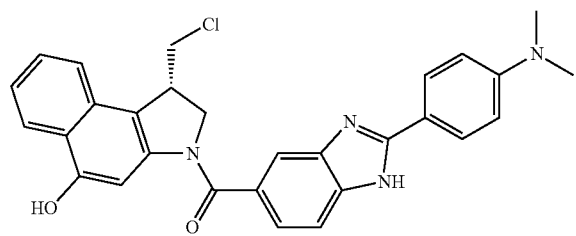

67

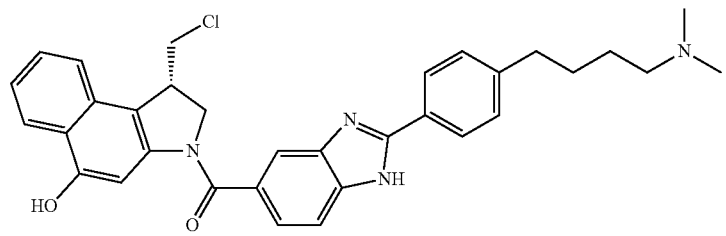

68

333 334
-continued
69
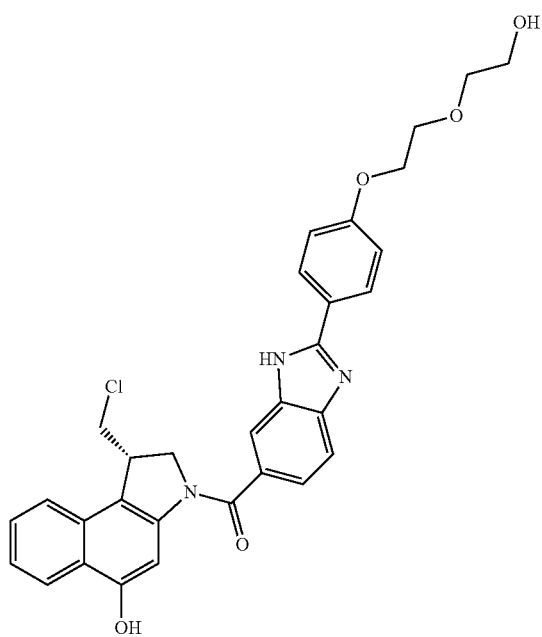
70
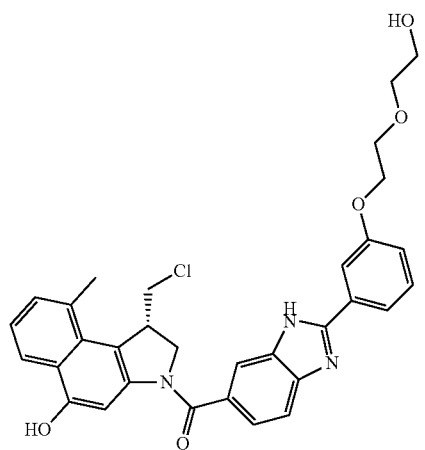
82
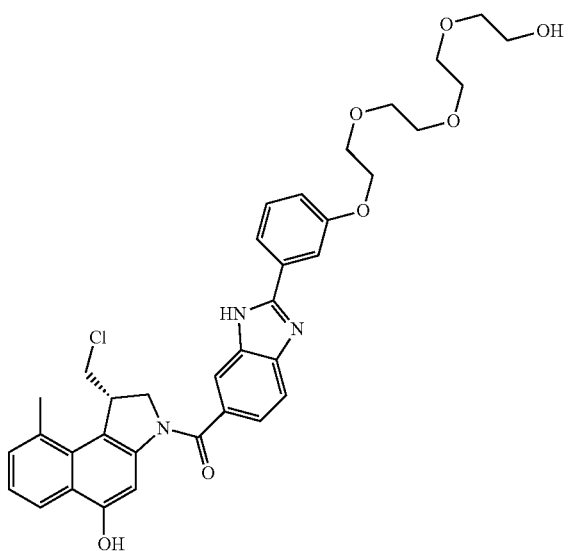

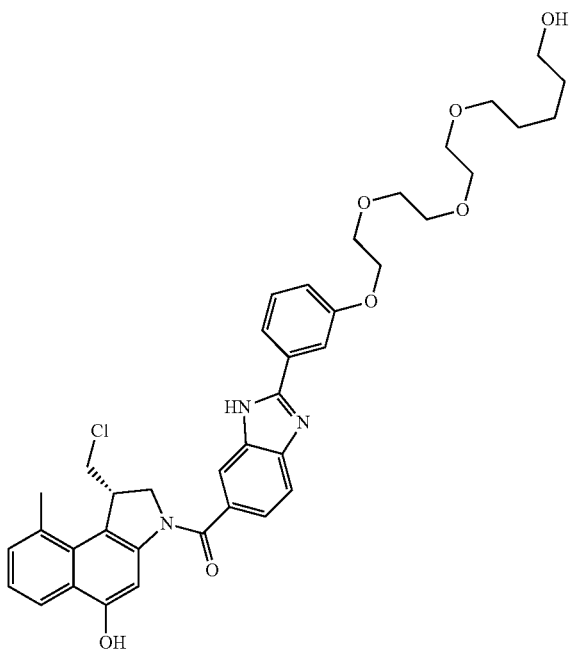
83
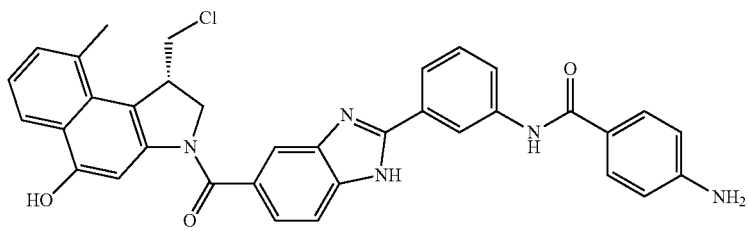
88
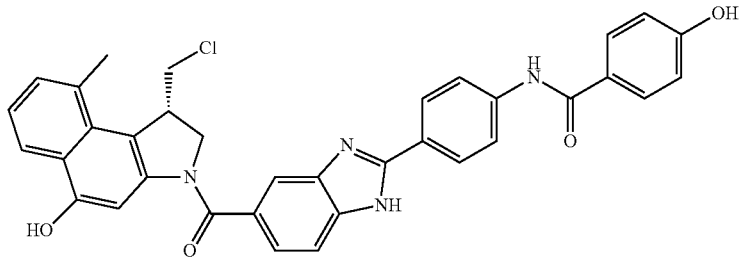
89
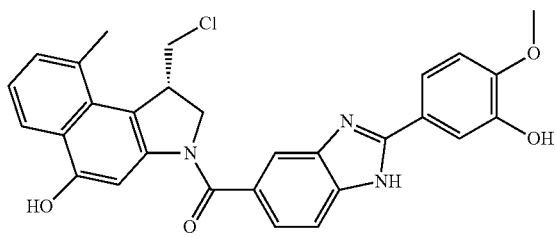
90
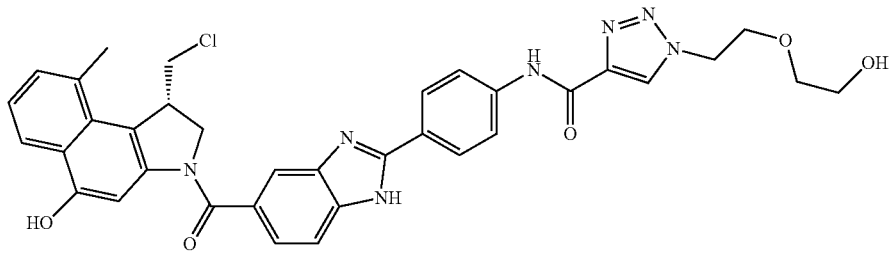
91

-continued
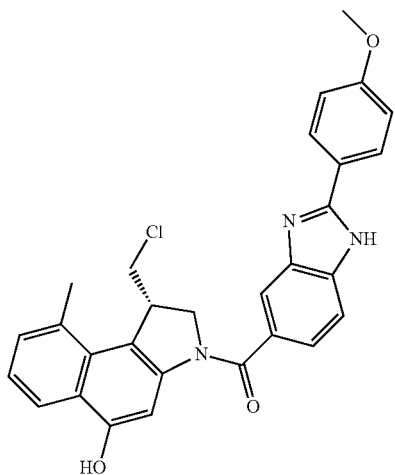
92
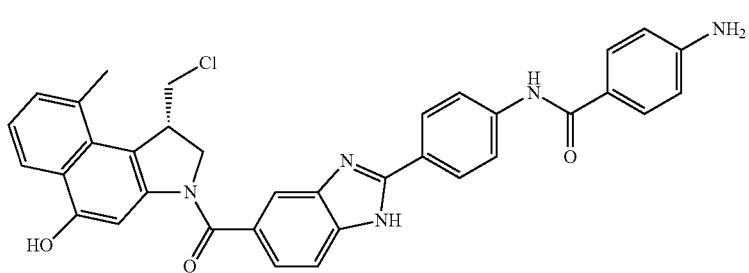
93
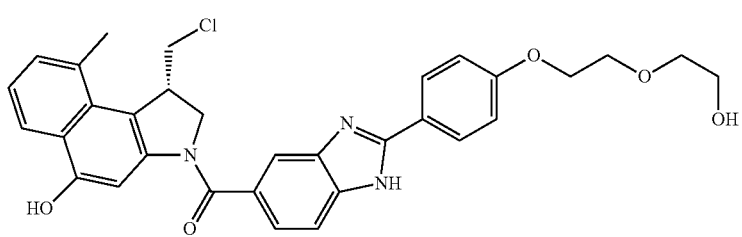
94
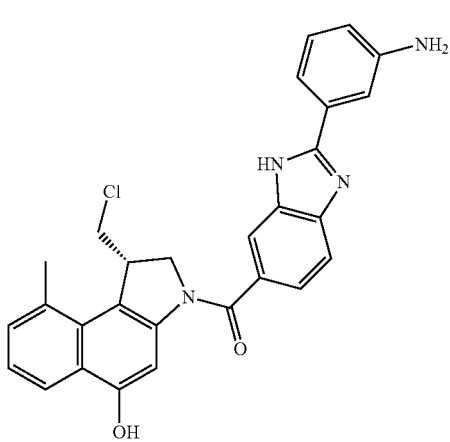
95
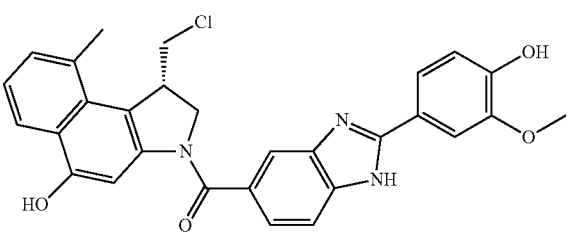
96

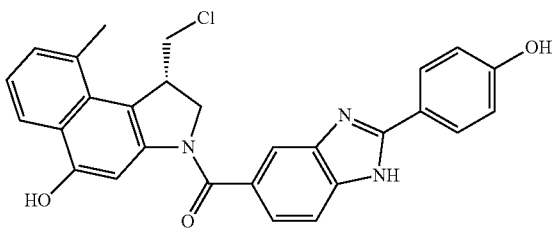

Compound 67: ¹H NMR (300 MHz, DMSO-d₆), δ (ppm): 2.76 (3 H, s, 9-Me), 3.10 (6 H, s, NMe), 3.60 (1 H, t, J=9.9 Hz, H-10), 3.77 (1 H, d, J=10.3 Hz, H-10), 4.00 (1 H, bs, H-1), 4.20 (1 H, t, J=7.7 Hz, H-2), 4.32 (1 H, t, J=8.2 Hz, H-2), 6.98 (2 H, d, J=9.5 Hz, H-3"), 7.23 (1 H, t, J=6.9 Hz, H-7), 7.34 (1 H, J=6.9 Hz, H-8), 7.55 (1 H, bs, H-4), 7.72 (1 H, d, J=9.0 Hz, H-7'), 7.83 (1 H, d, J=8.6 Hz, H-6'), 7.96 (1 H, s, H-4'), 8.03 (1 H, d, J=8.6 Hz, H-6), 8.14 (2 H, d, J=9.0 Hz), 10.39 (1 H, s, NH); MS (ESI) m/z=511 [M+H]⁺;

Compound 68: ¹H NMR (300 MHz, DMSO-d₆), δ (ppm): 2.15 (2 H, m, OCH₂CH₂), 2.76 (3 H, s, 9-Me), 2.84 (6 H, d, J=4.8 Hz, NMe), 3.25 (2 H, m, NCH₂CH₂), 3.55 (1 H, t, J=11.0 Hz, H-10), 3.77 (1 H, d, J=11.0 Hz, H-10), 4.04 (1 H, d, J=11 Hz, H-2), 4.13-4.22 (3 H, m, H-1, OCH₂), 4.34 (1 H, m, H-2), 7.18 (2 H, d, J=9.1 Hz, H-3"), 7.22 (1 H, t, J=6.9 Hz, H-7), 7.33 (1 H, d, J=6.6 Hz, H-8), 7.54 (1 H, dd, J=8.5 Hz, J=0.5 Hz, H-6'), 7.60 (1 H, bs, H-4), 7.72 (1 H, d, J=8.1 Hz, H-7'), 7.90 (1 H, s, H-4'), 8.02 (1 H, d, J=8.4 Hz, H-6), 8.19 (2 H, d, J=9.3 Hz, H-2"), 9.45 (1 H, s, OH), 10.38 (1 H, s, NH); MS (ESI) m/z=569 [M+H]⁺;

Compound 69: ¹H NMR (300 MHz, DMSO-d₆), δ (ppm): 2.76 (3 H, s, 9-Me), 3.51 (5 H, m, 2×O—CH₂, H-10ₐ), 3.78 (3 H, m, O—CH₂, H-10ᵦ), 4.06 (1 H, d, J=10.8 Hz, H-1), 4.22 (3 H, m, O—CH₂, H-2ₐ), 4.33 (1 H, m, H-2ᵦ), 4.63 (1 H, m, OH), 7.10 (2 H, d, J=8.9 Hz, 2×CH), 7.21 (1 H, t, J=8.2 Hz, H-7'), 7.32 (1 H, d, J=7.0 Hz, H-8'), 7.44 (1 H, d, J=8.9 Hz, CH), 7.57 (1 H, m, CH), 7.77 (1 H, s, H-4'), 8.01 (1 H, d, J=8.2 Hz, H-6'), 8.14 (2 H, d, J=8.9 Hz, 2×CH), 10.40 (1 H, s, OH), 12.01 (1 H, bs), 12.53 (1 H, bs); MS (ESI) m/z=615.6 [M+H]⁺;

Compound 70: ¹H NMR (300 MHz, DMSO-d₆), δ (ppm): 2.76 (3 H, s, 9-Me), 3.51-3.60 (5 H, m, 2×OCH₂, H-10ₐ), 3.74-3.85 (3 H, m, OCH₂, H-10ᵦ), 4.06 (1 H, m, H-1), 4.14-4.25 (3 H, m, OCH₂, H-2ₐ), 4.35 (1 H, m, H-2ᵦ), 4.65 (1 H, m, OH), 7.11 (1 H, d, J=9.1 Hz, CH), 7.22 (1 H, t, J=8.1 Hz, H-7'), 7.33 (1 H, d, J=7.1 Hz, H-8'), 7.50 (3 H, m, 3×CH), 7.65 (1 H, d, J=8.1 Hz), 7.80 (3 H, m, 3×CH), 8.00 (2 H, m, H-4', H-6'), 10.36 (1 H, s, OH), 13.18 (1 H, s, NH); MS (ESI) m/z=572.5 [M+H]⁺;

Compound 82: ¹H NMR (300 MHz, DMSO-d₆), δ (ppm): 2.76 (3 H, s, 9-Me), 3.35-3.65 (13 H, m, 6×CH₂O, H-10), 3.73-3.85 (3 H, m, H-10, CH₂O), 4.06 (1 H, m, H-2), 4.13-4.25 (3 H, m, H-2, CH₂O), 4.35 (1 H, m, H-1), 4.57 (1 H, t, J=5.4 Hz, OH), 7.12 (1 H, d, J=8.2 Hz, H-4"), 7.22 (1 H, t, J=7.7 Hz, H-7), 7.32 (1 H, d, J=6.8 Hz, H-8), 7.40-8.00 (7 H, m, H-4, H-4', H-5', H-6', H-2", H-5", H-6"), 8.02 (1 H, d, J=7.9 Hz, H-6), 10.36 (1 H, s, OH), 12.17 (1 H, s, NH); MS (ESI) m/z=660 [M+H]⁺;

Compound 83: ¹H NMR (300 MHz, DMSO-d₆), δ (ppm): 2.76 (3 H, s, 9-Me), 3.37-3.65 (13 H, m, 6×CH₂O, H-10), 3.73-3.83 (3 H, m, H-10, CH₂O), 4.07 (1 H, m, H-2), 4.12-4.26 (3 H, m, H-2, CH₂O), 4.35 (1 H, m, H-1), 4.57 (1 H, t, J=5.4 Hz, OH), 7.15 (2 H, d, J=8.8 Hz, H-3"), 7.22 (1 H, t, J=7.7 Hz, H-7), 7.32 (1 H, d, J=6.9 Hz, H-8), 7.47 (1 H, m, H-6' tautomers), 7.60 (1 H, bs, H-4), 7.61+7.72 (1 H, d, J=8.3, H-7' tautomers), 7.76+7.93 (1 H, s, H-4' tautomers), 8.02 (1 H, d, J=8.4, H-6), 10.36 (1 H, s, OH), 13.03 (1 H, s, NH); MS (ESI) m/z=660 [M+H]⁺;

Compound 88: ¹H NMR (300 MHz, DMSO-d₆), δ (ppm): 2.76 (3 H, s, 9-Me), 3.49 (1 H, m, H-10), 3.78 (1 H, d, J=10.1 Hz, H-10), 4.03 (1 H, m, H-2), 4.20 (1 H, m, H-2), 4.34 (1 H, m, H-1), 6.71 (2 H, d, J=8.6 Hz, H-3'''), 7.23 (1 H, t, J=7.5 Hz, H-7), 7.33 (1 H, d, J=6.9 Hz, H-8), 7.50-7.75 (3 H, m, H-4, H-7', H-5"), 7.80-7.98 (5 H, m, H-6', H-4", H-6", H2'''), 8.00-8.07 (2 H, m, H-6, H-4'), 8.83 (1 H, s, H-2"), 10.16 (1 H, s, OH), 10.40 (1 H, bs, NH); MS (ESI) m/z=602 [M+H]⁺;

Compound 89: ¹H NMR (300 MHz, DMSO-d₆), δ (ppm): 2.76 (3 H, s, 9-Me), 3.56 (1 H, m, H-10), 3.78 (1 H, d, J=9.2 Hz, H-10), 4.07 (1 H, m, H-2), 4.18 (1 H, m, H-2), 4.34 (1 H, m, H-1), 6.89 (2 H, d, J=8.7 Hz, H-3'''), 7.21 (1 H, t, J=7.7 Hz, H-7), 7.32 (1 H, d, J=6.8 Hz, H-8), 7.49 (1 H, m, H-6'), 7.60 (1 H, bs, H-4), 7.63+7.74 (1 H, d, J=8.2 Hz, H-7' tautomers), 7.79+7.95 (1 H, s, H-4' tautomers), 7.89 (2 H, d, J=8.7 Hz, H-2'''), 7.98 (2 H, d, J=8.8 Hz, H-3"), 8.02 (1 H, d, J=8.2 Hz, H-6), 8.18 (2 H, d, J=8.8 Hz, H-2"), 10.15 (1 H, s, OH), 10.24 (1 H, s, OH), 10.37 (1 H, bs, NH); MS (ESI) m/z=603 (M+H⁺);

Compound 90: ¹H NMR (300 MHz, DMSO-d₆), δ (ppm): 2.76 (3 H, s, 9-Me), 3.54 (1 H, m, H-10), 3.78 (1 H, d, J=10.7 Hz, H-10), 3.86 (3 H, s, OMe), 4.07 (1 H, d, J=11.0 Hz, H-2), 4.18 (1 H, m, H-2), 4.35 (1 H, m, H-1), 7.11 (1 H, d, J=8.4 Hz, H-5"), 7.21 (1 H, dd, J=6.7 Hz, 8.0 Hz, H-7), 7.32 (1 H, d, J=6.7 Hz, H-8), 7.46 (1 H, d, J=8.4 Hz, H-7'), 7.57 (1 H, bs, H-4), 7.60-7.70 (2 H, m, H-2", H-6"), 7.74 (1 H, m, H-6'), 7.91 (1 H, bs, H-4'), 8.01 (1 H, d, J=8.0 Hz, H-6), 9.33 (1 H, s, OH), 10.36 (1 H, s, OH), 12.96 (1 H, s, NH); MS (ESI) m/z=514 [M+H]⁺;

Compound 91: ¹H NMR (300 MHz, DMSO-d₆), δ (ppm): 2.76 (3 H, s, 9-Me), 3.46 (4 H, bs, 2×CH₂O), 3.56 (1 H, m, H-10), 3.77 (1 H, m, H-10), 3.88 (2 H, t, J=5.2 Hz, CH₂O), 4.08 (1 H, m, H-2), 4.20 (1 H, m, H-2), 4.35 (1 H, m, H-1), 4.64 (3 H, m, CH₂O, OH), 7.21 (1 H, t, J=7.7 Hz, H-7), 7.33 (1 H, d, J=6.7 Hz, H-8), 7.49 (1 H, m, H-7'), 7.60 (1 H, bs, H-4), 7.62+7.74 (1 H, d, J=7.9 Hz, H-6' tautomers), 7.79+7.96 (1 H, s, H-4' tautomers), 8.02 (1 H, d, J=8.0 Hz, H-6), 8.05 (2 H, d, J=8.8, H-2"), 8.18 (2 H, d, J=8.8 Hz, H-3"), 8.75 (1 H, s, triazole-H), 10.36 (1 H, s, NH), 10.70 (1 H, s, OH), 13.11 (1 H, bs, NH); MS (ESI) m/z=666 [M+H]⁺;

Compound 92: ¹H NMR (300 MHz, DMSO-d₆), δ (ppm): 2.76 (3 H, s, 9-Me), 3.55 (1 H, m, H-10), 3.78 (1 H, m, H-10), 3.86 (3 H, s, OMe), 4.07 (1 H, m, H-2), 4.18 (1 H, m, H-2), 4.35 (1 H, m, H-1), 7.14 (2 H, d, J=8.8 Hz, H-3"), 7.21 (1 H, dd, J=6.9 Hz, 8.2 Hz, H-7), 7.31 (1 H, d, J=6.9 Hz, H-8), 7.46+7.48 (1 H, d, J=8.2 Hz, H-6', tautomers), 7.56 (1 H, bs, H-4), 7.61+7.73 (1 H, d, J=8.2, H-7', tautomers), 7.76+7.93 (1 H, s, H-4' tautomers), 8.02 (1 H, d, J=8.2 Hz, H-6), 8.16 (2 H, d, J=8.8 Hz, H-2''), 10.36 (1 H, bs, OH), 13.02 (1 H, s, NH); MS (ESI) m/z=498 (M+H$^+$);

Compound 93: $^1$H NMR (300 MHz, DMSO-d$_6$), δ (ppm): 2.76 (3 H, s, 9-Me), 3.48 (1 H, m, H-10), 3.78 (1 H, d, J=10.6 Hz, H-10), 4.01 (1 H, m, H-2), 4.21 (1 H, m, H-2), 4.33 (1 H, m, H-1), 6.68 (2 H, d, J=8.6 Hz, H-3'''), 7.23 (1 H, t, J=7.7 Hz, H-7), 7.33 (1 H, d, J=6.7 Hz, H-8), 7.74 (1 H, d, J=8.3 Hz, H-7'), 7.70 (1 H, bs, H-4), 7.79 (2 H, d, J=8.6 Hz, H-2'''), 7.89 (1 H, d, J=8.3 Hz, H-6'), 8.02 (1 H, d, J=7.0 Hz, H-6), 8.04 (1 H, s, H-4'), 8.10 (2 H, d, J=8.9 Hz, H-3''), 8.26 (2 H, d, J=8.9 Hz, H-2''), 10.25 (1 H, s, OH), 10.41 (1 H, bs, NH); MS (ESI) m/z=602 [M+H]$^+$;

Compound 94: $^1$H NMR (300 MHz, DMSO-d$_6$), δ (ppm): 2.76 (3 H, s, 9-Me), 3.52 (4 H, bs, 2×CH$_2$O), 3.56 (1 H, m, H-10), 3.70-3.81 (3 H, m, H-10, CH$_2$O), 4.06 (1 H, d, J=10.5 Hz, H-2), 4.13-4.23 (3 H, m, H-2, CH$_2$O), 4.35 (1 H, m, H-1), 4.60 (1 H, bs, OH), 7.15 (2 H, d, J=8.8 Hz, H-3''), 7.22 (1 H, t, J=8.2 Hz, H-7), 7.33 (1 H, d, J=6.9 Hz, H-8), 7.47 (1 H, d, J=8.4 Hz, H-2''), 7.60 (1 H, bs, H-4), 7.65 (1 H, bs, H-7'), 7.85 (1 H, bs, H-4'), 8.02 (1 H, d, J=8.0 Hz, H-6), 8.15 (2 H, d, J=8.8, H-3''), 10.36 (1 H, s, OH); MS (ESI) m/z=572 [M+H]$^+$;

Compound 95: $^1$H NMR (300 MHz, DMSO-d$_6$), δ (ppm): 2.75 (3 H, s, 9-Me), 3.59 (1 H, m, H-10), 3.77 (1 H, d, J=10.4 Hz, H-10), 4.02 (1 H, m, H-2), 4.20 (1 H, m, H-2), 4.34 (1 H, m, H-1), 7.15 (1 H, d, J=8.0 Hz, H-4''), 7.23 (1 H, t, J=7.8 Hz, H-7), 7.33 (1 H, d, J=7.0 Hz, H-8), 7.49 (1 H, t, J=7.8 Hz, H-5''), 7.60-7.80 (4 H, m, H-4, H-7', H-2'', H-6''), 7.85 (1 H, d, J=8.3 Hz, H-6'), 8.01 (1 H, s, H-4'), 8.02 (1 H, d, J=8.0 Hz, H-6), 10.42 (1 H, s, OH); MS (ESI) m/z=483 [M+H]$^+$;

Compound 96: $^1$H NMR (300 MHz, DMSO-d$_6$), δ (ppm): 2.75 (3 H, s, 9-Me), 3.54 (1 H, m, H-10), 3.78 (1 H, d, J=10.9 Hz, H-10), 3.90 (3 H, s, OMe), 4.07 (1 H, d, J=10.7 Hz, H-2), 4.18 (1 H, m, H-2), 4.35 (1 H, m, H-1), 6.94 (1 H, d, J=8.2 Hz, H-5''), 7.21 (1 H, d, J=7.7 Hz, H-7), 7.32 (1 H, d, J=6.7 Hz, H-8), 7.47 (1 H, d, J=8.9 Hz, H-6'), 7.55 (1 H, bs, H-4), 7.60-7.70 (2 H, m, H-6'', H-7'), 7.78 (1 H, s, H-2''), 7.84 (1 H, s, H-4'), 8.02 (1 H, d, J=8.1 Hz, H-6), 9.61 (1 H, s, OH), 10.36 (1 H, s, OH), 12.97 (1 H, s, NH); MS (ESI) m/z=514 [M+H]$^+$;

Compound 97: $^1$H NMR (300 MHz, DMSO-d$_6$), δ (ppm): 2.75 (3 H, s, 9-Me), 3.54 (1 H, m, H-10), 3.77 (1 H, d, J=9.7 Hz, H-10), 4.06 (1 H, d, J=10.9 Hz, H-2), 4.18 (1 H, m, H-2), 4.35 (1 H, m, H-1), 6.94 (2 H, d, J=8.7 Hz, H-3''), 7.21 (1 H, t, J=7.6 Hz, H-7), 7.31 (1 H, d, J=6.7 Hz, H-8), 7.47 (1 H, d, J=8.2 Hz, H-6'), 7.56 (1 H, bs, H-4), 7.65 (1 H, d, J=8.2, H-7'), 7.83 (1 H, s, H-4'), 8.01 (1 H, d, J=7.9 Hz, H-6), 8.04 (2 H, d, J=8.7 Hz, H-2''), 10.05 (1 H, s, OH), 10.36 (1 H, s, OH), 13.06 (1 H, bs, NH); MS (ESI) m/z=484 [M+H]$^+$.

Example 7

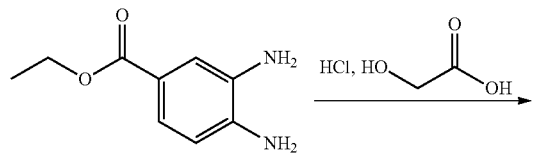

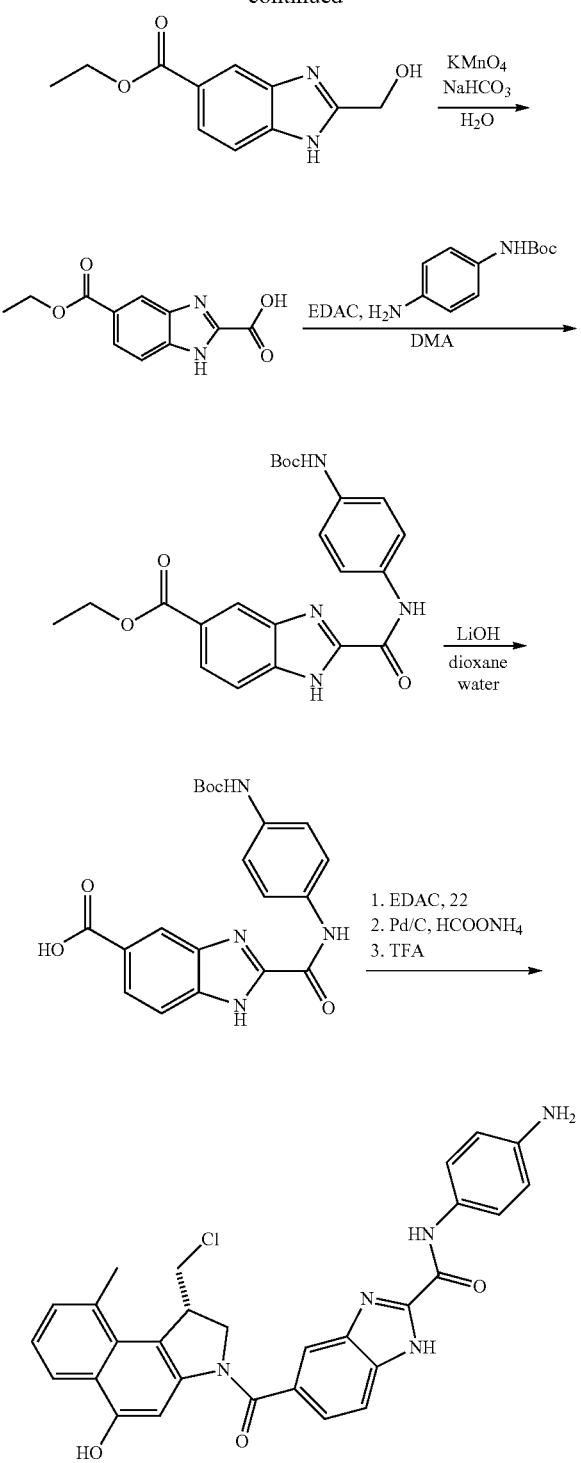

Compound 33: $^1$H NMR (400 MHz, DMSO-d$_6$), δ (ppm): 2.75 (3 H, s, 9-Me), 3.06-3.13 (1 H, m, H-10), 3.78 (1 H, d, J=11.5 Hz, H-10), 4.04 (1 H, m, H-1), 4.19 (1 H, t, J=8.2 Hz, H-2), 4.33 (1 H, t, J=9.3 Hz, H-2), 7.00 (2 H, bs, Ph-H), 7.23 (1 H, t, J=7.5 Hz, H-7), 7.33 (1 H, d, J=7.0 Hz, H-8), 7.60-8.50 (8 H, m), 10.38 (1 H, s, OH), 10.91 (1 H, s, NH); MS (ESI) m/z=526 [M+H]$^+$.

Example 8
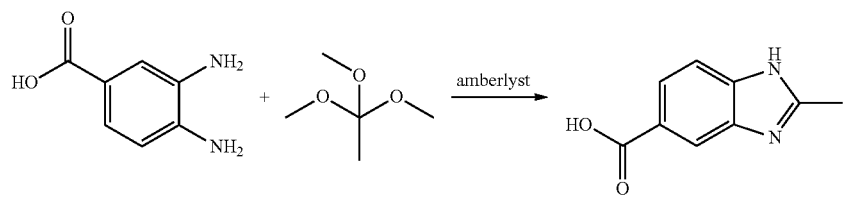
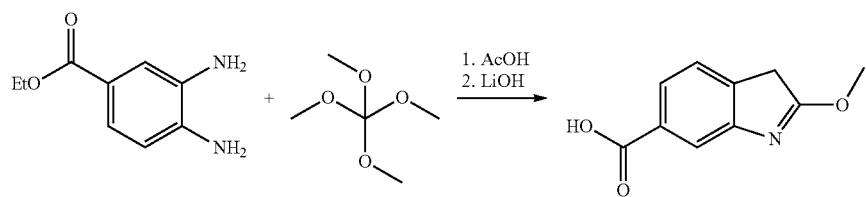
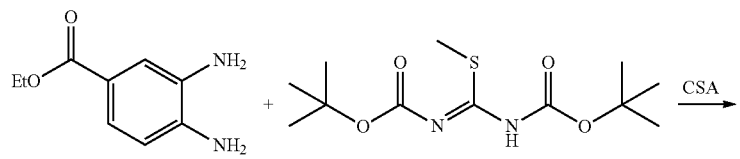
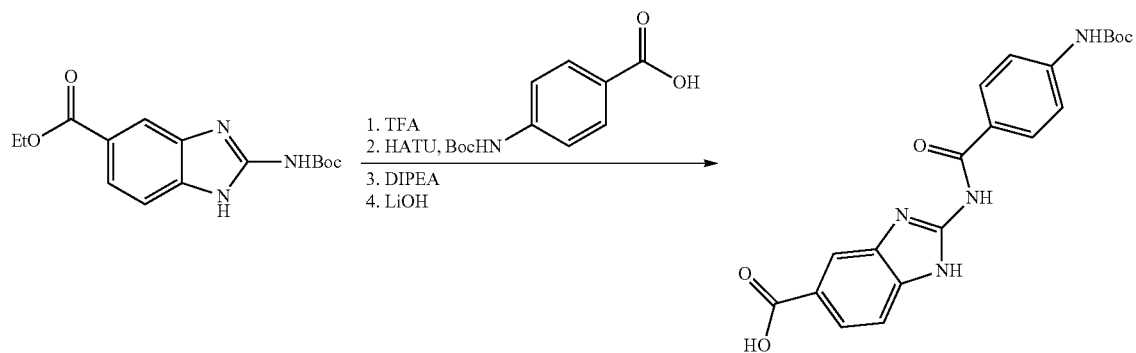
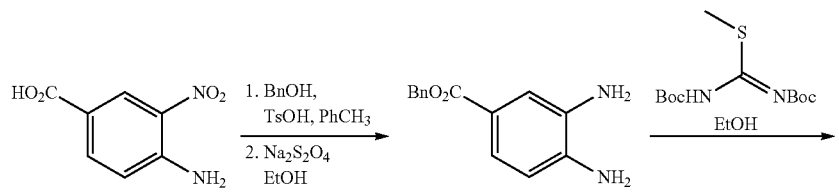
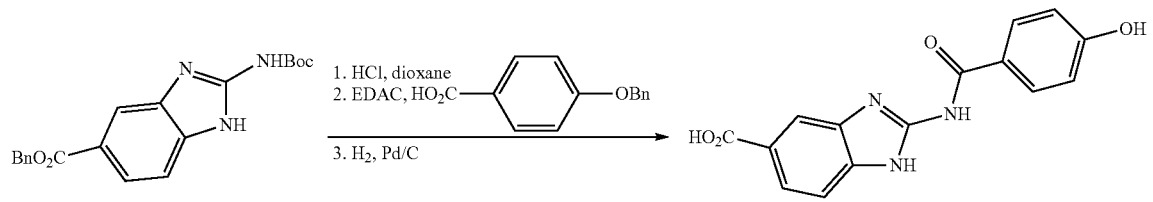

-continued
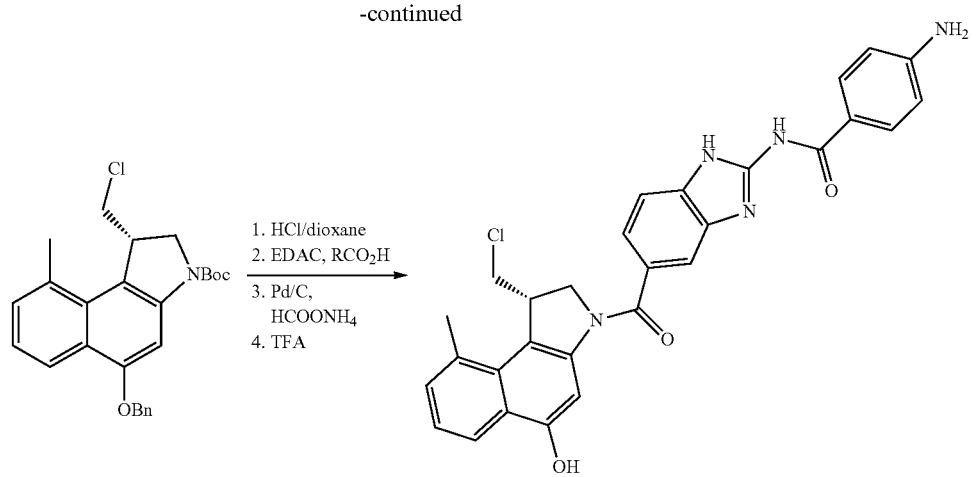
34
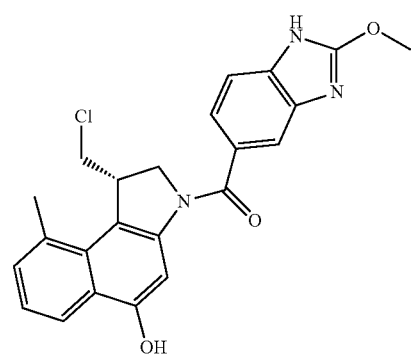
35
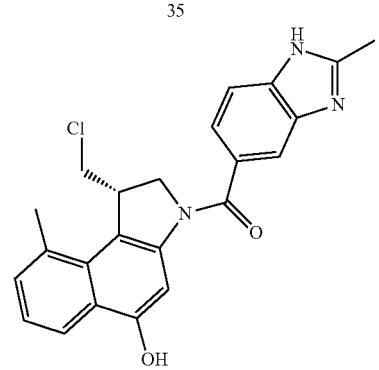
36
Compound 34: ¹H NMR (300 MHz, DMSO), δ (ppm): 2.76 (3 H, s, 9-Me), 3.50 (1 H, t, J=9.3 Hz, H-10), 3.78 (1 H, d, J=13.5 Hz, H-10), 4.06 (1 H, d, J=11.7 Hz, H-2), 4.15-4.22 (1 H, m, H-2), 4.29-4.36 (1 H, m, H-1), 5.96 (2 H, s, NH$_2$), 6.61 (2 H, d, J=9.0 Hz, H-2″), 7.21 (1 H, t, J=7.2 Hz, H-7), 7.33 (1 H, d, J=7.2 Hz, H-8), 7.38-7.78 (4 H, m, H-4, H-4′, H-6′, H-7′), 7.90 (2 H, d, J=9.0 Hz, H-1″), 8.02 (1 H, d, J=9.6 Hz, H-6), 10.35 (1 H, s, OH), 11.58 (1 H, s, NH), 12.45 (1 H, s, NH); MS (ESI) m/z=526.2 [M+H]⁺;
Compound 35: ¹H NMR (300 MHz, DMSO), δ (ppm): 2.75 (3 H, s, 9-Me), 3.33 (3 H, s, OMe), 3.45-3.55 (1 H, m, H-10), 3.77 (1 H, m, H-10), 4.04 (1 H, m, H-2), 4.17-4.21 (1 H, m, H-2), 4.29-4.36 (1 H, m, H-1), 7.06-7.51 (6 H, m, H-4, H-7, H-8, H-4′, H-6′, H-7′), 8.01 (1 H, m, H-6), 10.34-10.36 (1 H, m, OH), 11.05-11.14 (1 H, m, NH); MS (ESI) m/z=422.1 [M+H]⁺.
Example 9
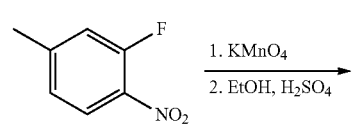

347
-continued
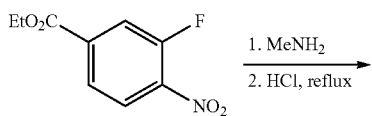
348
-continued
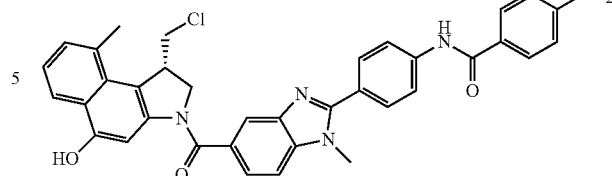
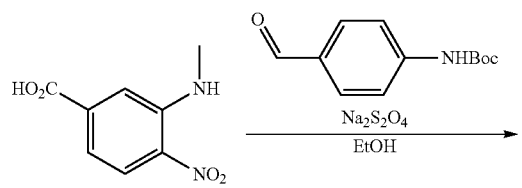
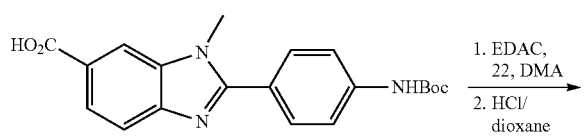
Compound 87: $^1$H NMR (300 MHz, DMSO-$d_6$), δ (ppm): 2.76 (3 H, s, 9-Me), 3.49 (1 H, m, H-10), 3.74 (1 H, m, H-10), 3.96 (1 H, m, H-2), 4.09 (3 H, s, N-Me), 4.19 (1 H, m, H-2), 4.34 (1 H, m, H-1), 6.67 (2 H, d, J=8.6 Hz, H-3'''), 7.24 (1 H, t, J=7.6 Hz, H-7), 7.32 (1 H, d, J=6.9 Hz, H-8), 7.70 (1 H, bs, H-4), 7.79 (2 H, d, J=8.6 Hz, H-2'''), 7.84 (1 H, d, J=8.8 Hz, H-7'), 7.96 (2 H, d, J=8.8 Hz, H-3''), 8.04 (1 H, d, J=8.1 Hz, H-6), 8.06-8.10 (2 H, m, H-6', H-7'), 8.13 (2 H, d, J=8.8 Hz, H-2''), 10.23 (1 H, s, OH) 10.44 (1 H, s, NH); MS (ESI) m/z=616 [M+H]$^+$.
Example 10
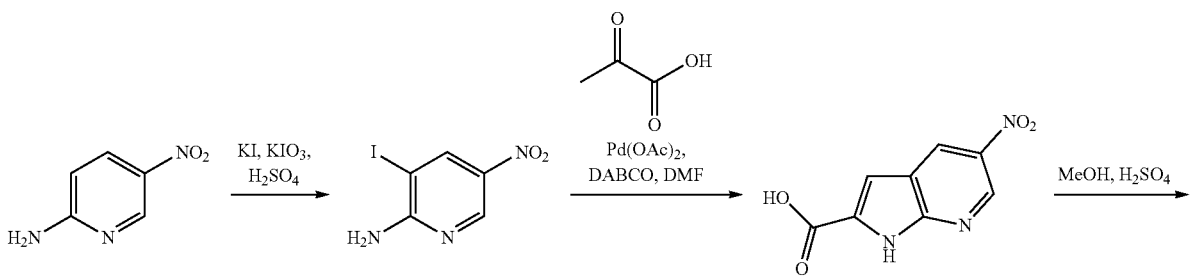
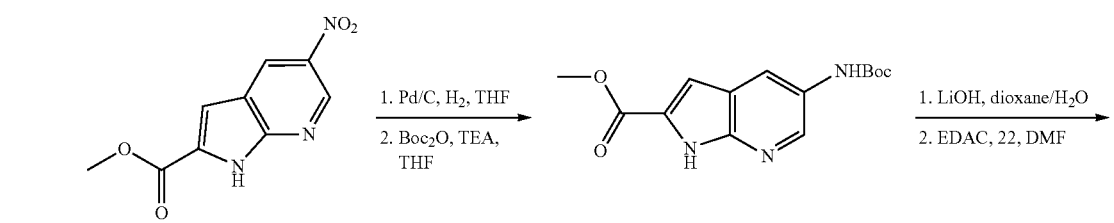
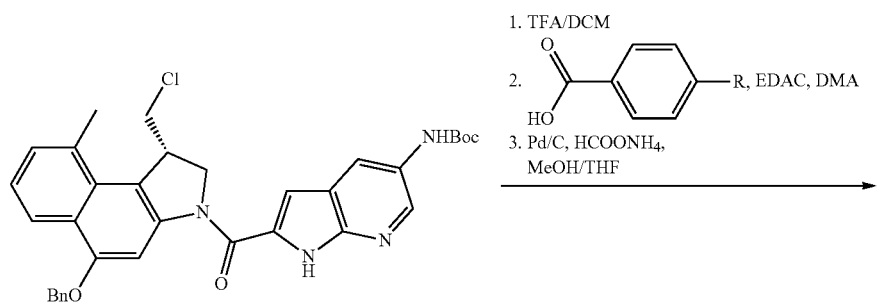

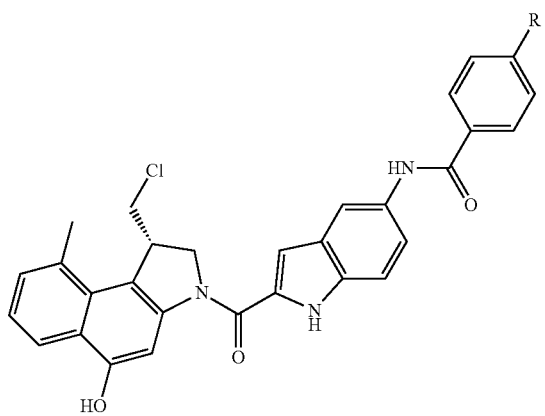
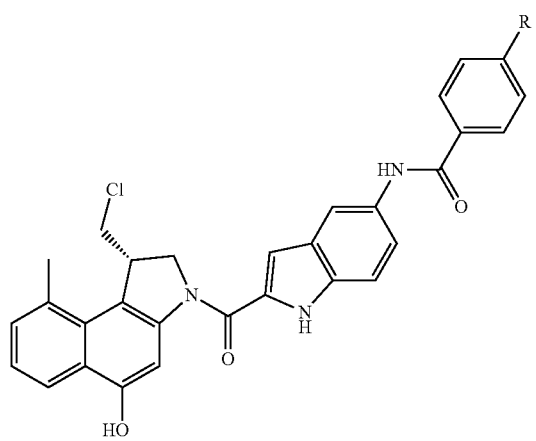
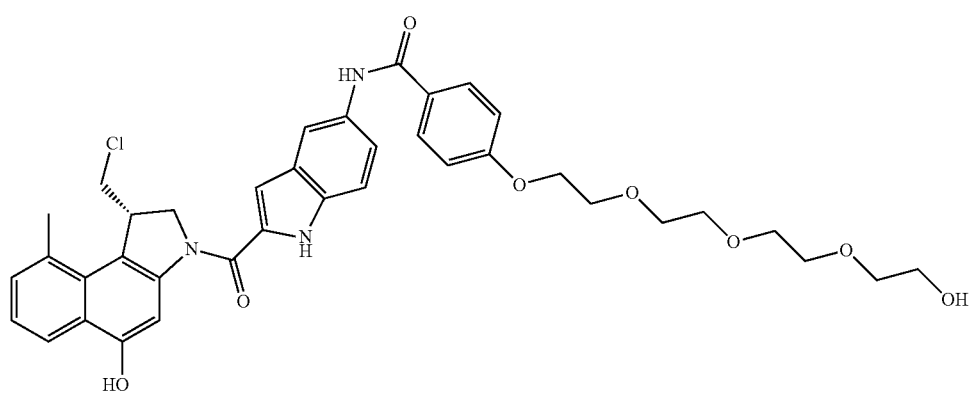

73
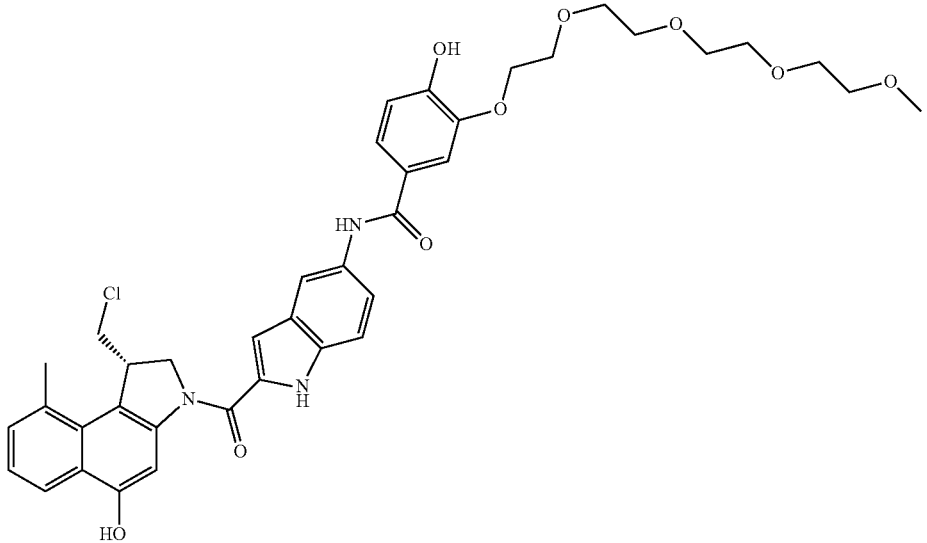
74
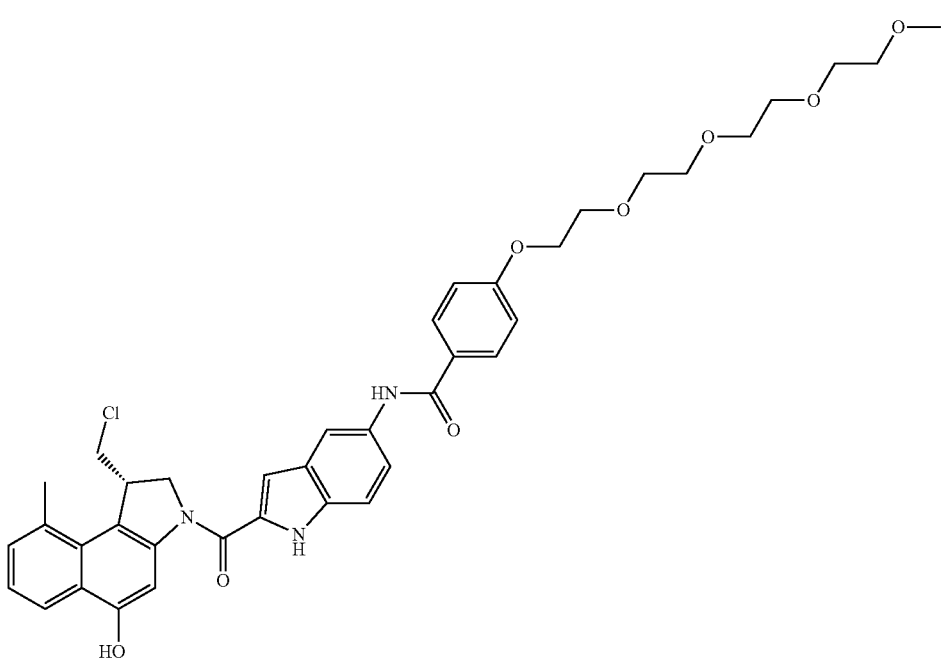
75
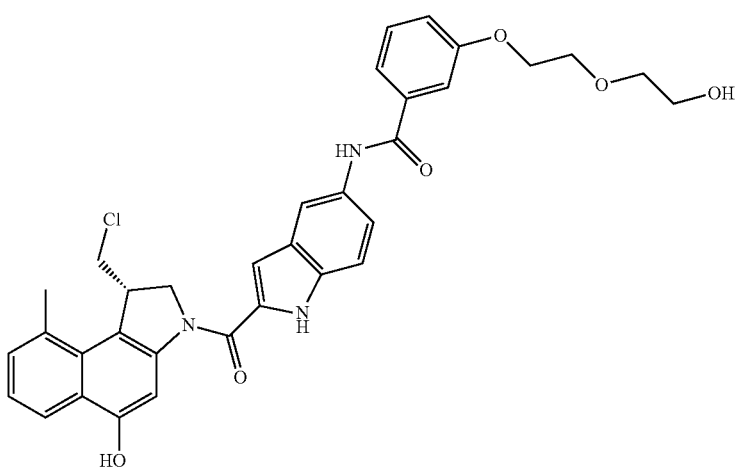

76

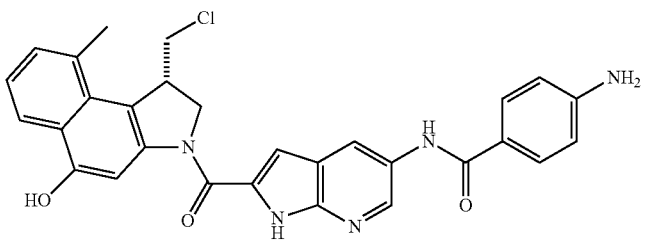

77

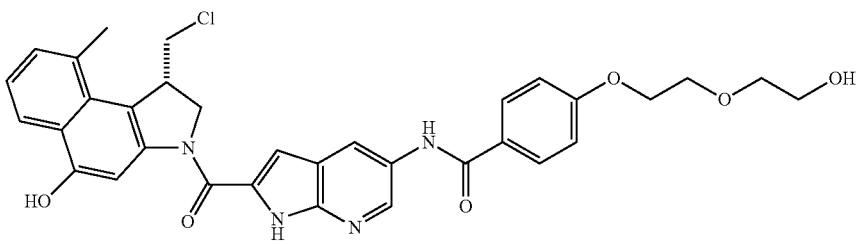

Compound 71: $^1$H NMR (300 MHz, DMSO-d$_6$), δ (ppm): 2.79 (3 H, s, 9-Me), 3.52 (1 H, m, H-10$_a$), 3.80 (1 H, m, H-10$_b$), 4.31 (1 H, m, H-2$_a$), 4.49 (1 H, m, H-1), 4.65 (1 H, m, H-2$_b$), 6.89 (2 H, d, J=8.4 Hz, 2×CH), 7.16 (1 H, s, CH), 7.25 (1 H, t, J=7.5 Hz, H-7'), 7.35 (1 H, m, H-8'), 7.90 (3 H, m, 2×CH, H-4'), 8.05 (1 H, d, J=8.4 Hz, H-6'), 8.50 (1 H, m, CH), 8.63 (1 H, m, CH), 10.10 (1 H, s, OH), 10.14 (1 H, s, NH), 10.47 (1 H, s, OH), 12.24 (1 H, s, NH);

Compound 72: $^1$H NMR (300 MHz, DMSO), δ (ppm): 2.79 (3 H, s, 9-Me), 3.39-3.78 (17 H, m, H-10, H-10, OH), 4.21 (2 H, t, J=5.1 Hz, OCH$_2$), 4.31 (1 H, t, J=11.4 Hz, H-2), 4.48 (1 H, d, J=11.1 Hz, H-2), 4.66 (1 H, m, H-1), 7.10 (2 H, d, J=9.0 Hz, H-2"), 7.16 (1 H, s, H-3'), 7.25 (1 H, t, J=6.9 Hz, H-7), 7.34 (1 H, d, J=6.6 Hz, H-8), 7.90-8.06 (4 H, m, H-4, H-6, H-1"), 8.53 (1 H, s, H-4'), 8.65 (1 H, s, H-6'), 10.26 (1 H, s, NH) 10.47 (1 H, s, OH), 12.27 (1 H, s, NH); MS (ESI) m/z=703.5 [M+H]$^+$;

Compound 73: $^1$H NMR (300 MHz, DMSO-d$_6$), δ (ppm): 2.79 (3 H, s, 9-Me), 3.22 (3 H, s, OMe), 3.39-3.65 (13 H, m, 6×CH$_2$, H-10$_a$), 3.81 (3 H, m, OCH$_2$, H-10$_b$), 4.20 (2 H, m, OCH$_2$), 4.31 (1 H, m, H-2$_a$), 4.49 (1 H, d, J=10.8 Hz, H-1), 4.66 (1 H, m, H-2), 6.92 (1 H, d, J=8.3 Hz, CH), 7.16 (1 H, d, J=2.2 Hz, CH), 7.24 (1 H, t, J=6.9 Hz, H-7'), 7.35 (1 H, m, H-8'), 7.55 (1 H, d, J=8.3 Hz, CH), 7.61 (1 H, m, CH), 7.91 (1 H, s, H-4'), 8.05 (1 H, d, J=7.5 Hz, H-6'), 8.44 (1 H, d, J=2.2 Hz, CH), 8.62 (1 H, d, J=2.2 Hz, CH), 9.69 (1 H, s, NH), 10.12 (1 H, s, OH), 10.47 (1 H, s, OH), 12.25 (1 H, s, NH); MS (ESI) m/z=733.5 [M+H]$^+$;

Compound 74: $^1$H NMR (300 MHz, DMSO-d$_6$), δ (ppm): 2.79 (3 H, s, 9-Me), 3.24 (3 H, s, OMe), 3.40-3.64 (13 H, m, 6×CH$_2$, H-10$_a$), 3.79 (3 H, m, OCH$_2$, H-10$_b$), 4.19 (2 H, m, OCH$_2$), 4.31 (1 H, m, H-2$_a$), 4.49 (1 H, d, J=10.9 Hz, H-1), 4.66 (1 H, m, H-2), 7.07 (1 H, d, J=8.2 Hz, CH), 7.16 (1 H, d, J=7.0 Hz, H-8'), 7.50 (2 H, m, CH), 7.93 (1 H, bs, H-4'), 8.05 (1 H, d, J=8.2 Hz, H-6'), 8.51 (1 H, d, J=2.3 Hz, CH), 8.63 (1 H, d, J=2.3 Hz, CH), 9.28 (1 H, s, NH), 10.18 (1 H, s, OH), 10.47 (1 H, s, OH), 12.24 (1 H, s, NH); MS (ESI) m/z=733.5 [M+H]$^+$;

Compound 75: $^1$H NMR (300 MHz, DMSO-d$_6$), δ (ppm): 2.79 (3 H, s, 9-Me), 3.53 (5 H, m, 2×OCH$_2$, H-10$_a$), 3.79 (3 H, m, OCH$_2$, H-10$_b$), 4.21 (2 H, m, OCH$_2$), 4.31 (1 H, m, H-2$_a$), 4.49 (1 H, d, J=10.6 Hz, H-1), 4.63 (2 H, m, OH, H-2$_b$), 7.18 (1 H, s, CH), 7.20 (1 H, m, CH), 7.25 (1 H, t, J=7.2 Hz, H-7'), 7.35 (1 H, d, J=6.9 Hz, H-8'), 7.47 (1 H, t, J=8.1 Hz, CH), 7.59 (2 H, m, 2×CH), 7.94 (1 H, s, H-4'), 8.05 (1 H, d, J=8.1 Hz, H-6'), 8.54 (1 H, d, J=2.4 Hz, CH), 8.66 (1 H, d, J=2.4 Hz, CH), 10.37 (1 H, s, NH), 10.47 (1 H, s, OH), 12.28 (1 H, s, NH); MS (ESI) m/z=615.5 [M+H]$^+$;

Compound 76: $^1$H NMR (300 MHz, DMSO-d$_6$), δ (ppm): 2.79 (3 H, s, 9-Me), 3.51 (1 H, t, J=10.7 Hz, H-10), 3.80 (1 H, d, J=11.3 Hz, H-10), 4.31 (1 H, t, J=8.7 Hz, H-1), 4.49 (1 H, d, J=10.5 Hz, H-2), 4.66 (1 H, dd, J=10.5 Hz, 10.0 Hz, H-2), 5.76 (2 H, s, NH$_2$), 6.62 (2 H, d, J=8.7 Hz, H-3"), 7.15 (1 H, d, J=2.18 Hz, H-3'), 7.25 (1 H, dd, J=8.7 Hz, 7.0 Hz, H-7), 7.35 (1 H, d, J=7.0 Hz, H-8), 7.77 (2 H, d, J=8.6 Hz, H-2"), 7.93 (1 H, s, H-4), 8.04 (1 H, d, J=8.2 Hz, H-6), 8.50 (1 H, d, J=2.2 Hz, H-4'), 8.63 (1 H, d, J=2.4 Hz, H-6'), 9.92 (1 H, s, OH), 10.47 (1 H, s, NH), 12.20 (1 H, s, NH); MS (ESI) m/z=526 [M+H]$^+$;

Compound 77: $^1$H NMR (300 MHz, DMSO-d$_6$), δ (ppm): 2.79 (3 H, s, 9-Me), 3.47-3.58 (5 H, m, CH$_2$, H-10), 3.75-3.85 (3 H, m, CH$_2$, H-10), 4.20 (2 H, m, CH$_2$), 4.31 (1 H, t, J=7.5 Hz, H-1), 4.49 (1 H, d, J=10.9 Hz, H-2), 4.60-4.71 (2 H, m, H-2, OH), 7.10 (2 H, d, J=9.5 Hz, H-3"), 7.17 (1 H, d, J=2.0 Hz, H-3'), 7.25 (1 H, dd, J=7.1 Hz, 8.5 Hz, H-7), 7.35 (1 H, d, J=7.1 Hz, H-8), 7.94 (1 H, s, H-4), 8.00 (2 H, d, J=8.9 Hz, H-2"), 8.05 (1 H, d, J=8.3 Hz, H-6), 8.53 (1 H, d, J=2.3 Hz, H-4'), 8.65 (1 H, d, J=2.4 Hz, H-6'), 10.25 (1 H, s, NH), 10.47 (1 H, s, OH), 12.26 (1 H, s, NH); MS (ESI) m/z=615 [M+H]$^+$.

Example 11
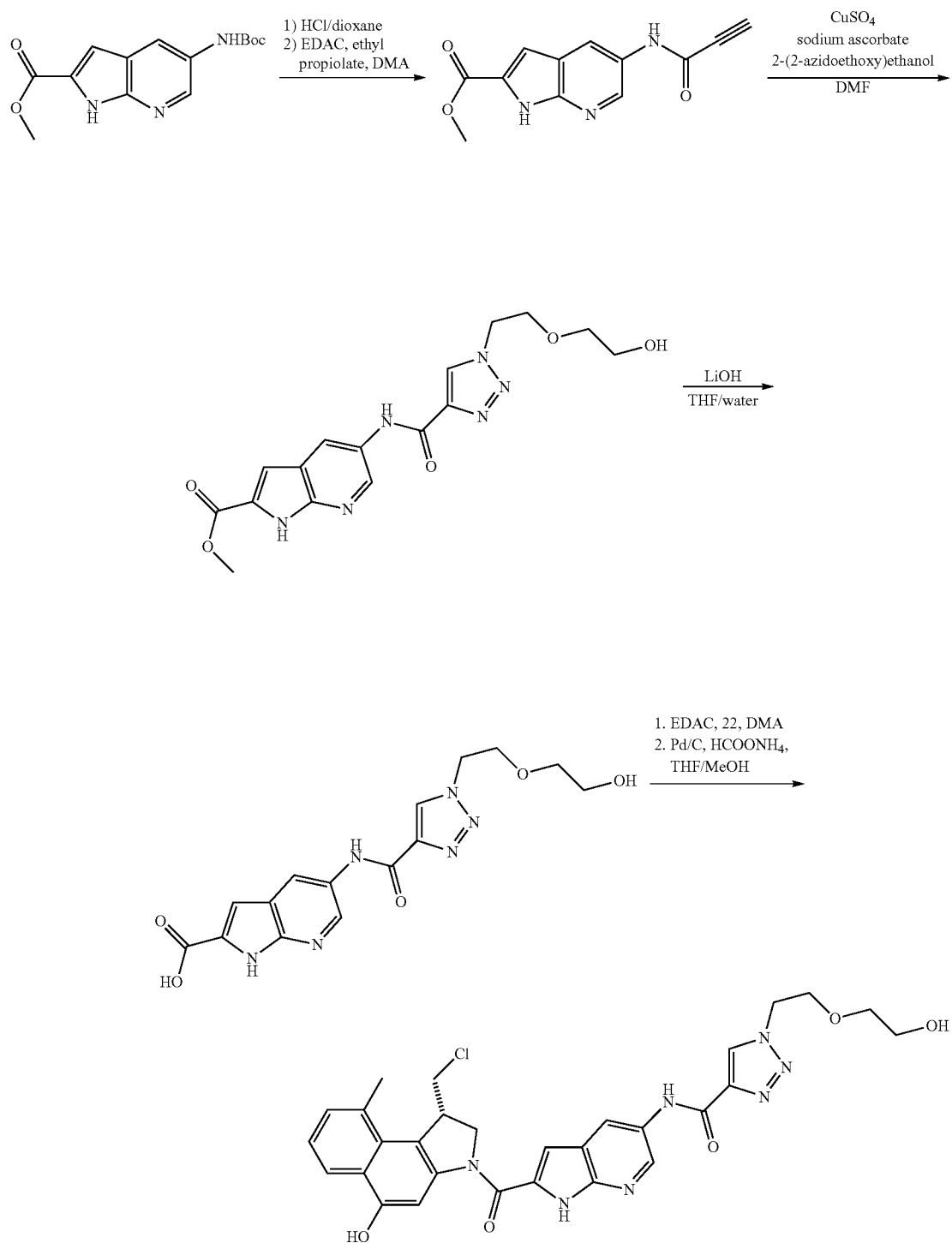
Compound 47: $^1$H NMR (400 MHz, DMSO-d$_6$), δ (ppm): 2.79 (3 H, s, 9-Me), 3.44-3.55 (5 H, m, H-10, 2×OCH$_2$), 3.79 (1 H, d, J=11.5 Hz, H-10), 3.89 (2 H, t, J=5.0 Hz, OCH$_2$), 4.31 (1 H, t, J=8.9 Hz, H-1), 4.48 (1 H, d, J=10.6 Hz, H-2), 4.62-4.69 (4 H, m, H-2, OH, OCH$_2$), 7.17 (1 H, d, J=2 Hz, H-3'), 7.25 (1 H, dd, J=7.0 Hz, 8.3 Hz, H-7), 7.35 (1 H, d, J=7.0 Hz, H-8), 7.93 (1 H, s, H-4), 8.05 (1 H, d, J=8.3 Hz, H-6), 8.56 (1 H, d, J=2 Hz, H-4'), 8.72-8.73 (2 H, m, H-6', triazole-H), 10.47 (1 H, s, OH), 10.64 (1 H, s, NH), 12.28 (1 H, s, NH); MS (ESI) m/z=590 [M+H]$^+$.

357 358
Example 12
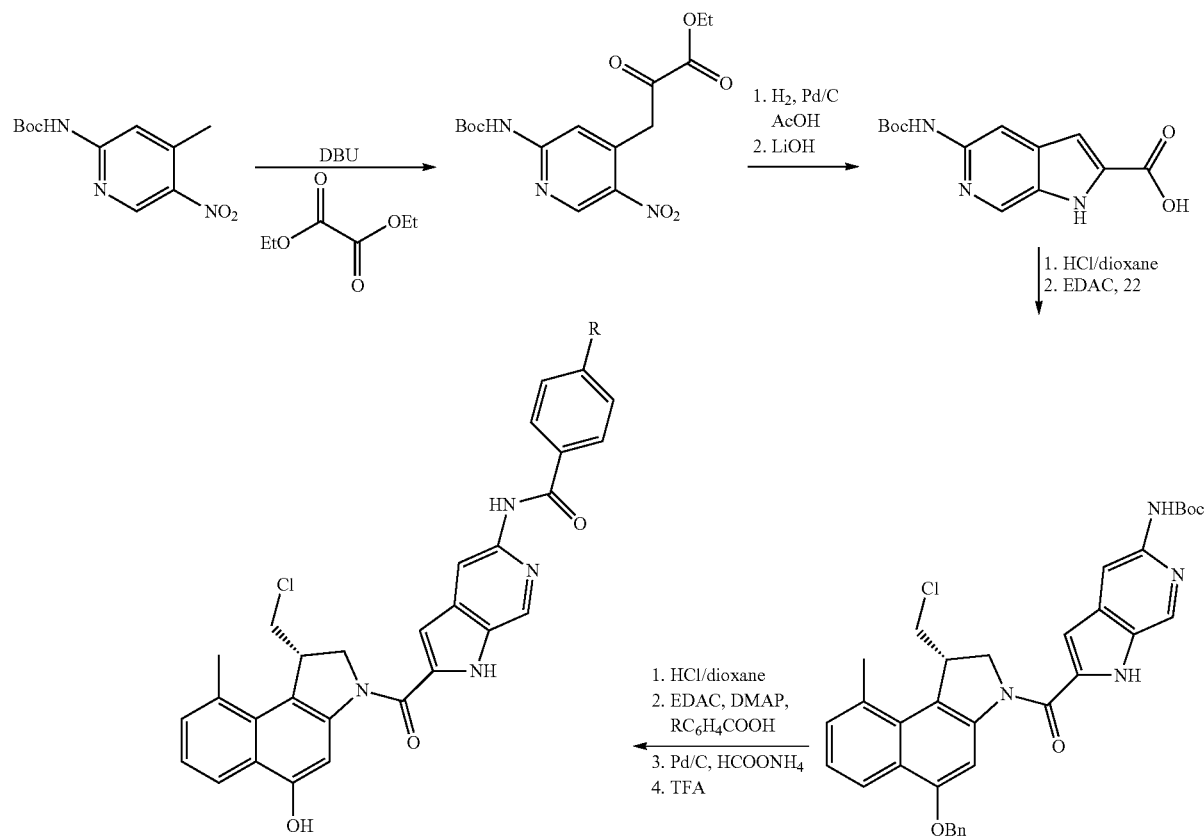
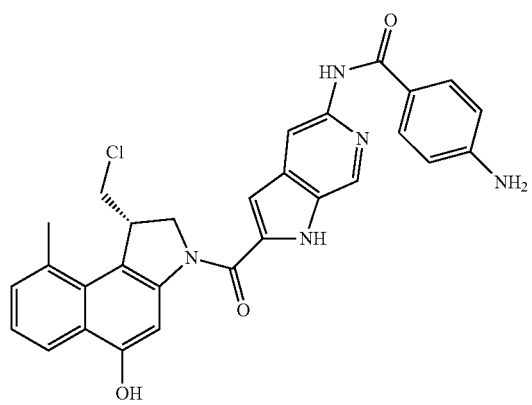
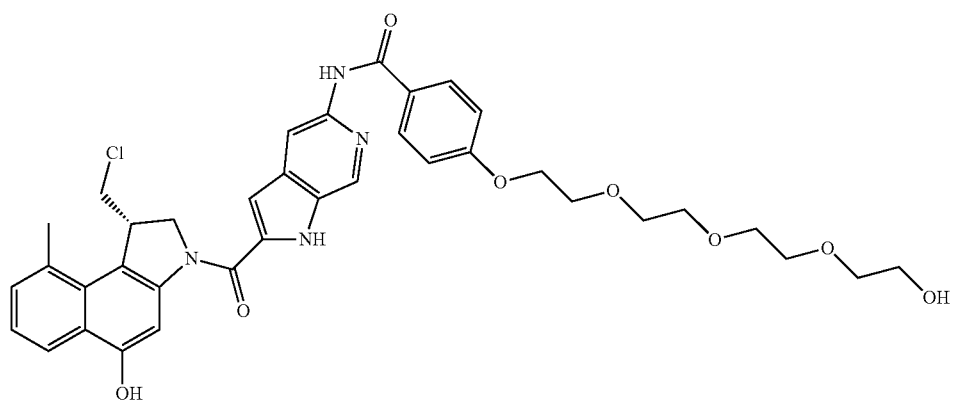

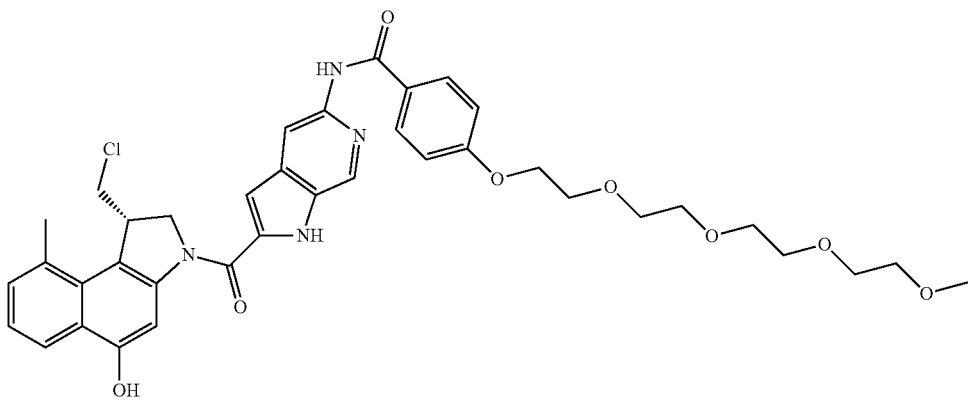

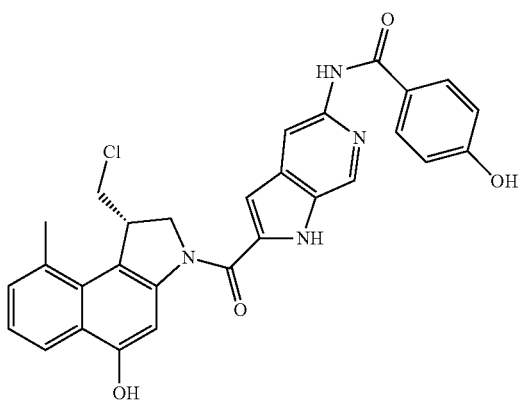

Compound 58: ¹H NMR (300 MHz, DMSO), δ (ppm): 2.79 (3 H, s, 9-Me), 3.60 (1 H, m, H-10), 3.80 (1 H, m, H-10), 4.36 (1 H, m, H-2), 4.47 (1 H, m, H-2), 4.68 (1 H, m, H-1), 6.68 (2 H, d, J=8.7 Hz, H-2''), 7.26 (1 H, t, J=6.9 Hz, H-7), 7.37 (1 H, d, J=6.6 Hz, H-8), 7.47 (1 H, s, H-3'), 7.90 (2 H, d, J=8.7 Hz, H-1''), 7.95-8.10 (2 H, m, H-4, H-6), 8.25 (1 H, s, H-4'), 8.90 (1 H, s, H-7'), 10.56 (1 H, s OH), 11.25 (1 H, s, NH), 12.99 (1 H, s, NH); MS (ESI) m/z=526.3 [M+H]⁺;

Compound 59: ¹H NMR (300 MHz, DMSO), δ (ppm): 2.79 (3 H, s, 9-Me), 3.58 (1 H, m, H-10), 3.79 (1 H, m, H-10), 4.34 (1 H, m, H-2), 4.47 (1 H, m, H-2), 4.67 (1 H, m, H-1), 6.93 (2 H, d, J=8.7 Hz, H-2''), 7.27 (1 H, t, J=7.2 Hz, H-7), 7.35-7.42 (1 H, m, H-8, H-3'), 7.98-8.08 (4 H, m, H-4, H-6, H-1''), 8.41 (1 H, s, H-4'), 8.86 (1 H, s, H-7'), 10.16 (1 H, s, OH), 10.56 (1 H, s OH), 11.15 (1 H, s, NH), 12.80 (1 H, s, NH); MS (ESI) m/z=527.4 [M+H]⁺;

Compound 60: ¹H NMR (300 MHz, DMSO), δ (ppm): 2.80 (3 H, s, 9-Me), 3.39-3.62 (14 H, m, H-10, OH), 3.77 (3 H, m, H-10), 4.23 (2 H, t, J=4.2 Hz), 4.36 (1 H, t, J=6.9 Hz, H-2), 4.49 (1 H, d, J=10.8 Hz, H-2), 4.70 (1 H, m, H-1), 7.12 (2 H, d, J=8.7 Hz, H-2''), 7.27 (1 H, t, J=7.2 Hz, H-7), 7.35-7.42 (2 H, m, H-8, H-3'), 7.97-8.13 (4 H, m, H-4, H-6, H-1''), 8.38 (1 H, s, H-4'), 8.86 (1 H, s, H-7'), 10.54 (1 H, s OH), 11.20 (1 H, s, NH), 12.78 (1 H, s, NH); MS (ESI) m/z=703.5 [M+H]⁺;

Compound 61: ¹H NMR (300 MHz, DMSO), δ (ppm): 2.79 (3 H, s, 9-Me), 3.24 (3 H, s, OMe), 3.40-3.62 (13 H, m, H-10), 3.76-3.82 (3 H, m, H-10), 4.19 (2 H, t, J=4.5 Hz), 4.34 (1 H, t, J=7.5 Hz, H-2), 4.53 (1 H, d, J=12.0 Hz, H-2), 4.70 (1 H, m, H-1), 7.06 (2 H, d, J=8.7 Hz, H-2''), 7.23-7.28 (2 H, H-7, H-3'), 7.35 (1 H, d, J=6.9 Hz, H-8), 7.97-8.07 (4 H, m, H-4, H-6, H-1''), 8.45 (1 H, s, H-4'), 8.68 (1 H, s, H-7'), 10.41 (1 H, s, NH), 10.59 (1 H, s OH), 12.17 (1 H, s, NH); MS (ESI) m/z=717.7 [M+H]⁺.

Example 13

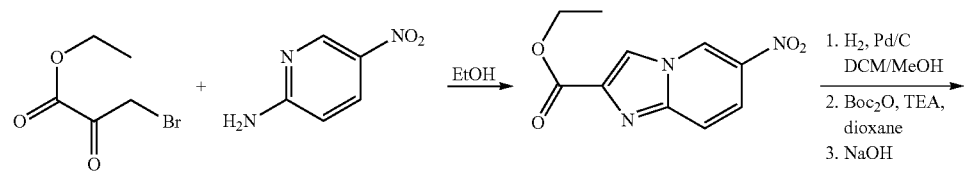

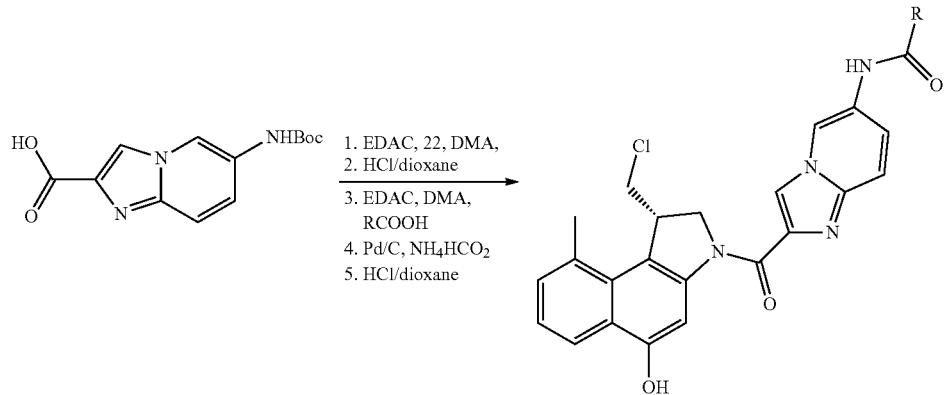
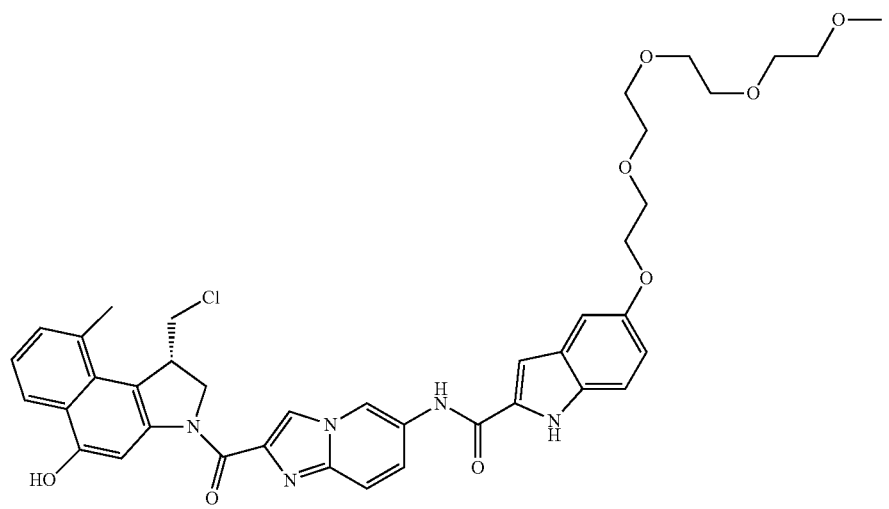
81
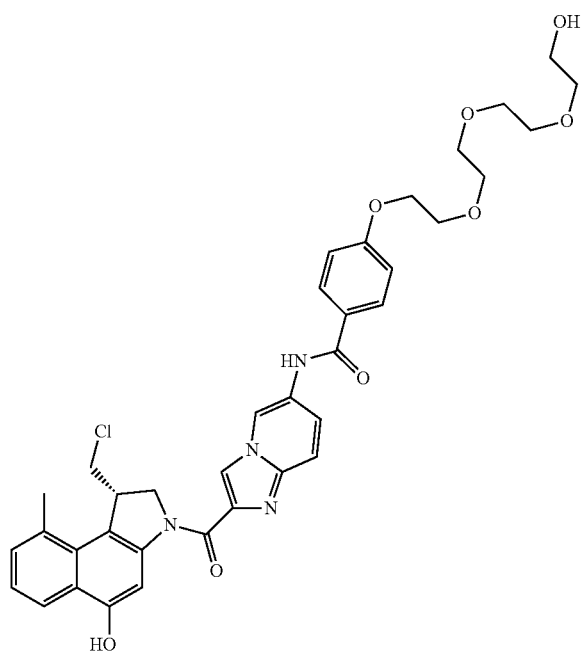
84

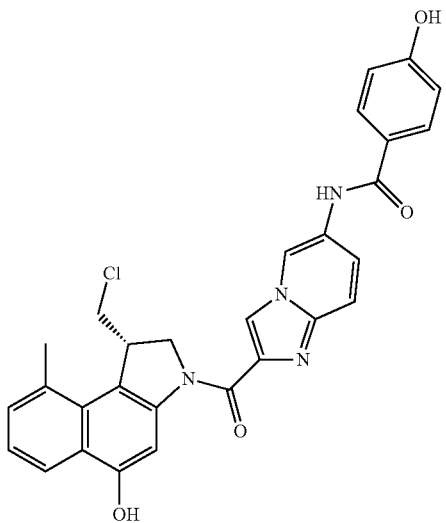

85

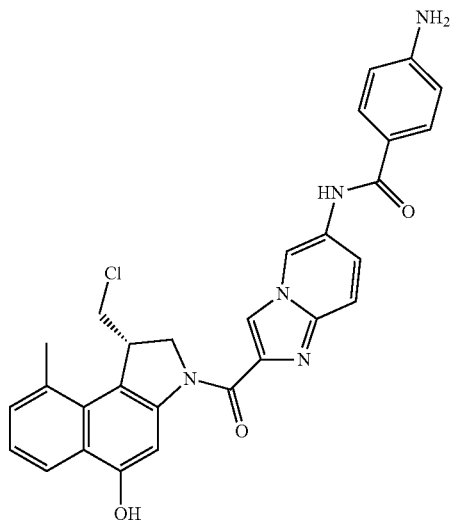

86

Compound 81: $^1$H NMR (300 MHz, DMSO-d$_6$), δ (ppm): 2.79 (3 H, s, 9-Me), 3.23 (3 H, s, OMe), 3.38-3.64 (13 H, m, 6×OCH$_2$, H-10$_a$), 3.78 (3 H, m, OCH$_2$, H-10$_b$), 4.12 (2 H, m, OCH$_2$), 4.30 (1 H, m, H-2$_a$), 4.58 (1 H, m, H-1), 5.06 (1 H, d, J=11.9 Hz, H-2$_b$), 6.92 (1 -H, dd, J=2.3 Hz, 9.1 Hz CH), 7.18 (1 H, s, CH), 7.23 (1 H, t, J=7.2 Hz, H-7'), 7.36 (3 H, m, 2×CH, H-8'), 7.62 (1 H, dd, J=2.0 Hz, 9.9 Hz, CH), 7.76 (1 H, d, J=9.7 Hz, CH), 8.05 (1 H, d, J=7.9 Hz, H-6'), 8.10 (1 H, bs, H-4'), 8.70 (1 H, s, CH), 9.42 (1 H, s, CH), 10.37 (1 H, s, OH), 10.42 (1 H, s, NH), 11.64 (1 H, s, NH); MS (ESI) m/z=756.5 [M+H]$^+$;

Compound 84: $^1$H NMR (300 MHz, DMSO-d$_6$), δ (ppm): 2.78 (3 H, s, 9-Me), 3.37-3.65 (13 H, m, 6×CH$_2$O, H-10), 3.71-3.81 (3 H, m, CH$_2$O, H-10), 4.20 (1 H, t, J=4.5 Hz, CH$_2$O), 4.30 (1 H, t, J=8.2 Hz, H-1), 4.52-4.62 (2 H, m, H-2, OH), 5.05 (1 H, d, J=11.8 Hz, H-2), 7.12 (2 H, d, J=8.8 Hz, H-3''), 7.23 (1 H, t, J=7.7 Hz, H-7), 7.33 (1 H, d, J=6.7 Hz, H-8), 7.57 (1 H, dd, J=1.8 Hz, 9.7 Hz, H-6'), 7.73 (1 H, d, J=9.7 Hz, H-7'), 8.00 (2 H, d, J=8.8 Hz, H-2''), 8.04 (1 H, d, J=8.4 Hz, H-6), 8.09 (1 H, bs, H-4), 8.66 (1 H, s, H-3'), 9.46 (1 H, s, H-4'), 10.28 (1 H, s, NH), 10.42 (1 H, s, OH); MS (ESI) m/z=703 [M+H]$^+$;

Compound 85: $^1$H NMR (300 MHz, DMSO-d$_6$), δ (ppm): 2.78 (3 H, s, 9-Me), 3.42 (1 H, t, J=10.5 Hz, H-10), 3.75 (1 H, d, J=11.0 Hz, H-10), 4.30 (1 H, t, J=8.9 Hz, H-1), 4.57 (1 H, dd, J=7.6 Hz, 11.8 Hz, H-2), 5.04 (1 H, d, J=11.8 Hz, H-2), 6.89 (1 H, d, J=8.7 Hz, H-3''), 7.23 (1 H, t, J=7.6 Hz, H-7), 7.33 (1 H, d, J=6.8 Hz, H-8), 7.57 (1 H, dd, J=1.8 Hz, 9.7 Hz, H-6'), 7.71 (1 H, d, J=9.7 Hz, H-7'), 7.90 (2 H, d, J=8.7 Hz, H-2''), 8.04 (1 H, d, J=8.1 Hz, H-6), 8.09 (1 H, bs, H-4), 8.66 (1 H, s, H-3'), 9.44 (1 H, s, H-4'), 10.17 (1 H, s, OH), 10.18 (1 H, s, NH), 10.42 (1 H, s, OH); MS (ESI) m/z=527 [M+H]$^+$;

Compound 86: $^1$H NMR (300 MHz, DMSO-d$_6$), δ (ppm): 2.78 (3 H, s, 9-Me), 3.44 (1 H, t, J=10.6 Hz, H-10), 3.76 (1 H, d, J=10.3 Hz, H-10), 4.32 (1 H, t, J=7.4 Hz, H-1), 4.58 (1 H, dd, J=7.4 Hz, 11.2 Hz, H-2), 4.96 (1 H, d, J=11.2 Hz, H-2), 5.93 (1 H, bs, NH$_2$), 6.63 (2 H, d, J=8.4 Hz, H-3''), 7.24 (1 H, t, J=7.6 Hz, H-7), 7.33 (1 H, d, J=6.7 Hz, H-8), 7.73 (2 H, m, H-6', H-7'), 8.04 (1 H, d, J=8.2 Hz, H-6), 8.08 (1 H, bs, H-4), 8.74 (1 H, s, H-3'), 9.51 (1 H, s, H-4'), 10.05 (1 H, s, NH), 10.45 (1 H, s, OH); MS (ESI) m/z=526 [M+H]$^+$.

Example 14

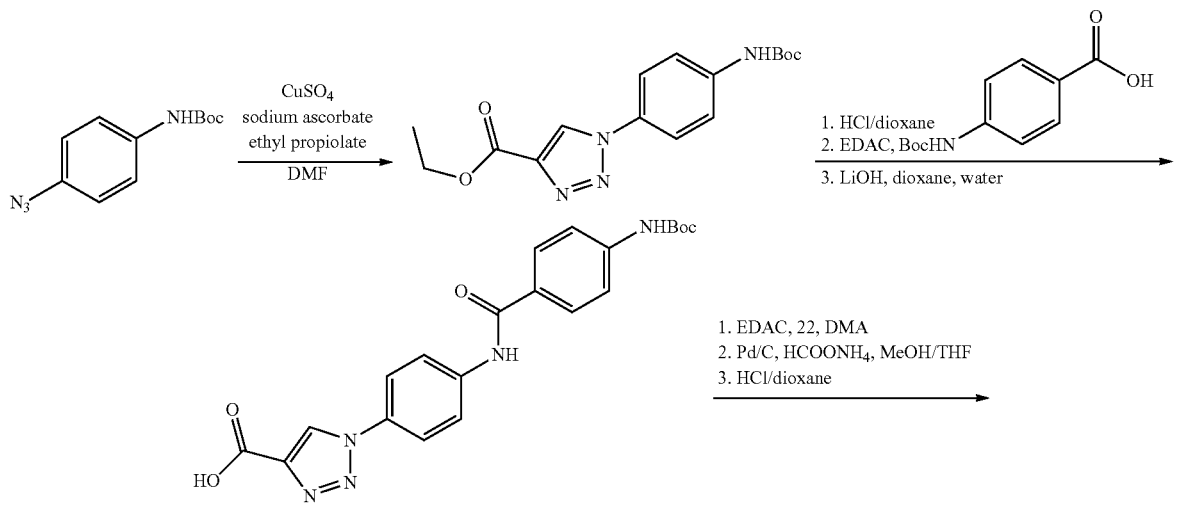

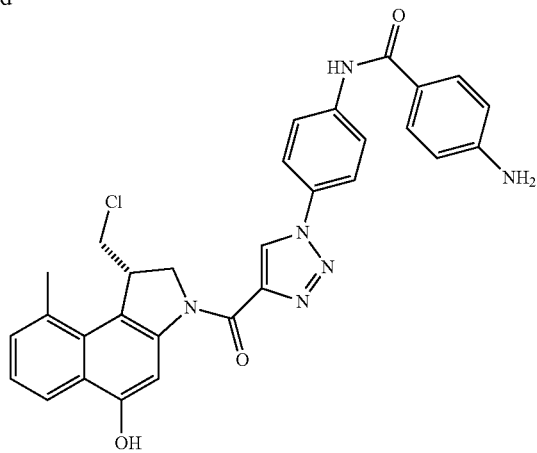
40
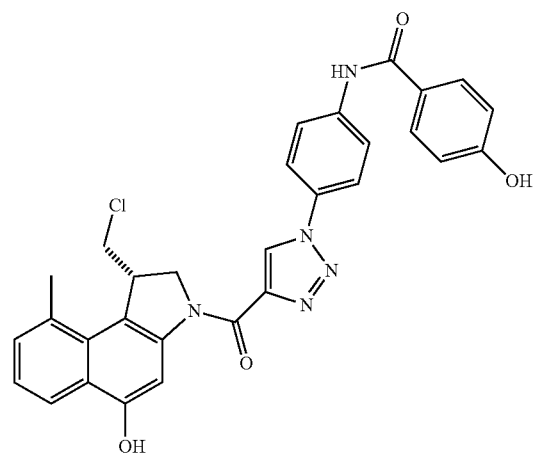
41
Compound 40: ¹H NMR (400 MHz, DMSO-d₆), δ (ppm): 2.79 (3 H, s, 9-Me), 3.50 (1 H, m, H-10), 3.79 (1 H, d, J=11.5 Hz, H-10), 4.36 (1 H, t, J=8.9 Hz, H-1), 4.61 (1 H, t, J=9.5 Hz, H-2), 4.92 (1 H, d, J=11.5 Hz, H-2), 6.88 (2 H, d, J=8.5 Hz, Ar—H), 7.25 (1 H, dd, J=7.0 Hz, 8.5 Hz, H-7), 7.35 (1 H, d, J=7.0 Hz, H-8), 7.80 (2 H, d, J=8.9 Hz, Ar—H), 7.95-8.14 (8 H, m, H-4, H-6, Ar—H, NH₂), 9.40 (1 H, s, triazole-H), 10.14 (1 H, s, OH), 10.50 (1 H, s, NH); MS (ESI) m/z=553 [M+H]⁺;
Compound 41: ¹H NMR (400 MHz, DMSO-d₆), δ (ppm): 2.79 (3 H, s, 9-Me), 3.50 (1 H, t, J=9.8 Hz, H-10), 3.79 (1 H, d, J=11.5 Hz, H-10), 4.36 (1 H, t, J=8.9 Hz, H-1), 4.61 (1 H, t, J=9.5 Hz, H-2), 4.92 (1 H, d, J=11.0 Hz, H-2), 6.90 (2 H, d, J=8.5 Hz, Ar—H), 7.25 (1 H, dd, J=7.0 Hz, 8.5 Hz, H-7), 7.35 (1 H, d, J=7.0 Hz, H-8), 7.90 (2 H, d, J=8.6 Hz, Ar—H), 7.98-8.14 (6 H, m, H-4, H-6, Ar—H), 9.40 (1 H, s, triazole-H), 10.16 (1 H, s, NH), 10.29 (1 H, s, OH), 10.49 (1 H, s, OH); MS (ESI) m/z=554 [M+H]⁺.
Example 15
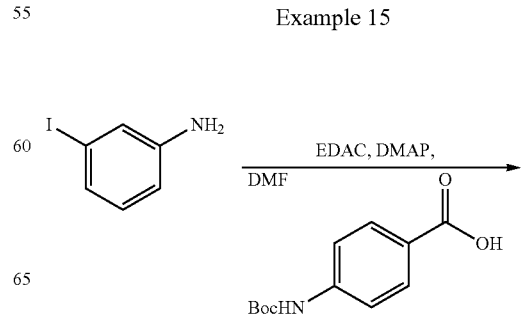

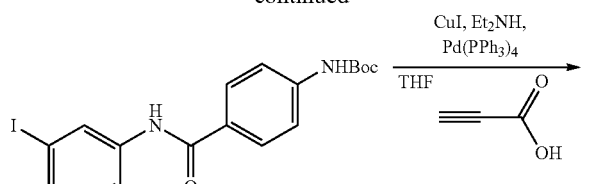

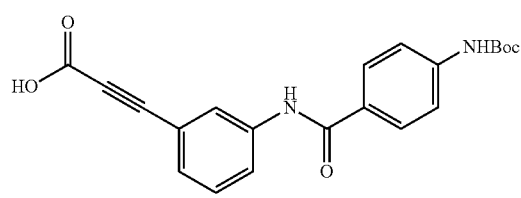

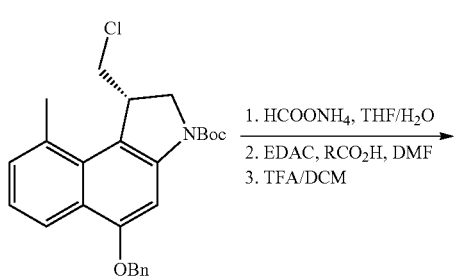

62

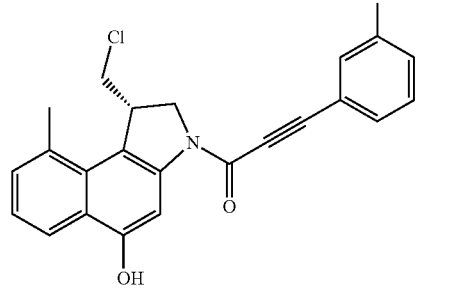

63

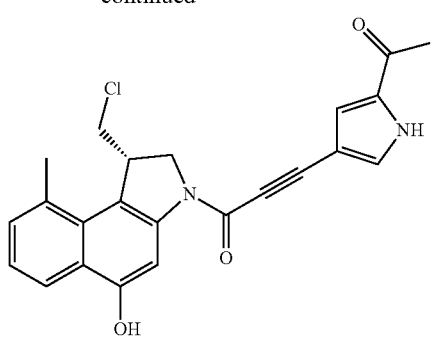

64

Compound 62: $^1$H NMR (300 MHz, DMSO-$d_6$), δ (ppm): 2.76 (3 H, s, 9-Me), 3.58 (1 H, m, H-10$_a$), 3.80 (1 H, m, H-10$_b$), 4.34 (1 H, m, H-1), 4.44 (1 H, m, H-2$_a$), 4.54 (1 H, m, H-2$_b$), 6.62 (2 H, d, J=8.9 Hz, 2×CH), 7.25 (1 H, t, J=7.6 Hz, H-7'), 7.36 (1 H, m, H-8'), 7.46 (1 H, t, J=8.4 Hz, CH), 7.74 (2 H, d, J=8.4 Hz, 2×CH), 7.92 (1 H, d, J=8.4 Hz, CH), 7.99 (1 H, s, H-4'), 8.04 (1 H, d, J=8.4 Hz, H-6'), 8.15 (1 H, s, CH), 9.98 (1 H, s, NH), 10.53 (1 H, bs, OH); MS (ESI) m/z=510.1 [M+H]$^+$;

Compound 63: $^1$H NMR (300 MHz, DMSO-$d_6$), δ (ppm): 2.25 (6 H, s, Me$_2$N), 2.67 (2 H, t, J=5.7 Hz, CH$_2$NMe$_2$), 2.76 (3 H, s, 9-Me), 3.57 (1 H, t, J=10.2 Hz, H-10$_a$), 3.81 (1 H, m, H-10$_b$), 4.13 (2 H, t, J=5.7 Hz, OCH$_2$), 4.33 (1 H, m, H-1), 4.43 (1 H, m, H-2$_a$), 4.53 (1 H, m, H-2$_b$), 7.16 (1 H, d, J=8.3 Hz, CH), 7.25 (3 H, m, H-7', 2×CH), 7.35 (1 H, m, H-8'), 7.43 (1 H, t, J=7.9 Hz, CH), 7.98 (1 H, s, H-4'), 8.04 (1 H, d, J=6.8 Hz, H-6'), 10.53 (1 H, s, OH); MS (ESI) m/z=427.2 [M+H]$^+$;

Compound 64: $^1$H NMR (300 MHz, DMSO-$d_6$), δ (ppm): 2.41 (3 H, s, CH$_3$CO), 2.76 (3 H, s, 9-Me), 3.51 (1 H, m, H-10$_a$), 3.79 (1 H, m, H-10$_b$), 4.33 (2 H, m, H-2$_a$, H-1), 4.49 (1 H, m, H-2$_b$), 7.23 (1 H, t, J=8.2 Hz, H-7'), 7.31-7.38 (2 H, m, CH, H-8'), 7.69 (1 H, m, CH), 7.98 (1 H, s, H-4'), 8.02 (1 H, d, J=8.2 Hz, H-6), 10.48 (1 H, s, OH), 12.46 (1 H, bs, NH); MS (ESI) m/z=407.1 [M+H]$^+$.

Example 16

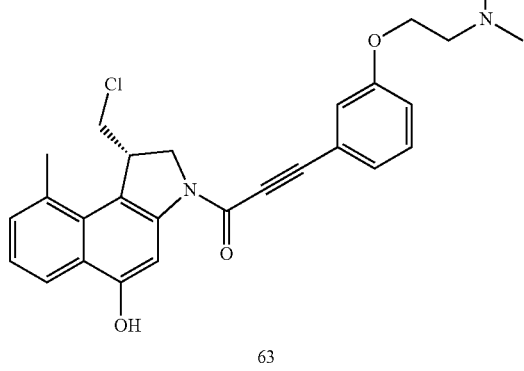

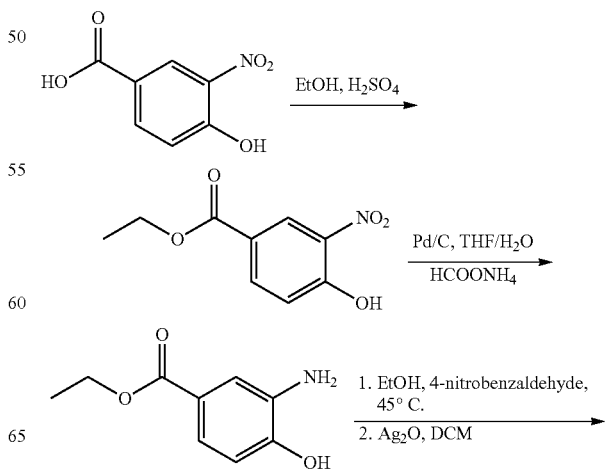

369
-continued
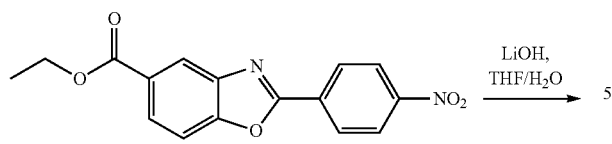
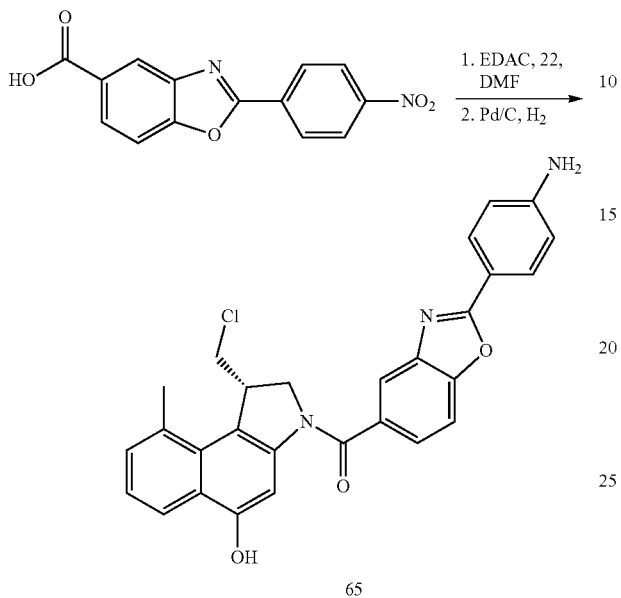
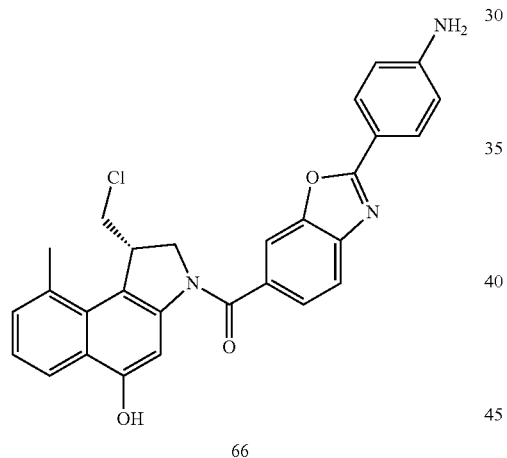
Compound 65: ¹H NMR (300 MHz, DMSO-$d_6$), δ (ppm): 2.75 (3 H, s, 9-Me), 3.59 (1 H, m, H-$10_a$), 3.76 (1 H, m, H-$10_b$), 4.02 (1 H, m, H-1), 4.18 (1 H, m, H-$2_a$), 4.33 (1 H, m, H-$2_b$), 6.07 (2 H, bs, NH$_2$), 6.70 (2 H, d, J=8.2 Hz, 2×CH), 7.18-7.35 (2 H, m, H-7', H-8'), 7.58 (1 H, d, J=8.2 Hz, CH), 7.80 (1 H, d, J=8.5 Hz, CH), 7.90 (2 H, d, J=8.5 Hz, 2×CH), 7.94 (1 H, s, H-4'), 8.02 (1 H, d, J=8.1 Hz, H-6'), 10.39 (1 H, bs, OH); MS (ESI) m/z=484.4 [M+H]⁺;
Compound 66: ¹H NMR (300 MHz, DMSO-$d_6$), δ (ppm): 2.75 (3 H, s, 9-Me), 3.60 (1 H, m, H-$10_a$), 3.77 (1 H, m, H-$10_b$), 4.00 (1 H, m, H-1), 4.19 (1 H, m, H-$2_a$), 4.33 (1 H, m, H-$2_b$), 6.06 (2 H, bs, NH$_2$), 6.71 (2 H, d, J=8.6 Hz, 2×CH), 7.22 (1 H, t, J=7.6 Hz, H-7'), 7.32 (1 H, d, J=6.6 Hz, H-8'), 7.39 (1 H, m, CH), 7.59 (1 H, m, CH), 7.80 (1 H, d, J=8.2 Hz, CH), 7.90 (1 H, d, J=8.6 Hz, 2×CH), 7.95 (1 H, s, H-4'), 8.02 (1 H, d, J=8.2 Hz, H-6'), 10.40 (1 H, bs, OH); MS (ESI) m/z=484.2 [M+H]⁺.
Example 17
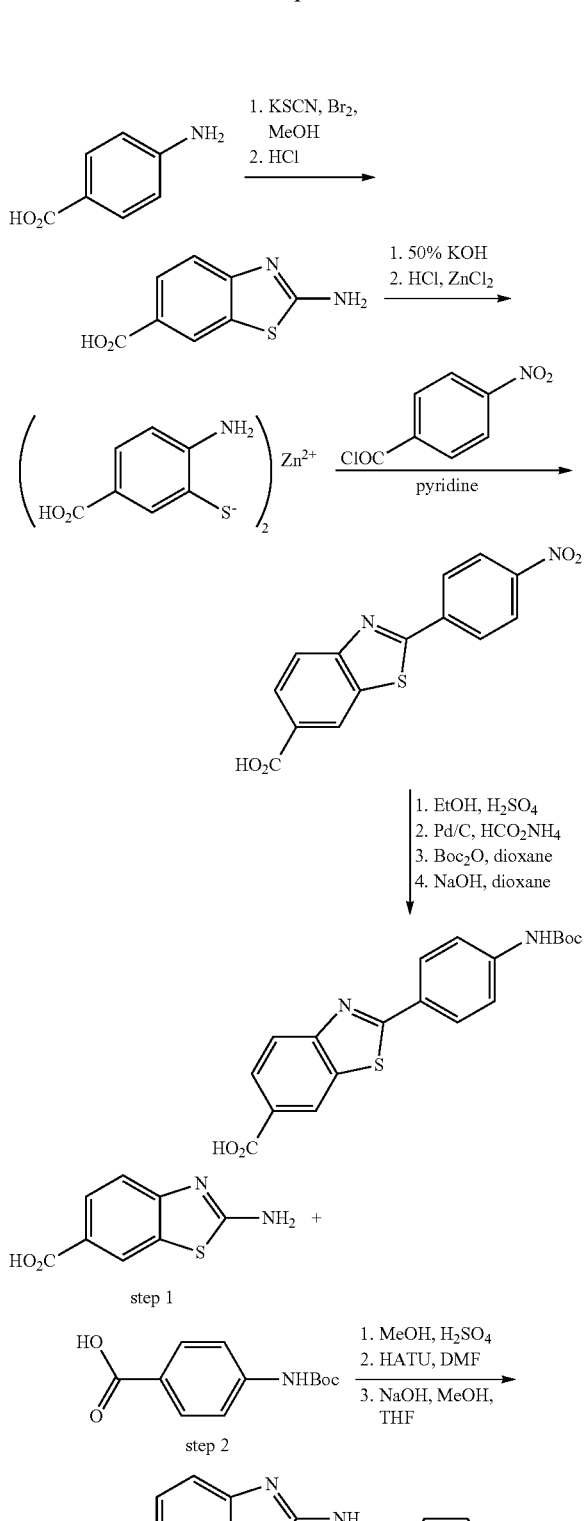

-continued

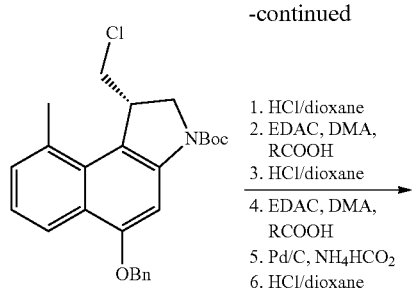
1. HCl/dioxane
2. EDAC, DMA, RCOOH
3. HCl/dioxane
4. EDAC, DMA, RCOOH
5. Pd/C, NH₄HCO₂
6. HCl/dioxane

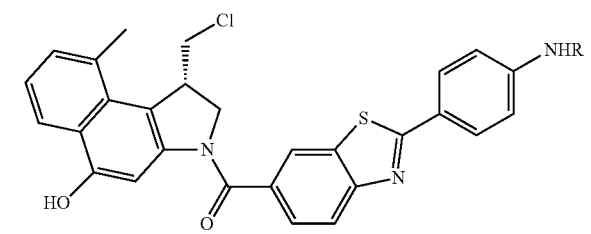
98

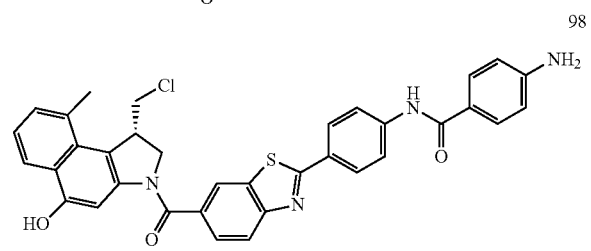
99

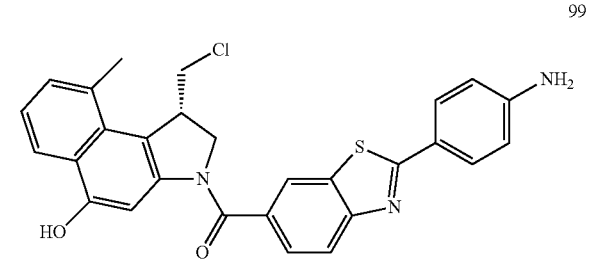
100

Compound 98: $^1$H NMR (300 MHz, DMSO-$d_6$), δ (ppm): 2.76 (3 H, s, 9-Me), 3.58 (1 H, m, H-10), 3.78 (1 H, d, J=10.6 Hz, H-10), 4.01 (1 H, m, H-2), 4.21 (1 H, m, H-2), 4.37 (1 H, m, H-1), 6.77 (2 H, d, J=8.5 Hz, H-3'''), 7.23 (1 H, t, J=7.6 Hz, H-7), 7.33 (1 H, d, J=6.8 Hz, H-8), 7.75-7.85 (3 H, m, H-4', H-2'''), 7.98-8.08 (3 H, m, H-6, H-3''), 8.12 (2 H, d, J=8.8, H-2''), 8.14 (1 H, d, J=8.2, H-5'), 8.47 (1 H, s, H-7'), 10.22 (1 H, s, OH), 10.42 (1 H, bs, NH); MS (ESI) m/z=618 [M+H]⁺;

Compound 99: $^1$H NMR (300 MHz, DMSO-$d_6$), δ (ppm): 2.75 (3 H, s, 9-Me), 3.59 (1 H, m, H-10), 3.77 (1 H, d, J=10.4 Hz, H-10), 4.01 (1 H, m, H-2), 4.21 (1 H, m, H-2), 4.35 (1 H, m, H-1), 6.75 (2 H, d, J=8.6 Hz, H-3''), 7.22 (1 H, t, J=7.7 Hz, H-7), 7.33 (1 H, d, J=6.7 Hz, H-8), 7.70 (1 H, bs, H-4), 7.72 (1 H, d, J=8.4 Hz, H-5'), 7.84 (2 H, d, J=8.6 Hz, H-2''), 7.90-8.10 (2 H, m, H-6, H-4'), 8.37 (1 H, s H-7'), 10.40 (1 H, s, OH); MS (ESI) m/z=500 [M+H]⁺;

Compound 100: $^1$H NMR (300 MHz, DMSO-$d_6$), δ (ppm): 2.76 (3 H, s, 9-Me), 3.69 (1 H, m, H-10), 3.78 (1 H, m, H-10), 4.03 (1 H, m, H-2), 4.19 (1 H, m, H-2), 4.37 (1 H, m, H-1), 6.68 (2 H, d, J=8.7 Hz, H-3''), 7.23 (1 H, dd, J=6.7 Hz, 8.0 Hz, H-7), 7.33 (1 H, d, J=6.7 Hz, H-8), 7.60 (1 H, bs, H-4), 7.72 (1 H, dd, J=1.3 Hz, 8.4 Hz, H-6'), 7.84 (1 H, d, J=8.4 Hz, H-7'), 7.94 (2 H, d, J=8.7 Hz, H-6''), 8.02 (1 H, d, J=8.0 Hz, H-2''), 8.34 (1 H, d, J=1.3 Hz, H-6), 10.39 (1 H, bs, OH), 12.53 (1 H, s, NH); MS (ESI) m/z=543 [M+H]⁺.

Example 18

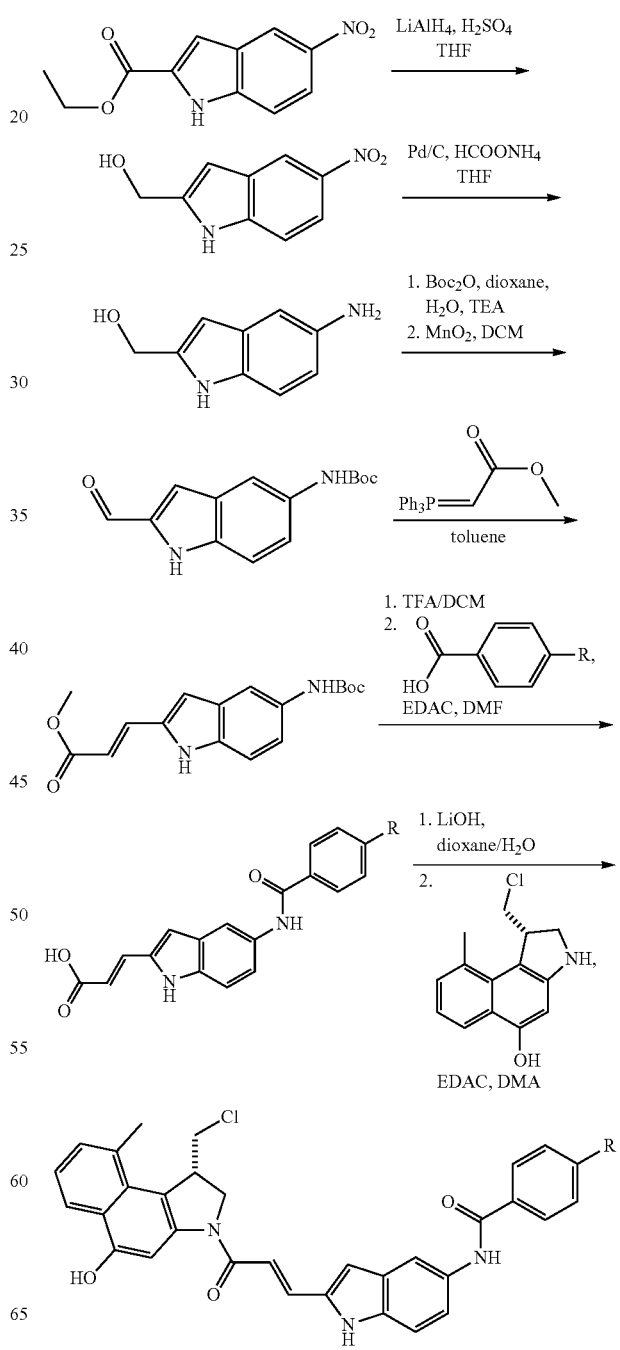

-continued

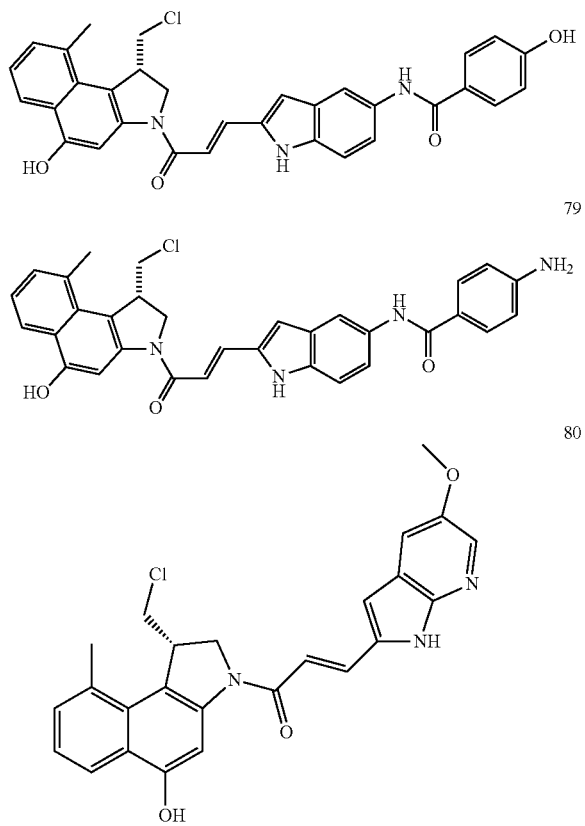

Compound 78: ¹H NMR (300 MHz, DMSO-$d_6$), δ (ppm): 2.79 (3 H, s, 9-Me), 3.50 (1 H, m, H-10), 3.76 (1 H, d, J=10.4 Hz, H-10), 4.31-4.40 (2 H, m, H-1, H-2), 4.47-4.54 (1 H, m, H-2), 6.86 (2 H, d, J=8.5 Hz, H-3″), 6.91 (1 H, s, H-3′), 7.18-7.27 (2 H, m, H-7, CH=CH), 7.33 (1 H, d, J=6.6 Hz, H-8), 7.38 (1 H, d, J=9.0 Hz, H-7′), 7.50 (1 H, dd, J=9.0 Hz, 1.8 Hz, H-6′), 7.67 (1 H, d, J=14.9 Hz, CH=CH), 7.87 (2 H, d, J=8.9 Hz, H-2″), 7.99-8.06 (2 H, m, H-4′, H-6), 8.20 (1 H, bs, H-4), 9.89 (1 H, s, NH), 10.03 (1 H, s, OH), 10.43 (1 H, s, OH), 11.61 (1 H, s, NH); MS (ESI) m/z=552 [M+H]⁺;

Compound 79: ¹H NMR (300 MHz, DMSO-$d_6$), δ (ppm): 2.79 (3 H, s, 9-Me), 3.49 (1 H, t, J=9.4 Hz, H-10), 3.76 (1 H, d, J=10.6 Hz, H-10), 4.31-4.41 (2 H, m, H-1, H-2), 4.45-4.55 (1 H, m, H-2), 5.70 (2 H, bs, NH₂), 6.61 (2 H, d, J=8.8 Hz, H-3″), 6.89 (1 H, s, H-3′), 7.17-7.27 (2 H, m, H-7, CH=CH), 7.30-7.40 (2 H, m, H-8, H-7′), 7.50 (1 H, dd, J=8.9 Hz, 2.1 Hz, H-6′), 7.67 (1 H, d, J=15.0 Hz, CH=CH), 7.74 (2 H, d, J=8.7 Hz, H-2″), 7.98-8.05 (2 H, m, H-6, H-4′), 8.21 (1 H, bs, H-4), 9.66 (1 H, s, NH), 10.44 (1 H, s, OH), 11.59 (1 H, s, NH); MS (ESI) m/z=551 [M+H]⁺;

Compound 80: ¹H NMR (300 MHz, DMSO-$d_6$), δ (ppm): 2.78 (3 H, s, 9-Me), 3.47 (1 H, m, H-10$_a$), 3.75 (1 H, d, J=11.1 Hz, H-10$_b$), 3.83 (3 H, s, OMe), 4.34 (2 H, m, H-2$_a$, HA), 4.53 (1 H, m, H-2$_b$), 6.85 (1 H, d, J=2.0 Hz, CH) 7.21 (1 H, t, J=7.9 Hz, H-7′), 7.31 (1 H, s, H-8′), 7.37 (1 H, d, J=15.3 Hz, =CH—), 7.57 (1 H, d, J=3.2 Hz, CH), 7.65 (1 H, d, J=15.3 Hz, =CH—), 8.03 (1 H, d, J=7.9 Hz, H-6′), 8.07 (1 H, d, J=3.2 Hz, CH), 8.21 (1 H, bs, H-4′), 10.43 (1 H, s, OH), 12.12 (1 H, s, NH); MS (ESI) m/z=448.1 [M+H]⁺.

Example 19

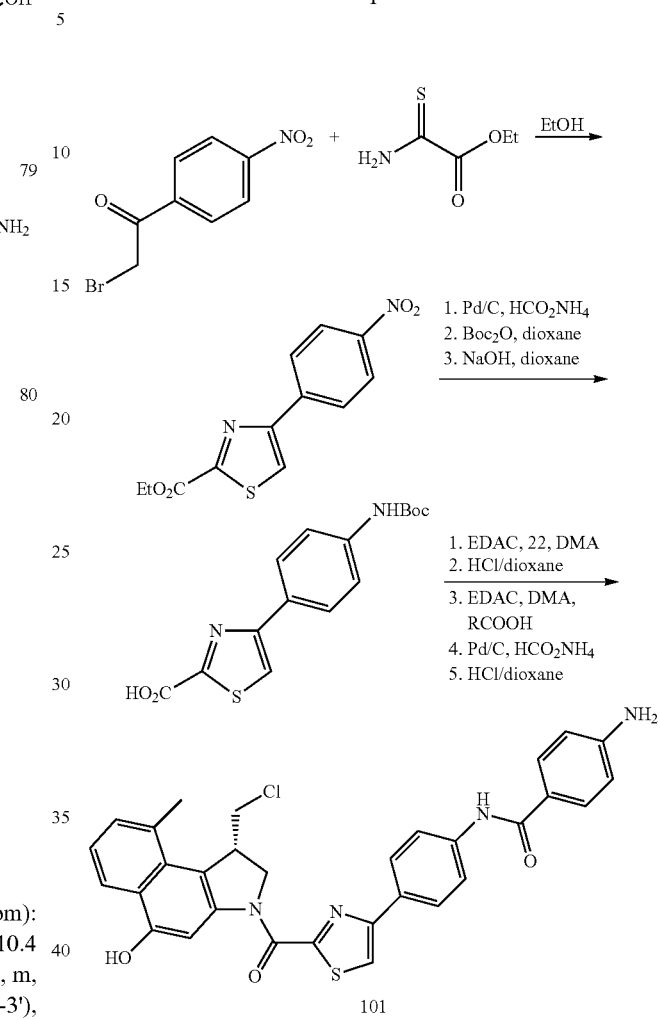

Compound 101: ¹H NMR (300 MHz, DMSO-$d_6$), δ (ppm): 2.81 (3 H, s, 9-Me), 3.58 (1 H, t, J=10.9 Hz, H-10), 3.81 (1 H, d, J=10.9 Hz, H-10), 4.43 (1 H, t, J=7.3 Hz, H-1), 4.71 (1 H, dd, J=7.2, 12.1 Hz, H-2), 5.36 (1 H, d, J=12.1 Hz, H-2), 6.71 (2 H, d, J=8.2 Hz, H-3‴), 7.23 (1 H, t, J=7.6 Hz, H-7), 7.33 (1 H, d, J=6.7 Hz, H-8), 7.78 (2 H, d, J=8.2 Hz, H-2‴), 7.91 (2 H, d, J=8.7 Hz, H-2″), 8.01 (2 H, d, J=8.7 Hz, H-3″), 8.07 (1 H, d, J=8.0 Hz, H-6), 8.14 (1 H, s, H-4), 8.42 (1 H, s, H-5′-thiazole), 9.97 (1 H, s, NH), 10.53 (1 H, s, OH); MS (ESI) m/z=569 [M+H]⁺.

Example 20

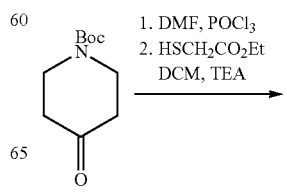

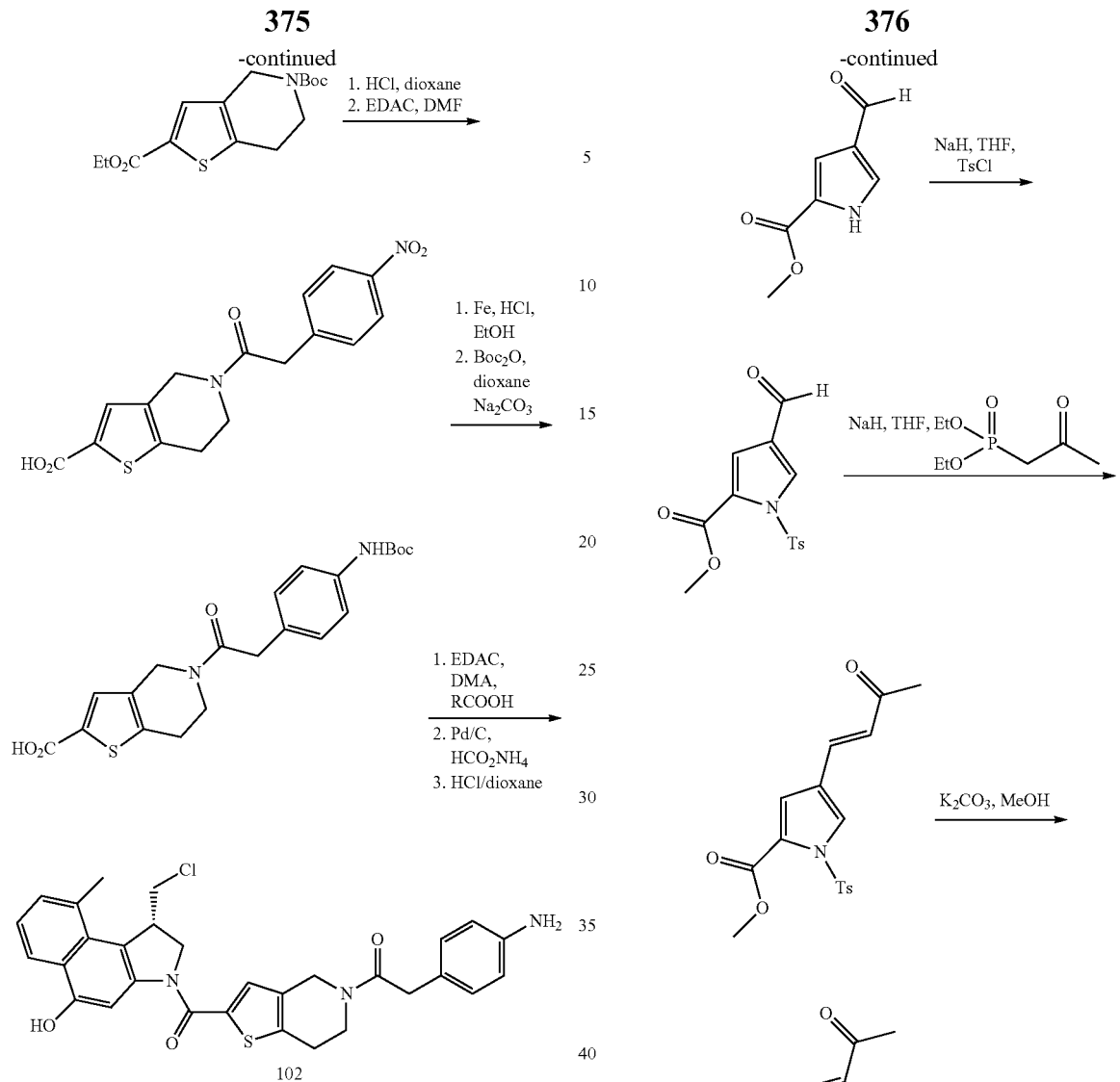
Compound 102: $^1$H NMR (300 MHz, DMSO-$d_6$), δ (ppm): 2.65-2.85 (2 H, m, thiophene-CH$_2$), 2.76 (3 H, s, 9-Me), 3.47 (1 H, m, H-10), 3.58-3.65 (2 H, m, CH$_2$N), 3.72-3.84 (3 H, m, CH$_2$N, H-10), 4.27 (1 H, m, H-1), 4.38 (1 H, m, H-2), 4.50-4.70 (3 H, m, CH$_2$C=O, H-1), 4.97 (2 H, bs, NH$_2$), 6.50 (2 H, m, H-2"), 6.91 (1 H, m, H-3"), 7.23 (1 H, t, J=7.6 Hz, H-7), 7.33 (1 H, d, J=6.9 Hz, H-8), 7.58 (1 H, bs, H-4), 7.87 (1 H, s, H-2'), 8.03 (1 H, s, H-6), 10.42 (1 H, s, OH); MS (ESI) m/z=546 [M+H]$^+$.
Example 21
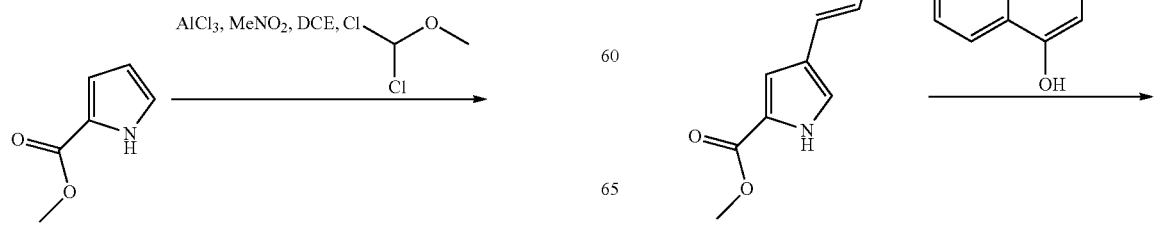

-continued

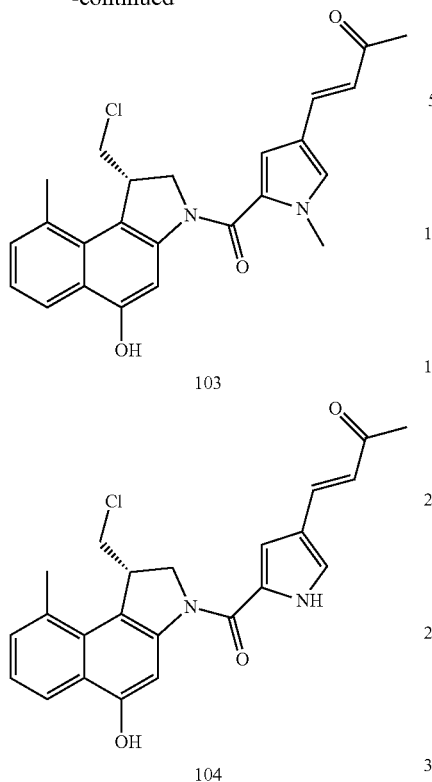

103

104

Compound 103: $^1$H NMR (200 MHz, CDCl$_3$), δ (ppm): 2.34 (3 H, s, Me), 2.82 (3 H, s, 9-Me), 3.30 (1 H, t, J=11.0 Hz), 3.68 (1 H, d, J=11.3 Hz), 3.95 (3 H, s, Me), 4.12 (1 H, m, H-1), 4.43 (1 H, t, J=6.90 Hz, H-2), 4.56 (1 H, d, J=11.0 Hz, H-2), 6.46 (1 H, d, J=16.1 Hz), 6.87 (1 H, d, J=1.7 Hz), 7.11 (1 H, d, J=1.7 Hz), 7.28 (1 H, m, H-7), 7.31 (1 H, s, H-8), 7.45 (1 H, d, J=16.1 Hz), 7.66 (1 H, s, H-4), 8.15 (1 H, d, J=8.9 Hz, H-6); MS (ESI) m/z=423.1 [M+H]$^+$;

Compound 104: $^1$H NMR (300 MHz, DMSO), δ (ppm): 2.26 (3 H, s, Me), 2.78 (3 H, s, 9-Me), 3.46 (1 H, t, J=11.0 Hz), 3.78 (1 H, d, J=11.7 Hz), 4.29 (1 H, t, J=7.75 Hz, H-2), 4.44 (1 H, d, J=10.7 Hz, H-2), 4.60 (1 H, m, H-1), 6.60 (1 H, d, J=16.1 Hz), 7.21 (1 H, d, J=7.0 Hz, H-7), 7.25 (1 H, s), 7.33 (1 H, d, J=6.9 Hz, H-8), 7.52 (1 H, d, J=3.0 Hz, H-12), 7.60 (1 H, d, J=16.3 Hz, H-14), 7.98 (1 H, s, H-4), 8.02 (1 H, d, J=8.5 Hz, H-6), 10.41 (1 H, s, NH); MS (ESI) m/z=409.2 [M+H]$^+$.

Example 22

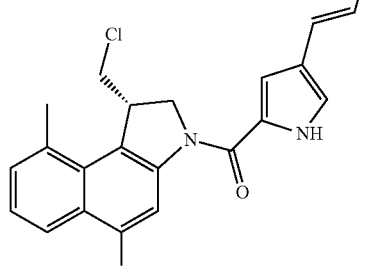

-continued

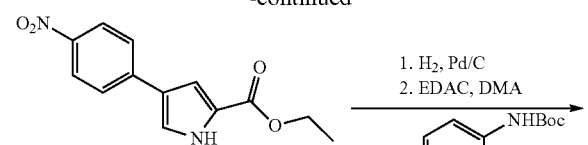

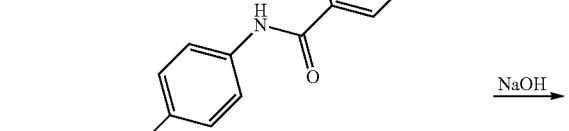

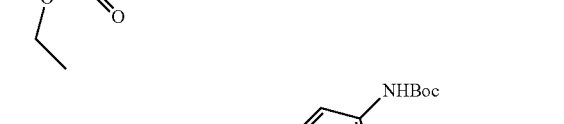

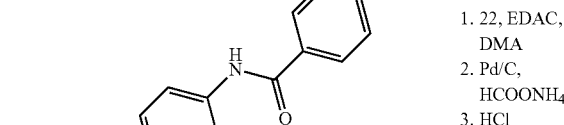

105

Compound 105: $^1$H NMR (400 MHz, DMSO), δ (ppm): 2.73 (3 H, s, 9-Me), 3.61 (1 H, m, H-10), 3.74 (1 H, d, J=10.8 Hz, H-10), 4.24 (1 H, m), 4.45 (1 H, d), 4.61 (1 H, t), 6.62 (2 H, d), 7.15 (2 H, t), 7.18 (1 H, d), 7.43 (1 H, s), 7.57 (2 H, d), 7.70 (4H, d), 7.94 (1 H, s), 7.98 (1 H, d), 9.73 (1 H, s, NH), 10.35 (1 H, s, OH), 11.77 (1 H, s, NH); MS (ESI) m/z=551.3 [M+H]$^+$.

Example 23

In vitro IC$_{50}$ assay: Cells in the log phase of growth were seeded into 96-well culture plates in 0.1 mL of complete media and allowed to attach overnight at 37° C. Compounds diluted in culture media were added to each well in a volume of 0.1 mL to get a final volume of 0.2 mL/well. After cells were exposed to the compounds for 96 hours, 0.1 mL of media was removed and 0.01 mL of MTT reagent was added. The plates were then returned to the incubator for 4 hours. Detergent reagent (0.1 mL) was then added and the plates incubated at 37° C. overnight in the dark to solublize the cells and purple formazan crystals. The absorbance was measured at 570 nm. IC$_{50}$ values for selected compounds are listed in Table A.

TABLE A

IC$_{50}$ values (nM) of selected compounds against MCF-7, N87, and PC-3 cell lines

| Compound | DNA binder class | MCF-7 | N87 | PC-3 |
|---|---|---|---|---|
| A | DB1 | 0.085 | 0.156 | 0.212 |
| B | DB1 | 0.025 | 0.144 | 0.145 |
| C | DB1 | 0.037 | 0.173 | 0.120 |
| D | DB1 | 0.010 | 0.087 | 0.168 |
| E | DB1 | 0.050 | 0.185 | 0.176 |
| F | DB2 | 0.093 | 0.427 | 0.341 |
| G | DB2 | 0.069 | 0.556 | 0.581 |
| H | DB6 | 0.037 | 0.162 | 0.166 |
| I | DB6 | 0.050 | 0.359 | 0.292 |

REFERENCES

1 Boger, D. L.; Johnson, D. S.; Wrasidlo, W. *Bioorg. Med. Chem. Lett.* 1994, 4, 631-636.
2 McGovren, J. P., Clarke, G. L., Pratt, E. A., DeKoning, T. F. *J. Antibiot.* 1984, 37, 63-70.
3 Carter, P.; Smith, L.; Ryan, M. *Endocr.-Relat. Cancer* 2004, 11, 659-687.
4 Bagshawe, K. D. *Drug Dev. Res.* 1995, 34, 220-230.
5 Melton, R.; Connors, T.; Knox, R. J. *S.T.P. Pharma Sciences*, 1999, 13-33.
6 Huber, B. E.; Richards, C. A.; Krenitsky, T. A. *Proc. Natl. Acad. Sci. USA,* 1991, 88, 8039-8043.
7 Bagshawe, K. D.; Springer, C. J.; Searle, F.; Antoniw, P.; Sharma, S. K.; Melton, R. G.; Sherwood, R. F. *Br. J. Cancer,* 1988, 58, 700-703.
8 Duncan, R. *Nat. Rev. Drug Discov.* 2003, 2, 347-360.
9 Toki, B. E.; Cerveny, C. G.; Wahl, A. F.; Senter, P. D. *J. Org. Chem.,* 2002, 67, 1866-1872.
10 See for some recently disclosed cyclization spacers for example WO 2005/079398, WO 2005/105154, and WO 2006/012527.
11 Greenwald, R. B., Choe, Y. H., McGuire, J., Conover, C. D. *Adv. Drug Delivery Rev.* 2003, 55, 217-250.
12 Kingsbury, W. D.; Boehm; J. C.; Mehta, R. J.; Grappel, S. F.; Gilvarg, C. *J. Med. Chem.* 1984, 27, 1447-1451.
13 Greenwald, R. B.; Zhao, H.; Yang, K.; Reddy, P.; Martinez, A. *J. Med. Chem.* 2004, 47, 726-734.
14 (a) Franke, A. E.; Sievers, E. L.; and Scheinberg, D. A. *Cancer Biother. Radiopharm.* 2000, 15, 459-476. (b) Murray, J. L. *Semin. Oncol.* 2000, 27, 2564-2570. (c) Breitling, F., and Dubel, S., *Recombinant Antibodies,* John Wiley and Sons, New York, 1998.
15 Ringsdorf, H. *J. Polym. Sci., Polym. Symp.* 1975, 51, 135-153.
16 Elvira, C.; Gallardo, A.; San Roman, J.; Cifuentes, A. *Molecules* 2005, 10, 114-125.
17 Remington's Pharmaceutical Science (15th ed., Mack Publishing, Easton, Pa., 1980) (incorporated by reference in its entirety for all purposes)

The invention claimed is:
1. A compound of formula (I) or (II):

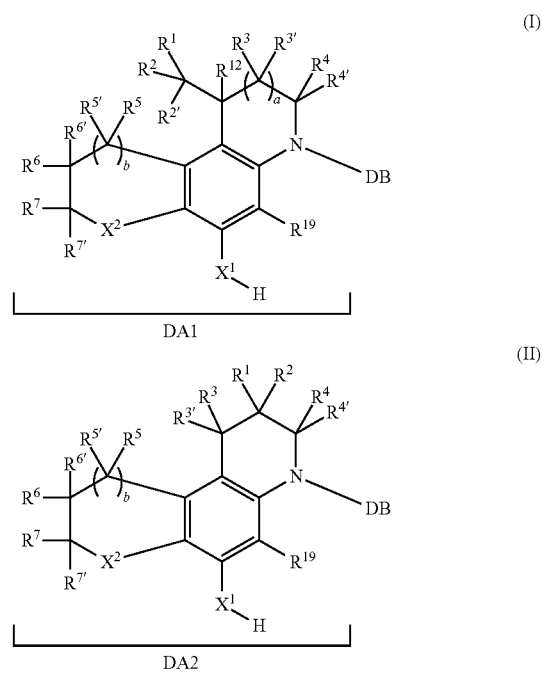

or a pharmaceutically acceptable salt, hydrate, or solvate thereof, wherein R$^1$ is a leaving group;

R$^2$, R$^{2'}$, R$^3$, R$^{3'}$, R$^4$, R$^{4'}$, R$^{12}$, and R$^{19}$ are independently selected from H, OH, SH, NH$_2$, N$_3$, NO$_2$, NO, CF$_3$, CN, C(O)NH$_2$, C(O)H, C(O)OH, halogen, R$^a$, SR$^a$, S(O)R$^a$, S(O)$_2$R$^a$, S(O)OR$^a$, S(O)$_2$OR$^a$, OS(O)R$^a$, OS(O)$_2$R$^a$, OS(O)OR$^a$, OS(O)$_2$OR$^a$, OR$^a$, NHR$^a$, N(R$^a$)R$^b$, $^+$N(R$^a$)(R$^b$)R$^c$, P(O)(OR$^a$)(OR$^b$), OP(O)(OR$^a$)(OR$^b$), SiR$^a$R$^b$R$^c$, C(O)R$^a$, C(O)OR$^a$, C(O)N(R$^a$)R$^b$, OC(O)R$^a$, OC(O)OR$^a$, OC(O)N(R$^a$)R$^b$, N(R$^a$)C(O)R$^b$, N(R$^a$)C(O)OR$^b$, and N(R$^a$)C(O)N(R$^b$)R$^c$, wherein R$^a$, R$^b$, and R$^c$ are independently selected from H and optionally substituted C$_{1-3}$ alkyl or C$_{1-3}$ heteroalkyl, or R$^3$+R$^{3'}$ and/or R$^4$+R$^{4'}$ are independently selected from =O, =S, =NOR$^{18}$, =C(R$^{18}$)R$^{18'}$, and =NR$^{18}$, R$^{18}$ and R$^{18'}$ being independently selected from H and optionally substituted C$_{1-3}$ alkyl, two or more of R$^2$, R$^{2'}$, R$^3$, R$^{3'}$, R$^4$, R$^{4'}$, and R$^{12}$ optionally being joined by one or more bonds to form one or more optionally substituted carbocycles and/or heterocycles;

X$^2$ is selected from O, C(R$^{14}$)(R$^{14'}$), and NR$^{14'}$, wherein R$^{14}$ and R$^{14'}$ have the same meaning as defined for R$^7$ and are independently selected, or R$^{14'}$ and R$^{7'}$ are absent resulting in a double bond between the atoms designated to bear R$^{7'}$ and R$^{14'}$;

R$^5$, R$^{5'}$, R$^6$, R$^{6'}$, R$^7$, and R$^{7'}$ are independently selected from H, OH, SH, NH$_2$, N$_3$, NO$_2$, NO, CF$_3$, CN, C(O)NH$_2$, C(O)H, C(O)OH, halogen, R$^e$, SR$^e$, S(O)R$^e$, S(O)$_2$R$^e$, S(O)OR$^e$, S(O)$_2$OR$^e$, OS(O)R$^e$, OS(O)$_2$R$^e$, OS(O)OR$^e$, OS(O)$_2$OR$^e$, OR$^e$, NHR$^e$, N(R$^e$)R$^f$, $^+$N(R$^e$)(R$^f$)R$^g$, P(O)(OR$^e$)(OR$^f$), OP(O)(OR$^e$)(OR$^f$), SiR$^e$R$^f$R$^g$, C(O)R$^e$, C(O)OR$^e$, C(O)N(R$^e$)R$^f$, OC(O)R$^e$, OC(O)OR$^e$, OC(O)N(R$^e$)R$^f$, N(R$^e$)R$^f$, N(R$^e$)C(O)R$^f$, N(R$^e$)C(O)OR$^f$, N(R$^e$)C(O)N(R$^f$)R$^g$, and a water-soluble group, wherein R$^e$, R$^f$, and R$^g$ are independently selected from H and optionally substituted (CH$_2$CH$_2$O)$_{ee}$CH$_2$CH$_2$X$^{13}$R$^{e1}$, C$_{1-15}$ alkyl, C$_{1-15}$ heteroalkyl, C$_{3-15}$ cycloalkyl, C$_{1-15}$ heterocycloalkyl, C$_{5-15}$ aryl, or C$_{1-15}$ heteroaryl, wherein ee is selected from 1 to 1000, X$^{13}$ is selected from O, S, and NR$^{f1}$, and R$^{f1}$ and R$^{e1}$ are independently selected from H and C$_{1-3}$ alkyl, one or more of the optional substituents in R$^e$, R$^f$, and/or R$^g$ optionally being a water-soluble group, two or more of R$^e$, R$^f$, and R$^g$ optionally being joined by one or more bonds to form one or more optionally substituted carbocycles and/or heterocycles, or R$^5$+R$^{5'}$ and/or R$^6$+R$^{6'}$ and/or R$^7$+R$^{7'}$ are independently selected from =O, =S, =NOR$^{e3}$, =C(R$^{e3}$)R$^{e4}$, and =NR$^{e3}$, R$^{e3}$ and R$^{e4}$ being independently selected from H and optionally substituted C$_{1-3}$ alkyl, or R$^{5'}$+R$^{6'}$ and/or R$^{6'}$+R$^{7'}$ and/or R$^{7'}$+R$^{14'}$ are absent, resulting in a double bond between the atoms designated to bear R$^{5'}$ and R$^{6'}$, and/or R$^{6'}$ and R$^{7'}$, and/or R$^{7'}$ and R$^{14'}$, respectively, two or more of R$^5$, R$^{5'}$, R$^6$, R$^{6'}$, R$^7$, R$^{7'}$, R$^{14}$, and R$^{14'}$ optionally being joined by one or more bonds to form one or more optionally substituted carbocycles and/or heterocycles;

X$^1$ is selected from O, S, and NR$^{13}$, wherein R$^{13}$ is selected from H and optionally substituted C$_{1-8}$ alkyl or C$_{1-8}$ heteroalkyl and not joined with any other substituent;

wherein DB is selected from the group consisting of:

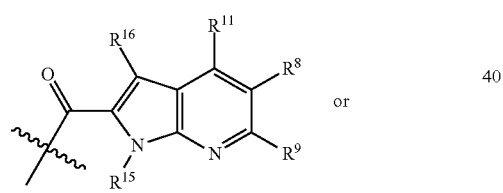 or

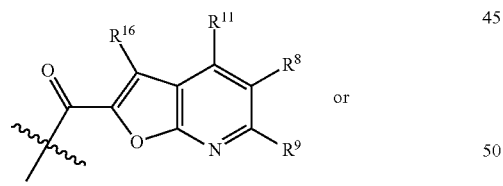 or

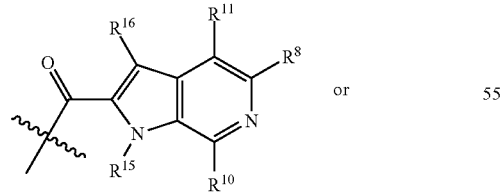 or

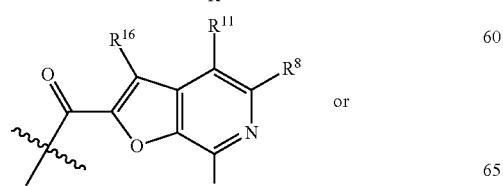 or

-continued

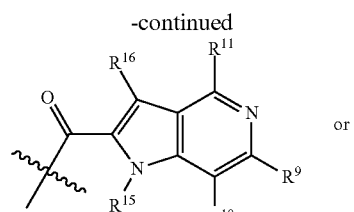 or

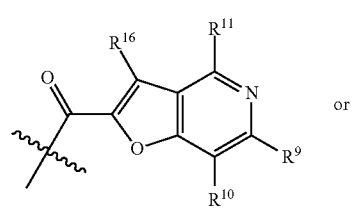 or

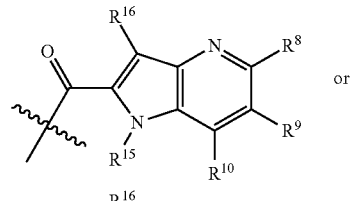 or

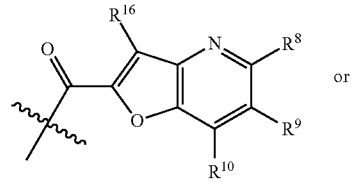 or

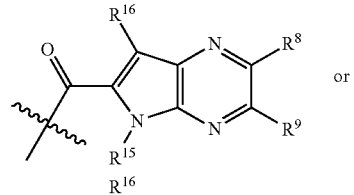 or

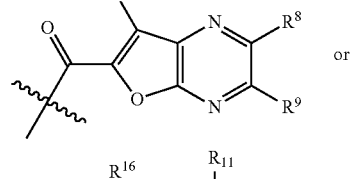 or

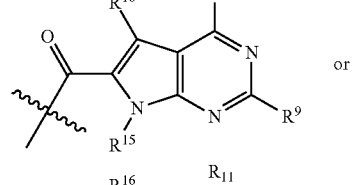 or

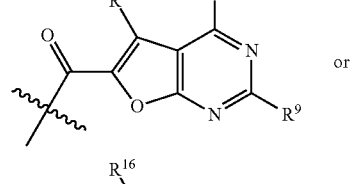 or

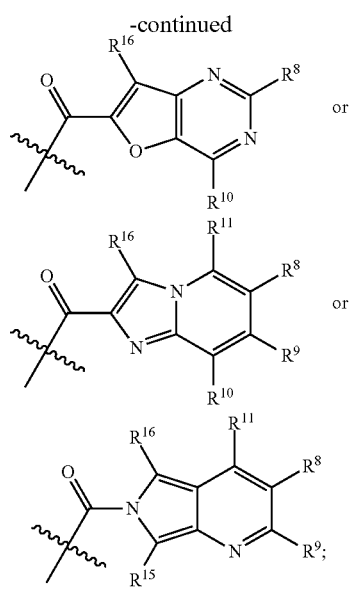

$R^8$, $R^9$, $R^{10}$, $R^{11}$, $R^{15}$, and $R^{16}$ are each independently selected from H, OH, SH, $NH_2$, $N_3$, $NO_2$, NO, $CF_3$, CN, $C(O)NH_2$, C(O)H, C(O)OH, halogen, $R^h$, $SR^h$, $S(O)R^h$, $S(O)_2R^h$, $S(O)OR^h$, $S(O)_2OR^h$, $OS(O)R^h$, $OS(O)_2R^h$, $OS(O)OR^h$, $OS(O)_2OR^h$, $OR^h$, $NHR^h$, $N(R^h)R^i$, $^+N(R^h)(R^i)R^j$, $P(O)(OR^h)(OR^i)$, $OP(O)(OR^h)(OR^i)$, $SiR^hR^iR^j$, $C(O)R^h$, $C(O)OR^h$, $C(O)N(R^h)R^i$, $OC(O)R^h$, $OC(O)OR^h$, $OC(O)N(R^h)R^i$, $N(R^h)C(O)R^i$, $N(R^h)C(O)OR^i$, $N(R^h)C(O)N(R^i)R^j$, and a water-soluble group, wherein $R^h$, $R^i$, and $R^j$ are independently selected from H and optionally substituted $(CH_2CH_2O)_{ee}CH_2CH_2X^{13}R^{e1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, one or more of the optional substituents in $R^h$, $R^i$, and/or $R^j$ optionally being a water-soluble group, two or more of $R^h$, $R^i$, and $R^j$ optionally being joined by one or more bonds to form one or more optionally substituted carbocycles and/or heterocycles, one of $R^2$, $R^{2'}$, $R^3$, and $R^{3'}$ and one of $R^5$ and $R^{5'}$ may optionally be joined by one or more bonds to form one or more optionally substituted carbocycles and/or heterocycles;

a and b are independently selected from 0 and 1;

wherein for each group that is optionally substituted, the substituent, when present, is selected from the group consisting of OH, =O, =S, $=NR^k$, $=N-OR^k$, SH, $NH_2$, $NO_2$, NO, $N_3$, $CF_3$, CN, OCN, SCN, NCO, NCS, $C(O)NH_2$, C(O)H, C(O)OH, halogen, $R^k$, $SR^k$, $S(O)R^k$, $S(O)OR^k$, $S(O)_2R^k$, $S(O)_2OR^k$, $OS(O)R^k$, $OS(O)OR^k$, $OS(O)_2R^k$, $OS(O)_2OR^k$, $S(O)N(R^k)R^l$, $OS(O)N(R^k)R^l$, $S(O)_2N(R^k)R^l$, $OS(O)_2N(R^k)R^l$, $OP(O)(OR^k)(OR^l)$, $P(O)(OR^k)(OR^l)$, $OR^k$, $NHR^k$, $N(R^k)R^l$, $^+N(R^k)(R^l)R^m$, $Si(R^k)(R^l)(R^m)$, $C(O)R^k$, $C(O)OR^k$, $C(O)N(R^k)R^l$, $OC(O)R^k$, $OC(O)OR^k$, $OC(O)N(R^k)R^l$, $N(R^k)C(O)R^l$, $N(R^k)C(O)OR^l$, $N(R^k)C(O)N(R^l)R^m$, a water-soluble group, and the thio derivatives of these substituents, and protonated, charged, and deprotonated forms of any of these substituents, wherein $R^k$, $R^l$, and $R^m$ are independently selected from H and optionally substituted $-(CH_2CH_2O)_{yy}CH_2CH_2X^{17}R^{yy}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, or a combination thereof, wherein yy is selected from 1 to 1000, $X^{17}$ is independently selected from O, S, and $NR^{zz}$, and $R^{zz}$ and $R^{yy}$ are independently selected from H and $C_{1-3}$ alkyl, two or more of $R^k$, $R^l$, and $R^m$ optionally being joined by one or more bonds to form one or more optionally substituted carbocycles and/or heterocycles; and wherein the water-soluble group is selected from the group consisting of polyalcohols, straight chain or cyclic saccharides, primary, secondary, tertiary, or quaternary amines and polyamines, sulfate groups, sulfonate groups, sulfinate groups, carboxylate groups, phosphate groups, phosphonate groups, phosphinate groups, ascorbate groups, glycols, and polyethers.

2. The compound according to claim 1 wherein DB is selected from

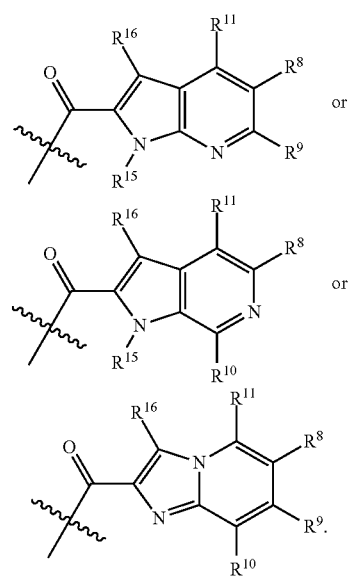

3. The compound according to claim 1 which is a compound of the formula

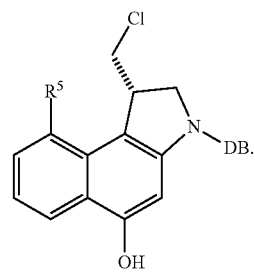

4. The compound according to claim 1 wherein $R^5$ is selected from methyl, ethyl, propyl, isopropyl, nitro, $CF_3$, F, Cl, Br, cyano, methoxy, ethoxy, propoxy, isopropoxy, amino ($NH_2$), methylamino, formyl, hydroxymethyl, and dimethylamino.

5. The compound according to claim 1 wherein at least one of the substituents $R^1$, $R^5$, $R^{5'}$, $R^6$, $R^{6'}$, $R^7$, $R^{7'}$, $R^{14}$, $R^{14'}$, $R^8$, $R^9$, $R^{10}$, $R^{11}$, $R^{15}$, and $R^{16}$ contains a $X^{14}(CH_2CH_2O)_{\!f\!f}CH_2CH_2X^{14}$ moiety, wherein ff is selected from 1 to 1000 and each $X^{14}$ is independently selected from

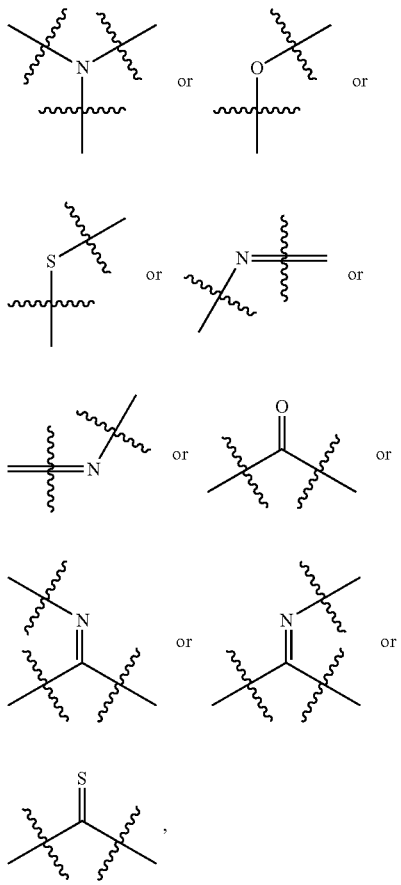

that is connected to the attachment site of said substituent either via a direct bond or via a moiety, being part of said same substituent, that does not comprise a disulfide, a hydrazone, a hydrazide, an ester, a natural amino acid, or a peptide containing at least one natural amino acid.

6. The compound according to claim 1 wherein at least one of the substituents $R^1$, $R^5$, $R^{5'}$, $R^6$, $R^{6'}$, $R^7$, $R^{7'}$, $R^{14}$, $R^{14'}$, $R^8$, $R^9$, $R^{10}$, $R^{11}$, $R^{15}$, and $R^{16}$ contains a triazole moiety.

7. A pharmaceutical composition comprising a compound according to claim 1 and a pharmaceutically acceptable carrier.

8. The compound according to claim 1 wherein DB is

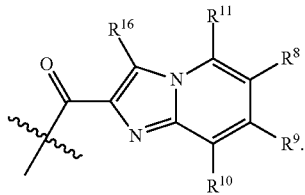

9. The compound according to claim 3, wherein DB is selected from

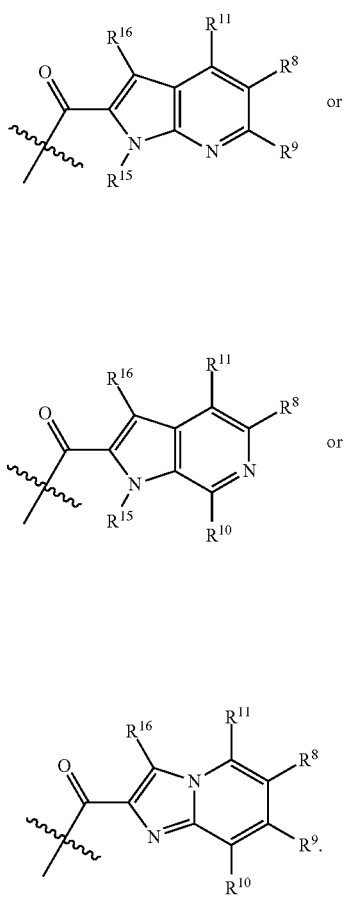

10. The compound according to claim 9 wherein DB is

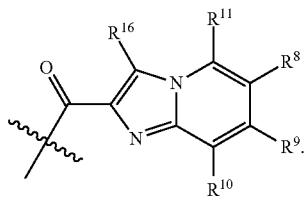

11. The compound according to claim 3 wherein $R^5$ is selected from methyl, ethyl, propyl, isopropyl, nitro, $CF_3$, F, Cl, Br, cyano, methoxy, ethoxy, propoxy, isopropoxy, amino ($NH_2$), methylamino, formyl, hydroxymethyl, and dimethylamino.

12. The compound according to claim 9 wherein the compound is selected from the group consisting of the compounds of formula 71, 72, 73, 74, 75, 76, and 77:

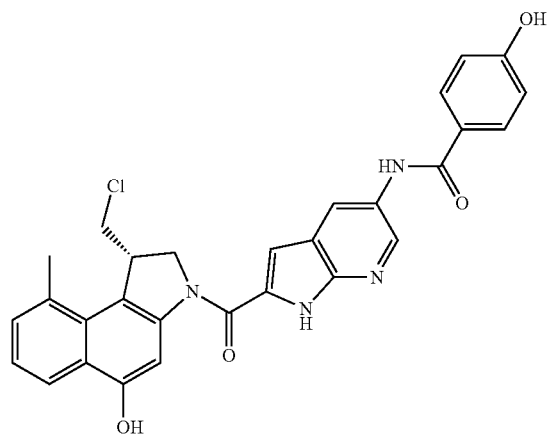
71
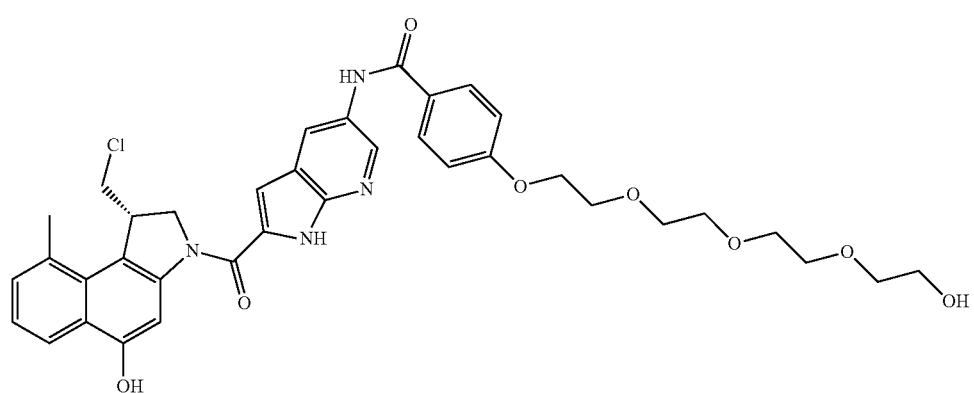
72
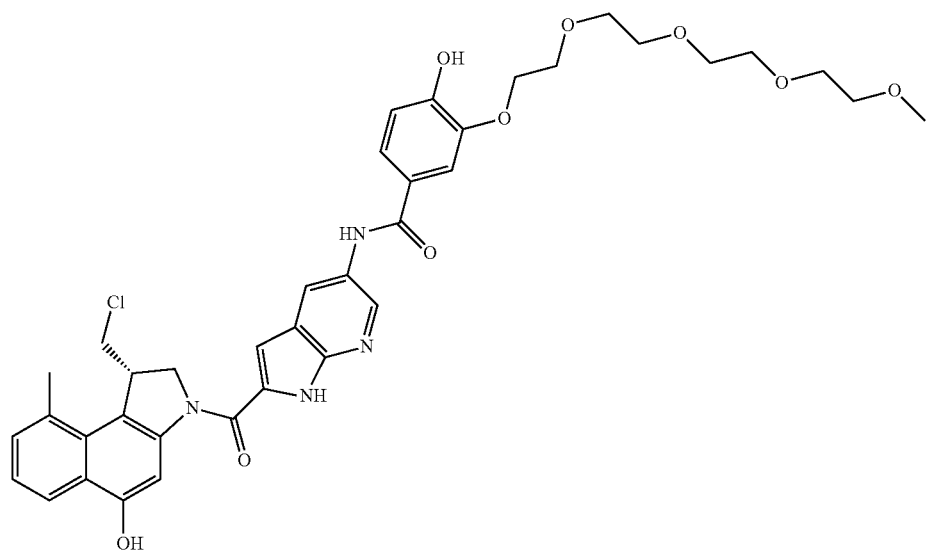
73

-continued
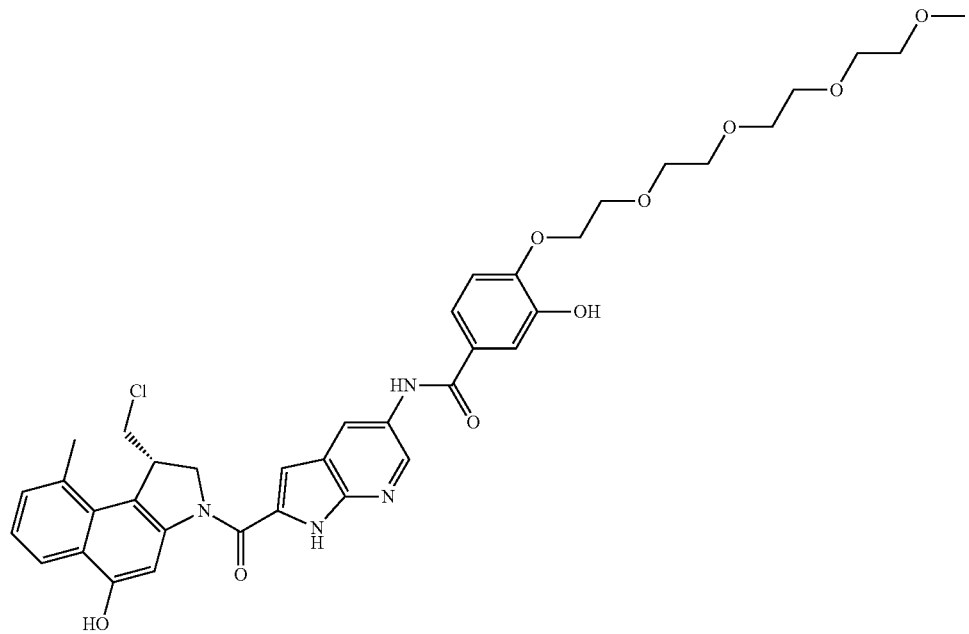
74
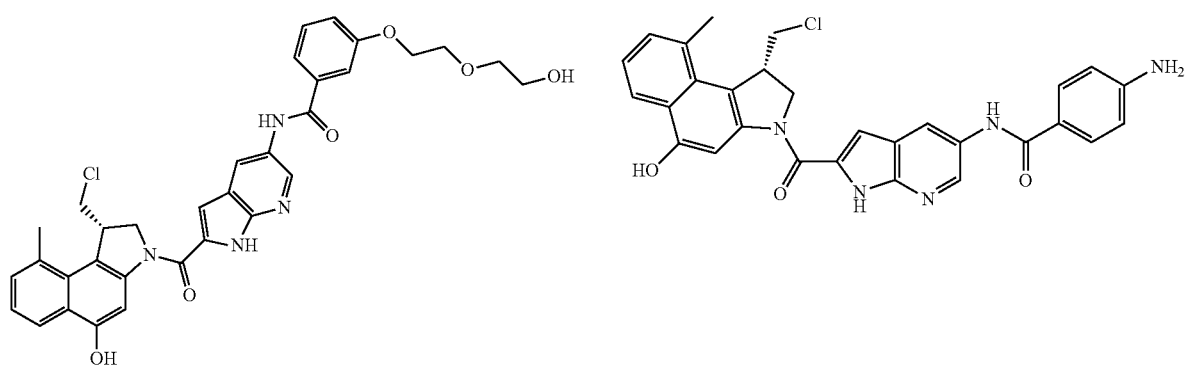
75
76
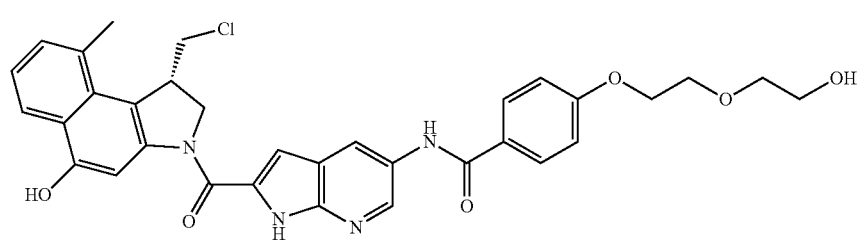
77
13. The compound according to claim 9 wherein the compound is selected from the group consisting of the compounds of formula 58, 59, 60, and 61:

58
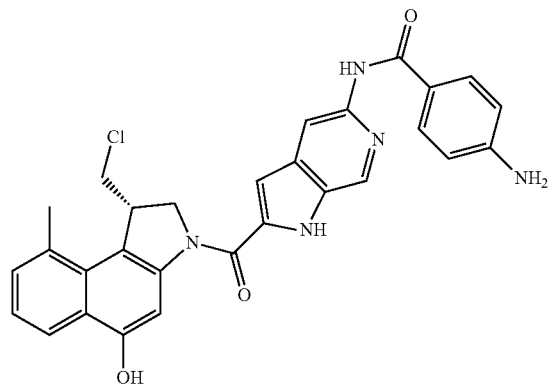
60
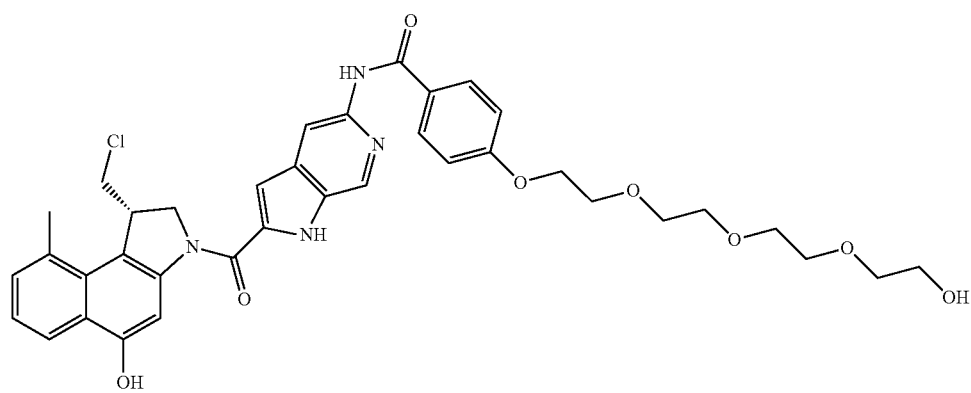
61
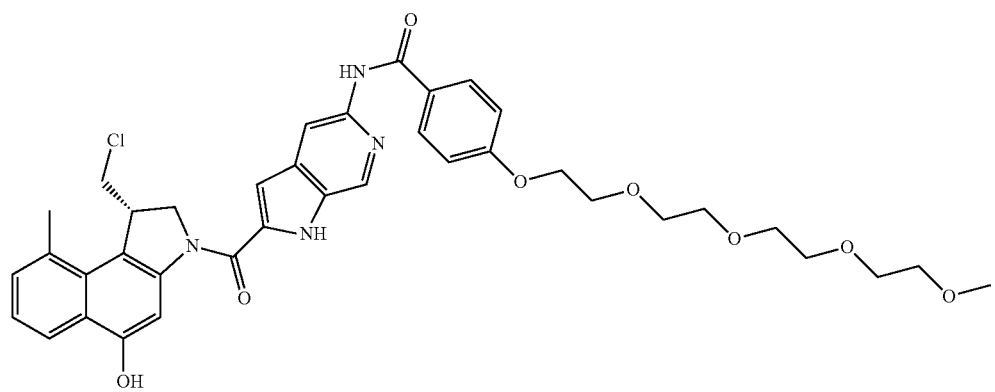
59
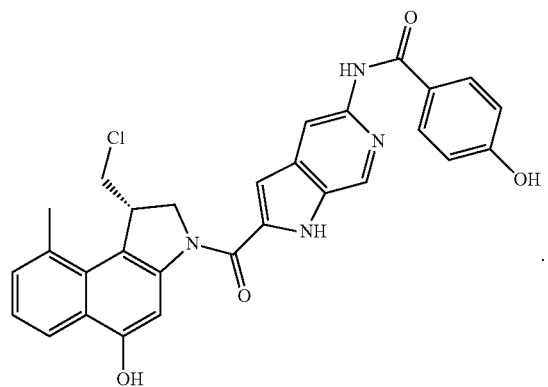
14. The compound according to claim 10 wherein the compound is selected from the group consisting of the compounds of formula 81, 84, 85, and 86:

81
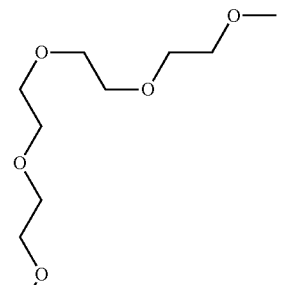
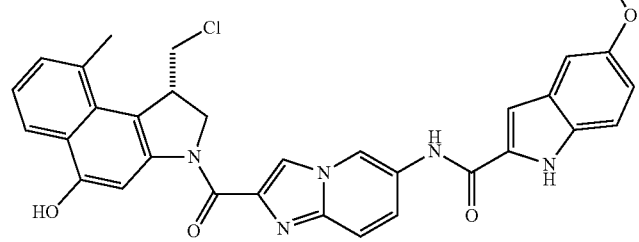
84
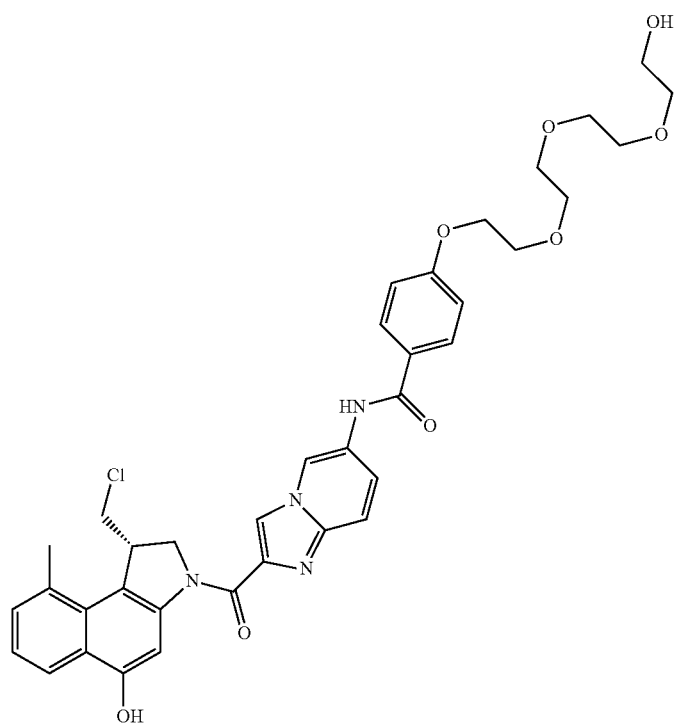

-continued
85
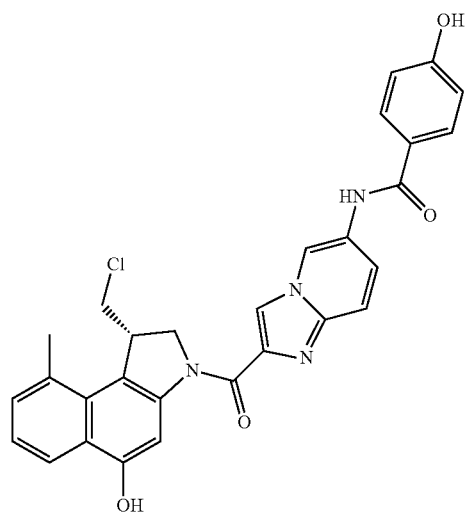
86
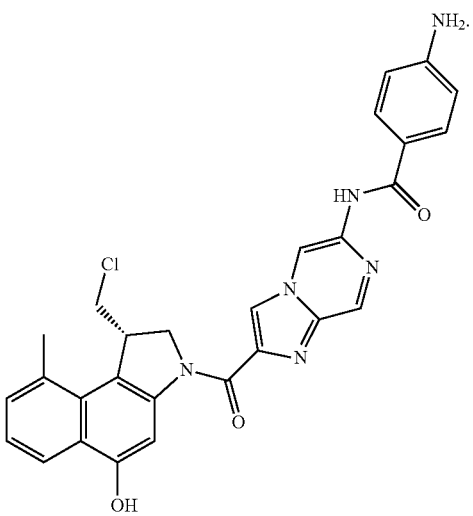
86
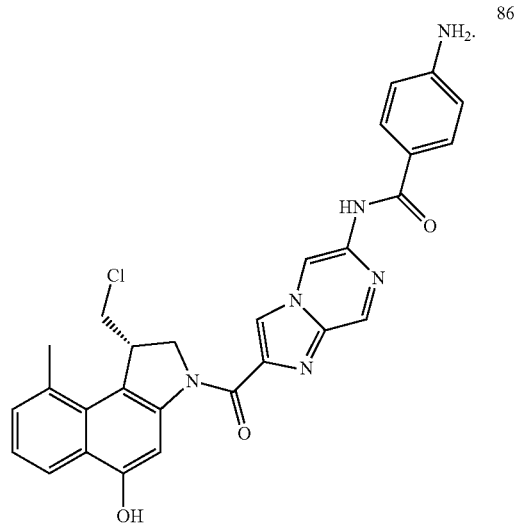 [SMILES: Cc1cccc2c(O)cc3c(c12)[C@H](CCl)CN3C(=O)c1cn2cc(NC(=O)c3ccc(N)cc3)ncc2n1]
* * * * *